(12) United States Patent
Chen et al.

(10) Patent No.: US 10,555,948 B2
(45) Date of Patent: Feb. 11, 2020

(54) NANOCARRIERS AND THEIR PROCESSING FOR DIAGNOSTICS AND THERAPEUTICS

(71) Applicant: Rhode Island Hospital, Providence, RI (US)

(72) Inventors: Qian Chen, Barrington, RI (US);
Yupeng Chen, Mansfield, MA (US);
Hongchuan Yu, Mansfield, MA (US);
Michael G. Ehrlich, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 15/687,289

(22) Filed: Aug. 25, 2017

(65) Prior Publication Data

US 2018/0193344 A1    Jul. 12, 2018

Related U.S. Application Data

(63) Continuation of application No. 14/659,071, filed on Mar. 16, 2015, now Pat. No. 9,775,842.
(Continued)

(51) Int. Cl.
*A61K 9/00* (2006.01)
*A61K 31/519* (2006.01)
(Continued)

(52) U.S. Cl.
CPC .......... *A61K 31/519* (2013.01); *A61K 9/0019* (2013.01); *A61K 9/0092* (2013.01); *A61K 9/08* (2013.01); *A61K 9/5123* (2013.01); *A61K 9/5146* (2013.01); *A61K 47/6949* (2017.08); *A61K 49/0095* (2013.01); *C12Q 1/6881* (2013.01); *C12Q 1/6883* (2013.01); *C12Q 1/6886* (2013.01); *G01N 33/6893* (2013.01); *C12N 15/113* (2013.01); *C12N 15/1137* (2013.01); *C12N 15/1138* (2013.01); *C12N 2310/14* (2013.01); *C12N 2320/32* (2013.01);
(Continued)

(58) Field of Classification Search
CPC .................................................. A61K 31/519
See application file for complete search history.

(56) References Cited

U.S. PATENT DOCUMENTS 6,696,565 B2    2/2004   Fenniri
8,795,691 B2    8/2014   Webster et al.
(Continued)

FOREIGN PATENT DOCUMENTS

WO          9219195 A1      11/1992
WO          WO-0182899 A2   11/2001
(Continued)

OTHER PUBLICATIONS

GenBank Accession No. NM_007365.2.
(Continued)

*Primary Examiner* — Paul W Dickinson
(74) *Attorney, Agent, or Firm* — Mintz Levin Cohn Ferris Glovsky and Popeo, P.C.; Ingrid A. Beattie; Joohee Lee

(57) ABSTRACT

The compositions and methods of the invention provide compositions and methods for preferential targeting of tissues to delivery therapeutic or diagnostic agents. For example, such compounds are useful in the treatment of joint disorders those affecting articulating joints, e.g., injury-induced osteoarthritis as well as autoimmune diseases affecting joint tissue such as rheumatoid arthritis.

32 Claims, 60 Drawing Sheets

Specification includes a Sequence Listing.

Related U.S. Application Data

(60) Provisional application No. 62/113,335, filed on Feb. 6, 2015, provisional application No. 61/953,495, filed on Mar. 14, 2014.

(51) Int. Cl.

| | |
|---|---|
| C12Q 1/6881 | (2018.01) |
| A61K 49/00 | (2006.01) |
| C12Q 1/6883 | (2018.01) |
| C12Q 1/6886 | (2018.01) |
| A61K 47/69 | (2017.01) |
| G01N 33/68 | (2006.01) |
| A61K 9/51 | (2006.01) |
| A61K 9/08 | (2006.01) |
| C12N 15/113 | (2010.01) |

(52) U.S. Cl.
CPC . C12Q 2600/106 (2013.01); C12Q 2600/158 (2013.01); C12Q 2600/178 (2013.01); C12Y 304/24812 (2013.01); G01N 2800/102 (2013.01); Y02A 50/401 (2018.01)

(56) References Cited

U.S. PATENT DOCUMENTS

| | | |
|---|---|---|
| 9,775,842 B2 | 10/2017 | Chen et al. |
| 2006/0210552 A1 | 9/2006 | Demopulos et al. |
| 2010/0125100 A1 | 5/2010 | Bergey et al. |
| 2011/0177169 A1 | 7/2011 | Anderson et al. |
| 2011/0213121 A1 | 9/2011 | Kwon et al. |
| 2012/0171121 A1 | 7/2012 | Webster |
| 2013/0274226 A1 | 10/2013 | Cheng et al. |
| 2014/0171482 A1 | 6/2014 | Webster et al. |

FOREIGN PATENT DOCUMENTS

| | | |
|---|---|---|
| WO | WO-2008109347 A2 | 9/2008 |
| WO | WO-2012094304 A1 | 7/2012 |

OTHER PUBLICATIONS

GenBank Accession No. NM_012387.2.
GenBank Accession No. NM_016233.2.
GenBank Accession No. NM_018724.3.
GenBank Accession No. NP_000408.1.
GenBank Accession No. NP_000566.3.
GenBank Accession No. NP_000567.1.
GenBank Accession No. NP_000568.1.
GenBank Accession No. NP_000575.1.
GenBank Accession No. NP_000585.2.
GenBank Accession No. NP_000591 .1.
GenBank Accession No. NP_000609.1.
GenBank Accession No. NP_000651.3.
GenBank Accession No. NP_000868.1.
GenBank Accession No. NP_001020537.2.
GenBank Accession No. NP_001056.1.
GenBank Accession No. NP_001129071.1.
GenBank Accession No. NP_001139410.1.
GenBank Accession No. NP_001191.1.
GenBank Accession No. NP_0011932.
GenBank Accession No. NP_001278736.1.
GenBank Accession No. NP_001446.1.
GenBank Accession No. NP_001710.1.
GenBank Accession No. NP_001926.2.
GenBank Accession No. NP_002413.1.
GenBank Accession No. NP_002418.1.
GenBank Accession No. NP_004985.2.
GenBank Accession No. NP_005090.3.
GenBank Accession No. NP_008969.2.
GenBank Accession No. NP_031391.2.
GenBank Accession No. NP_036519.2.
GenBank Accession No. NP_057317.2.
GenBank Accession No. NP_061194.2.
Chen et al. Self-assembled rosette nanotube/hydrogel composites for cartilage tissue engineering. Tissue Eng Part C Methods. Dec. 2010;16(6):1233-43.
Comper. Physiochemical aspects of cartilage extra cellular matrix. Cartilage: Molecular Aspects 1991;59-96.
Fenniri et al., Helical rosette nanotubes: design, self-assembly, and characterization. J Am Chem Soc. Apr. 25, 2001;123(16):3854-5.
Fine et al., Enhanced endothelial cell functions on rosette nanotube-coated titanium vascular stents. Int J Nanomedicine. 2009;4:91-7.
GenBank Accession No. AAA36755.1.
GenBank Accession No. AAA51943.1.
GenBank Accession No. AAB05605.1.
GenBank Accession No. AAC50137.1.
GenBank Accession No. AAH18149.1.
GenBank Accession No. AAI14481.1.
GenBank Accession No. AAO92293.1.
GenBank Accession No. ABQ15210.1.
GenBank Accession No. ADZ73424.1.
GenBank Accession No. AF480527.1.
GenBank Accession No. AY242126.1.
GenBank Accession No. BC018149.2.
GenBank Accession No. BC071670.1.
GenBank Accession No. BC114480.1.
GenBank Accession No. EF534714.1.
GenBank Accession No. HQ267233.1.
GenBank Accession No. JQ768366.1.
GenBank Accession No. L78440.1.
GenBank Accession No. LM608509.1.
GenBank Accession No. M55994.1.
GenBank Accession No. M74777.1.
GenBank Accession No. NM_000417.2.
GenBank Accession No. NM_000575.3.
GenBank Accession No. NM_000576.2.
GenBank Accession No. NM_000577.4.
GenBank Accession No. NM_000584.3.
GenBank Accession No. NM_000594.3.
GenBank Accession No. NM_000600.3.
GenBank Accession No. NM_000618.3.
GenBank Accession No. NM_000660.5.
GenBank Accession No. NM_000877.3.
GenBank Accession No. NM_001025366.2.
GenBank Accession No. NM_001065.3.
GenBank Accession No. NM_001135599.2.
GenBank Accession No. NM_001145938.1.
GenBank Accession No. NM_001200.2.
GenBank Accession No. NM_001202.3.
GenBank Accession No. NM_001291807.1.
GenBank Accession No. NM_001455.3.
GenBank Accession No. NM_001719.2.
GenBank Accession No. NM_001935.3.
GenBank Accession No. NM_002422.3.
GenBank Accession No. NM_002427.3.
GenBank Accession No. NM_003789.3.
GenBank Accession No. NM_004994.2.
GenBank Accession No. NM_005099.4.
GenBank Accession No. NR_029501.1.
GenBank Accession No. NR_029620.1.
GenBank Accession No. NR_029681.1.
GenBank Accession No. NR_029693.1.
GenBank Accession No. NR_029854.1.
GenBank Accession No. U25994.1.
Journeay et al., Low inflammatory activation by self-assembling Rosette nanotubes in human Calu-3 pulmonary epithelial cells. Small. Jun. 2008;4(6):817-23.
Journeay et al., Rosette nanotubes show low acute pulmonary toxicity in vivo. Int J Nanomedicine. 2008;3(3):373-83.
Moralez et al., Helical rosette nanotubes with tunable stability and hierarchy. J Am Chem Soc. Jun. 15, 2005;127(23):8307-9.

(56) References Cited

OTHER PUBLICATIONS

Shvedova et al., Unusual inflammatory and fibrogenic pulmonary responses to single-walled carbon nanotubes in mice. Am J Physiol Lung Cell Mol Physiol. Nov. 2005;289(5):L698-708.

Torzilli et al., Effect of proteoglycan removal on solute mobility in articular cartilage. J Biomech. Sep. 1997;30(9):895-902.

Tyagi et al., Multicolor molecular beacons for allele discrimination. Nat Biotechnol. Jan. 1998;16(1):49-53.

Zhang et al., Arginine-glycine-aspartic acid modified rosette nanotube-hydrogel composites for bone tissue engineering. Biomaterials. Mar. 2009;30(7):1309-20.

Zhang et al., Cell behaviors on polysaccharide-wrapped single-wall carbon nanotubes: a quantitative study of the surface properties of biomimetic nanofibrous scaffolds. ACS Nano. Oct. 27, 2009;3(10):3200-6.

Cabral et al., Accumulation of sub-100 nm polymeric micelles in poorly permeable tumours depends on size. Nat Nanotechnol. Oct. 23, 2011;6(12):815-23.

Honary et al., Effect of Zeta Potential on the Properties of Nano-Drug Delivery Systems—A Review (Part 1). Tropical Journal of Pharmaceutical Research. Apr. 2013;12(2):255-64.

Honary et al., Effect of Zeta Potential on the Properties of Nano-Drug Delivery Systems—A Review (Part 2). Tropical Journal of Pharmaceutical Research. Apr. 2013;12(2):265-73.

Periyasamy et al., Nanomaterials for the Local and Targeted Delivery of Osteoarthritis Drugs. Journal of Nanomaterials. 2012.

FIG. 4
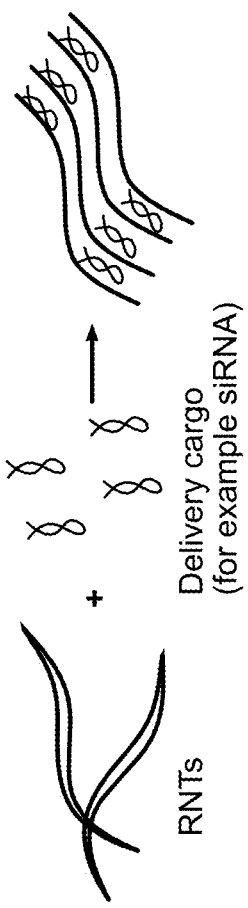
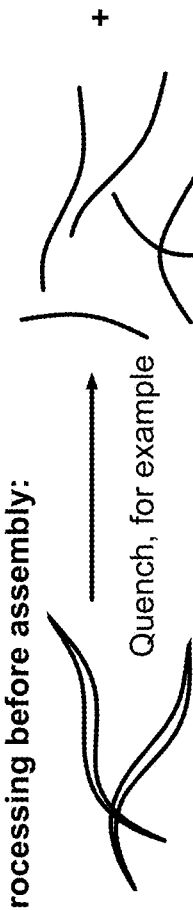
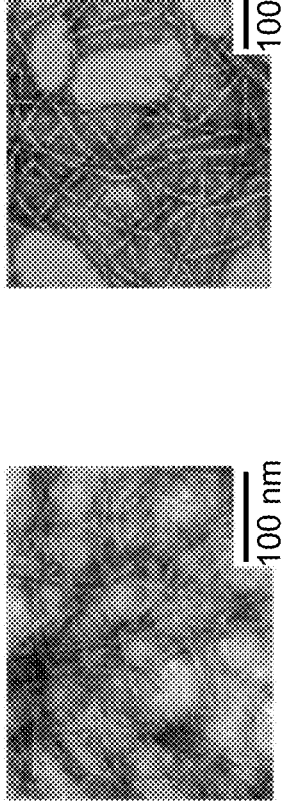
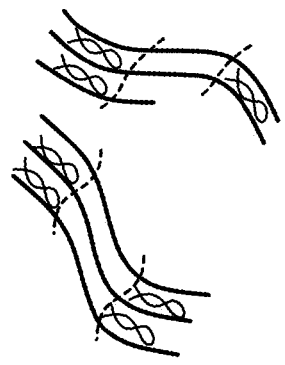
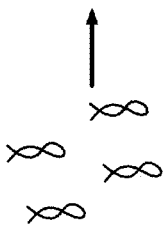
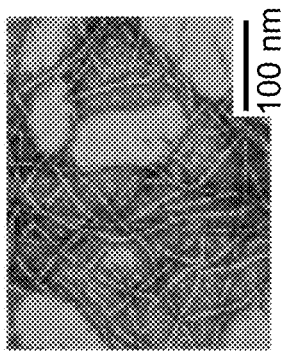
General assembly mechanism:
RNTs + Delivery cargo (for example siRNA) → Assembly between RNTs and delivery cargos. → Eventually, smaller nanopieces can be generated.
Processing before assembly:
Quench, for example
Long and bundled RNTs
Shorten and broken RNTs

FIG. 4 (continued)

Processing during assembly:

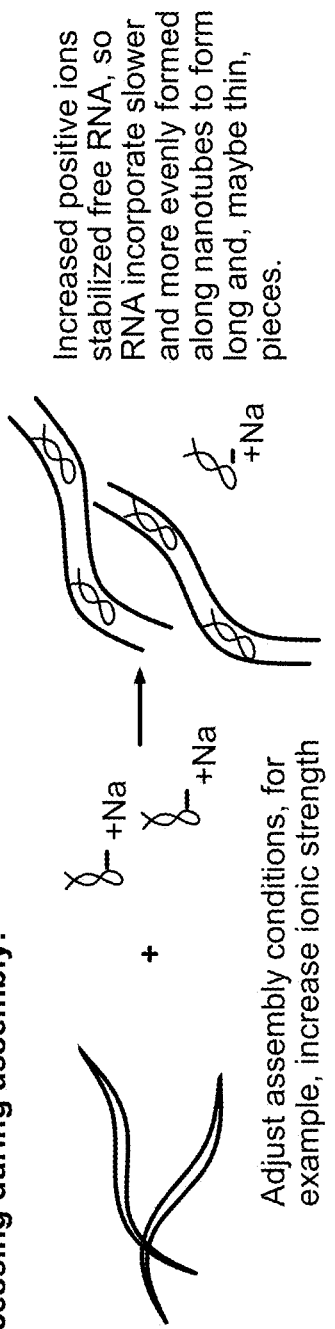

Adjust assembly conditions, for example, increase ionic strength

Increased positive ions stabilized free RNA, so RNA incorporate slower and more evenly formed along nanotubes to form long and, maybe thin, pieces.

Processing after assembly:

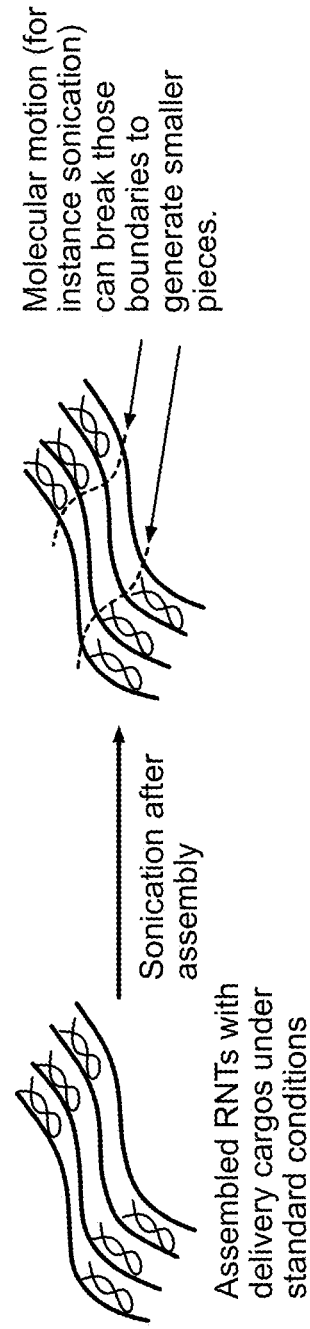

Assembled RNTs with delivery cargos under standard conditions

Sonication after assembly

Molecular motion (for instance sonication) can break those boundaries to generate smaller pieces.

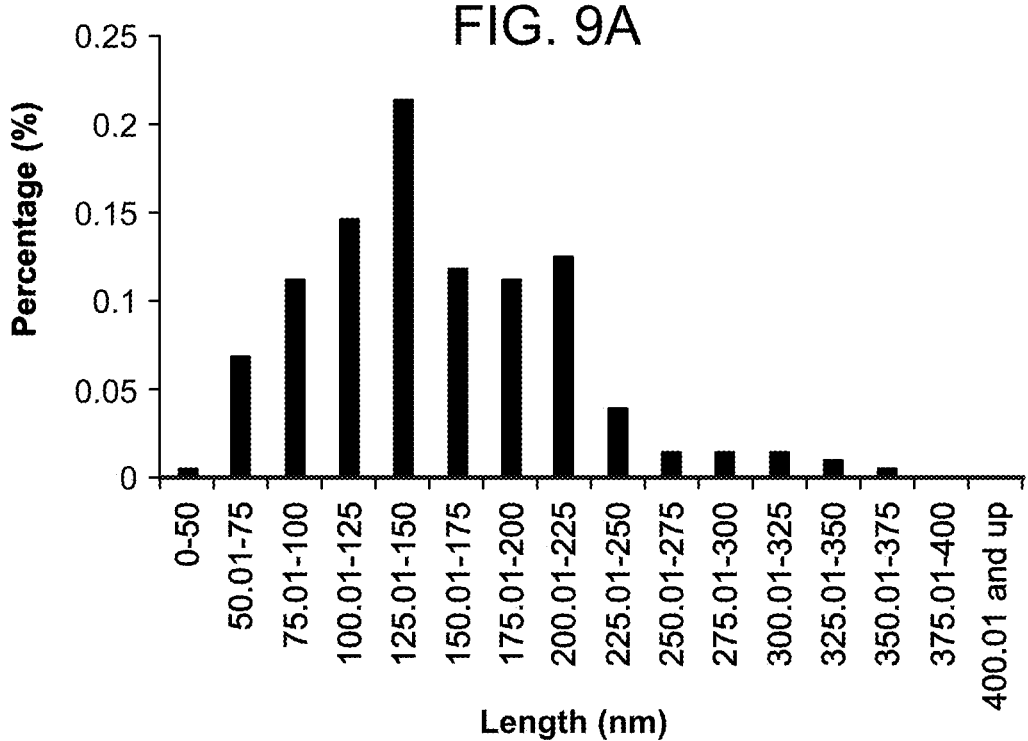
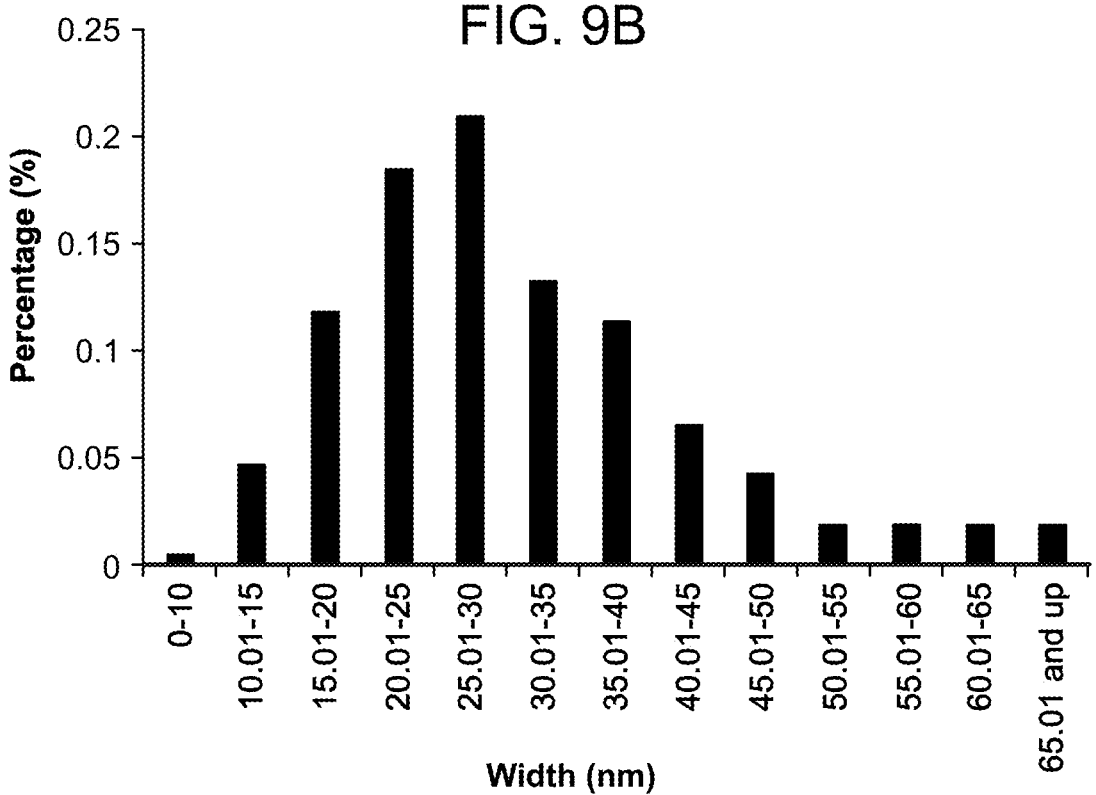

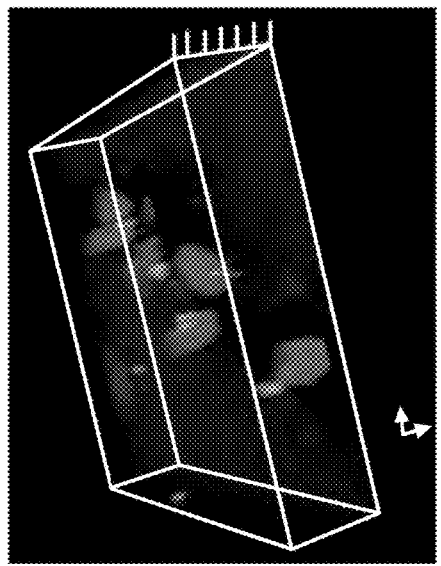
FIG. 15A
FIG. 15B
FIG. 15C
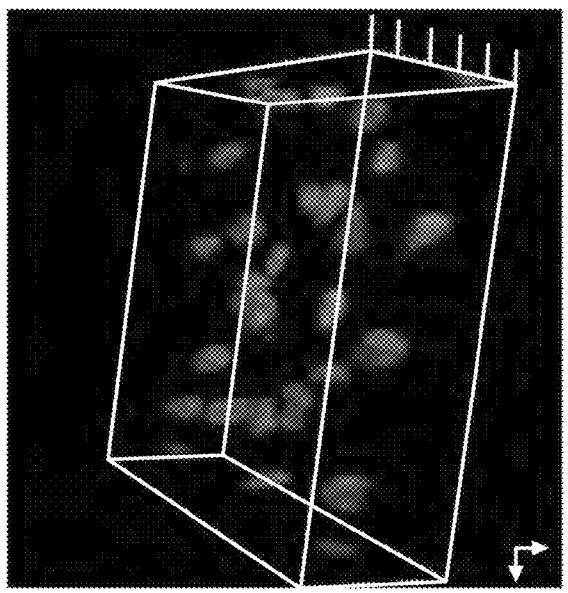
FIG. 16A
FIG. 16B

No stimulation

IL-1β stimulation

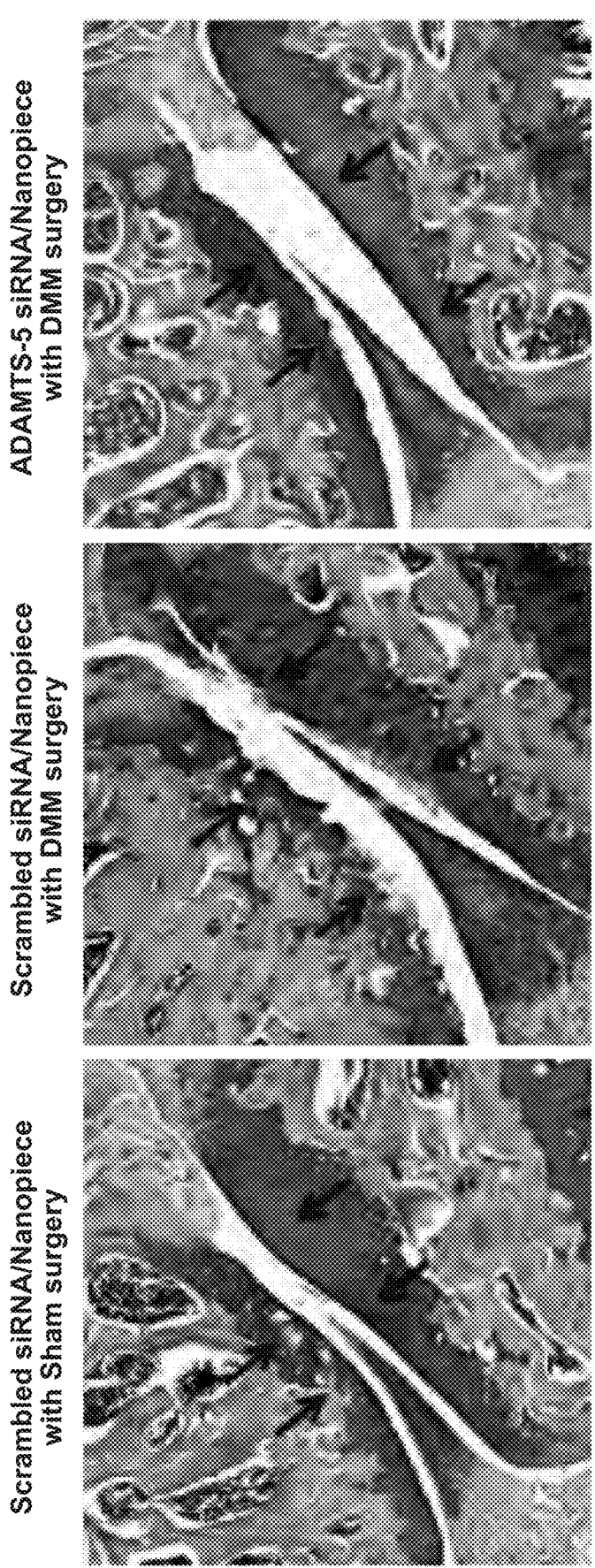

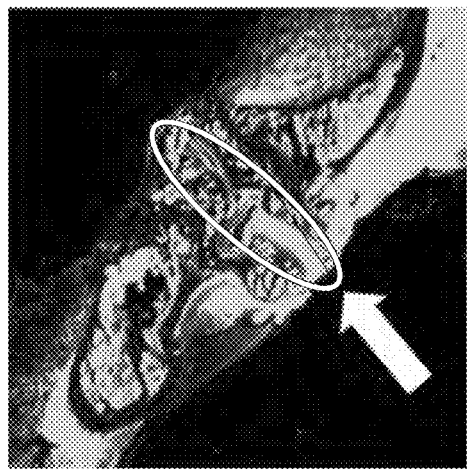
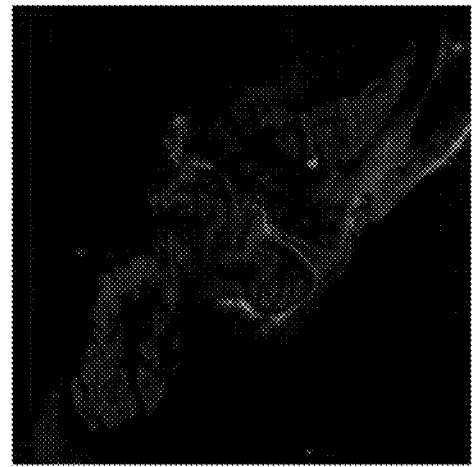
FIG. 37A
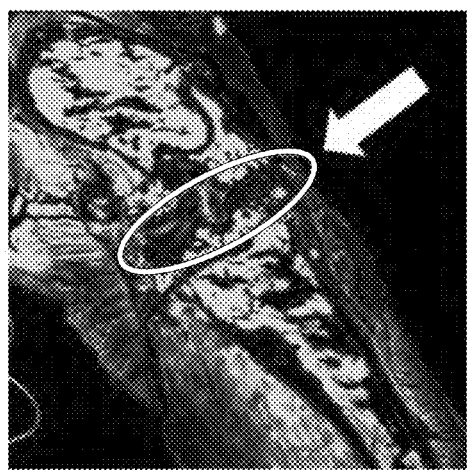
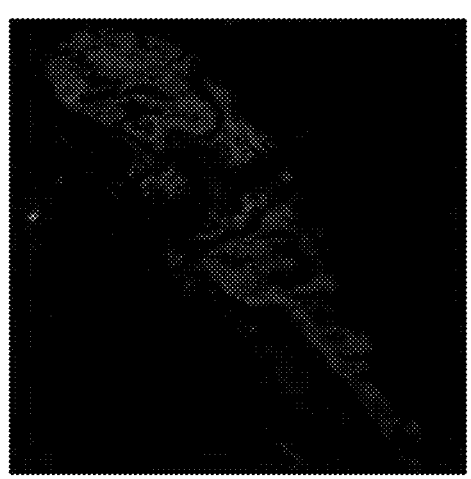
FIG. 37B

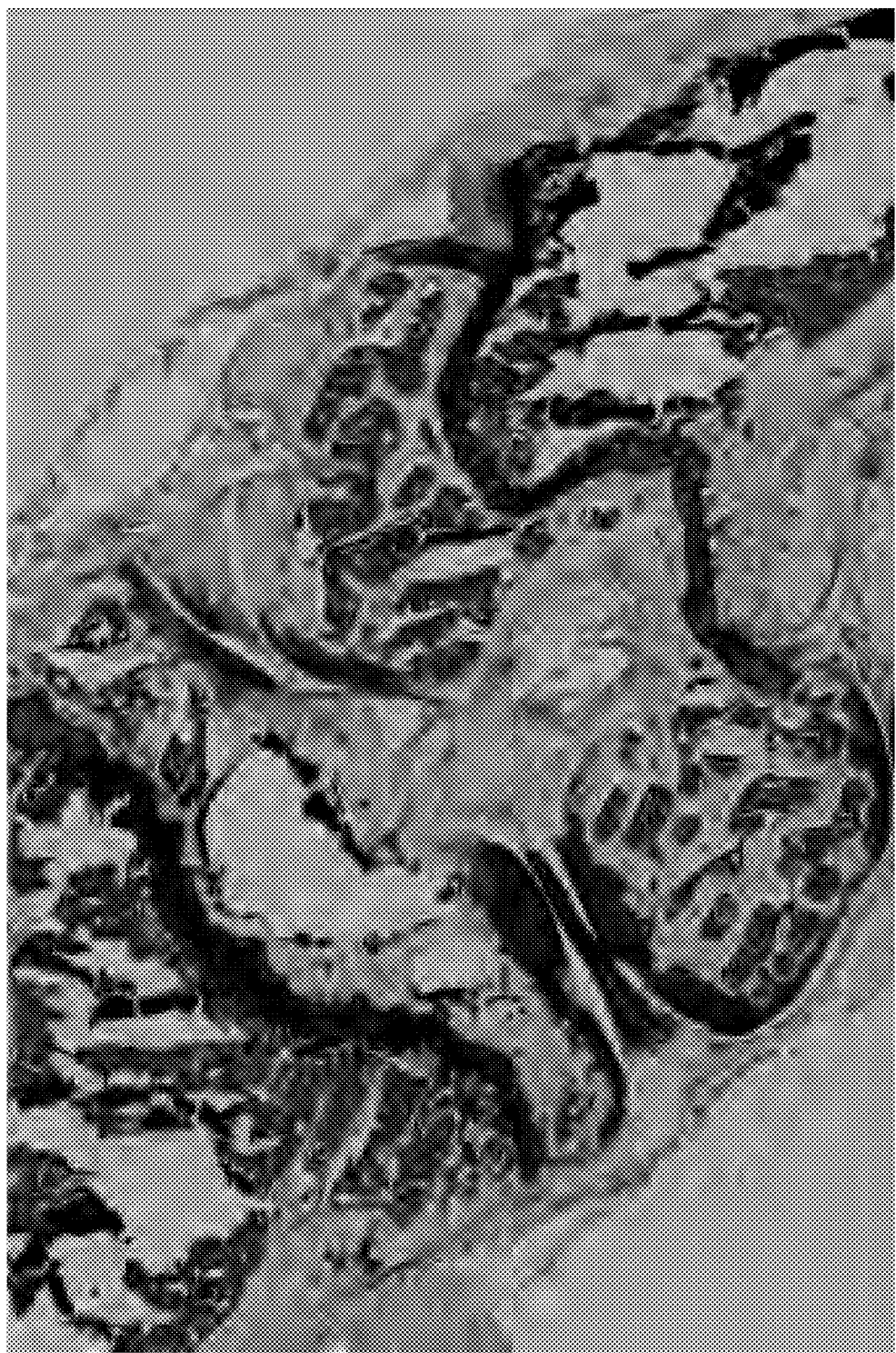
FIG. 38 — DMM knee 30 days after surgery

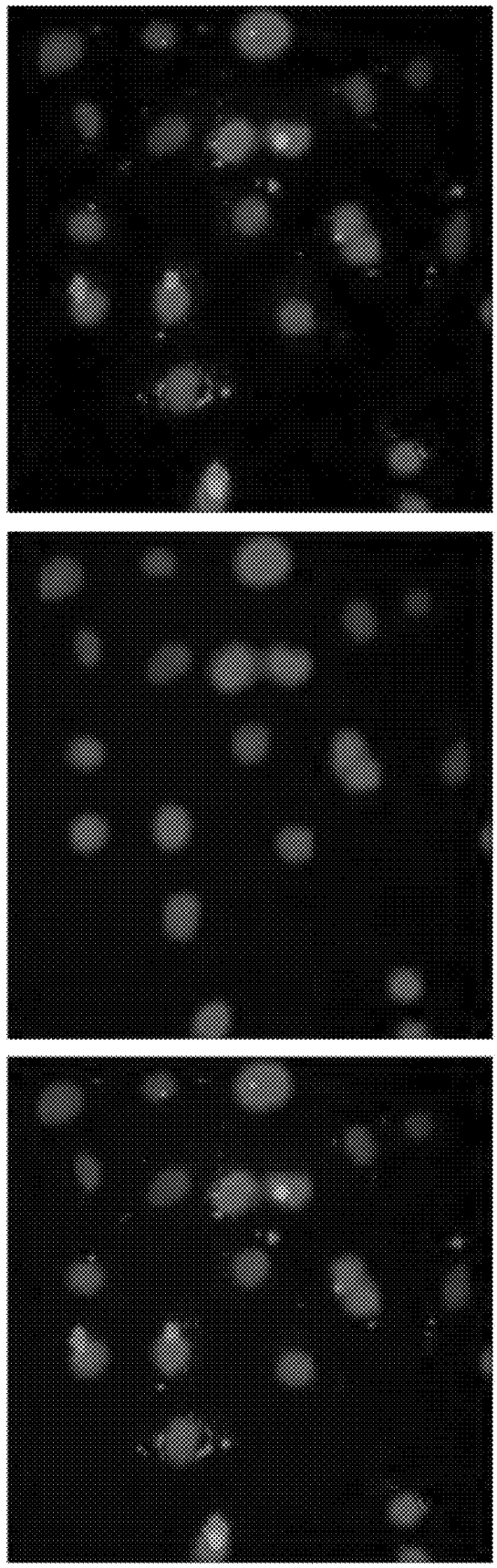

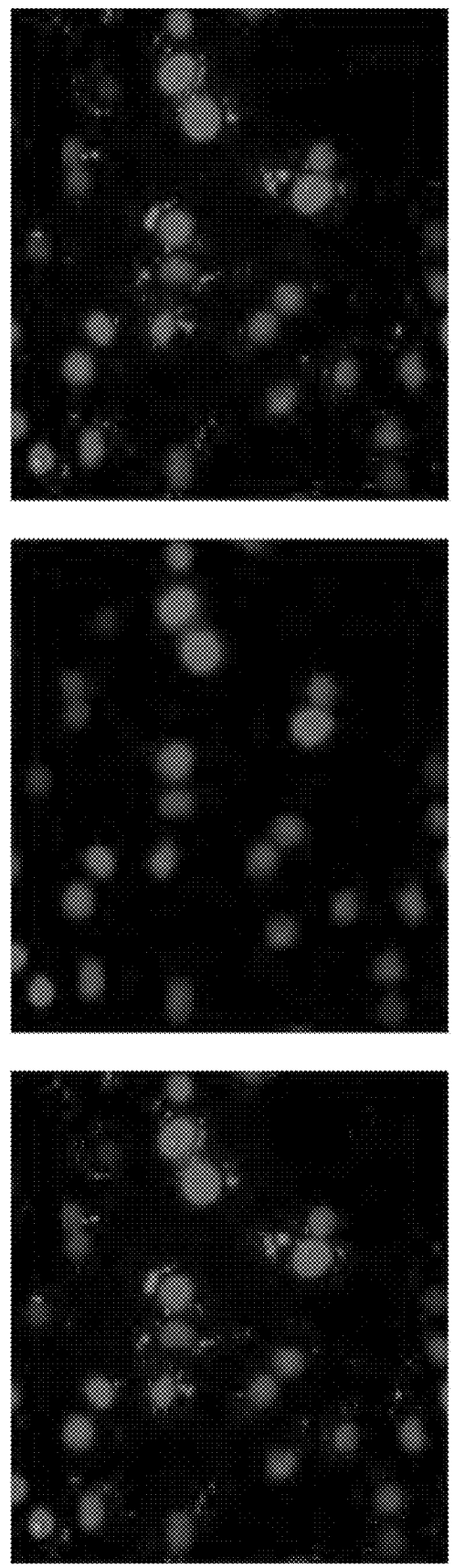
FIG. 40A Red channel
FIG. 40B Green channel
FIG. 40C Red + Green

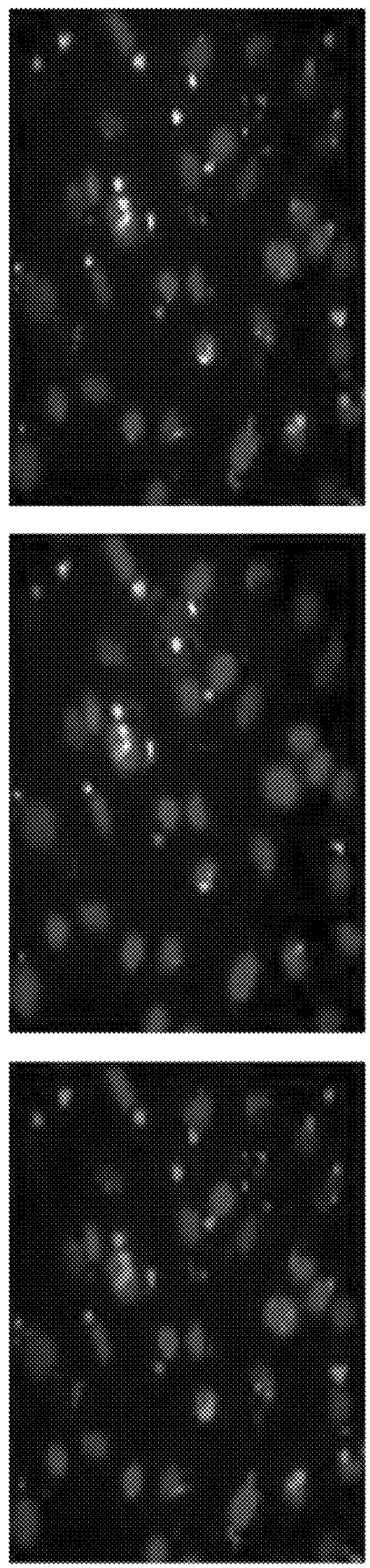

Relative ADAMTS-5 expression level in DMM knee

FIG. 44A
No stimulation
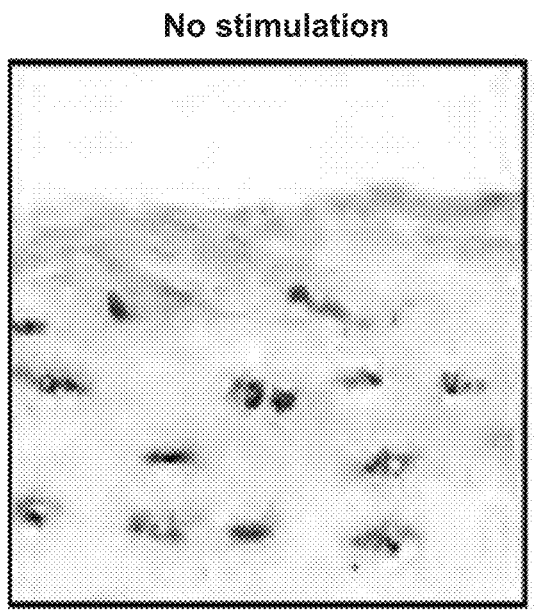
FIG. 44B
Stimulation+non-targeting siRNA/NPs
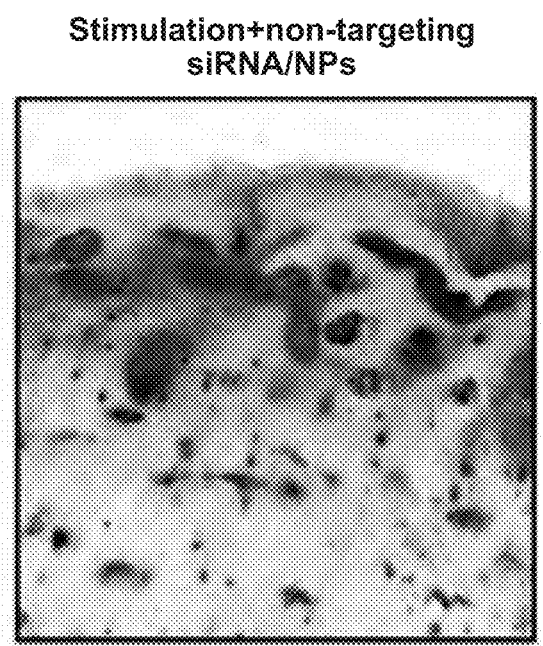
Stimulation+ADAMTS4/NPs
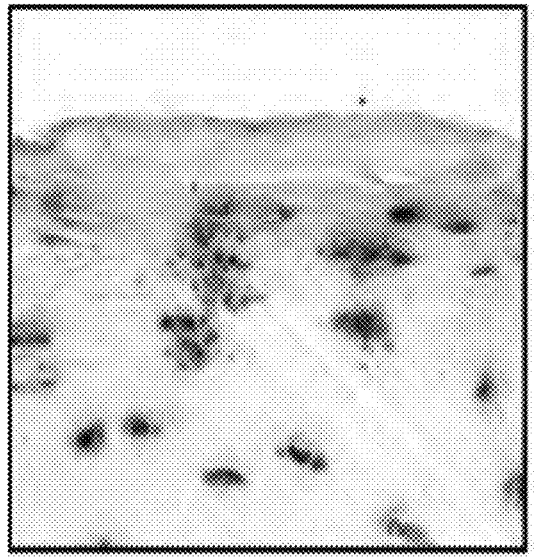
Stimulation+ADAMTS4&5/NPs
FIG. 44C
FIG. 44D Stimulation+non-targeting siRNA/NPs Stimulation+ADAMTS4&5/NPs No stimulation Stimulation+ADAMTS4/NPs

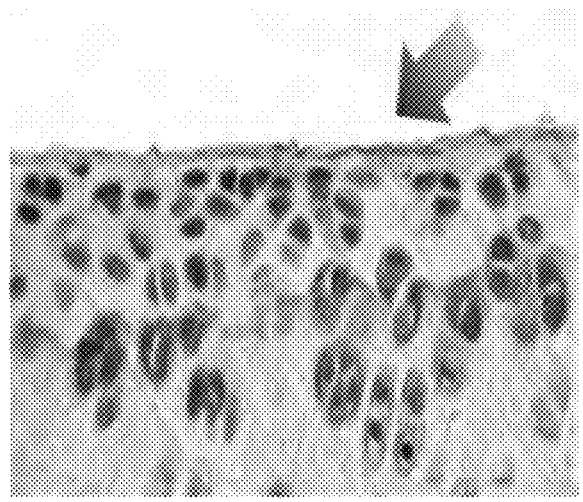
FIG. 46A  Sham with ADAMTS5 siRNA/NPs
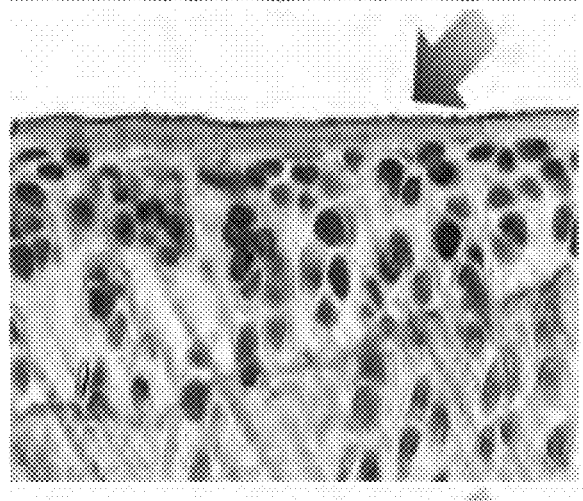
FIG. 46B  DMM with non-targeting siRNA/NPs
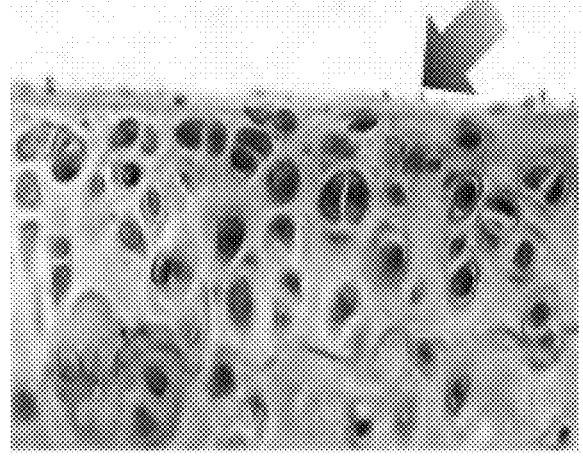
FIG. 46C  DMM with ADAMTS5 siRNA/NPs

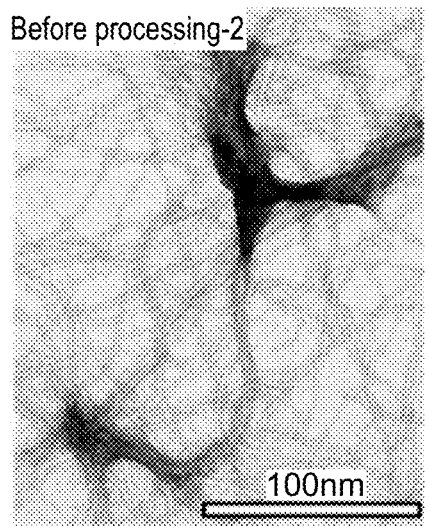
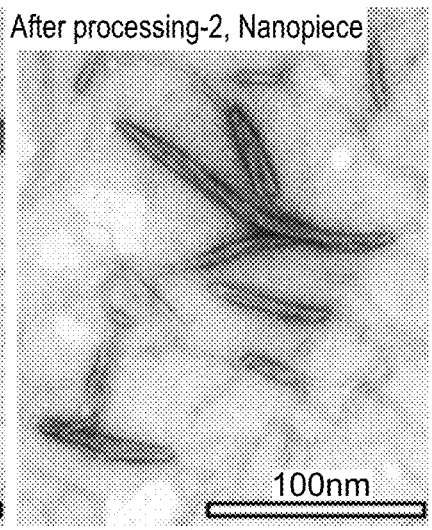
FIG. 49A     FIG. 49B
FIG. 50
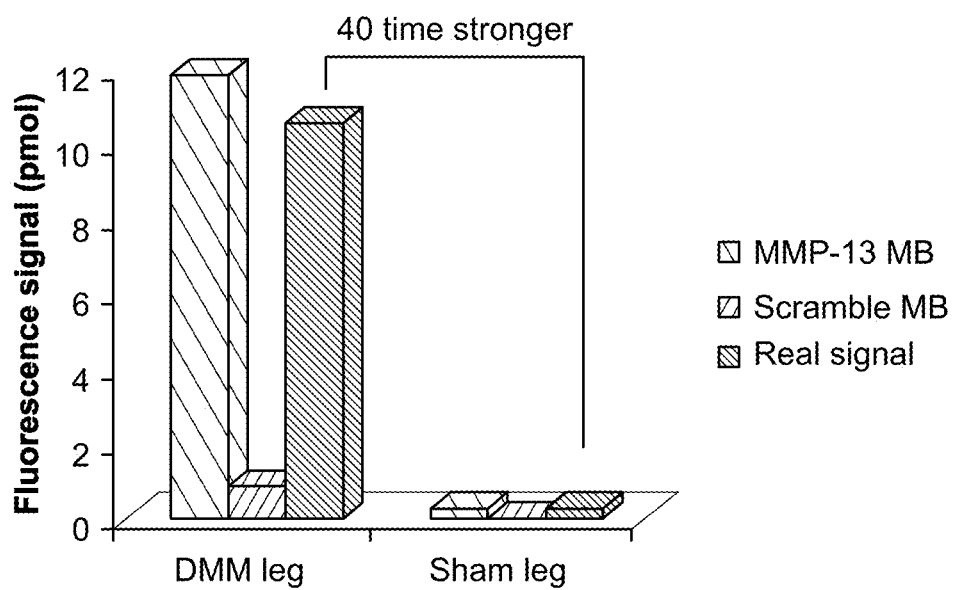

Molecular beacon
(no fluorescence before
targeting the gene)

Target gene

Molecular beacon
(Fluorescence after
targeting the gene)

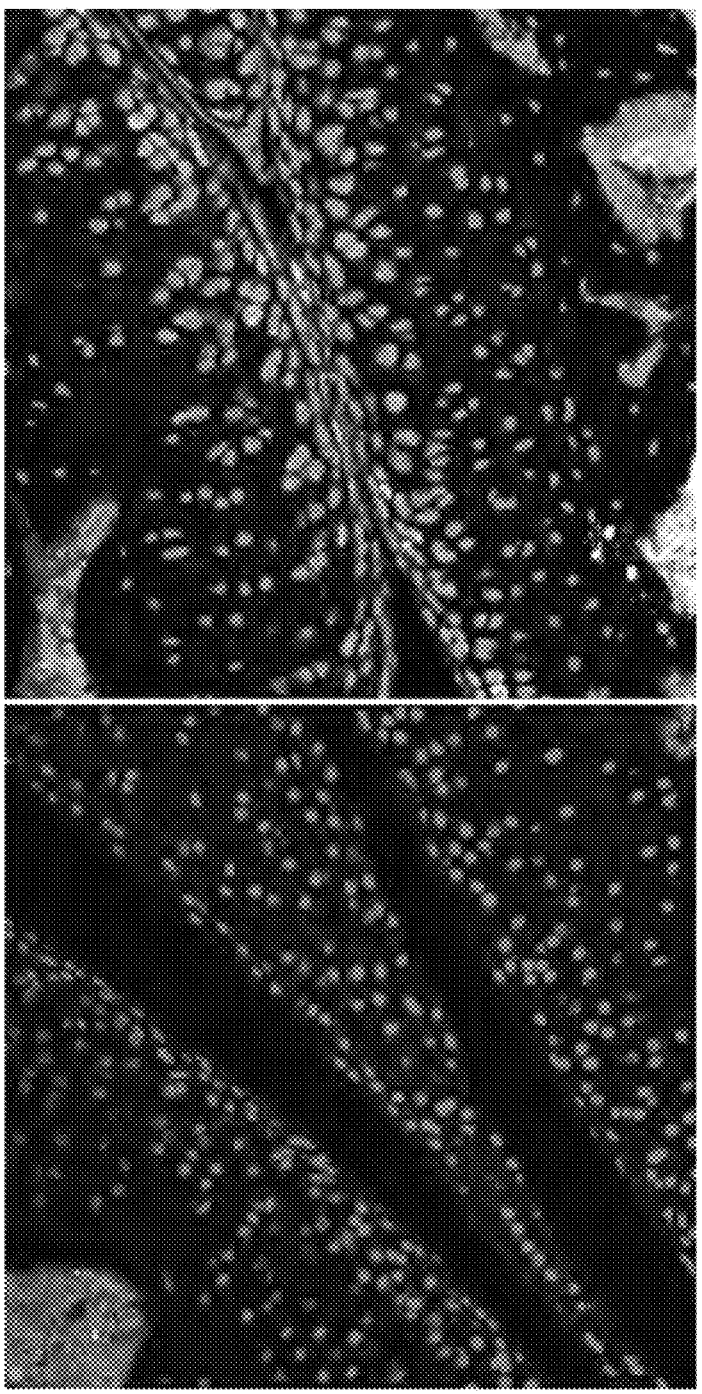

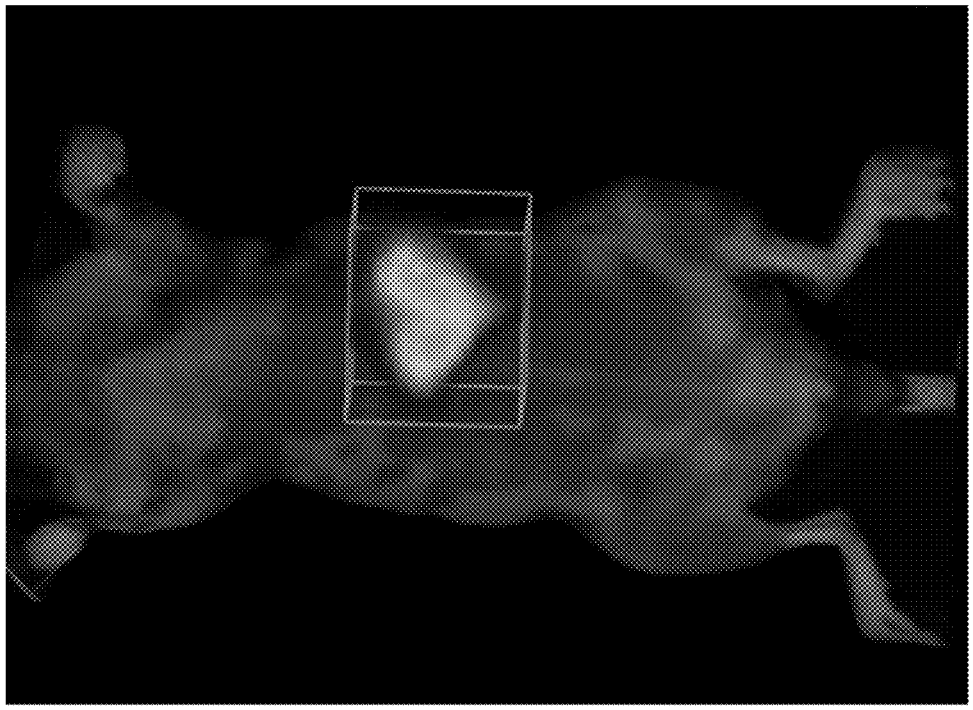
FIG. 62B Lipo delivery
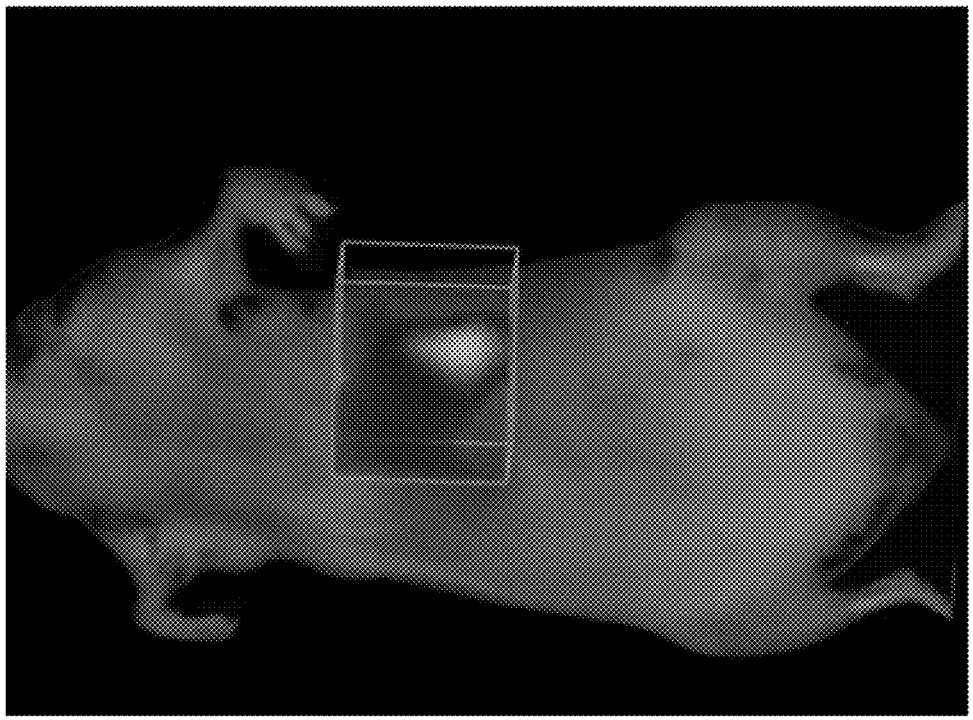
FIG. 62A NP delivery

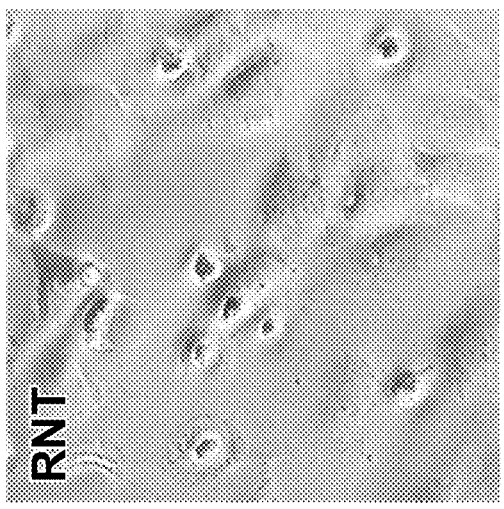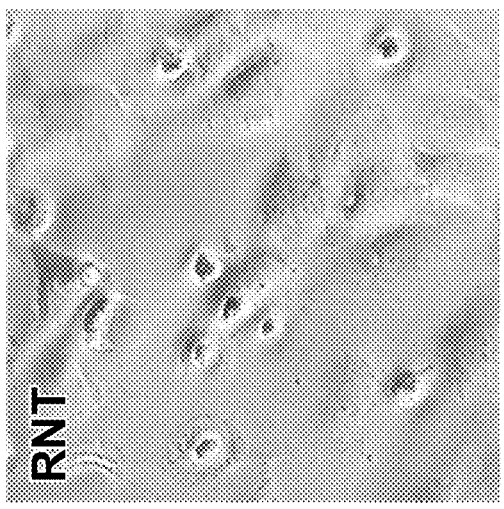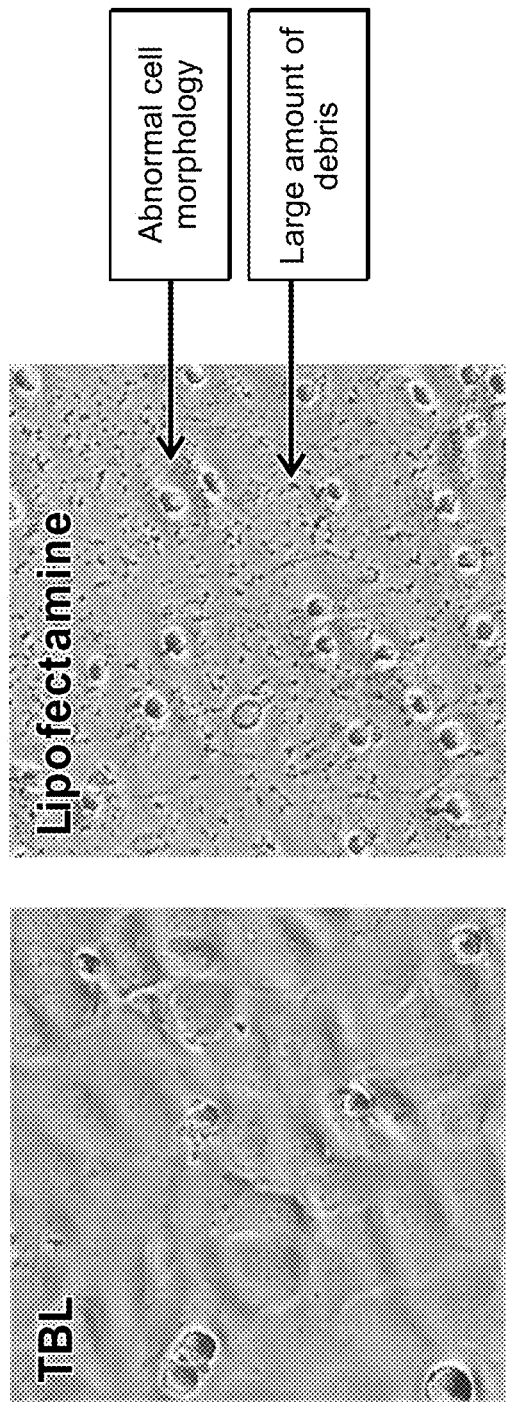

NANOCARRIERS AND THEIR PROCESSING FOR DIAGNOSTICS AND THERAPEUTICS

RELATED APPLICATIONS

This application is a Continuation application of U.S. patent application Ser. No. 14/659,071, filed Mar. 16, 2015 which claims the benefit of priority under 35 U.S.C. § 119(e) to U.S. Provisional Application No. 62/113,335, filed Feb. 6, 2015 and Provisional Application No. 61/953,495, filed Mar. 14, 2014, which are incorporated herein by reference in their entirety.

STATEMENT OF GOVERNMENT INTERESTS

This invention was made with government support under P20 RR024484 and P 20 GM104937 awarded by the National Institutes of Health. The government has certain rights in the invention.

INCORPORATION-BY-REFERENCE OF SEQUENCE LISTING

The contents of the text file named "21486_622C01US_SL.txt", which was created on Aug. 25, 2017, and is 351 KB in size, are hereby incorporated by reference in their entireties.

FIELD OF THE INVENTION

This invention relates to nanoparticles for delivering agents into cells or bodily tissues.

BACKGROUND

Although progress in drug delivery using nanotechnology has been documented, several challenges remain, particularly with regard to tissue targeting and toxicity. Current delivery systems suffer from significant hindrances such as low targeting efficiency. A major reason for these drawbacks is that tissues have extracellular matrix.

SUMMARY OF THE INVENTION

The compositions and methods of the invention provide a solution to long standing challenges in selective delivery of agents using nanotechnology. Accordingly, the invention features compounds, assemblies of such compounds, a system, or method for selective drug delivery to any bodily tissue (including those that include extracellular matrix tissue) comprising a nanoparticle. Nanoparticles such as rosette nanopieces, lipid nanoparticles, and polymeric nanoparticles composition comprise a cargo compound, wherein a positively-charged nanoparticle and cargo complex composition with net positive charge at pH 7-7.5 localizes or penetrates a negatively-charged tissue or wherein a negatively-charged (or weakly positively-charged) nanoparticle and cargo complex composition with net negative (or weak positive) charge at pH 7-7.5 localizes to or penetrates a positively-charged tissue. "Negatively charged" means zeta-potential of equal or smaller than 0 mV (which is minus "−" mV). "Positively charged" means zeta-potential of equal or larger than 0 mV (which is plus "+" mV). "Weakly positive" means zeta potential of 0 mV to +30 mV. The nanoparticle is tuned to preferentially localize to and deliver its cargo to a target bodily tissue. For example, a relatively negatively charged nanoparticle is used to preferentially localize to, accumulate, and/or penetrate a positively-charged tissue; a relatively positively charged nanoparticle is used to preferentially localize to, accumulate, and/or penetrate a negatively-charged tissue. For example, localization of the cargo-containing nanopiece is at least 10%, 20%, 50%, 75%, 2-fold, 5-fold, 8-fold, 10-fold or more to a target tissue compared to the the level of localization/delivery of the cargo in the absence of the nanoparticle. Thus, the nanopieces are selectively localized to a desired bodily tissue and deliver the cargo there.

The drug or agent delivered comprises a diagnostic reagent or a therapeutic compound. In one example, a net positive charge comprises a Zeta potential in the range of +0 mV and +60 mV (e.g., 0.1 mV, 1, 5, 10, 20, 30, 45, 60 mV); exemplary negatively charged tissues include cartilage tissue or a chondrocyte cell. In another example, a charge comprising a Zeta potential in the range of −60 mV and +30 mV (e.g., −60, −50, −40, −30, −20, −10, 1, 10, 20, 30 mV) is used to selectively or preferentially target positively charged tissues; exemplary positively charged tissues include neuronal tissue or a neuron.

Also within the invention is a system for selective drug delivery to a bodily tissue comprising a nanoparticle composition comprising a cargo compound, the composition being sized to localize or penetrate a target tissue. The nanoparticle is at least 0.1 nm in at least one dimension. For example, a size of ≤150 nm (e.g., 0.1, 10, 25, 50, 75, 100, 125, 150 nm) in at least one dimension localizes to or penetrates synovium, ocular tissue, dermatologic tissue, mucosal tissue, or pulmonary tissue, a size of ≤100 nm (e.g., 0.1, 10, 25, 50, 75, 100 nm) in at least one dimension localizes to or penetrates kidney tissue, or a size of ≤30 nm (0.1, 2, 5, 10, 20, 25, 30 nm) in at least one dimension localizes to or penetrates heart tissue. A size of ≤90 nm (0.1, 2, 5, 10, 25, 50, 75, 80, 90 nm) in at least one dimension localizes to or penetrates cartilage with inflammation or defect, and a size of ≤30 nm (0.1, 2, 5, 10, 20, 25, 30 nm) in at least one dimension localizes to or penetrates healthy, intact cartilage.

The system or method includes the treatment of joint disorders those affecting articulating joints, e.g., injury-induced osteoarthritis as well as autoimmune diseases affecting joint tissue such as rheumatoid arthritis. The compositions and methods of the invention further provide a solution to long standing challenges in the treatment of diseases and/or disorders affecting the epithelial, connective, muscles and/or nervous tissues in the body. The invention provides methods of introducing a therapeutic or diagnostic agent into a cell or tissue or tissue matrix using rosette nanotubes or components of rosette nanotubes. Embodiments of the present disclosure include the formation of a composite or complex or combination of one or more agents, such as therapeutic or diagnostic agents, and a rosette nanotube or a component of a rosette nanotube, where the one or more agents are attached to or otherwise bound to the rosette nanotube or component of a rosette nanotube. Embodiments of the present disclosure are further directed to a product made by the process of mixing together rosette nanotubes as described herein or modules forming rosette nanotubes as described herein and one or more agents in aqueous media under conditions which cause the rosette nanotubes or components of rosette nanotubes to combine with the one or more agents to form a complex or combination in aqueous media where the one or more agents are attached or otherwise bound through steric, ionic, or other forces to the rosette nanotube a component of a rosette nanotube. According to one aspect, the one or more agents are bound by noncovalent forces.

The nanopiece compositions are made from nanotubes made from modules that self-assemble, e.g., compounds comprising Formula I (module I) or compounds comprising Formula II (module II). Nanotubes according to the present disclosure include compounds of Formula I below:

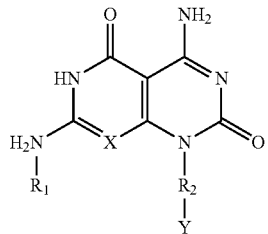

wherein X is CH or nitrogen; n is an integer of, 1, 2, 3, or 4; $R_2$ is hydrogen or a linker group for example $(CH_2)_n$ or other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. For example, one subset of compounds of formula (I) includes those in which X is nitrogen. In another example, one subset of compounds of formula (I) includes those in which $(CH_2)_n$ is the linker group. In another embodiment, one subset of compounds of formula (I) includes those in which $(CH_2)_n$ is the linker group and n is 2. In another example, one subset of compounds of formula (I) includes those in which Y is an amino acid selected from lysine, arginine and histidine. In another embodiment, one subset of compounds of formula (I) includes those in which X is nitrogen, $(CH_2)_n$ is the linker group, n is 2 and Y is an amino acid selected from lysine, arginine and histidine.

Compounds within the scope of the invention include those where the Y group can be connected to the linker group either by the amino group or the carboxyl group of the amino acid or polypeptide. An exemplary linker group is shown in the formula below.

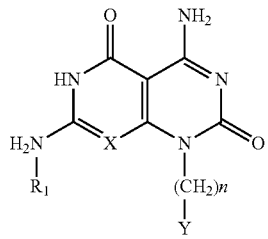

An exemplary module within the scope of formula I is shown in FIG. 1 along with a schematic representation of a nanotube and an image of nanotubes formed from the exemplary module.

Alternative linker groups $R_2$ can join the Y group to the carbon of the $(CH_2)_n$ group or the N atom either by the amino group or the carboxyl group of the amino acid or polypeptide.

Alternative $R_2$ groups within the scope of the present disclosure are selected from a group comprising:

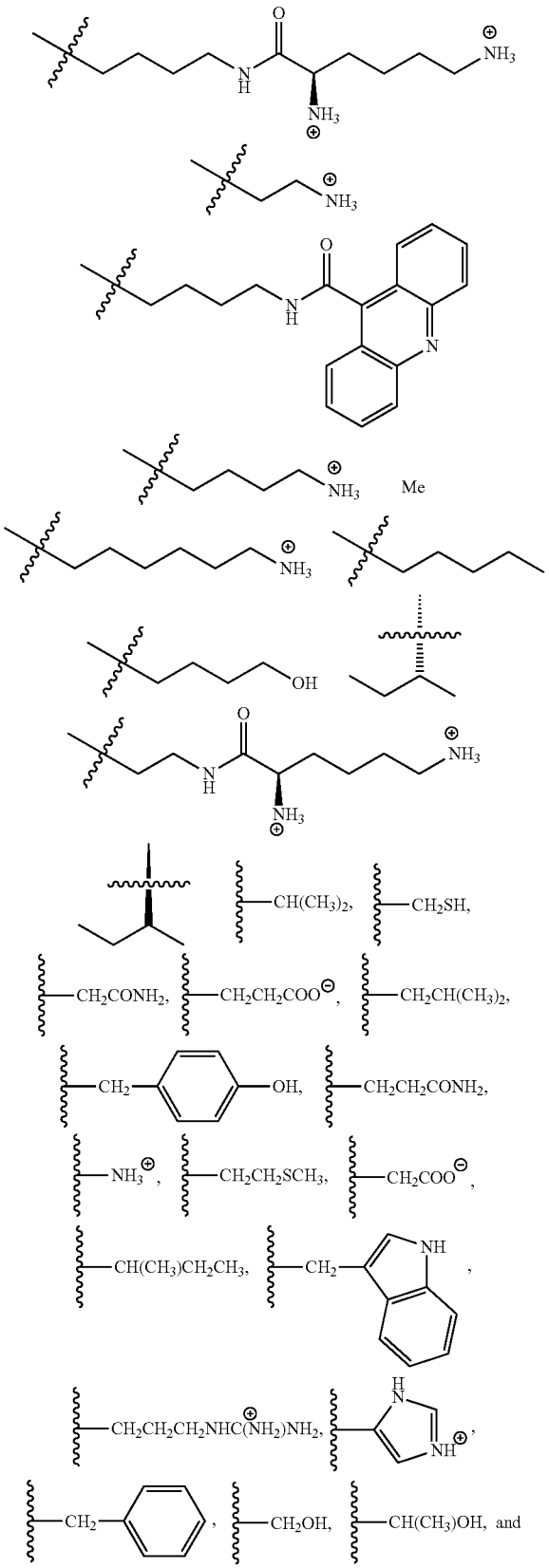

-continued

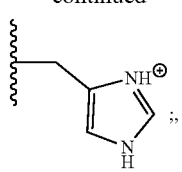

wherein Y is absent.

Compounds of Formula I can be prepared by the methods described in U.S. Pat. No. 6,696,565 hereby incorporated by reference herein in its entirety alone or combined with methods known to those of skill in the art. Additional description is provided in U.S. Pat. No. 8,795,691 and/or U.S. Patent Publication 20140171482 (U.S. Ser. No. 13/977, 138), each of which is hereby incorporated by reference. Rosette nanotubes are made by assembly of compounds of Formula (I).

Exemplary compounds of Formula I are shown below:

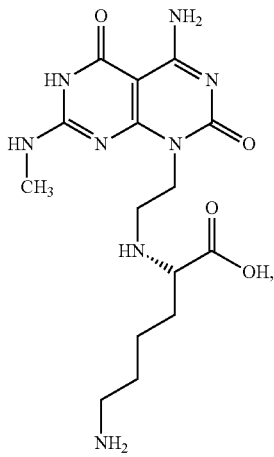

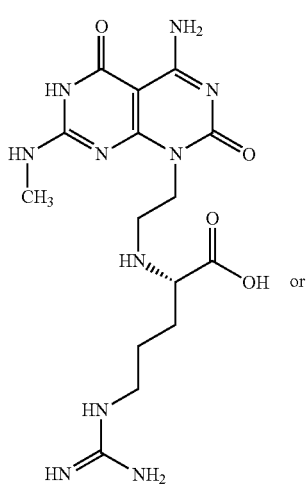

-continued

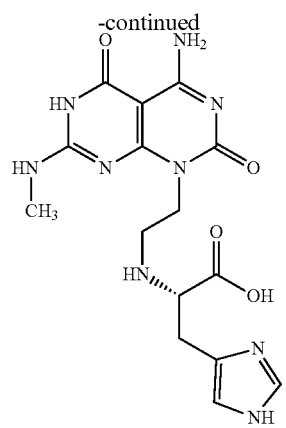

Modules according to the present disclosure also include compounds of Formula II below:

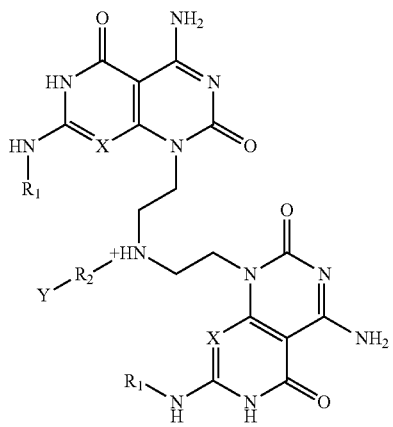

wherein X is CH or nitrogen; $R_2$ is hydrogen or a linker group for example $(CH_2)_n$ where n is an integer of, 1, 2, 3, or 4 or $(CH_2)_3CO$ other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such alkyl, straight or branched chain, saturated or unsaturated; and salts thereof. For example, one subset of compounds of formula (II) includes those in which X is nitrogen. In another example, one subset of compounds of formula (II) includes those in which $(CH_2)_n$ is the linker group. In another embodiment, one subset of compounds of formula (II) includes those in which $(CH_2)_n$ is the linker group and n is 2. In another example, one subset of compounds of formula (II) includes those in which Y is an amino acid selected from lysine, arginine and histidine. In another embodiment, one subset of compounds of formula (II) includes those in which X is nitrogen, $(CH_2)_n$ is the linker group, n is 2 and Y is an amino acid selected from lysine, arginine and histidine.

Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

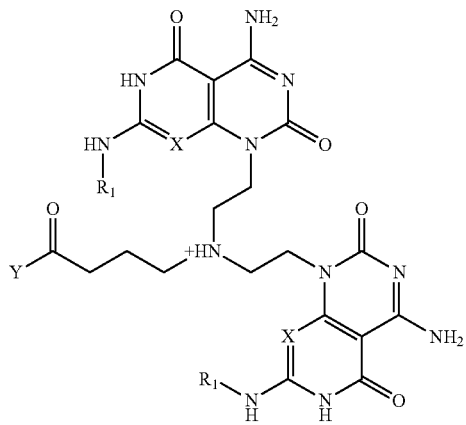

Compounds within the scope of the present disclosure include those where the Y group can be connected to the linker group either by the amino group or the carboxyl group of the amino acid or polypeptide. Alternative $R_2$ groups within the scope of the present disclosure are selected from a group comprising:

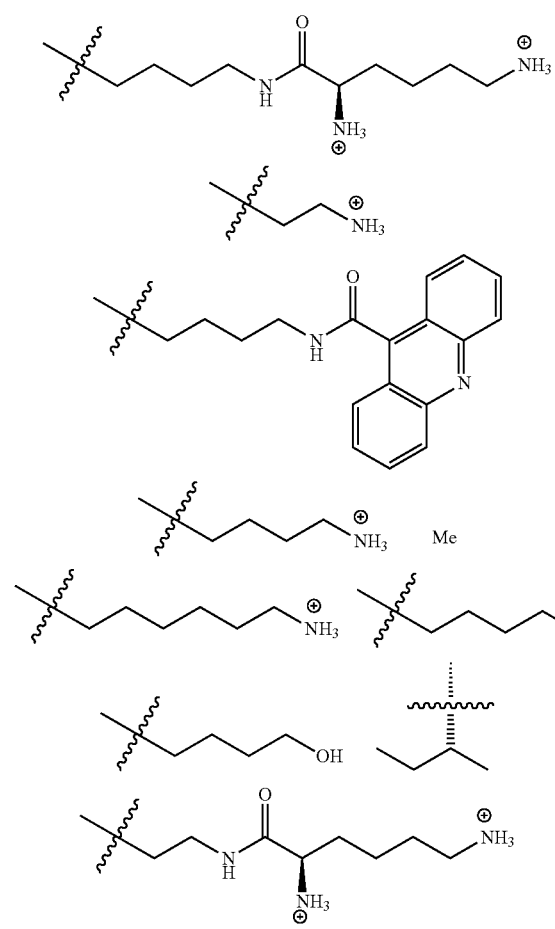

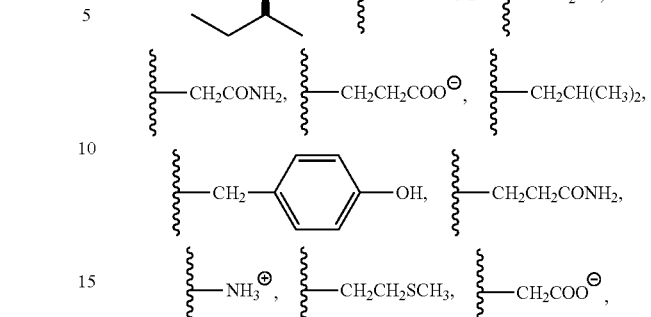

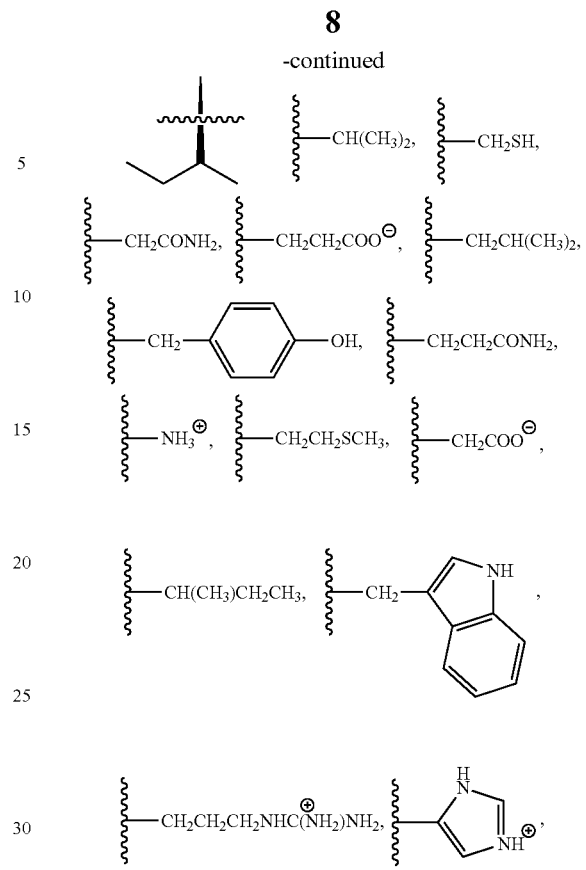

wherein Y is absent. TBL structures are made by the assembly of compounds of Formula (II).

Exemplary compounds of Formula II are shown below:

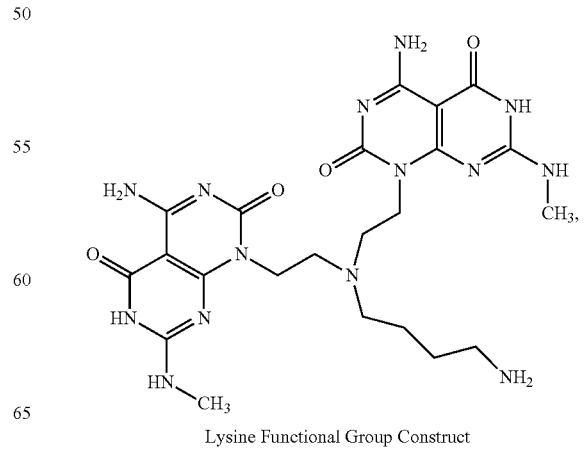

Lysine Functional Group Construct

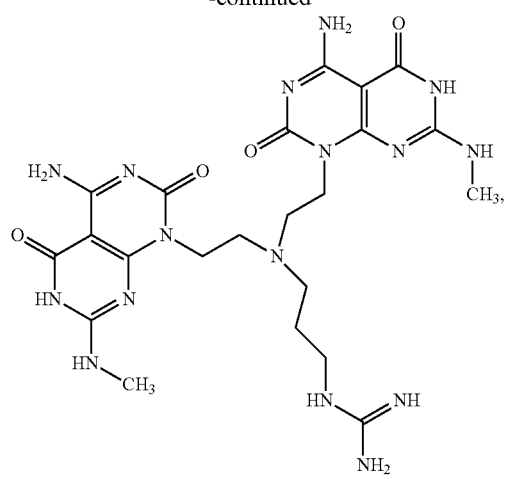
Arginine Functional Group Construct
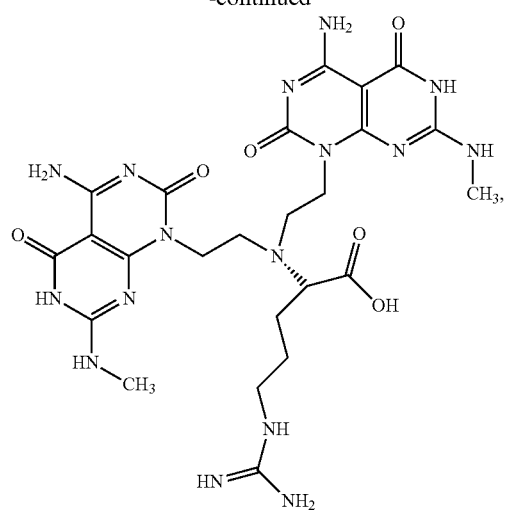
Arginine Amino Acid Construct
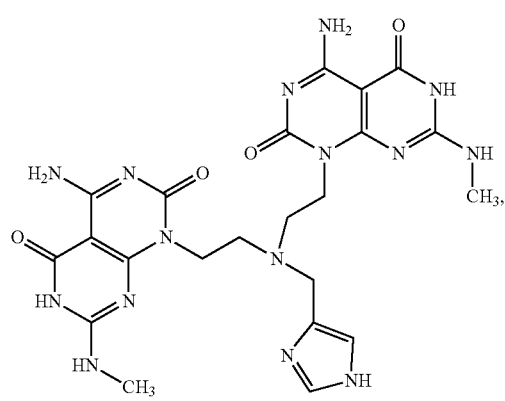
Histidine Functional Group Construct
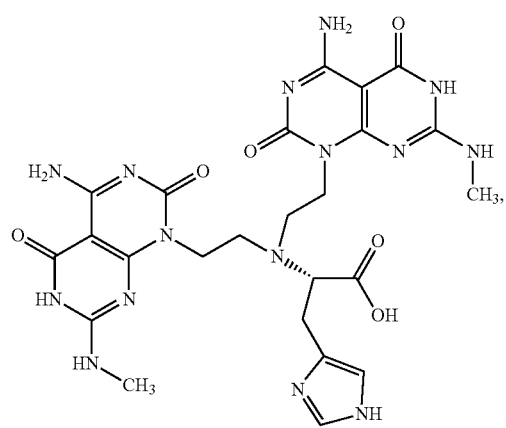
Histidine Amino Acid Construct
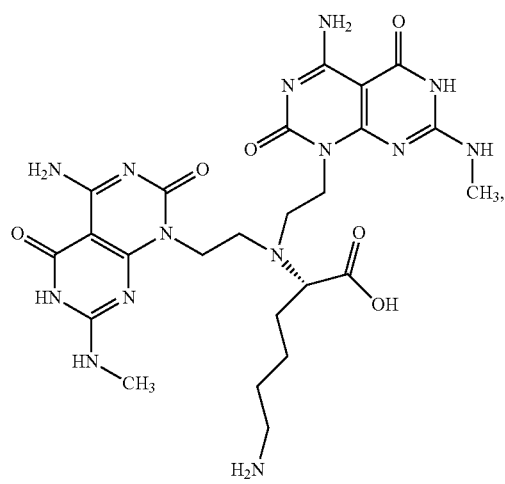
Lysine Amino Acid Construct
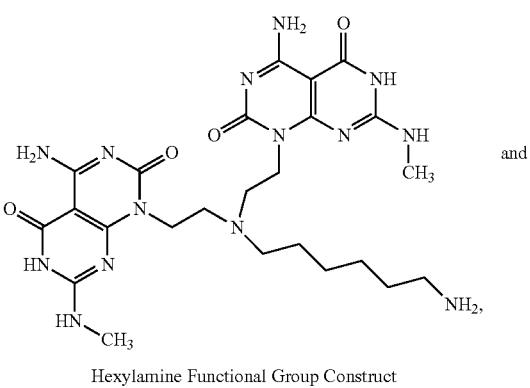
and
Hexylamine Functional Group Construct -continued

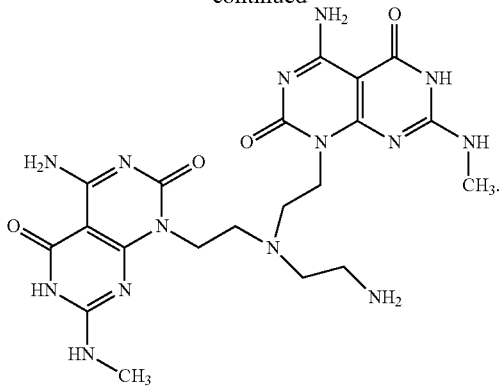

Ethylamine Functional Group Construct

In some embodiments, compounds of formula II comprise amino acid functional group constructs. These compounds contain functional groups present in natural occurring amino acid side chains or may contain the the entire amino acid side chain. For example, the lysine functional group constructs contains the entire amino acid side chain functionality ($-CH_2CH_2CH_2CH_2NH_3^+$), whereas the histidine functional group constructs contains the entire side chain or only contains the heteroaryl imidazole group present in histidine.

In some embodiments, compounds of formula II comprise amino acid constructs. These compounds contain the entire the amino acid or may contain modified and/or unnatural amino acids. For example, the lysine amino acid analog contains the entire amino acid functionality of lysine, whereas the histidine amino acid constructs contains a modified histidine amino acid.

In some embodiments the compounds of formula II are preferred over the compounds of formula I.

In some embodiments the compound of formula II is the Lysine Functional Group Construct

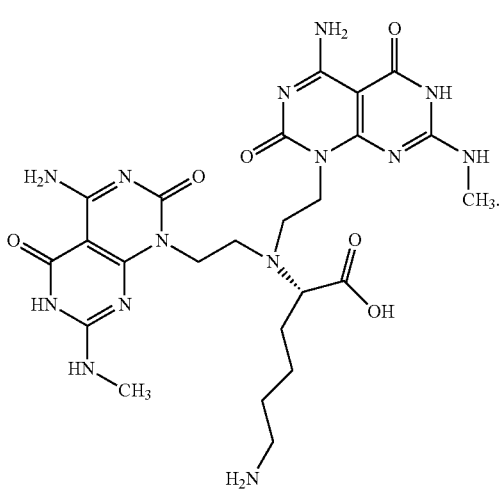 [SMILES: CNc1nc2c(c(N)nc(=O)n2CCN(CCn2c(=O)nc(N)c3c(=O)[nH]c(NC)nc32)[C@@H](CCCCN)C(=O)O)c(=O)[nH]1]

In some embodiments, the nanoparticles are constructed from lipid and/or polymeric components.

A three-dimensional representation of such modules is shown in FIG. 65. Embodiments further include delivering the composite into living cells. Embodiments further include a method of treating an individual requiring treatment comprising administering a complex of a rosette nanotube or a component of a rosette nanotube and one or more therapeutic agents to the individual in a manner to introduce the complex into cells or tissues of the individual. Embodiments further include a method of diagnosing an individual requiring diagnosis comprising administering a complex of a rosette nanotube or a component of a rosette nanotube and one or more diagnostic agents to the individual in a manner to introduce the complex into cells or tissues of the individual.

Rosette nanotubes or RNTs include nanotubes formed from modules having twin bases with a linker or TBL. Such rosette nanotubes may be referred to herein as "TBLs." According to this aspect, the agent is delivered into the cell. According to one aspect, the agent is released from the rosette nanotube after entry into the cell. According to an additional aspect, the agent remains attached to, bound to, or complexed with or combined with the rosette nanotube or component of a rosette nanotube.

Lipid nanoparticles comprise a lipid core and surfactant, in which the lipid core may include fatty acids, acrylglycerols, steroids, waxes, and mixtures of all above; and surfactants may contain a positively charged amino group, negatively charged phosphate or carboxylic acid. According to one aspect, a complex is produced by combining modules of a self-assembled rosette nanotube and one or more agents in media where the modules self-assemble into a rosette nanotube or components of a rosette nanotube which incorporates the one or more agents to form a complex of a rosette nanotube or component of a rosette nanotube and the one or more agents. According to an additional aspect, a complex is produced by combining a self-assembled rosette nanotube and one or more agents in media whereupon the one or more agents are incorporated into the rosette nanotube to form a complex of a rosette nanotube and one or more agents. The complex may then be contacted to cells whereupon the complex enters the cells. Without wishing to be bound by scientific theory, it is believes that the complex may enter cells by endocytosis. According to certain embodiments, the cells may be transformed cells, recombinant cells, malignant cells, or cells from primary cell lines. The transfection method may be performed on cells in vitro or in vivo.

The modules may be any of those known to persons of ordinary skill in the art such as GAC motifs and A/\T motifs, unmodified or modified to include moieties or side chains, which self-assemble into helical rosette nanotubes. According to one embodiment, modules are placed into an aqueous medium where they self assemble into a substructure such as a ring structure, such as a rosette, and the ring structures then self-assemble by stacking one on top of another to form a tubular structure, commonly referred to as a nanotube. Such modules, substructures and nanometer scale molecular structures and their self-assembly is described in U.S. Pat. No. 6,696,565, Fenniri et al, *J. Am. Chem. Soc.* 2001, 123, 3854-3855, Moralez et al., *J. Am. Chem. Soc.,* 2005, 127, 8307-8309, Fine et al., *International Journal of Nanomedicine* 2009:4 91-97; and Zhang et al., *Biomaterials* 2009; 30(7):1309-1320 each of which are hereby incorporated by reference in their entireties for all purposes.

Rosette nanotubes of the present disclosure are very stable in water and lack virus-related safety concerns and toxicity at amounts of about 1 µg/ml. See *Int. J. Nanomedicine,* 2008, 3(3):373-383; *Small.* 2008, 4(6):817-823; and *Am. J. Physiol Lung Cell Mol. Physiol.* 2005, November, 289(5): L698-708 each of which are hereby incorporated by reference in their entireties.

According to one aspect of the present disclosure, methods are provided where the self-assembly of precursors or modules incorporates the agent into or otherwise complexes the agent with, the self-assembled rosette nanotube or components of the rosette nanotube. According to another aspect, fully assembled rosette nanotubes can be incubated with one or more or a plurality of agents and the one or more or plurality of agents can complex with the fully assembled rosette nanotube to form a composite. According to one further aspect, the one or more or plurality of agents are joined to or bound to the self-assembled rosette nanotube through steric, ionic, van der Waals, dispersion or other noncovalent interactions to form a rosette nanotube or component of a rosette nanotube and agent complex useful as a complex to be administered to an individual. In another aspect of the invention, the agents comprise a therapeutic agent such as nucleic acid, peptide or small molecule. In a further aspect of the invention, the therapeutic agent comprises an IL-1 receptor antagonist. In yet a further aspect of the invention, the agent comprises a diagnostic agent such as a molecular probe or a molecular beacon. For example, the molecular beacon or probe comprises MMP-13 or ADAMTS-5.

According to certain aspects of the invention, a method for treating joint disease comprises administration of an effective amount of a composition containing a nanotube rosette-agent complex. Such a method of diagnosing joint disease comprises administration of an effective amount of a composition containing a nanotube rosette-agent complex. Another aspect of the invention comprises joint disease such as autoimmune, degenerative, inflammatory, infectious, cancerous, viral, fungal, injured, trauma, genetic, trauma, mechanical, nutritional or mal-alignment derived. Another embodiment of the invention describes joint disease comprising rheumatoid arthritis, osteoarthritis, juvenile onset of rheumatoid arthritis (JRA), psoriatic arthritis, reactive arthritis, septic arthritis, tendinitis, or herniation. Therapeutic agents are used to treat joint disease, e.g., such agents include analgesic agents, anti-inflammatory agents, immunosuppresive agents, antifungal agents, antibiotic agents, lubricants, anti-cancer agents, NMDA receptor antagonists, or antiviral agents.

According to certain aspects of the invention, a method for treating tissue and/or organ disease comprises administration of an effective amount of a composition containing a nanotube rosette-agent complex. Such a method of diagnosing tissue and/or organ disease comprises administration of an effective amount of a composition containing a nanotube rosette-agent complex. Another aspect of the invention comprises a tissue and/or organ disease such as autoimmune, degenerative, inflammatory, infectious, cancerous, viral, fungal, injured, trauma, genetic, trauma, mechanical, nutritional or mal-alignment derived. Another embodiment of the invention describes tissue and/or muscle disease comprising the eye, skin, brain, spine, intestine, kidney, liver, and stomach. Another aspect of the invention describes therapeutic agents to treat joint, tissue and/or organ disease, e.g., agents include analgesic agents, anti-inflammatory agents, immunosuppresive agents, antifungal agents, antibiotic agents, lubricants, anti-cancer agents, NMDA receptor antagonists, or antiviral agents.

According to certain aspects, rosette nanotubes are functionalized with a nucleic acid, such as DNA or small RNA to form a complex, for example RNA is bound to the rosette nanotube, the complex is translocated into a cell or tissue, and the intracellular small RNA (e.g., siRNA) is present within the cell in an amount sufficient for gene silencing resulting in the inhibition of the production of target proteins. In this aspect, the rosette nanotube is a delivery vehicle or carrier for the small RNA into a cell for RNA interference purposes. Alternatively, the nucleic acid can be expressed by the cell. For example, the cell comprises synoviocytes or chondrocytes. Alternatively, the target tissue is cartilage. According to certain aspects, methods and technologies are provided to process and assemble rosette nanotubes (RNTs) for cargo delivery for diagnostic and therapeutic purpose. Methods are directed to achieve inter-/intra-cellular delivery in vitro and in vivo. According to certain aspects, a complex of rosette nanotubes (RNTs) and cargo agents are prepared. The cargo agents include diagnostic molecules, for instance, oligomer based molecular beacons; or therapeutic molecules such as nucleic acid, peptide, or small molecules. Such diagnostic agents and therapeutic agents are well known to those of skill in the art. Such incorporation between RNTs and the cargo reagent are facilitated by electrostatic force, π-π interactions or hydrophilic/hydrophobic effects to form relatively stable entities, which are referred to herein as "Nanopieces". According to certain aspects, methods are provided to make rosette nanotubes of certain size (with or without an agent (e.g., cargo composition) that are suitable for trans-matrix e.g., extracelluar matrix, tissue delivery. For example, methods are provided for altering at least one dimension or other parameter of Nanopieces such as width to infiltrate the pore size of the target tissue matrix.

According to certain aspects, methods and technologies are provided to process and assemble rosette nanotubes (RNTs) for cargo delivery for diagnostic and therapeutic purpose. Methods are directed to achieve inter-/intra-cellular delivery in vitro and in vivo. According to certain aspects, a complex of rosette nanotubes (RNTs) and cargo agents are prepared. The cargo agents include diagnostic molecules, for instance, oligomer based molecular beacons; or therapeutic molecules such as nucleic acid, peptide, or small molecules. Such diagnostic agents and therapeutic agents are well known to those of skill in the art. Such incorporation between RNTs and the cargo reagent are facilitated by electrostatic force, π-π interactions or hydrophilic/hydrophobic effects to form relatively stable entities, which are referred to herein as "Nanopieces". According to certain aspects, methods are provided to make rosette nanotubes of certain size with or without an agent that are suitable for trans-matrix tissue delivery. For example, methods are provided for altering at least one dimension parameter of Nanopieces such as width to infiltrate the pore size of the target tissue matrix.

According to certain aspects, methods are provided for making rosette nanotubes of certain lengths and size parameters such as 1) before assembly, controlling the length and bundle of RNTs via changing physical and/or chemical conditions such as temperature, molecule motion/vibration (like sonication) and pH; 2) during assembly, adjusting assembly conditions via changing physical and/or chemical conditions including concentrations, pH and ionic strength to enhance/reduce the formation and stacking of Nanopieces; 3) after assembly, breaking long or stacked Nanopieces by via changing physical and/or chemical conditions including enhancing molecule motion/vibration (like sonication).

According to certain aspects, methods are provided for trans-matrix/tissue delivery or a complex of a rosette nanotube or component or piece thereof by controlling the ratio between RNTs and cargo reagents so that the forming Nanopieces present surface charges that are suitable for attraction, localization, penetration, or retention in the tissue or one or more cells of the tissue. For example, since many tissues or cells contain negatively charged molecules (like proteoglycan), positively charged RNT can be fabricated and used to assemble with negatively charged nucleic acid cargo in certain ratios, resulting in a positive charged Nanopiece for delivery. In this manner, Nanopieces localize to, bind to, and accumulate onto/into the matrix/tissue resulting in much longer retention time to achieve more effective delivery. Therefore, the highly effective and versatile trans-matrix/tissue delivery was achieved by processed Nanopieces. The term "Nanopiece" may be used herein to refer to rosette nanotubes which may be processed into certain dimensions or components of rosette nanotubes.

According to certain aspects, methods are provided for the use of rosette nanotubes or Nanopieces for diagnostic applications insofar as molecular probes can be delivered via Nanopieces to detect a specific gene expression (or protein activity). By co-delivery of a negative control for non-specific signal and an internal positive control, a target gene expression can be accurately diagnosed in a real-time, in-situ and non-invasive manner.

According to certain aspects, therapeutic applications are envisioned, such as knocking down one or multiple disease gene expression (such as via siRNA, miRNA or anti-sense delivery), e.g., inhibiting the expression of one or more genes or gene products associated with aberrantly high expression in a disease state compared to a normal state up-regulating one or multiple beneficial gene/protein (such as via DNA, mRNA or protein delivery); or through a combination of both.

According to certain aspects, methods are provided for making rosette nanotubes of certain lengths and size parameters such as 1) before assembly, controlling the length and bundle of RNTs via changing physical and/or chemical conditions such as temperature, molecule motion/vibration (like sonication) and pH; 2) during assembly, adjusting assembly conditions via changing physical and/or chemical conditions including concentrations, pH and ionic strength to enhance/reduce the formation and stacking of Nanopieces; 3) after assembly, breaking long or stacked Nanopieces by via changing physical and/or chemical conditions including enhancing molecule motion/vibration (like sonication).

According to certain aspects, method are provided for trans-matrix/tissue delivery or a complex of a rosette nanotube or component or piece thereof by controlling the ratio between RNTs and cargo reagents so that the forming Nanopieces present surface charges that are suitable for retention in the tissue. For example, since many tissues or cells contain negatively charged molecules (like proteoglycan), positively charged RNT can be used to assemble with negatively charged nucleic acid cargo in certain ratios, resulting in a positive charged Nanopiece for delivery (see Table 1). In this manner, Nanopieces associate with, bind to and/or accumulate onto/into the matrix/tissue resulting in much longer retention time to achieve more effective delivery. Therefore, the highly effective and versatile trans-matrix/tissue delivery was achieved by processed Nanopieces.

According to certain aspects, methods are provided for the use of rosette nanotubes or Nanopieces for diagnostic applications insofar as molecular probes can be delivered via Nanopieces to detect a specific gene expression (or protein activity). By co-delivery of a negative control for non-specific signal and an internal positive control, a target gene expression can be accurately diagnosed in a real-time, in-situ and non-invasive manner.

According to certain aspects, therapeutic applications are envisioned, such as knocking down one or multiple disease gene expression (such as via siRNA delivery); up-regulating one or multiple beneficial gene/protein (such as via DNA, mRNA or protein delivery); or through a combination of both.

According to certain aspects, depending on the processing conditions, different sizes of rosette nanotubes, e. g. Nanopieces can be created for different delivery proposes, such as to enter a cellular or tissue matrix. For example, cartilage tissue matrix has about 60 nm mesh size of the collagen II fibrillar network (Comper et al in *Cartilage*: Molecular Aspects (eds Hall, B. & Newman, S.) 59-96 (CRC Press, Boston, 1991)) and about 20 nm spacing between the side chains of the proteoglycan network (Torzilli et al *J. Biomech.* 30, 895-902 (1997)). Nanopieces with small sizes (at least one dimension smaller than 60 nm and/or 20 nm) showed excellent efficiency and function in intra-cartilage matrix delivery of siRNA. Secondly, through adjusting the ratio between RNTs and cargo reagents, overall positive charged surface enabled Nanopieces to adhere with negatively charged matrix/tissue components resulting longer retention time. Thirdly, Nanopieces can deliver a variety of cargo types and can deliver multiple cargo reagents at the same time. Fourthly, using non-covalent or covalent coating on Nanopieces can achieve a longer stability in the systemic circulation and penetrate into the targeted tissue matrix and/or organ more efficiently. Lastly, processed Nanopieces demonstrated successful delivery under conditions: in vitro, ex vivo and in vivo. Therefore, methods are provided for the use of Nanopieces for trans-matrix/tissue delivery.

According to certain aspects, complexes of rosette nanotubes or components of nanotubes or Nanopieces and agents can be used for research purposes as well as used for an effective delivery agent (especially in vivo) for molecular diagnosis and therapeutics. According to certain aspects, complexes of rosette nanotubes or components of nanotubes or Nanopieces and agents can be used for therapeutic purposes for treating various diseases, such as by delivery of interleukin-1 receptor antagonist (IL-1Ra), the natural protein inhibitor of IL-1, to modulate IL-1-based inflammation as a therapy for arthritis. For example, the cargo comprises IL-1R SiRNA. Complexes of rosette nanotubes or components of nanotubes or Nanopieces and agents can be used to deliver siRNA to knockdown the disease protein to achieve effective treatment.

According to certain aspects, complexes of rosette nanotubes or components of nanotubes or Nanopieces and agents can be used for diagnostics, such as by delivery of molecular probes or molecular beacons. Methods are provided to deliver molecular beacons into chondrocytes inside cartilage matrix as well as tissues and/or organs such as heart, stomach, kidney, liver, lung, spleen, brain, intestine, spine, rib cage, and limb. With co-delivery of multiple molecular beacons to detect disease gene expression as target, non-specific signal as negative control and house-keeping gene as internal positive control, target gene expression level can be quantified in a real-time, in-situ and non-invasive manner.

Embodiments of the present disclosure are directed to complexes of a self-assembled rosette nanotube and one or more or a plurality of agents. Such agents include biologically active agents and/or diagnostic agents. The complexes are administered to an individual where the biologically active agent and/or diagnostic agent are delivered to a site within the individual, including into the cell of an individual, and are made available for therapeutic or diagnostic purposes. According to one aspect, the agent dissociates from the rosette nanotube to treat an individual or to provide a diagnostic capability. According to an additional aspect, the agent remains attached to, bound to, or complexed with or combined with the rosette nanotube.

According to one aspect, a delivery complex is produced by combining modules of a self-assembled rosette nanotube and one or more agents, such as therapeutic or diagnostic agents, in media where the modules self-assemble into a rosette nanotube which incorporates the one or more agents to form a complex of a rosette nanotube and the one or more agents. According to an additional aspect, a delivery complex is produced by combining a self-assembled rosette nanotube and one or more agents, such as therapeutic or diagnostic agents, in media whereupon the one or more agents are incorporated into the rosette nanotube to form a complex of a rosette nanotube and one or more agents. The delivery complex may then be administered to an individual for therapeutic or diagnostic purposes. It is a further object of the present invention to create complexes of agents rosette nanotubes or components of rosette nanotubes that can be delivered into target cells and intracellular matrices where the agent can function. It is a further object of the present invention to provide methods of treating individuals using a delivery system of a complex of rosette nanotubes or components of rosette nanotubes and agents, where the agent enters the cell. These and other objects, features, and advantages of the invention or certain embodiments of the invention will be apparent to those skilled in the art from the following disclosure and description of exemplary embodiments.

It is a further object of the present invention to create complexes of agents rosette nanotubes or components of rosette nanotubes that can be delivered into target cells and intracellular matrices where the agent can function. It is a further object of the present invention to provide methods of treating individuals using a delivery system of a complex of rosette nanotubes or components of rosette nanotubes and agents, where the agent enters the cell. Thus, the invention encompasses a composition comprising a cargo molecule and a nanostructure comprising Formula I or Formula II for selective, e.g., preferential, delivery of a therapeutic drug or diagnostic agent to a target bodily tissue. Alternatively, the non-structure comprises a lipid or a polymer rather than a compound or Formula I or II.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 4 illustrates scheme 1, which displays an assembly mechanism and processing approaches.

FIG. 9A is a bar graph of the size distribution of Nanopieces processed after assembly (increasing sonication time).

FIG. 9B is a bar graph of the width distribution of Nanopieces processed after assembly (increasing sonication time).

FIGS. 15A-15C are a series of images showing effective delivery of processed GAPDH molecular beacon/RNT Nanopieces into human cartilage tissue matrix and inside chondrocytes.

FIGS. 16A and 16B are a series of images showing effective delivery of processed GAPDH molecular beacon/RNT Nanopieces into chicken cartilage tissue matrix and inside chondrocytes.

FIGS. 35A-35C area series of images showing histology of mouse knee joints. ADAMTS-5 siRNA/Nanopiece greatly inhibited cartilage degeneration after DMM surgery.

FIG. 37A and FIG. 37B are a series of images showing a comparison with fluorescence signal from scrambled molecular beacon, signal from MMP-13 molecular beacon indicating the area of MMP-13 expression and articular cartilage degeneration.

FIG. 38 is an image of histology staining of a mouse knee joint after DMM surgery. The area of cartilage degeneration is the same as what was indicated by MMP-13 molecular beacon.

FIGS. 39A-39C are a series of images showing GAPDH and Scrambled molecular beacon delivered by Nanopieces into chondrocytes with stimulation.

FIGS. 40A-40C are a series of images showing GAPDH and ADAMTS-5 molecular beacon delivered by Nanopieces into chondrocytes without stimulation.

FIGS. 41A-41C are a series of images showing GAPDH and ADAMTS-5 molecular beacon was delivered by Nanopieces into chondrocytes with stimulation.

FIGS. 44A-44D are a series of images illustrating immunohistochemistry results (staining is epitope from aggrecan cleavage) of human articular cartilage. ADAMTS-4 siRNA and combination of ADAMTS-4&5 siRNA/Nanopieces greatly inhibited Aggrecan cleavage with cytokine stimulation.

FIGS. 46A-46C are a series of images showing immunohistochemistry results (staining is epitope from aggrecan cleavage) of mouse knee joints. ADAMTS-5 siRNA/Nanopieces greatly inhibited Aggrecan cleavage after DMM surgery.

FIG. 49A and FIG. 49B are a series of images showing the generation of Nanopieces before and after "processing-2".

FIG. 50 is a graph showing quantitative analysis of fluorescence signal in mouse knee.

FIG. 60A and FIG. 60B are an image showing the delivery of small Nanopieces into articular cartilage to result in fluorescence compared to controls (MB only).

FIG. 62A and FIG. 62B are images showing the decreased liver capture with small Nanopieces compared with lipid vehicles.

FIGS. 66A-66D are a series of images showing that cells with Nanopiece (RNT or TBL) delivery maintain normal cell morphology, indicating excellent biocompatibility of Nanopiece; while delivery with lipid-based vehicles led to abnormal cell morphology and large amount of debris, suggesting cyto-toxicity of lipid-based vehicles.

DETAILED DESCRIPTION

Figure 2:
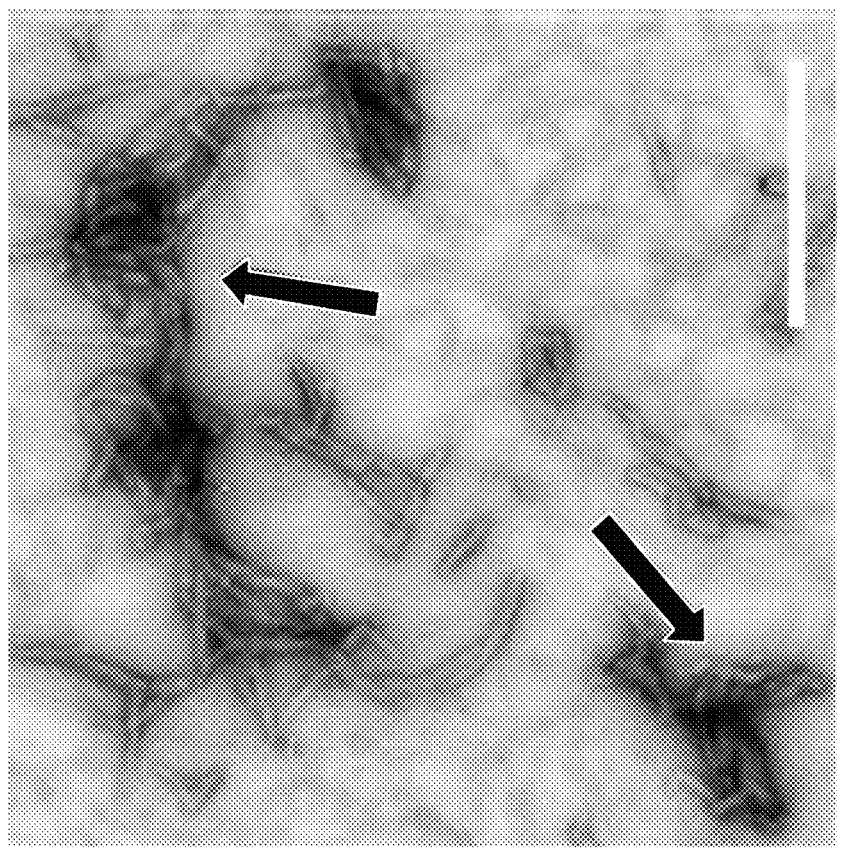
FIG. 2 is an illustration showing an assembly between RNTs with plasmid DNA.

The compositions and methods of the invention provide compositions and methods for preferential targeting of tissues to delivery therapeutic agents. The structures, e.g., nanopieces, are constructed to comprise a charge and/or size such that the structures preferentially associate with or bind to specific bodily tissues. For example, the invention provides methods for the delivery of Nanopieces and their cargo to/into joints, tissue and/or organs. A successful delivery into cells does not always necessarily mean that a successful delivery into tissue is achieved to obtain an efficacious therapeutic or diagnostic outcome. One major reason is that tissues unlike cells have an extracellular matrix. For example, Nanopieces with large size or inappropriate surface charge may not penetrate the tissue efficiently enough to cause a therapeutic or diagnostic response. Drug molecules released from nanotubes prior to tissue penetration do not diffuse into enough depth of the tissue to reach a significant amount of cells. The invention solves such problems and provides methods to package drug molecules within nanotubes/nanorods that are selectively designed to alter their surface charge and/or their size to be small enough to penetrate the tissue matrix. So in this manner it is not the drug molecules that are released from the nanotubes and then diffuse into the tissue but it is the actual Nanopieces/nanorods (containing cargo, e.g., drug) that penetrate the tissue. The invention further provides methods of processing nanotubes/nanorods to control of size and other properties of Nanopieces (like surface charge and coating), in order to efficiently deliver their cargo into joints, tissues and/or organs to achieve an effective therapy or diagnosis. These Nanopieces (Nanopieces) may contain nucleic acid, peptides, proteins and aromatic or negatively charged small molecules. Because different tissues have different surface charge, it is important to control the surface charge of Nanopieces via the ratio of delivery cargos and amount of nanorods. Nanopieces, which are too large may have difficulties in penetrating the tissue matrix and improper surface charge of Nanopieces may be repulsive to the target tissue matrix or perhaps the Nanopieces are not stable in the bodily fluids or blood. The table below describes exemplary nanopieces for preferential localization to and delivery to exemplary bodily tissues.

Selective Delivery of Nanopieces to Target Tissues

TABLE 1

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| Cartilage/chondrocyte | General range: at least one dimension between 1 nm and 90 nm Preferred range: at least one dimension between 1 nm and 30 nm | General range: between +0 mV and +60 mV Preferred range: between +8 mV and +40 mV | Ratio: 4.4~30 µg RNTs per 0.1 nmol RNA (Preferred ratio: 6.6~20 µg RNTs per 0.1 nmol RNA) Sonication power: 10%~100% (for a 700 W sonicator) Sonication time: 10 s~30 mins Ionic strength of assembly solution: 0~308 mmol/L At least one of pre-processing methods (such as heating, sonication or quench): required | siRNA, other nucleic acids, molecular beacons and peptides/proteins (ADAMTS-5 siRNA, MMP-13 oligo molecular beacon, IL-1Ra protein) | Negatively charged |
| Synovium | General range: at least one dimension between 1 nm and 150 nm Preferred range: at least one dimension | General range: between +0 mV and +60 mV Preferred range: | Ratio: 4.4~30 µg RNTs per 0.1 nmol RNA (Preferred ratio: 4.4~20 µg RNTs per 0.1 nmol | siRNA, other nucleic acids, molecular beacons and | |

TABLE 1-continued

| Target Tissue/Cell Type | Nanopiece Structure Size | Nanopiece Charge (Zeta potential) | Processing details to achieve desired length/width/charge* | Preferred payload/ cargo | Other/ notes |
|---|---|---|---|---|---|
| | between 10 nm and 100 nm | between +0 mV and +40 mV | RNA) Sonication power: 1~100% (for a 700 W sonicator) Sonication time: 5 s~30 mins Ionic strength of assembly solution: no requirement At least one of pre-processing methods (such as heating, sonication or quench): not required | peptides/ proteins (IL-1 or TNF-α siRNA, IL-1 or TNF-α oligo molecular beacon, IL-1Ra protein) | |
| Neurons | General range: at least one dimension between 1 nm and 150 nm Preferred range: at least one dimension between 10 nm and 100 nm | General range: between −60 mV and +30 mV Preferred range: between −40 mV and +30 mV | Ratio: 0.1~15 μg RNTs per 0.1 nmol RNA (Preferred ratio: 1~15 μg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | Neurons generally positively charged |
| Brain/BBB | General range: at least one dimension between 1 nm and 100 nm Preferred range: at least one dimension between 1 nm and 30 nm | General range: between −30 mV and +40 mV Preferred range: between +8 mV and +40 mV | Ratio: 1~20 μg RNTs per 0.1 nmol RNA (Preferred ratio: 4.4~20 μg RNTs per 0.1 nmol RNA) Sonication power: 10~100% (for a 700 W sonicator) Sonication time: 10 s~30 mins Ionic strength of assembly solution: 0~308 mmol/L At least one of pre-processing methods (such as heating, sonication or quench): required | siRNA, other nucleic acids, molecular beacons and peptides/ proteins | |
| Ocular tissue | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 μg RNTs per 0.1 nmol RNA (Preferred ratio: 4.4~20 μg RNTs per 0.1 nmol RNA) Sonication | siRNA, other nucleic acids, molecular beacons and peptides/ proteins | |

TABLE 1-continued

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| | | | power: 1~100% (for a 700 W sonicator) Sonication time: 5 s~30 mins Ionic strength of assembly solution: no requirement At least one of pre-processing methods (such as heating, sonication or quench): not required | | |
| Derm tissue, skin, etc. | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | |
| Tumor | General range: at least one dimension between 1 nm and 1200 nm Preferred range: at least one dimension between 10 nm and 200 nm | General range: between −60 mV and +60 mV Preferred range: between −30 mV and +60 mV | Ratio: 0.1~30 µg RNTs per 0.1 nmol RNA (Preferred ratio: 1~30 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | Tumors may be acidic |
| Kidney | General range: at least one dimension between 1 nm and 100 nm Preferred range: at least one dimension between 10 nm and 200 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 5~100% (for a 700 W | siRNA, other nucleic acids, molecular beacons and peptides/ proteins | |

TABLE 1-continued

| Target Tissue/Cell Type | Nanopiece Structure Size | Nanopiece Charge (Zeta potential) | Processing details to achieve desired length/width/charge* | Preferred payload/ cargo | Other/ notes |
|---|---|---|---|---|---|
| | | | sonicator) Sonication time: 5 s~30 mins Ionic strength of assembly solution: no requirement At least one of pre-processing methods (such as heating, sonication or quench): not required | | |
| Mucous membrane | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | |
| Lung | General range: at least one dimension between 10 nm and 150 nm Preferred range: at least one dimension between 20 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~50% (for a 700 W sonicator) Sonication time: 5 s~3 mins Ionic strength of assembly solution: no requirement At least one of pre-processing methods (such as heating, sonication or quench): not required | siRNA, other nucleic acids, molecular beacons and peptides/ proteins | |
| Heart | General range: at least one dimension between 1 nm and 90 nm Preferred range: at least one dimension between 1 nm and 30 nm | General range: between +0 mV and +60 mV Preferred range: between +8 mV and +40 mV | Ratio: 4.4~30 µg RNTs per 0.1 nmol RNA (Preferred ratio: 6.6~20 µg RNTs per 0.1 nmol RNA) Sonication power: 10%~100% (for a 700 W sonicator) | siRNA, other nucleic acids, molecular beacons and peptides/ proteins | |

TABLE 1-continued

| Target Tissue/Cell Type | Nanopiece Structure Size | Nanopiece Charge (Zeta potential) | Processing details to achieve desired length/width/ charge* | Preferred payload/ cargo | Other/ notes |
| --- | --- | --- | --- | --- | --- |
| | | | Sonication time: 10 s~30 mins Ionic strength of assembly solution: 0~308 mmol/L At least one of pre-processing methods (such as heating, sonication or quench): required | | |

Diagnostic Applications

Molecular beacons or molecular beacon probes are oligonucleotide hybridization probes that report the presence of specific nucleic acids. Molecular beacons are hairpin shaped molecules with an internally quenched fluorophore whose fluorescence is restored when they bind to a target nucleic acid sequence. The use of molecular beacons is a non-radioactive method for detecting specific sequences of nucleic acids. They are useful in situations where it is either not possible or desirable to isolate the probe-target hybrids from an excess of the hybridization probes such as in the context of clinical diagnostics.

A typical molecular beacon probe is 25 nucleotides long. The middle 15 nucleotides are complementary to the target DNA or RNA and do not base pair with one another, while the five nucleotides at each terminus are complementary to each other rather than to the target DNA. A typical molecular beacon structure can be divided in 4 parts. Loop: a 18-30 base pair region of the molecular beacon that is complementary to the target sequence. Stem: the beacon stem is formed by the attachment, to both termini of the loop, of two short (5 to 7 nucleotide residues) oligonucleotides that are complementary to each other. 5' fluorophore: located at the 5' end of the molecular beacon, a fluorescent dye is covalently attached. 3' quencher (non-fluorescent): the quencher dye part of the beacon is covalently attached to the 3' end of the molecular beacon. When the beacon is in closed loop shape, the quencher resides in proximity to the fluorophore, which results in quenching the fluorescent emission of the latter.

If the nucleic acid to be detected is complementary to the strand in the loop, the event of hybridization occurs. The duplex formed between the nucleic acid and the loop is more stable than that of the stem because the former duplex involves more base pairs. This causes the separation of the stem and hence of the fluorophore and the quencher. Once the fluorophore is distanced from the quencher, illumination of the hybrid with light results in the fluorescent emission. The presence of the emission reports that the event of hybridization has occurred and hence the target nucleic acid sequence is present in the test sample. Molecular beacons are useful in SNP detection, real-time nucleic acid detection, real-time PCR quantification, allelic discrimination and identification, multiplex PCR assays, and for diagnostics. Nanopieces containing molecular beacons or other non-radioactive or radioactive detectable markers are particularly useful in diagnostic clinical assays.

MMP

MMP13 is involved in the progression of osteoarthritis. Matrix metalloproteinase (MMP) 13 is a major enzyme that targets cartilage for degradation. Compared to other MMPs, the expression of MMP13 is relatively more restricted to connective tissue. It not only targets type II collagen in cartilage for degradation, but also degrades proteoglycan, types IV and type IX collagen, osteonectin and perlecan in cartilage. Clinical investigation revealed that patients with articular cartilage destruction have high MMP13 expression, indicating that increased MMP13 is associated with cartilage degradation. MMP13-overexpressing transgenic mice developed a spontaneous OA-like articular cartilage destruction phenotype. The ADAMTS (a disintegrin and metalloproteinase with thrombospondin motifs) family of aggrecanases also contributes to proteoglycan/aggrecan depletion and are associated with cartilage degradation during OA. ADAMTS4 and 5 were identified as the major aggrecanases during OA development.

ADAMTS5

ADAMTS5 is a member of the ADAMTS (a disintegrin and metalloproteinase with thrombospondin motifs) protein family and a major aggrecanase in human cartilage. Members of the family share several distinct protein modules, including a propeptide region, a metalloproteinase domain, a disintegrin-like domain, and a thrombospondin type 1 (TS) motif. Individual members of this family differ in the number of C-terminal TS motifs, and some have unique C-terminal domains. The enzyme encoded by this gene contains two C-terminal TS motifs and functions as aggrecanase to cleave aggrecan, a major proteoglycan of cartilage.

ADAMTS5 plays a role in arthritis, e.g., it plays a key role in aggrecan degradation in cartilage. For example, genetically modified mice in which the catalytic domain of ADAMTS5 was deleted are resistant to cartilage destruction in an experimental model of osteoarthritis. ADAMTS5 is the major aggrecanase in mouse cartilage in a mouse model of inflammatory arthritis. ADAMTS5 is also useful as a biomarker for prediction of the response to infliximab (IFX) in patients with rheumatoid arthritis.

Fabrication of Tissue-Targeted Nanoparticles

Examples for the preparation of nanopieces for use in individual tissues are described below.

Cartilage/Chondrocytes:
1) 30 μg RNTs in 50 μL water were heated to 99° C. for 3 mins, and then mixed with 0.1 nmol MMP-13 molecular beacon. The resulting mixture was sonicated at 100% power for 10 s.

2) 4.4 µg RNTs in 1 µL water were sonicated at 50% power of a 700 W sonicator for 10 mins, and then mixed with 0.1 nmol miRNA-140. The resulting mixture was sonicated at 100% power for 30 mins.
3) 10 µg RNTs in 10 µL water were sonicated at 100% power of a 700 W sonicator for 5 mins, and then mixed with 0.1 nmol ADAMTS-5 siRNA. The resulting mixture was sonicated at 100% power for 3 mins.

Synovium:
1) 30 µg RNTs in 50 µL water were heated to 99° C. for 3 mins, and then mixed with 0.1 nmol IL-1β molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol IL-1 receptor antagonist protein. The resulting mixture was sonicated at 1% power for 10 s.
3) 10 µg RNTs in 10 µL water were sonicated at 100% power of a 700 W sonicator for 5 mins, and then mixed with 0.1 nmol TNF-α siRNA. The resulting mixture was sonicated at 100% power for 60 s.

Neurons:
1) 15 µg RNTs in 50 µL water at 1% power of a 700 W sonicator for 30 mins, and then mixed with 0.1 nmol VEGF molecular beacon. The resulting mixture was sonicated at 100% power for 60 s.
2) 0.1 µg RNTs in 1 µL saline were heated to 99° C. for 3 mins, and then mixed with 0.1 nmol IL-1 receptor siRNA on ice. The resulting mixture was sonicated at 100% power for 30 mins.
3) 10 µg RNTs were sonicated in 10 µL water at 100% power of a 700 W sonicator for 5 mins, and then mixed with 0.1 nmol MMP-1 siRNA. The resulting mixture was sonicated at 100% power for 3 mins.

Brain/BBB:
1) 20 µg RNTs in 50 µL water were heated to 99° C. for 3 mins, and then mixed with 0.1 nmol MMP-9 molecular beacon on ice. The resulting mixture was sonicated at 100% power for 60 s.
2) 1 µg RNTs in 1 µL saline were sonicated at 10% power of a 700 W sonicator for 10 mins, and then mixed with 0.1 nmol VEGF mRNA. The resulting mixture was sonicated at 10% power for 10 s.
3) 10 µg RNTs in 10 µL water were sonicated at 100% power of a 700 W sonicator for 5 mins, and then mixed with 0.1 nmol TNF-α siRNA. The resulting mixture was sonicated at 100% power for 60 s.

Ocular Tissue:
1) 30 µg RNTs in 50 µL water were heated to 99° C. for 3 mins, and then mixed with 0.1 nmol VEGF molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol VEGF antagonist protein. The resulting mixture was sonicated at 1% power for 10 s.
3) 10 µg RNTs in 10 µL water were sonicated at 100% power of a 700 W sonicator for 5 mins, and then mixed with 0.1 nmol VEGF siRNA. The resulting mixture was sonicated at 100% power for 60 s.

Derm Tissue/Skin:
1) 30 µg RNTs in 50 µL water were heated to 99° C. for 3 mins, and then mixed with 0.1 nmol IL-1β molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol IL-6 siRNA. The resulting mixture was sonicated at 1% power for 10 s.
3) 10 µg RNTs in 10 µL water were sonicated at 100% power of a 700 W sonicator for 5 mins, and then mixed with 0.1 nmol IL-8 siRNA. The resulting mixture was sonicated at 100% power for 60 s.

Tumor:
1) 30 µg RNTs in 50 µL water at 1% power of a 700 W sonicator for 30 mins, and then mixed with 0.1 nmol VEGF molecular beacon. The resulting mixture was sonicated at 100% power for 60 s.
2) 0.1 µg RNTs in 1 µL saline were heated to 99° C. for 3 mins, and then mixed with 0.1 nmol TNF-α siRNA on ice. The resulting mixture was sonicated at 100% power for 30 mins.
3) 10 µg RNTs were sonicated in 10 µL water at 100% power of a 700 W sonicator for 5 mins, and then mixed with 0.1 nmol MMP-1 siRNA. The resulting mixture was sonicated at 100% power for 3 mins.

Kidney:
1) 30 µg RNTs in 50 µL water were heated to 99° C. for 3 mins, and then mixed with 0.1 nmol IL-12 molecular beacon on ice. The resulting mixture was sonicated at 100% power for 60 s.
2) 4.4 µg RNTs in 1 µL saline were sonicated at 5% power of a 700 W sonicator for 10 mins, and then mixed with 0.1 nmol IL-1 receptor associated protein siRNA. The resulting mixture was sonicated at 1% power for 10 s.
3) 10 µg RNTs in 10 µL water were sonicated at 100% power of a 700 W sonicator for 5 mins, and then mixed with 0.1 nmol IL-8 siRNA. The resulting mixture was sonicated at 100% power for 60 s.

Mucous Membrane:
1) 30 µg RNTs in 50 µL water were heated to 99° C. for 3 mins, and then mixed with 0.1 nmol MMP-13 molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol MMP-9 siRNA. The resulting mixture was sonicated at 1% power for 10 s.
3) 10 µg RNTs in 10 µL water were sonicated at 100% power of a 700 W sonicator for 5 mins, and then mixed with 0.1 nmol MMP-1 siRNA. The resulting mixture was sonicated at 100% power for 60 s.

Lung:
1) 30 µg RNTs in 50 µL water were heated to 99° C. for 3 mins, and then mixed with 0.1 nmol TNF-α molecular beacon on ice. The resulting mixture was sonicated at 50% power for 60 s.
2) 4.4 µg RNTs in 1 µL saline were sonicated at 1% power of a 700 W sonicator for 3 mins, and then mixed with 0.1 nmol MMP-9 siRNA. The resulting mixture was sonicated at 1% power for 5 s.
3) 10 µg RNTs in 10 µL water were sonicated at 50% power of a 700 W sonicator for 1 mins, and then mixed with 0.1 nmol MMP-1 siRNA. The resulting mixture was sonicated at 100% power for 60 s.

Heart:
1) 30 µg RNTs in 50 µL water were were heated to 99° C. for 3 mins, and then mixed with 0.1 nmol VEGF molecular beacon. The resulting mixture was sonicated at 100% power for 10 s.
2) 4.4 µg RNTs in 1 µL water were sonicated at 50% power of a 700 W sonicator for 10 mins, and then mixed with 0.1 nmol miRNA-365. The resulting mixture was sonicated at 100% power for 30 mins.

3) 10 μg RNTs in 10 μL water were sonicated at 100% power of a 700 W sonicator for 5 mins, and then mixed with 0.1 nmol IL-1α siRNA. The resulting mixture was sonicated at 100% power for 3 mins.

Coating of Nanopieces, which is another important factor for tissue delivery can also be used to improve the tissue delivery. For example polyethylene glycol (PEG) and dextran are coatings often used.

The invention further provides methods for making composites of rosette nanotubes or components or rosette nanotubes or rosette Nanopieces and therapeutic or diagnostic agents including those known in the art. For example, agents include nucleic acids (DNA or RNA), wherein the RNA can be small RNA such as siRNA and miRNA. In particular, disclosed herein are novel siRNA transport complexes, comprising an unexpectedly advantageous transport vehicle. Methods of the present invention include contacting a transfection complex described herein with one or more cells, where the transfection complex includes a rosette nanotube and one or more nucleic acids such as DNA and RNA, for example siRNA. The rosette nanotube is a carrier that is formed from self-assembled modules as described below and those modules recognized in the art.

Compounds/Modules for Self-Assembly

Modules according to the present disclosure include compounds of Formula I below:

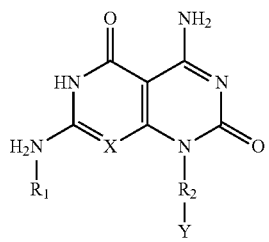

Wherein X is CH or nitrogen, preferably nitrogen; $R_2$ is hydrogen or a linker group for example $(CH_2)_n$ or other linker groups described herein, preferably $(CH_2)_n$; n is an integer of, 1, 2, 3, or 4, n=2 is preferred; Y is absent when $R_2$ is hydrogen or is an amino acid or polypeptide having an amino group covalently bound to an α-carbon of the amino acid and the amino group is covalently bound to the linker group $R_2$, Y is preferred to be lysine arginine, and histidine; and $R_1$ is hydrogen or an aliphatic moiety, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. Compounds within the scope of the invention include those where the Y group can be connected to the linker group either by the amino group or the carboxyl group of the amino acid or polypeptide. An exemplary linker group is shown in the formula below.

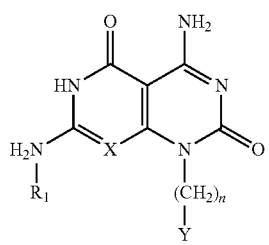

An exemplary module within the scope of Formula I is shown in FIG. 4 along with a schematic representation of a nanotube and an image of nanotubes formed from the exemplary module.

Alternative linker groups $R_2$ can join the Y group to the carbon of the $(CH_2)_n$ group or the N atom either by the amino group or the carboxyl group of the amino acid or polypeptide.

Alternative $R_2$ groups within the scope of the present disclosure are selected from a group comprising:

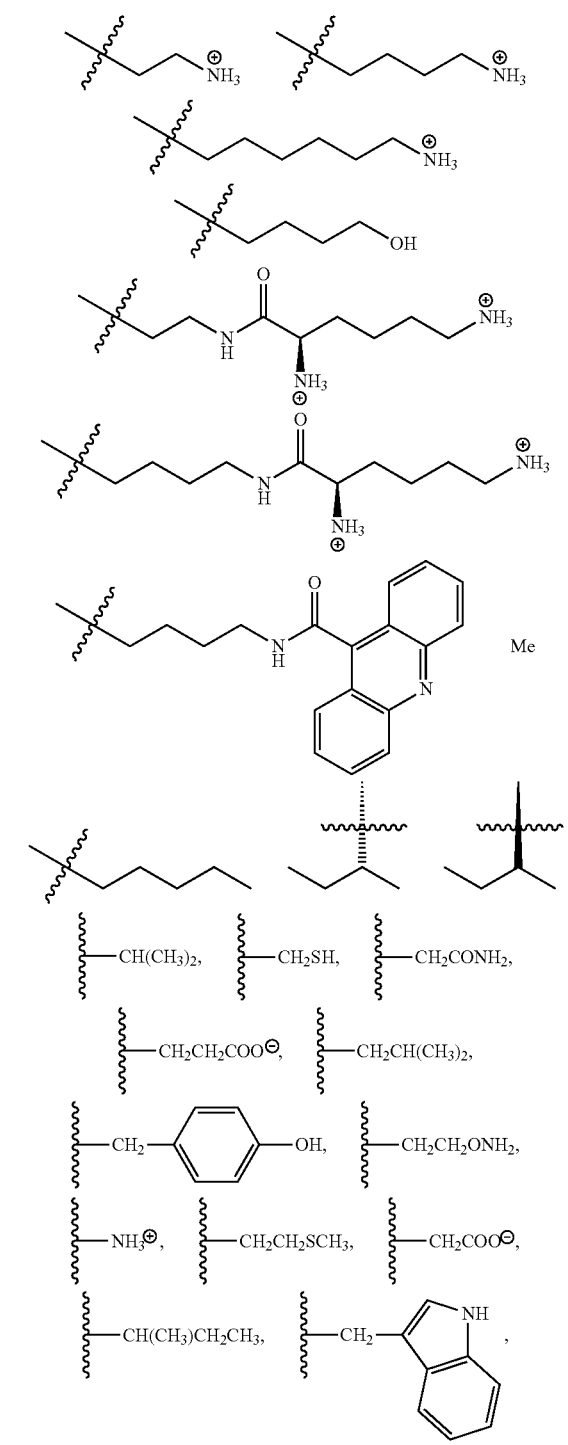

-continued

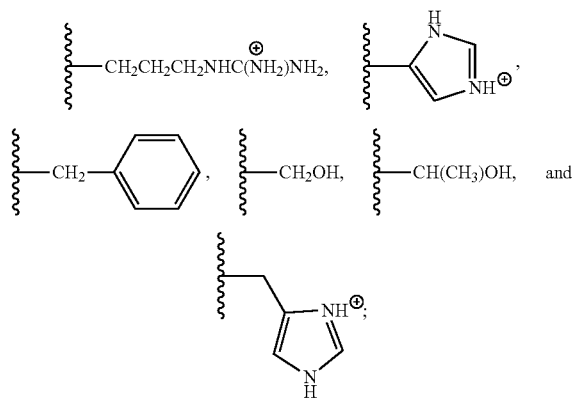 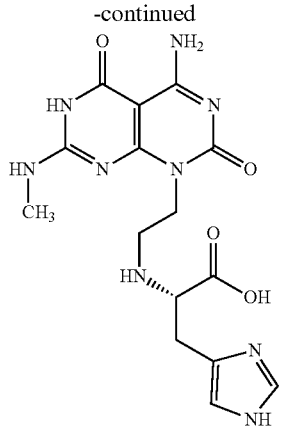

wherein Y is absent.

Compounds of Formula I can be prepared by the methods described in U.S. Pat. No. 6,696,565 hereby incorporated by reference herein in its entirety alone or combined with methods known to those of skill in the art. Rosette nanotubes are made by assembly of compounds of Formula (I).

Exemplary compounds of Formula I are shown below:

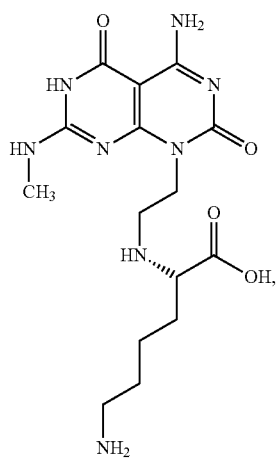

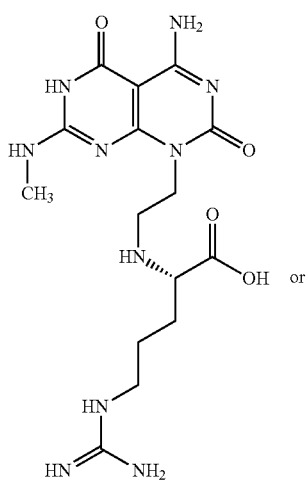

-continued

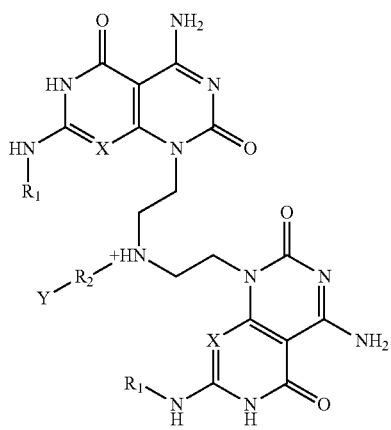

Modules according to the present disclosure also include compounds of Formula II below:

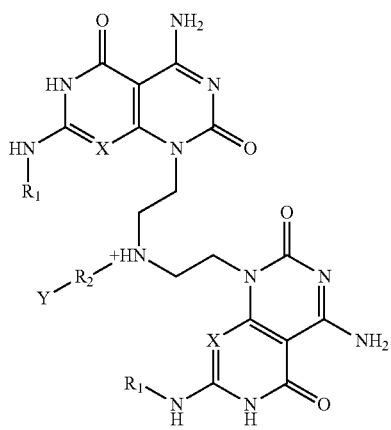

Wherein X is CH or nitrogen preferably nitrogen; $R_2$ is hydrogen or a linker group for example $(CH_2)_n$, preferably $(CH_2)_n$; where n is an integer of, 1, 2, 3, or 4 or $(CH_2)_3CO$ or other linker groups described herein, n=2 is preferred; Y is absent when $R_2$ is hydrogen or is an amino acid or polypeptide having an amino group covalently bound to an α-carbon of the amino acid and the amino group is covalently bound to the linker group $R_2$, Y is preferred to be lysine arginine, and histidine; and $R_1$ is hydrogen or an aliphatic moiety, such alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

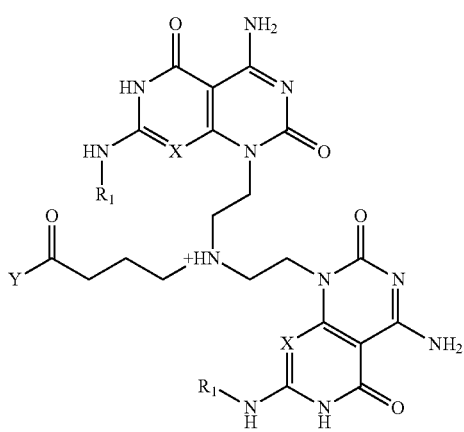

Compounds within the scope of the present disclosure include those where the Y group can be connected to the linker group either by the amino group or the carboxyl group of the amino acid or polypeptide. Alternative $R_2$ groups within the scope of the present disclosure are selected from a group comprising:

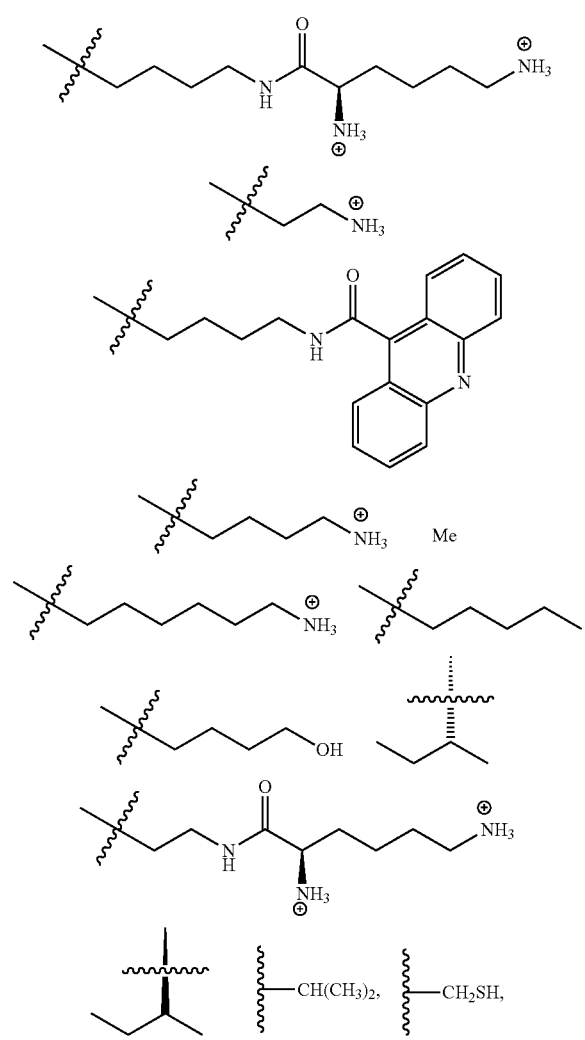

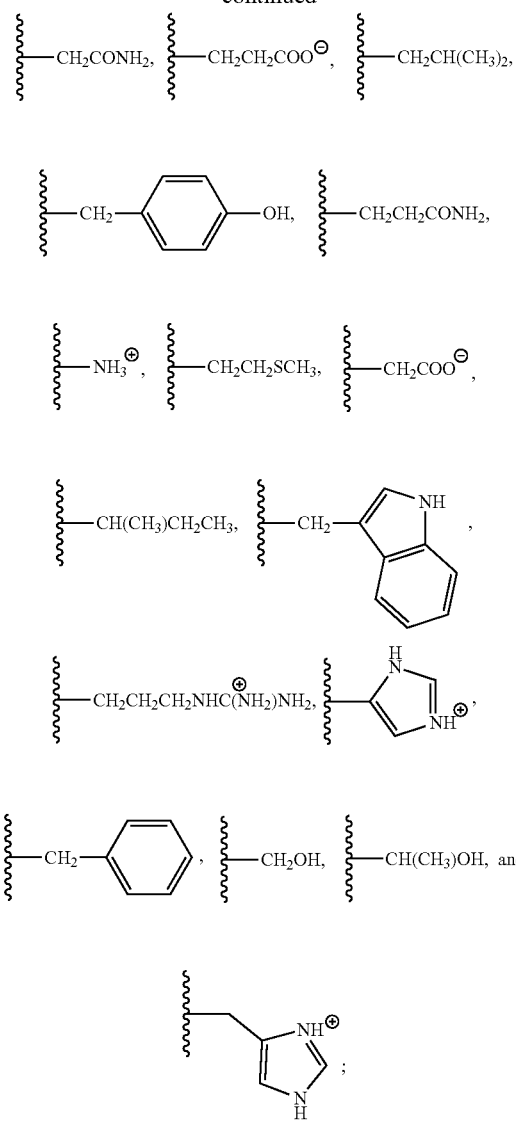

wherein Y is absent. TBL structures are made by the assembly of compounds of Formula (II).

Exemplary compounds of Formula II are shown below:

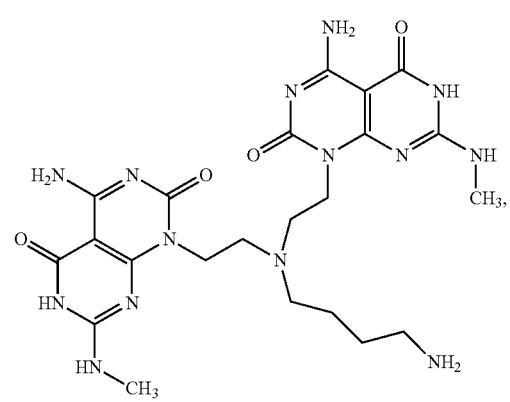

Lysine Functional Group Construct

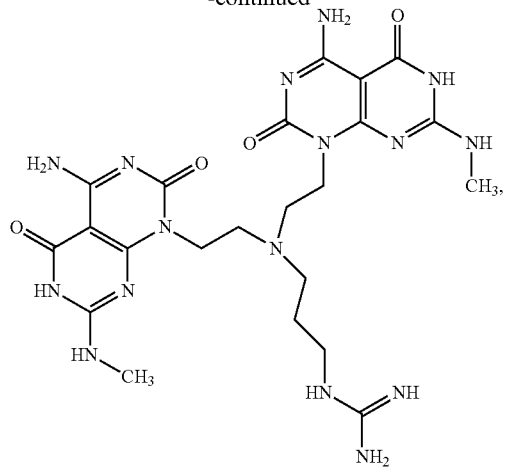
Arginine Functional Group Construct
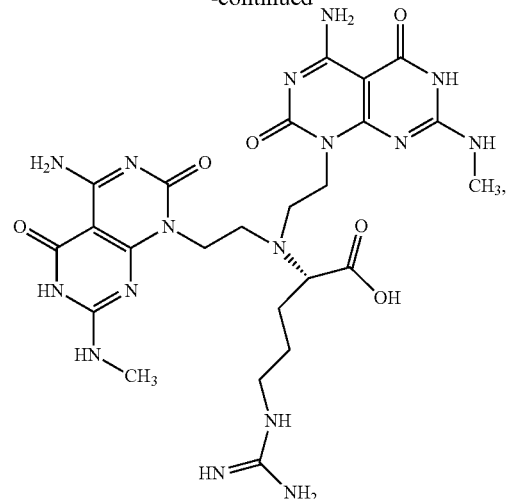
Arginine Amino Acid Construct
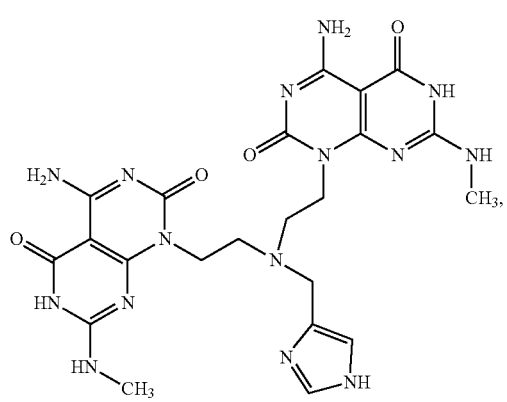
Histidine Functional Group Construct
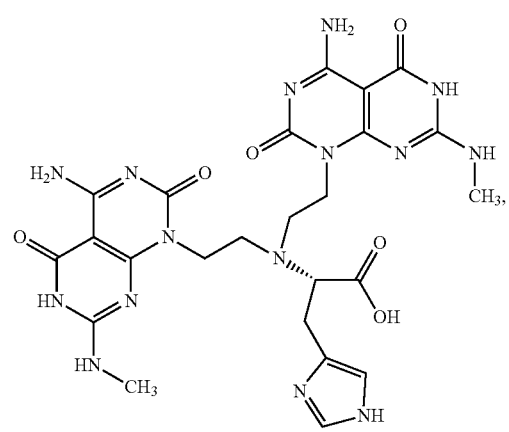
Histidine Amino Acid Construct
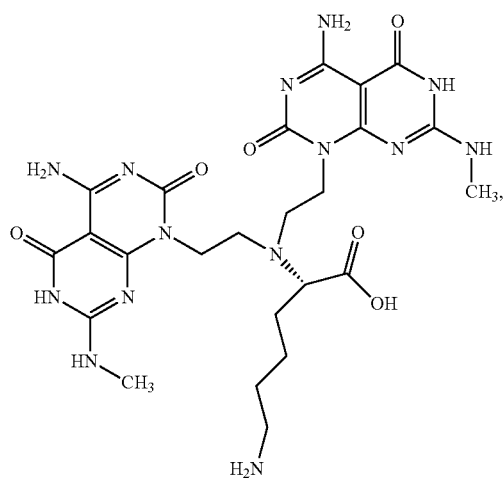
Lysine Amino Acid Construct
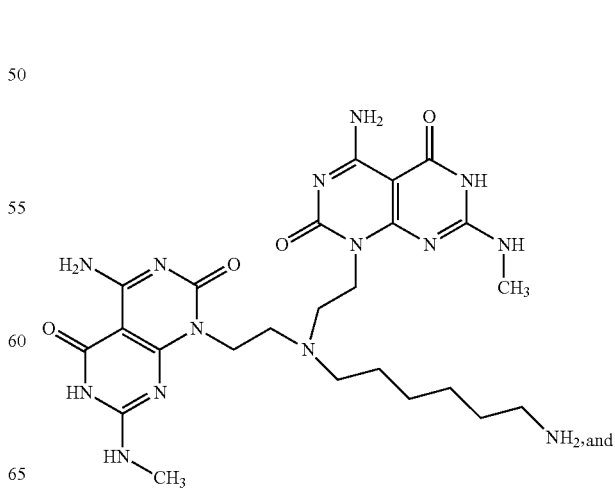
Hexylamine Functional Group Construct -continued

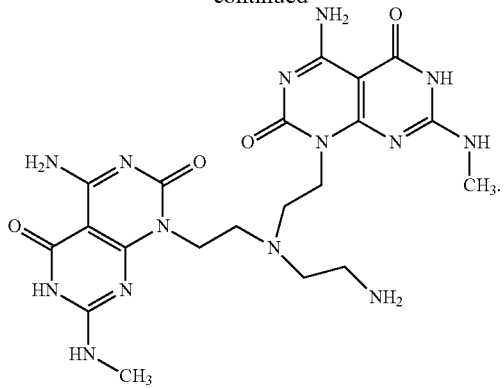

Ethylamine Functional Group Construct

In some embodiments, compounds of formula II comprise amino acid functional group constructs. These compounds contain functional groups present in natural occurring amino acid side chains or may contain the the entire amino acid side chain. For example, the lysine functional group construct contains the entire amino acid side chain functionality ($-CH_2CH_2CH_2CH_2NH_3^+$), whereas the histidine functional group construct only contains the heteroaryl imidazole group present in histidine.

In some embodiments, compounds of formula II comprise amino acid analogs. These compounds contain the entire the amino acid or may contain modified and/or unnatural amino acids. For example, the lysine amino acid analog contains the entire amino acid functionality of lysine, whereas the histidine amino acid analog contains a modified histidine amino acid.

In some embodiments the compounds of formula II are preferred over the compounds of formula I.

In some embodiments the compound of formula II is the Lysine Functional Group Construct:

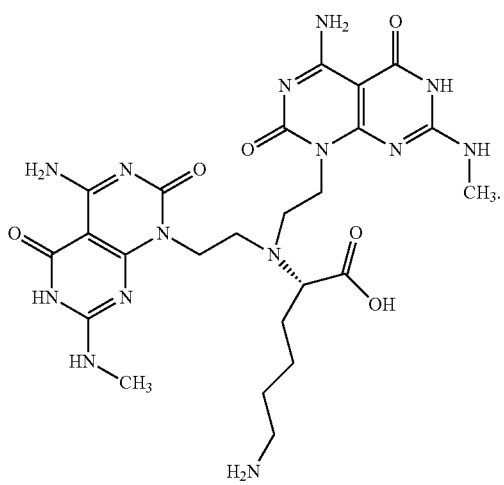 [SMILES: CNc1nc2c(c(N)nc(=O)n2CCN(CCn2c(=O)nc(N)c3c(=O)[nH]c(NC)nc32)[C@@H](CCCCN)C(=O)O)c(=O)[nH]1]

According to certain aspects of the present disclosure, the structure of Formula II is referred to as a twin base with a linker (TBL) or twin base linkers insofar as two similar double ring structures are present as shown in Formula II and are linked to an amino acid or polypeptide. However, it is to be understood that the two double ring structures need not be identical insofar as they may have different X and $R_1$ groups.

Embodiments of the present disclosure involve making composites of rosette nanotubes or components or rosette nanotubes or rosette Nanopieces and therapeutic or diagnostic agents including those known in the art and including nucleic acids, such as DNA or RNA. RNA can be small RNA including siRNA and miRNA. In particular, disclosed herein are novel siRNA transport complexes, comprising an unexpectedly advantageous transport vehicle. Methods of the present invention include contacting a transfection complex described herein with one or more cells, where the transfection complex includes a rosette nanotube and one or more nucleic acids such as DNA and RNA, for example siRNA. The rosette nanotube is a carrier that is formed from self-assembled modules as described below and those modules are recognized in the art.

TBL or twin base linkers comprise structures shown in Formula II and are linked to an amino acid, amino acid side chain structure, or polypeptide; compounds of Formula I may also be linked to an amino acid, amino acid side chain structure, or polypeptide. However, it is to be understood that the two double ring structures need not be identical insofar as they may have different X, Y, and $R_1$ groups.

Amino acids can be divided into amino acid containing hydrophilic side chains, hydrophobic side chains, and electrically charged side chains. See chart below, wherein the side chains are shaded:

According to aspects of the present disclosure, modules (compounds) according to Formula I and Formula II self-assemble into substructures also called supermacrocycles which themselves will self-assemble into nanometer scale architectures or structures such as discrete nanotubular assemblies in water or aqueous solutions. Supermacrocycles are defined herein as being a number of organic molecules covalently or noncovalently bound together so as to form a ring structure. For example, compounds of Formula I will self-assemble into a 6-mer ring structure, sometimes referred to as a rosette. The process of forming nanotubes with the modules of the present disclosure is hierarchical. In particular, the modules of the present invention first self-assemble into supermacrocycles, and then the supermacrocycles self-assembly into nanotubes. Such self-assembly is described in U.S. Pat. No. 6,696,565. For the compounds of Formula II referred to as twin base linkers, the compounds will also assemble into a 6-mer ring structure. However, a single supermacrocycle formed will include two base layers owing to the presence of the two bases in each of the compound of Formula II.

Examples of modules of the present disclosure comprise the compounds of Formula I and Formula II and may include low molecular weight synthetic DNA base analogues referred to by the nomenclature C∧G (Fenniri et al, *J. Am. Chem. Soc.* 2001, 123, 3854-3855) and A∧T. The C∧G moiety, referred to as a single CG motif, possesses the Watson-Crick donor-donor-acceptor of guanine and the acceptor-acceptor-donor of cytosine and undergoes a self-assembly process, fueled by an array of hydrogen bonds, to produce a six-membered supermacrocycle or rosette. Stacking of these rosettes produced a nanotube of very high aspect ratio. Compounds within the scope of the present invention include a twin GAC motif denoted as $(C∧G)_2$. Like the single C∧G motif, the twin C∧G motif $(C∧G)_2$ also possesses the Watson-Crick donor-donor-acceptor of guanine and the acceptor-acceptor-donor of cytosine and undergoes a self-assembly process, fueled by an array of hydrogen bonds, to produce a six-membered supermacrocycle or ring structure (rosette) of twin configuration. Stacking of these twin rosettes produces a nanotube of very high aspect ratio and higher stability. Analogously, The A/\T moiety, referred to as a single AT motif, also possesses the Watson-Crick donor-donor-acceptor of adenine and the acceptor-acceptor-donor of thymine and undergoes a self-assembly process as well, fueled by an array of hydrogen bonds, to produce a six-membered supermacrocycle or rosette. Stacking of these rosettes produces a nanotube of very high aspect ratio. Compounds within the scope of the present invention include a twin A/\T motif denoted as $(A/\backslash T)_2$. Like the single A/\T motif, the twin A/\T motif $(A/\backslash T)_2$ also possesses the Watson-Crick donor-donor-acceptor of adenine and the acceptor-acceptor-donor of thymine and undergoes a self-assembly process, fueled by an array of hydrogen bonds, to produce a six-membered supermacrocycle or ring structure (rosette) of twin configuration. Stacking of these twin rosettes also produces a nanotube of very high aspect ratio and higher stability.

It should be understood that the above described Formula I and/or Formula II demonstrate that electrostatic, stacking and hydrophobic interactions can be effectively orchestrated by hydrogen bonds to direct the hierarchical assembly and organization of helical nanotubular architectures in an aqueous milieu. Helical nanotubular architectures within the scope of the present invention include those formed entirely from compounds of Formula I. Helical nanotubular architectures within the scope of the present invention include those formed entirely from compounds of Formula II. Further, helical nanotubular architectures within the scope of the present invention include those formed from one or more of the compounds of Formula I and one or more of the compounds of Formula II. For example, a supermacrocycle ring substructure having particular amino acid or polypeptide side chains formed from the compounds of Formula I can be stacked with a supermacrocycle ring substructure having particular amino acid or polypeptide side chains formed from compounds of Formula II. The rosette substructures formed from the compounds of Formula I and Formula II can be stacked in any desired sequence to form nanotubular structures of the present invention. Utilizing this aspect of the present invention, a wide variety of structurally different modules (e. g, compounds) can be synthesized and self-assembled into supermacrocycles and then nanotubular structures according to methods of the present invention.

Another aspect of the invention is the conversion of nanotubes to nanorods by altering pH, temperature, and usage of physical methods (e.g., sonication, heating and blending) to prepare different sizes of Nanopieces.

Before assembly with delivery cargo, length of nanotubes (based on either Formula I or II) range in size from 1 nm to 999 micron, e.g., 10 nm to 999 nm. Outer width of nantoubes range in size from 0.5 nm to 100 nm, e.g., 1 nm to 10 nm. Inner diameter of nanotubes range in size from 1 angstrom to 10 nm, e.g., 0.5 nm to 5 nm.

After assembly with delivery cargo, length of Nanopieces (based on either Formula I or II) range in size from 1 nm to 999 micron, e.g., 10 nm to 999 nm. Width of Nanopieces range in size from 1 nm to 999 nm, e.g., 10 nm to 100 nm.

Another aspect of the invention is the packaging of drug molecules, e.g., therapeutics and diagnostics, with nanotubes to alter their surface charge and more importantly process these nanotubes into Nanopieces of the right shape and size to penetrate tissue matrix. Therefore, it is not the drug molecules that are released from nanotubes that diffuse into tissue, it is the Nanopieces themselves that penetrate the tissue. Control of the surface charge of the Nanopieces is done via the ratio of delivery cargo and nanotubes and/or nanorods. A further aspect of the invention is the use of coatings for the Nanopieces for tissue delivery. For example, polyethylene glycol and/or dextran are coatings that when used can improve tissue delivery.

A further aspect of the invention is the delivery of cargo into cells. These drug molecules can be nucleic acid, peptides, proteins, aromatic small molecules or negatively charged small molecules.

In some embodiments, the prepared module of the invention has an overall yield of no less than 60%, e.g., no less than 70%, no less than 80%, or no less than 90%.

In some embodiments, the module of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

In some embodiments, the nanotube of the invention has an overall yield of no less than 60%, e.g., no less than 70%, no less than 80%, or no less than 90%.

In some embodiments, the nanotube of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

In some embodiments, the Nanopieces of the invention has an overall yield of no less than 60%, e.g., no less than 70%, no less than 80%, or no less than 90%.

In some embodiments, the Nanopieces of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

According to certain preferred aspects of the present invention, a nanotube is prepared from single base ring structures and twin base ring structures in any desired order. The nanotube can have one or more single base ring structures and one or more twin base ring structures. Likewise, a nanotube within the scope of the present invention can include a plurality of single base ring structures formed from compounds of Formula I and a plurality of twin base ring structures formed from compounds of Formula II stacked together, e.g. one next to the other via hydrogen bonding, to form the nanotube.

Nanotube-Agent Complexes

According to certain aspects, nucleic acids or polypeptides includes small RNA being a duplex of between about 10 to about 30 nucleic acids, between about 15 to about 25 nucleic acids and between about 20 to about 23 nucleic acids, and any values and ranges in between whether overlapping or not. The small RNA can be formed by one or more oligonucleotides. Small RNA includes RNA commonly referred to as interference RNA, dsRNA, ssRNA, saRNA, siRNA or miRNA or their derivatives, analogs, mimics and inhibitors. According to certain aspects, siRNA is involved in the RNA interference (RNAi) pathway, where it interferes with the expression of a specific gene. In addition to their role in the RNAi pathway, siRNAs also act in the RNAi-related pathways. siRNA within the scope of the present disclosure includes double stranded RNA of about 21 nucleotides with a 2 nucleotide 3' overhang on either end of the siRNA. Each siRNA strand has a 5' phosphate group and a 3' hydroxyl (—OH) group. The structure is the result of processing by dicer, an enzyme that converts either long dsRNAs or small hairpin RNAs into siRNAs. Particular exemplary sequences of siRNA are readily available to those of skill in the art through published literature and siRNA is commercially available from, for example, Qiagen. It is to be understood that the present disclosure is not to be limited to any particular siRNA sequence, but rather the present disclosure broadly describes the incorporation of siRNA into or with rosette nanotubes. One of skill in the art will readily recognize that all siRNA sequences, given the similar structure and function of covalently connected nucleotides, can be incorporated into or complexed with rosette nanotubes using the methods described herein and that an exhaustive listing of publicly known siRNA sequences need not be provided herein.

According to additional aspects, DNA includes any DNA desired to be expressed by a cell. DNA includes genes having known functions and expressing known proteins. Likewise, DNA suitable for transfecting a cell will be apparent to those of skill in the art of transfection and gene expression.

Manufacture and Use of Transfection Complexes

The present disclosure is directed to methods of forming a transfection complex, for example, by mixing one or more nucleic acids with fully formed rosette nanotubes or modules that self-assemble into rosette nanotubes, such as the compounds of Formula I or Formula II. According to one aspect, fully formed rosette nanotubes in the form of a powder is dissolved in water and heated to boiling. The solution is then cooled to room temperature. One or more nucleic acids in the form of a solution is then added to the solution of nanotubes at a suitable temperature and for a suitable period of time until a complex of the nanotube and one or more nucleic acids forms. Suitable ratios of the nucleic acid to nanotube include about 0.01:1 (wt/wt) to about 1:0.1 (wt/wt).

The invention is further directed to transfection complexes, which include small RNA, such as siRNA and a rosette nanotube. Transfection complexes in accordance with the present invention may include any of the rosette nanotubes of the present invention in combination with small RNA known to those of skill in the art.

According to certain aspects, cells within the scope of the present invention that can be transfected include osteoblasts, fibroblasts, stem cells, neuronal cells, connective tissue cells, keratinocytes, cardiac myocytes, chondrocytes, proteoglycans, synoviocytes, adipose, phagocytic, blood monocytes, mesenchymal stem cells, neural stem cells, islet cells, hepatocytes, smooth muscle cells, urothelial cells, neurons, Schwann cells, microgial cells, cancerous and non-cancerous cells, epithelial cells, endothelial cells, myofibroblasts, osteoclasts, macrophages, leukocytes, osteocytes, astrocytes etc. and the like. Additional cells include bacterial cells such as *Staphylococcus aureus, Staphylococcus epidermis, Pseudomonas aeruginosa*, MRSA, *E. coli*, candida (yeast), *Candida albacans, Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium*, tuberculosis, *Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium*, Enterobacteriaceae, *Staphylococcus saprophyticus* and the like. The above list is intended to be exemplary and not exhaustive. One of skill in the art will readily be able to identify additional cells within the scope of the present disclosure, which is directed to toward cells present in joints, tissue and/or organs.

In general, a cell to be transfected includes, but is not limited to, any animal, plant or bacterial cell that is susceptible to intracellular delivery of DNA or RNA such as siRNA using the transfection complex of the present invention either in vitro or in vivo. For example, cells from different species such as human, mouse, rat, pig, chicken, etc. may be used according to the present disclosure. Likewise, cells from different tissues or organs, such as cartilage (e.g., ear, nose, rib cage, bronchial tube, intervertebral disc, hyaline, fibrous, elastic), connective tissue (e.g. loose, dense, adipose, fibrous, elastic, lymphoid), conjunctive tissue, fibers (e.g., collagenous, elastic, reticular), synovium, neuronal tissue, muscle tissue, ligament, tendon, busae, fibroblast, beast cells, macrophages from the immune system, and astrocytes from the neuronal system may be used. Likewise, primary cells obtained directly from animals, plants or bacteria may be used and cell lines, such as commercially available immortalized cell, may be used. Likewise, normal cells may be used and diseased cells may be used, such as cancer cells. For example, suitable cellular targets include, without limitation, epithelial cells, endothelial cells, keratinocytes, fibroblasts, muscle cells, hepatocytes, blood cells such as T lymphocytes, B lymphocytes, monocytes, macrophages, neutrophils, eosinophils, megakaryocytes, granulocytes, various stem or progenitor cells, in particular hematopoietic stem or progenitor cells, e.g., as obtained from bone marrow, umbilical cord blood, peripheral blood, fetal liver, and the like. In certain aspects, the cell is selected from the group consisting of synoviocytes, fibroblasts, monocytes, chondrocytes, collagen, endothelial cells, connective tissue cells, neuronal cells, muscle cells, hematopoietic stem cells and tumor cells.

According to certain embodiments, the cells include one or more cells selected from the group consisting of transformed, recombinant, malignant, and primary cell lines. It is believed that the rosette nanotubes of the present invention will be effective as carriers of DNA or RNA such as siRNA in most, if not all cell types and cell lines. Since complexes of the rosette nanotubes and nucleic acids are composed of covalently bound base pairs, one of skill would expect that such complexes will be universally recognized by all cell types for transfecting purposes.

Methods of transfecting cells in accordance with the present invention may also include forming the transfection complex by combining in aqueous media the modules of the rosette nanotube and one or more DNA sequences and/or one or more RNA sequences. The complex is allowed to form. Cells are then contacted with the complex. According to one aspect, one of skill in the art will recognize from the benefit of the present disclosure that doses, concentrations, ratios and conditions of RNT/nucleic acids incorporation can be within ranges. For example, between about 1 µL to about 100 µL, for example 10 µL, of 1 mg/mL RNTs can be mixed with about 1 µL to about 100 µL, for example 20 µL, of 504 nucleic acids, such as siRNA, miRNA, nucleic acid probes or other nucleic acids, at a temperature of between about 0° C. to about 37° C. for between about 0.5 hours to about 48 hours and added into 1 mL cell culture medium for transfection. For example, the combination of RNT and nucleic acids can be maintained at 4° C. for 24 hours or can be maintained at room temperature for two hours. Mixing can be accomplished by simple mixing, mixing while heating to about 60° C. to about 100° C., sonication or other methods known to those of skill in the art. If heated, the combination may then be subjected to a temperature of between about 0° C. to about 37° C. for between about 0.5 hours to about 48 hours to result in formation or assembly of the nanotube/nucleic acid complex. For example, nanotubes can be modified to modulate the surface charge of the nanotubes comprising one or more DNA sequence and/or one or more RNA sequences by varying the RNT/nucleic acid ratio. A skilled person in the arts would recognize that cartilage, for example, is a negatively charged tissue matrix and nanotube carrying an overall positive charge would increase the residence time of such Nanopieces in cartilage tissue.

Method of Treatment

The present invention also provides methods of treating tissue, organ and/or joint disease comprising using the complexes or compositions of the present invention. In particular, methods are provided for treating a patient having a tissue, organ or joint disease, by administering to the patient a therapeutically effective amount of a complex or composition of the present invention. For in vivo therapies based on local injection (e.g., intra-articularly, intratumoral, and intramuscularly) the RNT/small RNA complex is advantageously water soluble and so may be administered as an aqueous injection.

According to aspects of the present disclosure, composites of rosette nanotubes and small RNA can be combined with a pharmaceutically acceptable agent and administered as a delivery composition to an individual for therapeutic purposes.

In accordance with certain examples, complexes of the present invention can be incorporated into pharmaceutical compositions suitable for administration. Such compositions typically comprise the complexes disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Therapeutic Applications

Also encompassed are methods for treating a patient having a tissue, organ and/or joint disease, by administering to the patient cells that have been transfected by the methods disclosed herein. An aspect of an ex vivo delivery method of the present invention may include for example, (i) removing a cell from a subject; (ii) introducing siRNA into a cell by contacting the cell with a delivery composition (transfection complex or composition comprising such a transfection complex) comprising siRNA and a rosette nanotube; and (iii) reintroducing the cell into the subject. In addition, nanotubes having nucleic acids complexed therewith as described herein may be delivered in vivo to an individual in need of treatment where the nanotubes having nucleic acids complexed therewith enter cells within the individual and the nucleic acids regulate cellular expression of proteins. For example the nucleic acids may silence genes in a therapeutic manner to the extent that a protein is not expressed resulting in treatment or the nucleic acids may be expressed by the cell to produce proteins in a therapeutic manner resulting in treatment.

Examples of joint diseases (e.g. synovial, fibrous, cartilagenoius) potentially treatable with the complex, compositions, and methods include, but are not limited to the following: autoimmune, degenerative, inflammatory, infectious, cancerous, viral, fungal, injured or trauma derived. These joint diseases may be the primary disease or may be caused by an existing disease and/or illness. Examples include polymyalgia rheumatica, rheumatoid arthritis, multiple sclerosis, Charcot's Joint, osteoarthritis, juvenile onset of rheumatoid arthritis (JRA), system lupus erythematosus (SLE), psoriatic arthritis, inflammatory bowel disease (IBS) arthritis, Whipple's disease, intestinal lipodystrupjy, ankylosing spondylitis (AS), reactive arthritis, Still's disease, avascular necrosis, bursitis, fibromyalgia, gout, hemochromatosis, hypothyroidism, lupus, Lyme disease, Fifths disease, osteomalacia, osteomyelitis, Paget's disease of bone, pseudogout, rickets, septic arthritis, tendinitis, diabetes, Ehlers-Danlos syndrome, costochondritis, Perthes' disease, Marfan syndrome, rheumatic fever, tubercular arthritis, pigmented villonodular synovitis, scleroderma, polymyositis, erythema nodosum, neuropathic arthropathy, sickle-cell disease, acromegaly, amyloidosis, acute crystal synovitis, pyogenic bacterial infection, scurvy, hemophilia, achondroplasia, herniation, diffuse iodophatic skeletal hyperostosis (DISH), ganglion, lumbar spinal stenosis, sacroliac joint pain, SAPHO syndrome, polycythemia, Raynaud's phenomenon, hydroxyapatite, Behcet's syndrome, Felt's syndrome, hepatitis B, primary Sjoegrens, and polychondritis.

In another aspect of the invention, joint disease can also be the result of genetics, trauma (e.g., meniscus tears), mechanical injury (e.g., repetitive motion), nutrition deficiencies, and joint mal-alignment. Joints having suffered from an initial injury and/or trauma often develop joint disease over a period of time.

Examples of tissue diseases (e.g. epithelial, connective, muscle and nervous tissue) potentially treatable with the complex, compositions, and methods include, but are not limited to the following: autoimmune, degenerative, inflammatory, infectious, cancerous, viral, fungal, injured or trauma derived. These tissue and/or organ diseases may be the primary disease or may be caused by an existing disease and/or illness. Examples include amyloidosis, atrial fibrillation, convulsion, cramp, dermatomyositis, enchondroma, fibroma, lumbao, heritable connective tissue disorder (e.g., Marfan syndrome, Peyronie's disease, Ehlers-Danlos syndrome, Osteogenesis imperfecta, Stickler syndrome, Alport syndrome, Congenital contractural arachnodactyly), autoimmune connective tissue disorder (e.g., systemic lupus erythematosus (SLE), rheumatoid arthritis, Scleroderma, Sjoegren's syndrome, mixed connective tissue disease, psoriatic arthritis), scurvy, muscle disease (e.g., muscle tumour, muscular dystrophy, disuse atrophy, denervation atrophy, Duchenne muscular dystrophy, facioscapulohumoral muscular dystrophy), hepatic diseasemyasthenia gravis, myopathy, myositis, myositis ossificans, cancer, fibromyalgia, muscle fatigue, spasm, spasticity, sprain, strain, brain injury, spinal cord injury, gliomas, neuroepthelioma-tous, hypertension, cardiovascular disease, diabetes, Alzheimer's disease, cystitis, AIDS, rickets, and nerve sheath tumors. Examples of tissues, organs and/or body systems affected by disease and may be treated with the compositions, and methods described therein, but are not limited to the following: Immune system, senory organs (e.g., organs of taste, smell, sight, hearing), digestive system (e.g., mouth, fauces, pharynx, esophagus, abdomen, stomach, small intestine, large intestine, liver, pancreas), urogenital apparatus, endocrinological system, metabolism, cardiovascular system (e.g., heart, blood pressure, arteries), hematology (e.g., blood chemistry), urinary organs (e.g., kidneys, ureters, urinary bladder, male urethra, female urethra, male genital organs (e.g., testes and their covering, ductus deferens, vesiculae seminales, ejaculatory ducts, penis, prostate, bulbourethral glands), female genital organs (e.g., ovaries, uterine tube, uterus, vagina, clitoris, Bartholin's glands, external organs, mammae)), ductless glands (e.g., thyroid, parathyroid, thymus, hypophysis cerebri, pineal body, chromaphil and corticol systems, spleen), reproduction, respiratory (e.g., larynx, trachea, bronchi, pleurae, mediastinum, lungs), central nervous system (e.g., nerves, nerve fibers), skin, epithelial (e.g., simple, stratified, pseudostratified columnar, glandular), connective (e.g., loose connective (e.g., areolar, adipose, reticular), and dense connective (e.g., dense regular, dense irregular)), cartilage (e.g., Hyaline, elastic, fibrous), muscle (e.g., skeletal muscle (e.g., type I, II, IIa, IIx, IIb), cardiac muscle, smooth muscle), nervous (e.g., neuron (e.g., motor neurons, interneuron, sensory neuron), neuroglia, spinal cord, nerves, brain).

In another aspect of the invention, cancers can also reside in the joint, tissue and/or organ either as a primary tumor (e.g., sarcoma, hemangiopericytoma, connective tissue neoplasm, chondroma, chondrosarcoma) or as a result of metastasis of a primary tumor at a different location in the body of the subject.

Ex vivo and in vivo gene therapy with siRNA can also be used in joint, tissue, and/or organ disease. These RNAi applications toward joint disease include, but are not limited to, 1) targeting proteins or enzymes relevant in the disease state; 2) targeting or reducing expression of factors that are relevant in the disease state; and 3) targeting genes to maintain or restore joint health and homeostasis. For example, genes of the current invention may include ADAMTS (e.g., ADAMTS-4, ADAMTS-5), MMPs (e.g., MMP-1, MMP-3, MMP-9, MMP-13 and other MMPs), ILs (e.g., IL-1α, IL-1β, IL-2, IL-6, IL-8, IL-12, IL-15, IL-20, IL-21 and other ILs), IL receptors, IL receptor associated proteins, IL receptor antagonists, HLA-DRB1, PADI4, PTPN22, TNFAIP3, megakaryocyte stimulating factor, osteoprotegerin, activator of NF-α ligand, STAT4, CCR6, TNFR-1, TNFR-2, RIP, TRADD, PAD2-PAD4, FOX3, CD-25, FAP, DPP, CD26, MK2, SIRT-1, FoxO3a, miR-24, miR-125-5p, muR-203, miR-140, miR-365, miR-146a, miR-27a, TNF-α, HLA, collagen type II, aggrecan, prostaglandins, immunoglobulins, IFN-γ, GM-CSF, PDGF, FGF, VEGF, BMPs (e.g., BMP-2, BMP-4, BMP-7, and other BMPs), TGF-β, IGF-1, IGF-2 and, their related receptor protein and the like. For example, the following genes or proteins may promote arthritis such as rheumatoid arthritis: ADAMTS, MMPs, ILs, IL receptors, IL receptor associated proteins, HLA, DRB1, PADI4 gene, PTPN22 gene, TNFAIP3 gene, STAT4 gene, TNFR-1, TNFR-2, RIP, TRADD, PAD2-PAD4 proteins, CCR6 gene, miR-24, miR-125a-5p, mIR-365 and miR-203. Genes and protein can also prevent arthritis such as Juvenile idiopathic arthritis: FOXP3 and CD-25. Moreover, genes and proteins and their receptors and combinations thereof can also inhibit arthritis such as rheumatoid arthritis or osteoarthritis: IL receptor antagonists, MK2, FAP, DPP-4/CD26, SIRT-1/FoxO3a, miR-140 and miR-27a. Lastly, genes and proteins and their receptors and combinations thereof can mediate arthritis progression and joint tissue regeneration (such as cartilage regeneration): FGF, VEGF, BMPs, TGF-β, IGF-1, IGF-2, miR-146a.

Nanopieces deliver siRNA, antisense and/or anti-microRNA to knockdown genes and their related proteins and protein receptors (e.g., ADAMTS, MMPs, IL-1). In another example, Nanopieces deliver miRNA and/or mRNA to increase the level of genes and their related proteins and protein receptors. For example, genes and expression their respective encoded proteins and/or corresponding protein receptors that promote arthritis or other joint diseases can be knocked down; while genes and expression of their encoded proteins and/or corresponding protein receptors that inhibit arthritis or other joint diseases can be increased. Gene expression and production of encoded proteins and/or corresponding protein receptors that mediate arthritis progression and joint tissue regeneration can be adjusted (either knocked down or increased) depending on the needs or clinical condition of the patient.

Ex vivo and in vivo gene therapy with siRNA could also be used in cancer of tissue and/or organs. These RNAi applications toward cancer include, but are not limited to, 1) reducing expression of growth factors, reducing proteins that augment the cell cycle (e.g., Raf-1, PI-3 kinase), growth factor receptors (e.g., EGFR, Her-2), or proteins critical for supporting cells of the tumor (e.g., VEGF, VEGFR1-2 for tumor endothelial cells); 2) targeting or reducing expression of factors that are anti-apoptotic (e.g., BCL-2); and 3) targeting proteins or enzymes that reduce immune activation toward tumor.

Cancers or neoplasms contemplated within the scope of the disclosure include, but are not limited to, carcinomas (i.e., malignant tumors derived from epithelial cells such as, for example, common forms of breast, prostate, lung and colon cancer), sarcomas (i e, malignant tumors derived from connective tissue or mesenchymal cells), lymphomas (i.e., malignancies derived from hematopoietic cells), leukemias (i e, malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like.

Examples of specific neoplasms intended to be encompassed by the present invention include, but are not limited to, acute lymphoblastic leukemia, myeloid leukemia, acute childhood myeloid leukemia, adrenocortical carcinoma, AIDS-related cancers, AIDS-related lymphoma, anal cancer, appendix cancer, astrocytoma (e.g., cerebellar, cerebral), atypical teratoid/rhabdoid tumor, basal cell carcinoma, extrahepatic bile duct cancer, bladder cancer, bone cancer, osteosarcoma and malignant fibrous histiocytoma, brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors), breast cancer, bronchial tumors, Burkitt lymphoma, carcinoid tumor (e.g., gastrointestinal), carcinoma of unknown primary, central nervous system (e.g., atypical teratoid/rhabdoid tumor, embryonal tumors (e.g., lymphoma, primary), cerebellar astrocytoma, cerebral astrocytoma/malignant glioma, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, central nervous system embryonal tumors, endometrial cancer, ependymoblastoma, ependymoma, esophageal cancer, Ewing family of tumors, extracranial germ cell tumor, extragonadal germ cell tumor, extrahepatic bile duct cancer, eye cancer (e.g., intraocular melanoma, retinoblastoma), gallbladder cancer, gastric cancer, gastrointestinal tumor (e.g., carcinoid tumor, stromal tumor (gist), stromal cell tumor), germ cell tumor (e.g., extracranial, extragonadal, ovarian), gestational trophoblastic tumor, glioma (e.g., brain stem, cerebral astrocytoma), hairy cell leukemia, head and neck cancer, hepatocellular cancer, Hodgkin lymphoma, hypopharyngeal cancer, hypothalamic and visual pathway glioma, intraocular melanoma, islet cell tumors, Kaposi sarcoma, kidney cancer, large cell tumors, laryngeal cancer (e.g., acute lymphoblastic, acute myeloid), leukemia (e.g., acute myeloid, chronic lymphocytic, chronic myelogenous, hairy cell), lip and/or oral cavity cancer, liver cancer, lung cancer (e.g., non-small cell, small cell), lymphoma (e.g., AIDS-related, Burkitt, cutaneous T cell, Hodgkin, non-Hodgkin, primary central nervous system), Waldenström macroglobulinemia, malignant fibrous histiocytoma of bone and/or osteosarcoma, medulloblastoma, medulloepithelioma, melanoma, merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia (e.g., chronic, acute, multiple), chronic myeloproliferative disorders, nasal cavity and/or paranasal sinus cancer, nasopharyngeal cancer, neuroblastoma, non-Hodgkin lymphoma, non-small cell lung cancer, oral cancer, oral cavity cancer, oropharyngeal cancer, osteosarcoma and/or malignant fibrous histiocytoma of bone, ovarian cancer (e.g., ovarian epithelial cancer, ovarian germ cell tumor, ovarian low malignant potential tumor), pancreatic cancer (e.g., islet cell tumors), papillomatosis, paranasal sinus and/or nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell cancer, renal, pelvis and/or ureter, transitional cell cancer, respiratory tract carcinoma involving the nut gene on chromosome 15, retinoblastoma, rhabdomyosarcoma, salivary gland cancer, sarcoma (e.g., Ewing family of tumors, Kaposi, soft tissue, uterine), Sezary syndrome, skin cancer (e.g., non-melanoma, melanoma, merkel cell), small cell lung cancer, small intestine cancer, soft tissue sarcoma, squamous cell carcinoma, squamous neck cancer with occult primary, metastatic, stomach cancer; supratentorial primitive neuroectodermal tumors; T-cell lymphoma, cutaneous; testicular cancer, throat cancer; thymoma and/or thymic carcinoma, thyroid cancer, transitional cell cancer of the renal, pelvis and/or ureter; trophoblastic tumor, unknown primary site carcinoma, urethral cancer, uterine cancer, endometrial, uterine sarcoma, vaginal cancer, visual pathway and/or hypothalamic glioma, vulvar cancer, Waldenström macroglobulinemia, Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

Examples of primary cancers as joint disease comprise connective tissue neoplasm, hemangiopericytoma, sarcoma, chondroma, chondrosarcoma, bone and the like.

Examples of genetic and/or non-neoplastic diseases potentially treatable with the complex, compositions, and methods include, but are not limited to the following: adenosine deaminase deficiency; purine nucleoside phosphorylase deficiency; chronic granulomatous disease with defective p47phox; sickle cell with HbS, β-thalassemia; Faconi's anemia; familial hypercholesterolemia; phenylketonuria; ornithine transcarbamylase deficiency; apolipoprotein E deficiency; hemophilia A and B; muscular dystrophy; cystic fibrosis; Parkinsons, retinitis pigmentosa, lysosomal storage disease (e.g., mucopolysaccharide type 1, Hunter, Hurler and Gaucher), diabetic retinopathy, human immunodeficiency virus disease virus infection, acquired anemia, cardiac and peripheral vascular disease, osteoporosis and arthritis. In some of these examples of diseases, the therapeutic gene may encode a replacement enzyme or protein of the genetic or acquired disease, an antisense or ribozyme molecule, a decoy molecule, or a suicide gene product.

Recombinant cells may be produced using the complexes of the present invention. Resulting recombinant cells can be delivered to a subject by various methods known in the art. In certain embodiments, the recombinant cells are injected, e.g., subcutaneously or intra-articular. Recombinant blood cells (e.g., hematopoietic stem or progenitor cells) are preferably administered intravenously or intra-articular. The cells can also be encapsulated in a suitable vehicle and then implanted in the subject (see, e.g., Dionne et al. PCT Publication WO92/19195, dated Nov. 12, 1992). The amount of cells administered depends on a variety of factors known in the art, for example, the desired effect, subject state, rate of expression of the chimeric polypeptides, etc., and can readily be determined by one skilled in the art.

Another aspect of the present disclosure provides methods of introducing a therapeutic or diagnostic agent into a cell or tissue matrix using rosette nanotubes. Biologically active agents also called "therapeutic agents" or "drugs" are complexed with rosette nanotubes to form nanotube-drug complex, which can enter the cell and/or tissue and release the drug. A person of skill in the art will recognize the drug as being compounds which include any synthetic or natural element or are compounds which when introduced into the body causes a desired biological response, such as altering body function. Non-limiting examples of drugs or biologically active agents or therapeutic agents include anti-inflammatory agents (e.g., steroidal and non-steroidal), analgesics, anesthetics, chemotherapeutic agents, anti-proliferative agents, cytotoxic agents, steroidal agents, antifungal agents, antiviral agents, immunosuppressive agents, and include small molecules. Further non-limiting examples of drugs or biologically active agents or therapeutic agents include peptides (such as RGD, KRSR, YIGSR, IKVAV and the like), aromatic bioactive molecules such as tamoxifen, dexamethasone, vitamin K and the like, antibiotics such as penicillin, streptomycin, gentamycin and the like, glucosamine, chondroitin, cortisone, glucocorticoids, hydrocortisone, hyaluronic acid, hydrocortisone, gentamycin and the like, and proteins such as bone morphogenetic proteins, matrillins and the like. Drugs or biologically active agents or therapeutic agents may be hydrophobic or hydrophilic. According to one aspect, the rosette nanotubes include hydrophobic moieties within the core portion of the structure where hydrophobic drugs, biologically active agents or therapeutic agents may be located in the composite. According to another aspect, the rosette nanotubes of the present disclosure may have hydrophilic outer surfaces to facilitate administration of the complexes in physiological environments.

Examples of analgesic agents include opioid analgesics and adjuvent analgesics within the scope of the present disclosure that can be complexed with rosette nanotubes include clonidine, tizanidine, gapapentin, pregabalin, lamotrigine, oxcarbazepine, topiramate, levitiracetam, tigabine, zonisamide, carbamazepine, valprioc acid, phenytoin, amitriptyline, nortriptyline, desipramine, imipramine, doxepin, paroxetine, citalopram, escitalopram, fluoxetine, venlafaxine, duloxetine, bupriopion, mexiletine, lidocaine, baclofen, cyclobenzaprine, orphenadrine, metaxalone, methocarbamol, morphine, hydrocodone, hydromorphone, tramadol, oxycodone, oxymorphone, fentanyl, methadone, capsaicin, loperamide, naloxone, demerol, buprenorphine, butorphanol, codeine, levorphanol, meperidine, methadone, nabuphine, propoxyphene, and pentazocine.

Examples of non-opioid and anti-inflammatory agents within the scope of the present disclosure that can be complexed with rosette nanotubes include acetaminophen, aspirin, diflunisal, choline magnesium trisalicylate, salsalate, ibuprofen, naproxen, ketoprofen, fluriprofen, oxaprozin, indomethacin, sulindac, nabumetone, diclofenac, ketorolac, tolectin, piroxicam, meloxicam, mefenamic acid, meclofenamate, celecoxib, allopurinol, dextromethorphan, pegloticase, dexibuprofen, etodolac, fenoprofen, flufenamic acid, flupbiprofen, lornoxicam, loxoprofen, meclofenamic acid, piroxicam, tenoxicam, tolmetin, and tolfenamic acid.

Examples of immunosuppresive agents within the scope of the present disclosure that can be complexed with rosette nanotubes include alkylating agents, antimetabolites, high dose corticosteroids, azathioprine, mycophenolate mofetil, cyclosporine, methotrexate, leflunomide, cyclophosphamide, chlorambucil, nitrogen mustard, abacavir, abciximab, adalimumab, aldesleukin, altretamine, aminoglutethimide, amprevenir, anakinra, anastrozole, aspariginase, azathioprine, basiliximab, betamethasone, bleomycin, busulfan, capecitabine, carboplatin, carmustine, chlorambucil, cidofovir, cisplatin, cladribine, cortisone, cyclosporine, cytarabine, decarbazine, dacuzumab, dactinomycin, daunorubicin, delaviridine, dexamethasone, didanosine, doxorubicin, efavirenz, epirubicin, estramustine, etanercept, etoposide, exemestane, foxuridine, fludarabine, fluorouracil, flutamide, gemcitabine, gemtuzumab ozogamicin, hydrocortisone, hydroxychloroquine, hydroxyurea, idaubicin, ifosphamide, indinavir, infliximab, interferon alpha-2a, interferon alpha-2b, interferon beta-2b, interferon beta-2a, interferon gamma-1b, interleukin-2, irinotecan, isotretinoin, lamivudine, leflunomide, letrozole, leuprolide, mechloethamine, megestrol, melphalan, mercaptopurine, methotrexate, methylpregnisolone, mitomycin, mitotane, mitoxantrone, mycophenolate, nelfinavir, nevirapine, paclitaxel, pegaspargase, penicillamine, pentostatin, pimecroslimus, pipobroman, plicamycin, prednisolone, predisone, priliximab, procarbazine, ritonavir, rituximab, saquinavir, sargamomstim, stavudine, strepozocin, tacrolismus, temozolomide, teniposide, testolactone, thioguanine, thiotepa, trastuzumab, tretinoin, triamcinolone, uracil mustard, valrubicin, vinblastine, vincristine, vinorelbine, zalcitabine, zidovudine.

Examples of antifungal agents within the scope of the present disclosure that can be complexed with rosette nanotubes include polyene, azole, allylamine, morpholine, and antimetabolite antifungal agents, e.g., amphotericin B, candicin, filipin, hamycin, natamycin, nystatin rimocidin, bifonazole, butoconazole, clotrimazole, econozole, fenticonazole, isoconazole, ketoconazole, luiconazole, miconazole, omoconazole, oxiconazole, sertaconazole, sulconazole, tioconazole, albaconazole, fluconazole, isavuconazole, traconazole, posaconazole, ravuconazole, terconazole, voriconazole, abafungin, amorolfin, butenafine, naftifine, terbinafine, anidulafungin, caspofungin, micafungin, benzoic acid, ciclopirox, griseofulvin, tolnaftate, and undecylenic acid.

Examples of antibiotic agent within the scope of the present disclosure that can be complexed with rosette nanotubes include aminoglycosides (e.g., amikacin, gentamicin, kanamycine, neomygine, metilmicin, tobramycin, paromomycin, streptomycin, spectinomycin), anasamycins (e.g., geldanamycin, herbimycin, riflaximin), loracerbef, carbapenems (e.g., ertapenem, doripenem, cilastatin, meropenem), cephalosporin (e.g. cefadroxil, cefazolin, cephalexin, cefaclor, cefamandole, cefoxitin, cefprozil, cefuroxime, cefixime, cefdinir, cefdotoren, cefotaxime, ceftibuten, ceftizoxime, cefepime, ceftaroline, ceftobioprole, teichoplanin, vancomycin, telavancin, clindamycin, lincomycin, daptomycin, azithromycin, clarithromycin, dirithromycin, erythromycin, roxithromycin, troleandomycin, telithromycin, spiramycin, azetreonam, flurazolidone, linezolid, posizolid, radezolid, torezolid, ampicillin, azolocillin, carbenicillin, cloxacillin, dicloxaxillin, pencillin), polypeptides (e.g. bacitracin, colistin, polymyxin B), Quinolones (e.g., ciproflaxin, enoxacin, gemifloxacin, norfloxacin), sulfonamides (e.g., malfenide, sulfamethizole, sulfasalazine, sulfadiazine), tetracyclines (e.g., demeclocycline, minocycline, doxycycline, tetracycline), clofazimine, dapsone, capreomycin, cycloserine, ethambutol, ethionamide, isoniazid, pyrazinamide, riflampicin, rifabutin, rifapentine, streptomycin, arsphenamine, chloramthenicol, foffmycin, fusidic acid, metronidazole, mupirocin, platensimycin, thiamphenicol, tigecycline, tinidazole, and trimethoprim.

Examples of drugs within the scope of the present disclosure that can be complexed with rosette nanotubes include glucosamine, chondroitin, cortisone, glucocorticoids, hydrocortisone, hyaluronic acid, hydrocortisone, and lubricants (e.g. lubricin).

Examples of anti-cancer drugs within the scope of the present disclosure that can be complexed with rosette nanotubes include bortezomib ([(1R)-3-methyl-1-[[(2S)-1-oxo-3-phenyl-2-[(pyrazinylcarbonyl) amino]propyl]amino]butyl] boronic acid; MG-341; VELCADE®), MG-132 (N-[(phenylmethoxy)carbonyl]-L-leucyl-N-[(1S)-1-formyl-3-methylbutyl]-L-leucinamide); pyrimidine analogs (e.g., 5-fluorouracil, floxuridine, capecitabine, gemcitabine and cytarabine); purine analogs; folate antagonists and related inhibitors (e.g., mercaptopurine, thioguanine, pentostatin and 2-chlorodeoxyadenosine [cladribine]); folic acid analogs (e.g., methotrexate); antimitotic agents, including vinca alkaloids (e.g., vinblastine, vincristine, and vinorelbine) and alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC); microtubule disruptors (e.g., paclitaxel, docetaxel, vincristin, vinblastin, nocodazole, epothilones and navelbine, and teniposide); actinomycin, amsacrine, anthracyclines, bleomycin, busulfan, camptothecin, carboplatin, chlorambucil, cisplatin, cyclophosphamide, Cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP 16); dactinomycin (actinomycin D), daunorubicin, doxorubicin (adriamycin), idarubicin, anthracyclines, mitoxantrone, bleomycins, plicamycin (mithramycin) and mitomycin; L-asparaginase; antiplatelet agents;

platinum coordination complexes (e.g., cisplatin, carboplatin), procarbazine, hydroxyurea, mitotane, aminoglutethimide; hormones and hormone analogs (e.g., estrogen, tamoxifen, goserelin, bicalutamide, nilutamide); aromatase inhibitors (e.g., letrozole, anastrozole); anticoagulants (e.g., heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors); angiotensin receptor blockers; nitric oxide donors; anti-sense oligonucleotides; antibodies (e.g., trastuzumab (HERCEPTIN®), AVASTIN®, ERBITUX®); cell cycle inhibitors and differentiation inducers (e.g., tretinoin); mTOR (mammalian target of rapamycin) inhibitors (e.g., everolimus, sirolimus); topoisomerase inhibitors e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan); corticosteroids (e.g., cortisone, dexamethasone, hydrocortisone, methylpednisolone, prednisone, and prenisolone); growth factor signal transduction kinase inhibitors; mitochondrial dysfunction inducers; and caspase activators and the like.

Examples of anti-cancer drugs within the scope of the present disclosure that can be complexed with rosette nanotubes include alemtuzumab; aminoglutethimide; amsacrine; anastrozole; asparaginase; bevacizumab; bicalutamide; bleomycin; bortezomib; buserelin; busulfan; campothecin; capecitabine; carboplatin; carmustine; CeaVac; cetuximab; chlorambucil; cisplatin; cladribine; clodronate; colchicine; cyclophosphamide; cyproterone; cytarabine; dacarbazine; daclizumab; dactinomycin; daunorubicin; dienestrol; diethylstilbestrol; docetaxel; doxorubicin; edrecolomab; epirubicin; epratuzumab; erlotinib; estradiol; estramustine; etoposide; exemestane; filgrastim; fludarabine; fludrocortisone; fluorouracil; fluoxymesterone; flutamide; gemcitabine; gemtuzumab; genistein; goserelin; huJ591; hydroxyurea; ibritumomab; idarubicin; ifosfamide; IGN-101; imatinib; interferon; irinotecan; ironotecan; letrozole; leucovorin; leuprolide; levamisole; lintuzumab; lomustine; MDX-210; mechlorethamine; medroxyprogesterone; megestrol; melphalan; mercaptopurine; mesna; methotrexate; mitomycin; mitotane; mitoxantrone; mitumomab; nilutamide; nocodazole; octreotide; oxaliplatin; paclitaxel; pamidronate; pentostatin; pertuzumab; plicamycin; porfimer; procarbazine; raltitrexed; rituximab; streptozocin; sunitinib; suramin; tamoxifen; temozolomide; teniposide; testosterone; thalidomide; thioguanine; thiotepa; titanocene dichloride; topotecan; tositumomab; trastuzumab; tretinoin; vatalanib; vinblastine; vincristine; vindesine; and vinorelbine and the like.

Examples of NMDA receptor antagonists within the scope of the present disclosure that can be complexed with rosette nanotubes include LY 274614 (decahydro-6-(phosphonomethyl)-3-isoquinolinecarboxylic acid), LY 235959 [(3S,4aR,6S,8aR)-decahydro-6-(phosphonomethyl)-3-isoquinolinecarboxylic acid], LY 233053 ((2R,4S)-rel-4-(1H-tetrazol-5-yl-methyl)-2-piperidine carboxylic acid), NPC 12626 (α-amino-2-(2-phosphonoethyl)-cyclohexanepropanoic acid), reduced and oxidized glutathione, carbamathione, AP-5 (5-phosphono-norvaline), CPP (4-(3-phosphonopropyl)-2-piperazine-carboxylic acid), CGS-19755 (seifotel, cis-4(phono-methyl)-2-piperidine-carboxylic acid), CGP-37849 ((3E)-2-amino-4-methyl-5-phosphono-3-pentenoic acid), CGP 39551 ((3E)-2-amino-4-methyl-5-phosphono-3-pentenoic acid, 1-ethyl ester), SDZ 220-581 [(αS)-α-amino-2'-chloro-5-(phosphonomethyl)-[1,1'-biphenyl]-3-propanoic acid], and S-nitrosoglutathione, amantadine, aptiganel (CERESTAT®, CNS 1102), caroverine, dextrorphan, dextromethorphan, fullerenes, ibogaine, ketamine, lidocaine, memantine, dizocilpine (MK-801), neramexane (MRZ 2/579, 1,3,3,5,5-pentamethyl-cyclohexanamine), NPS 1506 (delucemine, 3-fluoro-γ-(3-fluorophenyl)-N-methyl-benzenepropanamine hydrochloride), phencyclidine, tiletamine and remacemide, acamprosate, arcaine, conantokin-G, eliprodil (SL 82-0715), haloperidol, ifenprodil, traxoprodil (CP-101,606), and Ro 25-6981 [(±)-(R,S)-α-(4-hydroxyphenyl)-β-methyl-4-(phenylmethyl)-1-piperidine propanol]; aminocyclopropanecarboxylic acid (ACPC), 7-chlorokynurenic acid, D-cycloserine, gavestinel (GV-150526), GV-196771A (4,6-dichloro-3-[(E)-(2-oxo-1-phenyl-3-pyrrolidinylidene)methyl]-1H-indole-2-carboxylic acid monosodium salt), licostinel (ACEA 1021), MRZ-2/576 (8-chloro-2,3-dihydropyridazino[4,5-b] quinoline-1,4-dione 5-oxide 2-hydroxy-N,N,N-trimethyl-ethanaminium salt), L-701,324 (7-chloro-4-hydroxy-3-(3-phenoxyphenyl)-2 (1H)-quinolinone), HA-966 (3-amino-1-hydroxy-2-pyrrolidinone), and ZD-9379 (7-chloro-4-hydroxy-2-(4-methoxy-2-methylphenyl)-1,2,5,10-tetra-hydropyridanizo[4,5-b] quinoline-1,10-dione, sodium salt); oxidized and reduced glutathione, S-nitrosoglutathione, sodium nitroprusside, ebselen, and disulfiram, DETC-MeSO, carbamathione; CNQX (1,2,3,4-tetrahydro-7-nitro-2,3-dioxo-6-quinoxalinecarbonitrile) and DNQX (1,4-dihydro-6,7-dinitro-2,3-quinoxalinedione) and the like.

Examples of subtype-specific NMDA receptor antagonists within the scope of the present disclosure that can be complexed with rosette nanotubes include arcaine, argiotoxin636, Co 101244 (PD 174494, Ro 63-1908, 1-[2-(4-hydroxyphenoxy)ethyl]-4-[(4-methylphenyl)methyl-4-piperidinol], despiramine, dextromethorphan, dextrorphan, eliprodil, haloperidol, ifenprodil, memantine, philanthotoxin343, Ro-25-6981 ([(±)-(R*, S*)-α-(4-hydroxyphenyl) β-methyl-4-(phenylmethyl)-1-piperidine propanol]), traxoprodil (CP-101,606), Ro 04-5595 (1-[2-(4-chlorophenyl)ethyl]-1,2,3,4-tetrahydro-6-methoxy-2-methyl-7-isoquinolinol), CPP [4-(3-phosphonopropyl)-2-piperazinecarboxylic acid], conantokin G, spermine, spermidine, NVP-AAM077 [[[[(1S)-1-(4-bromophenyl) ethyl]amino](1,2,3,4-tetrahydro-2,3-dioxo-5-quinoxalinyl) methyl]-phosphonic acid]; and 1-(phenanthrene-2-carbonyl) piperazine-2,3-dicarboxylic acid and the like.

Examples of anticonvulsants within the scope of the present disclosure that can be complexed with rosette nanotubes include barbiturates (e.g., mephobarbital and sodium pentobarbital); benzodiazepines, such as alprazolam (XANAX®), lorazepam, clonazepam, clorazepate dipotassium, and diazepam (VALIUM®); GABA analogs, such as tiagabine, gabapentin (an α2δ antagonist, NEURONTIN®), and β-hydroxypropionic acid; hydantoins, such as 5,5-diphenyl-2,4-imidazolidinedione (phenytoin, DILANTIN®) and fosphenytoin sodium; phenyltriazines, such as lamotrigine; succinimides, such as methsuximide and ethosuximide; 5H-dibenzazepine-5-carboxamide (carbamazepine); oxcarbazepine; divalproex sodium; felbamate; levetiracetam, primidone; zonisamide; topiramate; and sodium valproate.

Examples of psychiatric drugs within the scope of the present disclosure that can be complexed with rosette nanotubes include Abilify, Adapin, Adartrel, Adderall, Alepam, Alertec, Aloperidin, Alplax, Alprax, Alprazolam, Alviz, Alzolam, Amantadine, Ambien, Amisulpride, Amitriptyline, Amoxapine, Amfebutamone, Anafranil, Anatensol, Ansial, Ansiced, Antabus, Antabuse, Antideprin, Anxiron, Apo-Alpraz, Apo-Primidone, Apo-Sertral, Aponal, Apozepam, Aripiprazole, Aropax, Artane, Asendin, Asendis, Asentra, Ativan, Atomoxetine, Aurorix, Aventyl, Axoren, Beneficat, Benperidol, Bimaran, Bioperidolo, Biston, Brotopon, Bespar, Bupropion, Buspar, Buspimen, Buspinol, Buspirone, Buspisal, Cabaser, Cabergoline, Calepsin, Calcium carbonate, Calcium carbimide, Calmax, Carbamazepine, Carbatrol, Carbolith, Celexa, Chloraldurat, Chloralhydrat, Chlordiazepoxide, Chlorpromazine, Cibalith-S, Cipralex, Citalopram, Clomipramine, Clonazepam, Clozapine, Clozaril, Concerta, Constan, Convulex, Cylert, Dapotum, Daquiran, Daytrana, Defanyl, Dalmane, Damixane, Demolox, Depad, Depakene, Depakote, Depixol, Desyrel, Dostinex, dextroamphetamine, Dexedrine, Diazepam, Didrex, Divalproex, Dogmatyl, Dolophine, Droperidol, Edronax, Efectin, Effexor (Efexor), Eglonyl, Einalon S, Elavil, Elontril, Endep, Epanutin, Epitol, Equetro, Escitalopram, Eskalith, Eskazinyl, Eskazine, Etrafon, Eukystol, Eunerpan, Faverin, Fazaclo, Fevarin, Finlepsin, Fludecate, Flunanthate, Fluoxetine, Fluphenazine, Flurazepam, Fluspi, Fluspirilen, Fluvoxamine, Focalin, Gabapentin, Geodon, Gladem, Glianimon, Halcion, Halomonth, Haldol, Haloperidol, Halosten, Imap, Imipramine, Imovane, JJanimine, Jatroneural, Kalma, Keselan, Klonopin, Lamotrigine, Largactil, Lecital, Levomepromazine, Levoprome, Leponex, Lexapro, Libritabs, Librium, Linton, Liskantin, Lithane, Lithium, Lithizine, Lithobid, Lithonate, Lithotabs, Lorazepam, Loxapac, Loxapine, Loxitane, Ludiomil, Lunesta, Lustral, Luvox, Lyrica, Lyogen, Manegan, Manerix, Maprotiline, Mellaril, Melleretten, Melleril, Melneurin, Melperone, Meresa, Mesoridazine, Metadate, Methamphetamine, Methotrimeprazine, Methylin, Methylphenidate, Minitran, Mirapex, Mirapexine, Moclobemide, Modafinil, Modalina, Modecate, Moditen, Molipaxin, Moxadil, Murelax, Myidone, Mylepsinum, Mysoline, Nardil, Narol, Navane, Nefazodone, Neoperidol, Neurontin, Nipolept, Norebox, Normison, Norpramine, Nortriptyline, Novodorm, Olanzapine, Omca, Oprymea, Orap, Oxazepam, Pamelor, Parnate, Paroxetine, Paxil, Peluces, Pemoline, Pergolide, Permax, Permitil, Perphenazine, Pertofrane, Phenelzine, Phenytoin, Pimozide, Piportil, Pipotiazine, Pragmarel, Pramipexole, Pregabalin, Primidone, Prolift, Prolixin, Promethazine, Prothipendyl, Protriptyline, Provigil, Prozac, Prysoline, Psymion, Quetiapine, Ralozam, Reboxetine, Resimatil, Restoril, Restyl, Requip, Rhotrimine, Risperdal, Risperidone, Rispolept, Ritalin, Rivotril, Ropark, Ropinerole, Rubifen, Rozerem, Sediten, Seduxen, Selecten, Serax, Serenace, Serepax, Serenase, Serentil, Seresta, Serlain, Serlift, Seroquel, Seroxat, Sertan, Sertraline, Serzone, Sevinol, Sideril, Sifrol, Sigaperidol, Sinequan, Sinqualone, Sinquan, Sirtal, Solanax, Solian, Solvex, Songar, Stazepin, Stelazine, Stilnox, Stimuloton, Strattera, Sulpiride, Sulpiride Ratiopharm, Sulpiride Neurazpharm, Surmontil, Symbyax, Symmetrel, Tafil, Tavor, Taxagon, Tegretol, Telesmin, Temazepam, Temesta, Temposil, Terfluzine, Thioridazine, Thiothixene, Thombran, Thorazine, Timonil, Tofranil, Tradon, Tramadol, Tramal, Trancin, Tranax, Trankimazin, Tranquinal, Tranylcypromine, Trazalon, Trazodone, Trazonil, Trialodine, Trevilor, Triazolam, Trifluoperazine, Trihexane, Trihexyphenidyl, Trilafon, Trimipramine, Triptil, Trittico, Troxal, Tryptanol, Ultram, Valium, Valproate, Valproic acid, Valrelease, Vasiprax, Venlafaxine, Vestra, Vigicer, Vivactil, Wellbutrin, Xanax, Xanor, Xydep, Zamhexal, Zeldox, Zimovane, Zispin, Ziprasidone, Zolarem, Zoldac, Zoloft, Zolpidem, Zonalon, Zopiclone, Zotepine, Zydis, Zyprexa and the like.

Examples of miscellaneous drugs within the scope of the present disclosure that can be complexed with rosette nanotubes include nortriptyline, amytriptyline, fluoxetine (PROZAC®), paroxetine HCl (PAXIL®), trimipramine, oxcarbazepine (TRILEPTAL®), eperisone, misoprostol (a prostaglandin $E_1$ analog), latanoprost (a prostaglandin $F_2$ analog) melatonin, and steroids (e.g., pregnenolone, triamcinolone acetonide, methylprednisolone, and other anti-inflammatory steroids) and the like.

Examples of antiviral drugs within the scope of the present disclosure that can be complexed with rosette nanotubes include Abacavir, Aciclovir, Acyclovir, Adefovir, Amantadine, Amprenavir, Ampligen, Arbidol, Atazanavir, Atripla (fixed dose drug), Boceprevir, Cidofovir, Combivir (fixed dose drug), Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Pyramidine, Saquinavir, Stavudine, Synergistic enhancer (antiretroviral), Tea tree oil, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine and the like.

Ex vivo and in vivo therapy and/or diagnostics could also be used in joint disease. These therapeutic and diagnostic applications toward these joint diseases include, but are not limited to, 1) targeting proteins or enzymes relevant in the disease state; 2) targeting or reducing expression of factors that are relevant in the disease state; and 3) targeting genes to maintain or restore joint health and homeostasis. For example, Nanopieces delivery of molecular probes to detect expression of inflammatory markers (e.g., cytokines, MMP, ADAMS) and the like or delivery of therapeutic agents to treat pain, inflammation, infection and the like can be used.

In another example, in vivo imaging technology to detect molecular changes at early stages of arthritis without harming articular cartilage was demonstrated. Osteoarthritis (OA) is one of the most common causes of disability. However, the lack of tools for early diagnosis of OA hampers the prevention and treatment of the disease to decelerate articular cartilage loss and alleviate suffering of patients. The OA Biomarker Initiative has identified a series of biomarkers, including Matrix metalloproteinases (MMP), which are elevated in articular cartilage during OA pathogenesis. However, detection of MMP protein levels or activities in serum may not be sensitive enough, while the more sensitive detection of MMP transcripts requires invasive procedure to obtain biopsy of articular joint tissue. Therefore, there is an urgent need to develop sensitive in vivo imaging technology to detect molecular changes at early stages of arthritis without harming articular cartilage.

Figure 51:
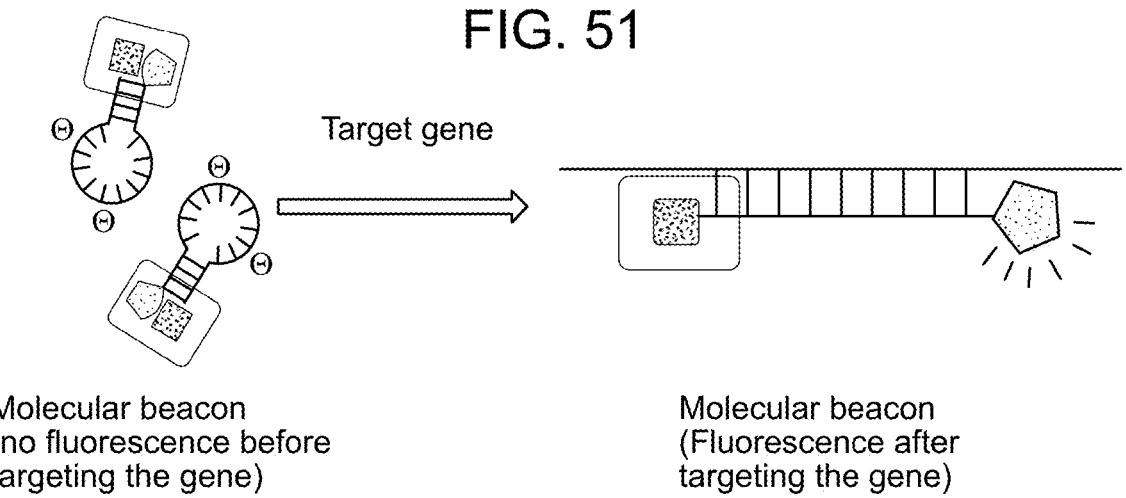
FIG. 51 is a scheme showing molecular beacon (MB) technology.
Figure 52:
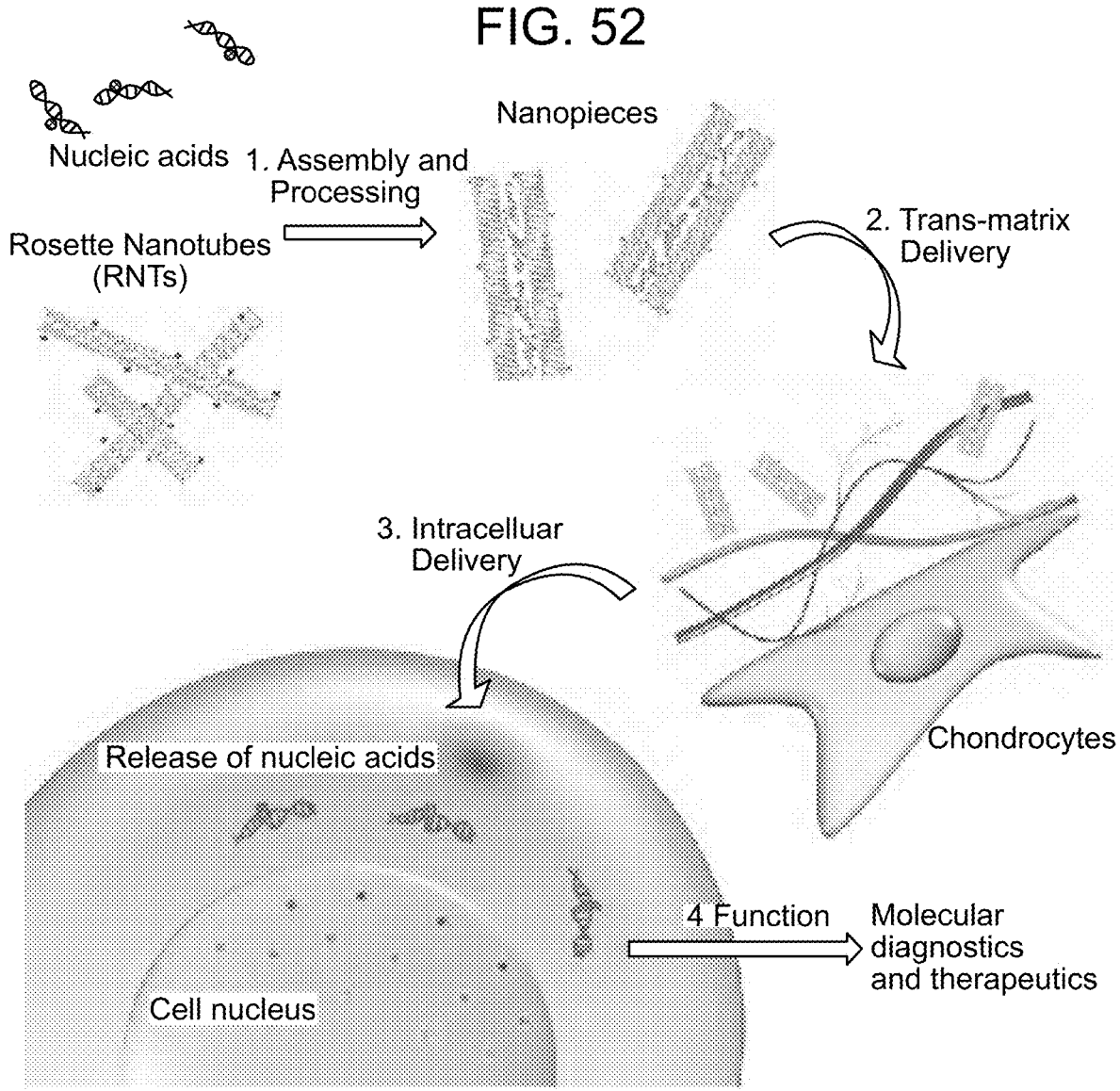
FIG. 52 is a scheme showing trans matrix delivery of Nanopieces into chondrocytes.

Specifically, Molecular beacon (MB) technology provided an intriguing possibility to detect the changes of mRNA levels in live animals in vivo. In fact, molecular beacon (MB) technology (FIG. 51) detected the changes of mRNA levels in live animals in vivo. The Molecular beacon comprises an oligonucleotides loop, double strand stem, and a fluorophore and quencher, which remains non-fluorescent due to the proximity of fluorophore and quencher. Upon entering a cell and hybridizing with its target mRNA, MB emits fluorescence after separation of the fluorophore and quencher (FIG. 52). However, prior to the invention, there was no report of detection of OA using MB due to the significant challenge of in vivo delivery of MB into joint tissues. Detection of OA using MB is challenging because of the in vivo delivery of MB into joint tissues. Early detection of OA in the Destabilizing Medial Meniscus (DMM) mouse OA model using MB to detect induction of MMP-13 transcript, a major matrix proteinase that degrades interstitial collagen matrix during arthritis was shown. In vivo delivery of MMP13 MB using Nanopieces derived from rosette nanotubes were used. Since cartilage is a very negatively charged tissue (containing a huge amount of proteoglycan), the negatively charged Nanopieces intend to bind and accumulate onto and/or into the matrix and/or tissue resulting in much longer retention time to achieve more effective delivery. Different sizes of Nanopieces can be created for different delivery proposes to get into the matrix. For example, cartilage tissue matrix has about 60 nm mesh size of the collagen II fibrillar network and about 20 nm spacing between the side chains of the proteoglycan network. Nanopieces with small sizes (at least one dimension smaller than 60 nm and/or 20 nm) showed excellent efficiency and function in intra-cartilage matrix delivery of siRNA. Adjusting the ratio between RNTs and cargo reagents to yield an overall positive charged surface enabled Nanopieces to adhere with negatively charged matrix and/or tissue components resulting longer retention time.

Intra-joint delivery was thereby achieved with these processed Nanopieces. Delivery of Molecular probes with Nanopiece detected a specific gene expression (or protein activity) along with the co-delivery of a negative control for non-specific signal and an internal positive control to accurately diagnose a target gene expression in a real-time, in-situ and non-invasive manner Matrix metalloproteinases (MMP) are the major enzymes that degrade the components of the extracellular matrix during arthritis progression. MMP-13, which is usually produced by cartilage and bone, degrade interstitial collagens (types I, II and III) in both OA and RA. Expression of MMP-13 is low in normal cells, whereas in pathologic condition excess MMP-13 production is associated with inflammation. mRNA level of MMP-13 are indicative for arthritis development and MMP-13 is as a good target in early diagnosis of arthritis. However, articular cartilage tissues need to be collected to show the up-regulation of MMP-13 mRNA levels. The combination of molecular beacon and Nanopieces technology detected of OA in vivo in a specific and sensitive manner without harming any joint tissues.

In another example, therapeutic agents complexed with nanotubes can knock down one or multiple disease gene expression (such as via siRNA delivery) and/or up-regulate one or multiple beneficial gene and/or protein (such as via DNA, mRNA or protein delivery) and deliver a variety of cargo types and can deliver multiple cargo reagents at the same time.

Accordingly, the rosette nanotubes of the present disclosure have hollow channels that can be used for drug encapsulation. Rosette nanotubes are able to incorporate water-insoluble drugs into their tubular structures by hydrophobic interactions with the core whereas their hydrophilic outer surface can shield such hydrophobic drugs in a physiological environment for subsequent prolonged release (even into the cell). Rosette nanotubes can also be chemically functionalized with peptides such as Arg-Gly-Asp-Ser-Lys, Lys-Arg-Ser-Arg-Lys, and Gly-Arg-Gly-Asp-Tyr-Lys to deliver growth factors for healthy tissue regeneration, such as healthy bone in osteosarcoma patients, after the delivery of drugs to kill cancer cells.

The rosette nanotubes may also be used in tissue engineering, where living cells are utilized as engineering materials. Applications for tissue engineering are used to repair or replace portions of whole tissues such as bone, cartilage, blood vessels, muscle, etc. Tissues are fabricated in the laboratory from combinations of engineered extracellular matrices ("scaffolds"), cells, and biologically active molecules destined for transplantation. For example, nasal chondrocytes can expand in culture to engineer a cartilage graft. The rosette nanotubes of the current disclosure can be used as scaffolds in tissue engineering methods, e.g. using nasal chondrocytes, as well as a transfer vehicle to deliver therapeutic agents to specific tissues, e.g. cartilage, when using tissue engineering techniques known to a skilled person in the art.

Genes and Proteins Used as Agents/Delivery Cargo

The following Genes and Proteins can be used as agents to complex with Nanotubes and Nanopieces:

The following Genes and Proteins can be used as target gene of siRNA which complex with Nanotubes and Nanopieces:

The mRNA transcript sequence encoding human ADAMTS-5, provided by Genbank Accession No. NM_007038.3, is incorporated herein by reference, and is shown below (SEQ ID NO: 1).

```
  1   ataaattcat tgttccacct cctcgcatct tcacagcgct cgcgctgctc tcggcgctcg
 61   cagctgccga ctggggatga cggcgggcag gaggagaccg cagccgaagg gacacagaca
121   cgccgcttca ccagctcgcc tcaggctgcc ccctgcatt  tttgttttaa tttttacggc
181   ttttccct   ctctttcttc ccttcctcct ggtcccagca gagccaagga aacccacaaa
241   ataagaaagg aagtgggccc cggagcttgg aacctccaca gccggcttgt ccagcgcagc
301   gcggggcgg  gaggctgcgc gcaccagttg ccagcccggt gcgcggtacc tttccttact
361   tttcttgaaa cagcgatcgt gcctgcattt ggtggttttt tggttttgt  tttttcctt
421   ttcccgtatt tgctgaatct ccactatccg acttttttt  tttaatcttt tctttccccc
```

```
 481   cccccccacc ccacctcttt ctggagcacg aatccaaaca ttttcccaag caacaaagaa
 541   aagttcgcac gctggcaccg cagcccggac aggctggcgc tgctgccggg ccccctccc
 601   tccgacactt gactcaatcc tgcaagcaag tgtgtgtgtg tccccatccc ccgccccgtt
 661   aacttcatag caaataacaa atacccataa agtcccagtc gcgcagcccc tccccgcggg
 721   cagcgcacta tgctgctcgg gtgggcgtcc ctgctgctgt gcgcgttccg cctgcccctg
 781   gccgcggtcg gccccgccgc gacacctgcc caggataaag ccgggcagcc tccgactgct
 841   gcagcagccg cccagccccg ccggcggcag ggggaggagg tgcaggagcg agccgagcct
 901   cccggccacc cgcacccccct ggcgcagcgg cgcaggagca aggggctggt gcagaacatc
 961   gaccaactct actccggcgg cggcaaggtg ggctacctcg tctacgcggg cggccggagg
1021   ttcctcttgg acctggagcg agatggttcg gtgggcattg ctggcttcgt gcccgcagga
1081   ggcgggacga gtgcgccctg gcgccaccgg agccactgct tctatcgggg cacagtggac
1141   ggtagtcccc gctctctggc tgtctttgac ctctgtgggg gtctcgacgg cttcttcgcg
1201   gtcaagcacg cgcgctacac cctaaagcca ctgctgcgcg accctgggc ggaggaagaa
1261   aagggggcgcg tgtacgggga tgggtccgca cggatcctgc acgtctacac ccgcgagggc
1321   ttcagcttcg aggccctgcc gccgcgcgcc agctgcgaaa ccccgcgtc cacaccggag
1381   gcccacgagc atgctccggc gcacagcaac ccgagcggac gcgcagcact ggcctcgcag
1441   ctcttggacc agtccgctct ctcgcccgct gggggctcag gaccgcagac gtggtggcgg
1501   cggcggcgcc gctccatctc ccgggcccgc caggtggagc tgcttctggt ggctgacgcg
1561   tccatggcgc ggttgtatgg ccggggcctg cagcattacc tgctgaccct ggcctccatc
1621   gccaataggc tgtacagcca tgctagcatc gagaaccaca tccgcctggc cgtggtgaag
1681   gtggtggtgc taggcgacaa ggacaagagc ctggaagtga gcaagaacgc tgccaccaca
1741   ctcaagaact tttgcaagtg gcagcaccaa cacaaccagc tgggagatga ccatgaggag
1801   cactacgatg cagctatcct gtttactcgg gaggatttat gtgggcatca ttcatgtgac
1861   accctgggaa tggcagacgt tgggaccata tgttctccag agcgcagctg tgctgtgatt
1921   gaagacgatg gcctccacgc agccttcact gtggctcacg aaatcggaca tttacttggc
1981   ctctcccatg acgattccaa attctgtgaa gagacctttg gttccacaga agataagcgc
2041   ttaatgtctt ccatccttac cagcattgat gcatctaagc cctggtccaa atgcacttca
2101   gccaccatca cagaattcct ggatgatggc catggtaact gtttgctgga cctaccacga
2161   aagcagatcc tgggccccga agaactccca ggacagacct acgatgccac ccagcagtgc
2221   aacctgacat tcgggcctga gtactccgtg tgtccggca tggatgtctg tgctcgcctg
2281   tggtgtgctg tggtacgcca gggccagatg gtctgtctga ccaagaagct gcctgcggtg
2341   gaagggacgc cttgtggaaa ggggagaatc tgcctgcagg gcaaatgtgt ggacaaaacc
2401   aagaaaaaat attattcaac gtcaagccat ggcaactggg gatcttgggg atcctggggc
2461   cagtgttctc gctcatgtgg aggaggagtg cagtttgcct atcgtcactg taataacccct
2521   gctcccagaa acaacggacg ctactgcaca gggaagaggg ccatctaccg ctcctgcagt
2581   ctcatgccct gcccacccaa tggtaaatca tttcgtcatg aacagtgtga ggccaaaaat
2641   ggctatcagt ctgatgcaaa aggagtcaaa acttttgtgg aatgggttcc caaatatgca
2701   ggtgtcctgc agcggatgt gtgcaagctg acctgcagag ccaaggcac tggctactat
2761   gtggtatttt ctccaaaggt gaccgatggc actgaatgta ggctgtacag taattccgtc
2821   tgcgtccggg ggaagtgtgt gagaactggc tgtgacggca tcattggctc aaagctgcag
2881   tatgacaagt gcggagtatg tggaggagac aactccagct gtacaaagat tgttggaacc
```

-continued

```
2941  tttaataaga aaagtaaggg ttacactgac gtggtgagga ttcctgaagg ggcaacccac
3001  ataaaagttc gacagttcaa agccaaagac cagactagat tcactgccta tttagccctg
3061  aaaaagaaaa acggtgagta ccttatcaat ggaaagtaca tgatctccac ttcagagact
3121  atcattgaca tcaatggaac agtcatgaac tatagcggtt ggagccacag ggatgacttc
3181  ctgcatggca tgggctactc tgccacgaag gaaattctaa tagtgcagat tcttgcaaca
3241  gaccccacta aaccattaga tgtccgttat agctttttg ttcccaagaa gtccactcca
3301  aaagtaaact ctgtcactag tcatggcagc aataaagtgg gatcacacac ttcgcagccg
3361  cagtgggtca cgggcccatg gctcgcctgc tctaggacct gtgacacagg ttggcacacc
3421  agaacggtgc agtgccagga tggaaaccgg aagttagcaa aaggatgtcc tctctcccaa
3481  aggccttctg cgtttaagca atgcttgttg aagaaatgtt agcctgtggt tatgatctta
3541  tgcacaaaga taactggagg attcagcact gatgcagtcg tggtgaacag gaggtctacc
3601  taacgcacag aaagtcatgc ttcagtgaca ttgtcaacag gagtccaatt atgggcagaa
3661  tctgctctct gtgaccaaaa gaggatgtgc actgcttcac gtgacagtgg tgaccttgca
3721  atatagaaaa acttgggagt tattgaacat cccctgggct tacaagaaac actgatgaat
3781  gtaaaatcag gggacatttg aagatggcag aactgtctcc cccttgtcac ctacctctga
3841  tagaatgtct ttaatggtat cataatcatt ttcacccata atacacagta gcttcttctt
3901  actgtttgta aatacattct cccttggtat gtcactttat atccctggt tctattaaaa
3961  tatccatata tatttctata aaaaagtgt ttgaccaaag taggtctgca gctatttcaa
4021  cttccttccg tttccagaaa gagctgtgga tatttactg gaaattaaga acttgctgct
4081  gttttaataa gatgtagtat attttctgac tacaggagat aaaatttcag tcaaaaaacc
4141  attttgacag caagtatctt ctgagaaatt ttgaaaagta aatagatctc agtgtatcta
4201  gtcacttaaa tacatacacg ggttcattta cttaaacctt tgactgcctg tattttttc
4261  aggtagctag ccaaattaat gcataatttc agatgtagaa gtagggtttg cgtgtgtgtg
4321  tgtgatcata ctcaagagtc taaaaactag tttccttgtg ttggaaattt aaaaggaaaa
4381  aaatcgtatt tcactgtgtt ttcaatttat attttcacaa ctactttctc tctccagagc
4441  tttcatctga tatctcacaa tgtatgatat acgtacaaaa cacacagcaa gttttctatc
4501  atgtccaaca cattcaacac tggtatacct cctaccagca agcctttaaa atgcatttgt
4561  gtttgcttat ttgttttgtt caagggttca gtaagaccta caatgttttg tatttcttga
4621  cttattttat tagaaacatt aaagatcact tggtagttag ccacattgag aagtggttat
4681  cattgttaat gtggttaatg ccaaaaagtg gttaatatta ataagactgt ttccacacca
4741  taggcaataa tttcttaatt taaaaaatct aagtatattc ctattgtact aaatattttt
4801  cccaactgga aagcacttga ttgtacccgt aagtgtttga gtgatgacat gtgatgattt
4861  tcagaaagtt gttgttttg tttccatagc ctgtttaagt aggttgtaag tttgaatagt
4921  tagacatgga aattatttta taagcacaca cctaaagata tcttttttaga tgataaaatg
4981  tacacccccc catcaccaac ctcacaactt agaaaatcta agttgtttga tttctttggg
5041  atttcttttg ttgtgaaaca ctgcaaagcc aattttctt tataaaaatt catagtaatc
5101  ctgccaaatg tgcctattgt taaagatttg catgtgaaga tcttagggaa ccactgtttg
5161  agttctacaa gctcatgaga gtttatttt attataagat gttttttaata taaagaatt
5221  atgtaactga tcactatatt acatcatttc agtgggccag gaaaatagat gtcttgctgt
5281  tttcagtatt ttcttaagaa attgctttta aaacaaataa ttgttttaca aaaccaataa
```

```
5341   ttatcctttg aattttcata gactgacttt gcttttgacg tagaaatttt ttttctcaat
5401   aaattatcac tttgagaaat gaggcctgta caaggctgat aacctatatg tgatggagat
5461   cacccaatgc caagggcaga aagcaaacct agttaaatag gtgagaaaaa aataataat
5521   cccagtgcca tttgtctgtg caaagagaat taggagagag gttaatgtta ctttttttcca
5581   ttttggaaat aattttaatc aagtaactca aatgtgacaa aatttatttt tattttttgt
5641   ggttatattc ccaacaacat taaaaaatac tcgaggcata aatgtagttg tctcctactc
5701   tgcttctctt actatactca tacatttta atatggttta tcaatgattc atgtttccct
5761   caaatagtga tggtttacac ctgtcatgga aacaatccta gagagctcag agcaattaaa
5821   ccactattcc atgcttttaa gtagttttct ccaccttttt cttatgagtc tcactagatt
5881   gactgaggaa tgtatgtcta aattcctgga gaagatgata tggattggaa actgaaattc
5941   agagaaatgg agtgttcaat agataccacg aattgtgaac aaagggaaaa ttctatacaa
6001   ctcaatctaa gtcagtccac tttgacttcg tactgtcttt cacctttcca ttgttgcatc
6061   ttgaattttt taaaatgtct agaattcagg atgctagggg ctacttcttt aaaaaaaaaa
6121   aaaaaaaaga attcgtctga aaatgctcag gtttgtaaga atctaatctc acttacataa
6181   ctaagcactc cataataagt tttattaagt acaaaggagg ccagaaaaaa tgacatttat
6241   ttcttctaga tcagaaaaat ttaaattaag ccctgccttg ctgtttagaa atatgtgggc
6301   attgttataa tttattcaat aaatttatgt tcctttgcct tcctgtggaa acagttttat
6361   cccactaaac taggaattag gggataaatc acaaacaaaa aaaagttgc agcactgaaa
6421   aaaagtaatt tattgttttt gcaactggta tgtgaatttg tgtgataaaa ttatttattc
6481   ttatttaaca aaaatatgtt caatttttc tatatttaaa atgttttgct gttgtcctac
6541   tttttaattt atgcttcatg tttgtgtata aagtacactt ttacactttg tgagtttaca
6601   taatatacag cactggttgc ttttgtattt ttttacagaa agctttctgt gtgaagcagg
6661   tgtatatgta tatattcctc atgtattctt attctgatac tatcattttt ctttccaagg
6721   aaattttaat ctgtcatgac caatagtgtt cattacttgt gcctatgata ataggttttt
6781   tacatcacat taacactatt ttttccaagt cacaaataag aaaaacactt attcaatgaa
6841   acaaggtgca agttttaaat ttgggtacac aaatagccta gaagcttcct acagacgcta
6901   agacacagcc aataatcaga tcctttcact tcatcgagaa acttggacaa gtcgatattg
6961   atgtattaga tgaaagttgt ctacacacaa cttctgaggg atacaaacga taataaaacc
7021   aaatgttgtc tgtttctcct ttagaaacac ctcctaaaat taatatcatt tagtctctag
7081   tgtctgtagg attctacaga tgagcacaaa tagattgggt ttgtataaca aatgctaata
7141   gtcataactg tttctacaaa tatggggtgt ccattaagag aatgtgatgt tttcctactg
7201   ctgttgaatc ccatggggtg attataggac ttgaaatagg cagagtcacc tctgatgaca
7261   tcagcttgcc tctgtgattt cacagtctga tcctggcaac aagacaaagc acccttggac
7321   acacagccaa tctctggttg tgatatttcc ccattgattc cttccttgtt aacaaggtca
7381   ttttaatggt tcaggtgagg acagcagcca gattcaaagt ccagaatttg tgctgttaca
7441   tagagttcac actgtcaaat aacattgaat ttaataatga tcaaattttt ctagtagtct
7501   ttggcagagt gtataatctc attggcatga ttggtgaata ttactaatct ctttataatg
7561   aaagatgctt tacaaatacc ttatatttgc taacatttca aaactactaa ataaatgaaa
7621   tagccatgtg tacagaaatg gtcatttaaa gctttaatag aaccaaattc aagacaatgt
7681   atcatttaga cacacagaaa aggaacttgt atgttttccc tattatttt ctcatttgcc
7741   aacaatctat agttttaggt tatcaaacag atagatcaac ttaactggct agtacattga
```

-continued

```
7801  aaaatcttcc taagaatcct tgttagcat aatctataga gataatttct caaattatat
7861  catcatgatg catataaact ctataatgta taattgtgtt tcatttattt aatgtatgag
7921  aacatattga aatacaaaac catgcattag ccaaaaaatt ggaatacagg tagtgttcag
7981  atcagcaaaa cattcagtct ggtaaatgcc tgcctggggc tatgatatca ttctcaatgc
8041  aggttttatg gaaaaactaa aagaatatgt tgttagatga tgttggtttt gaaaaaaaaa
8101  agacattaac atacacatta gttagcccag ttaattgcat tctactaata tagttgcaca
8161  ttagcaataa ttttgctgtc tctggtcttt attttgtggc ttcaactaac tggaccatgt
8221  ggactgtaaa ggtcaaatgg aaaaaacgag cagtggcccc tcatcctgta aggtactgct
8281  acatcagagt gacctaaaag tctaacactg tgaggaaaac tgtgatttgt aggaaaaaaa
8341  aaaaaaacaa ataaaaaaca gggcatgctt tttaattttt ttccactttc ctttggcaca
8401  cccaatgaac aattctaatt tttattgagg tgctaacatc tttcgtgacc gactgtcaaa
8461  tgtggtattt ttgagttact attttttctac atgatttac agtttgcaag aaagacctct
8521  aagctttgtg tcacggtagg gcacaacttg atactcaaaa tttgaaaaat aagcacatcc
8581  aatgattgtt ttgaccaaca gtggtcagtg acgtaaactg catgtgcatc tgaggacatt
8641  taaggggtca ttaaaatttg aggagcatca ggccggagta gcagactttt agatgagtca
8701  tatttcagca ttcactaagt cctcagcatt ccattcaaac tgtcgtgtat atttggcctg
8761  attttttttc aagctttgca ataatttatg ttattggtaa acacttggtg actatatctc
8821  agccttttct ttaacaactc acaatatatt agaaacacgt ctacctatac tgagagtata
8881  tttacaatag aagaacatac tgtatgtgac tttgtaaagc tagacttttg attaagaaat
8941  atataatctc tggatgctat ttttgcatta tacactcagg cacaacgtaa accttgatgg
9001  ctcatcttgc tacaattacg agttgaaaaa cactacttac gtatttgtat gacctattag
9061  tcagaggaaa tcatacatat gctttgtaaa tagactttgc agataactaa atagactgaa
9121  gaaatatgtt gcatttgata gaagcaattg cataaatatt tggtttctat attagagtct
9181  gtgagtaaag tcaagtaata aacctaagta ggtataacag atttttaaac cttgaaactt
9241  gctttgatgg tagagaaaat cattgaagat ttacatactg tatataagat gtaaaatgta
9301  cgctgcttat taccctcaat tttccagaag caatggtata taatgcagtt gaaaaaccaa
9361  aaatcttgga aaactaagac gggtcttgtt taaaatgtct ctcagctttg gcaaccttca
9421  aatcttaatc aactatttaa agcattactg tgtcttgtag cctgcattcc acaacagctc
9481  tgttattcag gtaaaagact tgaactgagc cgtttgggac ctatactgta atattttcat
9541  tgaggaacaa tatcctattt tgtaaagcat ttccctatgt gtgactttaa actgtaaaat
9601  taaacactgc ttttgtgggt tcagtgggca taataaatat aaattgtaaa ctaggttaaa
9661  gta
```

The amino acid sequence of human ADAMTS-5 (preproprotein), provided by Genbank Accession No. NP_008969.2, is incorporated herein by reference, and is shown below (SEQ ID NO: 2).

```
  1   mllgwaslll cafrlplaav gpaatpaqdk agqpptaaaa aqprrrqgee vqeraeppgh
 61   phplaqrrrs kglvqnidql ysgggkvgyl vyaggrrfll dlerdgsvgi agfvpagggt
121   sapwrhrshc fyrgtvdgsp rslavfdlcg gldgffavkh arytlkpllr gpwaeeekgr
181   vygdgsaril hvytregfsf ealpprasce tpastpeahe hapahsnpsg raalasqlld
```

-continued

```
241  qsalspaggs  gpqtwwrrrr  rsisrarqve  lllvadasma  rlygrglqhy  lltlasianr
301  lyshasienh  irlavvkvvv  lgdkdkslev  sknaattlkn  fckwqhqhnq  lgddheehyd
361  aailftredl  cghhscdtlg  madvgticsp  erscaviedd  glhaaftvah  eighllglsh
421  ddskfceetf  gstedkrlms  siltsidask  pwskctsati  teflddghgn  clldlprkqi
481  lgpeelpgqt  ydatqqcnit  fgpeysvcpg  mdvcarlwca  vvrqgqmvcl  tkklpavegt
541  pcgkgriclq  gkcvdktkkk  yystsshgnw  gswgswgqcs  rscgggvqfa  yrhcnnpapr
601  nngryctgkr  aiyrscslmp  cppngksfrh  eqceakngyq  sdakgvktfv  ewvpkyagvl
661  padvckltcr  akgtgyyvvf  spkvtdgtec  rlysnsvcvr  gkcvrtgcdg  iigsklqydk
721  cgvcggdnss  ctkivgtfnk  kskgytdvvr  ipegathikv  rqfkakdqtr  ftaylalkkk
781  ngeylingky  mistsetiid  ingtvmnysg  wshrddflhg  mgysatkeil  ivqilatdpt
841  kpldvrysff  vpkkstpkvn  svtshgsnkv  gshtsqpqwv  tgpwlacsrt  cdtgwhtrtv
901  qcqdgnrkla  kgcplsqrps  afkqcllkkc
```

(Signal peptide AA 1-6; proprotein AA 17-930; mature peptide AA 262-930).

The siRNA used to target human ADAMTS-5 mRNA include following sequences (SEQ ID NO: 3-6):

SEQ NO: 3:
5'-GCUCAAAGCUGCAGUAUGA-3'

SEQ NO: 4:
5'-GAAGUCCACUCCAAAAGUA-3'

SEQ NO: 5:
5'-GCACUACGAUGCAGCUAUC-3'

SEQ NO: 6:
5'-CGAAGGAAAUUCUAAUAGU-3'

The molecular beacon used to target human ADAMTS-5 mRNA includes the following sequences (SEQ ID NO: 7-9):

SEQ NO 7:
5'-CCGGTC TAACATTTCTTCAACAAGCA GACCGG-3'

SEQ NO 8:
5'-CCGGTC TTATACACAAACATGAAGCA GACCGG-3'

SEQ NO 9:
5'-CCGGTC TACATCTTATTAAAACAGCA GACCGG-3'

The mRNA transcript sequence encoding human ADAMTS-4, provided by Genbank Accession No. NM_005099.4, is incorporated herein by reference, and is shown below (SEQ ID NO: 10).

```
  1  ggggagaacc  cacagggaga  cccacagaca  catatgcacg  agagagacag  aggaggaaag
 61  agacagagac  aaaggcacag  cggaagaagg  cagagacagg  gcaggcacag  aagcggccca
121  gacagagtcc  tacagaggga  gaggccagag  aagctgcaga  agacacaggc  agggagagac
181  aaagatccag  gaaaggaggg  ctcaggagga  gagtttggag  aagccagacc  cctgggcacc
241  tctcccaagc  ccaaggacta  agtttttctcc  atttccttta  acggtcctca  gcccttctga
301  aaactttgcc  tctgaccttg  gcaggagtcc  aagcccccag  gctacagaga  ggagcttttcc
361  aaagctaggg  tgtggaggac  ttggtgccct  agacggcctc  agtccctccc  agctgcagta
421  ccagtgccat  gtcccagaca  ggctcgcatc  ccgggagggg  cttggcaggg  cgctggctgt
481  ggggagccca  accctgcctc  ctgctcccca  ttgtgccgct  ctcctggctg  gtgtggctgc
541  ttctgctact  gctggcctct  ctcctgccct  cagcccggct  ggccagcccc  ctcccccggg
601  aggaggagat  cgtgtttcca  gagaagctca  acgcagcgt  cctgcctggc  tcgggcgccc
661  ctgccaggct  gttgtgccgc  ttgcaggcct  ttggggagac  gctgctacta  gagctggagc
721  aggactccgg  tgtgcaggtc  gaggggctga  cagtgcagta  cctgggccag  gcgcctgagc
781  tgctgggtgg  agcagagcct  ggcacctacc  tgactggcac  catcaatgga  gatccggagt
841  cggtggcatc  tctgcactgg  gatgggggag  ccctgttagg  cgtgttacaa  tatcgggggg
901  ctgaactcca  cctccagccc  ctggagggag  gcacccctaa  ctctgctggg  ggacctgggg
961  ctcacatcct  acgccggaag  agtcctgcca  gcggtcaagg  tcccatgtgc  aacgtcaagg
```

```
1021  ctcctcttgg aagccccagc cccagacccc gaagagccaa gcgctttgct tcactgagta
1081  gatttgtgga gacactggtg gtggcagatg acaagatggc cgcattccac ggtgcggggc
1141  taaagcgcta cctgctaaca gtgatggcag cagcagccaa ggccttcaag cacccaagca
1201  tccgcaatcc tgtcagcttg gtggtgactc ggctagtgat cctggggtca ggcgaggagg
1261  ggccccaagt ggggcccagt gctgcccaga ccctgcgcag cttctgtgcc tggcagcggg
1321  gcctcaacac ccctgaggac tcggaccctg accactttga cacagccatt ctgtttaccc
1381  gtcaggacct gtgtggagtc tccacttgcg acacgctggg tatggctgat gtgggcaccg
1441  tctgtgaccc ggctcggagc tgtgccattg tggaggatga tgggctccag tcagccttca
1501  ctgctgctca tgaactgggt catgtcttca acatgctcca tgacaactcc aagccatgca
1561  tcagtttgaa tgggcctttg agcacctctc gccatgtcat ggcccctgtg atggctcatg
1621  tggatcctga ggagccctgt tcccctgca gtgcccgctt catcactgac ttcctggaca
1681  atggctatgg cactgtctc ttagacaaac cagaggctcc attgcatctg cctgtgactt
1741  tccctggcaa ggactatgat gctgaccgcc agtgccagct gaccttcggg cccgactcac
1801  gccattgtcc acagctgccg ccgccctgtg ctgccctctg gtgctctggc cacctcaatg
1861  gccatgccat gtgccagacc aaaacactcg cctgggccga tggcacaccc tgcgggcccg
1921  cacaggcctg catgggtggt cgctgcctcc acatggacca gctccaggac ttcaatattc
1981  cacaggctgg tggctgtggg ccttggggac catggggtga ctgctctcgg acctgtgggg
2041  gtggtgtcca gttctcctcc cgagactgca cgaggcctgt ccccggaat ggtggcaagt
2101  actgtgaggg ccgccgtacc cgcttccgct cctgcaacac tgaggactgc caactggct
2161  cagccctgac cttccgcgag gagcagtgtg ctgcctacaa ccaccgcacc gacctcttca
2221  agagcttccc agggcccatg gactgggttc ctcgctcac aggcgtggcc ccccaggacc
2281  agtgcaaact cacctgccag gcccaggcac tgggctacta ctatgtgctg agccacgg
2341  tggtagatgg gaccccctgt tccccggaca gctcctcggt ctgtgtccag ggccgatgca
2401  tccatgctgg ctgtgatcgc atcattggct ccaagaagaa gtttgacaag tgcatggtgt
2461  gcggagggga cggttctggt tgcagcaagc agtcaggctc cttcaggaaa ttcaggtacg
2521  gatacaacaa tgtggtcact atccccgcgg gggccaccca cattcttgtc cggcagcagg
2581  gaaaccctgg ccaccggagc atctacttgg ccctgaagct gccagatggc tcctatgccc
2641  tcaatggtga atacacgctg atgccctccc ccacagatgt ggtactgcct ggggcagtca
2701  gcttgcgcta cagcggggcc actgcagcct cagagacact gtcaggccat gggccactgg
2761  cccagccttt gacactgcaa gtcctagtgg ctgcaacccc caggacaca cgcctccgat
2821  acagcttctt cgtgccccgg ccgaccccttc aacgccacg ccccactccc caggactggc
2881  tgcaccgaag agcacagatt ctggagatcc ttcggcggcg ccctgggcg ggcaggaaat
2941  aacctcacta tcccggctgc cctttctggg caccgggggcc tcggacttag ctgggagaaa
3001  gagagagctt ctgttgctgc ctcatgctaa gactcagtgg ggaggggctg tgggcgtgag
3061  acctgccct cctctctgcc ctaatgcgca ggctggcccc gccctggttt cctgccctgg
3121  gaggcagtga tgggttagtg gatggaaggg gctgacagac agccctccat ctaaactgcc
3181  ccctctgccc tgcgggtcac aggagggagg gggaaggcag ggagggcctg ggccccagtt
3241  gtatttattt agtatttatt cacttttatt tagcaccagg aaggggaca aggactaggg
3301  tcctggggaa cctgaccct gacccctcat agccctcacc ctggggctag gaaatccagg
3361  gtggtggtga taggtataag tggtgtgtgt atgcgtgtgt gtgtgtgtga aaatgtgtgt
3421  gtgcttatgt atgaggtaca acctgttctg ctttcctctt cctgaatttt attttttggg
```

-continued

```
3481  aaaagaaaag tcaagggtag ggtgggcctt cagggagtga gggattatct ttttttttt
3541  ttctttcttt ctttcttttt ttttttttgag acagaatctc gctctgtcgc ccaggctgga
3601  gtgcaatggc acaatctcgg ctcactgcat cctccgcctc ccgggttcaa gtgattctca
3661  tgcctcagcc tcctgagtag ctgggattac aggctcctgc caccacgccc ggctaatttt
3721  tgttttgttt tgtttggaga cagagtctcg ctattgtcac cagggctgga atgatttcag
3781  ctcactgcaa ccttcgccac ctgggttcca gcaattctcc tgcctcagcc tcccgagtag
3841  ctgagattat aggcacctac caccacgccc ggctaatttt tgtatttta gtagagacgg
3901  ggtttcacca tgttggccag gctggtctcg aactcctgac cttaggtgat ccactcgcct
3961  tcatctccca aagtgctggg attacaggcg tgagccaccg tgcctggcca cgcccaacta
4021  attttttgtat ttttagtaga cacagggttt caccatgttg gccaggctgc tcttgaactc
4081  ctgacctcag gtaatcgacc tgcctcggcc tcccaaagtg ctgggattac aggtgtgagc
4141  caccacgccc ggtacatatt ttttaaattg aattctacta tttatgtgat ccttttggag
4201  tcagacagat gtggttgcat cctaactcca tgtctctgag cattagattt ctcatttgcc
4261  aataataata cctcccttag aagtttgttg tgaggattaa ataatgtaaa taaagaacta
4321  gcataacact caaaaaaaaa aaaaaaaaaa aaaaaaaaaa aaaaaaaaaa aaaaaaaaaa
4381  aaaaaaaaaa aaaaaaaaaa aaaaaaaaaa
```

The amino acid sequence of human ADAMTS-4 (preproprotein), provided by Genbank Accession No. NP_005090.3, is incorporated herein by reference, and is shown below (SEQ ID NO: 11).

```
  1  msqtgshpgr glagrwlwga qpclllpivp lswlvwllll llasllpsar lasplpreee
 61  ivfpeklngs vlpgsgapar llcrlqafge tlllelegds gvqvegltvq ylgqapellg
121  gaepgtyltg tingdpesva slhwdggall gvlqyrgael hlqpleggtp nsaggpgahi
181  lrrkspasgq gpmcnvkapl gspsprprra krfaslsrfv etivvaddkm aafhgaglkr
241  ylltvmaaaa kafkhpsirn pvslvvtrlv ilgsgeegpq vgpsaaqtlr sfcawqrgln
301  tpedsdpdhf dtailftrqd lcgvstcdtl gmadvgtvcd parscaived dglqsaftaa
361  helghvfnml hdnskpcisl ngplstsrhv mapvmahvdp eepwspcsar fitdfldngy
421  ghclldkpea plhlpvtfpg kdydadrqcq ltfgpdsrhc pqlpppcaal wcsghlngha
481  mcqtkhspwa dgtpcgpaqa cmggrclhmd qlqdfnipqa ggwgpwgpwg dcsrtcgggv
541  qfssrdctrp vprnggkyce grrtrfrscn tedcptgsal tfreeqcaay nhrtdlfksf
601  pgpmdwvpry tgvapqdqck ltcqaqalgy yyvleprvvd gtpcspdsss vcvqgrciha
661  gcdriigskk kfdkcmvcgg dgsgcskqsg sfrkfrygyn nvvtipagat hilvrqqgnp
721  ghrsiylalk lpdgsyalng eytlmpsptd vvlpgayslr ysgataaset lsghgplaqp
781  ltlqvlvagn pqdtrlrysf fvprptpstp rptpqdwlhr raqileilrr rpwagrk
```

The siRNA used to target human ADAMTS-4 mRNA includes the following sequences (SEQ ID NO: 12-15):

SEQ NO: 12:
5'-CCGCAAUCCUGUCAGCUUG-3'

SEQ NO: 13:
5'-GCGCUUUGCUUCACUGAGU-3'

SEQ NO: 14:
5'-GGACACACGCCUCCGAUAC-3'

SEQ NO: 15:
5'-GCACCGAAGAGCACAGAUU-3'

The molecular beacon used to target human ADAMTS-4 mRNA includes the following sequences (SEQ ID NO: 16-18):

SEQ NO: 16:
5'-CCGGTC TTTTCACACACACACACACG GACCGG-3'

SEQ NO: 17:
5'-CCGGTC TAAAAATACAAAAATTAGCC GACCGG-3'

SEQ NO: 18:
5'-CCGGTC TTGTCTCTGTCTCTTTCCTC GACCGG-3'

The mRNA transcript sequence encoding human MMP-13, provided by Genbank Accession No. NM_002427.3, is incorporated herein by reference, and is shown below (SEQ ID NO: 19).

```
   1 acaacagtcc ccaggcatca ccattcaaga tgcatccagg ggtcctggct gccttcctct
  61 tcttgagctg gactcattgt cgggccctgc cccttcccag tggtggtgat gaagatgatt
 121 tgtctgagga agacctccag tttgcagagc gctacctgag atcatactac catcctacaa
 181 atctcgcggg aatcctgaag gagaatgcag caagctccat gactgagagg ctccgagaaa
 241 tgcagtcttt cttcggctta gaggtgactg gcaaacttga cgataacacc ttagatgtca
 301 tgaaaaagcc aagatgcggg gttcctgatg tgggtgaata caatgttttc cctcgaactc
 361 ttaaatggtc caaaatgaat ttaacctaca gaattgtgaa ttacccct gatatgactc
 421 attctgaagt cgaaaaggca ttcaaaaaag ccttcaaagt ttggtccgat gtaactcctc
 481 tgaattttac cagacttcac gatggcattg ctgacatcat gatctctttt ggaattaagg
 541 agcatggcga cttctaccca tttgatgggc cctctggcct gctggctcat gcttttcctc
 601 ctgggccaaa ttatggagga gatgcccatt ttgatgatga tgaaacctgg acaagtagtt
 661 ccaaaggcta caacttgttt cttgttgctg cgcatgagtt cggccactcc ttaggtcttg
 721 accactccaa ggaccctgga gcactcatgt ttcctatcta cacctacacc ggcaaaagcc
 781 actttatgct tcctgatgac gatgtacaag ggatccagtc tctctatggt ccaggagatg
 841 aagaccccaa ccctaaacat ccaaaaacgc cagacaaatg tgaccttcc ttatcccttg
 901 atgccattac cagtctccga ggagaaacaa tgatctttaa agacagattc ttctggcgcc
 961 tgcatcctca gcaggttgat gcggagctgt ttttaacgaa atcatttggg ccagaacttc
1021 ccaaccgtat tgatgctgca tatgagcacc cttctcatga cctcatcttc atcttcagag
1081 gtagaaaatt ttgggctctt aatggttatg acattctgga aggttatccc aaaaaaatat
1141 ctgaactggg tcttccaaaa gaagttaaga ataaagtgc agctgttcac tttgaggata
1201 caggcaagac tctcctgttc tcaggaaacc aggtctggag atatgatgat actaaccata
1261 ttatggataa agactatccg agactaatag aagaagactt cccaggaatt ggtgataaag
1321 tagatgctgt ctatgagaaa aatggttata tctatttttt caacggaccc atacagtttg
1381 aatacagcat ctggagtaac cgtattgttc gcgtcatgcc agcaaattcc attttgtggt
1441 gttaagtgtc tttttaaaaa ttgttattta aatcctgaag agcatttggg gtaatacttc
1501 cagaagtgcg gggtagggga agaagagcta tcaggagaaa gcttggttct gtgaacaagc
```

```
1561  ttcagtaagt tatctttgaa tatgtagtat ctatatgact atgcgtggct ggaaccacat 1621  tgaagaatgt tagagtaatg aaatggagga tctctaaaga gcatctgatt cttgttgctg 1681  tacaaaagca atggttgatg atacttccca caccacaaat gggacacatg gtctgtcaat 1741  gagagcataa tttaaaaata tatttataag gaaattttac aagggcataa agtaaataca 1801  tgcatataat gaataaatca ttcttactaa aaagtataaa atagtatgaa aatggaaatt 1861  tgggagagcc atacataaaa gaaataaacc aaaggaaaat gtctgtaata atagactgta 1921  acttccaaat aaataatttt cattttgcac tgaggatatt cagatgtatg tgcccttctt 1981  cacacagaca ctaacgaaat atcaaagtca ttaaagacag gagacaaaag agcagtggta 2041  agaatagtag atgtggcctt tgaattctgt ttaattttca cttttggcaa tgactcaaag 2101  tctgctctca tataagacaa atattccttt gcatattata aaggataaag aaggatgatg 2161  tcttttatt aaaatatttc aggttcttca gaagtcacac attacaaagt taaaattgtt 2221  atcaaaatag tctaaggcca tggcatccct ttttcataaa ttatttgatt atttaagact 2281  aaaagttgca ttttaaccct attttaccta gctaattatt taattgtcca gtttgtcttg 2341  gatatatagg ctattttcta aagacttgta tagcatgaaa taaatatat cttataaagt 2401  ggaagtatgt atattaaaaa agagacatcc aaatttttt ttaaagcagt ctactagatt 2461  gtgatccctt gagatatgga aggatgcctt tttttctctg catttaaaaa aatcccccag 2521  cacttcccac agtgcctatt gatacttggg gagggtgctt ggcacttatt gaatatatga 2581  tcggccatca agggaagaac tattgtgctc agagacactg ttgataaaaa ctcaggcaaa 2641  gaaaatgaaa tgcatatttg caaagtgtat taggaagtgt ttatgttgtt tataataaaa 2701  atatattttc aacagacaaa aaaaaaaaaa aaaaa
```
                                                                    40

The amino acid sequence of human MMP-13 (collagenase 3 preproprotein), provided by Genbank Accession No. NP_002418.1, is incorporated herein by reference, and is shown below (SEQ ID NO: 20).

```
  1    mhpgvlaafl flswthcral plpsggdedd lseedlqfae rylrsyyhpt nlagilkena 61    assmterlre mqsffglevt gklddntldv mkkprcgvpd vgeynvfprt lkwskmnity 121    rivnytpdmt hsevekafkk afkvwsdvtp lnftrlhdgi adimisfgik ehgdfypfdg 181    psgllahafp pgpnyggdah fdddetwtss skgynlflva ahefghslgl dhskdpgalm 241    fpiytytgks hfmlpdddvq giqslygpgd edpnpkhpkt pdkcdpslsl daitslrget 301    mifkdrffwr lhpqqvdael fltksfwpel pnridaayeh pshdlififr grkfwalngy 361    dilegypkki selglpkevk kisaavhfed tgktlllfsgn qvwryddtnh imdkdyprli 421    eedfpgigdk vdavyekngy iyffngpiqf eysiwsnriv rvmpansilw c
```
(Signal protein AA 1-19; proprotein AA 20-471; mature peptide AA 104-471).

The siRNA used to target human MMP-13 mRNA includes the following sequences (SEQ ID NO: 21-24):

```
SEQ NO: 21:
5'-UUUCACACACACACACACGC-3'

SEQ NO: 22:
5'-UUUUCACACACACACACACG-3'

SEQ NO: 23:
5'-UAAAAAUACAAAAAUUAGCC-3'

SEQ NO: 24:
5'-UUUGUCUCUGUCUCUUUCCU-3'
```

The molecular beacon used to target human MMP-13 mRNA includes the following sequences (SEQ ID NO: 25-27):

```
SEQ NO 25:
5'-CCGGTC TACACACACCACTTATACCT GACCGG-3'

SEQ NO 26:
5'-CCGGTC TATAATCTCAGCTACTCGGG GACCGG-3'

SEQ NO 27:
5'-CCGGTC AAACAAAACAAAAATTAGCC GACCGG-3'
```

The mRNA transcript sequence encoding human MMP-1 variant 2, provided by Genbank Accession No. NM_001145938.1, is incorporated herein by reference, and is shown below (SEQ ID NO: 28).

```
   1 agcatgagtc agacagcctc tggcttctg gaagggcaag gactctatat atacagaggg
  61 agcttcctag ctgggatatt ggagcagcaa gaggctggga agccatcact taccttgcac
 121 tgagaaagaa gacaaaggca agttgaaaag cggagaaata gtggcccagt ggttgaaaaa
 181 ttgaagcaaa tgcaggaatt ctttgggctg aaagtgactg ggaaaccaga tgctgaaacc
 241 ctgaaggtga tgaagcagcc cagatgtgga gtgcctgatg tggctcagtt tgtcctcact
 301 gaggggaacc ctcgctggga gcaaacacat ctgacctaca ggattgaaaa ttacacgcca
 361 gatttgccaa gagcagatgt ggaccatgcc attgagaaag ccttccaact ctggagtaat
 421 gtcacacctc tgacattcac caaggtctct gagggtcaag cagacatcat gatatctttt
 481 gtcaggggag atcatcggga caactctcct tttgatggac ctggaggaaa tcttgctcat
 541 gcttttcaac caggcccagg tattggaggg gatgctcatt ttgatgaaga tgaaaggtgg
 601 accaacaatt tcagagagta caacttacat cgtgttgcag ctcatgaact cggccattct
 661 cttggactct cccattctac tgatatcggg gctttgatgt accctagcta caccttcagt
 721 ggtgatgttc agctagctca ggatgacatt gatggcatcc aagccatata tggacgttcc
 781 caaaatcctg tccagcccat cggcccacaa accccaaaag cgtgtgacag taagctaacc
 841 tttgatgcta taactacgat tcggggagaa gtgatgttct ttaaagacag attctacatg
 901 cgcacaaatc ccttctaccc ggaagttgag ctcaattca tttctgtttt ctggccacaa
 961 ctgccaaatg gcttgaagc tgcttacgaa tttgccgaca gagatgaagt ccggtttttc
1021 aaagggaata gtactgggc tgttcaggga cagaatgtgc tacacggata ccccaaggac
1081 atctacagct cctttggctt ccctagaact gtgaagcata tcgatgctgc tctttctgag
1141 gaaaacactg gaaaaaccta cttctttgtt gctaacaaat actggaggta tgatgaatat
1201 aaacgatcta tggatccagg ttatcccaaa atgatagcac atgactttcc tggaattggc
1261 cacaaagttg atgcagtttt catgaaagat ggatttttct atttctttca tggaacaaga
1321 caatacaaat tgatcctaa acgaagaga attttgactc tccagaaagc taatagctgg
1381 ttcaactgca ggaaaaattg aacattacta atttgaatgg aaaacacatg gtgtgagtcc
1441 aaagaaggtg ttttcctgaa gaactgtcta ttttctcagt catttttaac ctctagagtc
1501 actgatacac agaatataat cttatttata cctcagtttg catatttttt tactatttag
1561 aatgtagccc ttttttgtact gatataattt agttccacaa atggtgggta caaaagtca
1621 agtttgtggc ttatggattc ataggcca gagttgcaaa gatcttttcc agagtatgca
1681 actctgacgt tgatcccaga gagcagcttc agtgacaaac atatcctttc aagacagaaa
1741 gagacaggag acatgagtct ttgccggagg aaaagcagct caagaacaca tgtgcagtca
```

-continued

```
1801  ctggtgtcac cctggatagg caagggataa ctcttctaac acaaaataag tgttttatgt 1861  ttggaataaa gtcaaccttg tttctactgt tttatacact ttc
```

The amino acid sequence of human MMP-1 (interstitial collagenase isoform 2), provided by Genbank Accession No. NP_001139410.1, is incorporated herein by reference, and is shown below (SEQ ID NO: 29).

```
  1  mqeffglkvt gkpdaetlkv mkqprcgvpd vaqfvltegn prweqthlty rienytpdlp 61  radvdhaiek afqlwsnvtp ltftkvsegq adimisfvrg dhrdnspfdg pggnlahafq 121  pgpgiggdah fdederwtnn freynlhrva ahelghslgl shstdigalm ypsytfsgdv 181  qlaqddidgi qaiygrsqnp vqpigpqtpk acdskltfda ittirgevmf fkdrfymrtn 241  pfypevelnf isvfwpqlpn gleaayefad rdevrffkgn kywavqgqnv lhgypkdiys 301  sfgfprtvkh idaalseent gktyffvank ywrydeykrs mdpgypkmia hdfpgighkv 361  davfmkdgff yffhgtrqyk fdpktkrilt lqkanswfnc rkn
```

The siRNA used to target human MMP-1 variant 1 mRNA include following sequences (SEQ ID NO: 30-33):

```
SEQ NO: 30:
5'-UUAGCUUACUGUCACACGC-3'

SEQ NO: 31:
5'-UUAUAUUCAUCAUACCUCC-3'

SEQ NO: 32:
5'-UUGUCUUCUUUCUCAGUGC-3'

SEQ NO: 33:
5'-UUCGUAAGCAGCUUCAAGC-3'
```

The molecular beacon used to target human MMP-1 variant 1 mRNA includes the following sequences (SEQ ID NO: 34-36):

```
SEQ NO 34:
5'-CCGGTC TTCGTAAGCAGCTTCAAGC GACCGG-3'

SEQ NO 35:
5'-CCGGTC TAAAGAACATCACTTTCC GACCGG-3'

SEQ NO 36:
5'-CCGGTC TAAAACAGTAGAAACAAGG GACCGG-3'
```

The mRNA transcript sequence encoding human MMP-9, provided by Genbank Accession No. NM_004994.2, is incorporated herein by reference, and is shown below (SEQ ID NO: 37).

```
  1  agacacctct gccctcacca tgagcctctg gcagccctg gtcctggtgc tcctggtgct 61  gggctgctgc tttgctgccc ccagacagcg ccagtccacc cttgtgctct ccctggaga 121  cctgagaacc aatctcaccg acaggcagct ggcagaggaa tacctgtacc gctatggtta 181  cactcgggtg gcagagatgc gtggagagtc gaaatctctg gggcctgcgc tgctgcttct 241  ccagaagcaa ctgtccctgc ccgagaccgg tgagctggat agcgccacgc tgaaggccat 301  gcgaaccccca cggtgcgggg tcccagacct gggcagattc caaacctttg agggcgacct 361  caagtggcac caccacaaca tcacctattg gatccaaaac tactcggaag acttgccgcg 421  ggcggtgatt gacgacgcct ttgcccgcgc cttcgcactg tggagcgcgg tgacgccgct
```

```
 481   caccttcact cgcgtgtaca gccgggacgc agacatcgtc atccagtttg gtgtcgcgga
 541   gcacggagac gggtatccct tcgacgggaa ggacgggctc ctggcacacg cctttcctcc
 601   tggccccggc attcagggag acgcccattt cgacgatgac gagttgtggt ccctgggcaa
 661   gggcgtcgtg gttccaactc ggtttggaaa cgcagatggc gcggcctgcc acttcccctt
 721   catcttcgag ggccgctcct actctgcctg caccaccgac ggtcgctccg acggcttgcc
 781   ctggtgcagt accacggcca actacgacac cgacgaccgg tttggcttct gccccagcga
 841   gagactctac acccaggacg gcaatgctga tgggaaaccc tgccagtttc cattcatctt
 901   ccaaggccaa tcctactccg cctgcaccac ggacggtcgc tccgacggct accgctggtg
 961   cgccaccacc gccaactacg accgggacaa gctcttcggc ttctgcccga cccgagctga
1021   ctcgacggtg atgggggggca actcggcggg ggagctgtgc gtcttcccct tcactttcct
1081   gggtaaggag tactcgacct gtaccagcga gggccgcgga gatgggcgcc tctggtgcgc
1141   taccacctcg aactttgaca cgacaagaa gtggggcttc tgcccggacc aaggatacag
1201   tttgttcctc gtggcggcgc atgagttcgg ccacgcgctg gcttagatc attcctcagt
1261   gccggaggcg ctcatgtacc ctatgtaccg cttcactgag ggcccccct tgcataagga
1321   cgacgtgaat ggcatccggc acctctatgg tcctcgccct gaacctgagc cacggcctcc
1381   aaccaccacc acaccgcagc ccacggctcc cccgacggtc tgccccaccg acccccccac
1441   tgtccacccc tcagagcgcc ccacagctgg ccccacaggt ccccccctcag ctggccccac
1501   aggtcccccc actgctggcc cttctacggc cactactgtg cctttgagtc cggtggacga
1561   tgcctgcaac gtgaacatct tcgacgccat cgcggagatt gggaaccagc tgtatttgtt
1621   caaggatggg aagtactggc gattctctga gggcagggg agccggccgc agggcccctt
1681   ccttatcgcc gacaagtggc ccgcgctgcc ccgcaagctg gactcggtct ttgaggagcg
1741   gctctccaag aagcttttct tcttctctgg gcgccaggtg tgggtgtaca caggcgcgtc
1801   ggtgctgggc ccgaggcgtc tggacaagct gggcctggga gccgacgtgg cccaggtgac
1861   cggggccctc cggagtggca gggggaagat gctgctgttc agcgggcggc gcctctggag
1921   gttcgacgtg aaggcgcaga tggtggatcc ccggagcgcc agcgaggtgg accggatgtt
1981   ccccgggtg cctttggaca cgcacgacgt cttccagtac cgagagaaag cctatttctg
2041   ccaggaccgc ttctactggc gcgtgagttc ccggagtgag ttgaaccagg tggaccaagt
2101   gggctacgtg acctatgaca tcctgcagtg ccctgaggac tagggctccc gtcctgcttt
2161   ggcagtgcca tgtaaatccc cactgggacc aaccctgggg aaggagccag tttgccggat
2221   acaaactggt attctgttct ggaggaaagg gaggagtgga ggtgggctgg gccctctctt
2281   ctcacctttg tttttgttg gagtgtttct aataaacttg gattctctaa cctttaaaaa
2341   aaaaaaaaaa aaaaaaaaaa aaaaaaaaaa aaaaaaaaaa aaaaaaa
```

The amino acid sequence of human MMP-9 (preproprotein), provided by Genbank Accession No. NP_004985.2, is incorporated herein by reference, and is shown below (SEQ ID NO: 38).

```
  1   mslwqplvlv llvlgccfaa prqrqstivl fpgdlrtnit drqlaeeyly rygytrvaem
 61   rgeskslgpa lllqkqlsl petgeldsat lkamrtprcg vpdlgrfqtf egdlkwhhhn
121   itywiqnyse dlpravidda farafalwsa vtpltftrvy srdadiviqf gvaehgdgyp
181   fdgkdgllah afppgpgiqg dahfdddelw slgkgvvvpt rfgnadgaac hfpfifegrs
241   ysacttdgrs dglpwcstta nydtddrfgf cpserlytqd gnadgkpcqf pfifqgqsys
```

-continued

```
301  acttdgrsdg yrwcattany drdklfgfcp tradstvmgg nsagelcvfp ftflgkeyst
361  ctsegrgdgr lwcattsnfd sdkkwgfcpd qgyslflvaa hefghalgld hssvpealmy
421  pmyrftegpp lhkddvngir hlygprpepe prppttttpq ptapptvcpt gpptvhpser
481  ptagptgpps agptgpptag pstattvpls pvddacnvni fdaiaeignq lylfkdgkyw
541  rfsegrgsrp qgpfliadkw palprkldsv feerlskklf ffsgrqvwvy tgasvlgprr
601  ldklglgadv aqvtgalrsg rgkmllfsgr rlwrfdvkaq mvdprsasev drmfpgvpld
661  thdvfqyrek ayfcqdrfyw rvssrselnq vdqvgyvtyd ilqcped
```
(signal protein AA 1-19; proportein AA 20-707; mature protein 107-707)

The siRNA used to target human MMP-9 mRNA include following sequences (SEQ ID NO: 39-42):

```
SEQ NO: 39:
5'-UUGUCGCUGUCAAAGUUCGAG-3'

SEQ NO: 40:
5'-UUCUUGUCGCUGUCAAAGUUC-3'

SEQ NO: 41:
5'-UUCAACUCACUCCGGGAACUC-3'

SEQ NO: 42:
5'-UUCACGUCGUCCUUAUGCAAG-3'
```

The molecular beacon used to target human MMP-9 mRNA includes the following sequences (SEQ ID NO:43-45):

```
SEQ NO: 43:
5'-CCGGTC TTGTCGCTGTCAAAGTTCGGACCGG-3'

SEQ NO: 44:
5'-CCGGTC TTATTAGAAACACTCCAAC GACCGG-3'

SEQ NO: 45:
5'-CCGGTC ATTCACGTCGTCCTTATGC GACCGG-3'
```

The mRNA transcript sequence encoding human MMP-3, provided by Genbank Accession No. NM_002422.3, is incorporated herein by reference, and is shown below (SEQ ID NO: 46).

```
   1  ctacaaggag gcaggcaaga cagcaaggca tagagacaac atagagctaa gtaaagccag
  61  tggaaatgaa gagtcttcca atcctactgt tgctgtgcgt ggcagtttgc tcagcctatc
 121  cattggatgg agctgcaagg ggtgaggaca ccagcatgaa ccttgttcag aaatatctag
 181  aaaactacta cgacctcaaa aaagatgtga acagtttgt taggagaaag gacagtggtc
 241  ctgttgttaa aaaaatccga gaaatgcaga agttccttgg attggaggtg acggggaagc
 301  tggactccga cactctggag gtgatgcgca agcccaggtg tggagttcct gatgttggtc
 361  acttcagaac ctttcctggc atcccgaagt ggaggaaaac ccaccttaca tacaggattg
 421  tgaattatac accagatttg ccaaaagatg ctgttgattc tgctgttgag aaagctctga
 481  aagtctggga gaggtgact ccactcacat tctccaggct gtatgaagga gaggctgata
 541  taatgatctc ttttgcagtt agagaacatg gagacttta ccctttttgat ggacctggaa
 601  atgttttggc ccatgcctat gcccctgggc cagggattaa tggagatgcc actttgatg
 661  atgatgaaca atggacaaag gatacaacag ggaccaattt atttctcgtt gctgctcatg
 721  aaattggcca ctccctgggt ctctttcact cagccaacac tgaagctttg atgtacccac
 781  tctatcactc actcacagac ctgactcggt tccgcctgtc tcaagatgat ataaatggca
 841  ttcagtccct ctatggacct cccctgact ccccctgagac cccctggta cccacggaac
 901  ctgtccctcc agaacctggg acgccagcca actgtgatcc tgctttgtcc tttgatgctg
 961  tcagcactct gaggggagaa atcctgatct ttaaagacag gcacttttgg cgcaaatccc
1021  tcaggaagct tgaacctgaa ttgcatttga tctcttcatt ttggccatct cttccttcag
1081  gcgtggatgc cgcatatgaa gttactagca aggacctcgt tttcatttt aaggaaatc
1141  aattctgggc tatcagagga aatgaggtac gagctggata cccaagaggc atccacaccc
1201  taggtttccc tccaaccgtg aggaaaatcg atgcagccat ttctgataag gaaaagaaca
```

```
1261   aaacatattt ctttgtagag gacaaatact ggagatttga tgagaagaga aattccatgg 1321   agccaggctt tcccaagcaa atagctgaag actttccagg gattgactca aagattgatg 1381   ctgtttttga agaatttggg ttcttttatt tctttactgg atcttcacag ttggagtttg 1441   acccaaatgc aaagaaagtg acacacactt tgaagagtaa cagctggctt aattgttgaa 1501   agagatatgt agaaggcaca atatgggcac tttaaatgaa gctaataatt cttcacctaa 1561   gtctctgtga attgaaatgt tcgttttctc ctgcctgtgc tgtgactcga gtcacactca 1621   agggaacttg agcgtgaatc tgtatcttgc cggtcatttt tatgttatta cagggcattc 1681   aaatgggctg ctgcttagct tgcaccttgt cacatagagt gatctttccc aagagaaggg 1741   gaagcactcg tgtgcaacag acaagtgact gtatctgtgt agactatttg cttatttaat 1801   aaagacgatt tgtcagttat tttatctt
```

The amino acid sequence of human MMP-3 (preproprotein), provided by Genbank Accession No. NP_002413.1, is incorporated herein by reference, and is shown below (SEQ ID NO: 47).

```
  1    mkslpilllll cvavcsaypl dgaargedts mnlvqkylen yydlkkdvkq fvrrkdsgpv 61    vkkiremqkf lglevtgkld sdtlevmrkp rcgvpdvghf rtfpgipkwr kthltyrivn 121    ytpdlpkdav dsavekalkv weevtpltfs rlyegeadim isfavrehgd fypfdgpgnv 181    lahayapgpg ingdahfddd eqwtkdttgt nlflvaahei ghslglfhsa ntealmyply 241    hsltdltrfr lsqddingiq slygpppdsp etplvptepv ppepgtpanc dpalsfdays 301    tlrgeilifk drhfwrkslr klepelhlis sfwpslpsgv daayevtskd lvfifkgnqf 361    wairgnevra gyprgihtlg fpptvrkida aisdkeknkt yffvedkywr fdekrnsmep 421    gfpkqiaedf pgidskidav feefgffyff tgssqlefdp nakkvthtlk snswlnc
```
(signal peptide AA 1-17; proprotein AA 18-477; mature protein AA 100-477).

The siRNA used to target human MMP-3 mRNA include following sequences (SEQ ID NO: 48-51):

```
SEQ NO: 48:
5'-UUCAUCAUCAUCAAAGUGGG-3'

SEQ NO: 49:
5'-UAAUAACAUAAAAAUGACCG-3'

SEQ NO: 50:
5'-UAGUCUACACAGAUACAGUC-3'

SEQ NO: 51:
5'-UAUAUCAUCUUGAGACAGGC-3'
```

The molecular beacon used to target human MMP-3 mRNA includes the following sequences (SEQ ID NO: 52-54):

```
SEQ NO 52:
5'-CCGGTC TATATCATCTTGAGACAGGC GACCGG-3'

SEQ NO 53:
5'-CCGGTC TTTCTCTTCTCATCAAATCT GACCGG-3'

SEQ NO 54:
5'-CCGGTC TAACAAACTGTTTCACATCT GACCGG-3'
```

The mRNA transcript sequence encoding human IL-1 alpha, provided by Genbank Accession No. NM_000575.3, is incorporated herein by reference, and is shown below (SEQ ID NO: 55).

```
   1  accaggcaac accattgaag gctcatatgt aaaaatccat gccttccttt ctcccaatct
  61  ccattcccaa acttagccac tggcttctgg ctgaggcctt acgcatacct cccggggctt
 121  gcacacacct tcttctacag aagacacacc ttgggcatat cctacagaag accaggcttc
 181  tctctggtcc ttggtagagg gctactttac tgtaacaggc caggggtgga gagttctctc
 241  ctgaagctcc atcccctcta taggaaatgt gttgacaata ttcagaagag taagaggatc
 301  aagacttctt tgtgctcaaa taccactgtt ctcttctcta ccctgcccta accaggagct
 361  tgtcacccca aactctgagg tgatttatgc cttaatcaag caaacttccc tcttcagaaa
 421  agatggctca ttttccctca aaagttgcca ggagctgcca agtattctgc caattcaccc
 481  tggagcacaa tcaacaaatt cagccagaac acaactacag ctactattag aactattatt
 541  attaataaat tcctctccaa atctagcccc ttgacttcgg atttcacgat ttctcccttc
 601  ctcctagaaa cttgataagt ttcccgcgct tccctttttc taagactaca tgtttgtcat
 661  cttataaagc aaagggtga ataaatgaac caaatcaata acttctggaa tatctgcaaa
 721  caacaataat atcagctatg ccatctttca ctattttagc cagtatcgat ttgaatgaac
 781  atagaaaaat acaaaactga attcttccct gtaaattccc cgttttgacg acgcacttgt
 841  agccacgtag ccacgcctac ttaagacaat tacaaaaggc gaagaagact gactcaggct
 901  taagctgcca gccagagagg gagtcatttc attggcgttt gagtcagcaa agaagtcaag
 961  atggccaaag ttccagacat gtttgaagac ctgaagaact gttacagtga aaatgaagaa
1021  gacagttcct ccattgatca tctgtctctg aatcagaaat ccttctatca tgtaagctat
1081  ggcccactcc atgaaggctg catggatcaa tctgtgtctc tgagtatctc tgaaacctct
1141  aaaacatcca agcttacctt caaggagagc atggtggtag tagcaaccaa cgggaaggtt
1201  ctgaagaaga cacggttgag tttaagccaa tccatcactg atgatgacct ggaggccatc
1261  gccaatgact cagaggaaga aatcatcaag cctaggtcag caccttttag cttcctgagc
1321  aatgtgaaat acaactttat gaggatcatc aaatacgaat tcatcctgaa tgacgccctc
1381  aatcaaagta taattcgagc caatgatcag tacctcacgg ctgctgcatt acataatctg
1441  gatgaagcag tgaaatttga catgggtgct tataagtcat caaaggatga tgctaaaatt
1501  accgtgattc taagaatctc aaaaactcaa ttgtatgtga ctgcccaaga tgaagaccaa
1561  ccagtgctgc tgaaggagat gcctgagata cccaaaacca tcacaggtag tgagaccaac
1621  ctcctcttct tctgggaaac tcacggcact aagaactatt tcacatcagt tgcccatcca
1681  aacttgttta ttgccacaaa gcaagactac tgggtgtgct tggcaggggg gccacccctct
1741  atcactgact ttcagatact ggaaaaccag gcgtaggtct ggagtctcac ttgtctcact
1801  tgtgcagtgt tgacagttca tatgtaccat gtacatgaag aagctaaatc ctttactgtt
1861  agtcatttgc tgagcatgta ctgagccttg taattctaaa tgaatgttta cactctttgt
1921  aagagtggaa ccaacactaa catataatgt tgttatttaa agaacaccct atattttgca
1981  tagtaccaat cattttaatt attattcttc ataacaattt taggaggacc agagctactg
2041  actatggcta ccaaaaagac tctacccata ttacagatgg gcaaattaag gcataagaaa
2101  actaagaaat atgcacaata gcagttgaaa caagaagcca cagacctagg atttcatgat
2161  ttcatttcaa ctgtttgcct tctacttttca agttgctgat gaactcttaa tcaaatagca
2221  taagtttctg ggacctcagt tttatcattt tcaaaatgga gggaataata cctaagcctt
2281  cctgccgcaa cagtttttta tgctaatcag ggaggtcatt ttggtaaaat acttcttgaa
2341  gccgagcctc aagatgaagg caaagcacga aatgttattt tttaattatt atttatatat
2401  gtatttataa atatatttaa gataattata atatactata tttatgggaa ccccttcatc
```

-continued

```
2461   ctctgagtgt gaccaggcat cctccacaat agcagacagt gttttctggg ataagtaagt 2521   ttgatttcat taatacaggg cattttggtc caagttgtgc ttatcccata gccaggaaac 2581   tctgcattct agtacttggg agacctgtaa tcatataata aatgtacatt aattaccttg 2641   agccagtaat tggtccgatc tttgactctt ttgccattaa acttacctgg gcattcttgt 2701   ttcaattcca cctgcaatca agtcctacaa gctaaaatta gatgaactca actttgacaa 2761   ccatgagacc actgttatca aaactttctt ttctggaatg taatcaatgt ttcttctagg 2821   ttctaaaaat tgtgatcaga ccataatgtt acattattat caacaatagt gattgataga 2881   gtgttatcag tcataactaa ataaagcttg caacaaaatt ctctgacaaa aaaaaaaaaa 2941   aaa
```

The amino acid sequence of human IL-1 alpha (proprotein), provided by Genbank Accession No. NP_000566.3, is incorporated herein by reference, and is shown below (SEQ ID NO: 56).

```
  1    makvpdmfed lkncysenee dsssidhlsl nqksfyhvsy gplhegcmdq syslsisets 61    ktskltfkes mvvvatngkv lkkrrlslsq sitdddleai andseeeiik prsapfsfls 121    nvkynfmrii kyefilndal nqsiirandq yltaaalhnl deavkfdmga yksskddaki 181    tvilrisktq lyvtaqdedq pvllkempei pktitgsetn llffwethgt knyftsvahp 241    nlfiatkqdy wvclaggpps itdfqilenq a
(mature peptide AA 113-271).
```

The siRNA used to target human IL-1 alpha mRNA include following sequences (SEQ ID NO: 57-60):

```
SEQ NO: 57:
5'-UUUCUAUGUUCAUUCAACUC-3'

SEQ NO: 58:
5'-UCAUUCAACUCGAUACUGGC-3'

SEQ NO: 59:
5'-UUCAUUCAACUCGAUACUGG-3'

SEQ NO: 60:
5'-UAAUAGUUCUAAUAGUAGCU-3'
```

The molecular beacon used to target human IL-1 alpha mRNA includes the following sequences (SEQ ID NO: 61-63):

```
SEQ NO 61:
5'-CCGGTC TTTCTTAGTTTTCTTATGCC GACCGG-3'

SEQ NO 62:
5'-CCGGTC TAATAGTTCTAATAGTAGC GACCGG-3'

SEQ NO 63:
5'-CCGGTC TATGAACTGTCAACACTGC GACCGG-3'
```

The mRNA transcript sequence encoding human IL-1 beta, provided by Genbank Accession No. NM_000576.2, is incorporated herein by reference, and is shown below (SEQ ID NO: 64).

```
  1    accaaacctc ttcgaggcac aaggcacaac aggctgctct gggattctct tcagccaatc 61    ttcattgctc aagtgtctga agcagccatg gcagaagtac ctgagctcgc cagtgaaatg
```

-continued

```
 121   atggcttatt acagtggcaa tgaggatgac ttgttctttg aagctgatgg ccctaaacag 181   atgaagtgct ccttccagga cctggacctc tgccctctgg atggcggcat ccagctacga 241   atctccgacc accactacag caagggcttc aggcaggccg cgtcagttgt tgtggccatg 301   gacaagctga ggaagatgct ggttccctgc cacagacct tccaggagaa tgacctgagc 361   accttctttc ccttcatctt tgaagaagaa cctatcttct tcgacacatg ggataacgag 421   gcttatgtgc acgatgcacc tgtacgatca ctgaactgca cgctccggga ctcacagcaa 481   aaaagcttgg tgatgtctgg tccatatgaa ctgaaagctc tccacctcca gggacaggat 541   atggagcaac aagtggtgtt ctccatgtcc tttgtacaag gagaagaaag taatgacaaa 601   atacctgtgg ccttgggcct caaggaaaag aatctgtacc tgtcctgcgt gttgaaagat 661   gataagccca ctctacagct ggagagtgta gatcccaaaa attacccaaa gaagaagatg 721   gaaaagcgat ttgtcttcaa caagatagaa atcaataaca agctggaatt tgagtctgcc 781   cagttcccca actggtacat cagcacctct caagcagaaa acatgcccgt cttcctggga 841   gggaccaaag gcggccagga tataactgac ttcaccatgc aatttgtgtc ttcctaaaga

901   gagctgtacc cagagagtcc tgtgctgaat gtggactcaa tccctagggc tggcagaaag 961   ggaacagaaa ggttttttgag tacggctata gcctggactt tcctgttgtc tacaccaatg 1021   cccaactgcc tgccttaggg tagtgctaag aggatctcct gtccatcagc caggacagtc 1081   agctctctcc tttcagggcc aatccccagc ccttttgttg agccaggcct ctctcacctc 1141   tcctactcac ttaaagcccg cctgacagaa accacggcca catttggttc taagaaaccc 1201   tctgtcattc gctcccacat tctgatgagc aaccgcttcc ctatttattt atttatttgt 1261   ttgtttgttt tattcattgg tctaatttat tcaaggggg caagaagtag cagtgtctgt 1321   aaaagagcct agttttaat agctatggaa tcaattcaat ttggactggt gtgctctctt 1381   taaatcaagt cctttaatta agactgaaaa tatataagct cagattattt aaatgggaat 1441   atttataaat gagcaaatat catactgttc aatggttctg aaataaactt cactgaag
```

The amino acid sequence of human IL-1 beta (proprotein), provided by Genbank Accession No. NP_000567.1, is incorporated herein by reference, and is shown below (SEQ ID NO: 65).

```
  1   maevpelase mmayysgned dlffeadgpk qmkcsfqdld lcpldggiql risdhhyskg 61   frqaasvvva mdklrkmlvp cpqtfqendl stffpfifee epiffdtwdn eayvhdapvr 121   slnctlrdsq qkslvmsgpy elkalhlqgq dmeqqvvfsm sfvqgeesnd kipvalglke 181   knlylscvlk ddkptlqles vdpknypkkk mekrfvfnki einnklefes aqfpnwyist 241   sqaenmpvfl ggtkggqdit dftmqfvss (mature peptide AA 117-269)
```

The siRNA used to target human IL-1 beta mRNA includes the following sequences (SEQ ID NO: 66-69):

```
SEQ NO: 66:
5'-UUAUCAUCUUUCAACACGCAG-3'

SEQ NO: 67:
5'-UUUUACAGACACUGCUACUUC-3'

SEQ NO: 68:
5'-UUUGUCAUUACUUUCUUCUCC-3'

SEQ NO: 69:
5'-UACAGACACUGCUACUUCUUG-3'
```

The molecular beacon used to target human IL-1 beta mRNA includes the following sequences (SEQ ID NO: 70-72):

```
SEQ NO: 70:
5'-CCGGTC TTTTGTCATTACTTTCTTCTC GACCGG-3'

SEQ NO: 71:
5'-CCGGTC TTTCAGTCTTAATTAAAGGAC GACCGG-3'

SEQ NO: 72:
5'-CCGGTC TTACATAAATTAACTCAGCT GACCGG-3'
```

The mRNA transcript sequence encoding human IL-6, provided by Genbank Accession No. NM_000600.3, is incorporated herein by reference, and is shown below (SEQ ID NO: 73).

```
   1  aatattagag tctcaacccc caataaatat aggactggag atgtctgagg ctcattctgc
  61  cctcgagccc accgggaacg aaagagaagc tctatctccc ctccaggagc ccagctatga
 121  actccttctc cacaagcgcc ttcggtccag ttgccttctc cctggggctg ctcctggtgt
 181  tgcctgctgc cttcctgcc ccagtacccc caggagaaga ttccaaagat gtagccgccc
 241  cacacagaca gccactcacc tcttcagaac gaattgacaa acaaattcgg tacatcctcg
 301  acggcatctc agccctgaga aaggagacat gtaacaagag taacatgtgt gaaagcagca
 361  aagaggcact ggcagaaaac aacctgaacc ttccaaagat ggctgaaaaa gatggatgct
 421  tccaatctgg attcaatgag gagacttgcc tggtgaaaat catcactggt cttttggagt
 481  ttgaggtata cctagagtac ctccagaaca gatttgagag tagtgaggaa caagccagag
 541  ctgtgcagat gagtacaaaa gtcctgatcc agttcctgca gaaaaaggca aagaatctag
 601  atgcaataac cacccctgac ccaaccacaa atgccagcct gctgacgaag ctgcaggcac
 661  agaaccagtg gctgcaggac atgacaactc atctcattct gcgcagcttt aaggagttcc
 721  tgcagtccag cctgagggct cttcggcaaa tgta2E2tgg gcacctcaga ttgttgttgt
 781  taatgggcat tccttcttct ggtcagaaac ctgtccactg ggcacagaac ttatgttgtt
 841  ctctatggag aactaaaagt atgagcgtta ggacactatt ttaattattt ttaatttatt
 901  aatatttaaa tatgtgaagc tgagttaatt tatgtaagtc atatttatat ttttaagaag
 961  taccacttga aacattttat gtattagttt tgaaataata atggaaagtg gctatgcagt
1021  ttgaatatcc tttgtttcag agccagatca tttcttggaa agtgtaggct tacctcaaat
1081  aaatggctaa cttatacata tttttaaaga aatatttata ttgtatttat ataatgtata
1141  aatggttttt ataccaataa atggcatttt aaaaaattca gcaaaaaaaa aaaaaaaaa
1201  a
```

The amino acid sequence of human IL-6 (precursor), provided by Genbank Accession No. NP_000591.1, is incorporated herein by reference, and is shown below (SEQ ID NO: 74).

```
  1  mnsfstsafg pvafslglll vlpaafpapv ppgedskdva aphrqpltss eridkqiryi
 61  ldgisalrke tcnksnmces skealaennl nlpkmaekdg cfqsgfneet clvkiitgll
121  efevyleylq nrfesseeqa ravqmstkvl iqflqkkakn ldaittpdpt tnaslltklq
181  aqnqwlqdmt thlilrsfke flqsslralr qm (Signal peptide AA 1-29;
     mature peptide AA 30-212).
```

The siRNA used to target human IL-6 mRNA include following sequences (SEQ ID NO: 75-78):

```
SEQ NO: 75:
5'-UAAAAUAGUGUCCUAACGCUC-3'

SEQ NO: 76:
5'-UCACUACUCUCAAAUCUGUUC-3'

SEQ NO: 77:
5'-UUACUCUUGUUACAUGUCUCC-3'

SEQ NO: 78:
5'-UAACGCUCAUACUUUUAGUUC-3'
```

The molecular beacon used to target human IL-6 mRNA includes the following sequences (SEQ ID NO: 79-81):

```
SEQ NO 79:
5'-CCGGTC TTACTCTTGTTACATGTCYCC GACCTT-3'

SEQ NO 80:
5'-CCGGTC TTACTCTTGTTACATGTCTCC GACCTT-3'

SEQ NO 81:
5'-CCGGTC TACATAAAATGTTTCAAGTGG GACCTT-3'
```

The mRNA transcript sequence encoding human IL-8, provided by Genbank Accession No. NM_000584.3, is incorporated herein by reference, and is shown below (SEQ ID NO: 82).

```
  1  gagggtgcat aagttctcta gtagggtgat gatataaaaa gccaccggag cactccataa
 61  ggcacaaact ttcagagaca gcagagcaca caagcttcta ggacaagagc caggaagaaa
121  ccaccggaag gaaccatctc actgtgtgta aacatgactt ccaagctggc cgtggctctc
181  ttggcagcct tcctgatttc tgcagctctg tgtgaaggtg cagttttgcc aaggagtgct
241  aaagaactta gatgtcagtg cataaagaca tactccaaac ctttccaccc caaatttatc
301  aaagaactga gagtgattga gagtggacca cactgcgcca acacagaaat tattgtaaag
361  ctttctgatg gaagagagct ctgtctggac cccaaggaaa actgggtgca gagggttgtg
421  gagaagtttt tgaagagggc tgagaattca taaaaaaatt cattctctgt ggtatccaag
481  aatcagtgaa gatgccagtg aaacttcaag caaatctact tcaacacttc atgtattgtg
541  tgggtctgtt gtagggttgc cagatgcaat acaagattcc tggttaaatt tgaatttcag
601  taaacaatga atagttttc attgtaccat gaaatatcca gaacatactt atatgtaaag
661  tattatttat ttgaatctac aaaaaacaac aaataatttt taaatataag gattttccta
721  gatattgcac gggagaatat acaaatagca aaattgaggc caagggccaa gagaatatcc
781  gaactttaat ttcaggaatt gaatgggttt gctagaatgt gatatttgaa gcatcacata
```

```
 841   aaaatgatgg gacaataaat tttgccataa agtcaaattt agctggaaat cctggatttt 901   tttctgttaa atctggcaac cctagtctgc tagccaggat ccacaagtcc ttgttccact 961   gtgccttggt ttctccttta tttctaagtg gaaaagtat  tagccaccat cttacctcac 1021   agtgatgttg tgaggacatg tggaagcact ttaagttttt tcatcataac ataaattatt 1081   ttcaagtgta acttattaac ctatttatta tttatgtatt tatttaagca tcaaatattt 1141   gtgcaagaat ttggaaaaat agaagatgaa tcattgattg aatagttata aagatgttat 1201   agtaaattta ttttatttta gatattaaat gatgttttat tagataaatt tcaatcaggg 1261   tttttagatt aaacaaacaa acaattgggt acccagttaa attttcattt cagataaaca 1321   acaaataatt ttttagtata agtacattat tgtttatctg aaattttaat tgaactaaca 1381   atcctagttt gatactccca gtcttgtcat tgccagctgt gttggtagtg ctgtgttgaa 1441   ttacggaata atgagttaga actattaaaa cagccaaaac tccacagtca atattagtaa 1501   tttcttgctg gttgaaactt gtttattatg tacaaataga ttcttataat attatttaaa 1561   tgactgcatt tttaaataca aggctttata ttttaactt  taagatgttt ttatgtgctc 1621   tccaaatttt ttttactgtt tctgattgta tggaaatata aaagtaaata tgaaacattt 1681   aaaatataat ttgttgtcaa agtaaaaaaa aaaaaaa
```

The amino acid sequence of human IL-8(precursor), provided by Genbank Accession No. NP_000575.1, is incorporated herein by reference, and is shown below (SEQ ID NO: 83).

```
 1   mtsklavall aaflisaalc egavlprsak elrcqcikty skpfhpkfik elrviesgph
61   canteiivkl sdgrelcldp kenwvgrvve kflkraens
```

The siRNA used to target human IL-8 mRNA include following sequences (SEQ ID NO: 84-87):

SEQ NO: 84:
5'-UUUGUUUAAUCUAAAAACCC-3'

SEQ NO: 85:
5'-UUUACACACAGUGAGAUGGU-3'

SEQ NO: 86:
5'-UUCAAAUAUCACAUUCUAGC-3'

SEQ NO: 87:
5'-UUAUGCACUGACAUCUAAGU-3'

The molecular beacon used to target human IL-8 mRNA includes the following sequences (SEQ ID NO: 88-90):

SEQ NO 88:
5'-CCGGTC TATCACATTCTAGCAAACCC GACCGG-3'

SEQ NO 89:
5'-CCGGTC TACTAGAGAACTTATGCACC GACCGG-3'

SEQ NO 90:
5'-CCGGTC TAGTTCTAACTCATTATTCC GACCGG-3'

The mRNA transcript sequence encoding human IL-1R type 1 variant 1, provided by Genbank Accession No. NM_000877.3, is incorporated herein by reference, and is shown below (SEQ ID NO: 91).

```
   1  gtggccggcg gccggagccg actcggagcg cgcggcgccg gccgggagga gccggagagc
  61  ggccgggccg ggcggtgggg gcgccggcct gccccgcgcg ccccagggag cggcaggaat
 121  gtgacaatcg cgcgcccgcg caccgaagca ctcctcgctc ggctcctagg gctctcgccc
 181  ctctgagctg agccgggttc cgcccggggc tgggatccca tcaccctcca cggccgtccg
 241  tccaggtaga cgcaccctct gaagatggtg actccctcct gagaagctgg accccttggt
 301  aaaagacaag gccttctcca agaagaatat gaaagtgtta ctcagactta tttgtttcat
 361  agctctactg atttcttctc tggaggctga taaatgcaag gaacgtgaag aaaaaataat
 421  tttagtgtca tctgcaaatg aaattgatgt tcgtccctgt cctcttaacc caaatgaaca
 481  caaaggcact ataacttggt ataaagatga cagcaagaca cctgtatcta cagaacaagc
 541  ctccaggatt catcaacaca aagagaaact ttggtttgtt cctgctaagg tggaggattc
 601  aggacattac tattgcgtgg taagaaattc atcttactgc ctcagaatta aaataagtgc
 661  aaaatttgtg gagaatgagc ctaacttatg ttataatgca caagccatat ttaagcagaa
 721  actacccgtt gcaggagacg gaggacttgt gtgcccttat atggagtttt ttaaaaatga
 781  aaataatgag ttacctaaat tacagtggta taaggattgc aaacctctac ttcttgacaa
 841  tatacacttt agtggagtca agataggct catcgtgatg aatgtggctg aaaagcatag
 901  agggaactat acttgtcatg catcctacac atacttgggc aagcaatatc ctattacccg
 961  ggtaatagaa tttattactc tagaggaaaa caaacccaca aggcctgtga ttgtgagccc
1021  agctaatgag acaatggaag tagacttggg atcccagata caattgatct gtaatgtcac
1081  cggccagttg agtgacattg cttactggaa gtggaatggg tcagtaattg atgaagatga
1141  cccagtgcta ggggaagact attacagtgt ggaaaatcct gcaaacaaaa gaggagtac
1201  cctcatcaca gtgcttaata tatcggaaat tgaaagtaga ttttataaac atccatttac
1261  ctgttttgcc aagaatacac atggtataga tgcagcatat atccagttaa tatatccagt
1321  cactaatttc cagaagcaca tgattggtat atgtgtcacg ttgacagtca taattgtgtg
1381  ttctgttttc atctataaaa tcttcaagat tgacattgtg ctttggtaca gggattcctg
1441  ctatgatttt ctcccaataa aagcttcaga tggaaagacc tatgacgcat atatactgta
1501  tccaaagact gttggggaag ggtctacctc tgactgtgat atttttgtgt ttaaagtctt
1561  gcctgaggtc ttggaaaaac agtgtggata taagctgttc atttatggaa gggatgacta
1621  cgttgggaa gacattgttg aggtcattaa tgaaaacgta agaaaagca gaagactgat
1681  tatcatttta gtcagagaaa catcaggctt cagctggctg ggtggttcat ctgaagagca
1741  aatagccatg tataatgctc ttgttcagga tggaattaaa gttgtcctgc ttgagctgga
1801  gaaaatccaa gactatgaga aaatgccaga tcgattaaa ttcattaagc agaaacatgg
1861  ggctatccgc tggtcagggg actttacaca gggaccacag tctgcaaaga caaggttctg
1921  gaagaatgtc aggtaccaca tgccagtcca gcgacggtca ccttcatcta acaccagtt
1981  actgtcacca gccactaagg agaaactgca aagagaggct cacgtgcctc tcgggtagca
2041  tggagaagtt gccaagagtt ctttaggtgc ctcctgtctt atggcgttgc aggccaggtt
2101  atgcctcatg ctgacttgca gagttcatgg aatgtaacta tatcatcctt tatccctgag
2161  gtcacctgga atcagattat taagggaata agccatgacg tcaatagcag cccagggcac
2221  ttcagagtag agggcttggg aagatctttt aaaaaggcag taggcccggt gtggtggctc
2281  acgcctataa tcccagcact tgggaggct gaagtgggtg gatcaccaga ggtcaggagt
2341  tcgagaccag cccagccaac atggcaaaac cccatctcta ctaaaaatac aaaaatgagc
2401  taggcatggt ggcacacgcc tgtaatccca gctacacctg aggctgaggc aggagaattg
```

-continued

```
2461  cttgaaccgg ggagacggag gttgcagtga gccgagtttg ggccactgca ctctagcctg
2521  gcaacagagc aagactccgt ctcaaaaaaa gggcaataaa tgccctctct gaatgtttga
2581  actgccaaga aaaggcatgg agacagcgaa ctagaagaaa gggcaagaag gaaatagcca
2641  ccgtctacag atggcttagt taagtcatcc acagcccaag gcgggggcta tgccttgtct
2701  ggggaccctg tagagtcact gaccctggag cggctctcct gagaggtgct gcaggcaaag
2761  tgagactgac acctcactga ggaagggaga catattcttg gagaactttc catctgcttg
2821  tattttccat acacatcccc agccagaagt tagtgtccga agaccgaatt ttattttaca
2881  gagcttgaaa actcacttca atgaacaaag ggattctcca ggattccaaa gttttgaagt
2941  catcttagct ttccacagga gggagagaac ttaaaaaagc aacagtagca gggaattgat
3001  ccacttctta atgctttcct ccctggcatg accatcctgt cctttgttat tatcctgcat
3061  tttacgtctt tggaggaaca gctccctagt ggcttcctcc gtctgcaatg tcccttgcac
3121  agcccacaca tgaaccatcc ttcccatgat gccgctcttc tgtcatcccg ctcctgctga
3181  aacacctccc aggggctcca cctgttcagg agctgaagcc catgctttcc caccagcatg
3241  tcactcccag accacctccc tgccctgtcc tccagcttcc cctcgctgtc ctgctgtgtg
3301  aattcccagg ttggcctggt ggccatgtcg cctgccccca gcactcctct gtctctgctc
3361  ttgcctgcac ccttcctcct cctttgccta ggaggccttc tcgcattttc tctagctgat
3421  cagaatttta ccaaaattca gaacatcctc caattccaca gtctctggga gactttccct
3481  aagaggcgac ttcctctcca gccttctctc tctggtcagg cccactgcag agatggtggt
3541  gagcacatct gggaggctgg tctccctcca gctggaattg ctgctctctg agggagaggc
3601  tgtggtggct gtctctgtcc ctcactgcct tccaggagca atttgcacat gtaacataga
3661  tttatgtaat gctttatgtt taaaaacatt ccccaattat cttatttaat ttttgcaatt
3721  attctaattt tatatataga gaaagtgacc tattttttaa aaaaatcaca ctctaagttc
3781  tattgaacct aggacttgag cctccatttc tggcttctag tctggtgttc tgagtacttg
3841  atttcaggtc aataacggtc cccctcact ccacactggc acgtttgtga gaagaaaatga
3901  catttgcta ggaagtgacc gagtctagga atgcttttat tcaagacacc aaattccaaa
3961  cttctaaatg ttggaatttt caaaaattgt gtttagattt tatgaaaaac tcttctactt
4021  tcatctattc tttccctaga ggcaaacatt tcttaaaatg tttcattttc attaaaaatg
4081  aaagccaaat ttatatgcca ccgattgcag gacacaagca cagttttaag agttgtatga
4141  acatggagag gacttttggt ttttatattt ctcgtattta atatgggtga acaccaactt
4201  ttatttggaa taataatttt cctcctaaac aaaaacacat tgagtttaag tctctgactc
4261  ttgcctttcc acctgctttc tcctgggccc gctttgcctg cttgaaggaa cagtgctgtt
4321  ctggagctgc tgttccaaca gacagggcct agctttcatt tgacacacag actacagcca
4381  gaagcccatg gagcagggat gtcacgtctt gaaaagccta ttagatgttt tacaaattta
4441  attttgcaga ttattttagt ctgtcatcca gaaaatgtgt cagcatgcat agtgctaaga
4501  aagcaagcca atttggaaac ttaggttagt gacaaaattg gccagagagt gggggtgatg
4561  atgaccaaga attacaagta gaatggcagc tggaatttaa ggagggacaa gaatcaatgg
4621  ataagcgtgg gtggaggaag atccaaacag aaaagtgcaa agttattccc catcttccaa
4681  gggttgaatt ctggaggaag aagacacatt cctagttccc cgtgaacttc ctttgactta
4741  ttgtccccac taaaacaaaa caaaaaactt ttaatgcctt ccacattaat tagattttct
4801  tgcagttttt ttatggcatt ttttttaaga tgccctaagt gttgaagaag agtttgcaaa
```

```
                                      -continued
4861   tgcaacaaaa tatttaatta ccggttgtta aaactggttt agcacaattt atattttccc 4921   tctcttgcct ttcttatttg caataaaagg tattgagcca ttttttaaat gacattttg 4981   ataaattatg tttgtactag ttgatgaagg agttttttt  aacctgttta tataattttg 5041   cagcagaagc caaattttt  gtatattaaa gcaccaaatt catgtacagc atgcatcacg 5101   gatcaataga ctgtacttat tttccaataa aattttcaaa ctttgtactg ttaaaaaaaa 5161   aaaaaaaaaa
```

The amino acid sequence of human IL-1R type 1 isoform 1 precursor, provided by Genbank Accession No. NP_000868.1, is incorporated herein by reference, and is shown below (SEQ ID NO:92).

```
  1 mkvllrlicf iallisslea dkckereeki ilvssaneid vrpcplnpne hkgtitwykd
 61 dsktpvsteq asrihqhkek lwfvpakved sghyycvvrn ssyclrikis akfvenepnl
121 cynaqaifkq klpvagdggl vcpymeffkn ennelpklqw ykdckpllld nihfsgvkdr
181 livmnvaekh rgnytchasy tylgkqypit rviefitlee nkptrpvivs panetmevdl
241 gsqiqlicnv tgqlsdiayw kwngsvided dpvlgedyys venpankrrs tlitvlnise
301 iesrfykhpf tcfaknthgi daayiqliyp vtnfqkhmig icvtltviiv csvfiykifk
361 idivlwyrds cydflpikas dgktydayil ypktvgegst sdcdifvfkv lpevlekqcg
421 yklfiygrdd yvgedivevi nenvkksrrl iiilvretsg fswlggssee qiamynalvq
481 dgikvvllel ekiqdyekmp esikfikqkh gairwsgdft qgpqsaktrf wknvryhmpv
541 qrrspsskhq llspatkekl greahvplg
(Signal peptide 1-20; mature peptide AA 21-569).
```

The siRNA used to target human IL-1R type 1 variant 1 mRNA include following sequences (SEQ ID NO: 93-96):

```
SEQ NO: 93:
5'-UUUCUUCUCACAAACGUGCC-3'

SEQ NO: 94:
5'-UUAUACCAAGUUAUAGUGCC-3'

SEQ NO: 95:
5'-UUGUAAAACAUCUAAUAGGC-3'

SEQ NO: 96:
5'-UUUCCACACUGUAAUAGUCU-3'
```

The molecular beacon used to target human IL-1R type 1 variant 1 mRNA includes the following sequences (SEQ ID NO: 97-99):

```
SEQ NO 97:
5'-CCGGTC TTTCTTCTCACAAACGTGC GACCGG-3'

SEQ NO 98:
5'-CCGGTC TTAAACACAAAAATATCAC GACCGG-3'

SEQ NO 99:
5'-CCGGTC TTTCCACACTGTAATAGTC GACCGG-3'
```

The mRNA transcript sequence encoding human TNF-alpha, provided by Genbank Accession No. NM_000594.3, is incorporated herein by reference, and is shown below (SEQ ID NO: 100).

```
  1 cagacgctcc ctcagcaagg acagcagagg accagctaag agggagagaa gcaactacag
 61 accccccctg aaaacaaccc tcagacgcca catcccctga caagctgcca ggcaggttct
121 cttcctctca catactgacc cacggctcca ccctctctcc cctggaaagg acaccatgag
181 cactgaaagc atgatccggg acgtggagct ggccgaggag gcgctcccca agaagacagg
241 ggggccccag ggctccaggc ggtgcttgtt cctcagcctc ttctccttcc tgatcgtggc
301 aggcgccacc acgctcttct gcctgctgca ctttggagtg atcggccccc agagggaaga
361 gttcccagg gacctctctc taatcagccc tctggcccag gcagtcagat catcttctcg
421 aacccccgagt gacaagcctg tagcccatgt gtagcaaac cctcaagctg aggggcagct
481 ccagtggctg aaccgccggg ccaatgccct cctggccaat ggcgtggagc tgagagataa
541 ccagctggtg gtgccatcag agggcctgta cctcatctac tcccaggtcc tcttcaaggg
601 ccaaggctgc ccctccaccc atgtgctcct cacccacacc atcagccgca tcgccgtctc
661 ctaccagacc aaggtcaacc tcctctctgc catcaagagc cctgccaga gggagacccc
721 agagggggct gaggccaagc cctggtatga gcccatctat ctgggagggg tcttccagct
781 ggagaagggt gaccgactca gcgctgagat caatcggccc gactatctcg actttgccga
841 gtctgggcag gtctactttg ggatcattgc cctgtagga ggacgaacat ccaaccttcc
901 caaacgcctc ccctgcccca atccctttat tacccctcc ttcagacacc ctcaacctct
961 tctggctcaa aaagagaatt gggggcttag ggtcggaacc caagcttaga actttaagca
1021 acaagaccac cacttcgaaa cctgggattc aggaatgtgt ggcctgcaca gtgaagtgct
1081 ggcaaccact aagaattcaa actggggcct ccagaactca ctggggccta cagctttgat
1141 ccctgacatc tggaatctgg agaccaggga gcctttggtt ctggccagaa tgctgcagga
1201 cttgagaaga cctcacctag aaattgacac aagtggacct taggccttcc tctctccaga
1261 tgtttccaga cttccttgag acacggagcc cagccctccc catggagcca gctccctcta
1321 tttatgtttg cacttgtgat tatttattat ttatttatta tttatttatt tacagatgaa
1381 tgtatttatt tgggagaccg gggtatcctg ggggacccaa tgtaggagct gccttggctc
1441 agacatgttt tccgtgaaaa cggagctgaa caataggctg ttcccatgta gcccctggc
1501 ctctgtgcct tcttttgatt atgttttta aatatttat ctgattaagt tgtctaaaca
1561 atgctgattt ggtgaccaac tgtcactcat tgctgagcct ctgctcccca ggggagttgt
1621 gtctgtaatc gccctactat tcagtggcga gaaataaagt ttgcttagaa aagaaaaaaa
1681 aaaaaa
```

The amino acid sequence of human TNF-alpha, provided by Genbank Accession No. NP_000585.2, is incorporated herein by reference, and is shown below (SEQ ID NO:101).

```
  1 mstesmirdv elaeealpkk tggpqgsrrc lflslfsfli vagattlfcl lhfgvigpqr
 61 eefprdlsli splaqavrss srtpsdkpva hvvanpqaeg qlqwlnrran allangvelr
121 dnqlvvpseg lyliysqvlf kgqgcpsthv llthtisria vsyqtkvnll saikspcqre
181 tpegaeakpw yepiylggvf qlekgdrlsa einrpdyldf aesgqvyfgi ial
```

The siRNA used to target human TNF-alpha mRNA include following sequences (SEQ ID NO: 102-105):

SEQ NO: 102:
5'-AAUAAAUAAUCACAAGUGC-3'

SEQ NO: 103:
5'-UAAAAAACAUAAUCAAAAG-3'

SEQ NO: 104:
5'-UAAUAAAUAAUCACAAGUG-3'

SEQ NO: 105:
5'-UUUUCUUUUCUAAGCAAAC-3'

The molecular beacon used to target human TNF-alpha mRNA includes the following sequences (SEQ ID NO: 106-108):

SEQ NO 106:
5'-CCGGTC AAACATAATCAAAAGAAGG GACCGG-3'

SEQ NO 107:
5'-CCGGTC TAAAAAACATAATCAAAAG GACCGG-3'

SEQ NO 108:
5'-CCGGTC TATTTTAAAAAACATAATC GACCGG-3'

The mRNA transcript sequence encoding human VEGF A variant 1, provided by Genbank Accession No. NM_001025366.2, is incorporated herein by reference, and is shown below (SEQ ID NO: 109).

```
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 catttttttt taaaactgta ttgtttctcg ttttaattta tttttgcttg ccattcccca
 241 cttgaatcgg gccgacggct tggggagatt gctctacttc cccaaatcac tgtggatttt
 301 ggaaaccagc agaaagagga aagaggtagc aagagctcca gagagaagtc gaggaagaga
 361 gagacggggt cagagagagc gcgcgggcgt gcgagcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccgcg gcggacagtg gacgcggcgg cgagccgcgg gcaggggccg
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag aggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcc ccgaggcgcc
 961 gaggagagcg gccgccccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg gctgctgca atgacgaggg cctggagtgt
1321 gtgcccactg aggagtccaa catcaccatg cagattatgc ggatcaaacc tcaccaaggc
1381 cagcacatag agagatgag cttcctacag cacaacaaat gtgaatgcag accaaagaaa
1441 gatagagcaa gacaagaaaa aaaatcagtt cgaggaaagg gaaagggca aaaacgaaag
1501 cgcaagaaat cccggtataa gtcctggagc gtgtacgttg gtgcccgctg ctgtctaatg
1561 ccctggagcc tcctggcc catccctgt gggccttgct cagagcgag aaagcatttg
1621 tttgtacaag atccgcagac gtgtaaatgt tcctgcaaaa acacagactc gcgttgcaag
1681 gcgaggcagc ttgagttaaa cgaacgtact tgcagatgtg acaagccgag gcggtgagcc
1741 gggcaggagg aaggagcctc cctcagggtt tcgggaacca gatctctcac caggaaagac
```

-continued

```
1801 tgatacagaa cgatcgatac agaaaccacg ctgccgccac cacaccatca ccatcgacag 1861 aacagtcctt aatccagaaa cctgaaatga aggaagagga gactctgcgc agagcacttt 1921 gggtccggag ggcgagactc cggcggaagc attcccgggc gggtgaccca gcacggtccc 1981 tcttggaatt ggattcgcca ttttatttt cttgctgcta aatcaccgag cccggaagat 2041 tagagagttt tatttctggg attcctgtag acacacccac ccacatacat acatttatat 2101 atatatatat tatatatata taaaaataaa tatctctatt ttatatatat aaaatatata 2161 tattctttt ttaaattaac agtgctaatg ttattggtgt cttcactgga tgtatttgac 2221 tgctgtggac ttgagttggg aggggaatgt tcccactcag atcctgacag gaagaggag 2281 gagatgagag actctggcat gatcttttt ttgtcccact tggtggggcc agggtcctct 2341 cccctgccca ggaatgtgca aggccagggc atggggcaa atatgaccca gttttgggaa 2401 caccgacaaa cccagccctg cgctgagcc tctctacccc aggtcagacg gacagaaaga 2461 cagatcacag gtacagggat gaggacaccg gctctgacca ggagtttggg gagcttcagg 2521 acattgctgt gctttgggga ttccctccac atgctgcacg cgcatctcgc ccccaggggc 2581 actgcctgga agattcagga gcctgggcgg ccttcgctta ctctcacctg cttctgagtt 2641 gcccaggaga ccactggcag atgtcccggc gaagagaaga gacacattgt tggaagaagc 2701 agcccatgac agctccctt cctgggactc gccctcatcc tcttcctgct ccccttcctg 2761 gggtgcagcc taaaaggacc tatgtcctca caccattgaa accactagtt ctgtcccccc 2821 aggagacctg gttgtgtgtg tgtgagtggt tgaccttcct ccatcccctg gtccttccct 2881 tcccttcccg aggcacagag agacagggca ggatccacgt gcccattgtg gaggcagaga 2941 aaagagaaag tgttttatat acggtactta tttaatatcc ctttttaatt agaaattaaa 3001 acagttaatt taattaaaga gtagggtttt ttttcagtat tcttggttaa tatttaattt 3061 caactattta tgagatgtat cttttgctct ctcttgctct cttatttgta ccggttttg 3121 tatataaaat tcatgtttcc aatctctctc tccctgatcg gtgacagtca ctagcttatc 3181 ttgaacagat atttaatttt gctaacactc agctctgccc tccccgatcc cctggctccc 3241 cagcacacat tcctttgaaa taaggtttca atatacatct acatactata tatatatttg 3301 gcaacttgta tttgtgtgta tatatatata tatatgttta tgtatatatg tgattctgat 3361 aaaatagaca ttgctattct gttttttata tgtaaaaaca aaacaagaaa aaatagagaa 3421 ttctacatac taaatctctc tccttttta atttaatat ttgttatcat ttatttattg 3481 gtgctactgt ttatccgtaa taattgtggg gaaaagatat taacatcacg tctttgtctc 3541 tagtgcagtt tttcgagata ttccgtagta catatttatt tttaaacaac gacaaagaaa 3601 tacagatata tcttaaaaaa aaaaaagcat tttgtattaa agaatttaat tctgatctca 3661 aaaaaaaaa aaaaaaa
```

The amino acid sequence of human VEGF A isoform 1, provided by Genbank Accession No. NP_001020537.2, is incorporated herein by reference, and is shown below (SEQ ID NO:110).

```
  1 mtdrqtdtap spsyhllpgr rrtvdaaasr gqgpepapgg gvegvgargv alklfvqllg 61 csrfggavvr ageaepsgaa rsassgreep qpeegeeeee keeergpqwr lgarkpgswt 121 geaavcadsa paarpqala rasgrggrva rrgaeesgpp hspsrrgsas ragpgraset 181 mnfllswvhw slalllylhh akwsqaapma egggqnhhev vkfmdvyqrs ychpietlvd 241 ifqeypdeie yifkpscvpl mrcggccnde glecvptees nitmqimrik phqgqhigem
```

-continued

```
301 sflqhnkcec rpkkdrarqe kksvrgkgkg qkrkrkksry kswsvyvgar cclmpwslpg 361 phpcgpcser rkhlfvqdpq tckcsckntd srckarqlel nertcrcdkp rr
```

The siRNA used to target human VEGF Avariant 1 mRNA include following sequences (SEQ ID NO: 111-114):

```
SEQ NO: 111:
5'-UAAAACUCUCUAAUCUUCCGG-3'

SEQ NO: 112:
5'-UUCCUUCUCUUCUUCCUCCUC-3'

SEQ NO: 113:
5'-UAUACACACAAAUACAAGUUG-3'

SEQ NO: 114:
5'-UUAAAACGAGAAACAAUACAG-3'
```

The molecular beacon used to target human VEGF Avariant 1 mRNA includes the following sequences (SEQ ID NO: 115-117):

```
SEQ NO 115:
5'-CCGGTC TAAAACTCTCTAATCTTCC GACCGG-3'

SEQ NO 116:
5'-CCGGTC TTTGATCCGCATAATCTGC GACCGG-3'

SEQ NO 117:
5'-CCGGTC TTGAAATTAAATATTAACC GACCGG-3'
```

The mRNA transcript sequence encoding human TGF-beta 1, provided by Genbank Accession No. NM_000660.5, is incorporated herein by reference, and is shown below (SEQ ID NO: 118).

```
   1 agccggtccc cgccgccgcc gcccttcgcg ccctgggcca tctccctccc acctccctcc
  61 gcggagcagc cagacagcga gggccccggc cggggcagg ggggacgccc cgtccgggc
 121 accccccgg ctctgagccg cccgcggggc cggcctcggc ccggagcgga ggaaggagtc
 181 gccgaggagc agcctgaggc cccagagtct gagacgagcc gccgccgcc ccgccactgc
 241 ggggaggagg gggaggagga gcgggaggag ggacgagctg gtcgggagaa gaggaaaaaa
 301 acttttgaga cttttccgtt gccgctggga gccggaggcg cggggacctc ttggcgcgac
 361 gctgccccgc gaggaggcag gacttgggga ccccagaccg cctcccttg ccgccgggga
 421 cgcttgctcc ctccctgccc cctacacggg gtccctcagg cgcccccatt ccggaccagc
 481 cctcgggagt cgccgacccg gcctcccgca aagactttc cccagacctc gggcgcaccc
 541 cctgcacgcc gccttcatcc ccggcctgtc tcctgagccc ccgcgcatcc tagacccttt
 601 ctcctccagg agacggatct ctctccgacc tgccacagat cccctattca agaccaccca
 661 ccttctggta ccagatcgcg cccatctagg ttatttccgt gggatactga gacaccccg
 721 gtccaagcct cccctccacc actgcgccct tctccctgag gacctcagct ttccctcgag
 781 gccctcctac cttttgccgg gagacccca gccctgcag gggcggggcc tccccaccac
 841 accagccctg ttcgcgctct cggcagtgcc ggggggcgcc gcctccccca tgccgccctc
 901 cgggctgcgg ctgctgccgc tgctgctacc gctgctgtgg ctactggtgc tgacgcctgg
 961 ccggccggcc gcgggactat ccacctgcaa gactatcgac atggagctgg tgaagcggaa
1021 gcgcatcgag gccatccgcg gcagatcct gtccaagctg cggctcgcca gcccccgag
1081 ccaggggag gtgccgcccg gccgctgcc cgaggccgtg ctcgccctgt acaacagcac
1141 ccgcgaccgg gtggccgggg agagtgcaga accggagccc gagcctgagg ccgactacta
1201 cgccaaggag gtcacccgcg tgctaatggt ggaaacccac aacgaaatct atgacaagtt
1261 caagcagagt acacacagca tatatatgtt cttcaacaca tcagagctcc gagaagcggt
1321 acctgaaccc gtgttgctct ccgggcaga gctgcgtctg ctgaggctca agttaaaagt
1381 ggagcagcac gtggagctgt accagaaata cagcaacaat tcctggcgat acctcagcaa
1441 ccggctgctg gcacccagcg actcgccaga gtggttatct tttgatgtca ccggagttgt
1501 gcggcagtgg ttgagccgtg gaggggaaat tgagggcttt cgccttagcg cccactgctc
1561 ctgtgacagc agggataaca cactgcaagt ggacatcaac gggttcacta ccggccgccg
```

```
1621  aggtgacctg gccaccattc atggcatgaa ccggcctttc ctgcttctca tggccacccc 1681  gctggagagg gcccagcatc tgcaaagctc ccggcaccgc cgagccctgg acaccaacta 1741  ttgcttcagc tccacggaga agaactgctg cgtgcggcag ctgtacattg acttccgcaa 1801  ggacctcggc tggaagtgga tccacgagcc caagggctac catgccaact tctgcctcgg 1861  gccctgcccc tacatttgga gcctggacac gcagtacagc aaggtcctgg ccctgtacaa 1921  ccagcataac ccgggcgcct cggcggcgcc gtgctgcgtg ccgcaggcgc tggagccgct 1981  gcccatcgtg tactacgtgg gccgcaagcc caaggtggag cagctgtcca acatgatcgt 2041  gcgctcctgc aagtgcagct gaggtcccgc cccgccccgc cccgcccgg caggccggc 2101  cccacccgc cccgccccg ctgccttgcc catgggggct gtatttaagg cacccgtgc 2161  cccaagccca cctggggccc cattaaagat ggagagagga ctgcggatct ctgtgtcatt 2221  gggcgcctgc ctggggtctc catccctgac gttcccccac tcccactccc tctctctccc 2281  tctctgcctc ctcctgcctg tctgcactat tcctttgccc ggcatcaagg cacaggggac 2341  cagtggggaa cactactgta gttagatcta tttattgagc accttgggca ctgttgaagt 2401  gccttacatt aatgaactca ttcagtcacc atagcaacac tctgagatgc agggactctg 2461  ataacaccca ttttaaaggt gaggaaacaa gcccagagag gttaagggag gagttcctgc 2521  ccaccaggaa cctgctttag tgggggatag tgaagaagac aataaaagat agtagttcag 2581  gcc
```

The amino acid sequence of human TGF-beta 1 (precursor), provided by Genbank Accession No. NP_000651.3, is incorporated herein by reference, and is shown below (SEQ ID NO:119).

```
  1  mppsglrllp lllpllwllv ltpgrpaagl stcktidmel vkrkrieair gqilsklrla 61  sppsqgevpp gplpeavlal ynstrdrvag esaepepepe adyyakevtr vlmvethnei 121  ydkfkqsths iymffntsel reavpepvll sraelrllrl klkveqhvel yqkysnnswr 181  ylsnrllaps dspewlsfdv tgvvrqwlsr ggeiegfrls ahcscdsrdn tlqvdingft 241  tgrrgdlati hgmnrpflll matpleraqh lqssrhrral dtnycfsste knccvrqlyi 301  dfrkdlgwkw ihepkgyhan fclgpcpyiw sldtqyskvl alynqhnpga saapccvpqa 361  leplpivyyv grkpkveqls nmivrsckcs
```
(Signal peptide AA 1-29; mature peptide AA 30-278).

The siRNA used to target human TGF-beta 1 mRNA include following sequences (SEQ ID NO: 120-123):

SEQ NO: 120:
5'-UAUUGUCUUCUUCACUAUC-3'

SEQ NO: 121:
5'-UAGAUCUAACUACAGUAGU-3'

SEQ NO: 122:
5'-UAUAUGCUGUGUGUACUCU-3'

SEQ NO: 123:
5'-UAUAUAUGCUGUGUGUACU-3'

The molecular beacon used to target human TGF-beta 1 mRNA includes the following sequences (SEQ ID NO: 124-126):

SEQ NO 124:
5'-CCGGTC ATATATGCTGTGTGTACTC GACCGG-3'

SEQ NO 125:
5'-CCGGTC TTTTATTGTCTTCTTCACT GACCGG-3'

SEQ NO 126:
5'-CCGGTC TATATATGCTGTGTGTACT GACCGG-3'

The mRNA transcript sequence encoding human TGF-beta 2 variant 1, provided by Genbank Accession No. NM_001135599.2, is incorporated herein by reference, and is shown below (SEQ ID NO: 127).

```
   1 gtgatgttat ctgctggcag cagaaggttc gctccgagcg gagctccaga agctcctgac
  61 aagagaaaga cagattgaga tagagataga aagagaaaga gagaaagaga cagcagagcg
 121 agagcgcaag tgaaagaggc aggggagggg gatggagaat attagcctga cggtctaggg
 181 agtcatccag gaacaaactg aggggctgcc cggctgcaga caggaggaga cagagaggat
 241 ctattttagg gtggcaagtg cctacctacc ctaagcgagc aattccacgt tggggagaag
 301 ccagcagagg ttgggaaagg gtgggagtcc aagggagccc ctgcgcaacc ccctcaggaa
 361 taaaactccc cagccagggt gtcgcaaggc ctgccgttgt gatccgcagg gggtgaacgc
 421 aaccgcgacg gctgatcgtc tgtggctggg ttggcgtttg gagcaagaga aggaggagca
 481 ggagaaggag ggagctggag gctgaagcg tttgcaagcg gcggcggcag caacgtggag
 541 taaccaagcg ggtcagcgcg cgcccgccag ggtgtaggcc acggagcgca gctcccagag
 601 caggatccgc gccgcctcag cagcctctgc ggcccctgcg gcacccgacc gagtaccgag
 661 cgccctgcga agcgcaccct cctccccgcg gtgcgctggg ctcgccccca gcgcgcgcac
 721 acgcacacac acacacacac acacacacgc acgcacacac gtgtgcgctt ctctgctccg
 781 gagctgctgc tgctcctgct ctcagcgccg cagtggaagg caggaccgaa ccgctccttc
 841 tttaaatata taaatttcag cccaggtcag cctcggcggc cccctcacc gcgctcccgg
 901 cgcccctccc gtcagttcgc cagctgccag ccccgggacc ttttcatctc ttccctttg
 961 gccggaggag ccgagttcag atccgccact ccgcacccga gactgacaca ctgaactcca
1021 cttcctcctc ttaaatttat ttctacttaa tagccactcg tctcttttt tccccatctc
1081 attgctccaa gattttttt cttcttactc gccaaagtca gggttccctc tgcccgtccc
1141 gtattaatat ttccactttt ggaactactg gcctttctt tttaaaggaa ttcaagcagg
1201 atacgttttt ctgttgggca ttgactagat tgtttgcaaa agtttcgcat caaaaacaac
1261 aacaacaaaa aaccaaacaa ctctccttga tctatacttt gagaattgtt gatttctttt
1321 ttttattctg acttttaaaa acaactttt tttccacttt tttaaaaat gcactactgt
1381 gtgctgagcg cttttctgat cctgcatctg gtcacggtcg cgctcagcct gtctacctgc
1441 agcacactcg atatggacca gttcatgcgc aagaggatcg aggcgatccg cgggcagatc
1501 ctgagcaagc tgaagctcac cagtccccca gaagactatc ctgagcccga ggaagtcccc
1561 ccggaggtga tttccatcta caacagcacc agggacttgc tccaggagaa ggcgagccgg
1621 agggcggccg cctgcgagcg cgagaggagc gacgaagagt actacgccaa ggaggtttac
1681 aaaatagaca tgccgccctt cttccccctcc gaaactgtct gcccagttgt tacaacaccc
1741 tctggctcag tgggcagctt gtgctccaga cagtcccagg tgctctgtgg gtaccttgat
```

-continued

```
1801  gccatcccgc ccactttcta cagaccctac ttcagaattg ttcgatttga cgtctcagca
1861  atggagaaga atgcttccaa tttggtgaaa gcagagttca gagtctttcg tttgcagaac
1921  ccaaaagcca gagtgcctga caacggatt gagctatatc agattctcaa gtccaaagat
1981  ttaacatctc caacccagcg ctacatcgac agcaaagttg tgaaaacaag agcagaaggc
2041  gaatggctct ccttcgatgt aactgatgct gttcatgaat ggcttcacca taaagacagg
2101  aacctgggat ttaaaataag cttacactgt ccctgctgca cttttgtacc atctaataat
2161  tacatcatcc caaataaaag tgaagaacta gaagcaagat ttgcaggtat tgatggcacc
2221  tccacatata ccagtggtga tcagaaaact ataaagtcca ctaggaaaaa aaacagtggg
2281  aagaccccac atctcctgct aatgttattg ccctcctaca gacttgagtc acaacagacc
2341  aaccggcgga agaagcgtgc tttggatgcg gcctattgct ttagaaatgt gcaggataat
2401  tgctgcctac gtccacttta cattgatttc aagagggatc tagggtggaa atggatacac
2461  gaacccaaag ggtacaatgc caacttctgt gctggagcat gcccgtattt atggagttca
2521  gacactcagc acagcagggt cctgagctta taataccca taaatccaga agcatctgct
2581  tctccttgct gcgtgtccca agatttagaa cctctaacca ttctctacta cattggcaaa
2641  acacccaaga ttgaacagct ttctaatatg attgtaaagt cttgcaaatg cagctaaaat
2701  tcttggaaaa gtggcaagac caaaatgaca atgatgatga taatgatgat gacgacgaca
2761  acgatgatgc ttgtaacaag aaaacataag agagccttgg ttcatcagtg ttaaaaaatt
2821  tttgaaaagg cggtactagt tcagacactt tggaagtttg tgttctgttt gttaaaactg
2881  gcatctgaca caaaaaagt tgaaggcctt attctacatt tcacctactt tgtaagtgag
2941  agagacaaga agcaaatttt tttaaagaa aaaaataaac actggaagaa tttattagtg
3001  ttaattatgt gaacaacgac aacaacaaca acaacaacaa acaggaaaat cccattaagt
3061  ggagttgctg tacgtaccgt tcctatcccg cgcctcactt gattttctg tattgctatg
3121  caataggcac ccttcccatt cttactctta gagttaacag tgagttattt attgtgtgtt
3181  actatataat gaacgtttca ttgcccttgg aaaataaaac aggtgtataa agtggagacc
3241  aaatactttg ccagaaactc atggatggct taaggaactt gaactcaaac gagccagaaa
3301  aaaagaggtc atattaatgg gatgaaaacc caagtgagtt attatatgac cgagaaagtc
3361  tgcattaaga taaagaccct gaaaacacat gttatgtatc agctgcctaa ggaagcttct
3421  tgtaaggtcc aaaaactaaa aagactgtta ataaaagaaa ctttcagtca gaataagtct
3481  gtaagttttt ttttttcttt ttaattgtaa atggttcttt gtcagtttag taaaccagtg
3541  aaatgttgaa atgttttgac atgtactggt caaacttcag accttaaaat attgctgtat
3601  agctatgcta taggttttt cctttgtttt ggtatatgta accataccta tattattaaa
3661  atagatggat atagaagcca gcataattga aaacacatct gcagatctct tttgcaaact
3721  attaaatcaa aacattaact actttatgtg taatgtgtaa attttacca tattttttat
3781  attctgtaat aatgtcaact atgatttaga ttgacttaaa tttgggctct ttttaatgat
3841  cactcacaaa tgtatgtttc ttttagctgg ccagtacttt tgagtaaagc ccctatagtt
3901  tgacttgcac tacaaatgca tttttttttt aataacattt gccctacttg tgctttgtgt
3961  ttctttcatt attatgacat aagctacctg ggtccacttg tcttttcttt ttttgtttc
4021  acagaaaaga tgggttcgag ttcagtggtc ttcatcttcc aagcatcatt actaaccaag
4081  tcagacgtta acaaattttt atgttaggaa aaggaggaat gttatagata catagaaaat
4141  tgaagtaaaa tgttttcatt ttagcaagga tttagggttc taactaaaac tcagaatctt
4201  tattgagtta agaaaagttt ctctaccttg gtttaatcaa tatttttgta aaatcctatt
```

-continued

```
4261   gttattacaa agaggacact tcataggaaa catctttttc tttagtcagg tttttaatat
4321   tcagggggaa attgaaagat atatatttta gtcgattttt caaaagggga aaaaagtcca
4381   ggtcagcata agtcattttg tgtatttcac tgaagttata aggtttttat aaatgttctt
4441   tgaaggggaa aaggcacaag ccaatttttc ctatgatcaa aaaattcttt ctttcctctg
4501   agtgagagtt atctatatct gaggctaaag tttaccttgc tttaataaat aatttgccac
4561   atcattgcag aagaggtatc ctcatgctgg ggttaataga atatgtcagt ttatcacttg
4621   tcgcttattt agctttaaaa taaaaattaa taggcaaagc aatggaatat ttgcagtttc
4681   acctaaagag cagcataagg aggcgggaat ccaaagtgaa gttgtttgat atggtctact
4741   tctttttgg aatttcctga ccattaatta aagaattgga tttgcaagtt tgaaaactgg
4801   aaaagcaaga gatgggatgc cataatagta aacagccctt gtgttggatg taacccaatc
4861   ccagatttga gtgtgtgttg attattttt tgtcttccac ttttctatta tgtgtaaatc
4921   acttttattt ctgcagacat tttcctctca gataggatga cattttgttt tgtattattt
4981   tgtctttcct catgaatgca ctgataatat tttaaatgct ctattttaag atctcttgaa
5041   tctgtttttt tttttttaa tttgggggtt ctgtaaggtc tttatttccc ataagtaaat
5101   attgccatgg gagggggggtg gaggtggcaa ggaaggggtg aagtgctagt atgcaagtgg
5161   gcagcaatta tttttgtgtt aatcagcagt acaatttgat cgttggcatg gttaaaaaat
5221   ggaatataag attagctgtt ttgtattttg atgaccaatt acgctgtatt ttaacacgat
5281   gtatgtctgt ttttgtggtg ctctagtggt aaataaatta tttcgatgat atgtggatgt
5341   ctttttccta tcagtaccat catcgagtct agaaaacacc tgtgatgcaa taagactatc
5401   tcaagctgga aaagtcatac cacctttccg attgccctct gtgctttctc ccttaaggac
5461   agtcacttca gaagtcatgc tttaaagcac aagagtcagg ccatatccat caaggataga
5521   agaaatccct gtgccgtctt tttattccct tatttattgc tatttggtaa ttgtttgaga
5581   tttagtttcc atccagcttg actgccgacc agaaaaaatg cagagagatg tttgcaccat
5641   gctttggctt tctggttcta tgttctgcca acgccagggc caaaagaact ggtctagaca
5701   gtatcccctg tagccccata acttggatag ttgctgagcc agccagatat aacaagagcc
5761   acgtgctttc tggggttggt tgtttgggat cagctacttg cctgtcagtt tcactggtac
5821   cactgcacca caaacaaaaa aacccaccct atttcctcca atttttttgg ctgctaccta
5881   caagaccaga ctcctcaaac gagttgccaa tctcttaata aataggatta ataaaaaaag
5941   taattgtgac tcaaaaaaaa aaaaaa
```

The amino acid sequence of human TGF-beta 2 isoform 1 precursor, provided by Genbank Accession No. NP_001129071.1, is incorporated herein by reference, and is shown below (SEQ ID NO:128).

```
  1    mhycvlsafl ilhlvtvals lstcstldmd qfmrkrieai rgqilsklkl tsppedypep
 61    eevppevisi ynstrdllqe kasrraaace rersdeeyya kevykidmpp ffpsetvcpv
121    vttpsgsvgs lcsrqsqvlc gyldaipptf yrpyfrivrf dvsameknas nlvkaefrvf
181    rlqnpkarvp eqrielyqil kskdltsptq ryidskvvkt raegewlsfd vtdavhewlh
241    hkdrnlgfki slhcpcctfv psnnyiipnk seelearfag idgtstytsg dqktikstrk
301    knsgktphll lmllpsyrle sqqtnrrkkr aldaaycfrn vqdncclrpl yidfkrdlgw
361    kwihepkgyn anfcagacpy lwssdtqhsr vlslyntinp easaspccvs qdlepltily
421    yigktpkieq lsnmivksck cs
```

The siRNA used to target human TGF-beta 2 variant 1 mRNA include following sequences (SEQ ID NO: 129-132):

SEQ NO: 129:
5'-UAUCUCUAUCUCAAUCUGUC-3'

SEQ NO: 130:
5'-UUCUAUCUCUAUCUCAAUCU-3'

SEQ NO: 131:
5'-UUCUCUUUCUAUCUCUAUCU-3'

SEQ NO: 132:
5'-UCUAUCUCUAUCUCAAUCUG-3'

The molecular beacon used to target human TGF-beta 2 variant 1 mRNA includes the following sequences (SEQ ID NO: 133-135):

SEQ NO 133:
5'-CCGGTC TTCTATCTCTATCTCAATC GACCGG-3'

SEQ NO 134:
5'-CCGGTC TATCTCTATCTCAATCTGT GACCGG-3'

SEQ NO 135:
5'-CCGGTC TTCTCTTTCTATCTCTATC GACCGG-3'

The mRNA transcript sequence encoding human IGF-1 variant 4, provided by Genbank Accession No. NM_000618.3, is incorporated herein by reference, and is shown below (SEQ ID NO: 136).

```
   1 ttttgtagat aaatgtgagg attttctcta aatccctctt ctgtttgcta aatctcactg
  61 tcactgctaa attcagagca gatagagcct gcgcaatgga ataaagtcct caaaattgaa
 121 atgtgacatt gctctcaaca tctcccatct ctctggattt cttttttgctt cattattcct
 181 gctaaccaat tcattttcag actttgtact tcagaagcaa taggaaaaat cagcagtctt
 241 ccaacccaat tatttaagtg ctgcttttgt gatttcttga aggtgaagat gcacaccatg
 301 tcctcctcgc atctcttcta cctggcgctg tgcctgctca ccttcaccag ctctgccacg
 361 gctggaccgg agacgctctg cggggctgag ctggtggatg ctcttcagtt cgtgtgtgga
 421 gacaggggct tttatttcaa caagcccaca gggtatggct ccagcagtcg gagggcgcct
 481 cagacaggca tcgtggatga gtgctgcttc cggagctgtg atctaaggag gctggagatg
 541 tattgcgcac ccctcaagcc tgccaagtca gctcgctctg tccgtgccca gcgccacacc
 601 gacatgccca agacccagaa ggaagtacat tgaagaacg caagtagagg gagtgcagga
 661 aacaagaact acaggatgta ggaagaccct cctgaggagt gaagagtgac atgccaccgc
 721 aggatccttt gctctgcacg agttacctgt taaactttgg aacacctacc aaaaaataag
 781 tttgataaca tttaaaagat gggcgtttcc cccaatgaaa tacacaagta aacattccaa
 841 cattgtcttt aggagtgatt tgcaccttgc aaaaatggtc ctggagttgg tagattgctg
 901 ttgatctttt atcaataatg ttctataaa aagaaaaaa aatatatat atatatatat
 961 cttagtccct gcctctcaag agccacaaat gcatgggtgt tgtatagatc cagttgcact
1021 aaattcctct ctgaatcttg gctgctggag ccattcattc agcaaccttg tctaagtggt
1081 ttatgaattg tttccttatt tgcacttctt tctacacaac tcgggctgtt tgttttacag
1141 tgtctgataa tcttgttagt ctatacccac cacctcactt cataaccttt atatttgccg
1201 aatttggcct cctcaaaagc agcagcaagt cgtcaagaag cacaccaatt ctaacccaca
1261 agattccatc tgtggcattt gtaccaaata taagttggat gcattttatt ttagacacaa
1321 agctttattt ttccacatca tgcttacaaa aagaataat gcaaatagtt gcaactttga
1381 ggccaatcat tttttaggcat atgttttaaa catagaaagt ttcttcaact caaaagagtt
1441 ccttcaaatg atgagttaat gtgcaaccta attagtaact ttcctctttt tattttttcc
1501 atatagagca ctatgtaaat ttagcatatc aattatacag gatatatcaa acagtatgta
1561 aaactctgtt ttttagtata atggtgctat tttgtagttt gttatatgaa agagtctggc
1621 caaaacggta atacgtgaaa gcaaaacaat aggggaagcc tggagccaaa gatgacacaa
1681 ggggaagggt actgaaaaca ccatccattt gggaaagaag gcaaagtccc cccagttatg
1741 ccttccaaga ggaacttcag acacaaaagt ccactgatgc aaattggact ggcgagtcca
```

-continued

```
1801  gagaggaaac tgtggaatgg aaaaagcaga aggctaggaa ttttagcagt cctggtttct
1861  ttttctcatg gaagaaatga acatctgcca gctgtgtcat ggactcacca ctgtgtgacc
1921  ttgggcaagt cacttcacct ctctgtgcct cagtttcctc atctgcaaaa tgggggcaat
1981  atgtcatcta cctacctcaa aggggtggta taaggtttaa aaagataaag attcagattt
2041  tttttaccct gggttgctgt aagggtgcaa catcagggcg cttgagttgc tgagatgcaa
2101  ggaattctat aaataaccca ttcatagcat agctagagat tggtgaattg aatgctcctg
2161  acatctcagt tcttgtcagt gaagctatcc aaataactgg ccaactagtt gttaaaagct
2221  aacagctcaa tctcttaaaa cacttttcaa aatatgtggg aagcatttga ttttcaattt
2281  gattttgaat tctgcatttg gttttatgaa tacaaagata agtgaaaaga gagaaggaa
2341  aagaaaaagg agaaaaacaa agagatttct accagtgaaa ggggaattaa ttactctttg
2401  ttagcactca ctgactcttc tatgcagtta ctacatatct agtaaaacct cgtttaatac
2461  tataaataat attctattca ttttgaaaaa cacaatgatt ccttctttc taggcaatat
2521  aaggaaagtg atccaaaatt tgaaatatta aaataatatc taataaaaag tcacaaagtt
2581  atcttcttta acaaacttta ctcttattct tagctgtata tacatttttt taaaagtttg
2641  ttaaaatatg cttgactaga gtttccagtt gaaaggcaaa aacttccatc acaacaagaa
2701  atttcccatg cctgctcaga agggtagccc ctagctctct gtgaatgtgt tttatccatt
2761  caactgaaaa ttggtatcaa gaaagtccac tggttagtgt actagtccat catagcctag
2821  aaaatgatcc ctatctgcag atcaagattt tctcattaga acaatgaatt atccagcatt
2881  cagatctttc tagtcacctt agaactttt ggttaaaagt acccaggctt gattatttca
2941  tgcaaattct atattttaca ttcttggaaa gtctatatga aaaacaaaaa taacatcttc
3001  agttttctc ccactgggtc acctcaagga tcagaggcca ggaaaaaaaa aaaaaagact
3061  ccctggatct ctgaatatat gcaaaaagaa ggccccattt agtggagcca gcaatcctgt
3121  tcagtcaaca agtattttaa ctctcagtcc aacattattt gaattgagca cctcaagcat
3181  gcttagcaat gttctaatca ctatggacag atgtaaaaga aactatacat catttttgcc
3241  ctctgcctgt tttccagaca tacaggttct gtggaataag atactggact cctcttccca
3301  agatggcact tctttttatt tcttgtcccc agtgtgtacc ttttaaaatt attccctctc
3361  aacaaaactt tataggcagt cttctgcaga cttaacgtgt tttctgtcat agttagatgt
3421  gataattcta agagtgtcta tgacttattt ccttcactta attctatcca cagtcaaaaa
3481  tcccccaagg aggaaagctg aaagatgcac tgccatatta tctttcttaa cttttccaa
3541  cacataatcc tctccaactg gattataaat aaattgaaaa taactcatta taccaattca
3601  ctattttatt ttttaatgaa ttaaaactag aaaacaaatt gatgcaaacc ctggaagtca
3661  gttgattact atatactaca gcagaatgac tcagatttca tagaaaggag caaccaaaat
3721  gtcacaaccc aaaactttac aagctttgct tcagaattag attgctttat aattcttgaa
3781  tgaggcaatt tcaagatatt tgtaaaagaa cagtaaacat tggtaagaat gagctttcaa
3841  ctcataggct tatttccaat ttaattgacc atactggata cttaggtcaa atttctgttc
3901  tctcttcccc aaataatatt aaagtattat ttgaacttt taagatgagg cagttcccct
3961  gaaaaagtta atgcagctct ccatcagaat ccactcttct agggatatga aaatctctta
4021  acacccaccc tacatacaca gacacacaca cacacacaca cacacacaca cacacacaca
4081  ttcaccctaa ggatccaatg gaatactgaa aagaaatcac ttccttgaaa attttattaa
4141  aaaacaaaca aacaaacaaa aagcctgtcc acccttgaga atccttcctc tccttggaac
4201  gtcaatgttt gtgtagatga aaccatctca tgctctgtgg ctccagggtt tctgttacta
```

-continued

```
4261  ttttatgcac ttgggagaag gcttagaata aaagatgtag cacattttgc tttcccattt
4321  attgtttggc cagctatgcc aatgtggtgc tattgtttct ttaagaaagt acttgactaa
4381  aaaaaaaaga aaaaagaaa aaaagaaag catagacata ttttttttaaa gtataaaaac
4441  aacaattcta tagatagatg gcttaataaa atagcattag gtctatctag ccaccaccac
4501  ctttcaactt tttatcactc acaagtagtg tactgttcac caaattgtga atttggggt
4561  gcaggggcag gagttggaaa ttttttaaag ttagaaggct ccattgtttt gttggctctc
4621  aaacttagca aaattagcaa tatattatcc aatcttctga acttgatcaa gagcatggag
4681  aataaacgcg ggaaaaaaga tcttataggc aaatagaaga atttaaaaga taagtaagtt
4741  ccttattgat ttttgtgcac tctgctctaa aacagatatt cagcaagtgg agaaaataag
4801  aacaaagaga aaaaatacat agatttacct gcaaaaaata gcttctgcca aatccccctt
4861  gggtattctt tggcatttac tggtttatag aagacattct cccttcaccc agacatctca
4921  aagagcagta gctctcatga aaagcaatca ctgatctcat ttgggaaatg ttggaaagta
4981  tttccttatg agatggggt tatctactga taaagaaaga atttatgaga aattgttgaa
5041  agagatggct aacaatctgt gaagattttt tgtttcttgt ttttgttttt ttttttttt
5101  tactttatac agtctttatg aatttcttaa tgttcaaaat gacttggttc ttttcttctt
5161  ttttttatatc agaatgagga ataataagtt aaacccacat agactcttta aaactatagg
5221  ctagatagaa atgtatgttt gacttgttga agctataatc agactattta aaatgttttg
5281  ctattttaa tcttaaaaga ttgtgctaat ttattagagc agaacctgtt tggctctcct
5341  cagaagaaag aatctttcca ttcaaatcac atggctttcc accaatattt tcaaaagata
5401  aatctgattt atgcaatggc atcatttatt ttaaaacaga agaattgtga aagtttatgc
5461  ccctccccttg caaagaccat aaagtccaga tctggtaggg gggcaacaac aaaaggaaaa
5521  tgttgttgat tcttggtttt ggattttgtt ttgttttcaa tgctagtgtt taatcctgta
5581  gtacatattt gcttattgct atttttaatat tttataagac cttcctgtta ggtattagaa
5641  agtgatacat agatatcttt tttgtgtaat ttctatttaa aaaagagaga agactgtcag
5701  aagctttaag tgcatatggt acaggataaa gatatcaatt taaataacca attcctatct
5761  ggaacaatgc ttttgttttt taaagaaacc tctcacagat aagacagagg cccagggat
5821  ttttgaagct gtctttattc tgccccccatc ccaacccagc ccttattatt ttagtatctg
5881  cctcagaatt ttatagaggg ctgaccaagc tgaaactcta gaattaaagg aacctcactg
5941  aaaacatata tttcacgtgt tccctctttt ttttttttcct ttttgtgaga tgggggtctcg
6001  cactgtcccc caggctggag tgcagtggca tgatctcggc tcactgcaac ctccacctcc
6061  tgggtttaag cgattctcct gcctcagcct cctgagtagc tgggattaca ggcacccacc
6121  actatgcccg gctaattttt tggattttta atagagacgg ggttttacca tgttggccag
6181  gttggtctca aactcctgac cttgtgattt gcccgcctca gcctcccaaa ttgctgggat
6241  tacaggcatg agccaccaca ccctgcccat gtgttccctc ttaatgtatg attacatgga
6301  tcttaaacat gatccttctc tcctcattct tcaactatct ttgatggggt ctttcaaggg
6361  gaaaaaaatc caagcttttt taaagtaaaa aaaaaaaag agaggacaca aaaccaaatg
6421  ttactgctca actgaaatat gagttaagat gggagacagag tttctcctaa taaccggagc
6481  tgaattacct ttcactttca aaaacatgac cttccacaat ccttagaatc tgcctttttt
6541  tatattactg aggcctaaaa gtaaacatta ctcatttttat tttgcccaaa atgcactgat
6601  gtaaagtagg aaaaataaaa acagagctct aaaatcccctt tcaagccacc cattgacccc
```

```
-continued
6661   actcaccaac tcatagcaaa gtcacttctg ttaatccctt aatctgattt tgtttggata 6721   tttatcttgt acccgctgct aaacacactg caggagggac tctgaaacct caagctgtct 6781   acttacatct tttatctgtg tctgtgtatc atgaaaatgt ctattcaaaa tatcaaaacc 6841   tttcaaatat cacgcagctt atattcagtt tacataaagg ccccaaatac catgtcagat 6901   cttttggta  aaagagttaa tgaactatga gaattgggat tacatcatgt attttgcctc 6961   atgtatttt  atcacactta taggccaagt gtgataaata aacttacaga cactgaatta 7021   atttccctg  ctactttgaa accagaaaat aatgactggc cattcgttac atctgtctta 7081   gttgaaaagc atatttttta ttaaattaat tctgattgta tttgaaatta ttattcaatt 7141   cacttatggc agaggaatat caatcctaat gacttctaaa aatgtaacta attgaatcat 7201   tatcttacat ttactgttta ataagcatat tttgaaaatg tatggctaga gtgtcataat 7261   aaaatggtat atctttcttt agtaattaca ttaaaattag tcatgtttga ttaattagtt 7321   c
```

The amino acid sequence of human IGF-1 isoform 4 preproprotein, provided by Genbank Accession No. NP_000609.1, is incorporated herein by reference, and is shown below (SEQ ID NO:137).

```
  1    mgkisslptq lfkccfcdfl kvkmhtmsss hlfylalcll tftssatagp eticgaelvd 61    alqfvcgdrg fyfnkptgyg sssrrapqtg ivdeccfrsc dlrrlemyca plkpaksars 121    vraqrhtdmp ktqkevhlkn asrgsagnkn yrm
```

The siRNA used to target human IGF-1 variant 4 mRNA include following sequences (SEQ ID NO: 138-141):

```
SEQ NO: 138:
5'-UAAACUGAAUAUAAGCUGC-3'

SEQ NO: 139:
5'-UAAAAAAAUAUGUCUAUGC-3'

SEQ NO: 140:
5'-UUUAACAGGUAACUCGUGC-3'

SEQ NO: 141:
5'-UAACAAACUACAAAAUAGC-3'
```

The molecular beacon used to target human IGF-1 variant 4 mRNA includes the following sequences (SEQ ID NO: 142-144):

```
SEQ NO 142:
5'-CCGGTC TAAACTGAATATAAGCTGCG GACCGG-3'

SEQ NO 143:
5'-CCGGTC TTTAAATTCTTCTATTTGCC GACCGG-3'

SEQ NO 144:
5'-CCGGTC TAATCAACTGACTTCCAGGGGACCGG-3'
```

The mRNA transcript sequence encoding human BMP-2, provided by Genbank Accession No. NM_001200.2, is incorporated herein by reference, and is shown below (SEQ ID NO: 145).

```
   1  ccacaaaggg cacttggccc cagggctagg agagcgaggg gagagcacag ccacccgcct
  61  cggcggcccg ggactcggct cgactcgccg gagaatgcgc ccgaggacga cggggcgcca
 121  gagccgcggt gctttcaact ggcgagcgcg aatggggtg cactggagta aggcagagtg
 181  atgcgggggg gcaactcgcc tggcaccgag atcgccgccg tgcccttccc tggacccggc
 241  gtcgcccagg atggctgccc cgagccatgg gccgcggcgg agctagcgcg gagcgcccga
 301  ccctcgaccc ccgagtcccg gagccggccc cgcgcgggc cacgcgtccc tcgggcgctg
 361  gttcctaagg aggacgacag caccagcttc tcctttctcc cttcccttcc ctgccccgca
 421  ctcctccccc tgctcgctgt tgttgtgtgt cagcacttgg ctggggactt cttgaacttg
 481  cagggagaat aacttgcgca ccccactttg cgccggtgcc tttgccccag cggagcctgc
 541  ttcgccatct ccgagcccca ccgcccctcc actcctcggc cttgcccgac actgagacgc
 601  tgttcccagc gtgaaaagag agactgcgcg gccggcaccc gggagaagga ggaggcaaag
 661  aaaaggaacg gacattcggt ccttgcgcca ggtcctttga ccagagtttt tccatgtgga
 721  cgctctttca atggacgtgt ccccgcgtgc ttcttagacg gactgcggtc tcctaaaggt
 781  cgaccatggt ggccgggacc cgctgtcttc tagcgttgct gcttccccag gtcctcctgg
 841  gcggcgcggc tggcctcgtt ccggagctgg gccgcaggaa gttcgcggcg gcgtcgtcgg
 901  gccgcccctc atcccagccc tctgacgagg tcctgagcga gttcgagttg cggctgctca
 961  gcatgttcgg cctgaaacag agacccaccc ccagcaggga cgccgtggtg cccccctaca
1021  tgctagacct gtatcgcagg cactcaggtc agccgggctc acccgcccca gaccaccggt
1081  tggagagggc agccagccga gccaacactg tgcgcagctt ccaccatgaa gaatctttgg
1141  aagaactacc agaaacgagt gggaaaacaa cccggagatt cttctttaat ttaagttcta
1201  tccccacgga ggagtttatc acctcagcag agcttcaggt tttccgagaa cagatgcaag
1261  atgctttagg aaacaatagc agtttccatc accgaattaa tatttatgaa atcataaaac
1321  ctgcaacagc caactcgaaa ttccccgtga ccagactttt ggacaccagg ttggtgaatc
1381  agaatgcaag caggtgggaa agttttgatg tcaccccgc tgtgatgcgg tggactgcac
1441  agggacacgc caaccatgga ttcgtggtgg aagtggccca cttggaggag aaacaaggtg
1501  tctccaagag acatgttagg ataagcaggt ctttgcacca agatgaacac agctggtcac
1561  agataaggcc attgctagta acttttggcc atgatggaaa agggcatcct ctccacaaaa
1621  gagaaaaacg tcaagccaaa cacaaacagc ggaaacgcct taagtccagc tgtaagagac
1681  acccttttgta cgtggacttc agtgacgtgg ggtggaatga ctggattgtg ctccccccgg
1741  ggtatcacgc cttttactgc cacggagaat gccctttccc tctggctgat catctgaact
1801  ccactaatca tgccattgtt cagacgttgg tcaactctgt taactctaag attcctaagg
1861  catgctgtgt cccgacagaa ctcagtgcta tctcgatgct gtaccttgac gagaatgaaa
1921  aggttgtatt aaagaactat caggacatgg ttgtggaggg ttgtgggtgt cgctagtaca
1981  gcaaaattaa atacataaat atatatatat atatatattt tagaaaaaag aaaaaaacaa
2041  acaaacaaaa aaacccacc ccagttgaca ctttaatatt tcccaatgaa gactttattt
2101  atggaatgga atggaaaaaa aaacagctat tttgaaaata tatttatatc tacgaaaaga
2161  agttgggaaa acaaatatt taatcagaga attattcctt aaagatttaa aatgtattta
2221  gttgtacatt ttatatgggt tcaaccccag cacatgaagt ataatggtca gatttatttt
2281  gtatttattt actattataa ccacttttta ggaaaaaaat agctaatttg tatttatatg
2341  taatcaaaag aagtatcggg tttgtacata attttccaaa aattgtagtt gttttcagtt
2401  gtgtgtattt aagatgaaaa gtctacatgg aaggttactc tggcaaagtg cttagcacgt
```

-continued

```
2461  ttgctttttt gcagtgctac tgttgagttc acaagttcaa gtccagaaaa aaaaagtgga
2521  taatccactc tgctgacttt caagattatt atattattca attctcagga atgttgcaga
2581  gtgattgtcc aatccatgag aatttacatc cttattaggt ggaatatttg gataagaacc
2641  agacattgct gatctattat agaaactctc ctcctgcccc ttaatttaca gaaagaataa
2701  agcaggatcc atagaaataa ttaggaaaac gatgaacctg caggaaagtg aatgatggtt
2761  tgttgttctt ctttcctaaa ttagtgatcc cttcaaaggg gctgatctgg ccaaagtatt
2821  caataaaacg taagatttct tcattattga tattgtggtc atatatattt aaaattgata
2881  tctcgtggcc ctcatcaagg gttggaaatt tatttgtgtt ttacctttac ctcatctgag
2941  agctctttat tctccaaaga acccagtttt ctaacttttt gcccaacacg cagcaaaatt
3001  atgcacatcg tgttttctgc ccaccctctg ttctctgacc tatcagcttg cttttctttc
3061  caaggttgtg tgtttgaaca catttctcca aatgttaaac ctatttcaga taataaatat
3121  caaatctctg gcatttcatt ctataaagtc
```

The amino acid sequence of human BMP-2 preproprotein, provided by Genbank Accession No. NP_001191.1, is incorporated herein by reference, and is shown below (SEQ ID NO:146).

```
  1  mvagtrclla lllpqvllgg aaglvpelgr rkfaaassgr pssqpsdevl sefelrllsm
 61  fglkqrptps rdavvppyml dlyrrhsgqp gspapdhrle raasrantvr sfhheeslee
121  lpetsgkttr rfffnlssip teefitsael qvfreqmqda lgnnssfhhr iniyeiikpa
181  tanskfpvtr lldtrlvnqn asrwesfdvt pavmrwtaqg hanhgfvvev ahleekqgvs
241  krhvrisrsl hqdehswsqi rpllvtfghd gkghplhkre krqakhkqrk rlkssckrhp
301  lyvdfsdvgw ndwivappgy hafychgecp fpladhlnst nhaivqtivn svnskipkac
361  cvptelsais mlyldenekv vlknyqdmvv egcgcr (Signal protein AA 1-23;
     proprotein AA 24-396; mature protein AA 283-396).
```

The siRNA used to target human BMP-2 mRNA include following sequences (SEQ ID NO: 147-150):

```
SEQ NO: 147:
5'-UUGUGAACUCAACAGUAGC-3'

SEQ NO: 148:
5'-UUAAUUUUGCUGUACUAGC-3'

SEQ NO: 149:
5'-UAAAACACAAAUAAAUUUC-3'

SEQ NO: 150:
5'-UUCUUUCUGUAAAUUAAGG-3'
```

The molecular beacon used to target human BMP-2 mRNA includes the following sequences (SEQ ID NO: 151-153):

```
SEQ NO 151:
5'-CCGGTC TAATACAAAATAAATCTG GACCGG-3'

SEQ NO 152:
5'-CCGGTC AAAACACAAATAAATTTCC GACCGG-3'

SEQ NO 153:
5'-CCGGTC TTCATTCTCGTCAAGGTAC GACCGG-3'
```

The mRNA transcript sequence encoding human BMP-4 variant 1, provided by Genbank Accession No. NM_001202.3, is incorporated herein by reference, and is shown below (SEQ ID NO: 154).

```
   1  aagaggagga aggaagatgc gagaaggcag aggaggaggg agggagggaa ggagcgcgga
  61  gcccggcccg gaagctaggt gagtgtggca tccgagctga gggacgcgag cctgagacgc
 121  cgctgctgct ccggctgagt atctagcttg tctccccgat gggattcccg tccaagctat
 181  ctcgagcctg cagcgccaca gtccccggcc ctcgcccagg ttcactgcaa ccgttcagag
 241  gtccccagga gctgctgctg gcgagcccgc tactgcaggg acctatggag ccattccgta
 301  gtgccatccc gagcaacgca ctgctgcagc ttccctgagc ctttccagca gtttgttca
 361  agattggctg tcaagaatca tggactgtta ttatatgcct tgttttctgt caagacacca
 421  tgattcctgg taaccgaatg ctgatggtcg ttttattatg ccaagtcctg ctaggaggcg
 481  cgagccatgc tagtttgata cctgagacgg ggaagaaaaa agtcgccgag attcagggcc
 541  acgcgggagg acgccgctca gggcagagcc atgagctcct gcgggacttc gaggcgacac
 601  ttctgcagat gtttgggctg cgccgccgcc cgcagcctag caagagtgcc gtcattccgg
 661  actacatgcg ggatctttac cggcttcagt ctggggagga ggaggaagag cagatccaca
 721  gcactggtct tgagtatcct gagcgcccgg ccagccgggc caacaccgtg aggagcttcc
 781  accacgaaga acatctggag aacatcccag ggaccagtga aaactctgct tttcgtttcc
 841  tctttaacct cagcagcatc cctgagaacg aggtgatctc ctctgcagag cttcggctct
 901  tccgggagca ggtggaccag ggccctgatt gggaaagggg cttccaccgt ataaacattt
 961  atgaggttat gaagccccca gcagaagtgg tgcctgggca cctcatcaca cgactactgg
1021  acacgagact ggtccaccac aatgtgacac ggtgggaaac ttttgatgtg agccctgcgg
1081  tccttcgctg gacccgggag aagcagccaa actatgggct agccattgag gtgactcacc
1141  tccatcagac tcggacccac cagggccagc atgtcaggat tagccgatcg ttacctcaag
1201  ggagtgggaa ttgggcccag ctccggcccc tcctggtcac ctttggccat gatggccggg
1261  gccatgcctt gacccgacgc cggagggcca agcgtagccc taagcatcac tcacagcggg
1321  ccaggaagaa gaataagaac tgccggcgcc actcgctcta tgtggacttc agcgatgtgg
1381  gctggaatga ctggattgtg gccccaccag gctaccaggc cttctactgc catgggact
1441  gccccttttcc actggctgac cacctcaact caaccaacca tgccattgtg cagaccctgg
1501  tcaattctgt caattccagt atccccaaag cctgttgtgt gcccactgaa ctgagtgcca
1561  tctccatgct gtacctggat gagtatgata aggtggtact gaaaaattat caggagatgg
1621  tagtagaggg atgtgggtgc cgctgagatc aggcagtcct tgaggataga cagatataca
1681  caccacacac acacaccaca tacaccacac acacgttc ccatccactc acccacacac
1741  tacacagact gcttccttat agctggactt ttatttaaaa aaaaaaaaa aaaaggaaaa
1801  aatccctaaa cattcacctt gaccttattt atgactttac gtgcaaatgt tttgaccata
1861  ttgatcatat attttgacaa aatatattta taactacgta ttaaaagaaa aaaataaaat
1921  gagtcattat tttaaaggta aaaaaaaaaa aaaaaaa
```

The amino acid sequence of human BMP-4 preproprotein, provided by Genbank Accession No. NP_001193.2, is incorporated herein by reference, and is shown below (SEQ ID NO:155).

```
  1  mipgnrmlmv vllcqvllgg ashaslipet gkkkvaeiqg haggrrsgqs hellrdfeat
 61  llqmfglrrr pqpsksavip dymrdlyrlq sgeeeeeqih stgleyperp asrantvrsf
121  hheehlenip gtsensafrf lfnlssipen evissaelrl freqvdqgpd wergfhrini
181  yevmkppaev vpghlitrll dtrlvhhnvt rwetfdvspa vlrwtrekqp nyglaievth
241  lhqtrthqgq hvrisrslpq gsgnwaqlrp llvtfghdgr ghaltrrrra krspkhhsqr
301  arkknkncrr hslyvdfsdv gwndwivapp gyqafychgd cpfpladhln stnhaivqtl
361  vnsvnssipk accvptelsa ismlyldeyd kvvlknyqem vvegcgcr (Signal
     peptide AA 1-24)
```

The siRNA used to target human BMP-4 variant 1 mRNA include following sequences (SEQ ID NO: 156-159):

```
SEQ NO: 156:
5'-UAAUAAAACGACCAUCAGCA-3'

SEQ NO: 157:
5'-UAUCUGUCUAUCCUCAAGGA-3'

SEQ NO: 158:
5'-UUCUUAUUCUUCUUCCUGGC-3'

SEQ NO: 159:
5'-UAAUAAAACGACCAUCAGC-3'
```

The molecular beacon used to target human BMP-4 variant 1 mRNA includes the following sequences (SEQ ID NO: 160-162):

```
SEQ NO 160:
5'-CCGGTC TATCTGTCTATCCTCAAGG GACCGG-3'

SEQ NO 161:
5'-CCGGTC TCTCAGGTATCAAACTAGC GACCGG-3'

SEQ NO 162:
5'-CCGGTC TTTGTCAAAATATATGATC GACCGG-3'
```

The mRNA transcript sequence encoding human BMP-7, provided by Genbank Accession No. NM_001719.2, is incorporated herein by reference, and is shown below (SEQ ID NO: 163).

```
   1  agcgcgtacc actctggcgc tcccgaggcg gcctcttgtg cgatccaggg cgcacaaggc
  61  tgggagagcg ccccggggcc cctgctatcc gcgccggagg ttggaagagg gtgggttgcc
 121  gccgccgag  ggcgagagcg ccagaggagc gggaagaagg agcgctcgcc cgcccgcctg
 181  cctcctcgct gcctccccgg cgttggctct ctggactcct aggcttgctg gctgctcctc
 241  ccacccgcgc ccgcctcctc actcgccttt tcgttcgccg gggctgcttt ccaagccctg
 301  cggtgcgccc gggcgagtgc ggggcgaggg gcccggggcc agcaccgagc aggggcggg
 361  ggtccgggca gagcgcggcc ggccggggag gggccatgtc tggcgcgggc gcagcggggc
 421  ccgtctgcag caagtgaccg agcggcgcgg acggccgcct gcccctctg  ccacctgggg
 481  cggtgcgggc ccggagcccg gagcccgggt agcgcgtaga gccggcgcga tgcacgtgcg
 541  ctcactgcga gctgcggcgc cgcacagctt cgtggcgctc tgggcacccc tgttcctgct
 601  gcgctccgcc ctggccgact tcagcctgga caacgaggtg cactcgagct tcatccaccg
 661  gcgcctccgc agccaggagc ggcgggagat gcagcgcgag atcctctcca ttttgggctt
 721  gccccaccgc ccgcgcccgc acctccaggg caagcacaac tcggcaccca tgttcatgct
 781  ggacctgtac aacgccatgg cggtggagga gggcggcggg cccggcgggc agggcttctc
 841  ctaccccta  aaggccgtct tcagtaccca gggccccccc ctggccagcc tgcaagatag
 901  ccatttcctc accgacgccg acatggtcat gagcttcgtc aacctcgtgg aacatgacaa
 961  ggaattcttc cacccacgct accaccatcg agagttccgg tttgatcttt ccaagatccc
1021  agaaggggaa gctgtcacgg cagccgaatt ccggatctac aaggactaca tccgggaacg
1081  cttcgacaat gagacgttcc ggatcagcgt ttatcaggtg ctccaggagc acttgggcag
1141  ggaatcggat ctcttcctgc tcgacagccg taccctctgg gcctcggagg agggctggct
1201  ggtgtttgac atcacagcca ccagcaacca ctgggtggtc aatccgcggc acaacctggg
1261  cctgcagctc tcggtggaga cgctggatgg gcagagcatc aaccccaagt tggcgggcct
```

```
1321  gattgggcgg cacgggcccc agaacaagca gcccttcatg gtggctttct tcaaggccac
1381  ggaggtccac ttccgcagca tccggtccac ggggagcaaa cagcgcagcc agaaccgctc
1441  caagacgccc aagaaccagg aagccctgcg gatggccaac gtggcagaga acagcagcag
1501  cgaccagagg caggcctgta agaagcacga gctgtatgtc agcttccgag acctgggctg
1561  gcaggactgg atcatcgcgc ctgaaggcta cgccgcctac tactgtgagg gggagtgtgc
1621  cttccctctg aactcctaca tgaacgccac caaccacgcc atcgtgcaga cgctggtcca
1681  cttcatcaac ccggaaacgg tgcccaagcc ctgctgtgcg cccacgcagc tcaatgccat
1741  ctccgtcctc tacttcgatg acagctccaa cgtcatcctg aagaaataca gaaacatggt
1801  ggtccgggcc tgtggctgcc actagctcct ccgagaattc agacccttg gggccaagtt
1861  tttctggatc ctccattgct cgccttggcc aggaaccagc agaccaactg ccttttgtga
1921  gaccttcccc tccctatccc caactttaaa ggtgtgagag tattaggaaa catgagcagc
1981  atatggcttt tgatcagttt ttcagtggca gcatccaatg aacaagatcc tacaagctgt
2041  gcaggcaaaa cctagcagga aaaaaaaaca acgcataaag aaaaatggcc gggccaggtc
2101  attggctggg aagtctcagc catgcacgga ctcgtttcca gaggtaatta tgagcgccta
2161  ccagccaggc cacccagccg tgggaggaag ggggcgtggc aaggggtggg cacattggtg
2221  tctgtgcgaa aggaaaattg acccggaagt tcctgtaata aatgtcacaa taaaacgaat
2281  gaatgaaaat ggttaggacg ttacagatat attttcctaa acaatttatc cccatttctc
2341  ggtttatcct gatgcgtaaa cagaagctgt gtcaagtgga gggcggggag gtccctctcc
2401  attccctaca gttttcatcc tgaggcttgc agaggcccag tgtttaccga ggtttgccca
2461  aatccaagat ctagtgggag gggaaagagc aaatgtctgc tccgaggagg gcggtgtgtt
2521  gatctttgga ggaaaaatat gttctgttgt tcagctggat ttgccgtggc agaaatgaaa
2581  ctaggtgtgt gaaatacccg cagacatttg ggattggctt ttcacctcgc cccagtggta
2641  gtaaatccat gtgaaattgc agagggggaca aggacagcaa gtaggatgga acttgcaact
2701  caaccctgtt gttaagaagc accaatgggc cgggcacagt agctcccacc tgtaatccca
2761  gcactttggg aggctgaggt gggcggatca tttgaggtca ggagttcgag accagcctgg
2821  ccaacatggt gaaaccccat ctctactaaa aatacaaaaa ttagccgggc atggtggcac
2881  gcacctgtaa tcccagctac tctggaggct gaggcaggag aattgcttga ccccagagg
2941  tggaggttgc agtgagccaa gatcgtccca ctgcactcca gcttgggtga caaaacaaga
3001  ctccatctca aagaaaaaa aaacagcac caatgaagcc tagttctcca cgggagtggg
3061  gtgagcagga gcactgcaca tcgccccagt ggaccctctg gtctttgtct gcagtggcat
3121  tccaaggctg gccctggca agggcacccg tggctgtctc ttcatttgca gacctgatc
3181  agaagtctct gcaaacaaat ttgctccttg aattaagggg gagatggcat aataggaggt
3241  ctgatgggtg caggatgtgc tggacttaca ttgcaaatag aagccttgtt gagggtgaca
3301  tcctaaccaa gtgtcccgat ttggaggtgg catttctgac gtggctcttg gtgtaagcct
3361  gccttgcctt ggctggtgag tccataaat agtatgcact cagcctccgg ccacaaacac
3421  aaggcctagg ggagggctag actgtctgca aacgttttct gcatctgtaa agaaaacaag
3481  gtgatcgaaa actgtggcca tgtggaaccc ggtcttgtgg gggactgttt ctccatcttg
3541  actcagacag ttcctggaaa caccggggct ctgttttat tttctttgat gttttcttc
3601  tttagtagct tgggctgcag cctccactct ctagtcactg ggaggagta ttttttgtta
3661  tgtttggttt catttgctgg cagagctggg gcttttgtg tgatccctct tggtgtgagt
```

-continued

```
3721  tttctgaccc aaccagcctc tggttagcat catttgtaca tttaaacctg taaatagttg 3781  ttacaaagca aagagattat ttatttccat ccaaagctct tttgaacacc cccccccctt 3841  taatccctcg ttcaggacga tgagcttgct ttccttcaac ctgtttgttt tcttatttaa 3901  gactatttat taatggttgg accaatgtac tcacagctgt tgcgtcgagc agtccttagt 3961  gaaaattctg tataaataga caaatgaaa agggtttgac cttgcaataa aaggagacgt 4021  ttggttctgg caaaaaaaaa aaaaaaaa
```

The amino acid sequence of human BMP-7 precursor, provided by Genbank Accession No. NP_001710.1, is incorporated herein by reference, and is shown below (SEQ ID NO:164).

```
  1  mhvrslraaa phsfvalwap lfllrsalad fsldnevhss fihrrlrsqe rremqreils 61  ilglphrprp hlqgkhnsap mfmldlynam aveegggpgg qgfsypykav fstqgpplas 121  lqdshfltda dmvmsfvnlv ehdkeffhpr yhhrefrfdl skipegeavt aaefriykdy 181  irerfdnetf risvyqvlqe hlgresdlfl ldsrtlwase egwlvfdita tsnhwvvnpr 241  hnlglqlsve tldgqsinpk lagligrhgp qnkqpfmvaf fkatevhfrs irstgskqrs 301  qnrsktpknq ealrmanvae nsssdqrqac kkhelyvsfr dlgwqdwiia pegyaayyce 361  gecafplnsy mnatnhaivq tlvhfinpet vpkpccaptq lnaisvlyfd dssnvilkky 421  rnmvvracgc h (signal peptide AA 1-29; mature peptide AA 293-431).
```

The siRNA used to target human BMP-7 mRNA include following sequences (SEQ ID NO: 165-168):

```
SEQ NO: 165:
5'-UUCCUAAUACUCUCACACC-3'

SEQ NO: 166:
5'-UAACAAAAAAUACUCCUCC-3'

SEQ NO: 167:
5'-UAAAUAAGAAAACAAACAGG-3'

SEQ NO: 168:
5'-UUCCUAAUACUCUCACACCU-3'
```

The molecular beacon used to target human BMP-7 mRNA includes the following sequences (SEQ ID NO: 169-171):

```
SEQ NO 169:
5'-CCGGTC TAACAAAAAATACTCCTCCC GACCGG-3'

SEQ NO 170:
5'-CCGGTC TTGTAACAACUATTTACAGG GACCGG-3'

SEQ NO 171:
5'-CCGGTC TAAATAAGAAAACAAACAG GACCGG-3'
```

The mRNA transcript sequence encoding human IL-1 receptor antagonist variant 3, provided by Genbank Accession No. NM_000577.4, is incorporated herein by reference, and is shown below (SEQ ID NO: 172).

```
   1  gggcagctcc acccctgggag ggactgtggc ccaggtactg cccgggtgct actttatggg
  61  cagcagctca gttgagttag agtctggaag acctcagaag acctcctgtc ctatgaggcc
 121  ctccccatgg ctttagagac gatctgccga ccctctggga gaaaatccag caagatgcaa
 181  gccttcagaa tctgggatgt taaccagaag accttctatc tgaggaacaa ccaactagtt
 241  gctggatact tgcaaggacc aaatgtcaat ttagaagaaa agatagatgt ggtacccatt
 301  gagcctcatg ctctgttctt gggaatccat ggagggaaga tgtgcctgtc ctgtgtcaag
 361  tctggtgatg agaccagact ccagctggag gcagttaaca tcactgacct gagcgagaac
 421  agaaagcagg acaagcgctt cgccttcatc cgctcagaca gtgcccccac caccagtttt
 481  gagtctgccg cctgccccgg ttggttcctc tgcacagcga tggaagctga ccagcccgtc
 541  agcctcacca atatgcctga cgaaggcgtc atggtcacca aattctactt ccaggaggac
 601  gagtagtact gcccaggcct gcctgttccc attcttgcat ggcaaggact gcagggactg
 661  ccagtccccc tgccccaggg ctcccggcta tgggggcact gaggaccagc cattgagggg
 721  tggaccctca gaaggcgtca caacaacctg gtcacaggac tctgcctcct cttcaactga
 781  ccagcctcca tgctgcctcc agaatggtct ttctaatgtg tgaatcagag cacagcagcc
 841  cctgcacaaa gccttccat gtcgcctctg cattcaggat caaaccccga ccacctgccc
 901  aacctgctct cctcttgcca ctgcctcttc ctccctcatt ccaccttccc atgccctgga
 961  tccatcaggc cacttgatga cccccaacca agtggctccc acaccctgtt ttacaaaaaa
1021  gaaaagacca gtccatgagg gaggttttta agggtttgtg gaaaatgaaa attaggattt
1081  catgattttt tttttcagt ccccgtgaag gagagcccctt catttggaga ttatgttctt
1141  tcggggagag gctgaggact taaaatattc ctgcatttgt gaaatgatgg tgaaagtaag
1201  tggtagcttt tccctttcttt ttcttctttt tttgtgatgt cccaacttgt aaaaattaaa
1261  agttatggta ctatgttagc cccataattt ttttttcct tttaaaacac ttccataatc
1321  tggactcctc tgtccaggca ctgctgccca gcctccaagc tccatctcca ctccagattt
1381  tttacagctg cctgcagtac tttacctcct atcagaagtt tctcagctcc caaggctctg
1441  agcaaatgtg gctcctgggg gttcttttctt cctctgctga aggaataaat tgctccttga
1501  cattgtagag cttctggcac ttggagactt gtatgaaaga tggctgtgcc tctgcctgtc
1561  tcccccaccg ggctgggagc tctgcagagc aggaaacatg actcgtatat gtctcaggtc
1621  cctgcagggc caagcaccta gcctcgctct tggcaggtac tcagcgaatg aatgctgtat
1681  atgttgggtg caaagttccc tacttcctgt gacttcagct ctgttttaca ataaaatctt
1741  gaaaatgcct aaaaaaaaaa aaaaaaaaaa aaaaaaaaaa aaaaaaaaaa aaaaaaaaaa
1801  aa
```

The amino acid sequence of human IL-1 receptor antagonist isoform 3, provided by Genbank Accession No. NP_000568.1, is incorporated herein by reference, and is shown below (SEQ ID NO:173).

```
  1  maleticrps grksskmqaf riwdvnqktf ylrnnqlvag ylqgpnvnle ekidvvpiep
 61  halflgihgg kmclscvksg detrlqleav nitdlsenrk qdkrfafirs dsgpttsfes
121  aacpgwflct ameadqpvsl tnmpdegvmv tkfyfqede
```

The Pre-miRNA sequence of human microRNA140, provided by Genbank Accession NO: NR_029681.1, is incorporated herein by reference, and is shown below (SEQ ID NO: 174).

5'-UGUGUCUCUCUCUGUGUCCUGCCAGUGGUUUUACCCUAUGGUAGGUU
ACGUCAUGCUGUUCUACCACAGGGUAGAACCACGGACAGGAUACCGGGGC
ACC-3'

And mature microRNA140 (SEQ ID NO: 175).

5'-cagugguuuuacccuaugguag-3'

The Pre-miRNA sequence of human microRNA365, provided by Genbank Accession NO: NR_029854.1, is incorporated herein by reference, and is shown below (SEQ ID NO: 176).

5'-ACCGCAGGGAAAAUGAGGGACUUUUGGGGGCAGAUGUGUUUCCAUUC
CACUAUCAUAAUGCCCCUAAAAAUCCUUAUUGCUCUUGCA-3'

And mature microRNA365 (SEQ ID NO: 177):

5'-AGGGACUUUUGGGGGCAGAUGUG-3'

The Pre-miRNA sequence of human microRNA125a, provided by Genbank Accession NO: NR_029693.1, is incorporated herein by reference, and is shown below (SEQ ID NO: 178).

5'-UGCCAGUCUCUAGGUCCCUGAGACCCUUUAACCUGUGAGGA
CAUCCAGGGUCACAGGUGAGGUUCUUGGGAGCCUGGCGUCUGG
CC-3'

And two mature microRNA125a (SEQ ID NO: 179-180):

SEQ ID NO: 179: hsa-mir-125a-5p:
5'-ucccugagacccuuuaaccuguga-3'\

SEQ ID NO: 180: hsa-mir-125a-3p:
5'-acaggugagguucuugggagcc-3'

The mRNA sequence encoding human IL-15, provided by Genbank Accession No. BC018149.2, is incorporated herein by reference, and is shown below (SEQ ID NO: 181).

```
   1 actccgggtg gcaggcgccc gggggaatcc cagctgactc gctcactgcc ttcgaagtcc
  61 ggcgccccc gggagggaac tgggtggccg caccctcccg gctgcggtgg ctgtcgcccc
 121 ccaccctgca gccaggactc gatggaggta cagagctcgg cttctttgcc ttgggagggg
 181 agtggtggtg gttgaaaggg cgatggaatt ttccccgaaa gcctacgccc agggcccctc
 241 ccagctccag cgttaccctc cggtctatcc tactggccga gctgccccgc cttctcatgg
 301 ggaaaactta gccgcaactt caattttggg ttttccttt aatgacactt ctgaggctct
 361 cctagccatc ctcccgcttc cggaggagcg cagatcgcag gtccctttgc ccctggcgtg
 421 cgactcccta ctgcgctgcg ctcttacggc gttccaggct gctggctagc gcaaggcggg
 481 ccgggcaccc cgcgctccgc tgggagggtg agggacgcgc gtctggcggc cccagccaag
 541 ctgcgggttt ctgagaagac gctgtcccgc agccctgagg gctgagttct gcacccagtc
 601 aagctcagga aggccaagaa aagaatccat tccaatatat ggccatgtgg ctctttggag
 661 caatgttcca tcatgttcca tgctgctgac gtcacatgga gcacagaaat caatgttagc
 721 agatagccag cccatacaag atcgtattgt attgtaggag gcatcgtgga tggatggctg
 781 ctggaaaccc cttgccatag ccagctcttc ttcaatactt aaggatttac cgtggctttg
 841 agtaatgaga atttcgaaac cacatttgag aagtatttcc atccagtgct acttgtgttt
 901 acttctaaac agtcattttc taactgaagc tggcattcat gtcttcattt tgggctgttt
 961 cagtgcaggg cttcctaaaa cagaagccaa ctgggtgaat gtaataagtg atttgaaaaa
1021 aattgaagat cttattcaat ctatgcatat tgatgctact ttatatacgg aaagtgatgt
1081 tcacccccagt tgcaaagtaa cagcaatgaa gtgctttctc ttggagttac aagttatttc
1141 acttgagtcc ggagatgcaa gtattcatga tacagtagaa aatctgatca tcctagcaaa
1201 caacagtttg tcttctaatg ggaatgtaac agaatctgga tgcaaagaat gtgaggaact
1261 ggaggaaaaa aatattaaag aatttttgca gagttttgta catattgtcc aaatgttcat
1321 caacactct tgattgcaat tgattctttt taaagtgttt ctgttattaa caaacatcac
1381 tctgctgctt agacataaca aaacactcgg catttcaaat gtgctgtcaa aacaagtttt
1441 tctgtcaaga agatgatcag accttggatc agatgaactc ttagaaatga aggcagaaaa
1501 atgtcattga gtaatatagt gactatgaac ttctctcaga cttactttac tcattttttt
```

-continued

```
1561  aatttattat tgaaattgta catatttgtg gaataatgta aaatgttgaa taaaaatatg 1621  tacaagtgtt gttttttaag ttgcactgat attttacctc ttattgcaaa atagcatttg 1681  tttaagggtg atagtcaaat tatgtattgg tggggctggg taccaatgct gcaggtcaac 1741  agctatgctg gtaggctcct gcctgtgtgg aaccactgac tactggctct cattgacttc 1801  cttactaagc atagcaaaca gaggaagaat tgttatcag taagaaaag aagaactata 1861  tgtgaatcct cttctttaca ctgtaattta gttattgatg tataaagcaa ctgttatgaa 1921  ataagaaat tgcaataact ggcaaaaaaa aaaaaaaaaa aaaaaaaa
```

The atg start and stop codons are bolded and underlined.
The amino acid sequence of human IL-15, provided by Genbank Accession No. AAH18149.1, is incorporated herein by reference, and is shown below (SEQ ID NO: 182).

```
                                                    (SEQ ID NO: 182)
  1  mriskphlrs isiqcylcll lnshflteag ihvfilgcfs aglpkteanw vnvisdlkki 61  edliqsmhid atlytesdvh psckvtamkc fllelqvisl esgdasihdt venliilann 121  slssngnvte sgckeceele eknikeflqs fvhivqmfin ts
```

The mRNA sequence encoding human IL-20 (interleukin-20 precursor), provided by Genbank Accession No. NM_018724.3, is incorporated herein by reference, and is shown below (SEQ ID NO: 183).

```
   1  ctttgaattc ctagctcctg tggtctccag atttcaggcc taagatgaaa gcctctagtc 61  ttgccttcag ccttctctct gctgcgtttt atctcctatg gactccttcc actggactga 121  agacactcaa tttgggaagc tgtgtgatcg ccacaaacct tcaggaaata cgaaatggat 181  tttctgagat acggggcagt gtgcaagcca aagatggaaa cattgacatc agaatcttaa 241  ggaggactga gtctttgcaa gacacaaagc ctgcgaatcg atgctgcctc ctgcgccatt 301  tgctaagact ctatctggac agggtattta aaaactacca gaccctgac cattatactc 361  tccggaagat cagcagcctc gccaattcct ttcttaccat caagaaggac ctccggctct 421  gtcatgccca catgacatgc cattgtgggg aggaagcaat gaagaaatac agccagattc 481  tgagtcactt tgaaaagctg gaacctcagg cagcagttgt gaaggctttg ggggaactag 541  acattcttct gcaatggatg gaggagacag aataggagga aagtgatgct gctgctaaga 601  atattcgagg tcaagagctc cagtcttcaa tacctgcaga ggaggcatga ccccaaacca 661  ccatctcttt actgtactag tcttgtgctg gtcacagtgt atcttattta tgcattactt 721  gcttccttgc atgattgtct ttatgcatcc ccaatcttaa ttgagaccat acttgtataa 781  gatttttgta atatctttct gctattggat atatttatta gttaatatat ttatttattt 841  tttgctattt aatgtattta ttttttact tggacatgaa actttaaaaa aattcacaga 901  ttatatttat aacctgacta gagcaggtga tgtatttta tacagtaaaa aaaaaaaacc 961  ttgtaaattc tagaagagtg gctagggggg ttattcattt gtattcaact aaggacatat 1021  ttactcatgc tgatgctctg tgagatattt gaaattgaac caatgactac ttaggatggg 1081  ttgtggaata agttttgatg tggaattgca catctaccct acaattactg accatcccca 1141  gtagactccc cagtcccata attgtgtatc ttccagccag gaatcctaca cggccagcat 1201  gtatttctac aaataaagtt ttctttgcat aacaaaaaaa aaaaaaaaaa aa
```

The atg start and stop codons are bolded and underlined. The amino acid sequence of human IL-20 (interleukin-20 precursor), provided by Genbank Accession No. NP_061194.2, is incorporated herein by reference, and is shown below (SEQ ID NO: 184).

```
  1  mkasslafsl lsaafyllwt pstglktlnl gscviatnlq eirngfseir gsvqakdgni 61  dirilrrtes lqdtkpanrc cllrhllrly ldrvfknyqt pdhytlrkis slansfltik 121  kdlrlchahm tchcgeeamk kysqilshfe klepqaavvk algeldillq wmeete
```

The mRNA sequence encoding human PADI4 (protein-arginine deiminase type-4), provided by Genbank Accession No. NM_012387.2, is incorporated herein by reference, and is shown below (SEQ ID NO: 185).

```
                                                    (SEQ ID NO: 185)
   1  acagccagag ggacgagcta gcccgacgat ggcccagggg acattgatcc gtgtgacccc 61  agagcagccc acccatgccg tgtgtgtgct gggcaccttg actcagcttg acatctgcag 121  ctctgcccct gaggactgca cgtccttcag catcaacgcc tccccagggg tggtcgtgga 181  tattgcccac ggccctccag ccaagaagaa atccacaggt tcctccacat ggcccctgga 241  ccctggggta gaggtgaccc tgacgatgaa agtggccagt ggtagcacag gcgaccagaa 301  ggttcagatt tcatactacg gacccaagac tccaccagtc aaagctctac tctacctcac 361  cggggtggaa atctccttgt gcgcagacat caccgcacc ggcaaagtga agccaaccag 421  agctgtgaaa gatcagagga cctggacctg ggcccttgt ggacagggtg ccatcctgct 481  ggtgaactgt gacagagaca atctcgaatc ttctgccatg gactgcgagg atgatgaagt 541  gcttgacagc gaagacctgc aggacatgtc gctgatgacc ctgagcacga gaccccaa 601  ggacttcttc acaaaccata cactggtgct ccacgtggcc aggtctgaga tggacaaagt 661  gagggtgttt caggccacac ggggcaaaact gtcctccaag tgcagcgtag tcttgggtcc 721  caagtggccc tctcactacc tgatggtccc cggtggaaag cacaacatgg acttctacgt 781  ggaggccctc gctttcccgg acaccgactt cccggggctc attaccctca ccatctccct 841  gctggacacg tccaacctgg agctccccga ggctgtggtg ttccaagaca gcgtggtctt 901  ccgcgtggcg ccctggatca tgaccccaa cacccagccc cgcaggagg tgtacgcgtg 961  cagtattttt gaaaatgagg acttcctgaa gtcagtgact actctggcca tgaaagccaa 1021  gtgcaagctg accatctgcc ctgaggagga gaacatggat gaccagtgga tgcaggatga 1081  aatggagatc ggctacatcc aagccccaca caaaacgctg cccgtggtct tcgactctcc 1141  aaggaacaga ggcctgaagg agtttcccat caaacgcgtg atgggtccag attttggcta 1201  tgtaactcga gggccccaaa caggggtat cagtggactg gactcctttg ggaacctgga 1261  agtgagcccc ccagtcacag tcagggggcaa ggaatacccg ctgggcagga ttctcttcgg 1321  ggacagctgt tatcccagca atgacagccg gcagatgcac caggccctgc aggacttcct 1381  cagtgcccag caggtgcagg cccctgtgaa gctctattct gactggctgt ccgtgggcca 1441  cgtggacgag ttcctgagct ttgtgccagc acccgacagg aagggcttcc ggctgctcct 1501  ggccagcccc aggtcctgct acaaactgtt ccaggagcag cagaatgagg gccacgggga 1561  ggccctgctg ttcgaaggga tcaagaaaaa aaacagcag aaaataaaga acattctgtc 1621  aaacaagaca ttgagagaac ataattcatt tgtggagaga tgcatcgact ggaaccgcga 1681  gctgctgaag cgggagctgg gcctggccga gagtgacatc attgacatcc cgcagctctt 1741  caagctcaaa gagttctcta aggcggaagc ttttttcccc aacatggtga acatgctggt
```

-continued

```
1801  gctagggaag caccctgggca tccccaagcc cttcgggccc gtcatcaacg gccgctgctg 1861  cctggaggag aaggtgtgtt ccctgctgga gccactgggc ctccagtgca ccttcatcaa 1921  cgacttcttc acctaccaca tcaggcatgg ggaggtgcac tgcggcacca acgtgcgcag 1981  aaagcccttc tccttcaagt ggtggaacat ggtgccctga gcccatcttc cctggcgtcc 2041  tctccctcct ggccagatgt cgctgggtcc tctgcagtgt ggcaagcaag agctcttgtg 2101  aatattgtgg ctccctgggg gcggccagcc ctcccagcag tggcttgctt tcttctcctg 2161  tgatgtccca gtttcccact ctgaagatcc aacatggtc ctagcactgc acactcagtt 2221  ctgctctaag aagctgcaat aaagttttt taagtcactt tgtac
```

The atg start and stop codons are bolded and underlined.
The amino acid sequence of human PADI4 (protein-arginine deiminase type-4) provided by Genbank Accession No. NP_036519.2, is incorporated herein by reference, and is shown below (SEQ ID NO: 186).

(SEQ ID NO: 186)
```
  1  maqgtlirvt peqpthavcv lgtltqldic ssapedctsf sinaspgvvv diahgppakk 61  kstgsstwpl dpgvevtltm kvasgstgdq kvqisyygpk tppvkallyl tgveislcad 121  itrtgkvkpt ravkdqrtwt wgpcgqgail lvncdrdnle ssamdcedde vldsedlqdm 181  slmtlstktp kdfftnhtiv lhvarsemdk vrvfqatrgk lsskcsvvlg pkwpshylmv 241  pggkhnmdfy vealafpdtd fpglitltis lldtsnlelp eavvfqdsvv frvapwimtp 301  ntqppqevya csifenedfl ksvttlamka kcklticpee enmddqwmqd emeigyiqap 361  hktlpvvfds prnrglkefp ikrvmgpdfg yvtrgpqtgg isgldsfgnl evsppvtvrg 421  keyplgrilf gdscypsnds rqmhqalqdf lsaqqvqapv klysdwlsvg hvdeflsfvp 481  apdrkgfrll lasprscykl fqeqqneghg eallfegikk kkqqkiknil snktlrehns 541  fvercidwnr ellkrelgla esdiidipql fklkefskae affpnmvnml vlgkhlgipk 601  pfgpvingrc cleekvcsll eplglqctfi ndfftyhirh gevhcgtnvr rkpfsfkwwn 661  mvp
```

The mRNA sequence encoding human HLA-DRB1, provided by Genbank Accession No. HQ267233.1, is incorporated herein by reference, and is shown below (SEQ ID NO: 187).

```
  1  atggtgtgtc tgaggctccc tggaggctcc tgcatggcag ttctgacagt gacactgatg 61  gtgctgagct ccccactggc tttggctggg acaccagac cacgtttctt ggaggaggtt 121  aagtttgagt gtcatttctt caacgggacg gagcgggtgc ggttgctgga agacgcgtc 181  cataaccaag aggagtacgc gcgctacgac agcgacgtg gggagtaccg gcggtgacg 241  gagctggggc ggcctgatgc cgagtactgg aacagccaga aggacctcct ggagcggagg 301  cgtgccgcgg tggacaccta ctgcagacac aactacgggg ttggtgagag cttcacagtg 361  cagcggcgag ttcaacctaa ggtgactgtg tatccttcaa agaccagcc cctgcagcac 421  cacaacctcc tggtctgttc tgtgaatggt ttctatccag gcagcattga agtcaggtgg 481  ttccggaacg gccaggaaga gaagactggg gtggtgtcca cgggcctgat ccagaatgga 541  gactggacct tccagaccct ggtgatgctg gaaacagttc ctcagagtgg agaggtttac 601  acctgccaag tggagcaccc aagtgtgatg agccctctca cagtggaatg gagagcacgg
```

-continued
```
 661  tctgaatctg cacagagcaa gatgctgagt ggagtcgggg gctttgtgct gggcctgctc 721  ttccttgggg ccgggctgtt catctacttc aggaatcaga aggacactc tggacttccg 781  ccaacaggat tcctgagctg a
```

The atg start and stop codons are bolded and underlined. The amino acid sequence of human HLA-DRB1, provided by Genbank Accession No. ADZ73424.1, is incorporated herein be reference, and is shown below (SEQ ID NO: 188).

```
                                                       (SEQ ID NO: 188)
   1  mvclrlpggs cmavltvtlm vlssplalag dtrprfleev kfechffngt ervrllerrv 61  hnqeeyaryd sdvgeyravt elgrpdaeyw nsqkdllerr raavdtycrh nygvgesftv 121  qrrvqpkvtv ypsktqplqh hnllvcsvng fypgsievrw frngqeektg vvstgliqng 181  dwtfqtlvml etvpqsgevy tcqvehpsvm spltvewrar sesaqskmls gvggfvlgll 241  flgaglfiyf rnqkghsglp ptgfls
```

The mRNA sequence encoding human PTPN22 provided by Genbank Accession No. BC071670.1, is incorporated herein by reference, and is shown below (SEQ ID NO: 189).

```
    1  ggtgtctcgg ccatgacaca catttgacat gccctccctc aacctactta tagactattt 61  ttcttgctct gcagcatgga ccaaagagaa attctgcaga agttcctgga tgaggcccaa 121  agcaagaaaa ttactaaaga ggagtttgcc aatgaatttc tgaagctgaa aaggcaatct 181  accaagtaca aggcagacaa aacctatcct acaactgtgg ctgagaagcc caagaatatc 241  aagaaaaaca gatataagga tattttgccc tatgattata gccgggtaga actatccctg 301  ataacctctg atgaggattc cagctacatc aatgccaact tcattaaggg agtttatgga 361  cccaaggctt atattgccac cagggtcct ttatctacaa ccctcctgga cttctggagg 421  atgatttggg aatatagtgt ccttatcatt gttatggcat gcatggagta tgaaatggga 481  aagaaaaagt gtgagcgcta ctgggctgag ccaggagaga tgcagctgga atttggccct 541  ttctctgtat cctgtgaagc tgaaaaaagg aaatctgatt atataatcag gactctaaaa 601  gttaagttca atagtgaaac tcgaactatc taccagtttc attacaagaa ttggccagac 661  catgatgtac cttcatctat agaccctatt cttgagctca tctgggatgt acgttgttac 721  caagaggatg acagtgttcc catatgcatt cactgcagtg ctggctgtgg aaggactggt 781  gttatttgtg ctattgatta tacatggatg ttgctaaaag atgggagtca agcaaagcat 841  tgtattcctg agaaaaatca cactctccaa gcagactctt attctcctaa tttaccaaaa 901  agtaccacaa aagcagcaaa aatgatgaac caacaaagga caaaaatgga aatcaaagaa 961  tcttcttcct ttgactttag gacttctgaa ataagtgcaa agaagagct agttttgcac 1021  cctgctaaat caagcacttc ttttgacttt ctggagctaa attacagttt tgacaaaaat 1081  gctgacacaa ccatgaaatg gcagacaaag gcatttccaa tagttgggga gcctcttcag 1141  aagcatcaaa gtttggattt gggctctctt ttgtttgagg atgttctaa ttctaaacct 1201  gtaaatgcag caggaagata ttttaattca aaggtgccaa taacacggac caaatcaact 1261  cctttttgaat tgatacagca gagagaaacc aaggaggtgg acagcaagga aaacttttct 1321  tatttggaat ctcaaccaca tgattcttgt tttgtagaga tgcaggctca aaaagtaatg 1381  catgtttctt cagcagaact gaattattca ctgccatatg actctaaaca ccaaatacgt 1441  aatgcctcta atgtaaagca ccatgactct agtgctcttg gtgtatattc ttacatacct
```

-continued

```
1501  ttagtggaaa atccttattt ttcatcatgg cctccaagtg gtaccagttc taagatgtct
1561  cttgatttac ctgagaagca agatggaact gttttccctt cttctctgtt gccaacatcc
1621  tctacatccc tcttctctta ttacaattca catgattctt tatcactgaa ttctccaacc
1681  aatatttcct cactattgaa ccaggagtca gctgtactag caactgctcc aaggatagat
1741  gatgaaatcc ccctccact tcctgtacgg acacctgaat catttattgt ggttgaggaa
1801  gctggagaat tctcaccaaa tgttcccaaa tccttatcct cagctgtgaa ggtaaaaatt
1861  ggaacatcac tggaatgggg tggaacatct gaaccaaaga aatttgatga ctctgtgata
1921  cttagaccaa gcaagagtgt aaaactccga agtcctaaat cagaactaca tcaagatcgt
1981  tcttctcccc cacctcctct cccagaaaga actctagagt ccttctttct tgccgatgaa
2041  gattgtatgc aggcccaatc tatagaaaca tattctacta gctatcctga caccatggaa
2101  aattcaacat cttcaaaaca gacactgaag actcctggaa aaagtttcac aaggagtaag
2161  agtttgaaaa ttttgcgaaa catgaaaaag agtatctgta attcttgccc accaaacaag
2221  cctgcagaat ctgttcagtc aaataactcc agctcatttc tgaattttgg ttttgcaaac
2281  cgtttttcaa aacccaaagg accaaggaat ccaccaccaa cttggaatat ttaataaaac
2341  tccagattta taataatatg ggctgcaagt acacctgcaa ataaaactac tagaatactg
2401  ctagttaaaa taagtgctct atatgcataa tatcaaatat gaagatatgc taatgtgtta
2461  atagctttta aaagaaaagc aaaatgccaa taagtgccag ttttgcattt tcatatcatt
2521  tgcattgagt tgaaaactgc aaataaaagt ttgtcacttg agcttatgta cagaatgcta
2581  tatgagaaac acttttagaa tggatttatt tttcattttt gccagttatt tttattttct
2641  tttacttttt tacataaaca taaacttcaa aaggtttgta agatttggat ctcaactaat
2701  ttctacattg ccagaatata ctataaaaag ttaaaaaaaa aacttacttt gtgggttgca
2761  atacaaactg ctcttgacaa tgactattcc ctgacagtta ttttgccta aatggagtat
2821  accttgtaaa tcttcccaaa tgttgtggaa aactggaata ttaagaaaat gagaaattat
2881  atttattaga ataaaatgtg caaataatga caattatttg aatgtaacaa ggaattcaac
2941  tgaaatcctg ataagtttta accaaagtca ttaaattacc aattctagaa aagtaatcaa
3001  tgaaatataa tagctatctt ttggtagcaa aagatataaa ttgtatatgt ttatacagga
3061  tctttcagat catgtgcaat ttttatctaa ccaatcagaa atactagttt aaaatgaatt
3121  tctatatgaa tatggatctg ccataagaaa atctagttca actctaattt tatgtagtaa
3181  ataaattggc aggtaattgt ttttacaaag aatccacctg acttccccta atgcattaaa
3241  aatatttta tttaaataac tttatttata acttttagaa acatgtagta ttgtttaaac
3301  atcatttgtt cttcagtatt tttcatttgg aagtccaata gggcaaattg aatgaagtat
3361  tattatctgt ctcttgtagt acaatgtatc caacagacac tcaataaact ttttggttgt
3421  taaaaaaaaa aaaaaa
```

The atg start and stop codons are bolded and underlined.
The amino acid sequence of human PTPN22, provided by Genbank Accession No. AAH716701.1, is incorporated herein by reference, and is shown below (SEQ ID NO: 190).

(SEQ ID NO: 190)
```
  1  mdqreilqkf ldeaqskkit keefaneflk lkrqstkyka dktypttvae kpknikknry
 61  kdilpydysr velslitsde dssyinanfi kgvygpkayi atqgplsttl ldfwrmiwey
121  svliivmacm eyemgkkkce rywaepgemq lefgpfsvsc eaekrksdyi irtlkvkfns
```

-continued

```
 181 etrtiyqfhy knwpdhdvps sidpileliw dvrcyqedds vpicihcsag cgrtgvicai 241 dytwmllkdg sqakhcipek nhtlqadsys pnlpksttka akmmnqqrtk meikesssfd 301 frtseisake elvlhpakss tsfdflelny sfdknadttm kwqtkafpiv geplqkhqsl 361 dlgsllfegc snskpvnaag ryfnskvpit rtkstpfeli qqretkevds kenfsylesq 421 phdscfvemq aqkvmhvssa elnyslpyds khqirnasnv khhdssalgv ysyiplvenp 481 yfsswppsgt sskmsldlpe kqdgtvfpss llptsstslf syynshdsls lnsptnissl 541 lnqesavlat apriddeipp plpvrtpesf ivveeagefs pnvpkslssa vkvkigtsle 601 wggtsepkkf ddsvilrpsk svklrspkse lhqdrssppp plpertlesf fladedcmqa 661 qsietystsy pdtmenstss kqtlktpgks ftrskslkil rnmkksicns cppnkpaesv 721 qsnnsssfln fgfanrfskp kgprnppptw ni
```

The mRNA sequence encoding human TNFAIP3 provided by Genbank Accession No. BC114480.1, is incorporated herein by reference, and is shown below (SEQ ID NO: 191).

```
    1 ccggagaggt gttggagagc aca atg gctg aacaagtcct tcctcaggct ttgtatttga 61 gcaatatgcg gaaagctgtg aagatacggg agagaactcc agaagacatt tttaaaccta 121 ctaatgggat cattcatcat tttaaaacca tgcaccgata cacactggaa atgttcagaa 181 cttgccagtt ttgtcctcag tttcgggaga tcatccacaa agccctcatc gacagaaaca 241 tccaggccac cctggaaagc cagaagaaac tcaactggtg tcgagaagtc cggaagcttg 301 tggcgctgaa aacgaacggt gacggcaatt gcctcatgca tgccacttct cagtacatgt 361 ggggcgttca ggacacagac ttggtactga ggaaggcgct gttcagcacg ctcaaggaaa 421 cagacacacg caactttaaa ttccgctggc aactggagtc tctcaaatct caggaatttg 481 ttgaaacggg gctttgctat gatactcgga actggaatga tgaatgggac aatcttatca 541 aaatggcttc cacagacaca cccatggccc gaagtggact tcagtacaac tcactggaag 601 aaatacacat atttgtcctt tgcaacatcc tcagaaggcc aatcattgtc atttcagaca 661 aaatgctaag aagtttggaa tcaggttcca atttcgcccc tttgaaagtg ggtggaattt 721 acttgcctct ccactggcct gcccaggaat gctacagata ccccattgtt ctcggctatg 781 acagccatca tttttgtaccc ttggtgaccc tgaaggacag tgggcctgaa atccgagctg 841 ttccacttgt taacagagac cggggaagat ttgaagactt aaaagttcac tttttgacag 901 atcctgaaaa tgagatgaag gagaagctct taaaagagta cttaatggtg atagaaatcc 961 ccgtccaagg ctgggaccat ggcacaactc atctcatcaa tgccgcaaag ttggatgaag 1021 ctaacttacc aaaagaaatc aatctggtag atgattactt tgaacttgtt cagcatgagt 1081 acaagaaatg gcaggaaaac agcgagcagg ggaggagaga ggggcacgcc cagaatccca 1141 tggaaccttc cgtgccccag ctttctctca tggatgtaaa atgtgaaacg cccaactgcc 1201 ccttcttcat gtctgtgaac acccagcctt tatgccatga gtgctcagag aggcggcaaa 1261 agaatcaaaa caaactccca aagctgaact ccaagccggg ccctgagggg ctccctggca 1321 tggcgctcgg ggcctctcgg ggagaagcct atgagccctt ggcgtggaac cctgaggagt 1381 ccactggggg gcctcattcg gccccaccga cagcacccag cccttttctg ttcagtgaga 1441 ccactgccat gaagtgcagg agcccggct gccccttcac actgaatgtg cagcacaacg 1501 gattttgtga acgttgccac aacgcccggc aacttcacgc cagccacgcc ccagaccaca
```

```
1561  caaggcactt ggatcccggg aagtgccaag cctgcctcca ggatgttacc aggacattta
1621  atgggatctg cagtacttgc ttcaaaagga ctacagcaga ggcctcctcc agcctcagca
1681  ccagcctccc tccttcctgt caccagcgtt ccaagtcaga tccctcgcgg ctcgtccgga
1741  gcccctcccc gcattcttgc cacagagctg gaaacgacgc cctgctggc tgcctgtctc
1801  aagctgcacg gactcctggg gacaggacgg ggacgagcaa gtgcagaaaa gccggctgcg
1861  tgtattttgg gactccagaa aacaagggct tttgcacact gtgtttcatc gagtacagag
1921  aaaacaaaca ttttgctgct gcctcaggga aagtcagtcc cacagcgtcc aggttccaga
1981  acaccattcc gtgcctgggg agggaatgcg gcacccttgg aagcaccatg tttgaaggat
2041  actgccagaa gtgtttcatt gaagctcaga atcagagatt tcatgaggcc aaaaggacag
2101  aagagcaact gagatcgagc cagcgcagag atgtgcctcg aaccacacaa agcacctcaa
2161  ggcccaagtg cgcccgggcc tcctgcaaga acatcctggc ctgccgcagc gaggagctct
2221  gcatggagtg tcagcatccc aaccagagga tgggccctgg ggccaccgg ggtgagcctg
2281  cccccgaaga ccccccccaag cagcgttgcc gggccccgc ctgtgatcat tttggcaatg
2341  ccaagtgcaa cggctactgc aacgaatgct ttcagttcaa gcagatgtat ggctaaccgg
2401  aaacaggtgg gtcacctcct gcaagaagtg gggcctcgag ctgtcagtca tcatggtgct
2461  atcctctgaa cccctcagct gccactgcaa cagtgggctt aagggtgtct gagcaggaga
2521  ggaaagataa gctcttcgtg gtgcccacga tgctcaggtt tggtaacccg ggagtgttcc
2581  caggtggcct tagaaagcaa agcttgtaac tggcaaggga tgatgtcaga ttcagcccaa
2641  ggttcctcct ctcctaccaa gcaggaggcc aggaacttct tggacttgg aaggtgtgcg
2701  gggactggcc gaggcccctg caccctgcgc atcaggactg cttcatcgtc ttggctgaga
2761  aagggaaaag acacacaagt cgcgtgggtt ggagaagcca gagccattcc acctcccctc
2821  ccccagcatc tctcagagat gtgaagccag atcctcatgg cagcgaggcc ctctgcaaga
2881  agctcaagga agctcaggga aaatgacgt attcagagag tgtttgtagt tcatggtttt
2941  tccctacctg cccggttcct ttcctgagga cccggcagaa atgcagaacc atccatggac
3001  tgtgattctg aggctgctga gactgaacat gttcacattg acagaaaaac aagctgctct
3061  ttataatatg caccttttaa aaaattagaa tatttactg ggaagacgtg taactctttg
3121  ggttattact gtctttactt ctaaagaagt tagcttgaac tgaggagtaa aagtgtgtac
3181  atatataata taccttaca ttatgtatga gggattttt taaattatat tgaaatgctg
3241  ccctagaagt acaataggaa ggctaaataa taataacctg ttttctggtt gttgttgggg
3301  catgagcttg tgtatacact gcttgcataa actcaaccag ctgccttttt aaagggagct
3361  ctagtccttt ttgtgtaatt cactttattt atttattac aaacttcaag attatttaag
3421  cgaagatatt tcttcagctc tggggaaaat gccacagtgt tctcctgaga gaacatcctt
3481  gctttgagtc aggctgtggg caagttcctg accacaggga gtaaattggc ctctttgata
3541  cacttttgct tgcctcccca ggaaagaagg aattgcatcc aaggtataca tacatattca
3601  tcgatgtttc gtgcttctcc ttatgaaact ccagctatgt aataaaaaac tatactctgt
3661  gttctgttaa tgcctctgag tgtcctacct ccttggagat gagatagga aggagcaggg
3721  atgagactgg caatggtcac agggaaagat gtggccttt tgatggttt tattttctgt
3781  taacactgtg tcctgggggg gctgggaagt cccctgcatc ccatg
```

The atg start and stop codons are bolded and underlined.
The amino acid sequence of human TNFAIP3, provided by Genbank Accession No. AAI14481.1, is incorporated herein be reference, and is shown below (SEQ ID NO: 192).

```
  1  maeqvlpqal ylsnmrkavk irertpedif kptngiihhf ktmhrytlem frtcqfcpqf
 61  reiihkalid rniqatlesq kklnwcrevr klvalktngd gnclmhatsq ymwgvqdtdl
121  vlrkalfstl ketdtrnfkf rwqleslksq efvetglcyd trnwndewdn likmastdtp
181  marsglqyns leeihifvlc nilrrpiivi sdkmlrsles gsnfaplkvg giylplhwpa
241  qecyrypivl gydshhfvpl vtlkdsgpei ravplvnrdr grfedlkvhf ltdpenemke
301  kllkeylmvi eipvqgwdhg tthlinaakl deanlpkein lvddyfelvq heykkwqens
361  eqgrreghaq npmepsvpql slmdvkcetp ncpffmsvnt qplchecser rqknqnklpk
421  lnskpgpegl pgmalgasrg eayeplawnp eestggphsa pptapspflf settamkcrs
481  pgcpftlnvq hngfcerchn arqlhashap dhtrhldpgk cqaclqdvtr tfngicstcf
541  krttaeassss lstslppsch qrsksdpsrl vrspsphsch ragndapagc lsqaartpgd
601  rtgtskcrka gcvyfgtpen kgfctlcfie yrenkhfaaa sgkvsptasr fqntipclgr
661  ecgtlgstmf egycqkcfie aqnqrfheak rteeqlrssq rrdvprttqs tsrpkcaras
721  cknilacrse elcmecqhpn qrmgpgahrg epapedppkq rcrapacdhf gnakcngycn
781  ecfqfkqmyg
```

The mRNA sequence encoding human STAT4 provided by Genbank Accession No. L78440.1, is incorporated herein by reference, and is shown below (SEQ ID NO: 193).

```
   1  gctttctcct agggactgtg aggggcgctt ctgactttgg acttgagcac tgcctgggac
  61  ctgtgctgag agagcgctag catgtctcag tggaatcaag tccaacagtt agaaatcaag
 121  tttttggagc aggtggatca attctatgat gacaactttc ccatggaaat tcggcatctg
 181  ttggcccaat ggattgaaaa tcaagactgg gaggcagctt ctaacaatga aaccatggca
 241  acgattcttc ttcaaaactt gttaatacaa ctggatgaac agttaggtcg tgtttccaaa
 301  gagaaaaacc tactcttgat acacaatcta aaaagaatta ggaaggtcct tcagggaaaa
 361  tttcatggaa atccaatgca tgtagctgtg ttatttcaa actgtttaag ggaagagagg
 421  agaatattgg ctgcagccaa catgcctgtc caggggcctc tagagaaatc cttacaaagt
 481  tcttcagttt cagaaagaca gaggaatgtg gagcacaaag tggctgccat taaaaacagt
 541  gtgcagatga cagaacaaga taccaaatac ttagaagatc tgcaagacga atttgactac
 601  aggtataaaa caattcagac aatggatcag agtgacaaga tagtgccat ggtgaatcag
 661  gaagttttga cactgcagga aatgcttaac agcctcgatt tcaagagaaa ggaggctctc
 721  agtaaaatga cccaaatcat ccatgagaca gacctgttaa tgaacaccat gctcatagaa
 781  gagctgcaag actggaagcg gcggcagcaa atcgcctgca tcggggtcc actccacaat
 841  gggctcgacc agcttcagaa ctgctttaca ctattggcag aaagtctttt ccaactgaga
 901  aggcaattgg agaaactaga ggagcaatct accaaaatga catatgaagg tgatcccatt
 961  ccaatgcaaa gaactcacat gctagaaaga gtcaccttct gatctacaa ccttttcaag
1021  aactcatttg tggttgagcg acagccatgt atgccaaccc accctcagag gccgttggta
1081  cttaaaaccc taattcagtt cactgtaaaa ctaaggctac taataaaatt gccagaacta
1141  aactatcagg taaaggttaa ggcatcaatt gacaagaatg tttcaactct aagcaaccga
1201  agatttgtac tttgtggaac taatgtcaaa gccatgtcta ttgaagaatc ttccaatggg
1261  agtctctcag tagaatttcg acatttgcaa ccaaggaaa tgaagtccag tgctggaggt
1321  aaaggaaatg agggctgtca catggtgact gaagaacttc attccataac gtttgaaaca
```

```
1381  cagatctgcc tctatggcct gaccatagat ttggagacca gctcattgcc tgtggtgatg 1441  atttccaatg tcagtcagtt acctaatgct gggcatcca tcatttggta caacgtgtca 1501  accaacgatt cccagaactt ggttttcttt aataatcctc cacctgccac attgagtcaa 1561  ctactggagg tgatgagctg gcagttttca tcgtacgttg gtcgtggtct taactcagat 1621  caactccata tgctggcaga aagcttaca gtccaatcta gctacagtga tggtcacctc 1681  acctgggcca agttctgcaa ggaacattta cctggtaaat catttacctt ttggacatgg 1741  cttgaagcaa tattggatct aattaagaaa cacattcttc cctttggat tgatgggtat 1801  gtcatgggct tgttagcaa agagaaggaa cggctgttgc taaaggataa aatgcctggc 1861  accttttttat taagattcag tgaaagccat ctcggaggaa taactttcac ctgggtggac 1921  cattctgaaa gtggggaagt gagattccac tctgtagaac cctacaataa aggccggttg 1981  tctgctctgc cattcgctga catcctgcga gactacaaag ttattatggc tgaaaacatt 2041  cctgaaaacc ctctgaagta cctatatcct gacattccca agacaaagc cttcggtaaa 2101  cactacagct ctcagccttg cgaagtttca agaccaacag aaagggggtga caaaggttat 2161  gttccttctg tttttatccc catctcaaca atccgaagtg attcaacaga gccacattct 2221  ccatcagacc ttcttcccat gtctccaagt gtgtatgcgg tgttgagaga aaacctgagt 2281  cccacaacaa ttgaaactgc aatgaagtct ccttattctg ctgaatgaca ggataaactc 2341  tgacgcacca agaaaggaag caaatgaaaa agtttaaaga ctgttctttg cccaataacc 2401  acattttatt tcttcagctt tgtaaatacc aggttctagg aaatgtttga catctgaagc 2461  tctcttcaca ctcccgtggc actcctcaat tgggagtgtt gtgactgaaa tgcttgaaac 2521  caaagcttca gataaacttg caagataaga caactttaag aaaccagtgt taataacaat 2581  attaacag
```

The atg start and stop codons are bolded and underlined. The amino acid sequence of human STAT4, provided by Genbank Accession No. AAB05605.1, is incorporated herein by reference, and is shown below (SEQ ID NO: 194).

```
  1  msqwnqvqql eikfleqvdq fyddnfpmei rhllaqwien qdweaasnne tmatillqnl 61  liqldeqlgr vskeknllli hnlkrirkvl qgkfhgnpmh vavvisnclr eerrilaaan 121  mpvqgpleks lqsssyserq rnvehkvaai knsvqmteqd tkyledlqde fdyryktiqt 181  mdqsdknsam vnqevltlqe mlnsldfkrk ealskmtqii hetdllmntm lieelqdwkr 241  rqqiaciggp lhngldqlqn cftllaeslf qlrrqlekle eqstkmtyeg dpipmqrthm 301  lervtfliyn lfknsfvver qpcmpthpqr plvlktliqf tvklrllikl pelnyqvkvk 361  asidknvstl snrrfvlcgt nvkamsiees sngslsvefr hlqpkemkss aggkgnegch 421  mvteelhsit fetqiclygl tidletsslp vvmisnvsql pnawasiiwy nvstndsqnl 481  vffnnpppat lsqllevmsw qfssyvgrgl nsdqlhmlae kltvqssysd ghltwakfck 541  ehlpgksftf wtwleaildl ikkhilplwi dgyvmgfvsk ekerllkdk mpgtfllrfs 601  eshlggitft wvdhsesgev rfhsvepynk grlsalpfad ilrdykvima enipenplky 661  lypdipkdka fgkhyssqpc evsrptergd kgyvpsvfip istirsdste phspsdllpm 721  spsvyavlre nlspttieta mkspysae
```

The mRNA sequence encoding human CCR6 provided by Genbank Accession No. AY242126.1, is incorporated herein by reference, and is shown below (SEQ ID NO: 195).

```
  1    atgagcgggg aatcaatgaa tttcagcgat gttttcgact ccagtgaaga ttattttgtg
 61    tcagtcaata cttcatatta ctcagttgat tctgagatgt tactgtgctc cttgcaggag
121    gtcaggcagt tctccaggct atttgtaccg attgcctact ccttgatctg tgtctttggc
181    ctcctgggga atattctggt ggtgatcacc tttgctttt ataagaaggc caggtctatg
241    acagacgtct atctcttgaa catggccatt gcagacatcc tctttgttct tactctccca
301    ttctgggcag tgagtcatgc cactggtgcg tgggttttca gcaatgccac gtgcaagttg
361    ctaaaaggca tctatgccat caactttaac tgcgggatgc tgctcctgac ttgcattagc
421    atggaccggt acatcgccat tgtacaggcg actaagtcat tccggctccg atccagaaca
481    ctaccgcgca gcaaaatcat ctgccttgtt gtgtggggc tgtcagtcat catctccagc
541    tcaacttttg tcttcaacca aaaatacaac acccaaggca gcgatgtctg tgaacccaag
601    taccagactg tctcggagcc catcaggtgg aagctgctga tgttggggct tgagctactc
661    tttggtttct ttatcccttt gatgttcatg atattttgtt acacgttcat tgtcaaaacc
721    ttggtgcaag ctcagaattc taaaaggcac aaagccatcc gtgtaatcat agctgtggtg
781    cttgtgtttc tggcttgtca gattcctcat aacatggtcc tgcttgtgac ggctgcaaat
841    ttgggtaaaa tgaaccgatc ctgccagagc gaaaagctaa ttggctatac gaaaactgtc
901    acagaagtcc tggctttcct gcactgctgc ctgaaccctg tgctctacgc ttttattggg
961    cagaagttca gaaactactt tctgaagatc ttgaaggacc tgtggtgtgt gagaaggaag
1021   tacaagtcct caggcttctc ctgtgccggg aggtactcag aaaacatttc tcggcagacc
1081   agtgagaccg cagataacga caatgcgtcg tccttcacta tgtga
```

The atg start and stop codons are bolded and underlined.
The amino acid sequence of human CCR6, provided by Genbank Accession No. AAO92293.1, is incorporated herein by reference, and is shown below (SEQ ID NO: 196).

```
  1    msgesmnfsd vfdssedyfv svntsyysvd semllcslqe vrqfsrlfvp iayslicvfg
 61    llgnilvvit fafykkarsm tdvyllnmai adilfvltlp fwayshatga wvfsnatckl
121    lkgiyainfn cgmllltcis mdryiaivqa tksfrlrsrt lprskiiclv vwglsviiss
181    stfvfnqkyn tqgsdvcepk yqtvsepirw kllmlglell fgffiplmfm ifcytfivkt
241    lvqaqnskrh kairviiavv lvflacqiph nmvllvtaan lgkmnrscqs ekligytktv
301    tevlaflhcc lnpvlyafig qkfrnyflki lkdlwcvrrk yksgfscag rysenisrqt
361    setadndnas sftm
```

The mRNA sequence encoding human TNFR-1 (tumor necrosis factor receptor 1) provided by Genbank Accession No. NM_001065.3, is incorporated herein by reference, and is shown below (SEQ ID NO: 197).

```
  1    ctcctccagc tcttcctgtc ccgctgttgc aacactgcct cactcttccc ctcccaccctt
 61    ctctcccctc ctctctgctt taattttctc agaattctct ggactgaggc tccagttctg
121    gcctttgggg ttcaagatca ctgggaccag gccgtgatct ctatgcccga gtctcaaccc
181    tcaactgtca ccccaaggca cttgggacgt cctggacaga ccgagtcccg ggaagcccca
241    gcactgccgc tgccacactg ccctgagccc aaatggggga gtgagaggcc atagctgtct
301    ggcatgggcc tctccaccgt gctgacctg ctgctgccac tggtgctcct ggagctgttg
361    gtgggaatat accctcagg ggttattgga ctggtccctc acctagggga cagggagaag
```

-continued

```
 421   agagatagtg tgtgtcccca aggaaaatat atccaccctc aaaataattc gatttgctgt
 481   accaagtgcc acaaaggaac ctacttgtac aatgactgtc caggcccggg gcaggatacg
 541   gactgcaggg agtgtgagag cggctccttc accgcttcag aaaaccacct cagacactgc
 601   ctcagctgct ccaaatgccg aaaggaaatg ggtcaggtgg agatctcttc ttgcacagtg
 661   gaccgggaca ccgtgtgtgg ctgcaggaag aaccagtacc ggcattattg gagtgaaaac
 721   cttttccagt gcttcaattg cagcctctgc ctcaatggga ccgtgcacct ctcctgccag
 781   gagaaacaga acaccgtgtg cacctgccat gcaggtttct ttctaagaga aaacgagtgt
 841   gtctcctgta gtaactgtaa gaaaagcctg gagtgcacga agttgtgcct accccagatt
 901   gagaatgtta agggcactga ggactcaggc accacagtgc tgttgcccct ggtcattttc
 961   tttggtcttt gccttttatc cctcctcttc attggtttaa tgtatcgcta ccaacggtgg
1021   aagtccaagc tctactccat tgtttgtggg aaatcgacac ctgaaaaaga gggggagctt
1081   gaaggaacta ctactaagcc cctggcccca aacccaagct tcagtcccac tccaggcttc
1141   accccccacc tgggcttcag tcccgtgccc agttccacct tcacctccag ctccacctat
1201   accccggtg actgtcccaa ctttgcggct ccccgcagag aggtggcacc accctatcag
1261   ggggctgacc ccatccttgc gacagccctc gcctccgacc ccatcccaa ccccttcag
1321   aagtgggagg acagcgccca caagccacag agcctagaca ctgatgaccc cgcgacgctg
1381   tacgccgtgg tggagaacgt gccccccgttg cgctggaagg aattcgtgcg gcgcctaggg
1441   ctgagcgacc acgagatcga tcggctggag ctgcagaacg ggcgctgcct gcgcgaggcg
1501   caatacagca tgctggcgac ctggaggcgg cgcacgccgc ggcgcgaggc cacgctggag
1561   ctgctggac gcgtgctccg cgacatggac ctgctgggct gcctggagga catcgaggag
1621   gcgctttgcg gccccgccgc cctcccgccc gcgcccagtc ttctcagatg aggctgcgcc
1681   cctgcgggca gctctaagga ccgtcctgcg agatcgcctt ccaacccac tttttctgg
1741   aaaggagggg tcctgcaggg gcaagcagga gctagcagcc gcctacttgg tgctaaccc
1801   tcgatgtaca tagcttttct cagctgcctg cgcgccgccg acagtcagcg ctgtgcgcgc
1861   ggagagaggt gcgccgtggg ctcaagagcc tgagtgggtg gtttgcgagg atgagggacg
1921   ctatgcctca tgcccgtttt gggtgtcctc accagcaagg ctgctcgggg gcccctggtt
1981   cgtccctgag ccttttttcac agtgcataag cagttttttt tgtttttgtt ttgtttttgtt
2041   ttgtttttaa atcaatcatg ttacactaat agaaacttgg cactcctgtg ccctctgcct
2101   ggacaagcac atagcaagct gaactgtcct aaggcagggg cgagcacgga acaatggggc
2161   cttcagctgg agctgtggac ttttgtacat acactaaaat tctgaagtta aagctctgct
2221   cttggaaaaa aaaaaaaaaa aaaaaaaaa aaaaaaa
```

The atg start and stop codons are bolded and underlined.
The amino acid sequence of human TNFR-1 (tumor necrosis factor receptor 1), provided by Genbank Accession No. NP_001056.1, is incorporated herein by reference, and is shown below (SEQ ID NO: 198).

```
  1   mglstvpdll lplvllellv giypsgvigl vphlgdrekr dsvcpqgkyi hpqnnsicct
 61   kchkgtylyn dcpgpgqdtd crecesgsft asenhlrhcl scskcrkemg qveissctvd
121   rdtvcgcrkn qyrhywsenl fqcfncslcl ngtvhlscqe kqntvctcha gfflrenecv
181   scsnckksle ctklclpqie nvkgtedsgt tvllplviff glcllsllfi glmyryqrwk
241   sklysivcgk stpekegele gtttkplapn psfsptpgft ptlgfspvps stftssstyt
```

-continued

```
301  pgdcpnfaap rrevappyqg adpilatala sdpipnplqk wedsahkpqs ldtddpatly 361  avvenvpplr wkefvrrlgl sdheidrlel qngrclreaq ysmlatwrrr tprreatlel 421  lgrvlrdmdl lgcledieea lcgpaalppa psllr  Signal peptide AA 1-21;
     mature peptide AA 22-455).
```

The mRNA sequence encoding human TNFR-2 provided by Genbank Accession No. M55994.1, is incorporated herein by reference, and is shown below (SEQ ID NO: 199).

```
   1   gaattcggcg cagcggagcc tggagagaag gcgctgggct gcgagggcgc gagggcgcga 61   gggcaggggg caaccggacc ccgcccgcac ccatggcgcc cgtcgccgtc tgggccgcgc 121   tggccgtcgg actggagctc tgggctgcgg cgcacgcctt gcccgcccag gtggcattta 181   caccctacgc cccggagccc gggagcacat gccggctcag agaatactat gaccagacag 241   ctcagatgtg ctgcagcaag tgctcgccgg ccaacatgc aaaagtcttc tgtaccaaga 301   cctcggacac cgtgtgtgac tcctgtgagg acagcacata cacccagctc tggaactggg 361   ttcccgagtg cttgagctgt ggctcccgct gtagctctga ccaggtggaa actcaagcct 421   gcactcggga acagaaccgc atctgcacct gcaggccgg ctggtactgc gcgctgagca 481   agcaggaggg gtgccggctg tgcgcgccgc tgcgcaagtg ccgcccgggc ttcggcgtgg 541   ccagaccagg aactgaaaca tcagacgtgg tgtgcaagcc ctgtgccccg gggacgttct 601   ccaacacgac ttcatccacg gatatttgca ggccccacca gatctgtaac gtggtggcca 661   tccctgggaa tgcaagcagg gatgcagtct gcacgtccac gtcccccacc cggagtatgg 721   ccccagggc agtacactta ccccagccag tgtccacacg atcccaacac acgcagccaa 781   ctccagaacc cagcactgct ccaagcacct ccttcctgct cccaatgggc cccagccccc 841   cagctgaagg gagcactggc gacttcgctc ttccagttgg actgattgtg ggtgtgacag 901   ccttgggtct actaataata ggagtggtga actgtgtcat catgacccag gtgaaaaaga 961   agcccttgtg cctgcagaga aagccaagg tgcctcactt gcctgccgat aaggcccggg 1021   gtacacaggg ccccgagcag cagcacctgc tgatcacagc gccgagctcc agcagcagct 1081   ccctggagag ctcggccagt gcgttggaca aagggcgcc cactcggaac cagccacagg 1141   caccaggcgt ggaggccagt ggggccgggg aggcccgggc cagcaccggg agctcagatt 1201   cttcccctgg tggccatggg acccaggtca atgtcacctg catcgtgaac gtctgtagca 1261   gctctgacca cagctcacag tgctcctccc aagccagctc acaatgggga gacacagatt 1321   ccagcccctc ggagtccccg aaggacgagc aggtccccct ctccaaggag gaatgtgcct 1381   ttcggtcaca gctggagacg ccagagaccc tgctggggag caccgaagag aagccctgc 1441   cccttggagt gcctgatgct gggatgaagc ccagttaacc aggccggtgt gggctgtgtc 1501   gtagccaagg tgggctgagc cctggcagga tgaccctgcg aaggggccct ggtccttcca 1561   ggcccccacc actaggactc tgaggctctt tctgggccaa gttcctctag tgccctccac 1621   agccgcagcc tccctctgac ctgcaggcca agagcagagg cagcgggttg tggaaagcct 1681   ctgctgccat ggtgtgtccc tctcggaagg ctggctgggc atggacgttc ggggcatgct 1741   ggggcaagtc cctgactctc tgtgacctgc ccgcccagc tgcacctgcc agcctggctt 1801   ctggagccct tgggtttttt gtttgtttgt ttgtttgttt gtttgtttct cccctgggc 1861   tctgccccag ctctggcttc cagaaaaccc cagcatcctt ttctgcagag gggctttctg 1921   gagaggaggg atgctgcctg agtcacccat gaagacagga cagtgcttca gcctgaggct
```

-continued

```
1981    gagactgcgg gatggtcctg gggctctgtg cagggaggag gtggcagccc tgtagggaac
2041    ggggtccttc aagttagctc aggaggcttg gaaagcatca cctcaggcca ggtgcagtcc
2101    ctcacgccta tgatcccagc actttgggag gctgaggcgg gtggatcacc tgaggttagg
2161    agttcgagac cagcctggcc aacatggtaa acccatct ctactaaaaa tacagaaatt
2221    agccgggcgt ggtggcgggc acctatagtc ccagctactc agaagcctga ggctgggaaa
2281    tcgtttgaac ccgggaagcg gaggttgcag ggagccgaga tcacgccact gcactccagc
2341    ctgggcgaca gagcgagagt ctgtctcaaa agaaaaaaaa aaaaaaccga attc
```

The atg start and stop codons are bolded and underlined. The amino acid sequence of human TNFR-2, provided by Genbank Accession No. AAA36755.1, is incorporated herein by reference, and is shown below (SEQ ID NO: 200).

```
1      mapvavwaal avglelwaaa halpaqvaft pyapepgstc rlreyydqta qmccskcspg
61     qhakvfctkt sdtvcdsced stytqlwnwv peclscgsrc ssdqvetqac treqnrictc
121    rpgwycalsk qegcrlcapl rkcrpgfgva rpgtetsdvv ckpcapgtfs nttsstdicr
181    phqicnvvai pgnasrdavc tstsptrsma pgavhlpqpv strsqhtqpt pepstapsts
241    fllpmgpspp aegstgdfal pvglivgvta lglliigvvn cvimtqvkkk plclqreakv
301    phlpadkarg tqgpeqqhll itapssssss lessasaldr raptrnqpqa pgveasgage
361    arastgssds spgghgtqvn vtcivnvcss sdhssqcssq asstmgdtds spsespkdeq
421    vpfskeecaf rsqletpetl lgsteekplp lgvpdagmkp s (Signal peptide AA
       1-22; mature peptide AA 23-461).
```

The mRNA sequence encoding human cell death protein (RIP) provided by Genbank Accession No. U25994.1, is incorporated herein by reference, and is shown below (SEQ ID NO: 201).

```
1      gacgtgaaga gtttaaagaa agagtattca aacgaaaatg cagttgtgaa gagaatgcag
61     tctcttcaac ttgattgtgt ggcagtacct tcaagccggt caaattcagc cacagaacag
121    cctggttcac tgcacagttc ccagggactt gggatgggtc ctgtggagga gtcctggttt
181    gctccttccc tggagcaccc acaagaagag aatgagccca gcctgcagag taaactccaa
241    gacgaagcca actaccatct ttatggcagc cgcatggaca ggcagacgaa acagcagccc
301    agacagaatg tggcttacaa cagagaggag gaaaggagac gcagggtctc ccatgaccct
361    tttgcacagc aaagaccta cgagaatttt cagaatacag agggaaaagg cactgtttat
421    tccagtgcag ccagtcatgg taatgcagtg caccagccat cagggctcac cagccaacct
481    caagtactgt atcagaacaa tggattatat agctcacatg gctttggaac aagaccactg
541    gatccaggaa cagcaggtcc cagagtttgg tacaggccaa ttccaagtca tatgcctagt
601    ctgcataata tcccagtgcc tgagaccaac tatctaggaa attctcccac catgccattc
661    agctccttgc caccaacaga tgaatctata aaatatacca tatacaatag tactggcatt
721    cagattggag cctacaatta tatggagatt ggtgggacga gttcatcact actagacagc
781    acaaatacga acttcaaaga agagccagct gctaagtacc aagctatctt tgataatacc
841    actagtctga cggataaaca cctggaccca atcagggaaa atctgggaaa gcactggaaa
901    aactgtgccc gtaaactggg cttcacacag tctcagattg atgaaattga ccatgactat
961    gagcgagatg gactgaaaga aaaggtttac cagatgctcc aaaagtgggt gatgagggaa
```

-continued

```
1021   ggcataaagg gagccacggt ggggaagctg gcccaggcgc tccaccagtg ttccaggatc 1081   gaccttctga gcagcttgat ttacgtcagc cagaactaac cctggatggg ctacggcagc 1141   tgaagtggac gcctcactta gtggataacc cagaaagtt ggctgcctca gagcattcag 1201   aattctgtcc tcactgatag gggttctgtg tctgcagaaa
```

The atg start and stop codons are bolded and underlined.
The amino acid sequence of human RIP, provided by Genbank Accession No. AAC50137.1, is incorporated herein by reference, and is shown below (SEQ ID NO: 202).

```
  1   dvkslkkeys nenavvkrmq slqldcvavp ssrsnsateq pgslhssqgl gmgpveeswf 61   apslehpqee nepslqsklq deanyhlygs rmdrqtkqqp rqnvaynree errrrvshdp 121   faqqrpyenf qntegkgtvy ssaashgnav hqpsgltsqp qvlyqnngly sshgfgtrpl 181   dpgtagprvw yrpipshmps lhnipvpetn ylgnsptmpf sslpptdesi kytiynstgi 241   qigaynymei ggtssslids tntnfkeepa akyqaifdnt tsltdkhldp irenlgkhwk 301   ncarklgftq sqideidhdy erdglkekvy qmlqkwvmre gikgatvgkl aqalhqcsri 361   dllssliyvs qn
```

The mRNA sequence encoding human TRADD provided by Genbank Accession No. NM_003789.3, is incorporated herein by reference, and is shown below (SEQ ID NO: 203).

```
   1   gcacaccecgg aagcggcgga gtagagcgga gcctggcggg cgtgggaacc caggcccccgc 61   cgaggcggcc aggaggtgag atggcagctg gcaaaatgg gcacgaagag tgggtgggca 121   gcgcatacct gtttgtggag tcctcgctgg acaaggtggt cctgtcggat gcctacgcgc 181   acccccagca gaaggtggca gtgtacaggg ctctgcaggc tgccttggca gagagcggcg 241   ggagcccgga cgtgctgcag atgctgaaga tccaccgcag cgacccgcag ctgatcgtgc 301   agctgcgatt ctgcgggcgg cagccctgtg gccgcttcct ccgcgcctac cgcgaggggg 361   cgctgcgcgc cgcgctgcag aggagcctgg cggccgcgct cgcccagcac tcggtgccgc 421   tgcaactgga gctgcgcgcc ggcgccgagc ggctggacgc tttgctggcg gacgaggagc 481   gctgtttgag ttgcatccta gcccagcagc ccgaccggcc ccgggatgaa gaactggctg 541   agctggagga tgcgctgcga aatctgaagt gcggctcggg ggcccggggt ggcgacgggg 601   aggtcgcttc ggccccttg cagcccccgg tgccctctct gtcggaggtg aagccgccgc 661   cgccgccgcc acctgcccag acttttctgt tccagggtca gcctgtagtg aatcggccgc 721   tgagcctgaa ggaccaacag acgttcgcgc gctctgtggg tctcaaatgg cgcaaggtgg 781   ggcgctcact gcagcgaggc tgccgggcgc tgcgggaccc ggcgctggac tcgctggcct 841   acgagtacga gcgcgaggga ctgtacgagc aggccttcca gctgctgcgg cgcttcgtgc 901   aggccgaggg ccgccgcgcc acgctgcagc gcctggtgga ggcactcgag gagaacgagc 961   tcaccagcct ggcagaggac ttgctgggcc tgaccgatcc caatggcggc ctggcctaga 1021   ccaggggtgc agccagcttt tggagaacct ggatggcctt agggttcctt ctgcggctat 1081   tgctgaaccc ctgtccatcc acgggaccct gaaactccac ttggcctatc tgctggacct 1141   gctggggcag agttgattgc cttccccagg agccagacca ctgggggtgc atcattgggg 1201   attctgcctc aggtactttg atagagtgtg gggtgggggg gacctgcttt ggagatcagc 1261   ctcaccttct cccatcccag aagcggggct tacagccagc ccttacagtt tcactcatga
```

-continued

```
1321  agcaccttga tctttggtgt cctggacttc atcctgggtg ctgcagatac tgcagtgaag 1381  taaaacagga atcaatcttg cctgccccca gctcacactc agcgtgggac cccgaatgtt 1441  aagcaatgat aataaagtat aacacggatt ttgatgtgag aaaaaaaaaa aaaaaa
```

The atg start and stop codons are bolded and underlined. The amino acid sequence of human TRADD, provided by Genbank Accession No. NP_00370.1, is incorporated herein by reference, and is shown below (SEQ ID NO: 204).

```
  1  maagqnghee wvgsaylfve ssldkvvlsd ayahpqqkva vyralqaala esggspdvlq 61  mlkihrsdpq livqlrfcgr qpcgrflray regalraalq rslaaalaqh svplqlelra 121  gaerldalla deerclscil aqqpdrlrde elaeledalr nlkcgsgarg gdgevasapl 181  qppvpslsev kppppppppaq tflfqgqpvv nrplslkdqq tfarsvglkw rkvgrslqrg 241  cralrdpald slayeyereg lyeqafqllr rfvqaegrra tlqrlveale eneltslaed 301  llgltdpngg la
```

The mRNA sequence encoding human PADI2 (protein-arginine deiminase type-2) provided by Genbank Accession No. NM_007365.2, is incorporated herein by reference, and is shown below (SEQ ID NO: 205).

```
   1  gcaggctgct ggagaaggcg cacctgctgc aggtgctccc ggccgccccg gaccagcgag 61  cgcgggcact gcggcgggga ggatgctgcg cgagcggacc gtgcggctgc agtacgggag 121  ccgcgtggag gcggtgtacg tgctgggcac ctacctctgg accgatgtct acagcgcggc 181  cccagccggg gcccaaacct tcagcctgaa gcactcggaa cacgtgtggg tggaggtggt 241  gcgtgatggg gaggctgagg aggtggccac caatggcaag cagcgctggc ttctctcgcc 301  cagcaccacc ctgcgggtca ccatgagcca ggcgagcacc gaggccagca gtgacaaggt 361  caccgtcaac tactatgacg aggaagggag cattcccatc gaccaggcgg ggctcttcct 421  cacagccatt gagatctccc tggatgtgga cgcagaccgg gatggtgtgg tggagaagaa 481  caacccaaag aaggcatcct ggacctgggg ccccgagggc caggggggcca tcctgctggt 541  gaactgtgac cgagagacac cctggttgcc caaggaggac tgccgtgatg agaaggtcta 601  cagcaaggaa gatctcaagg acatgtccca gatgatcctg cggaccaaag gccccgaccg 661  cctccccgcc ggatacgaga tagttctgta catttccatg tcagactcag acaaagtggg 721  cgtgttctac gtggagaacc cgttcttcgg ccaacgctat atccacatcc tgggccggcg 781  gaagctctac catgtggtca agtacacggg tggctccgcg gagctgctgt tcttcgtgga 841  aggcctctgt ttccccgacg agggcttctc aggcctggtc tccatccatg tcagcctgct 901  ggagtacatg gcccaggaca ttcccctgac tcccatcttc acggacaccg tgatattccg 961  gattgctccg tggatcatga cccccaacat cctgcctccc gtgtcggtgt ttgtgtgctg 1021  catgaaggat aattacctgt tcctgaaaga ggtgaagaac cttgtggaga aaaccaactg 1081  tgagctgaag gtctgcttcc agtacctaaa ccgaggcgat cgctggatcc aggatgaaat 1141  tgagtttggc tacatcgagg cccccataa aggcttcccc gtggtgctgg actctccccg 1201  agatggaaac ctaaaggact tccctgtgaa ggagctcctg ggcccagatt ttggctacgt 1261  gacccgggag cccctctttg agtctgtcac cagccttgac tcatttggaa acctggaggt 1321  cagtccccca gtgaccgtga acggcaagac ataccgcctt ggccgcatcc tcatcgggag 1381  cagctttcct ctgtctggtg gtcggaggat gaccaaggtg gtgcgtgact tcctgaaggc
```

-continued

```
1441  ccagcaggtg caggcgcccg tggagctcta ctcagactgg ctgactgtgg gccacgtgga
1501  tgagttcatg tcctttgtcc ccatccccgg cacaaagaaa ttcctgctac tcatggccag
1561  cacctcggcc tgctacaagc tcttccgaga gaagcagaag gacggccatg gagaggccat
1621  catgttcaaa ggctggggtg gatgagcag caagcgaatc accatcaaca agattctgtc
1681  caacgagagc cttgtgcagg agaacctgta cttccagcgc tgcctagact ggaaccgtga
1741  catcctcaag aaggagctgg gactgacaga gcaggacatc attgacctgc ccgctctgtt
1801  caagatggac gaggaccacc gtgccagagc cttcttccca aacatggtga acatgatcgt
1861  gctggacaag gacctgggca tccccaagcc attcgggcca caggttgagg aggaatgctg
1921  cctggagatg cacgtgcgtg gcctcctgga gccctgggc ctcgaatgca ccttcatcga
1981  cgacatttct gcctaccaca aatttctggg ggaagtccac tgtggcacca acgtccgcag
2041  gaagcccttc accttcaagt ggtggcacat ggtgccctga cctgccaggg gccctggcgt
2101  ttgcctcctt cgcttagttc tccagaccct ccctcacacg cccagagcct tctgctgaca
2161  tggactggac agccccgctg ggagaccttt gggacgtggg gtggaatttg gggtatctgt
2221  gccttgccct ccctgagagg ggcctcagtg tcctctgaag ccatccccag tgagcctcga
2281  ctctgtccct gctgaaaata gctgggccag tgtctctgta gccctgacat aaggaacaga
2341  acacaacaaa acacagcaaa ccatgtgccc aaactgctcc ccaaagaatt ttgagtctct
2401  aatctgacac tgaatgaggg gagaagggaa ggagattctg ggattgccag ttcttccagc
2461  agccatgctc tgaaaatcaa ggtagaatcc atggaaaggg accccaggac cccgggaccc
2521  tagacgtatc ttgaactgcc atcgtcattt caaatacatc tccctcaggg tttccaggtg
2581  gccaccccca attattcatt ccttaccaac ctctcaaatc ctcttggctt tctctctgca
2641  gtgtggacac tgttggctag tcctccccac tccctgaggg tccagtaagt tagcttagaa
2701  ccttcctgga aacatttcat ctgagcaggt ttccccacgt gtgggatgct ccttttgcct
2761  catctgtctc agggatgcag gctcccccgc atgcatgggg atttctcccc agaccagcat
2821  acttgtgacc tgagagttca atgcgtaaag atgcccctgg tcagccatat ccatcttctc
2881  ttgcctggtc cttgattctc tggccgctcc ctgaccttcc tccttccact gccttgactt
2941  tcttcctttt tattcctggt gccatctgtc caggcagcta gacaagaact tgttcgccag
3001  cagccagatt caggccttcc caggggcata taagtgacc agcccctcct ctccggacat
3061  cagatccaac acataaggac cctggcctac cctccagccc aacagccagt tctgggtcag
3121  ctgccaactt aggggtggtt tgattatccc attgaaattc accagtgcct ttgccaaaga
3181  ccctctcatt tggacatacc cagattcatt ccctggctcc aactgaaaag actcagtttc
3241  aatcgttaaa agttccttta gggccagaag aataaatgaa ttataatccc attttgaaga
3301  accgatttat aaccaatgaa aaggttataa tgtaatttat attcttggag gaacaagatt
3361  ttcatttggg attatttcct tcaaccattc aacaaacatt tgttgtatgc cactaagcgc
3421  caggcacggc gttgggctct gcaaacacag tggttagtag cagtctggac ctggtcccta
3481  ctggcatgga acccatcact ccccaacatg caaagcccac atttaaaggc cagcctctgc
3541  cccttcagtg atgcgctctt tagaaatgcc agtccactat attcagaaat ccgcagggca
3601  caaaacttcc agcaagtcac tgttgtggtg aaatgggcag tgggggtggg gggtcttctt
3661  taaacaggcc cccttcccat ctacctagcc agtacccatc caatgagtcc ccagagcctc
3721  cagaagctgt tgtctcctct ctggggacag cagctcctgc ctttggagc caaagcccca
3781  gatctctcca gccccagagc tgaaaacacc aagtgcctat ttgagggtgt ctgtctggag
```

```
                               -continued
3841    acttagagtt  tgtcatgtgt  gtgtgtgtgt  ttggttaatg  tgggtttatg  ggttttcttt 3901    cttttttttc  ttttttttt   tagtctacat  taggggaag   tgagcgcctc  ccatgtgcag 3961    acagtgtgtc  tttatagatt  tttctaaggc  tttccccaat  gatgtcggta  atttctgatg 4021    tttctgaagt  tcccaggact  cacacacccg  ttcccatctc  acttgcccac  ccagtgtgac 4081    aaccctcggt  gtggatatac  ccccgtggac  tcatggctct  tccccacccc  cactttctat 4141    aaatgtaggc  ctagaatacg  cttctctgtt  gcaaaactca  gctaagttcc  tgcttccacc 4201    ttgatgttga  aatatcttat  gtaagagggc  agggatgtc   gtgaagatgg  caagaagaac 4261    acagtttcaa  atttctggaa  aagagcctgt  ggtggagatc  taaagatgtt  tagggaagag 4321    ctcgactaaa  gaacaatgaa  ataaatggtc  caaggggaag  tca
```

The atg start and stop codons are bolded and underlined. The amino acid sequence of human PADI2 (protein-arginine deiminase type-2), provided by Genbank Accession No. NP_031391.2, is incorporated herein by reference, and is shown below (SEQ ID NO: 206).

```
  1    mlrertvrlq  ygsrveavyv  lgtylwtdvy  saapagaqtf  slkhsehvwv  evvrdgeaee 61    vatngkqrwl  lspsttlrvt  msgasteass  dkvtvnyyde  egsipidqag  lfltaieisl 121    dvdadrdgvv  eknnpkkasw  twgpegqgai  llvncdretp  wlpkedcrde  kvyskedlkd 181    msqmilrtkg  pdrlpagyei  vlyismsdsd  kvgvfyvenp  ffgqryihil  grrklyhvvk 241    ytggsaellf  fveglcfpde  gfsglvsihv  slleymaqdi  pltpiftdtv  ifriapwimt 301    pnilppvsvf  vccmkdnylf  lkevknlvek  tncelkvcfq  ylnrgdrwiq  deiefgyiea 361    phkgfpvvld  sprdgnlkdf  pvkellgpdf  gyvtreplfe  svtsldsfgn  levsppvtvn 421    gktyplgril  igssfplsgg  rrmtkvvrdf  lkaqqvqapv  elysdwltvg  hvdefmsfvp 481    ipgtkkflll  mastsacykl  frekqkdghg  eaimfkglgg  msskritink  ilsneslvqe 541    nlyfqrcldw  nrdilkkelg  lteqdiidlp  alfkmdedhr  araffpnmvn  mivldkdlgi 601    pkpfgpqvee  ecclemhvrg  lleplglect  fiddisayhk  flgevhcgtn  vrrkpftfkw 661    whmvp
```

The mRNA sequence encoding human PAD3 (PADI3) provided by Genbank Accession No. NM_016233.2, is incorporated herein by reference, and is shown below (SEQ ID NO: 207).

```
  1    agtgttgggg  ttggcggcca  cagctaagtc  caacaccagc  atgtcgctgc  agagaatcgt 61    gcgtgtgtcc  ctggagcatc  ccaccagcgc  ggtgtgtgtg  gctggcgtgg  agaccctcgt 121    ggacatttat  gggtcagtgc  ctgagggcac  agaaatgttt  gaggtctatg  ggacgcctgg 181    cgtggacatc  tacatctctc  ccaacatgga  gagggccgg   gagcgtgcag  acaccaggcg 241    gtggcgcttt  gacgcgactt  tggagatcat  cgtggtcatg  aactcccca   gcaatgacct 301    caacgacagc  catgttcaga  tttcctacca  ctccagccat  gagcctctgc  ccctggccta 361    tgcggtgctc  tacctcacct  gtgttgacat  ctctctggat  tgcgacctga  actgtgaggg 421    aaggcaggac  aggaactttg  tagacaagcg  gcagtgggtc  tggggccca   gtgggtatgg 481    cggcatcttg  ctggtgaact  gtgaccgtga  tgatccgagc  tgtgatgtcc  aggacaattg 541    tgaccagcac  gtgcactgcc  tgcaagacct  ggaagacatg  tctgtcatgg  tcctgcggac 601    gcagggccct  gcagccctct  ttgatgacca  caaacttgtc  ctccatacct  ccagctatga
```

```
                     -continued
 661  tgccaaacgg gcacaggtct tccacatctg cggtcctgag gatgtgtgtg aggcctatag
 721  gcatgtgctg ggccaagata aggtgtccta tgaggtaccc cgcttgcatg gggatgagga
 781  gcgcttcttc gtggaaggcc tgtccttccc tgatgccggc ttcacaggac tcatctcctt
 841  ccatgtcact ctgctggacg actccaacga ggatttctcg gcatccccta tcttcactga
 901  cactgtggtg ttccgagtgg caccctggat catgacgccc agcactctgc caccectaga
 961  ggtgtatgtg tgccgtgtga ggaacaacac gtgttttgtg gatgcggtgg cagagctggc
1021  caggaaggcc ggctgcaagc tgaccatctg cccacaggcc gagaaccgca acgaccgctg
1081  gatccaggat gagatggagc tgggctacgt tcaggcgccc acaagaccc tcccggtggt
1141  ctttgactcc ccaaggaatg gggaactgca ggatttccct tacaaaagaa tcctgggtcc
1201  agattttggt tacgtgactc gggaaccacg cgacaggtct gtgagtggcc tggactcctt
1261  tgggaacctg gaggtcagcc ctccagtggt ggccaatggg aaagagtacc ccctggggag
1321  gatcctcatt gggggcaacc tgcctgggtc aagtggccgc agggtcaccc aggtggtgcg
1381  ggacttcctc catgcccaga aggtgcagcc ccccgtggag ctctttgtgg actggttggc
1441  cgtgggccat gtggatgagt ttctgagctt tgtccctgcc cccgatggga agggcttccg
1501  gatgctcctg gccagccctg gggcctgctt caagctcttc caggaaaagc agaagtgtgg
1561  ccacgggagg gccctcctgt tccagggggt tgttgatgat gagcaggtca agaccatctc
1621  catcaaccag gtgctctcca ataaagacct catcaactac aataagtttg tgcagagctg
1681  catcgactgg aaccgtgagg tgctgaagcg ggagctgggc ctggcagagt gtgacatcat
1741  tgacatccca cagctcttca agaccgagag gaaaaaagca acggccttct ccctgacttt
1801  ggtgaacatg ctggtgctgg ggaagcacct gggcatcccc aagccctttg ggcccatcat
1861  caatggctgc tgctgcctgg aggagaaggt gcggtccctg ctggagccgc tgggcctcca
1921  ctgcaccttc attgatgact tcactccata ccacatgctg catggggagg tgcactgtgg
1981  caccaatgtg tgcagaaagc ccttctcttt caagtggtgg aacatggtgc ctgagacag
2041  ctcccaccca ccatcctgtc ccctggggc gggcattggc ccaggtggtg gagacagaga
2101  caggcccctg aacgataagc accaagagac cccaaggctc cagatggaac actgagggtg
2161  accgtccctc tcagaagcct tttccctgga agtgtccatg cctcacctgc aacccatgtg
2221  gttctcagac ttgaatcttc tcggcccccc aaaaagaagg acctcatttc ttatagcctc
2281  tcctgtgatt caacacaacc catggagatg tccccttctc actctgaaat catccatttg
2341  gggacaaatc cacattgggg tctagaaaca tccacgtatc tcatcagcca tcttgtcctg
2401  tgcatcctaa cagaggaagg atccatgatt ctgctttggt ccaattgctt cctctctgca
2461  gaggaacaac cctaaaacca gaccactcca cgcaggacag gcaggagaga ttcttcctaa
2521  agcctccccc ataaaaaggg agctgtggat ccacttagat cagggcggaa ccatctttca
2581  cccggccaag ctcctgccca gatgttgacc ctcacccagc gtgagctgtc acatagtagg
2641  agcttctaga tgcatgtgga agcaatgaga gttgtccctt agccttataa actccccatg
2701  atctgacatg cagaaatcca gccttgtcca gaatcctcct ggaatttctt ggagacgaaa
2761  gtatctgggg gattgttggg tactagggag actgggtaca agggtgaaaa gtagttccca
2821  taatacacat ggttgactat ggtgatccac cttgtgatgg ttaatattag gtgtctggag
2881  aaggttgctt cattggccct gggacttctc tctgcaggag gagagaacgc tgcctctcct
2941  ctggattggt ctcaggctct ctgttggcct ttggtcagcg tttccacatc ctgctctgct
3001  gcaggagagg gggctaaggg gctggatcca ccaaggcagc tcacagcggg aaaactctgg
3061  gaatgaacca ctgaattcag gggatggggg tggggggcg gttctcgagg tgtgtgccag
```

-continued

```
3121  ctacacgtgt gttctgtatg ggtccagctg cgtttccatc actcgctaat aaatcaacag 3181  aaacacaaa
```

The atg start and stop codons are bolded and underlined.
The amino acid sequence of human PADI3 (PAD3), provided by Genbank Accession No. NP_057317.2, is incorporated herein by reference, and is shown below (SEQ ID NO: 208).

```
  1  mslqrivrvs lehptsavcv agvetivdiy gsvpegtemf evygtpgvdi yispnmergr 61  eradtrrwrf datleiivvm nspsndlnds hvqisyhssh eplplayavl yltcvdisld 121  cdlncegrqd rnfvdkrqwv wgpsgyggil lvncdrddps cdvqdncdqh vhclqdledm 181  svmvlrtqgp aalfddhklv lhtssydakr aqvfhicgpe dvceayrhvl gqdkvsyevp 241  rlhgdeerff veglsfpdag ftglisfhvt llddsnedfs aspiftdtvv frvapwimtp 301  stlpplevyv crvrnntcfv davaelarka gcklticpqa enrndrwiqd emelgyvqap 361  hktlpvvfds prngelqdfp ykrilgpdfg yvtreprdrs vsgldsfgnl evsppvvang 421  keyplgrili ggnlpgssgr rvtqvvrdfl haqkvqppve lfvdwlavgh vdeflsfvpa 481  pdgkgfrmll aspgacfklf qekqkcghgr allfqgvvdd eqvktisinq vlsnkdliny 541  nkfvqscidw nrevlkrelg laecdiidip qlfkterkka taffpdlvnm lvlgkhlgip 601  kpfgpiingc ccleekvrsl leplglhctf iddftpyhml hgevhcgtnv crkpfsfkww 661  nmvp
```

The mRNA sequence encoding human FOXP3 provided by Genbank Accession No. EF534714.1, is incorporated herein by reference, and is shown below (SEQ ID NO: 209).

```
   1  atgcccaacc ccaggcctgg caagccctcg gcccttcct tggcccttgg cccatcccca 61  ggagcctcgc ccagctggag ggctgcaccc aaagcctcag acctgctggg ggcccggggc 121  ccaggggggaa ccttccaggg ccgagatctt cgaggcgggg cccatgcctc ctcttcttcc 181  ttgaacccca tgccaccatc gcagctgcag ctgcccacac tgccctagt catggtggca 241  ccctccgggg cacggctggg ccccttgccc cacttacagg cactcctcca ggacaggcca 301  catttcatgc accagctctc aacggtggat gcccacgccc ggaccctgt gctgcaggtg 361  caccccctgg agagcccagc catgatcagc ctcacaccac caccaccgc cactgggtc 421  ttctccctca aggcccggcc tggcctccca cctgggatca acgtggccag cctggaatgg 481  gtgtccaggg agccggcact gctctgcacc ttcccaaatc ccagtgcacc caggaaggac 541  agcacccttt cggctgtgcc ccagagctcc tacccactgc tggcaaatgg tgtctgcaag 601  tggcccggat gtgagaaggt cttcgaagag ccagaggact tcctcaagca ctgccaggcg 661  gaccatcttc tggatgagaa gggcagggca caatgtctcc tcagagaga gatggtacag 721  tctctggagc agcagctggt gctggagaag gagaagctga gtgccatgca ggcccacctg 781  gctgggaaaa tggcactgac caaggcttca tctgtggcat catccgacaa gggctcctgc 841  tgcatcgtag ctgctggcag ccaaggccct gtcgtcccag cctggtctgg ccccggggag 901  gcccctgaca gcctgtttgc tgtccggagg cacctgtggg gtagccatgg aaacagcaca 961  ttcccagagt tcctccacaa catggactac ttcaagttcc acaacatgcg accccctttc 1021  acctacgcca cgctcatccg ctgggccatc ctggaggctc cagagaagca gcggacactc
```

```
-continued
1081   aatgagatct accactggtt cacacgcatg tttgccttct tcagaaacca tcctgccacc 1141   tggaagaacg ccatccgcca caacctgagt ctgcacaagt gctttgtgcg ggtggagagc 1201   gagaaggggg ctgtgtggac cgtggatgag ctggagttcc gcaagaaacg gagccagagg 1261   cccagcaggt gttccaaccc tacacctggc ccctga
```

The atg start and stop codons are bolded and underlined.
The amino acid sequence of human FOXP3, provided by Genbank Accession No. ABQ15210.1, is incorporated herein by reference, and is shown below (SEQ ID NO: 210).

```
  1   mpnprpgkps apslalgpsp gaspswraap kasdllgarg pggtfqgrdl rggahassss
 61   lnpmppsqlq lptlplvmva psgarlgplp hlqallqdrp hfmhqlstvd ahartpvlqv
121   hplespamis ltppttatgv fslkarpglp pginvaslew vsrepallct fpnpsaprkd
181   stlsavpqss ypllangvck wpgcekvfee pedflkhcqa dhlldekgra qcllqremvq
241   sleqqlvlek eklsamqahl agkmaltkas svassdkgsc civaagsqgp vvpawsgpre
301   apdslfavrr hlwgshgnst fpeflhnmdy fkfhnmrppf tyatlirwai leapekqrtl
361   neiyhwftrm faffrnhpat wknairhnls lhkcfvrves ekgavwtvde lefrkkrsqr
421   psrcsnptpg p
```

The mRNA sequence encoding human IL2RA (CD-25) provided by Genbank Accession No. NM_000417.2, is incorporated herein by reference, and is shown below (SEQ ID NO: 211).

```
                                                              (SEQ ID NO: 211)
  1   ggcagtttcc tggctgaaca cgccagccca atacttaaag agagcaactc ctgactccga 61   tagagactgg atggaccccac aagggtgaca gcccaggcgg accgatcttc ccatcccaca 121   tcctccggcg cgatgccaaa aagaggctga cggcaactgg gccttctgca gagaaagacc 181   tccgcttcac tgccccggct ggtcccaagg gtcaggaaga tggattcata cctgctgatg 241   tggggactgc tcacgttcat catggtgcct ggctgccagg cagagctctg tgacgatgac 301   cgccagaga tcccacacgc cacattcaaa gccatggcct acaaggaagg aaccatgttg 361   aactgtgaat gcaagagagg tttccgcaga ataaaaagcg ggtcactcta tatgctctgt 421   acaggaaact ctagccactc gtcctgggac aaccaatgtc aatgcacaag ctctgccact 481   cggaacacaa cgaaacaagt gacacctcaa cctgaagaac agaaagaaag gaaaaccaca 541   gaaatgcaaa gtccaatgca gccagtggac caagcgagcc ttccaggtca ctgcaggaa 601   cctccaccat gggaaaatga agccacagag agaatttatc atttcgtggt ggggcagatg 661   gtttattatc agtgcgtcca gggatacagg gctctacaca gaggtcctgc tgagagcgtc 721   tgcaaaatga cccacgggaa gacaaggtgg acccagcccc agctcatatg cacaggtgaa 781   atggagacca gtcagtttcc aggtgaagag aagcctcagg caagcccccga aggccgtcct 841   gagagtgaga cttcctgcct cgtcacaaca acagattttc aaatacagac agaaatggct 901   gcaaccatgg agacgtccat atttacaaca gagtaccagg tagcagtggc cggctgtgtt 961   ttcctgctga tcagcgtcct cctcctgagt gggctcacct ggcagcggag acagaggaag 1021  agtagaagaa caatctagaa aaccaaaaga caagaatttt cttggtaaga gccgggaac 1081  agacaacaga agtcatgaag cccaagtgaa atcaaaggtc taaatggtc gcccaggaga 1141  catccgttgt gcttgcctgc gttttggaag ctctgaagtc acatcacagg acacggggca
```

```
-continued
1201  gtggcaacct tgtctctatg ccagctcagt cccatcagag agcgagcgct acccacttct
1261  aaatagcaat ttcgccgttg aagaggaagg gcaaaaccac tagaactctc catcttattt
1321  tcatgtatat gtgttcatta aagcatgaat ggtatggaac tctctccacc ctatatgtag
1381  tataaagaaa agtaggttta cattcatctc attccaactt cccagttcag gagtcccaag
1441  gaaagcccca gcactaacgt aaatacacaa cacacacact ctaccctata caactggaca
1501  ttgtctgcgt ggttcctttc tcagccgctt ctgactgctg attctcccgt tcacgttgcc
1561  taataaacat ccttcaagaa ctctgggctg ctacccagaa atcattttac ccttggctca
1621  atcctctaag ctaaccccct tctactgagc cttcagtctt gaatttctaa aaaacagagg
1681  ccatggcaga ataatctttg ggtaacttca aaacggggca gccaaaccca tgaggcaatg
1741  tcaggaacag aaggatgaat gaggtcccag gcagagaatc atacttagca aagtttacc
1801  tgtgcgttac taattggcct ctttaagagt tagtttcttt gggattgcta tgaatgatac
1861  cctgaatttg gcctgcacta atttgatgtt tacaggtgga cacacaaggt gcaaatcaat
1921  gcgtacgttt cctgagaagt gtctaaaaac accaaaaagg gatccgtaca ttcaatgttt
1981  atgcaaggaa ggaaagaaag aaggaagtga agagggagaa gggatggagg tcacactggt
2041  agaacgtaac cacggaaaag agcgcatcag gcctggcacg gtggctcagg cctataaccc
2101  cagctcccta ggagaccaag gcgggagcat ctcttgaggc caggagtttg agaccagcct
2161  gggcagcata gcaagacaca tccctacaaa aaattagaaa ttggctggat gtggtggcat
2221  acgcctgtag tcctagccac tcaggaggct gaggcaggag gattgcttga gcccaggagt
2281  tcgaggctgc agtcagtcat gatggcacca ctgcactcca gcctgggcaa cagagcaaga
2341  tcctgtcttt aaggaaaaaa agacaagatg agcataccag cagtccttga acattatcaa
2401  aaagttcagc atattagaat caccgggagg ccttgttaaa agagttcgct gggcccatct
2461  tcagagtctc tgagttgttg gtctggaata gagccaaatg ttttgtgtgt ctaacaattc
2521  ccaggtgctg ttgctgctgc tactattcca ggaacacact ttgagaacca ttgtgttatt
2581  gctctgcacg cccacccact ctcaactccc acgaaaaaaa tcaacttcca gagctaagat
2641  ttcggtggaa gtcctggttc catatctggt gcaagatctc ccctcacgaa tcagttgagt
2701  caacattcta gctcaacaac atcacacgat taacattaac gaaaattatt catttgggaa
2761  actatcagcc agttttcact tctgaagggg caggagagtg ttatgagaaa tcacggcagt
2821  tttcagcagg gtccagattc agattaaata actattttct gtcatttctg tgaccaacca
2881  catacaaaca gactcatctg tgcactctcc ccctccccct tcaggtatat gttttctgag
2941  taaagttgaa aagaatctca gaccagaaaa tatagatata tatttaaatc ttacttgagt
3001  agaactgatt acgacttttg ggtgttgagg ggtctataag atcaaaactt ttccatgata
3061  atactaagat gttatcgacc atttatctgt ccttctctca aaagtgtatg gtggaatttt
3121  ccagaagcta tgtgatacgt gatgatgtca tcactctgct gttaacatat aataaattta
3181  ttgctattgt ttataaaaga ataaatgata tttttt
```

The atg start and stop codons are bolded and underlined. The amino acid sequence of human IL2RA (CD-25), provided by Genbank Accession No. NP_000408, is incorporated herein by reference, and is shown below (SEQ ID NO: 212).

```
                                                   (SEQ ID NO: 212)
  1  mdsyllmwgl ltfimvpgcq aelcddddppe iphatfkama ykegtmlnce ckrgfrriks 61  gslymlctgn sshsswdnqc qctssatrnt tkqvtpqpee qkerkttemq spmqpvdqas
```

-continued

```
121  lpghcreppp weneateriy hfvvgqmvyy qcvqgyralh rgpaesvckm thgktrwtqp 181  qlictgemet sqfpgeekpq aspegrpese tsclvtttdf qiqtemaatm etsiftteyq 241  vavagcvfll isvillsglt wqrrqrksrr ti   (Signal protein AA 1-21;
                                           mature protein AA 22-272).
```

The mRNA sequence encoding human FAP (fibroblast activation protein) provided by Genbank Accession No. NM_001291807.1, is incorporated herein by reference, and is shown below (SEQ ID NO: 213).

```
   1  aagaacgccc ccaaaatctg tttctaattt tacagaaatc ttttgaaact tggcacggta
  61  ttcaaaagtc cgtggaaaga aaaaaacctt gtcctggctt cagcttccaa ctacaaagac
 121  agacttggtc cttttcaacg gttttcacag atccagtgac ccacgctctg aagacagaat
 181  tagctaactt tcaaaaacat ctggaaaaat gaagacttgg gtaaaaatcg tatttggagt
 241  tgccacctct gctgtgcttg ccttattggt gatgtgcatt gtcttacgcc cttcaagagt
 301  tcataactct gaagaaaata caatgagagc actcacactg aaggatattt taaatggaac
 361  attttcttat aaaacatttt ttccaaactg gatttcagga caagaatatc ttcatcaatc
 421  tgcagataac aatatagtac tttataatat tgaaacagga caatcatata ccattttgag
 481  taatagaacc atgctttgga gatactctta cacagcaaca tattacatct atgaccttag
 541  caatggagaa tttgtaagag gaaatgagct tcctcgtcca attcagtatt tatgctggtc
 601  gcctgttggg agtaaattag catatgtcta tcaaaacaat atctatttga acaaagacc
 661  aggagatcca ccttttcaaa taacatttaa tggaagagaa ataaaaatat ttaatggaat
 721  cccagactgg gtttatgaag aggaaatgct tgctacaaaa tatgctctct ggtggtctcc
 781  taatggaaaa ttttggcat atgcggaatt taatgatacg gataccag ttattgccta
 841  ttcctattat ggcgatgaac aatatcctag aacaataaat attccatacc caaggctgg
 901  agctaagaat cccgttgttc ggatatttat tatcgatacc acttaccctg cgtatgtagg
 961  tccccaggaa gtgcctgttc cagcaatgat agcctcaagt gattattatt tcagttggct
1021  cacgtgggtt actgatgaac gagtatgttt gcagtggcta aaaagagtcc agaatgtttc
1081  ggtcctgtct atatgtgact tcaggaagag actggcagac tgggattgtc caaagaccca
1141  ggagcatata aagaaaagca gaactggatg ggctggtgga ttctttgttt caacaccagt
1201  tttcagctat gatgccattt cgtactacaa aatatttagt gacaaggatg ctacaaaca
1261  tattcactat atcaaagaca ctgtggaaaa tgctattcaa attacaagtg gcaagtggga
1321  ggccataaat atattcagag taacacagga ttcactgttt tattctagca atgaatttga
1381  agaataccct ggaagaagaa acatctacag aattagcatt ggaagctatc ctccaagcaa
1441  gaagtgtgtt acttgccatc taaggaaaga aaggtgcaa tattacacag caagtttcag
1501  cgactacgcc aagtactatg cacttgtctg ctacggccca ggcatcccca tttccaccct
1561  tcatgatgga cgcactgatc aagaaattaa aatcctggaa gaaacaagg aattggaaaa
1621  tgctttgaaa aatatccagc tgcctaaaga ggaaattaag aaacttgaag tagatgaaat
1681  tactttatgg tacaagatga ttcttcctcc tcaatttgac agatcaaaga agtatcctt
1741  gctaattcaa gtgtatggtg gtccctgcag tcagagtgta aggtctgtat ttgctgttaa
1801  ttggatatct tatcttgcaa gtaaggaagg gatggtcatt gccttggtgg atggtcgagg
1861  aacagctttc caaggtgaca aactcctcta tgcagtgtat cgaaagctgg gtgtttatga
1921  agttgaagac cagattacag ctgtcagaaa attcatagaa atgggtttca ttgatgaaaa
```

-continued

```
1981  aagaatagcc atatggggct ggtcctatgg aggatacgtt tcatcactgg cccttgcatc 2041  tggaactggt cttttcaaat gtggtatagc agtggctcca gtctccagct gggaatatta 2101  cgcgtctgtc tacacagaga gattcatggg tctcccaaca aaggatgata atcttgagca 2161  ctataagaat tcaactgtga tggcaagagc agaatatttc agaaatgtag actatcttct 2221  catccacgga acagcagatg ataatgtgca ctttcaaaac tcagcacaga ttgctaaagc 2281  tctggttaat gcacaagtgg atttccaggc aatgtggtac tctgaccaga accacggctt 2341  atccggcctg tccacgaacc acttatacac ccacatgacc cacttcctaa agcagtgttt 2401  ctctttgtca gactaaaaac gatgcagatg caagcctgta tcagaatctg aaaaccttat 2461  ataaacccct cagacagttt gcttatttta ttttttatgt tgtaaaatgc tagtataaac 2521  aaacaaatta atgttgttct aaaggctgtt aaaaaaaaga tgaggactca gaagttcaag 2581  ctaaatattg tttacatttt ctggtactct gtgaaagaag agaaaaggga gtcatgcatt 2641  ttgctttgga cacagtgttt tatcacctgt tcatttgaag aaaaataata aagtcagaag 2701  ttcaagtgct aaaaaaaaaa aaaaaaaaaa aaaaaaaaa
```

The atg start and stop codons are bolded and underlined. The amino acid sequence of human FAP (fibroblast activation protein), provided by Genbank Accession No. NP_001278736.1, is incorporated herein by reference, and is shown below (SEQ ID NO: 214).

```
  1  mktwvkivfg vatsavlall vmcivlrpsr vhnseentmr altlkdilng tfsyktffpn 61  wisggeylhg sadnnivlyn ietggsytil snrtmlwrys ytatyyiydl sngefvrgne 121  lprpiqylcw spvgsklayv yqnniylkqr pgdppfqitf ngrenkifng ipdwvyeeem 181  latkyalwws pngkflayae fndtdipvia ysyygdeqyp rtinipypka gaknpvvrif 241  iidttypayv gpqevpvpam iassdyyfsw ltwvtdervc lqwlkrvqnv svlsicdfre 301  dwqtwdcpkt qehieesrtg waggffvstp vfsydaisyy kifsdkdgyk hihyikdtve 361  naiqitsgkw eainifrvtq dslfyssnef eeypgrrniy risigsypps kkcvtchlrk 421  ercqyytasf sdyakyyalv cygpgipist lhdgrtdqei kileenkele nalkniqlpk 481  eeikklevde itlwykmilp pqfdrskkyp lliqvyggpc sqsvrsvfav nwisylaske 541  gmvialvdgr gtafqgdkll yavyrklgvy evedqitavr kfiemgfide kriaiwgwsy 601  ggyvsslala sgtglfkcgi avapvsswey yasvyterfm glptkddnle hyknstvmar 661  aeyfrnvdyl lihgtaddnv hfqnsaqiak alvnaqvdfq amwysdqnhg lsglstnhly 721  thmthflkqc fslsd
```

The mRNA sequence encoding human DPP4 (dipeptidyl peptidase 4) provided by Genbank Accession No. NM_001935.3, is incorporated herein by reference, and is shown below (SEQ ID NO: 215).

```
  1  ctttcactgg caagagacgg agtcctgggt ttcagttcca gttgcctgcg gtgggctgtg 61  tgagtttgcc aaagtcccct gccctctctg ggtctcggtt ccctcgcctg tccacgtgag 121  gttggaggag ctgaacgccg acgtcatttt tagctaagag ggagcagggt ccccgagtcg 181  ccggcccagg gtctgcgcat ccgaggccgc gcgcccttc ccctccccca cggctcctcc 241  gggccccgca ctctgcgccc cggctgccgc ccagcgccct acaccgccct caggggggccc 301  tcgcgggctc cccccggccg ggatgccagt gccccgcgcc acgcgcgcct gctcccgcgc
```

-continued

```
 361  cgcctgccct gcagcctgcc cgcggcgcct ttatacccag cgggctcggc gctcactaat
 421  gtttaactcg gggccgaaac ttgccagcgg cgagtgactc caccgcccgg agcagcggtg
 481  caggacgcgc gtctccgccg cccgcggtga cttctgcctg cgctccttct ctgaacgctc
 541  acttccgagg agacgccgac gatgaagaca ccgtggaagg ttcttctggg actgctgggt
 601  gctgctgcgc ttgtcaccat catcaccgtg cccgtggttc tgctgaacaa aggcacagat
 661  gatgctcag ctgacagtcg caaaacttac actctaactg attacttaaa aaatacttat
 721  agactgaagt tatactcctt aagatggatt tcagatcatg aatatctcta caaacaagaa
 781  aataatatct tggtattcaa tgctgaatat ggaaacagct cagttttctt ggagaacagt
 841  acatttgatg agtttggaca ttctatcaat gattattcaa tatctcctga tgggcagttt
 901  attctcttag aatacaacta cgtgaagcaa tggaggcatt cctacacagc ttcatatgac
 961  atttatgatt taaataaaag gcagctgatt acagaagaga ggattccaaa caacacacag
1021  tgggtcacat ggtcaccagt gggtcataaa ttggcatatg tttggaacaa tgacatttat
1081  gttaaaattg aaccaaattt accaagttac agaatcacat ggacggggaa agaagatata
1141  atatataatg gaataactga ctgggtttat gaagaggaag tcttcagtgc ctactctgct
1201  ctgtggtggt ctccaaacgg cactttttta gcatatgccc aatttaacga cacagaagtc
1261  ccacttattg aatactcctt ctactctgat gagtcactgc agtacccaaa gactgtacgg
1321  gttccatatc caaaggcagg agctgtgaat ccaactgtaa agttctttgt tgtaaataca
1381  gactctctca gctcagtcac caatgcaact tccatacaaa tcactgctcc tgcttctatg
1441  ttgataggg atcactactt gtgtgatgtg acatgggcaa cacaagaaag aatttctttg
1501  cagtggctca ggaggattca gaactattcg gtcatggata tttgtgacta tgatgaatcc
1561  agtggaagat ggaactgctt agtggcacgg caacacattg aaatgagtac tactggctgg
1621  gttggaagat ttaggcctc agaacctcat tttacccttg atggtaatag cttctacaag
1681  atcatcagca atgaagaagg ttacagacac atttgctatt ccaaataga taaaaaagac
1741  tgcacattta ttacaaaagg cacctgggaa gtcatcggga tagaagctct aaccagtgat
1801  tatctatact acattagtaa tgaatataaa ggaatgccag gaggaaggaa tctttataaa
1861  atccaactta gtgactatac aaaagtgaca tgcctcagtt gtgagctgaa tccggaaagg
1921  tgtcagtact attctgtgtc attcagtaaa gaggcgaagt attatcagct gagatgttcc
1981  ggtcctggtc tgccctcta tactctacac agcagcgtga atgataaagg gctgagagtc
2041  ctggaagaca attcagcttt ggataaaatg ctgcagaatg tccagatgcc ctccaaaaaa
2101  ctggacttca ttatttgaa tgaaacaaaa ttttggtatc agatgatctt gcctcctcat
2161  tttgataaat ccaagaaata tcctctacta ttagatgtgt atgcaggccc atgtagtcaa
2221  aaagcagaca ctgtcttcag actgaactgg gccacttacc ttgcaagcac agaaaacatt
2281  atagtagcta gctttgatgg cagaggaagt ggttaccaag gagataagat catgcatgca
2341  atcaacagaa gactgggaac atttgaagtt gaagatcaaa ttgaagcagc cagacaattt
2401  tcaaaaatgg gatttgtgga caacaaacga attgcaattt ggggctggtc atatggaggg
2461  tacgtaacct caatggtcct gggatcggga agtggcgtgt tcaagtgtgg aatagccgtg
2521  gcgcctgtat cccggtggga gtactatgac tcagtgtaca cagaacgtta catgggtctc
2581  ccaactccag aagacaacct tgaccattac agaaattcaa cagtcatgag cagagctgaa
2641  aatttaaac aagttgagta cctccttatt catgaacag cagatgataa cgttcactt
2701  cagcagtcag ctcagatctc aaagccctg gtcgatgttg gagtggattt ccaggcaatg
```

-continued

```
2761  tggtatactg atgaagacca tggaatagct agcagcacag cacaccaaca tatatatacc
2821  cacatgagcc acttcataaa acaatgtttc tctttacctt agcacctcaa aataccatgc
2881  catttaaagc ttattaaaac tcattttgt tttcattatc tcaaaactgc actgtcaaga
2941  tgatgatgat ctttaaaata cacactcaaa tcaagaaact taaggttacc tttgttccca
3001  aatttcatac ctatcatctt aagtagggac ttctgtcttc acaacagatt attaccttac
3061  agaagtttga attatccggt cgggttttat tgtttaaaat catttctgca tcagctgctg
3121  aaacaacaaa taggaattgt ttttatggag gctttgcata gattccctga gcaggatttt
3181  aatcttttc taactggact ggttcaaatg ttgttctctt ctttaaaggg atggcaagat
3241  gtgggcagtg atgtcactag ggcagggaca ggataagagg gattagggag agaagatagc
3301  agggcatggc tgggaaccca agtccaagca taccaacacg agcaggctac tgtcagctcc
3361  cctcggagaa gagctgttca cagccagact ggcacagttt tctgagaaag actattcaaa
3421  cagtctcagg aaatcaaata tgcaaagcac tgacttctaa gtaaaaccac agcagttgaa
3481  aagactccaa agaaatgtaa gggaaactgc cagcaacgca ggcccccagg tgccagttat
3541  ggctataggt gctacaaaaa cacagcaagg gtgatgggaa agcattgtaa atgtgctttt
3601  aaaaaaaaat actgatgttc ctagtgaaag aggcagcttg aaactgagat gtgaacacat
3661  cagcttgccc tgttaaaaga tgaaaatatt tgtatcacaa atcttaactt gaaggagtcc
3721  ttgcatcaat ttttcttatt tcatttcttt gagtgtctta attaaaagaa tattttaact
3781  tccttggact cattttaaaa aatggaacat aaaatacaat gttatgtatt attattccca
3841  ttctacatac tatggaattt ctcccagtca tttaataaat gtgccttcat tttttcagaa
3901  aaaaaaaaaa aaa
```

The atg start and stop codons are bolded and underlined. The amino acid sequence of human DPP-4 (dipeptidyl peptidase 4), provided by Genbank Accession No. NP_001926.2, is incorporated herein by reference, and is shown below (SEQ ID NO: 216).

```
  1  mktpwkvllg llgaaalvti itvpvvllnk gtddatadsr ktytltdylk ntyrlklysl
 61  rwisdheyly kqennilvfn aeygnssvfl enstfdefgh sindysispd gqfilleyny
121  vkqwrhsyta sydiydlnkr qliteeripn ntqwvtwspv ghklayvwnn diyvkiepnl
181  psyritwtgk ediiyngitd wvyeeevfsa ysalwwspng tflayaqfnd tevplieysf
241  ysdeslqypk tvrvpypkag avnptvkffv vntdslssvt natsiqitap asmligdhyl
301  cdvtwatqer islqwlrriq nysvmdicdy dessgrwncl varqhiemst tgwvgrfrps
361  ephftldgns fykiisneeg yrhicyfqid kkdctfitkg twevigieal tsdylyyisn
421  eykgmpggrn lykiqlsdyt kvtclscelp percqyysys fskeakyyql rcsgpglply
481  tlhssvndkg lrvlednsal dkmlqnvqmp skkldfiiln etkfwyqmil pphfdkskky
541  pllldvyagp csqkadtvfr lnwatylast eniivasfdg rgsgyqgdki mhainrrlgt
601  fevedqieaa rqfskmgfvd nkriaiwgws yggyvtsmvl gsgsgvfkcg iavapvsrwe
661  yydsvytery mglptpednl dhyrnstvms raenfkqvey llihgtaddn vhfqqsaqis
721  kalvdvgvdf qamwytdedh giasstahqh iythmshfik qcfslp
```

The mRNA sequence encoding human CD26 provided by Genbank Accession No. M74777.1, is incorporated herein by reference, and is shown below (SEQ ID NO: 217).

```
   1  gacgccgacg atgaagacac cgtggaaggt tcttctggga ctgctgggtg ctgctgcgct
  61  tgtcaccatc atcaccgtgc ccgtggttct gctgaacaaa ggcacagatg atgctacagc
 121  tgacagtcgc aaaacttaca ctctaactga ttacttaaaa aatacttata gactgaagtt
 181  atactcctta agatggattt cagatcatga atatctctac aaacaagaaa ataatatctt
 241  ggtattcaat gctgaatatg gaaacagctc agttttcttg gagaacagta catttgatga
 301  gtttggacat tctatcaatg attattcaat atctcctgat gggcagttta ttctcttaga
 361  atacaactac gtgaagcaat ggaggcattc ctacacagct tcatatgaca tttatgattt
 421  aaataaaagg cagctgatta cagaagagag gattccaaac aacacacagt gggtcacatg
 481  gtcaccagtg ggtcataaat tggcatatgt tggaacaat gacatttatg ttaaaattga
 541  accaaattta ccaagttaca gaatcacatg gacggggaaa gaagatataa tatataatgg
 601  aataactgac tgggtttatg aagaggaagt cttcagtgcc tactctgctc tgtggtggtc
 661  tccaaacggc actttttag catatgccca atttaacgac acagaagtcc cacttattga
 721  atactccttc tactctgatg agtcactgca gtacccaaag actgtacggg ttccatatcc
 781  aaaggcagga gctgtgaatc caactgtaaa gttctttgtt gtaaatacag actctctcag
 841  ctcagtcacc aatgcaactt ccatacaaat cactgctcct gcttctatgt gataggggga
 901  tcactacttg tgtgatgtga catgggcaac acaagaaaga atttctttgc agtggctcag
 961  gaggattcag aactattcgg tcatggatat ttgtgactat gatgaatcca gtggaagatg
1021  gaactgctta gtggcacggc aacacattga aatgagtact actggctggg ttggaagatt
1081  taggcctcca gaacctcatt ttacccttga tggtaatagc ttctacaaga tcatcagcaa
1141  tgaagaaggt tacagacaca tttgctattt ccaaatagat aaaaagact gcacatttat
1201  tacaaaaggc acctgggaag tcatcgggat agaagctcta accagtgatt atctatacta
1261  cattagtaat gaatataaag gaatgccagg aggaaggaat ctttataaaa tccaacttag
1321  tgactataca aaagtgacat gcctcagttg tgagctgaat ccggaaaggt gtcagtacta
1381  ttctgtgtca ttcagtaaag aggcgaagta ttatcagctg agatgttccg gtcctggtct
1441  gcccctctat actctacaca gcagcgtgaa tgataaaggg ctgagagtcc tggaagacaa
1501  ttcagctttg gataaaatgc tgcagaatgt ccagatgccc tccaaaaaac tggacttcat
1561  tattttgaat gaaacaaaat tttggtatca gatgatcttg cctcctcatt ttgataaatc
1621  caagaaatat cctctactat tagatgtgta tgcaggccca tgtagtcaaa aagcagacac
1681  tgtcttcaga ctgaactggg ccacttacct tgcaagcaca gaaaacatta tagtagctag
1741  ctttgatggc agaggaagtg gttaccaagg agataagatc atgcatgcaa tcaacagaag
1801  actgggaaca tttgaagttg aagatcaaat tgaagcagcc agacaatttt caaaaatggg
1861  atttgtggac aacaaacgaa ttgcaatttg gggctggtca tatgagggt acgtaacctc
1921  aatggtcctg ggatcaggaa gtggcgtgtt caagtgtgga atagccgtgg cgcctgtatc
1981  ccgtgggag tactatgact cagtgtacac agaacgttac atgggtctcc caactccaga
2041  agacaaccct gaccattaca gaaattcaac agtcatgagc agagctgaaa attttaaaca
2101  agttgagtac ctccttattc atgggaacagc agatgataac gttcactttc agcagtcagc
2161  tcagatctcc aaagccctgg tcgatgttgg agtggatttc aggcaatgt ggtatactga
2221  tgaagaccat ggaatagcta gcagcacagc acaccaacat atatataccc acatgagcca
2281  cttcataaaa caatgtttct ctttacctta gcacctcaaa ataccatgcc atttaaagct
2341  tattaaaact cattttgtt ttcattatct caaaactgca ctgtcaagat gatgatgatc
2401  tttaaaatac acactcaaat caagaaactt aaggttacct ttgttcccaa atttcatacc
```

-continued

```
2461  tatcatctta agtagggact tctgtcttca caacagatta ttaccttaca gaagtttgaa
2521  ttatccggtc gggttttatt gtttaaaatc atttctgcat cagctgctga aacaacaaat
2581  aggaattgtt tttatggagg ctttgcatag attccctgag caggatttta atcttttttct
2641  aactggactg gttcaaatgt tgttctcttc tttaaaggga tggcaagatg tgggcagtga
2701  tgtcactagg gcagggacag gataagaggg attagggaga gaagatagca gggcatggct
2761  gggaacccaa gtccaagcat accaacacga ccaggctact gtcagctccc ctcggagaaa
2821  actgtgcagt ctgcgtgtga acagctcttc tcctttagag cacaatggat ctcgagggat
2881  cttccatacc taccagttct gcgcctcgag gccgcgactc taga
```

The atg start and stop codons are bolded and underlined.
The amino acid sequence of human CD26, provided by Genbank Accession No. AAA51943.1, is incorporated herein by reference, and is shown below (SEQ ID NO: 218).

```
  1  mktpwkvllg llgaaalvti itvpvvllnk gtddatadsr ktytltdylk ntyrlklysl
 61  rwisdheyly kqennilvfn aeygnssvfl enstfdefgh sindysispd gqfilleyny
121  vkqwrhsyta sydiydlnkr qliteeripn ntqwvtwspv ghklayvwnn diyvkiepnl
181  psyritwtgk ediiyngitd wvyeeevfsa ysalwwspng tflayaqfnd tevplieysf
241  ysdeslqypk tvrvpypkag avnptvkffv vntdslssvt natsiqitap asmligdhyl
301  cdvtwatqer islqwlrriq nysvmdicdy dessgrwncl varqhiemst tgwvgrfrps
361  ephftldgns fykiisneeg yrhicyfqid kkdctfitkg twevigieal tsdylyyisn
421  eykgmpggrn lykiqlsdyt kvtclscelp percqyysys fskeakyyql rcsgpglply
481  tlhssvndkg lrvlednsal dkmlqnvqmp skkldfiiln etkfwyqmil pphfdkskky
541  pllldvyagp csqkadtvfr lnwatylast eniivasfdg rgsgyqgdki mhainrrlgt
601  fevedqieaa rqfskmgfvd nkriaiwgws yggyvtsmvl gsgsgvfkcg iavapvsrwe
661  yydsvytery mglptpednl dhyrnstvms raenfkqvey llihgtaddn vhfqqsaqis
721  kalvdvgvdf qamwytdedh giasstahqh iythmshfik qcfslp
```

The mRNA sequence encoding human SIRT1 provided by Genbank Accession No. JQ768366.1, is incorporated herein by reference, and is shown below (SEQ ID NO: 219).

```
  1  atgattggca cagatcctcg aacaattctt aaagattat tgccggaaac aatacctcca
 61  cctgagttgg atgatatgac actgtggcag attgttatta atatcctttc agaaccacca
121  aaaaggaaaa aagaaaaga tattaataca attgaagatg ctgtgaaatt actgcaagag
181  tgcaaaaaaa ttatagttct aactggagct ggggtgtctg tttcatgtgg aatacctgac
241  ttcaggtcaa gggatggtat ttatgctcgc cttgctgtag acttcccaga tcttccagat
301  cctcaagcga tgtttgatat tgaatatttc agaaaagatc caagaccatt cttcaagttt
361  gcaaaggaaa tatatcctgg acaattccag ccatctctct gtcacaaatt catagccttg
421  tcagataagg aaggaaaact acttcgcaac tatacccaga acatagacac gctggaacag
481  gttgcgggaa tccaaggat aattcagtgt catggttcct ttgcaacagc atcttgcctg
541  atttgtaaat acaaagttga ctgtgaagct gtacgaggag ctcttttag tcaggtagtt
601  cctcgatgtc ctaggtgccc agctgatgaa ccgcttgcta tcatgaaacc agagattgtg
661  ttttttggtg aaaatttacc agaacagttt catagagcca tgaagtatga caaagatgaa
```

-continued

```
 721   gttgacctcc tcattgttat tgggtcttcc ctcaaagtaa gaccagtagc actaattcca
 781   agttccatac cccatgaagt gcctcagata ttaattaata gagaacettt gcctcatctg
 841   cattttgatg tagagcttct tggagactgt gatgtcataa ttaatgaatt gtgtcatagg
 901   ttaggtggtg aatatgccaa actttgctgt aaccctgtaa agctttcaga aattactgaa
 961   aaacctccac gaacacaaaa agaattggct tatttgtcag agttgccacc cacacctctt
1021   catgtttcag aagactcaag ttcaccagaa agaacttcac caccagattc ttcagtgatt
1081   gtcacacttt tagaccaagc agctaagagt aatgatgatt tagatgtgtc tgaatcaaaa
1141   ggttgtatgg aagaaaaacc acaggaagta caaacttcta ggaatgttga agtattgct
1201   gaacagatgg aaaatccgga tttgaagaat gttggttcta gtactgggga gaaaaatgaa
```

The atg start and stop codons are bolded and underlined.
The amino acid sequence of human SIRT1, provided by Genbank Accession No. JQ768366.1, is incorporated herein by reference, and is shown below (SEQ ID NO: 220).

```
  1   migtdprtil kdllpetipp pelddmtlwq ivinilsepp krkkrkdint iedavkllqe
 61   ckkiivltga gvsyscgipd frsrdgiyar lavdfpdlpd pqamfdieyf rkdprpffkf
121   akeiypgqfq pslchkfial sdkegkllrn ytqnidtleq vagiqriiqc hgsfatascl
181   ickykvdcea vrgalfsqvv prcprcpade plaimkpeiv ffgenlpeqf hramkydkde
241   vdllivigss lkvrpvalip ssiphevpqi linreplphl hfdvellgdc dviinelchr
301   lggeyaklcc npvklseite kpprtqkela ylselpptpl hvsedssspe rtsppdssvi
361   vtlldqaaks nddldvsesk gcmeekpqev qtsrnvesia eqmenpdlkn vgsstgekne
```

The mRNA sequence encoding human FoxO3a (forkhead box 03) provided by Genbank Accession No. NM_001455.3, is incorporated herein by reference, and is shown below (SEQ ID NO: 221).

```
  1   gcgcgaggcc gtcgattcgc tcgcggctcc atcgcggcct ggccgggggg cggtgtctgc
 61   tgcgccaggt tcgctggccg cacgtcttca ggtcctcctg ttcctgggag gcgggcgcgg
121   caggactggg aggtggcggc agcgggcgag gactcgccga ggacggggct ccggcccggg
181   ataaccaact ctccttctct cttctttggt gcttcccag gcggcggcgg cggcgccgg
241   gagccggagc cttcgcggcg tccacgtccc tcccccgctg caccccgccc cggcgcgaga
301   ggagagcgcg agagccccag ccgcgggcgg gcgggcggcg aagatggcag aggcaccggc
361   ttccccggcc ccgctctctc cgctcgaagt ggagctggac ccggagttcg agccccagag
421   ccgtccgcga tcctgtacgt ggcccctgca aaggccgag ctccaagcga gcctgccaa
481   gccctcgggg gagacggccg ccgactccat gatccccgag gaggaggacg atgaagacga
541   cgaggacggc ggggacgggg ccggctcggc catggcgatc ggcggcggcg gcgggagcgg
601   cacgctgggc tccgggctgc tccttgagga ctcggcccgg gtgctggcac ccggagggca
661   agaccccggg tctgggccag ccaccgcggc gggcgggctg agcgggggta cacaggcgct
721   gctgcagcct cagcaaccgc tgccaccgcc gcagccgggg cggctgggg ctccgggca
781   gccgaggaaa tgttcgtcgc ggcggaacgc ctggggaaac ctgtcctacg cggacctgat
841   cacccgcgcc atcgagagct ccccggacaa acggctcact ctgtcccaga tctacgagtg
901   gatggtgcgt tgcgtgccct acttcaagga taagggcgac agcaacagct ctgccggctg
```

```
 961 gaagaactcc atccggcaca acctgtcact gcatagtcga ttcatgcggg tccagaatga
1021 gggaactggc aagagctctt ggtggatcat caaccctgat gggggggaaga gcggaaaagc
1081 cccccggcgg cgggctgtct ccatggacaa tagcaacaag tataccaaga gccgtggccg
1141 cgcagccaag aagaaggcag ccctgcagac agcccccgaa tcagctgacg acagtccctc
1201 ccagctctcc aagtggcctg gcagccccac gtcacgcagc agtgatgagc tggatgcgtg
1261 gacggacttc cgttcacgca ccaattctaa cgccagcaca gtcagtggcc gcctgtcgcc
1321 catcatggca agcacagagt tggatgaagt ccaggacgat gatgcgcctc tctcgcccat
1381 gctctacagc agctcagcca gcctgtcacc ttcagtaagc aagccgtgca cggtggaact
1441 gccacggctg actgatatgg caggcaccat gaatctgaat gatgggctga ctgaaaacct
1501 catggacgac ctgctggata acatcacgct cccgccatcc cagccatcgc ccactggggg
1561 actcatgcag cggagctcta gcttcccgta taccaccaag ggctcgggcc tgggctcccc
1621 aaccagctcc tttaacagca cggtgttcgg accttcatct ctgaactccc tacgccagtc
1681 tcccatgcag accatccaag agaacaagcc agctaccttc tcttccatgt cacactatgg
1741 taaccagaca ctccaggacc tgctcacttc ggactcactt agccacagcg atgtcatgat
1801 gacacagtcg gaccccttga tgtctcaggc cagcaccgct gtgtctgccc agaattcccg
1861 ccggaacgtg atgcttcgca atgatccgat gatgtccttt gctgcccagc ctaaccaggg
1921 aagtttggtc aatcagaact gctccacca ccagcaccaa acccagggcg ctcttggtgg
1981 cagccgtgcc ttgtcgaatt ctgtcagcaa catgggcttg agtgagtcca gcagccttgg
2041 gtcagccaaa caccagcagc agtctcctgt cagccagtct atgcaaaccc tctcggactc
2101 tctctcaggc tcctccttgt actcaactag tgcaaacctg cccgtcatgg gccatgagaa
2161 gttccccagc gacttggacc tggacatgtt caatgggagc ttggaatgtg acatggagtc
2221 cattatccgt agtgaactca tggatgctga tgggttggat tttaactttg attccctcat
2281 ctccacacag aatgttgttg gtttgaacgt ggggaacttc actggtgcta agcaggcctc
2341 atctcagagc tgggtgccag gctgaaggat cactgaggaa ggggaagtgg gcaaagcaga
2401 ccctcaaact gacacaagac ctacagagaa accctttgc caaatctgct ctcagcaagt
2461 ggacagtgat accgtttaca gcttaacacc tttgtgaatc ccacgccatt ttcctaaccc
2521 agcagagact gttaatggcc ccttaccctg ggtgaagcac ttacccttgg aacagaactc
2581 taaaaagtat gcaaaatctt ccttgtacag ggtggtgagc cgcctgccag tggaggacag
2641 caccccctcag caccacccac cctcattcag agcacaccgt gagcccccgt cggccattct
2701 gtggtgtttt aatattgcga tggtttatgg gacgttttaa gtgttgttct tgtgtttgtt
2761 ttcctttgac tttctgagtt tttcacatgc attaacttgc ggtattttc tgttaaaatg
2821 ttaaccgtcc ttcccctagc aaatttaaaa acagaaagaa aatgttgtac cagttaccat
2881 tccgggttcg agcatcacaa gcttttgagc gcatggaact ccataaacta acaaattaca
2941 taaactaaag ggggattttc tttcttcttt tgtttggtag aaaattatcc ttttctaaaa
3001 actgaacaat ggcacaattg tttgctatgt gcaccgtcc aggacagaac cgtgcatagg
3061 caaaaggagt ggagcacagc gtccggccca gtgtgtttcc ggttctgagt cagggtgatc
3121 tgtggacggg acccccagcac caagtctacg ggtgccagat cagtagggcc tgtgatttcc
3181 tgtcagtgtc ctcagctaat gtgaacagtg ttggtctgct ggttagaaac tagaatattg
3241 atattttcag gaaagaaatc agctcagctc tccactcatt gccaaatgtc actaaagggt
3301 ttagttttaa ggagaaagaa aaggaaaaaa aaaaaaaaca aaaagtcct gttttgctt
3361 gcagaacaaa tgaacttaca ggtgagcatt aagcttgcag tgagaaatgt gcgaagagta
```

-continued

```
3421  aaaacccaag tcaatgctga ggcagttcta acttcactgt tttcctaaat acacatcctt
3481  gattattttc agccttgcta tataatctga tctgctagaa gtgtatgagt gagaggcaat
3541  agcatacaaa ctgatttttt aaatataagc ttaggttgta attgtacaag tgactcaatg
3601  gaagtacaaa atagggcagt tttaactttt ttttctgctt ctatggattt cattttgttg
3661  tgttttcaaa aagttatggt gctgtatagg tgctttctgt ttaacctgga aagtgtgatt
3721  atattcgtta ccttctttgg tagacggaat agttgggacc acctttggta cataagaaat
3781  tggtataacg atgctctgat tagcacagta tatgcatact tctccaaagt gatatatgaa
3841  gactcttttc tttgcataaa aagcattagg catataaatg tataaatata ttttatcatg
3901  tacagtacaa aaatggaacc ttatgcatgg gccttaggaa tacaggctag tatttcagca
3961  cagacttccc tgcttgagtt cttgctgatg cttgcaccgt gacagtgggc accaacacag
4021  acgtgccacc caacccctg cacacaccac cggccaccag gggccccctt gtgcgccttg
4081  gctttataac tcctctgggg gtgatattgg tggtgatcac agctcctagc ataatgagag
4141  ttccatttgg tattgtcaca cgtctcctgc ctcgcttggg ttgccatgtt tgagcgatgg
4201  ccctgttgat ttcaccctgc cttttactga atctgtaaat tgttgtgcaa ttgtggttat
4261  agtagactgt agcacattgc ctttctaaa ctgctacatg tttataatct tcattttaa
4321  agtatgtgta atttttttaa gtatgtattc tattcatatg gtctgcttgt cagtgagcca
4381  gacttgctta ctatattcct ttataataat gctagccact tcctggattc tttagtaatg
4441  tgctgtatgc aagaactttc cagtagcagt gaaggagggt tgcctctcca agcttcctaa
4501  gggatgctgc cctgtgtggg gatgcattgc agaggcacta gtagcatggg ggctagagtg
4561  gggagcgaga tgtaaaaggg tggggggata ggagaattcc agagtgcttc cagcattagg
4621  gtcctgagaa cttctgagtt cagagaaaca tgcaaagtga ctaacaaaat agctacttac
4681  ctttgcagtt ttacagaccc tgggagctgc tttgggagtg agaaaggcaa ccctccaatg
4741  tgtttcaact ttaaaatgtt gaattctttt cagacatggt atctcattta ttctcctttt
4801  ctagcgtttg ttgaatttca ggcagaatgt cttacagaat gtcctagaac cagattatca
4861  tttaatctga aacagctgag gaagggacag agaaggtaca agggcaaggc agcacaaaac
4921  agatcaggag aatgaagagg gaatgctttg gttttttgtt ttgttttgtt ttttcttttt
4981  caagtaacta aaacagcatc tacatgtaga gtgttgtgga gagctgagac cagggtaaag
5041  tcaagtgcag catcagtact gcgagaccca ccagcccctg gagagggtca gccgagaatc
5101  tggtagtgaa gcctgtctag ggtcccggca ccctcaccct cagccacctg cagagaggcc
5161  agggcccccag agactagcct ggttctgaag tgggcagggg tgctgccaga gccctctgcc
5221  ccttatgttg agaccctgct tcaggacag gccagccgtt ggccaccatg tcacattctg
5281  agtgagtgtc acaggtccct aacaataatt ttctgatctg gagcatatca gcagaatgct
5341  tagcctcaag gggcctggca gctgtaatgt ttgatttatg atgagaacta tccgaggcca
5401  cccttggcct ctaaataagc tgctctaggg agccgcctac ttttttgatga gaaattagaa
5461  gagtacctaa tgttgaaaac atgacatgcg ctcttgggat ctgctgttct ctccagggct
5521  ccagaacctg atacctgtta ccaaagctag gaaagagctt tatcacaagc cttcactgtc
5581  ctggcatgag aactggctgc caggctcagt gtaccccatt aactgtgaat gaatctgagc
5641  ttggtttcct ttattgcttc ctctgcaata tgattgctga aacacatttt aaaaattcag
5701  aagcttgtca ctcctgttaa tgggaggatc agtcacacat gtgtagtaca aggcggactt
5761  tgtgtttgtt tttggtgtta atttttagca ttgtgtgtgt tgcttcccca ccctgaggag
```

-continued

```
5821  aggacaccat ggcttactac tcaggacaag tatgccccgc tcagggtgtg atttcaggtg
5881  gcttccaaac ttgtacgcag tttaaagatg gtggggacag actttgcctc tacctagtga
5941  accccactta agaataagg agcatttgaa tctcttggaa aaggccatga agaataaagc
6001  agtcaaaaag aagtcctcca tgttggtgcc aaggacttgc gaggggaaat aaaaatgtta
6061  tccagcctga ccaacatgga gaaacccgt ctccattaaa aatacaaaat tagcctggca
6121  tggtggcgca tgcctgtaat cccagctact ctggaggctg aggcaggaga atcgcttgaa
6181  cccaggaggc ggaggtcgca gtgagccgag atcatgccag tgcactccag cctgggtaac
6241  aagagtgaaa ctccgtgtca aaaaaaaaa aaaaatgtta ctcatcctct ctgaaagcaa
6301  aaaggaaacc ctaacagctc tgaactctgg ttttattttt cttgctgtat ttgggtgaac
6361  attgtatgat taggcataat gttaaaaaaa aaatttttt tttggtagaa atgcaatcac
6421  cagtaaagag gtacgaaaaa gctagcctct ctcagagacc ggggaggcag agtactacta
6481  gaggaagtga agttctgatg gaatcatgcc tgtcaaatga ggtcttgaag cggatgccca
6541  aataaaagag tatattttat ctaaatctta agtgggtaac atttttatgca gtttaaatga
6601  atggaatatt ttcctcttgt ttagttgtat ctgtttgtat ttttctttga tgaatgattg
6661  gtcatgaggc ctcttgccac actccagaaa tacgtgtgcg gctgctttta agaactatgt
6721  gtctggtcac ttatttctct aaaattatct cattgcctgg caatcagtct tctcttgtat
6781  acttgtccta gcacattatg tacatgggaa atgtaaacaa atgtgaagga ggaccagaaa
6841  aattagttaa tatttaaaaa aatgtattgt gcattttggc ttcacatgtt taactttttt
6901  taagaaaaaa gttgcatgaa tggaaaaaaa aatctgtata cagtatctgt aaaaactatc
6961  ttatctgttt caattccttg ctcatatccc atataatcta gaactaaata tggtgtgtgg
7021  ccatatttaa acacctgaga gtcaagcagt tgagactttg atttgaagca cctcatcctt
7081  ctttcaatgc gaacactatc atatggcatt cttactgagg attttgtcta accatatgtt
7141  gccatgaatt aactctgccg cctttcttaa ggatcaaaac cagtttgatt tgggaatctt
7201  cccctttcca aatgaaatag agatgcagta cttaactttc cttggtgttt gtagatattg
7261  ccttgtgtat tccacttaaa accgtaatct agtttgtaaa agagatggtg acgcatgtaa
7321  ataaagcatc agtgacactc t
```

The atg start and stop codons are bolded and underlined. The amino acid sequence of human FoxO3a (forkhead box 03), provided by Genbank Accession No. NP_001446.1, is incorporated herein by reference, and is shown below (SEQ ID NO: 222).

```
                                                         (SEQ ID NO: 222)
  1  maeapaspap lspleveldp efepqsrprs ctwplqrpel qaspakpsge taadsmipee
 61  eddeddedgg gragsamaig ggggsgtlgs gllledsary lapggqdpgs gpataaggls
121  ggtqallqpq qplpppqpga aggsgqprkc ssrrnawgnl syadlitrai esspdkrltl
181  sqiyewmvrc vpyfkdkgds nssagwknsi rhnlslhsrf mrvqnegtgk sswwiinpdg
241  gksgkaprrr aysmdnsnky tksrgraakk kaalqtapes addspsqlsk wpgsptsrss
301  deldawtdfr srtnsnastv sgrlspimas teldevqddd aplspmlyss saslspsysk
361  pctvelprlt dmagtmnlnd gltenlmddl ldnitlppsq psptgglmqr sssfpyttkg
421  sglgsptssf nstvfgpssl nslrqspmqt iqenkpatfs smshygnqtl qdlltsdsls
481  hsdvmmtqsd plmsqastav saqnsrrnvm lrndpmmsfa aqpnqgslvn qnllhhqhqt
541  qgalggsral snsysnmgls essslgsakh qqqspvsgsm qtlsdslsgs slystsanlp
```

```
601  vmghekfpsd ldldmfngsl ecdmesiirs elmdadgldf nfdslistqn vvglnvgnft
661  gakqassqsw vpg
```

The mRNA sequence encoding human MiR-24 provided by Genbank Accession No. AF480527.1, is incorporated herein by reference, and is shown below (SEQ ID NO: 223).

```
                                              (SEQ ID NO: 223)
  1        tggctcagtt cagcaggaac ag
```

The mRNA sequence encoding human MiR-125a-5p (hsa-mir-125a) provided by Genbank Accession No. LM608509.1, is incorporated herein by reference, and is shown below (SEQ ID NO: 224).

```
  1   tgccagtctc taggtccctg agacccttta acctgtgagg acatccaggg tcacaggtga
 61   ggttcttggg agcctggcgt ctggcc
```

The mRNA sequence encoding human MiR-203a (MiR-203), provided by Genbank Accession No. NR_029620.1, is incorporated herein by reference, and is shown below (SEQ ID NO: 225).

```
  1   gtgttgggga ctcgcgcgct gggtccagtg gttcttaaca gttcaacagt tctgtagcgc
 61   aattgtgaaa tgtttaggac cactagaccc ggcgggcgcg gcgacagcga
```

The mRNA sequence encoding human MiR-140, provided by Genbank Accession No. NR_029681.1, is incorporated herein by reference, and is shown below (SEQ ID NO: 226).

```
  1   tgtgtctctc tctgtgtcct gccagtggtt ttaccctatg gtaggttacg tcatgctgtt
 61   ctaccacagg gtagaaccac ggacaggata ccggggcacc
```

The mRNA sequence encoding human MiR-27a, provided by Genbank Accession No. NR_029501.1, is incorporated herein by reference, and is shown below (SEQ ID NO: 227).

```
  1   ctgaggagca gggcttagct gcttgtgagc agggtccaca ccaagtcgtg ttcacagtgg
 61   ctaagttccg cccccag
```

Formulation and Dosing

In accordance with certain examples, a pharmaceutical composition of the invention is formulated to be compatible with its intended route of administration. Such pharmaceutical compositions may be administered by injection or infusion into a localized tissue site, e.g., into an articulating joint or by inhalation, transdermally, orally, rectally, transmucosally, intestinally, parenterally, intramuscularly, intra-articularly, subcutaneously, intravenously or other suitable methods that will be readily selected by the person of ordinary skill in the art, given the benefit of this disclosure. For example, solutions or suspensions used for parenteral, intradermal, intra-articular, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral and/or intra-articular preparation can be enclosed in ampules, disposable syringes or multiple dose vials made of glass or plastic.

A biologically acceptable medium includes, but is not limited to, any and all solvents, dispersion media, and the like which may be appropriate for the desired route of administration of the complexes of the present disclosure.

The use of such media for pharmaceutically active substances is known in the art. Except insofar as any conventional media or agent is incompatible with the activity of the small molecule, protein, polypeptide and/or peptide, its use in the pharmaceutical preparation of the invention is contemplated. Suitable vehicles and formulations are described, for example, in the book *Remington's Pharmaceutical Sciences* (Remington's Pharmaceutical Sciences. Mack Publishing Company, Easton, Pa., USA 1985). These vehicles include injectable formulations.

The complexes of the present invention may be administered by any suitable route. For example, a pharmaceutical preparation may be administered in tablets or capsules, by injection, by infusion, by inhalation, topically (e.g., by lotion or ointment), by suppository, by controlled release patch, or the like.

The complexes described herein may be administered to an individual (e.g., a human or animal such as a non-human primate) for therapy by any suitable route of administration, including orally, nasally, rectally, intravaginally, parenterally, intra-articularly, intracisternally, topically, buccally, sublingually, epidurally and the like. Intra-articular administration is useful for local treatment of disease and flare-up, e.g. pain in joints, synovitis and the like.

Regardless of the route of administration selected, the pharmaceutical compositions of the present invention are formulated into pharmaceutically acceptable dosage forms such as described below or by other conventional methods known to those of skill in the art. Actual dosage levels of the pharmaceutical compositions described herein may be varied so as to obtain an amount of the compound which is effective to achieve the desired therapeutic response for a particular patient, composition, and mode of administration, without being toxic to the patient.

Joint disease is treated using the complexes or compositions described herein. For example, methods are provided for treating a patient having a joint disease, by administering to the patient a therapeutically effective amount of a complex or composition of the present invention. For in vivo therapies based on local injection (e.g., intratumoral, intraarticularly, intramuscularly, into the peritoneal cavity, and aerosolized treatments) the RNT/small RNA complex is advantageously water soluble and so may be administered as an aqueous injection.

The selected dosage level will depend upon a variety of factors including the activity of a particular compound or ester, salt or amide thereof, the route of administration, the time of administration, the rate of excretion of the particular compound being employed, the duration of the treatment, other drugs, compounds and/or materials used in combination with the particular complex employed, the age, sex, weight, condition, general health and prior medical history of the patient being treated, and like factors well known in the medical arts. A physician, veterinarian or research scientist having ordinary skill in the art can readily determine and prescribe the effective amount of the pharmaceutical composition required. For example, the physician, veterinarian or research scientist could start doses of the compounds of the invention employed in the pharmaceutical composition at levels lower than that required in order to achieve the desired therapeutic effect and gradually increase the dosage until the desired effect is achieved. Furthermore, different delivery materials are used to administer different doses and dose ranges. For example, Nanopieces demonstrate good biocompatibility and low toxicity. Previous studies have demonstrated no significant toxicity with an administration of 25 µg delivery nanotubes (RNTs) in vivo (Journeay W S, et al. Int J Nanomedicine. 2008; 3(3):373-83). Even with a 50 µg dose, inflammation that resulted from RNTs was resolved after 7 days. In comparison, some conventional delivery materials such as carbon nanotubes, can cause inflammation at much lower doses the resulting in inflammation that can last for two months. In the current system, a 5 µg dose of RNT in Nanopiece was effective in the delivery of cargo. Therefore, the effective doses of RNT Nanopieces are significantly lower than their toxic doses, providing a good therapeutic index. Moreover, RNTs or TBLs showed a lower toxicity than lipid-based delivery vehicles. In FIGS. 66A-66D, ATDC5 cells were cultured with no additives (negative control), Nanopieces of 0.1 nmol non-targeting siRNA with 10 µg of RNT, Nanopieces of 0.1 nmol non-targeting siRNA with 2.5 µg TBL, or 0.1 nmol non-targeting siRNA with 6 µg Lipofectamine 2000. After 24 hours, ATDC5 cells cultured with Lipofectamine 2000 showed abnormal cell morphology and large amount of cell debris, however, cells cultured with either RNT nanopiece or TBL nanopiece presented normal morphology as the negative control.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient will range from about 0.0001 to about 100 mg per kilogram of body weight per day, or from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of biologically active agent can include a single treatment or, preferably, can include a series of treatments. It will also be appreciated that the effective dosage for treatment may increase or decrease over the course of a particular treatment. Changes in dosage may result from the results of diagnostic assays.

If desired, the effective daily dose of the active compound may be administered as one, two, three, four, five, six or more sub-doses administered separately at appropriate intervals throughout the day, optionally, in unit dosage forms. In certain embodiments, an effective dose is given every other day, twice a week, once a week or once a month.

A complex of the invention can be administered as such or in admixtures with pharmaceutically acceptable carriers and can also be administered in conjunction with other antimicrobial agents such as penicillin, cephalosporin, aminoglycosides, glycopeptides and the like. Conjunctive therapy includes sequential, simultaneous and separate administration of an active compound in such a way that the therapeutic effects of the first administered compound are still present when a subsequent administration is performed.

Another aspect of the present disclosure provides pharmaceutically acceptable compositions comprising a therapeutically effective amount of one or more of the complexes described herein, formulated together with one or more pharmaceutically acceptable carriers (additives) and/or diluents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection or intraarticularly as, for example, a sterile solution or suspension; (3) topical application, for example, as a cream, ointment or spray applied to the skin; or (4) intravaginally or intrarectally, for example, as a pessary, cream or foam. However, in certain embodiments the subject complexes may be simply dissolved or suspended in sterile water.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in compositions of the present invention.

Examples of pharmaceutically acceptable antioxidants include but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention may conveniently be presented in unit dosage form and may be prepared by any methods well known in the pharmaceutical art. The amount of active ingredient which can be combined with a carrier material to produce a single dosage form will vary depending upon the individual being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, from about 5 percent to about 70 percent, from about 10 percent to about 30 percent, from about 15 percent to about 25 percent, or from about 18 percent to about 22 percent. In an alternative embodiment, compounds of the present invention can be administered per se, e.g., in the absence of carrier material.

Methods of preparing the formulations or compositions of the present invention include the step of associating a complex described herein with a carrier and, optionally, one or more accessory ingredients. In general, the formulations are prepared by uniformly associating a complex of the present invention with liquid carriers, finely divided solid carriers, or both, and, optionally, shaping the product.

Formulations suitable for oral administration may be in the form of capsules, cachets, pills, tablets, lozenges (using a flavored basis, such as sucrose and acacia or tragacanth), powders, granules, as a solution or a suspension in an aqueous or non-aqueous liquid, as an oil-in-water or water-in-oil liquid emulsion, as an elixir or syrup, as pastilles (using an inert base, such as gelatin and glycerin, or sucrose and acacia) and/or as mouth washes and the like, each containing a predetermined amount of a complex of the present invention as an active ingredient. A complex of the present invention may also be administered as a bolus, electuary or paste.

Ointments, pastes, creams and gels may contain, in addition to a complex of the present disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a complex of the present disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a complex of the present invention to the body. Such dosage forms can be made by dissolving or dispersing the complex in the proper medium. Absorption enhancers can also be used to increase the flux of the complex across the skin. The rate of such flux can be controlled by either providing a rate controlling membrane or dispersing the complex in a polymer matrix or gel.

Pharmaceutical compositions of this invention suitable for parenteral administration comprise one or more complexes of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol asorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of the complexes in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions which are compatible with body tissue.

In accordance with certain examples, complexes of the present invention can be incorporated into pharmaceutical compositions suitable for administration. Such compositions typically comprise the complexes disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, intraarticularly, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intraarticularly, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

The present disclosure is directed to methods of forming a delivery complex, for example, by mixing one or more agents with fully formed rosette nanotubes or modules that self-assemble into rosette nanotubes, such as the compounds of Formula I or Formula II. According to one aspect, fully formed rosette nanotubes in the form of a powder is dissolved in water and heated to boiling. The solution is then cooled to room temperature. One or more agents is then added to the solution of nanotubes at a suitable temperature and for a suitable period of time until a complex of the nanotube and one or more agents forms. Suitable ratios of the nucleic acid to nanotube include about 0.01:1 (wt/wt) to about 1:0.1 (wt/wt).

Definitions

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amino, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Halogen", as used herein, refers to fluorine, chlorine, bromine, or iodine.

The term "optionally substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "amino acid" is inclusive of the 20 common amino acids, as well as "nonstandard amino acids," for example, D-amino acids and chemically (or biologically) produced derivatives of "common" amino acids, including for example, β-amino acids. Accordingly, amino acids according to the present disclosure include the commonly known amino acids such as glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), glutamine (Gln, Q) and the like. Amino acids also include stereoisomers thereof and compounds structurally similar to the amino acids or modifications or derivatives thereof. Exemplary amino acids within the scope of the present disclosure include lysine, arginine, serine, glycine, aspartate and the like. The amino acids of the present disclosure are modified only at their terminal amine group.

Amino acids are composed of amine (—$NH_2$) and carboxylic acid (—COOH) functional groups, along with a side-chain specific to each amino acid. The key elements of an amino acid are carbon, hydrogen, oxygen, and nitrogen, though other elements are found in the side-chains of certain amino acids.

In the structure shown below, Z represents a side-chain specific to each amino acid. The carbon atom next to the carboxyl group (which is therefore numbered 2 in the carbon chain starting from that functional group) is called the α-carbon. Amino acids containing an amino group bonded directly to the alpha carbon are referred to as alpha amino acids.

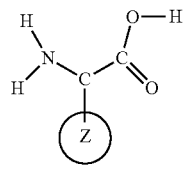

Figure 69:
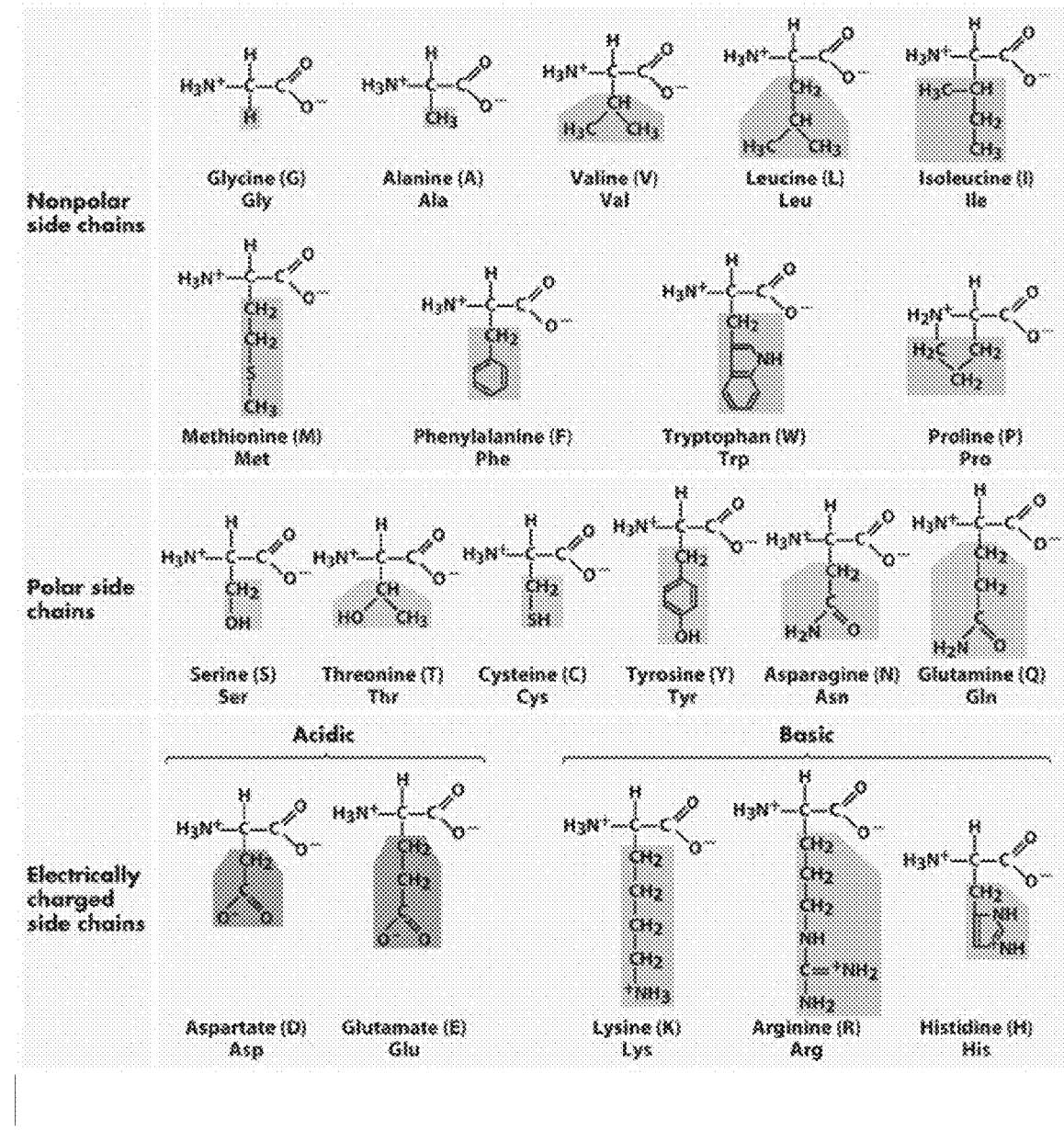
FIG. 69 shows amino acids containing hydrophilic side chains, hydrophobic side chains, and electrically charged side chains, respectively.

Amino acids can be divided into amino acid containing hydrophilic side chains, hydrophobic side chains, and electrically charged side chains. See FIG. 69, wherein the side chains are shaded.

The term "peptide" is inclusive of both straight and branched amino acid chains, as well as cyclic amino acid chains, which comprise at least 2 amino acid residues. The terms "peptide" and "polypeptide" are used interchangeably herein. Accordingly, polypeptides according to the present disclosure include two or more amino acids covalently linked together. According to one aspect, the two or more amino acids are covalently linked together at least in part by one or more peptide bonds. The polypeptides of the present disclosure are modified only at their terminal amine group. For example, the peptide or fragment of a full-length protein comprises 2, 5, 10, 50, 100, 200, 500 600, 700, 750, 800, 900, 1000 or more amino acids in length or up to the full length of a reference protein.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences. As used herein, one of skill in the art will understand that the term "nucleic acid probe" includes probes known as molecular beacons which include synthetic oligonucleotide hybridization probes that can report the presence of specific nucleic acids in homogenous solutions or in cells. Species of molecular beacons include hairpin shaped molecules with a detectable marker such as an internally quenched fluorophore whose fluorescence is restored when they bind to a target nucleic acid sequence. Technically, molecular beacons can be designed to target any gene and can be linked with fluorescent molecules of different fluorescence wavelengths.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety, sugar moiety or phosphate backbone.

The term "small RNA" is used as it is in the art, and includes a duplex of RNA (30 bases or less in each strand) that targets mRNA. Small RNA may be chemically or enzymatically synthesized. Small RNA in accordance with the present invention may be incorporated and then activated in RISC (RNA-induced silencing complex).

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

The word "transfect" is broadly used herein to refer to introduction of an exogenous compound, such as a polynucleotide sequence, into a prokaryotic or eukaryotic cell; the term includes, without limitation, introduction of an exogenous nucleic acid into a cell, which may result in a permanent or temporary alteration of genotype in an immortal or non-immortal cell line. Accordingly, embodiments of the present disclosure include the introduction of a polynucleotide sequence to either be expressed or to inhibit expression of a target gene.

As may be used herein, the terms "drug," biologically active agent," and "therapeutic agent" are used interchangeably and are intended to include, but are not limited to, those compounds recognized by persons of skill in the art as being biologically active agents, or drugs or therapeutic agents and include any synthetic or natural element or compound which when introduced into the body causes a desired biological response, such as altering body function.

As used herein, the terms "parenteral administration" and "administered parenterally" are intended to include, but are not limited to, modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal injection, intrasternal injection, infusion and the like.

As used herein, the terms "systemic administration," "administered systemically," "peripheral administration" and "administered peripherally" are intended to include, but are not limited to, the administration of a compound, drug or other material other than directly into the central nervous system, such that it enters an individual's system and, thus, is subject to metabolism and other like processes, such as, for example, subcutaneous administration.

The term "treatment," as used herein, is intended to include, but is not limited to, prophylaxis, therapy and cure. A patient or individual receiving treatment is any animal in need, such as humans, non-human primates, and other mammals such as horses, camels, cattle, swine, sheep, poultry, goats, rabbits, mice, guinea pigs, dogs, cats and the like.

As used herein, the term "therapeutically effective amount" is intended to include, but is not limited to, an amount of a compound, material, or composition comprising a complex of the present invention which is effective for producing a desired therapeutic effect in at least a subpopulation of cells in an animal and thereby altering (e.g., reducing or increasing) the biological consequences of one or more pathways in the treated cells, at a reasonable benefit/risk ratio.

As used herein, the term "pharmaceutically acceptable" is intended to include, but is not limited to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "pharmaceutically acceptable agent" (such as a salt, carrier, excipient or diluent) is a component which (1) is compatible with the RNT/small RNA composites in that it can be included in the delivery composition without eliminating the capacity of the RNT/small RNA composites to transfect cells and deliver small RNA; and (2) where the delivery composition is intended for therapeutic uses, is suitable for use with an animal (e.g., a human) without undue adverse side effects, such as toxicity, irritation, and allergic response. Side effects are "undue" when their risk outweighs the benefit provided by the pharmaceutical agent.

As used herein, the term "pharmaceutically acceptable carrier" is intended to include, but is not limited to, a pharmaceutically acceptable material, composition or vehicle, such as a liquid or solid filler, diluent, excipient, solvent or encapsulating material, involved in carrying or transporting the complexes of the present disclosure from one organ, or portion of the body, to another organ, or portion of the body. Each carrier must be "acceptable" in the sense of being compatible with the other ingredients of the formulation and not unduly dangerous to the patient. Examples of materials which can serve as pharmaceutically acceptable carriers include but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations, which could easily be determined by one of skill in the art.

Chemical compounds, polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" compound, nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified compositions are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, thin layer chromatography, or high-performance liquid chromatography (HPLC) analysis. For example, a purified compound refers to a one that has been separated from other proteins, lipids, and nucleic acids with which it is naturally associated. Preferably, the compound constitutes at least 10, 20, 50, 70, 80, 90, 95, 99-100% by dry weight of the purified preparation.

By "isolated nucleic acid" is meant a nucleic acid that is free of the genes which, in the naturally-occurring genome of the organism from which the DNA of the invention is derived, flank the gene. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

As used therein, the term "patient" is intended to include a mammal suffering from a disease. Such a mammal can be a human or another animal such as a companion animal (e.g., dog or cat) or a performance animal or livestock animal (e.g., an equine, bovine, porcine animal).

EXAMPLES

The following examples are specific embodiments of the present invention but are not intended to limit it.

Example 1

Nanopieces that include RNTs and exemplary cargo or payload compounds were manufactured. Cargo agents assemble with RNTs into Nanopieces. Then, taking siRNA Nanopiece as an example, it was demonstrated that Nanopieces can be intentionally processed into different sizes and charge for matrix penetration, e.g. preferential delivery of the cargo to specific tissue types. For example, Nanopieces with a net positive charge were made to deliver payload compounds to negatively charged tissue such as cartilage.

The relation between RNT/siRNA ratio and surface charge was evaluated. Selecting the ratio to result in a net positive charge on Nanopieces, Nanopieces have better binding and longer retention time on negatively charged tissue matrix (e.g., human articular cartilage).

For in vitro and in vivo delivery studies, cartilage was used as an example, because cartilage is an avascular tissue with high matrix component, which is a challenging tissue for drug delivery. Other target matrix and/or tissue can be used and the net charge of the Nanopiece tuned for preferential targeting to a selected tissue. It was shown that the processed Nanopieces were efficiently delivered into cartilage matrix from various species, as well as inside chondrocytes. The delivered Nanopieces were fully functional. A composite of polyethylene glycol (PEG) was used to increase Nanopiece delivery efficiency in a protein-rich environment (such as serum). Rat and mouse models showed that the processed Nanopieces successfully achieved trans-matrix and/or tissue delivery in vivo.

For diagnostics, MMP-13 molecular beacons for disease gene detection were co-delivered with non-targeting scrambled molecular beacons as a non-specific signal negative control and GAPDH molecular beacons as an internal house-keeping gene control. Fluorescence signal was accurately translated into gene expression level exemplary of a non-invasive approach to detect real-time, in-situ gene expression in living animals.

For therapeutics, cytokine (IL-1β) was used to stimulate cartilage degeneration mimicking arthritis, especially rheumatoid arthritis. With Nanopiece delivery of IL-1 receptor siRNA, IL-1 receptor expression was knocked down in chondrocytes in mouse cartilage in vivo, so that cartilage degeneration genes (such as MMP-13, MMP-9) were down-regulated and cartilage anabolic genes (such as Col II) were up-regulated.

Nanopieces were used to deliver ADAMTS-5 siRNA into knee joints of mice with cytokine (IL-1α and retinoic acid) stimulation. Cartilage degeneration was significantly inhibited. To mimic osteoarthritis progression, destabilization of medial meniscus (DMM) was conducted on knee joints of mice. With Nanopiece delivery of ADAMTS-5 siRNA, osteoarthritis progression was prevented. These data indicate the Nanopieces are useful to prevent and/or inhibit cartilage degeneration and arthritis progression.

Example 2

Successful assembly of RNTs into Nanopieces was shown, (see ARROWS) and they were used to deliver various types of cargo reagents including small nucleic acids (siRNA, FIG. 1), long nucleic acids (plasmid DNA, FIG. 2), peptide or protein (Matrilin-3, FIG. 3) as well as small molecules.

Example 2.1

Figure 1:
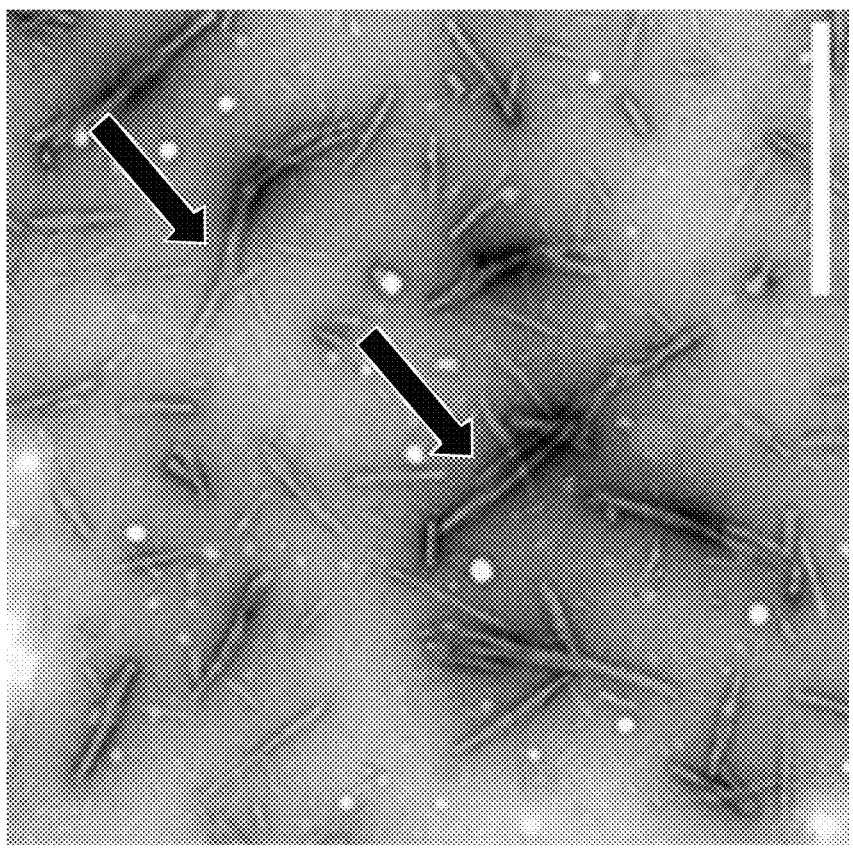
FIG. 1 is an illustration showing an assembly between RNTs with siRNA.

Nanopieces containing SiRNA as cargo were manufactured as follows. 2 μL of a 50 μM siRNA solution was mixed with 10 μL of a 1 mg/mL RNTs mixture. The resulting mixture was sonicated for 60 s. Dilution factors can range from 1 to 50 μL for preparing the siRNA-RNTs complex mixture and sonication times of the resulting mixture can vary from 1 to 600 s. Results are shown in FIG. 1.

Example 2.2

Nanopieces containing DNA were manufactured as follows. 0.5 μg DNA was mixed with 10 μL of a 1 mg/mL RNTs solution. The resulting mixture was sonicated for 60 s. Dilution factors can range from 1 to 50 μL for preparing the DNA-RNTs complex mixture and sonication times of the resulting mixture can vary from 1 to 600 s. Results are shown in FIG. 2.

Example 2.3

Figure 3:
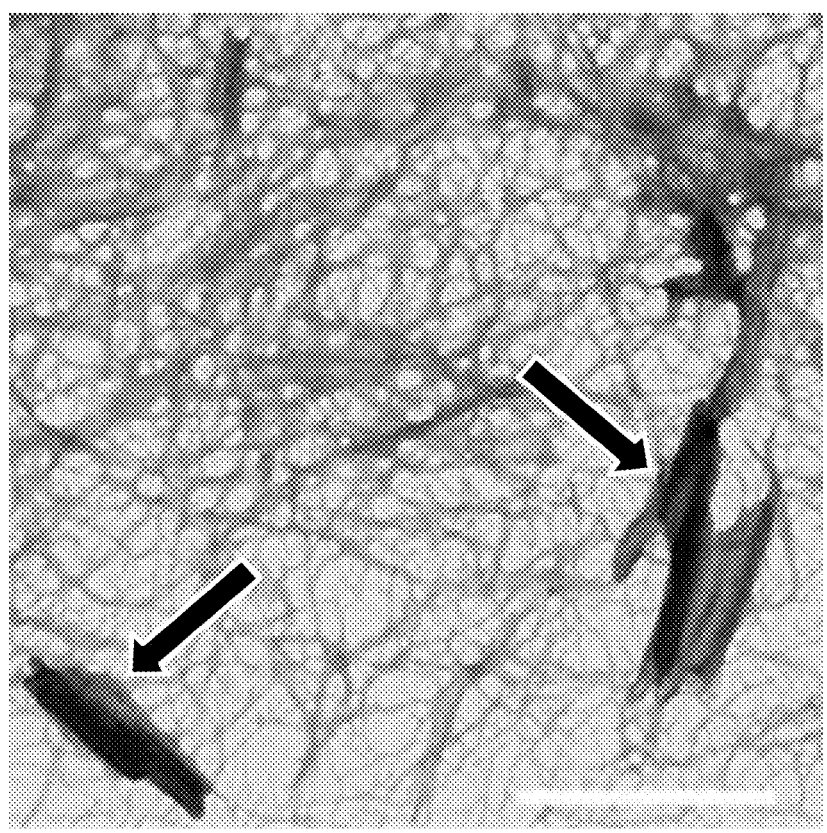
FIG. 3 is an illustration showing an assembly between RNTs with Matrilin-3.

Nanopieces containing Matrilin as cargo were manufactured as follows. 10 μL of a 100 μg/mL Matrilin (MATN) protein solution was mixed with 10 μL of a 1 mg/mL RNTs. The resulting mixture was then sonicated for 60 s. Dilution factors can range from 1 to 50 μL for preparing the MATN-RNTs complex mixture and sonication times of the resulting mixture can vary from 1 to 600 s. Results are shown in FIG. 3.

Example 3

Design and Processing of Nanopieces

Figure 5A:
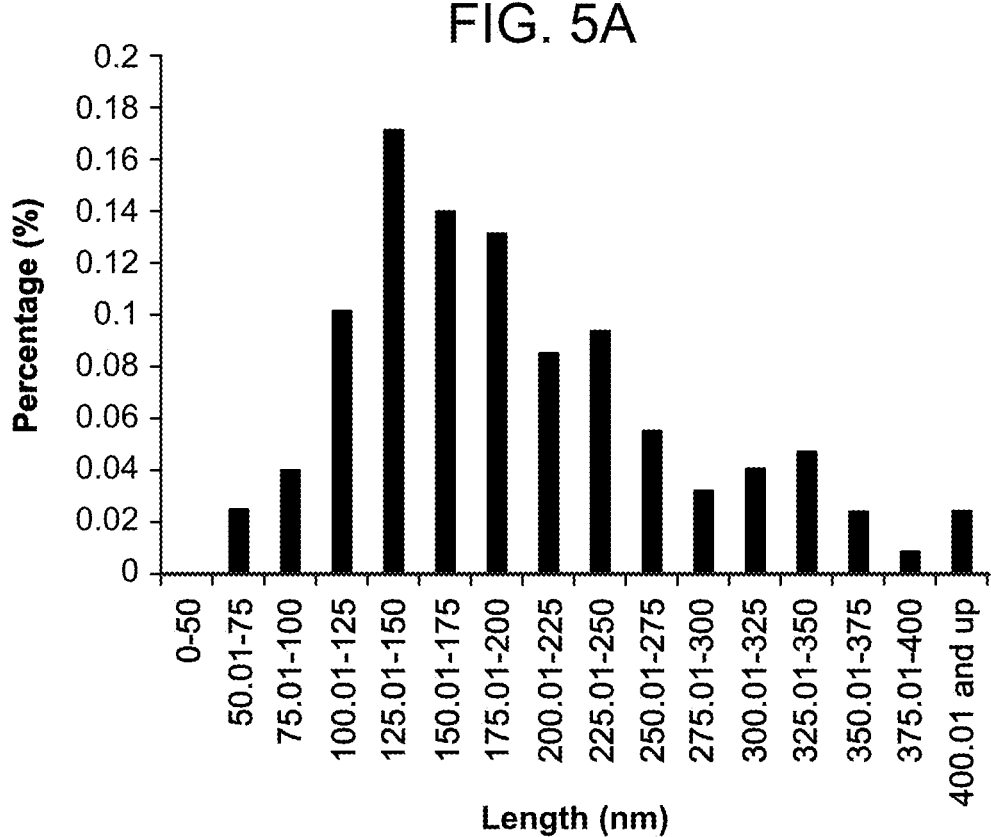
FIG. 5A is a bar graph of the size distribution of Nanopieces assembled under standard conditions.
Figure 5B:
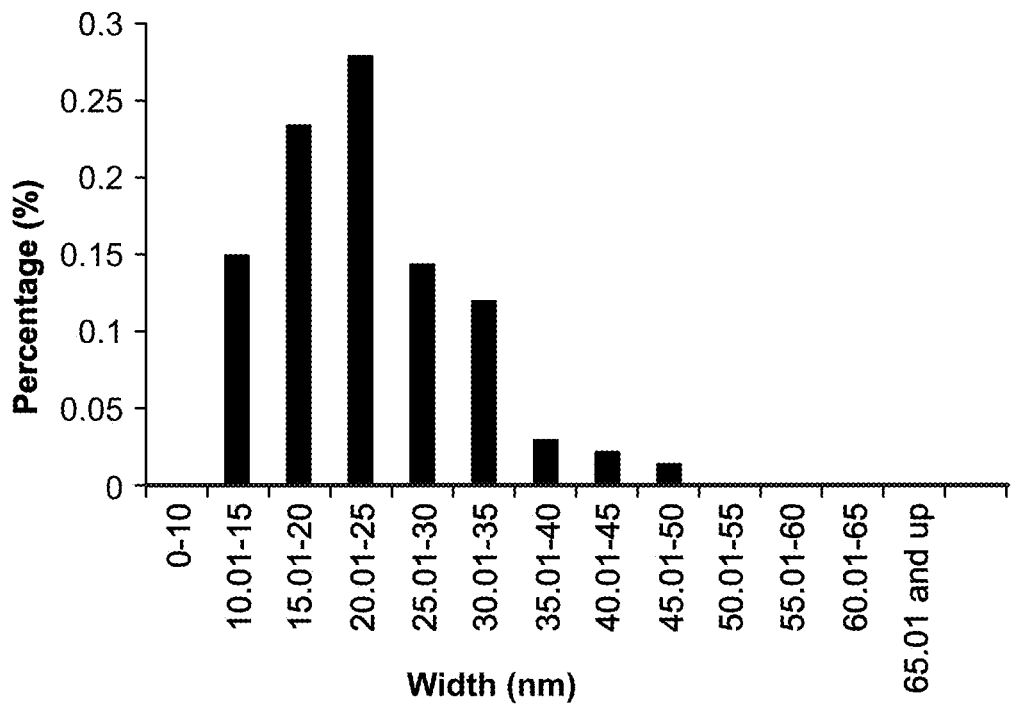
FIG. 5B is a bar graph of the width distribution of Nanopieces assembled under standard conditions.
Figure 10A:
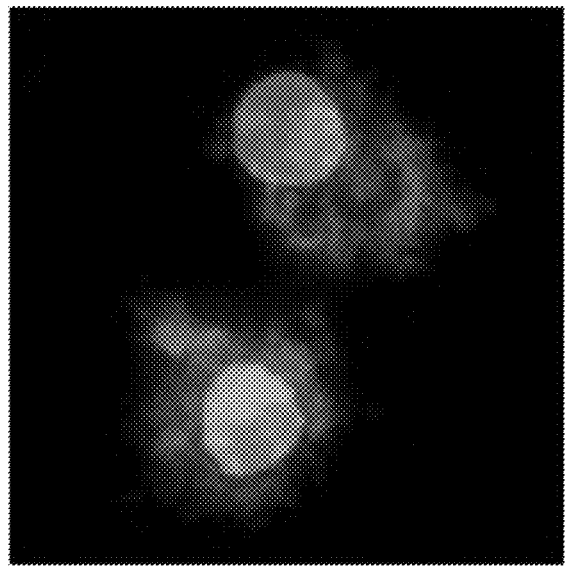
FIG. 10A and FIG. 10B are a series of images showing Nanopieces assembled before processing (FIG. 10A) and after processing with sonication (FIG. 10B) were delivered into cells.
Figure 10B:
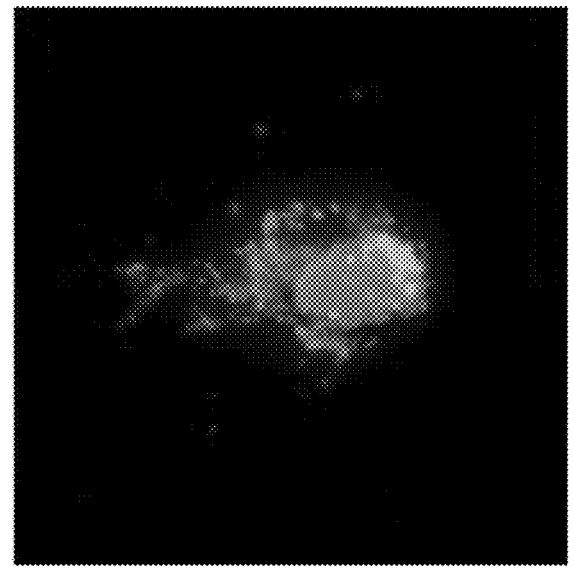

FIG. 4 shows an exemplary assembly mechanism. Processing methods were designed before, during and after assembly to manipulate the sizes of Nanopieces. Taking quench and sonication as examples of processing methods before assembly, FIGS. 6A-6B and FIGS. 7A-7B demonstrate the formation of smaller Nanopieces compared with those generated under standard conditions (FIG. 5A and FIG. 5B). FIGS. 8A-8B and FIGS. 9A-9B represent size distributions of examples of processing methods during and after assembly. Small Nanopieces were delivered into cells as shown in FIG. 10A and FIG. 10B.

Example 3.1

FIGS. 5A-9B demonstrate Nanopieces of different sizes and width that were imaged under a transmission electron microscope, and their length and width were analyzed with Image J software.

Nanopieces of different lengths and widths were prepared using the following exemplary procedures.

Example 3.1A 5 ug of RNT in 5 uL water was mixed with 50 pmol siRNA in 10 uL water, and then the mixture was sonicated for 2 min to produce Nanopieces (FIG. 5A and FIG. 5B)

Figure 6A:
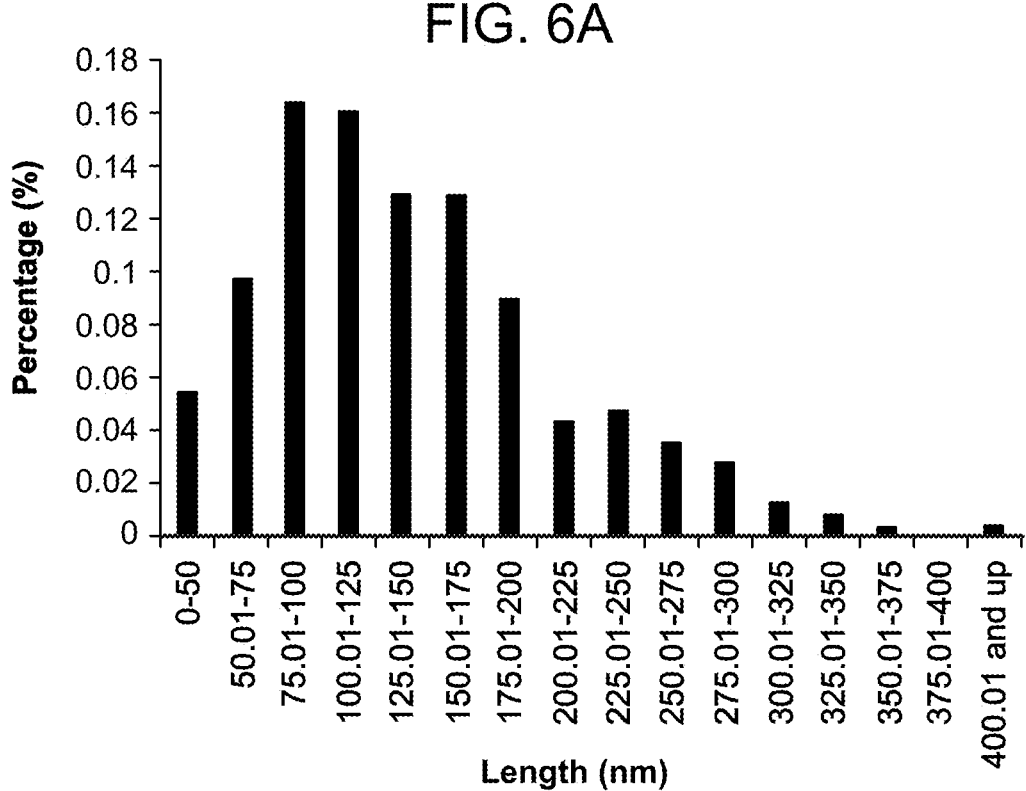
FIG. 6A is a bar a graph of the size distribution of Nanopieces processed before assembly (quench).
Figure 6B:
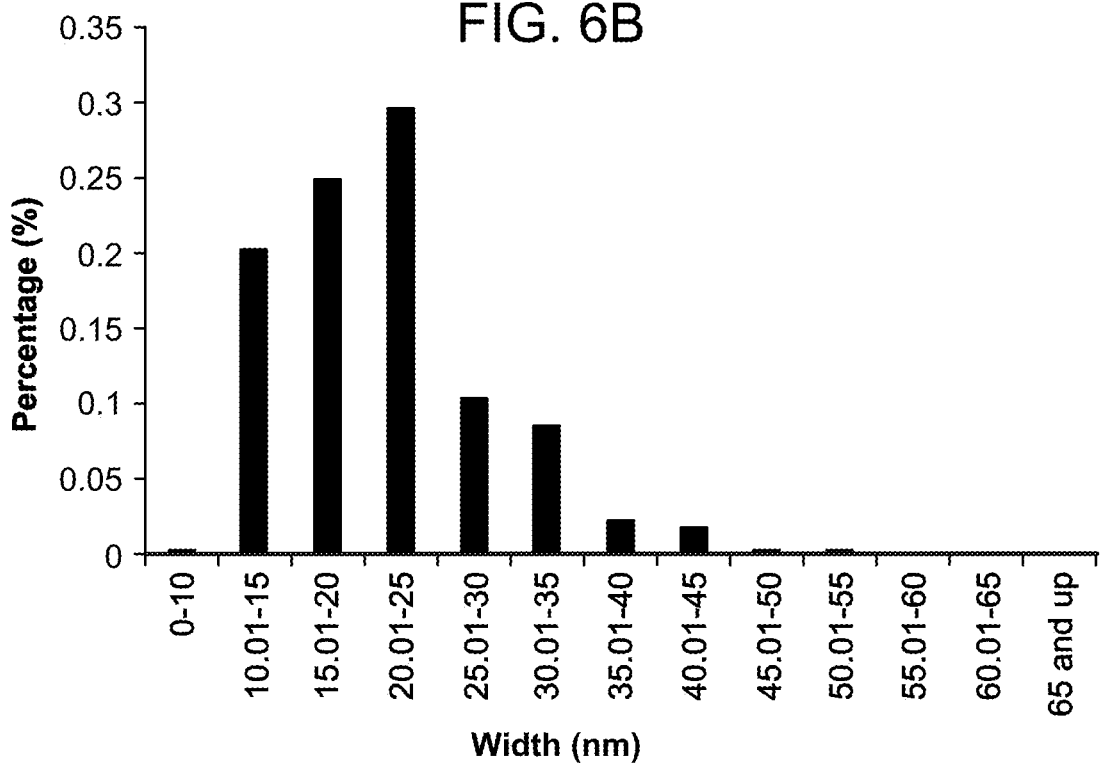
FIG. 6B is a bar graph of the width distribution of Nanopieces processed before assembly (quench).

Example 3.1B 5 ug of RNT in 5 uL water is heated to 95° C. for 10 min, and then the solution is immediately putted on ice. After totally cooling down to 0° C., RNT solution is mixed with 50 pmol siRNA in 10 uL water, and then the mixture is sonicated for 2 min to produce Nanopieces (FIG. 6A and FIG. 6B).

Figure 7A:
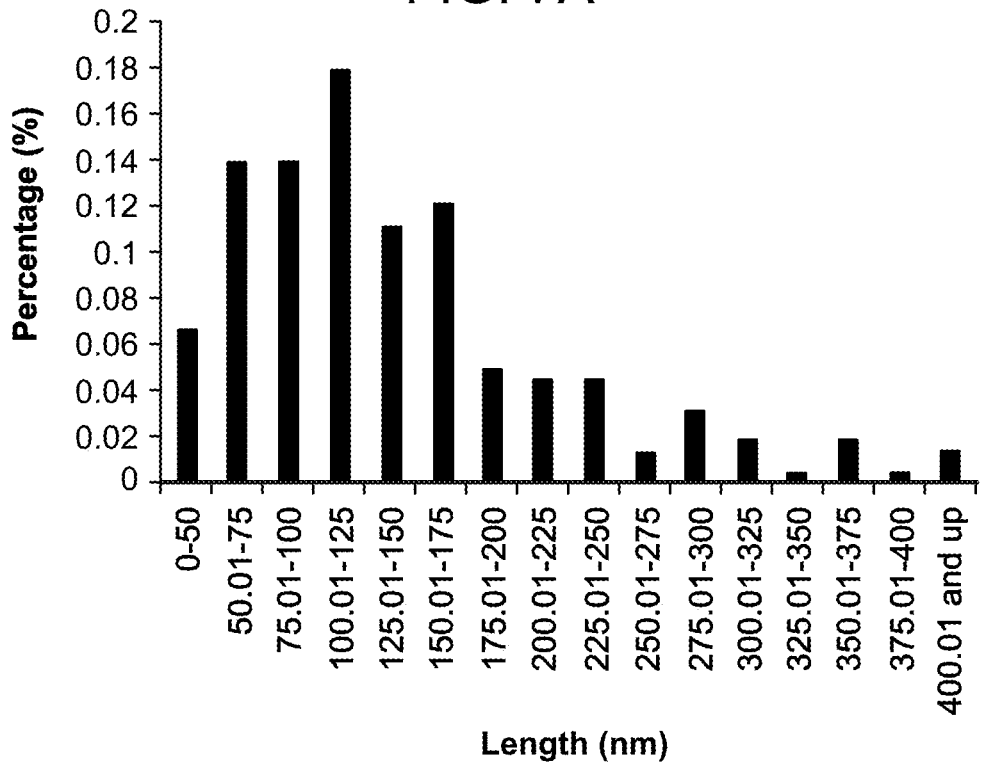
FIG. 7A is a bar graph of the size distribution of Nanopieces processed before assembly (sonication).
Figure 7B:
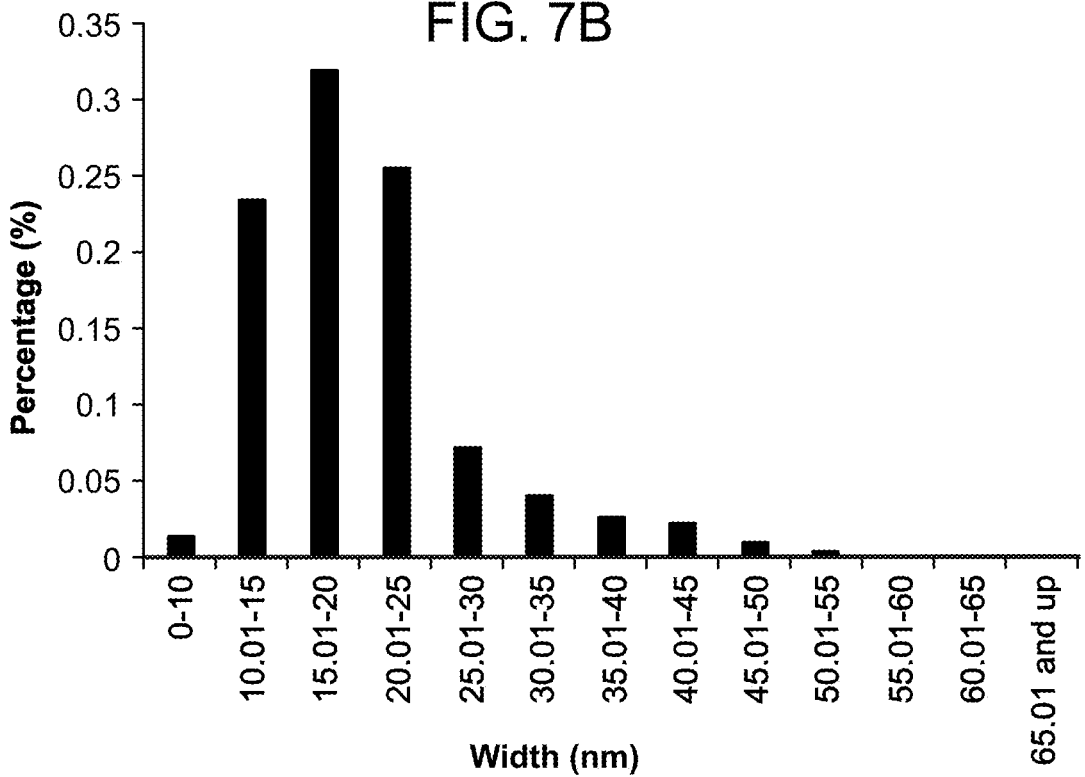
FIG. 7B is a bar graph of the width distribution of Nanopieces processed before assembly (sonication).

Example 3.1C 5 ug of RNT in 5 uL water is heated to 95° C. for 10 min, and then the solution is immediately subjected to sonication for 5 min. The resulting RNT solution is mixed with 50 pmol siRNA in 10 uL water, and then the mixture is sonicated for 2 min to produce Nanopieces (FIG. 7A and FIG. 7B).

Figure 8A:
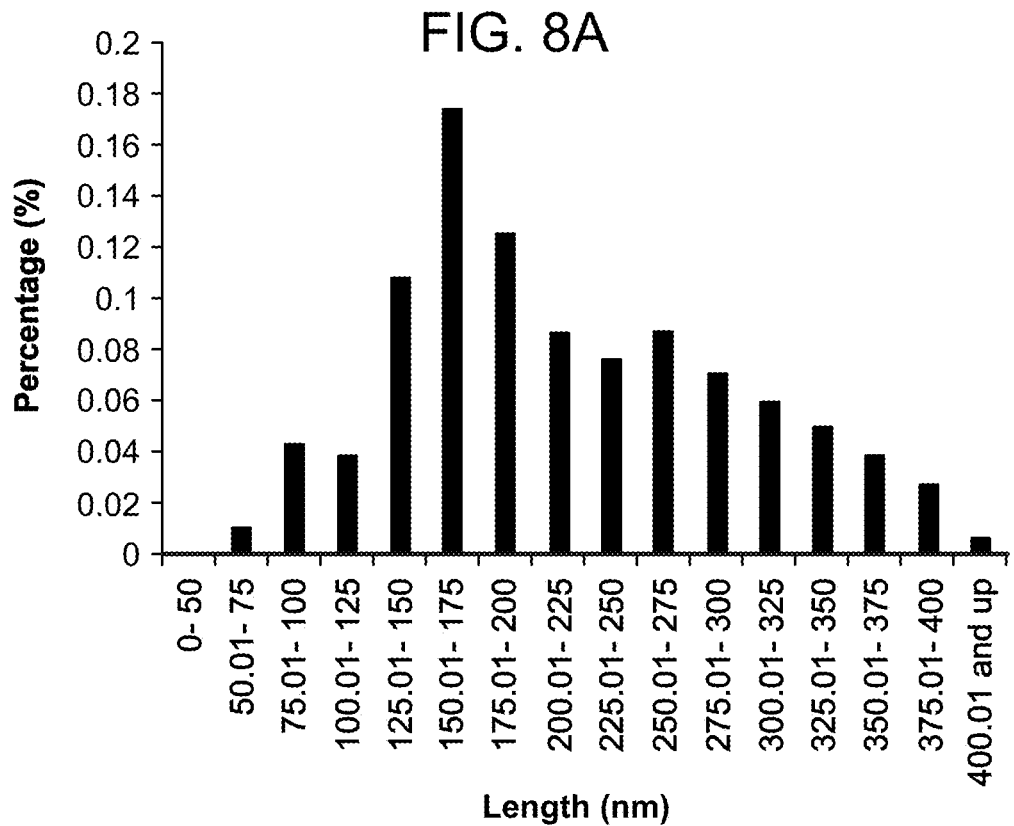
FIG. 8A is a bar graph of the size distribution of Nanopieces processed during assembly (increasing ionic strength).
Figure 8B:
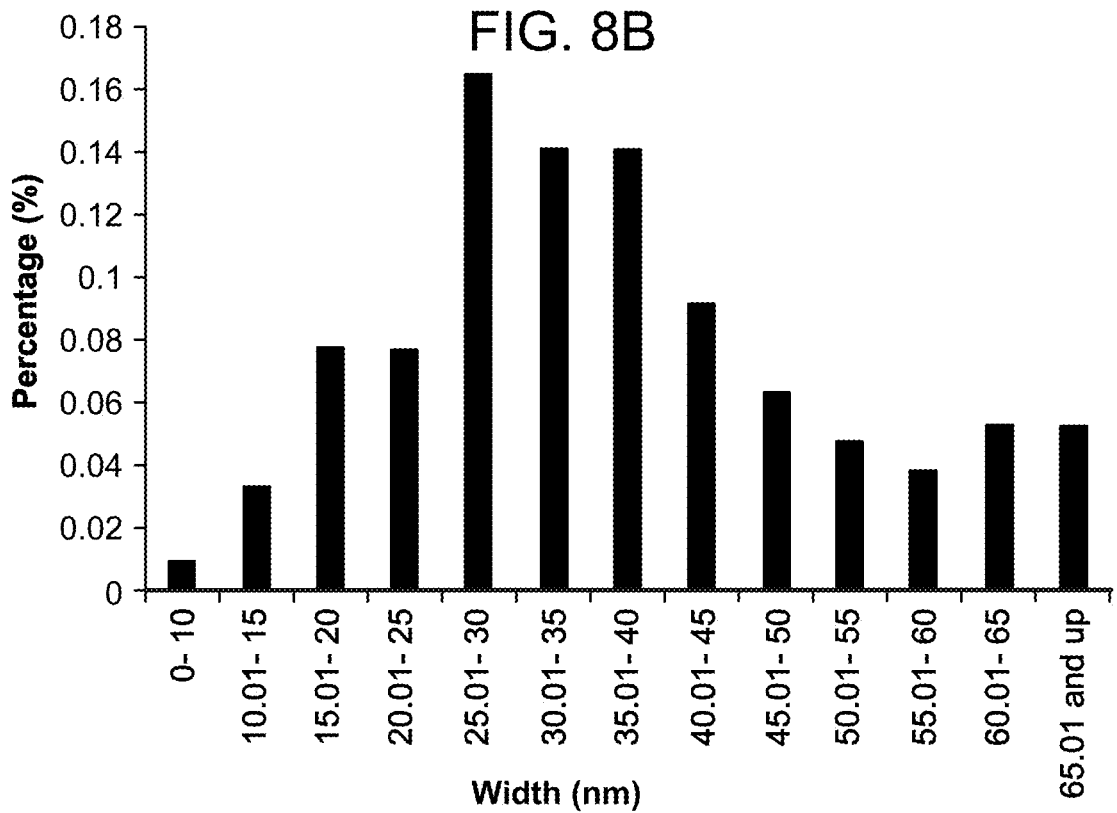
FIG. 8B is a bar graph of the width distribution of Nanopieces processed during assembly (increasing ionic strength).

Example 3.1D 5 ug of RNT in 5 uL in water is mixed with 50 pmol siRNA in 10 uL 0.9% saline, and then the mixture is sonicated for 2 min to produce Nanopieces (FIGS. 8A and 8B).

Example 3.1E 5 ug of RNT in 5 uL in water is mixed with 50 pmol siRNA in 10 uL water, and then the mixture is sonicated for 4 min to produce Nanopieces (FIGS. 9A and 9B).

Example 3.2

FIGS. 10A and 10B show that fluorescence labeled RNA was delivered into cells using unprocessed and processed Nanopieces. The Nanopieces were added to chondrocytes and the cells were maintained under standard cell culture conditions for 24 h. FIG. 10A shows unprocessed nanopeices, while FIG. 10B shows processed Nanopieces being delivered into cells.

Example 3.3

Various types of Nanopieces and their processing methods are described. Nanotubes are converted into nanorods. As shown in FIG. 4, the use of physical methods (sonication, blending, microwave and/or quenching) or chemical methods (altering pH, adding organic solvents, and/or adding of aromatic chemicals) convert nanotubes into homogenous shorter/longer nanorods to result in shorter/longer Nanopieces compared to standard conditions. (FIGS. 5A-FIG. 7B). Nanorods were produced via either sonicating RNTs, or heating RNTs to 90° C., and then quenching them on ice. RNTs or Nanorods were used to form Nanopieces. Nanopieces were characterized using transmission electron microscope and their length and width were analyzed with Image J software.

Example 3.4

Figure 11:
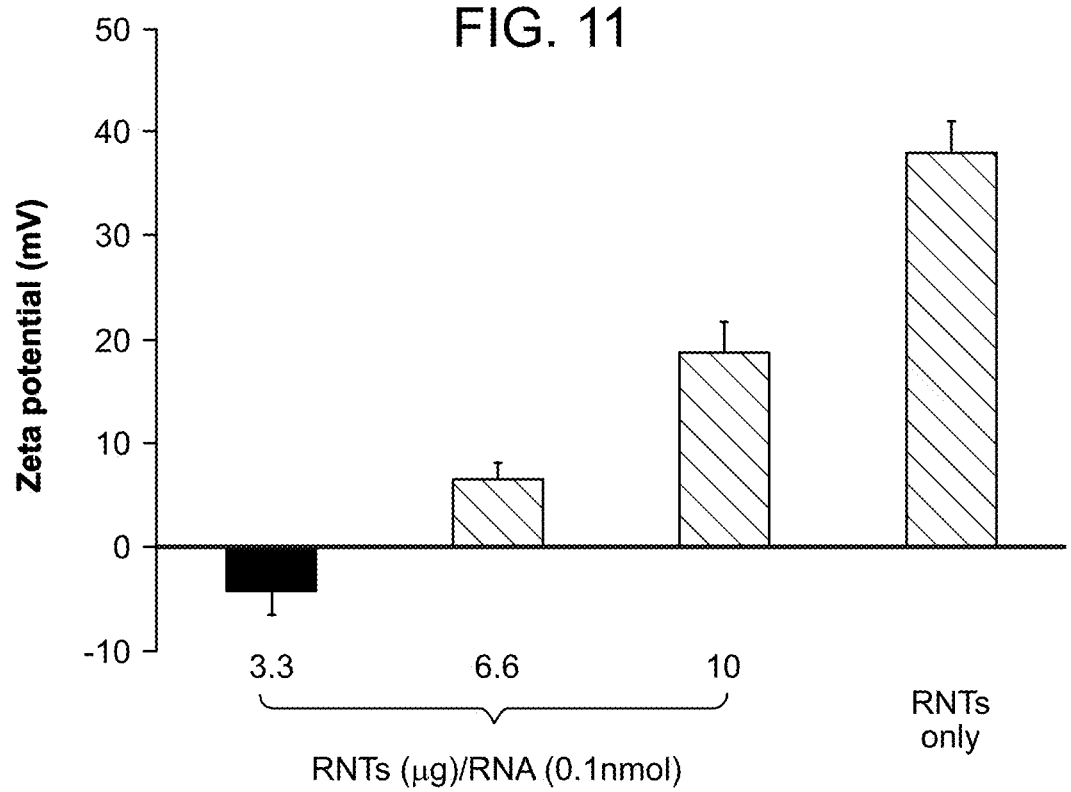
FIG. 11 is a graph showing the Zeta potential (reflecting surface charge) of Nanopieces with different RNT/siRNA ratios.

Various types of Nanopieces and their processing methods are used to customize the physical characteristics, e.g., length and width, and/or chemical characteristics e.g., surface charge of the delivery vehicle. Two major conditions can be altered: i) assembly conditions (ionic strength, pH and concentration) to achieve Nanopieces with various sizes; and ii) the ratio between nanotubes/nanorods and delivery cargos to achieve different surface charge for the delivery of cargo into different tissues. For example, an increase in ionic strength can be used in the assembly solution to generate longer and wider Nanopieces compared to when using standard conditions (FIG. 4, FIG. 7A and FIG. 7B). An increase in the ratio of RNTs over siRNA resulted in an increase of the surface positive charge of Nanopieces (FIG. 11). FIG. 8A and FIG. 8B show that RNTs and siRNA were dissolved in saline to form Nanopieces as described in the previous sections. Nanopieces were imaged under a transmission electron microscope, and their length and width were analyzed with Image J software. FIG. 11 shows the different ratios of RNTs and siRNA that were used to form Nanopieces. The surface charge (as measured by Zeta potential; mV) of Nanopieces was determined via Nano-sizer.

Example 3.5

Figures 56A, 56B, 56C:
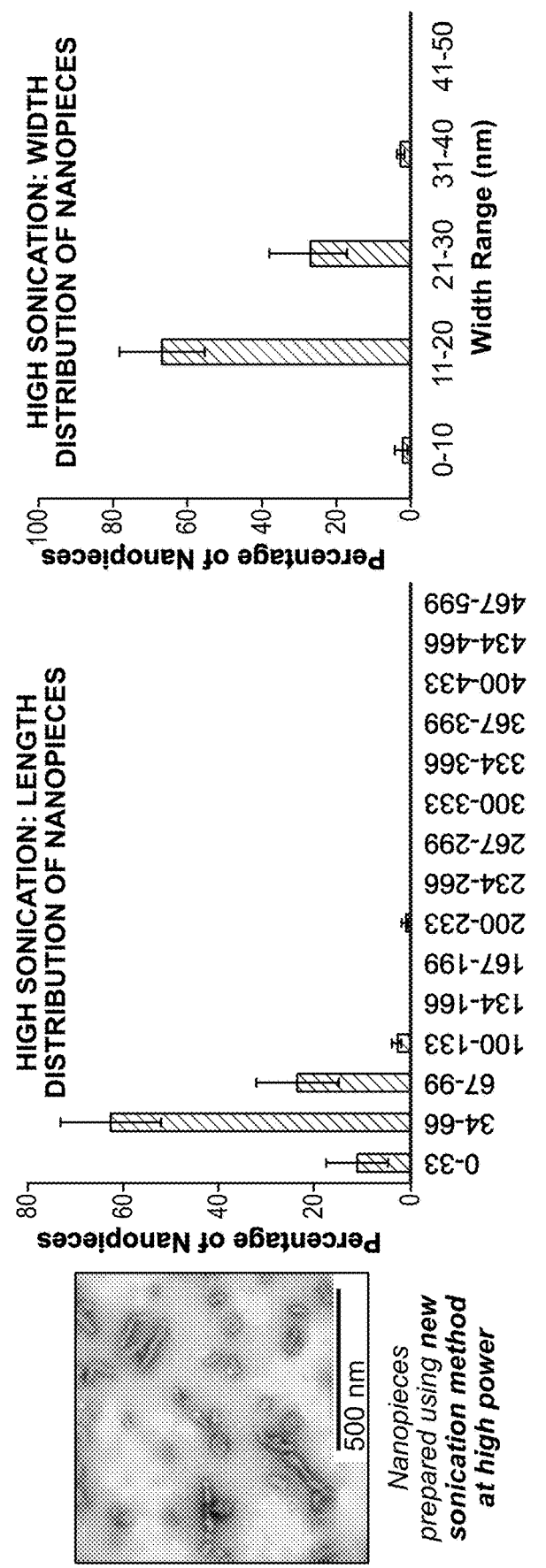
FIGS. 56A-56L are a series of graphs and images showing Nanopieces size and morphology with increasing sonication power.
Figures 56D, 56E, 56F:
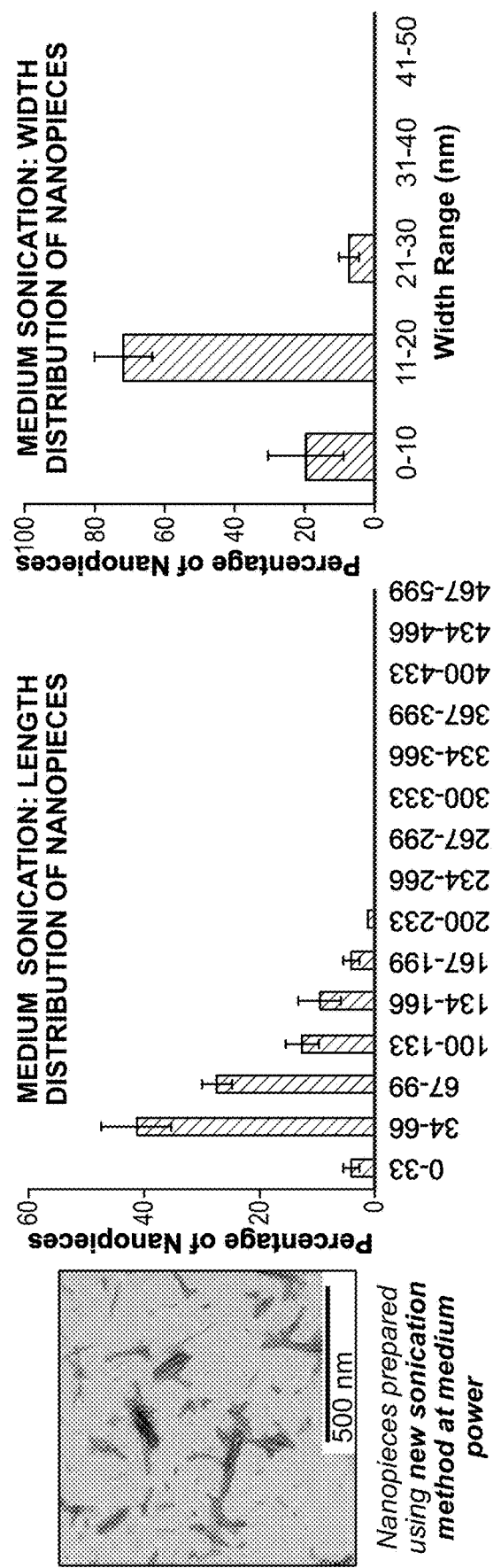
Figures 56G, 56H, 56I:
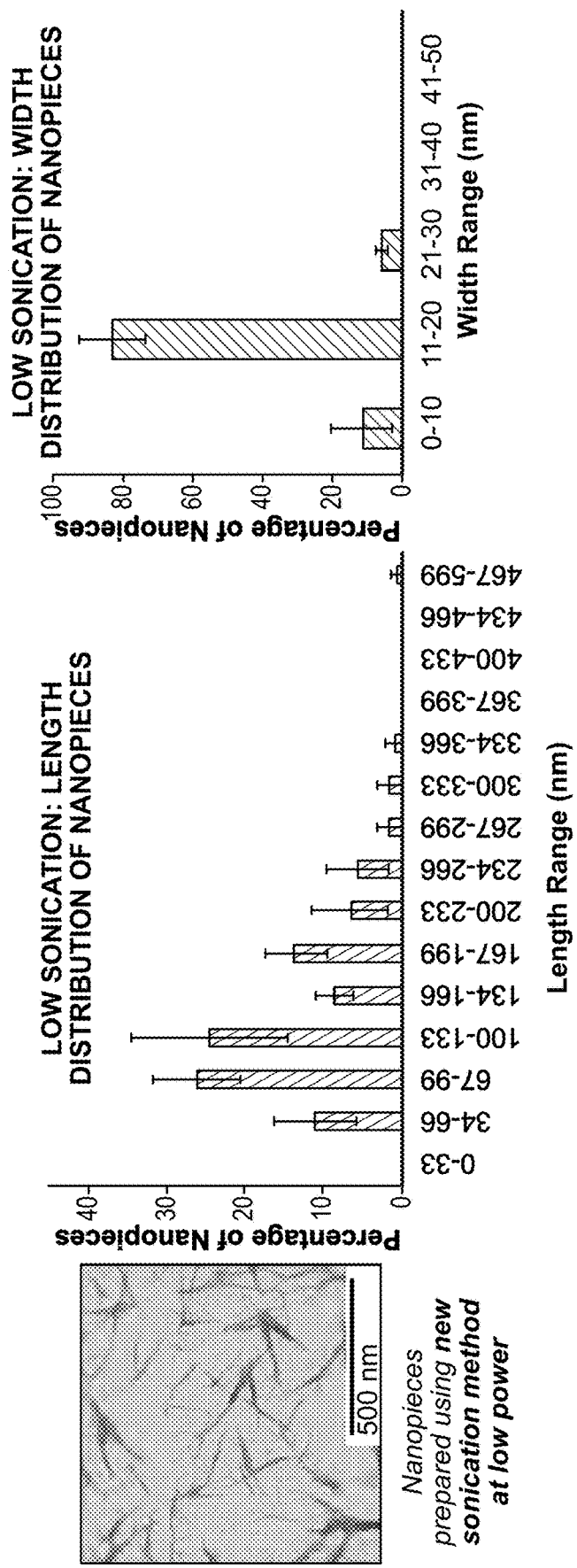
Figures 56J, 56K, 56L:
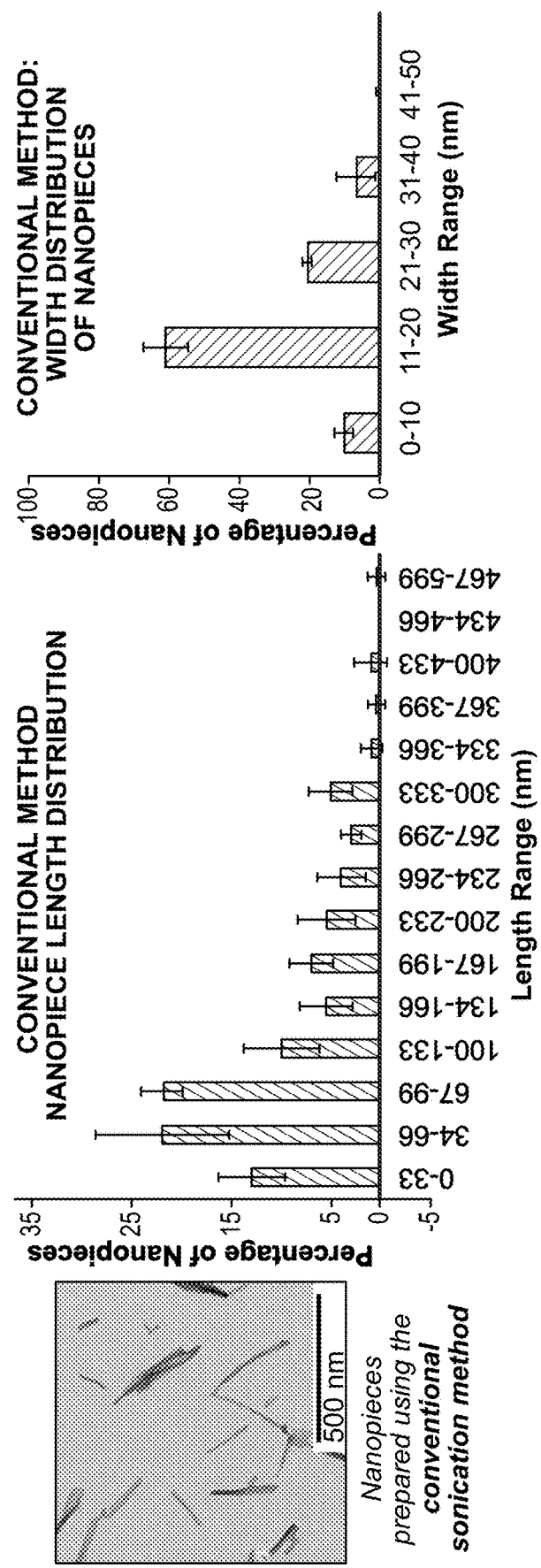
Figure 57:
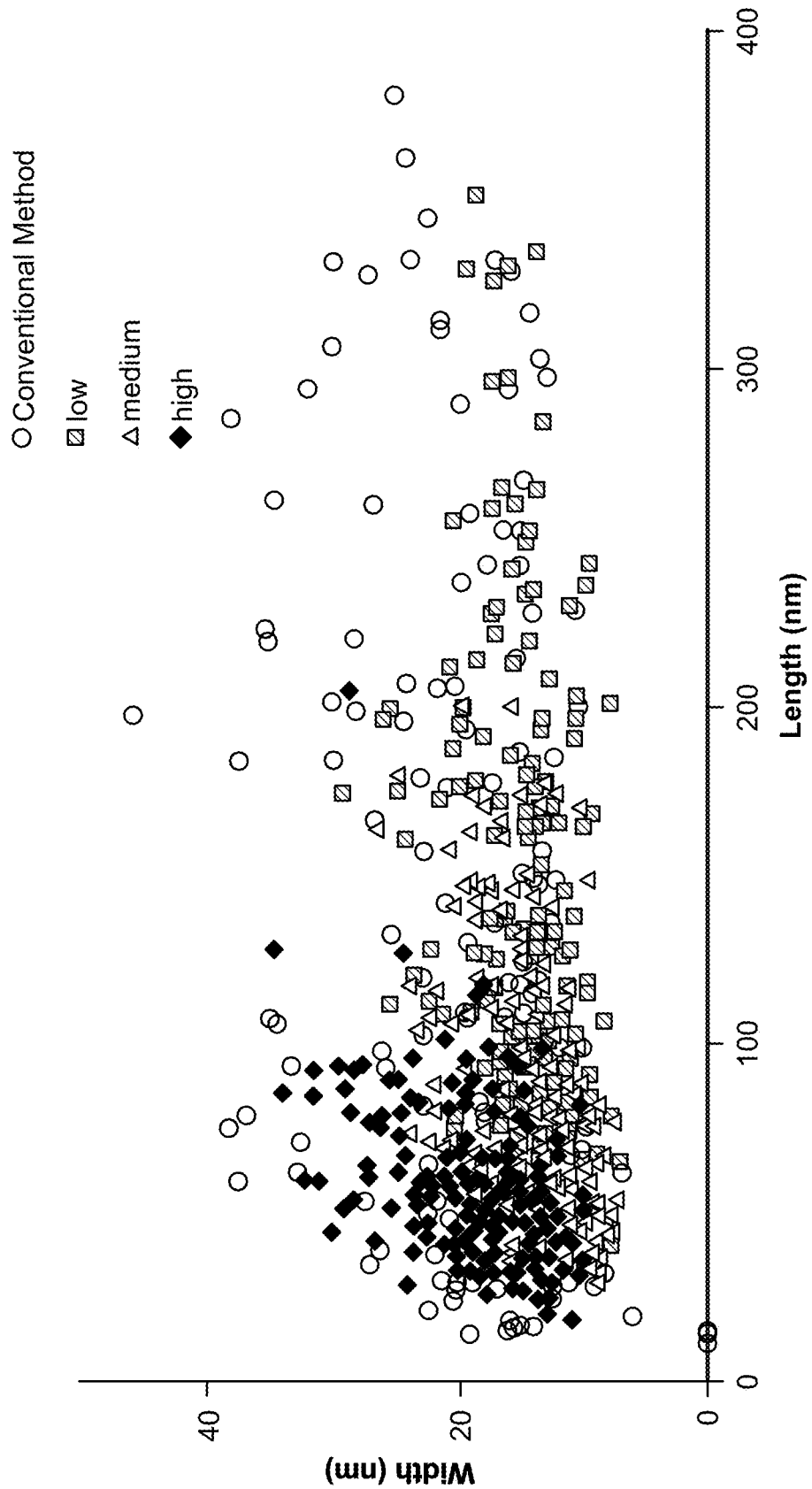
FIG. 57 is a scatter plot of Nanopieces size and morphology with increasing sonication power.

Processing after assembly included physical methods, e.g., using different power of sonication, heating, blending and/or microwave; or chemical methods, like altering of pH and adding of aromatic chemicals. For example, the use of low, medium and high power of sonication resulted in Nanopieces with different size (length) and morphology (aspect ratio, which is equal to length/width) (FIG. 4, FIGS. 56A-56L, and FIG. 57). FIGS. 56A-FIG. 57 show that Nanopieces were formed under standard conditions or were processed with different sonication powers (low power is 10% of maximum amplitude of a 700 W sonicator; medium is 50% and high is 100%). Nanopieces were imaged under a transmission electron microscope, and their length and width were analyzed with Image J software.

Example 3.6

Figure 20:
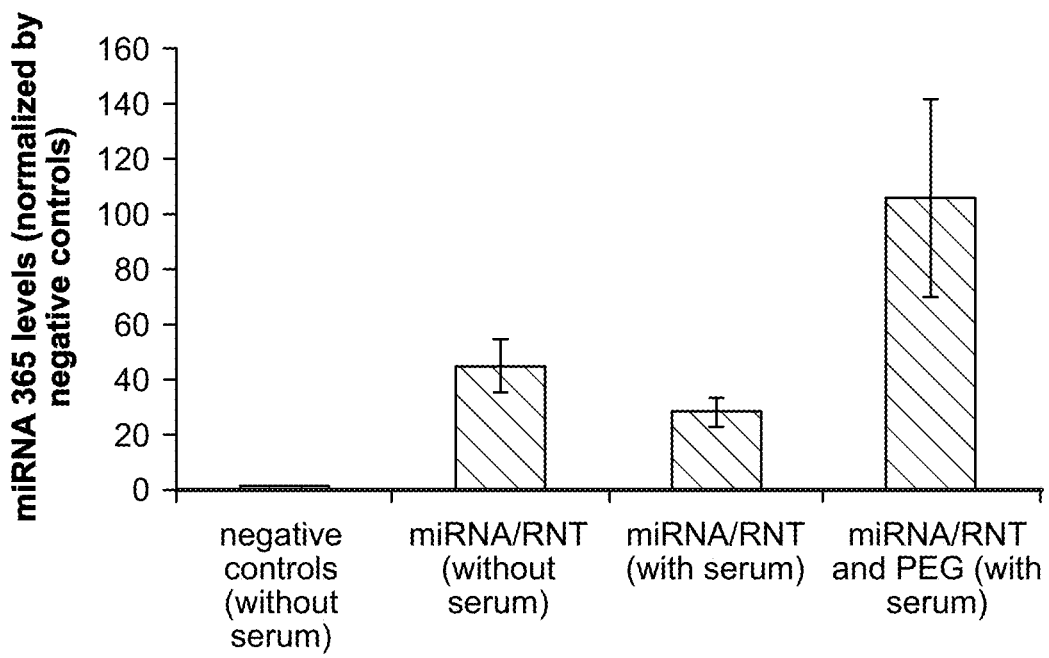
FIG. 20 is a graph showing functional delivery of processed miRNA365/RNT Nanopieces with and/or without PEG into human cartilage tissue matrix and inside chondrocytes in the serum and serum-free medium.
Figure 58:
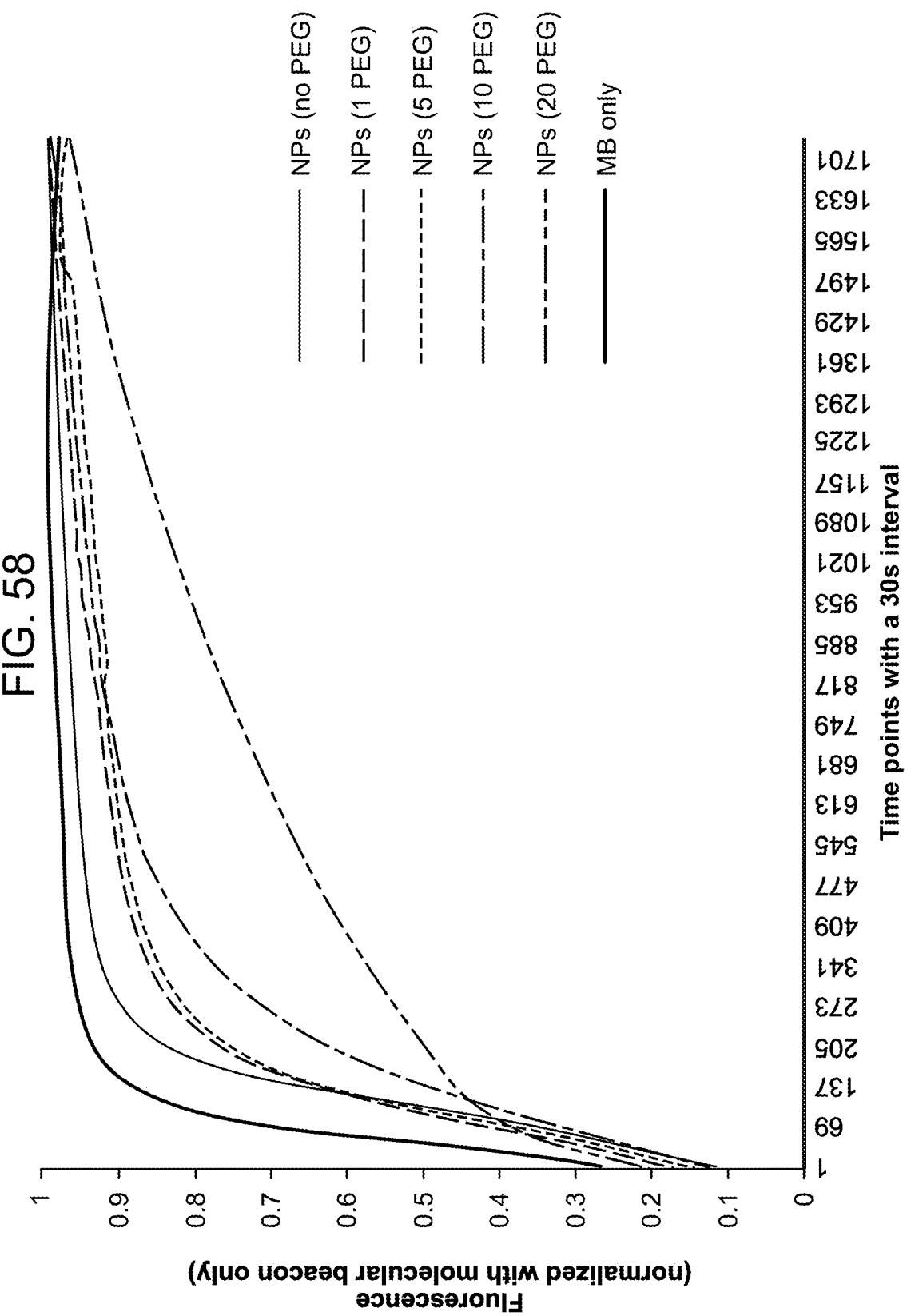
FIG. 58 is a line graph showing the stability of Nanopieces with different molar-excess ratios of PEG.
Figure 59:
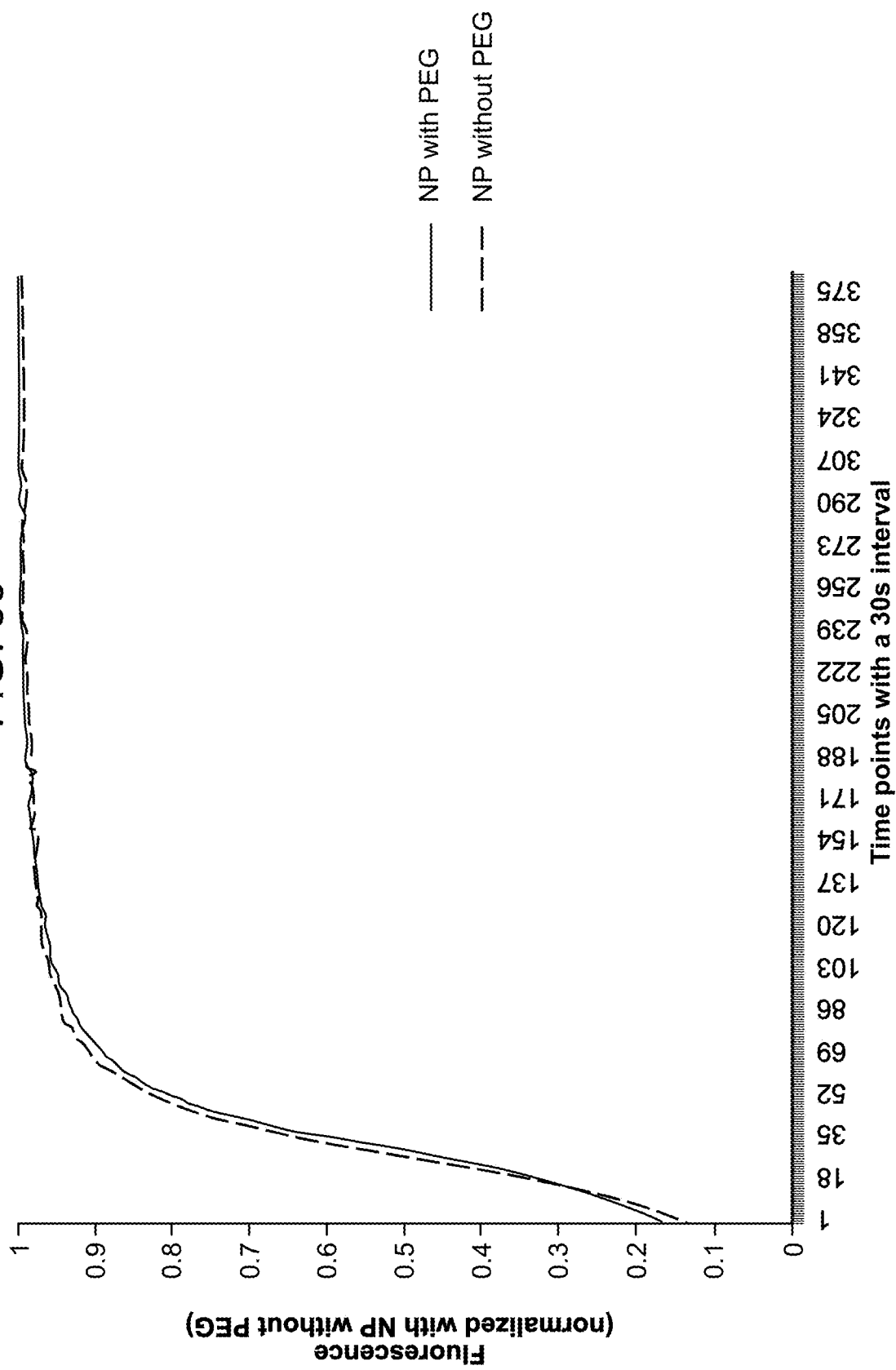
FIG. 59 is a line graph showing the stability of Nanopieces with and without non-covalent linked PEG.
Figures 61A, 61B:
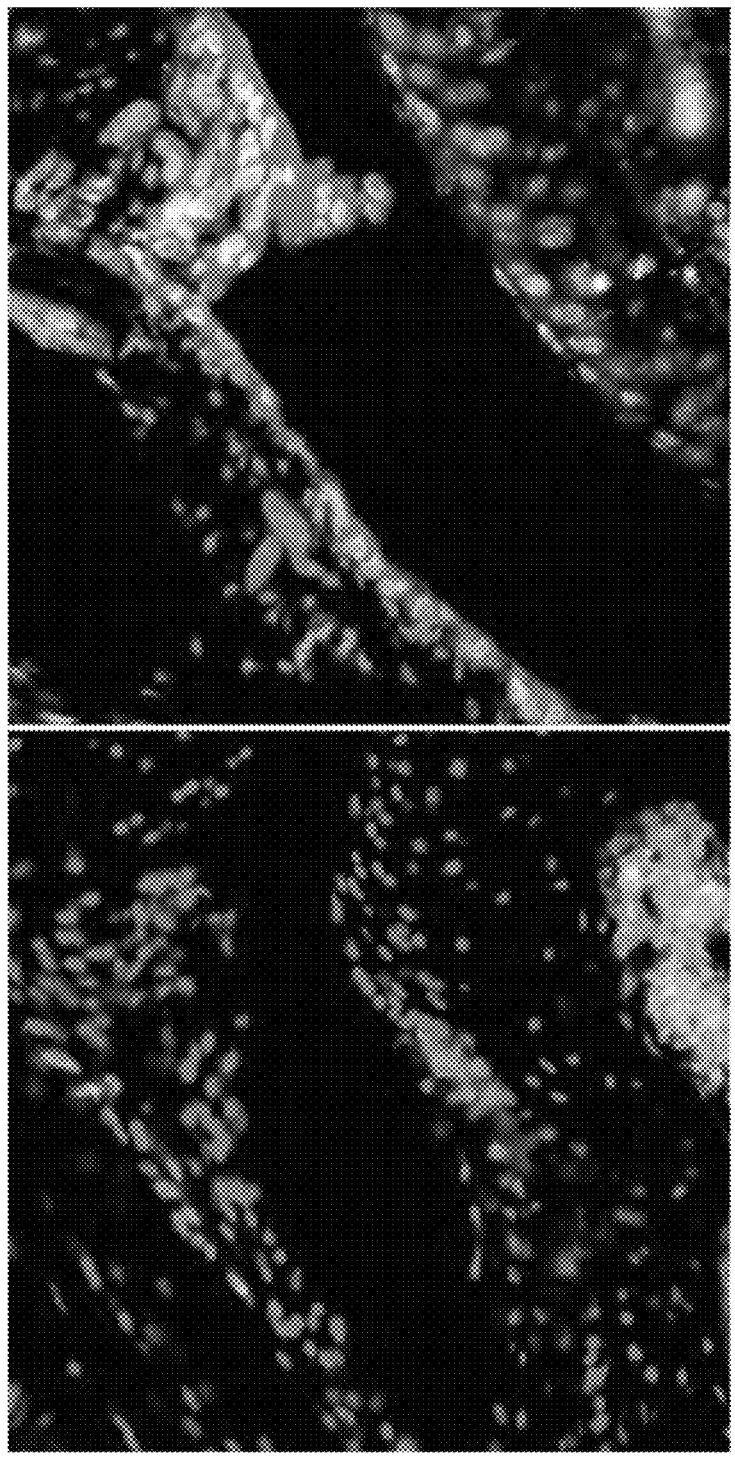
FIG. 61A and FIG. 61B are images showing the delivery of both large and small Nanopieces into synovium to result in fluorescence compared with controls (MB only).

Nanopieces are optionally coated. Coating of Nanopieces with PEG facilitated Nanopieces delivery into tissue matrix, especially in a protein-rich environment, such as in the presence of serum (FIG. 20). Although Nanopieces doubled the half-life of delivery cargos (such as molecular beacon, MB) in serum, a covalent linked PEG coating had a 6-time longer half-life than MB only (FIG. 58). Moreover, non-covalent linked PEG only had marginal difference on Nanopieces in terms of stability in serum (FIG. 59). FIG. 58-FIG. 59 show that molecular beacons delivered with/without Nanopieces were soaked in serum. For PEG coating, PEG (MW 400) was either covalently linked or non-covalently coated on Nanopieces. A fluorescence plate read was determined half-life of MBs.

Example 3.6

Nanopieces of different sizes and length were prepared using the following procedure:
Step A: Quench before assembly: heating 5 ug RNT in water to 50-99° C. for 10 s-10 mins, then immediately putting it on ice, and mixing with 50 pmol siRNA, then, sonicating for 30 s-2 mins to produce Nanopieces.
Step B: Sonication before assembly: sonicating 5 ug RNT in water to 50-99° C. for 10 s-10 mins, and mixing with 50 pmol siRNA, then, sonicating for 30 s-2 mins to produce Nanopieces.
Step C: Increase ionic strength: mixing 5 ug RNT with 50 pmol siRNA in saline, then, sonicating for 30 s-2 mins to produce Nanopieces.
Step D: Increase sonication time after assembly: mixing 5 ug RNT with 50 pmol siRNA, then, sonicating for 2 mins-10 mins to produce Nanopieces.
Modification of Parameters:

| | Size of Nanopieces | |
|---|---|---|
| Factors | High/Long | Low/Short |
| Heating temperature for quench | Small (Avg. length 10 nm~149 nm; Avg. width diameter 10~29 nm) | Large (Avg. length 150 nm~500 nm; Avg. width diameter 10~29 nm) |

| | | |
|---|---|---|
| Heating time for quench | Small (Avg. length 10 nm~149 nm; Avg. width diameter 10~29 nm) | Large (Avg. length 150 nm~500 nm; Avg. width diameter 10~29 nm) |
| Sonication time before assembly | Small (Avg. length 10 nm~149 nm; Avg. width diameter 10~29 nm) | Large (Avg. length 150 nm~500 nm; Avg. width diameter 10~29 nm) |
| Sonication power before assembly | Small (Avg. length 10 nm~149 nm; Avg. width diameter 10~29 nm) | Large (Avg. length 150 nm~500 nm; Avg. width diameter 10~29 nm) |
| Sonication time after assembly | Small (Avg. length 10 nm~149 nm; Avg. width diameter 10~29 nm) | Large (Avg. length 150 nm~500 nm; Avg. width diameter 10~29 nm) |
| Sonication power after assembly | Small (Avg. length 10 nm~149 nm; Avg. width diameter 10~29 nm) | Large (Avg. length 150 nm~500 nm; Avg. width diameter 10~29 nm) |
| Ionic strength | Vary Large (Avg. length 150 nm~999 micon; Avg. width diameter 30~100 nm) | Small (Avg. length 10 nm~149 nm; Avg. width diameter 10~29 nm) |

| | Charge of Nanopieces | |
|---|---|---|
| | Strong/High | Weak/Low |
| RNT/RNA ratio Negative charge from the cargo (such as RNA other nucleic acids or proteins) | Positive Negative | Negative Positive |

| Nanopiece properties | Size | | Surface Charge | |
|---|---|---|---|---|
| | Small | Large | Negative | Positive |
| Suitable cells or tissues | High and dense extracellular matrix content | Low and loose extracellular matrix content | Positively charged or neutral cell membrane/ extracellular matrix | Negatively charged or neutral cell membrane/ extracellular matrix |

Example 4

Surface Charge and Matrix/Tissue Binding

Figures 12A, 12B:
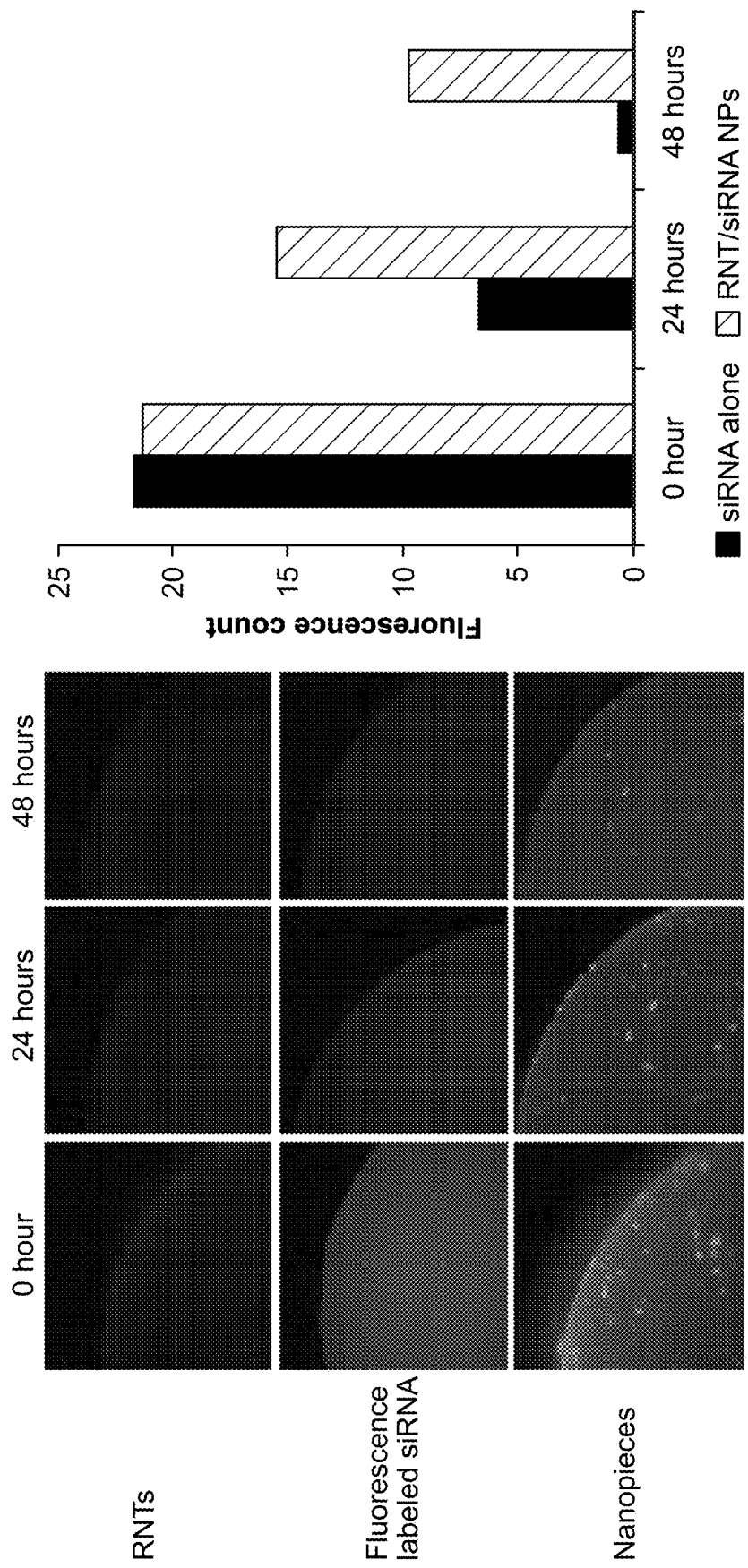
FIG. 12A shows a series of images and FIG. 12B shows a bar graph illustrating cartilage binding with RNTs, fluorescence labeled siRNA and RNT/siRNA Nanopieces on articular cartilage.

Surface charge of Nanopieces were tuned or customized via controlling RNT/delivery cargo ratio (e.g., RNT/siRNA as an example, FIG. 11). Adjusting 4.4 μg~30 μg RNTs per 0.1 nmol RNA yielded positively charged Nanopieces. These Nanopieces exhibited excellent binding to negatively charged tissue and/or matrix, as shown in FIG. 12A and FIG. 12B; light grey area and spots are the fluorescence signals from siRNA alone or siRNA. Nanopieces with more than 30 ug RNT per 0.1 nmol RNA are also positively charged. Generally, the ratio will not exceed 30 ug per 0.1 nmol RNA.

Example 4.1

Fluorescence labeled RNA with and without Nanopieces was added onto porcine articular cartilage for 1 h. Then, the cartilage was soaked in HBSS buffer at 37° C. The remaining RNA was analyzed using a fluorescence microscope.

Example 5

Trans-Matrix/Tissue Delivery

Figure 13B:
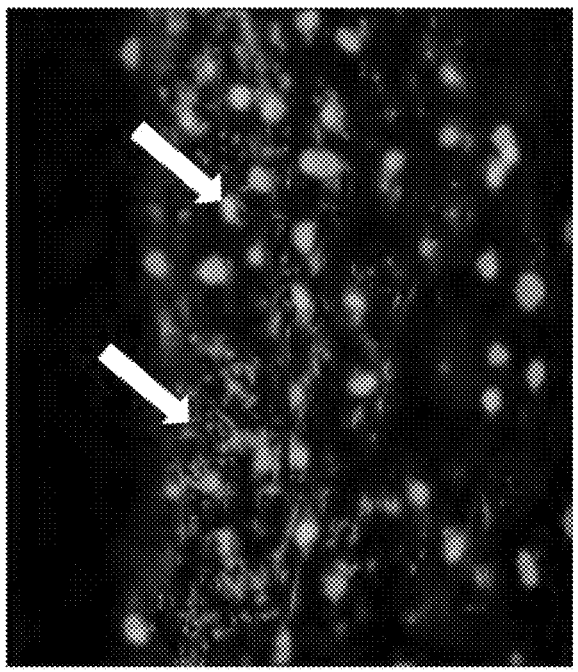
FIG. 13A and FIG. 13B are a series of images showing fluorescence labeled siRNA/RNT Nanopieces were delivered into porcine cartilage (Right) compared with controls (siRNA only).
Figure 13A:
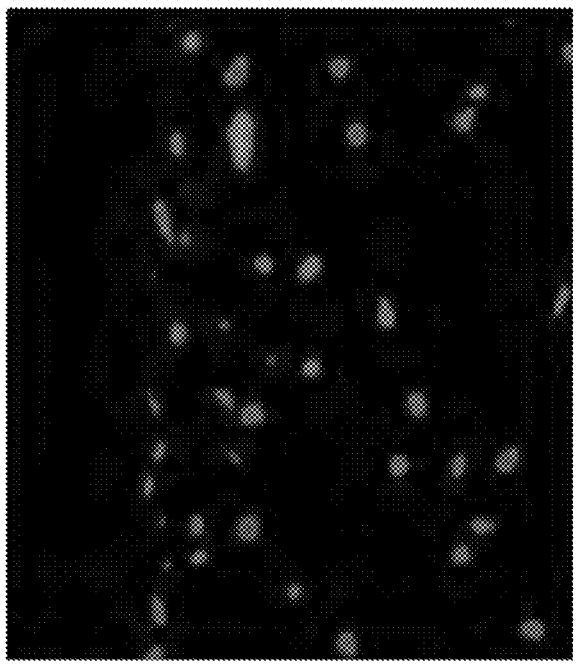

Results showed that processed fluorescence labeled siRNA/RNT Nanopieces successfully penetrated into cartilage (FIG. 13A and FIG. 13B). Moreover, it was further demonstrated that GAPDH molecular beacon/RNT Nanopieces not only penetrate into the tissue matrix but also inside cells (FIGS. 14A-FIGS. 16A and 16B). Effective trans-matrix and/or tissue delivery was demonstrated with a variety of species. Light grey areas within FIGS. 14A-FIGS. 16A and 16B around the cell nucleus are the fluorescence signals from molecular beacons.)

Example 5.1

Fluorescence labeled RNA was delivered with and without Nanopieces and was soaked with porcine cartilage. After 24 hours, the cartilage was sectioned and the individual sections were observed under a fluorescence microscope (FIG. 13A and FIG. 13B).

Example 5.2

Figure 14C:
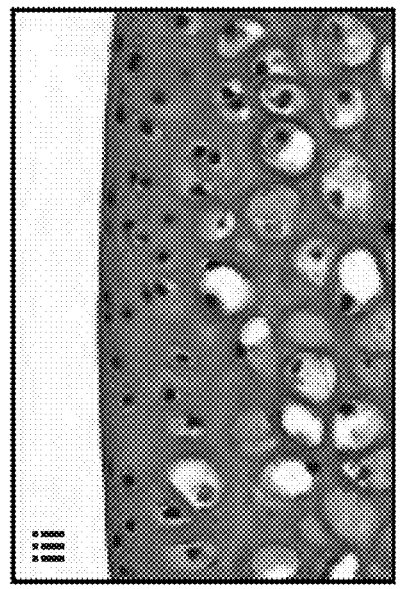
FIGS. 14A-14C are a series of images showing effective delivery of processed GAPDH molecular beacon/RNT Nanopieces into mouse cartilage tissue matrix and inside chondrocytes.
Figure 14B:
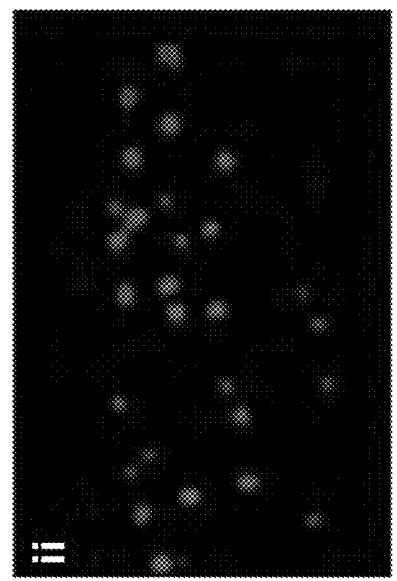
Figure 14A:
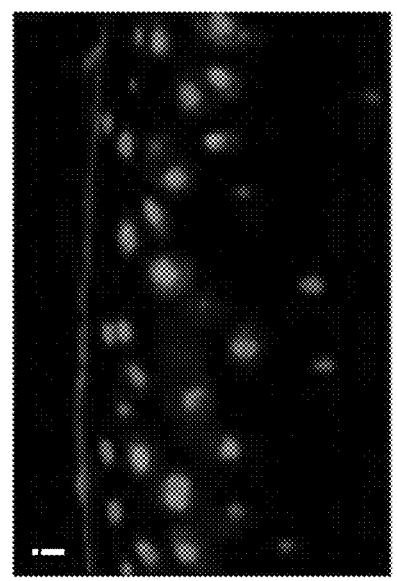

Fluorescence GAPDH molecular beacon was delivered with and without Nanopieces and soaked with mouse cartilage. After 24 hours, the cartilage was then sectioned and the individual sections were observed under a fluorescence microscope (FIGS. 14A-14C).

Example 5.3

Fluorescence GAPDH molecular beacon was delivered with and without Nanopieces and soaked with human cartilage. After 24 hours, the cartilage was then sectioned and the individual sections were observed under a fluorescence microscope (FIGS. 15A-15C).

Example 5.4

Fluorescence GAPDH molecular beacon was delivered with and without Nanopieces and soaked with chicken cartilage. After 24 hours, the cartilage was then sectioned and the individual sections were observed under a fluorescence microscope (FIG. 16A and FIG. 16B).

Example 5.5

Applications of various types of Nanopieces: Various types of Nanopieces can be used for delivery into different tissues or organs as desired. For example, co-injection of small Nanopieces (Avg. length ~110 nm, Avg. width ~20 nm) (SMALL means Avg. length 10 nm~149 nm; Avg. width diameter 10~29 nm) to deliver GAPDH MBs with fluorescence and very large Nanopieces (Avg. length ~250 nm, Avg. width ~33 nm) (LARGE means Avg. length 150 nm~999 micon; Avg. width diameter 30~100 nm) to deliver GAPDH MBs also with fluorescence into knee joints of mice were carried out. Small Nanopieces could be delivered into both cartilage and synovium, while large Nanopieces could only be delivered into synovium (FIG. 60A, FIG. 60B, FIG. 61A and FIG. 61B). (Bright area/spots around cell nuclei in FIG. 60A, FIG. 60B, FIG. 61A and FIG. 61B are the fluorescence signal from molecular beacons delivered via different sizes of Nanopieces.) Therefore, selective delivery into synovium with processed large Nanopieces was achieved.

Figure 63:
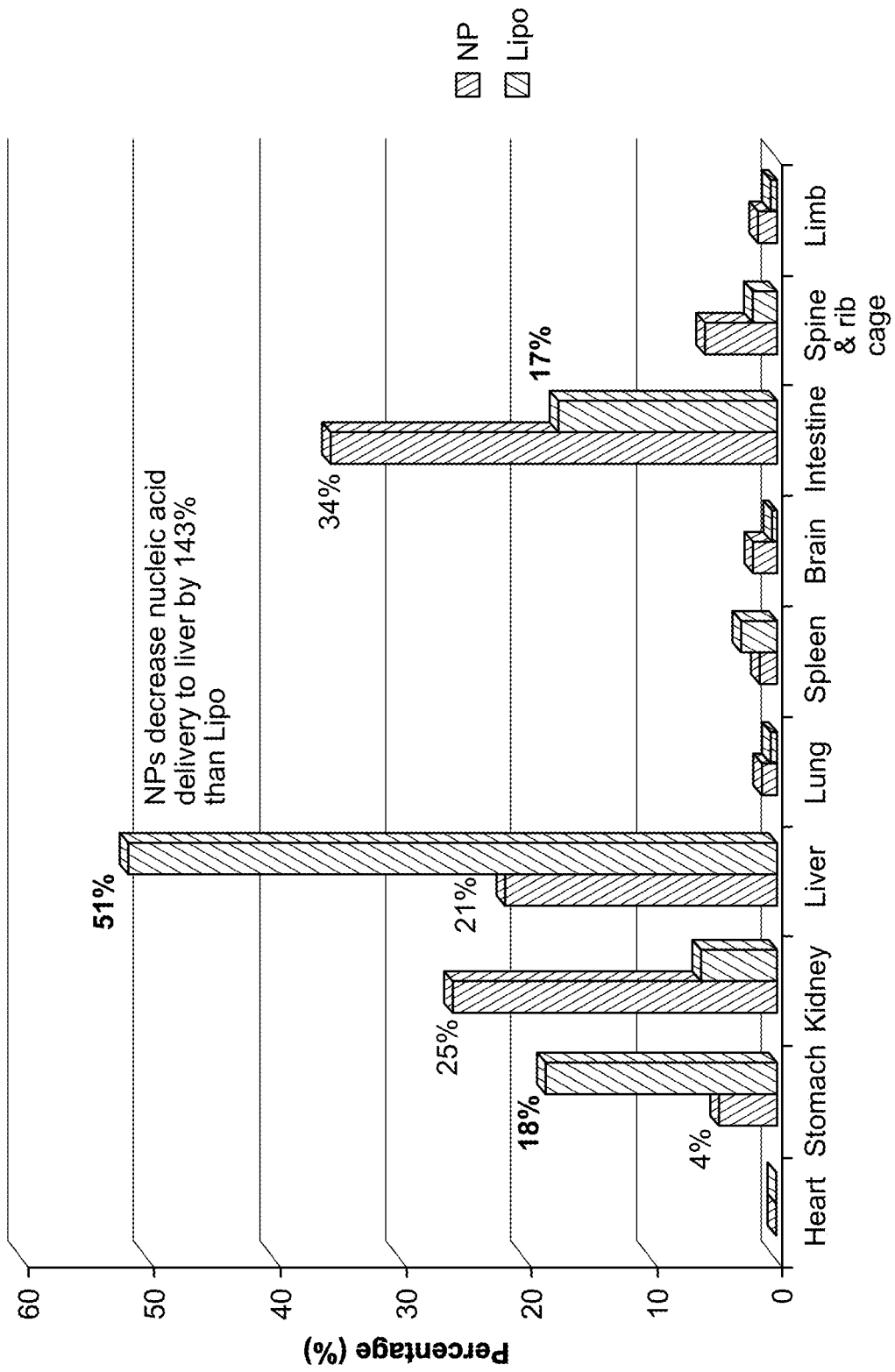
FIG. 63 is a bar graph showing the decreased liver capture with small Nanopieces compared to lipid vehicles.
Figure 64:
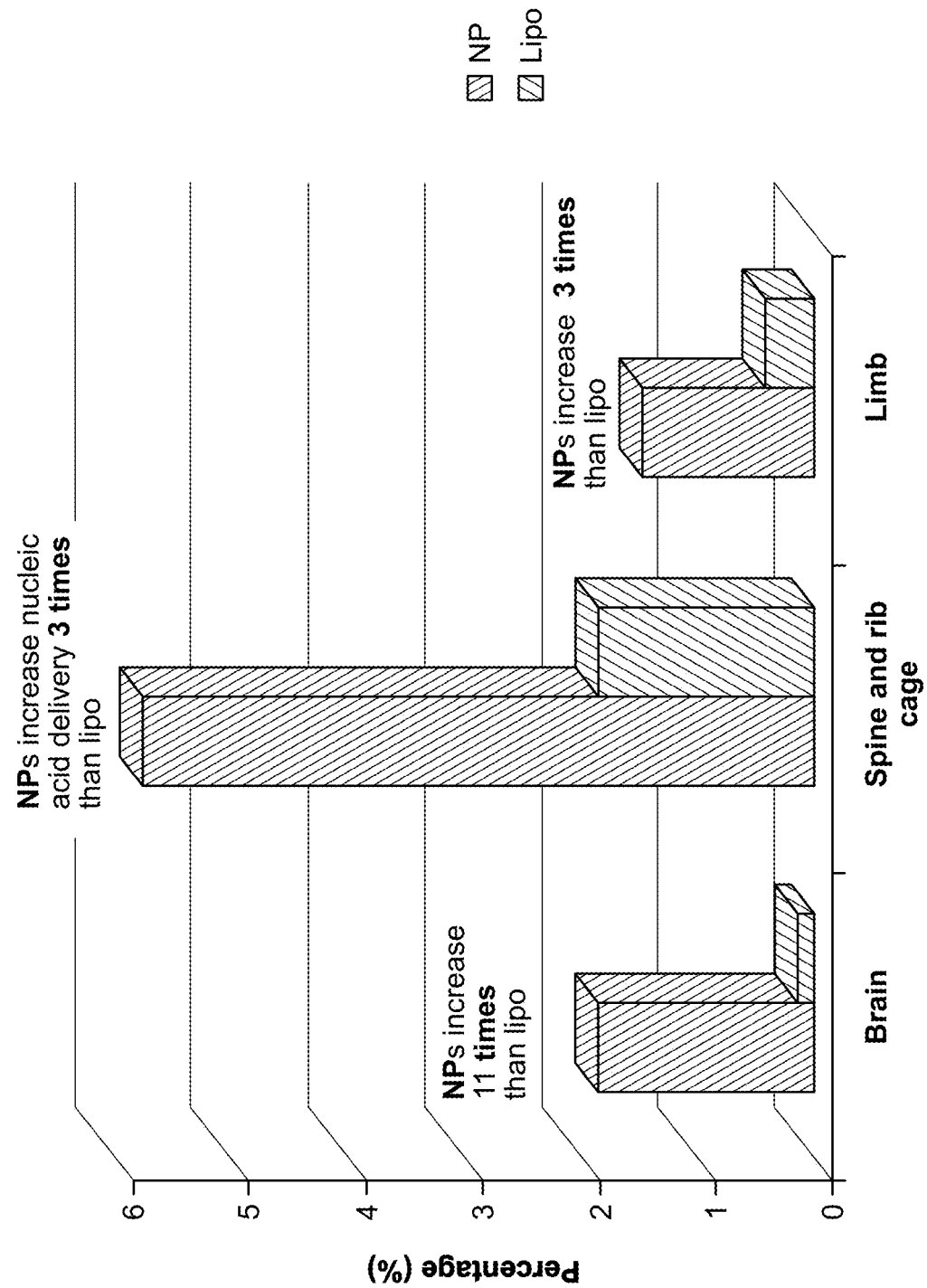
FIG. 64 is a bar graph showing increased delivery into tissues or organs with dense matrix with small Nanopieces.
Figure 65:
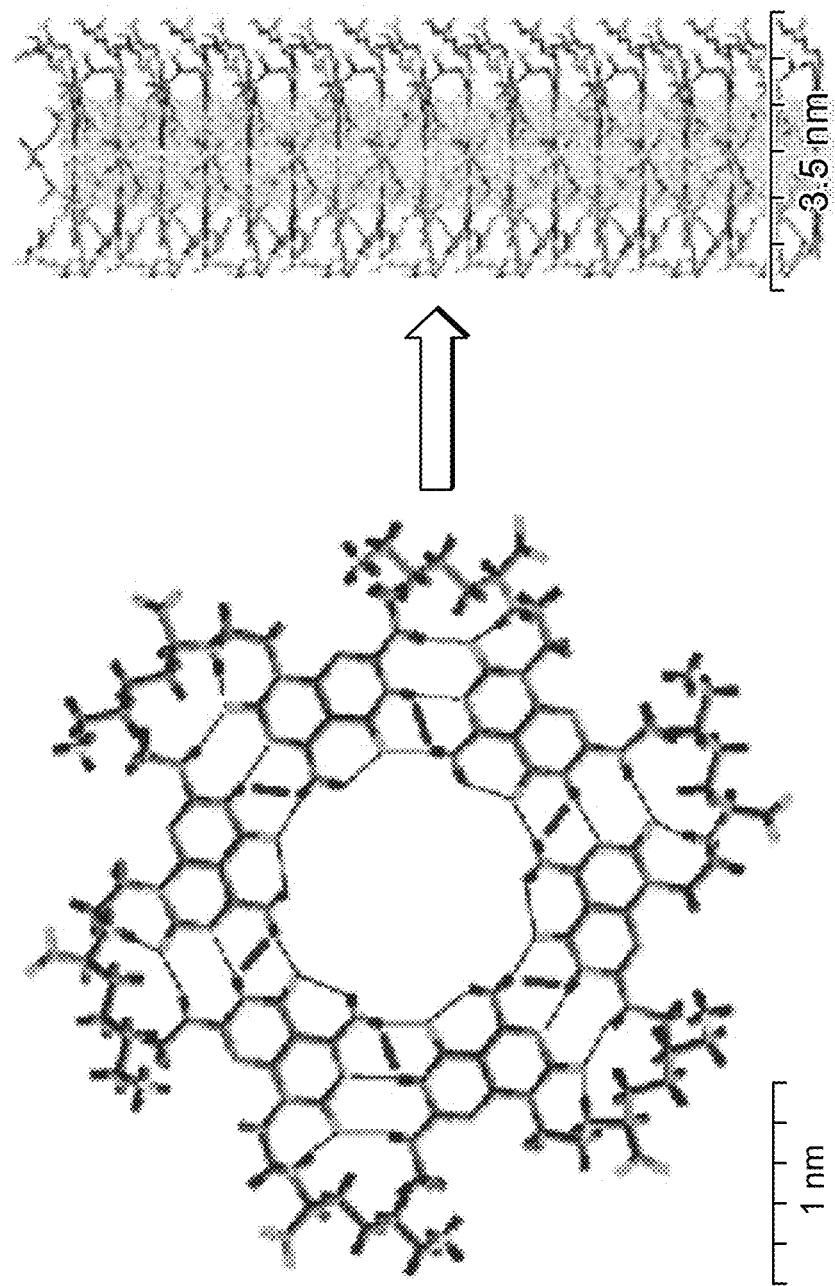
FIG. 65 is an illustration showing a structure of RNT. It is a long tubular structure with outside diameter of 3.5 nm, and inside diameter of 1.1 nm.

Another example was the use of small Nanopieces. Systemic injection of small Nanopieces into mice was carried out. Compared with conventional lipid delivery vehicles, small Nanopieces were found to be able to increase penetration into tissues and organs with dense matrix, which are difficult to infiltrate (such as brain, rib, spine and limb), as well as decreased liver capture (FIG. 62A, FIG. 62B and FIG. 63). FIG. 60A, FIG. 60B, FIG. 61A and FIG. 61B show fluorescence labeled GAPDH molecular beacon delivered with small Nanopieces and also fluorescence labeled GAPDH molecular beacon delivered with large Nanopieces were co-injected into mouse knee joints, and the fluorescence signal was observed under a fluorescence microscope. FIGS. 62A-FIG. 64 shows Far fluorescence labeled GAPDH molecular beacon delivered with Nanopieces or with lipid particles were injected into mice via resto-orbital injection. After 24 hours, the mice were sacrificed and dissected. The fluorescence signal in each organs or tissue was recorded and via a fluorescence molecular tomography.

Example 6

Function

Figure 17:
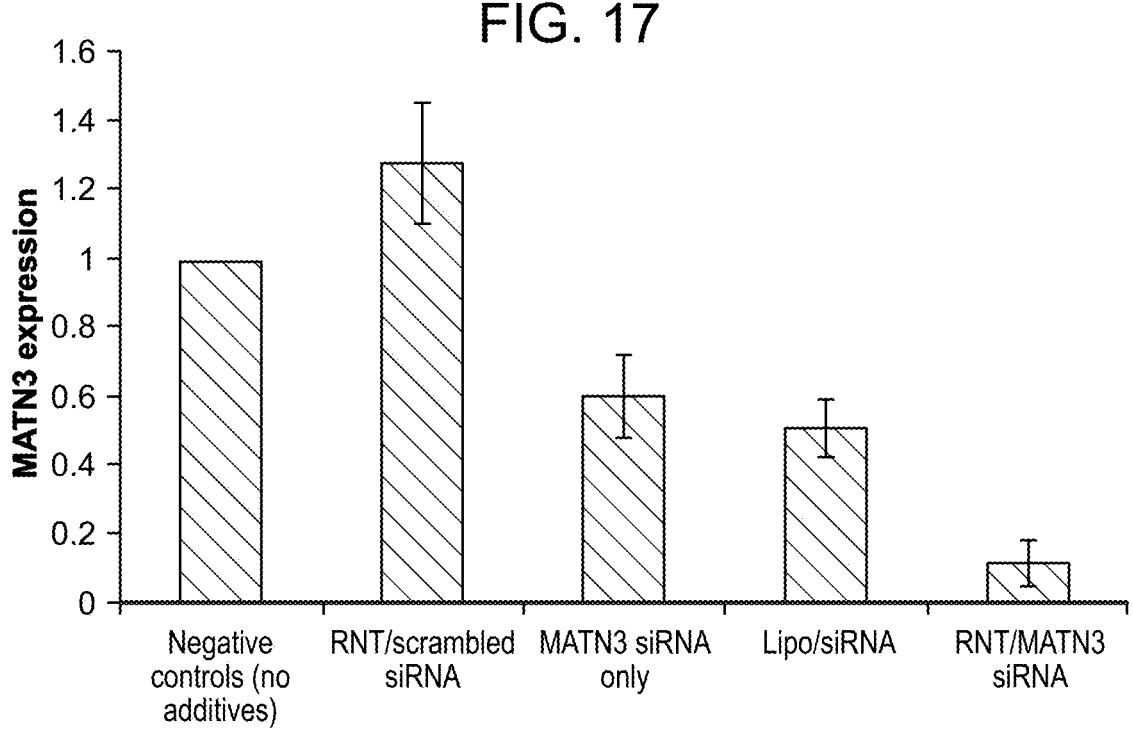
FIG. 17 is a graph showing functional delivery of processed MATN3 siRNA/RNT Nanopieces into mouse cartilage tissue matrix and inside chondrocytes.
Figure 18:
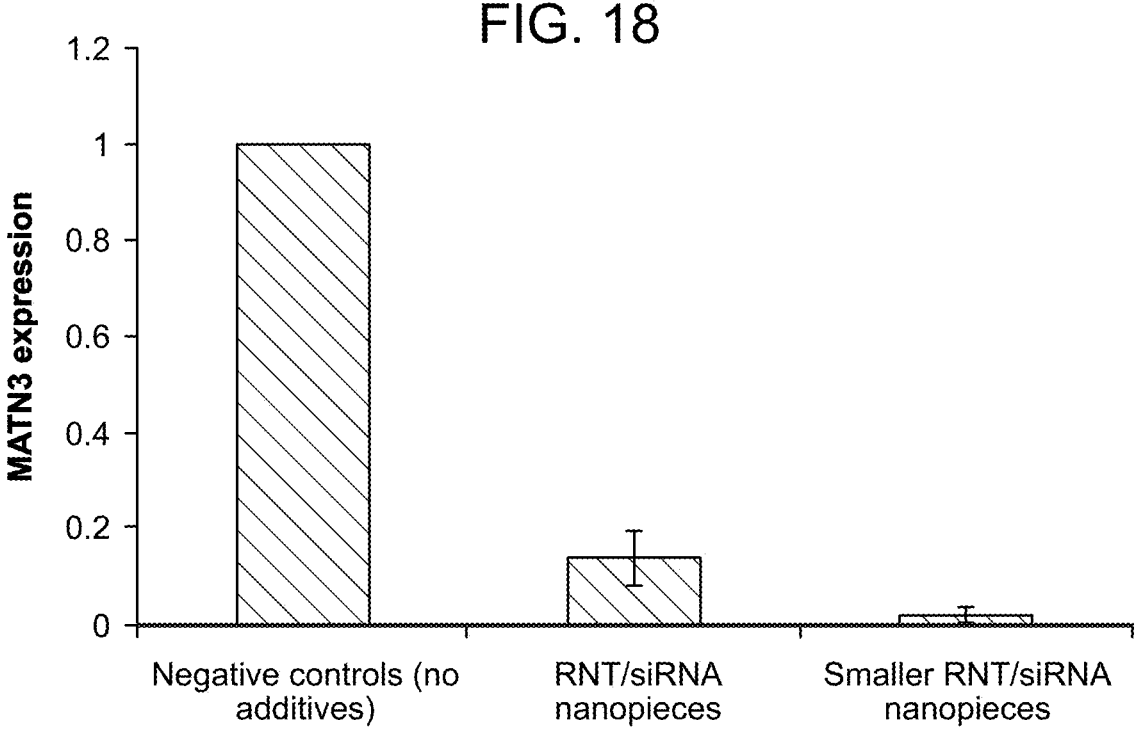
FIG. 18 is a graph showing functional delivery of processed MATN3 siRNA/RNT Nanopieces into mouse cartilage tissue matrix and inside chondrocytes.
Figure 19:
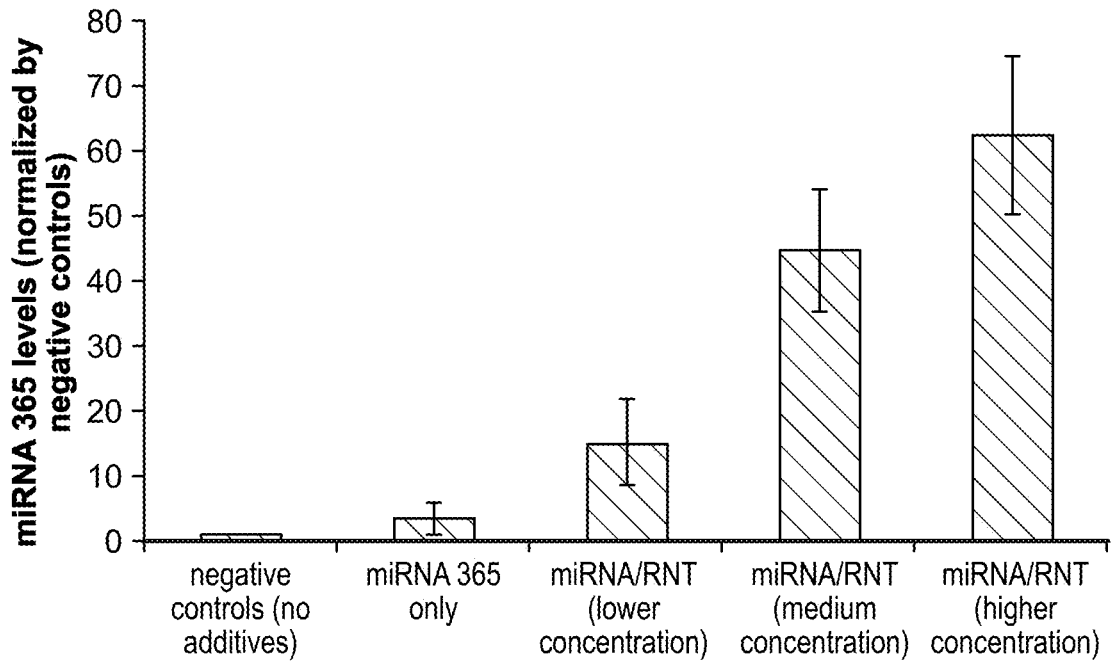
FIG. 19 is a graph showing functional delivery of processed miRNA365/RNT Nanopieces into human cartilage tissue matrix and inside chondrocytes.

Results showed delivery of Matrilin-3 (MATN3) siRNA/RNT Nanopieces into the mouse cartilage tissue matrix and cells with excellent biological function (FIG. 17 and FIG. 18). Moreover, miRNA-365/RNT Nanopieces were functional, when delivered into human cartilage tissue matrix and cells (FIG. 19). The smaller processed Nanopieces resulted in higher Nanopiece delivery efficacy.

Example 6.1

MATN-3 siRNA was delivered with and without Nanopieces or Lipofectamine 2000 and soaked with mouse cartilage. The MATN-3 gene expression was determined via real time RT-PCR (FIG. 17).

Example 6.2

MATN-3 siRNA was delivered with unprocessed or processed Nanopieces and was soaked with mouse cartilage. The MATN-3 gene expression was determined via real time RT-PCR (FIG. 18).

Example 6.3

Various doses of miR-365 (0.1, 0.5 and 1.0 nmol) were delivered with Nanopieces and were soaked with human cartilage. The miR-365 expression was determined via real time RT-PCR (FIG. 19).

Example 7

Compositions

FIG. 20 shows that a composite of PEG increases Nanopiece delivery efficiency in a protein-rich environment (such as serum).

Example 8

In Vivo Delivery

Figure 21:
FIG. 21 is an image showing injection of reagents into mouse knee joints.
Figure 22A:
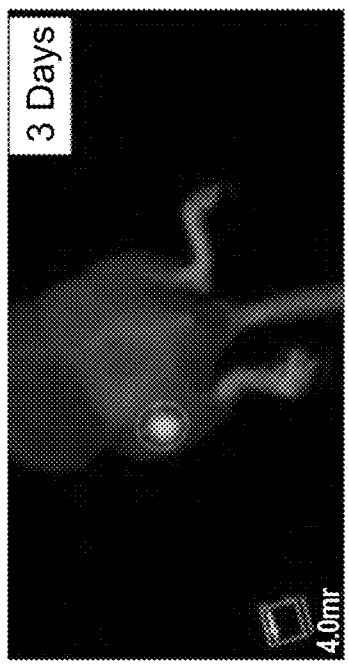
FIGS. 22A-22F are a series of images showing fluorescent signals in mouse cartilage tissue matrix over time by injecting processed RNT/beacon Nanopieces.
Figure 22B:
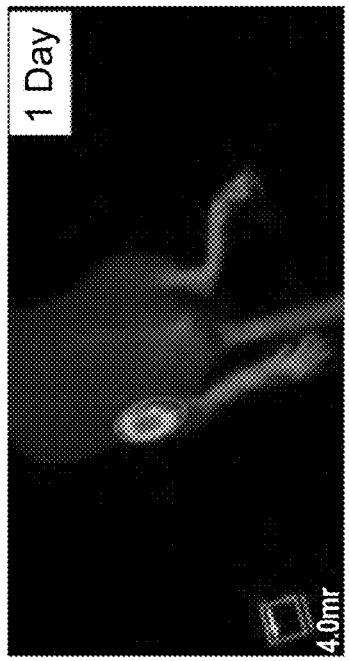
Figure 22C:
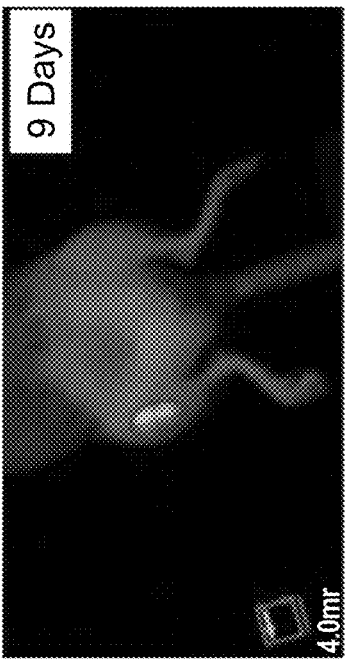
Figure 22D:
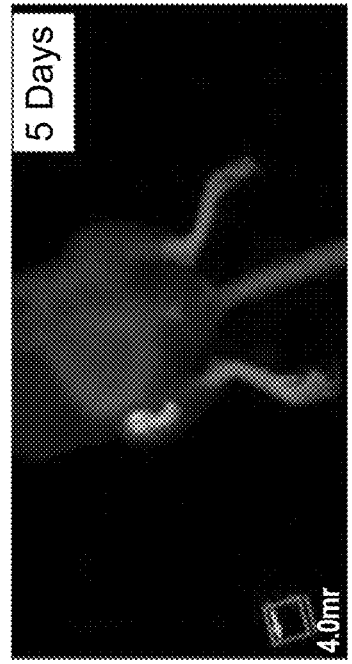
Figure 22E:
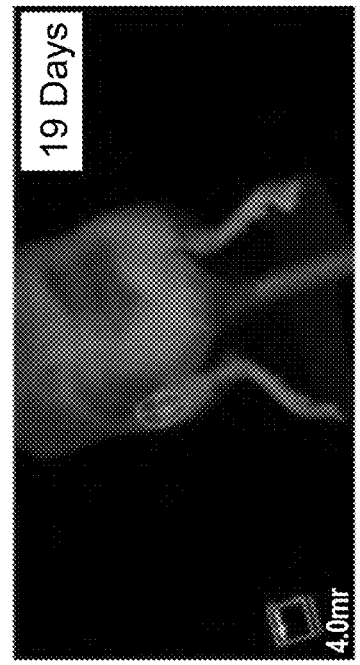
Figure 22F:
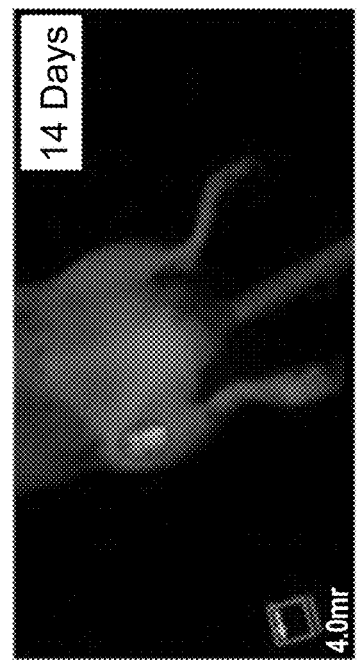
Figure 23B:
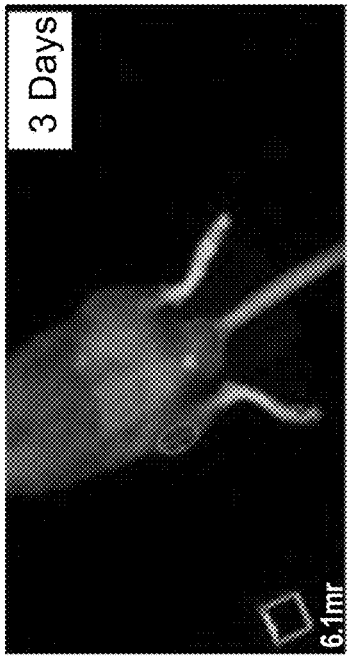
FIGS. 23A-23F are a series of images showing fluorescent signals in mouse cartilage tissue matrix over time by injecting molecular beacon only.
Figure 23D:
Figure 23F:
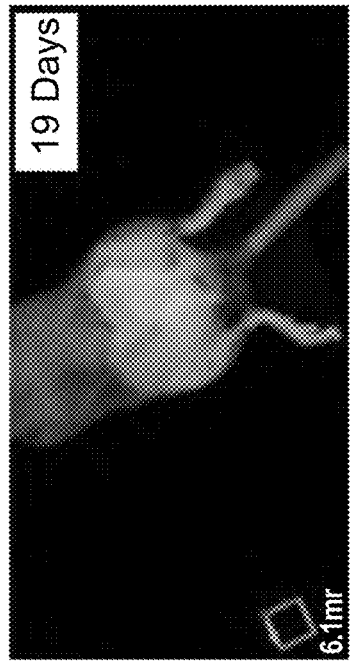
Figure 23A:
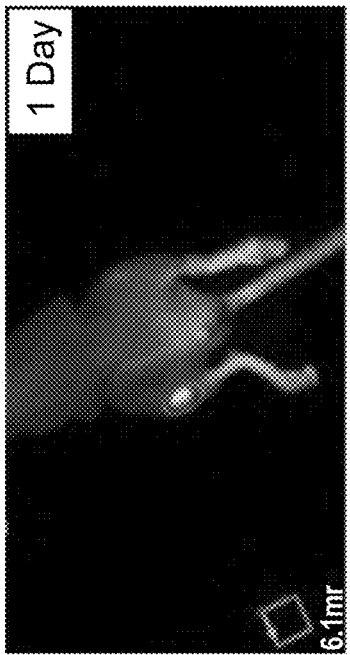
Figure 23C:
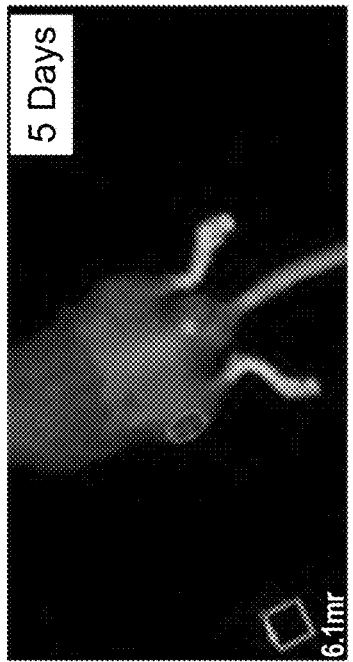
Figure 23E:
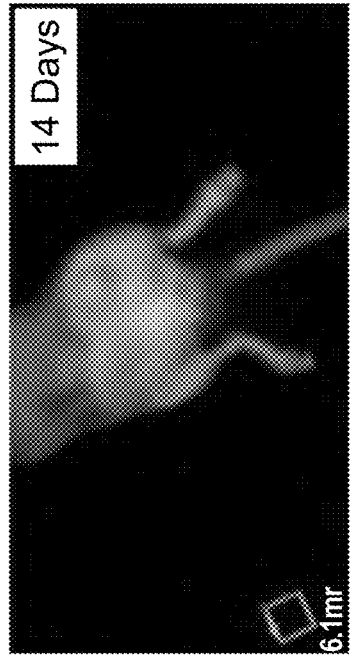
Figure 24:
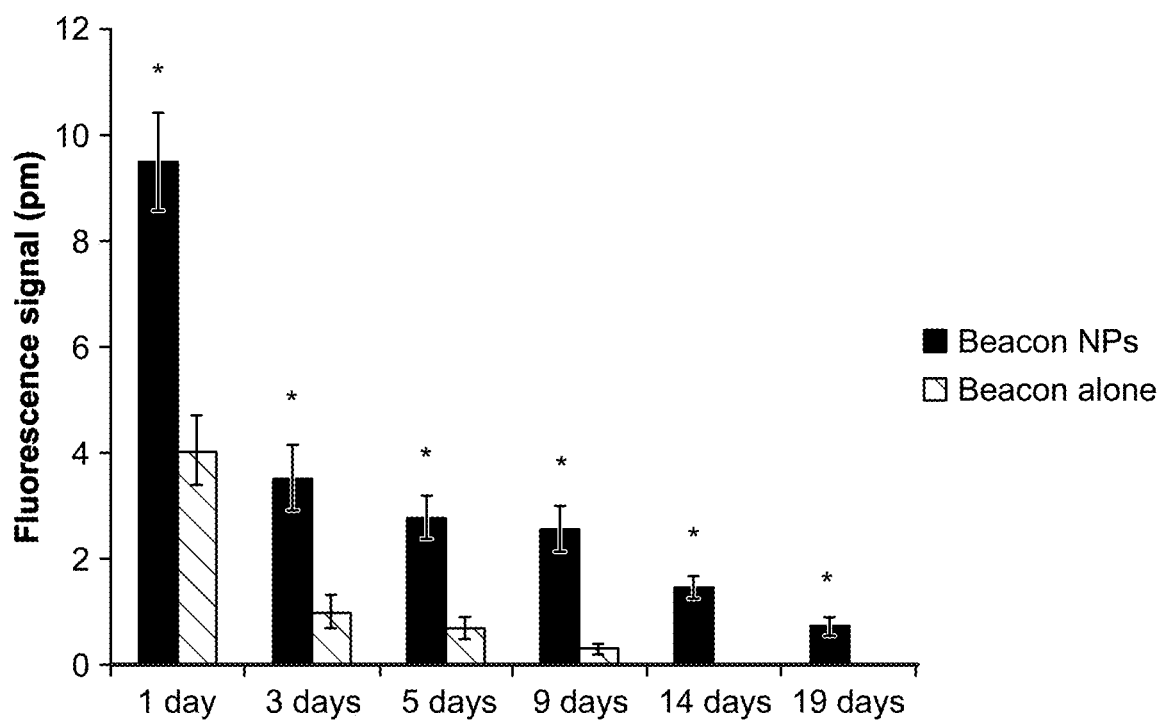
FIG. 24 is a graph showing quantitative fluorescent signals in mouse cartilage tissue matrix over time.
Figure 25B:
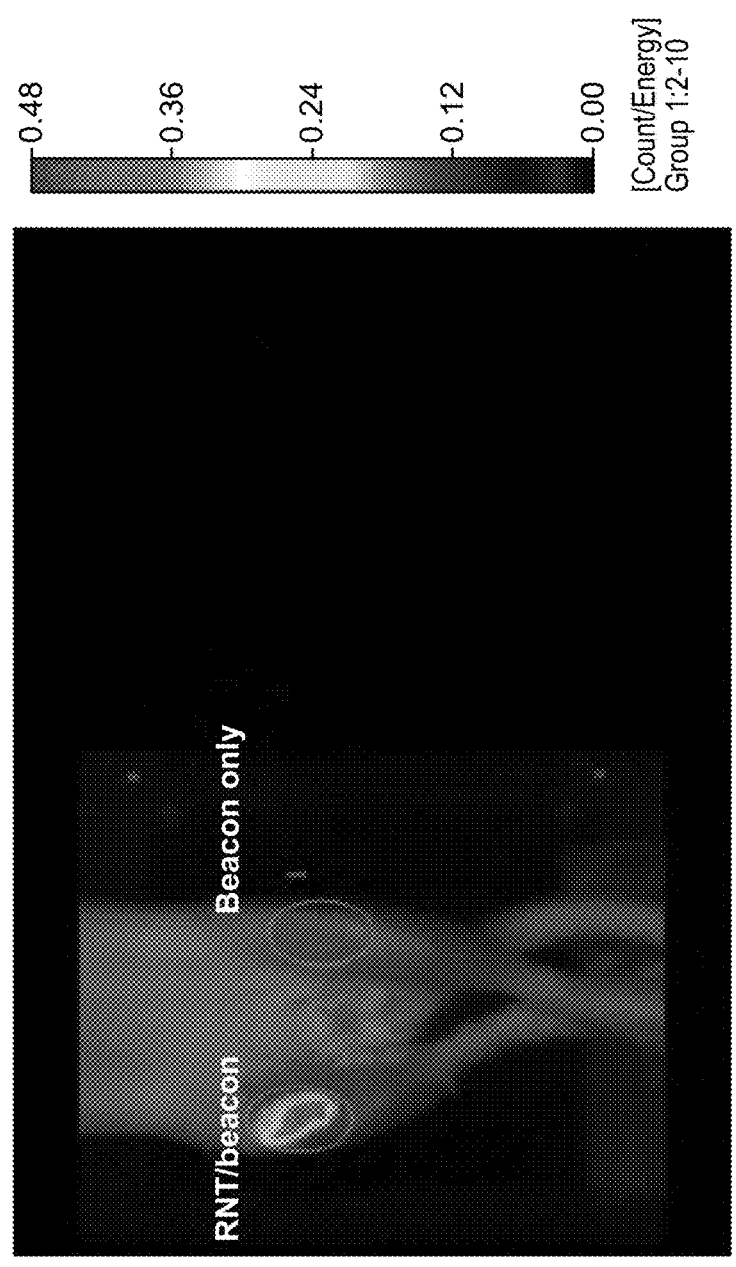
FIG. 25A is a graph and FIG. 25B is an image showing in vivo delivery of processed RNT/beacon Nanopieces into rat cartilage tissue matrix and inside chondrocytes compared with beacon only.
Figure 25A:
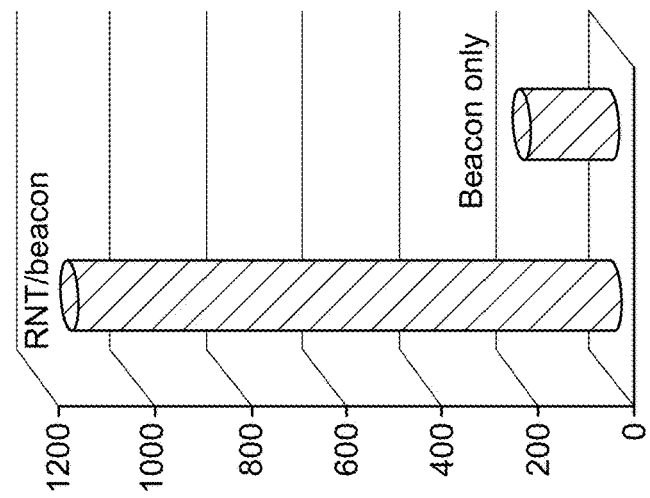
Figure 26B:
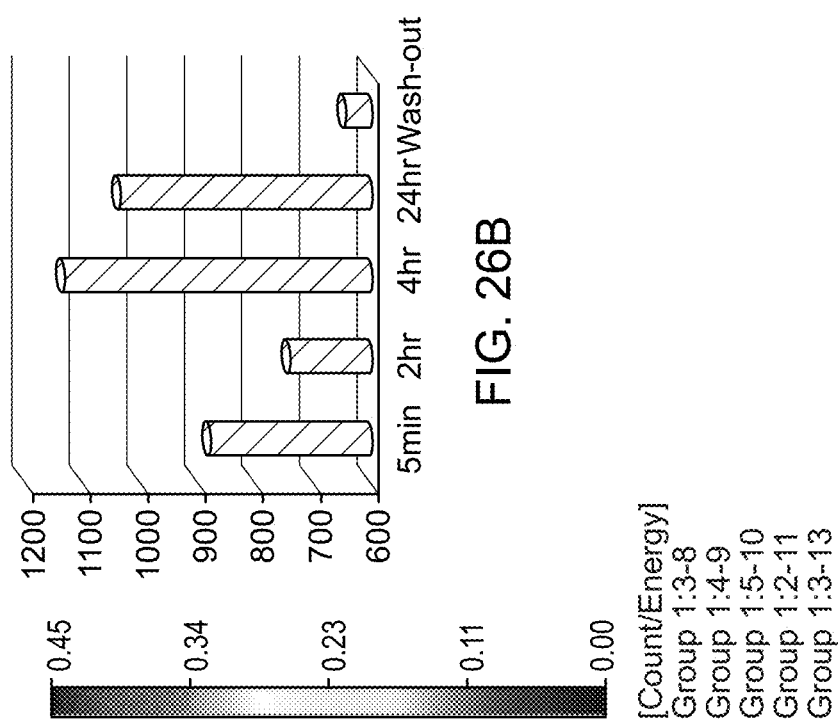
FIG. 26A is a series of images and 26B is a bar graph showing qualitative (Left) and quantitative (Right) in vivo delivery of processed RNT/beacon Nanopieces into rat cartilage tissue matrix and inside chondrocytes compared with beacon only.
Figure 26A:
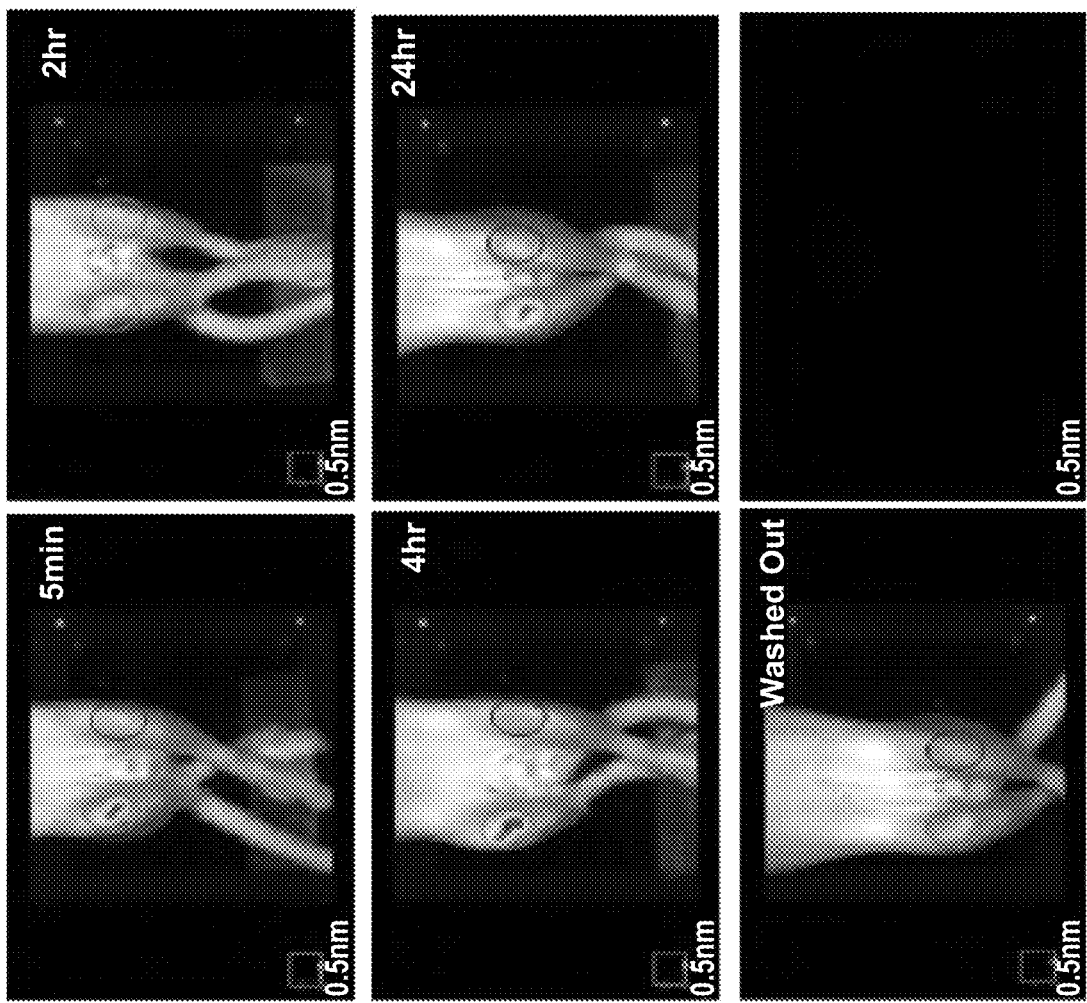
Figure 27:
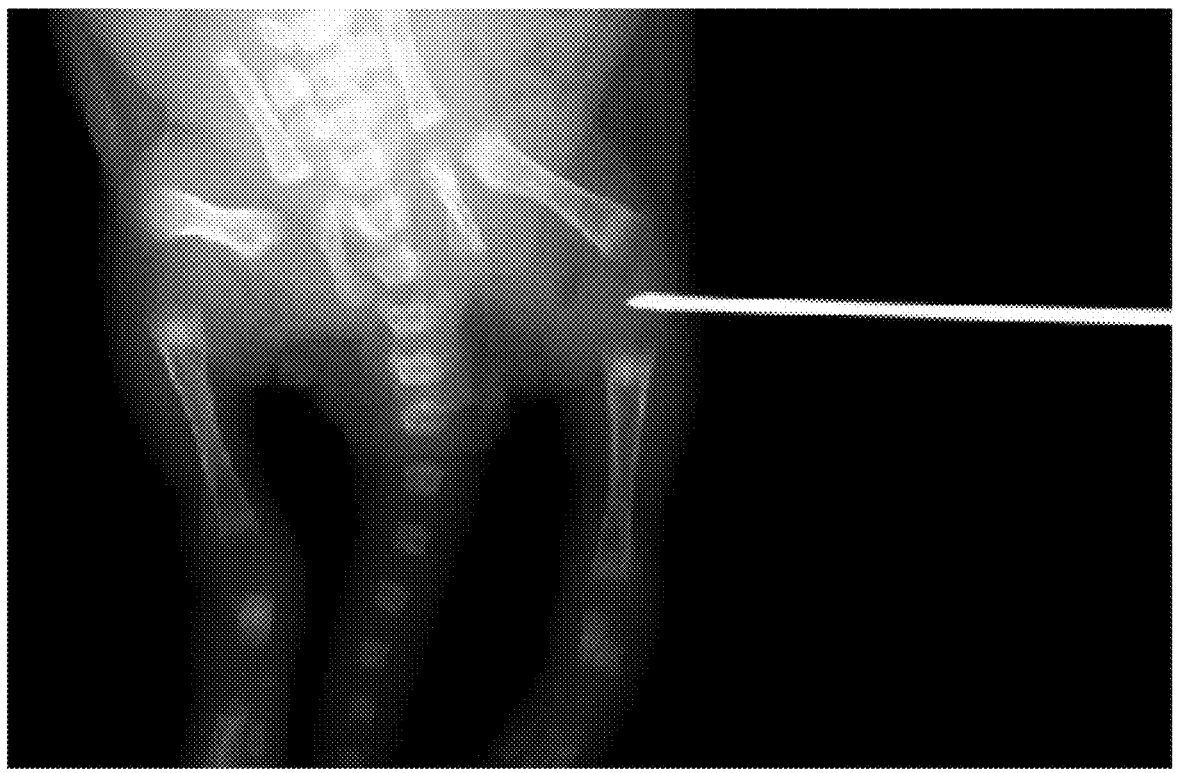
FIG. 27 is an image showing injection of reagents into baby mouse joints.

FIG. 21 and FIG. 27 show injection of Nanopieces into an articulating joint. Injection of GAPDH molecular beacon/ RNT Nanopieces into knee joints of a mouse (FIG. 21) resulted in a significant fluorescence signal compared with beacon only (in the absence of RNT Nanopieces). The signal lasted more than 2 weeks in the knees (FIGS. 22A-22F, FIGS. 23A-23F, and FIG. 24). In rats, a significant fluorescence signal was also obtained by injecting GAPDH molecular beacon/RNT Nanopieces into knee joints. The fluorescence signal was robust after washing out the adhered fluorescence molecules on the articular surface (FIGS. 25A-25B and FIGS. 26A-26B). Matrilin-3 siRNA Nanopieces were injected into knees of baby one-week-old mice and was found to be functional. Histology slides of cartilage sections confirmed the successful delivery of the Nanopieces (FIGS. 28A-28C; light grey areas around the cell nuclei illustrate the fluorescence signal from molecular beacons. Effective in vivo trans-matrix/tissue delivery of processed Nanopieces (Nanopieces) was demonstrated in these experiments.

Example 8.1

Fluorescence labeled GAPDH molecular beacon was delivered with and without Nanopieces and injected into mouse knee joints. The fluorescence signal was recorded via fluorescence molecular tomography (FIGS. 22A-22F, FIGS. 23A-23F, and FIG. 24).

Example 8.2

Fluorescence labeled GAPDH molecular beacon was delivered with and without Nanopieces and injected into rat knee joints. The fluorescence signal was recorded via fluorescence molecular tomography (FIGS. 25A-25B and FIG. 26A-26B).

Example 8.3

Figures 28A, 28B, 28C:
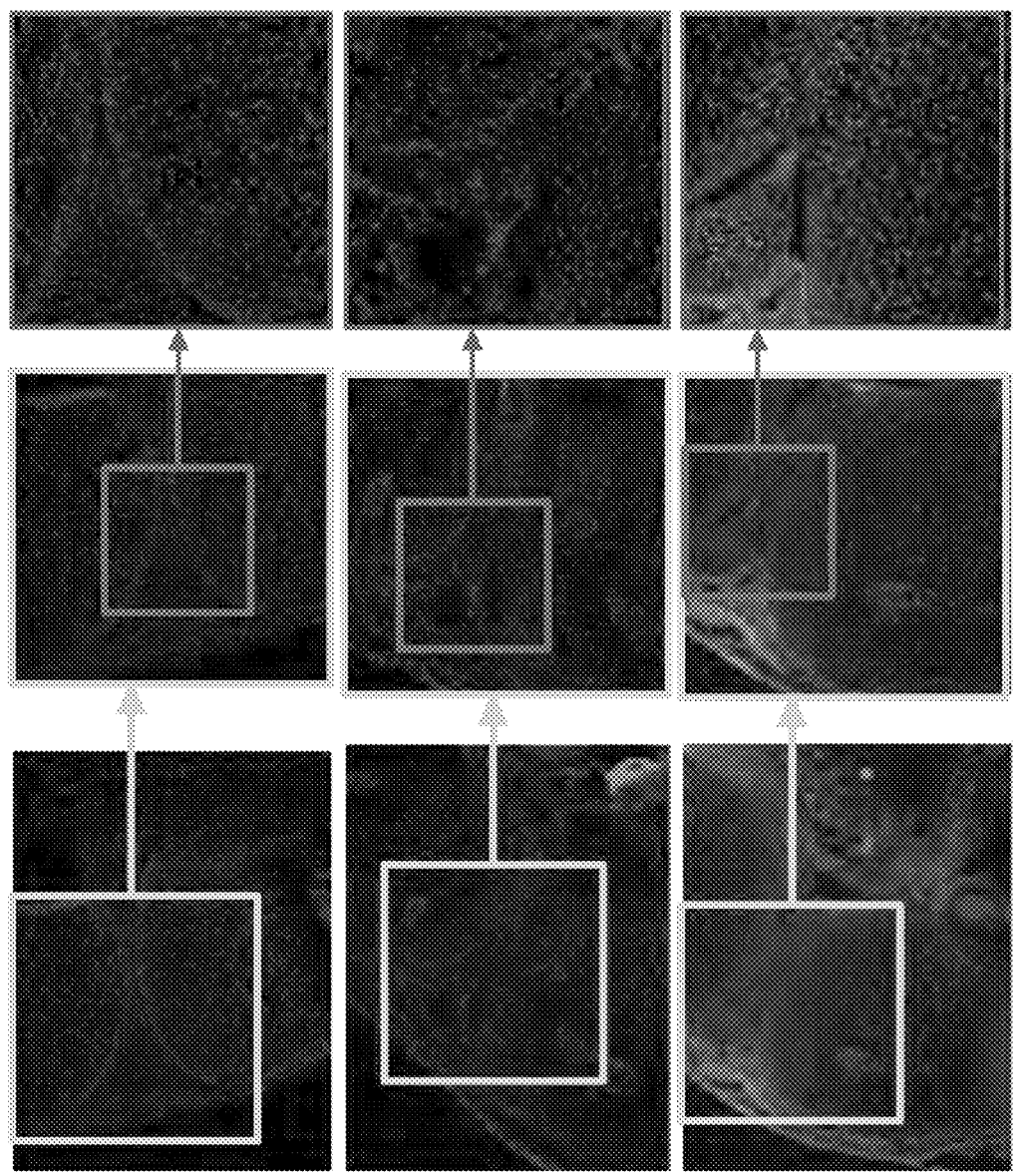
FIGS. 28A-28C are a series of images showing histology sections of cartilage delivered with RNTs only (Top), beacon only (Middle) and RNT/beacon Nanopieces (Bottom).

Fluorescence labeled GAPDH molecular beacon was delivered with and without Nanopieces and injected into baby mouse knee joints. The mouse was sacrificed and knee joint was sectioned for observation under a fluorescence microscope (FIG. 27 and FIGS. 28A-28C; light grey areas around the nuclei in FIGS. 28A-28C illustrate the fluorescence signal from molecular beacons.

Example 9

Diagnostics

Figure 29A:
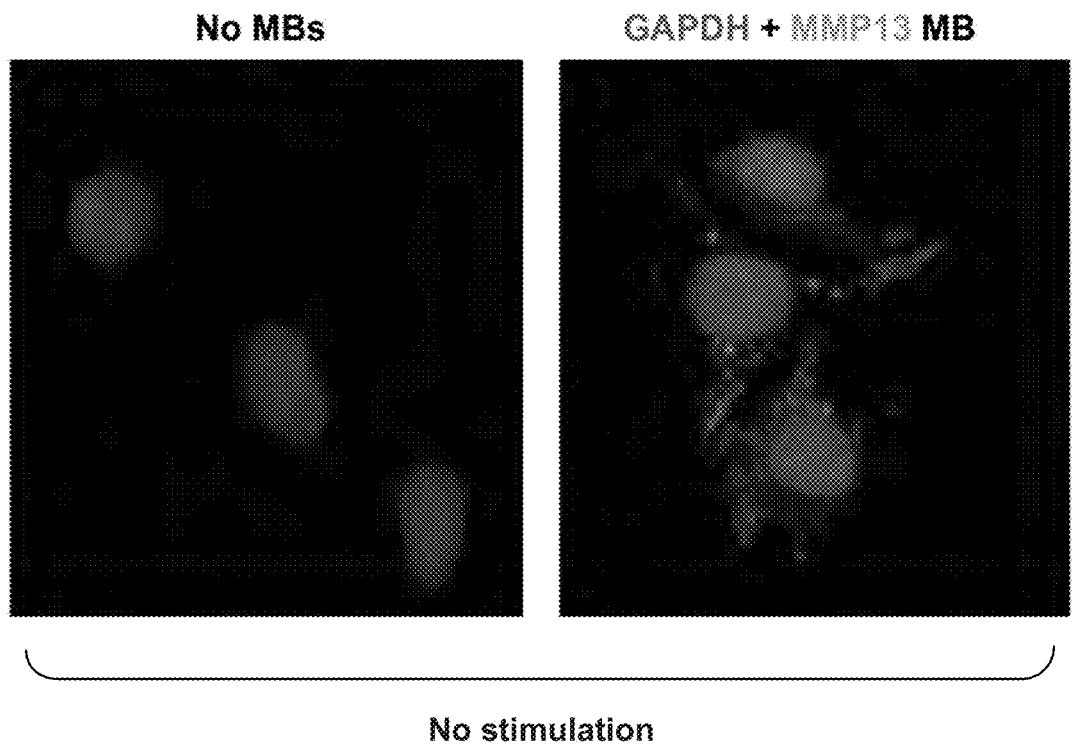
FIG. 29A and FIG. 29B are a series of images showing in vitro validation of MMP-13 molecular beacon.
Figure 29B:
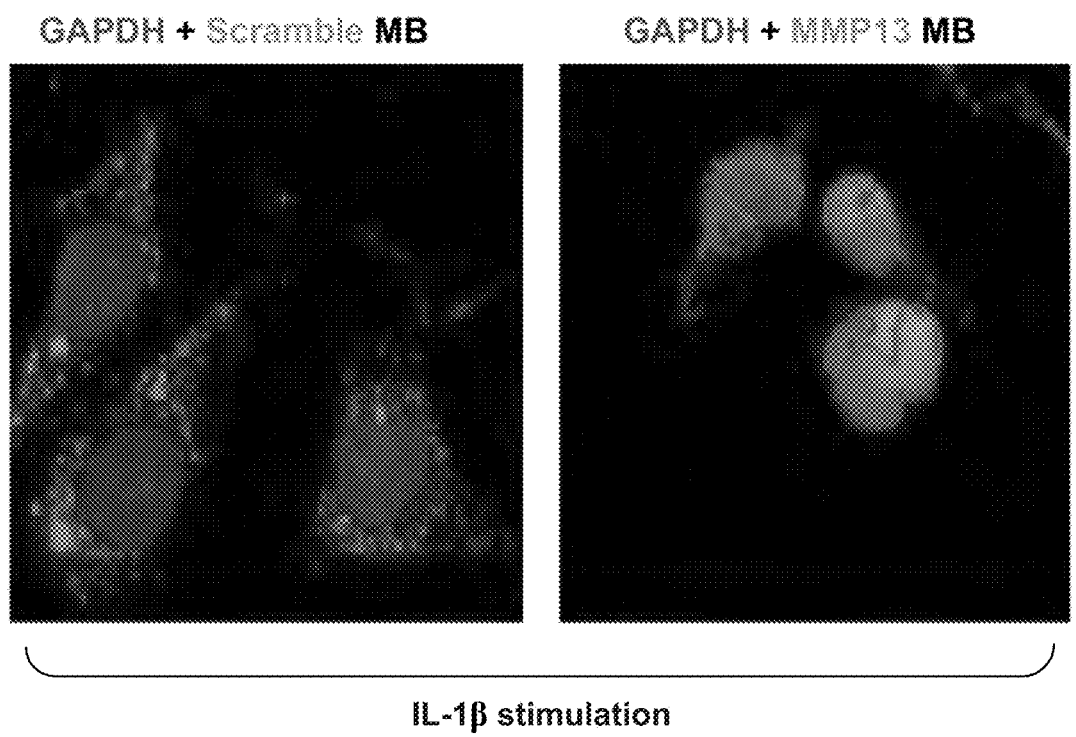

To detect OA progression, MMP-13 was selected as a target gene. MMP-13 molecular beacon was designed and its function validated in vitro. As shown in FIG. 29A and FIG. 29B, MMP-13 molecular beacon was delivered by methods described herein and found to emit fluorescence in chondrocytes after stimulation. Light areas shown in in FIG. 29A and FIG. 29B illustrate the fluorescence signal from molecular beacons. The MMP-13 molecular beacon was prepared according to the following procedure:

Step one: Pre-heat RNT nanotubes solution, then quench it by placing tube on ice.
Step two: Sonicate RNT nanotubes solution.
Step three: Dilute MMP-13 molecular beacon or IL-1beta receptor siRNA in water, then mix with RNT nanotubes solution in a certain ratio (50 pmol siRNA or 100 pmol molecular beacon to 5 ug RNT), then vertex well.
Step four: Sonicate the mixture described in Step three, then spin all liquid down. MMP-13 molecular beacon or IL-1beta receptor Nanopieces was assembled after Step four.

*Standard preparation only includes Step three and Step four. Joint preparation includes all steps.

Figure 30:
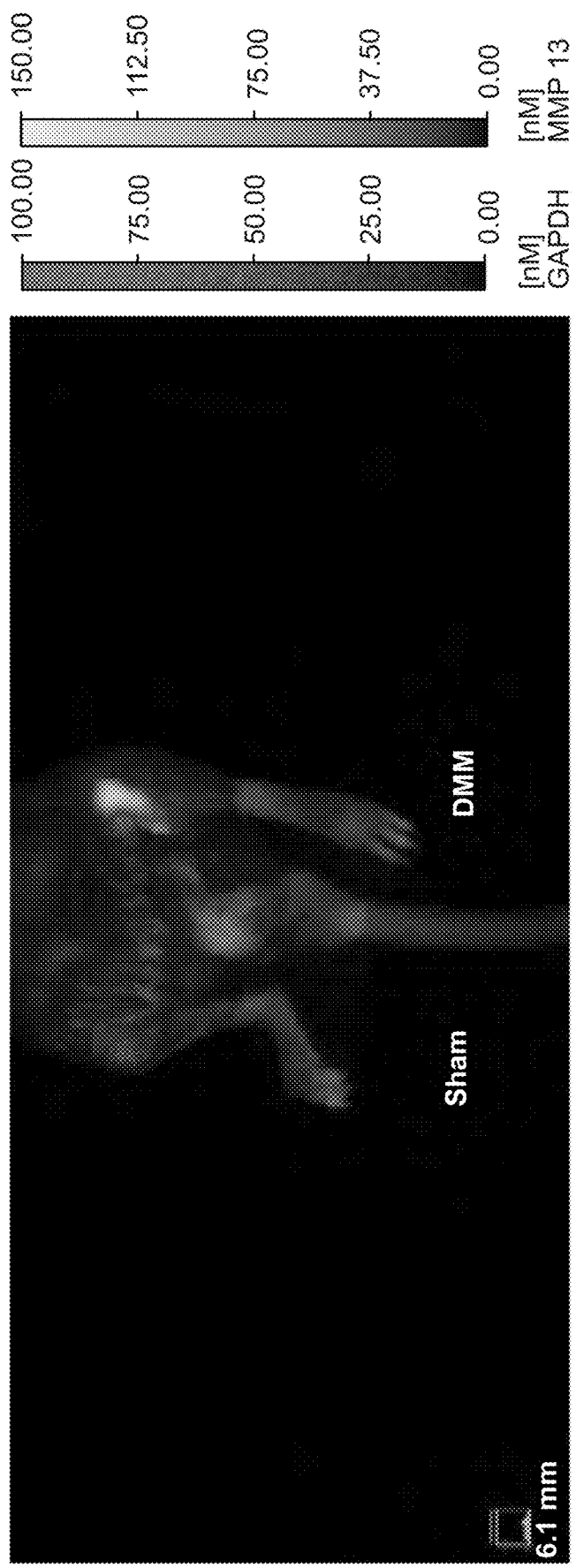
FIG. 30 is an image showing comparison of fluorescence signal between DMM and Sham knees (dark grey is GAPDH; light grey is MMP-13).
Figure 31:
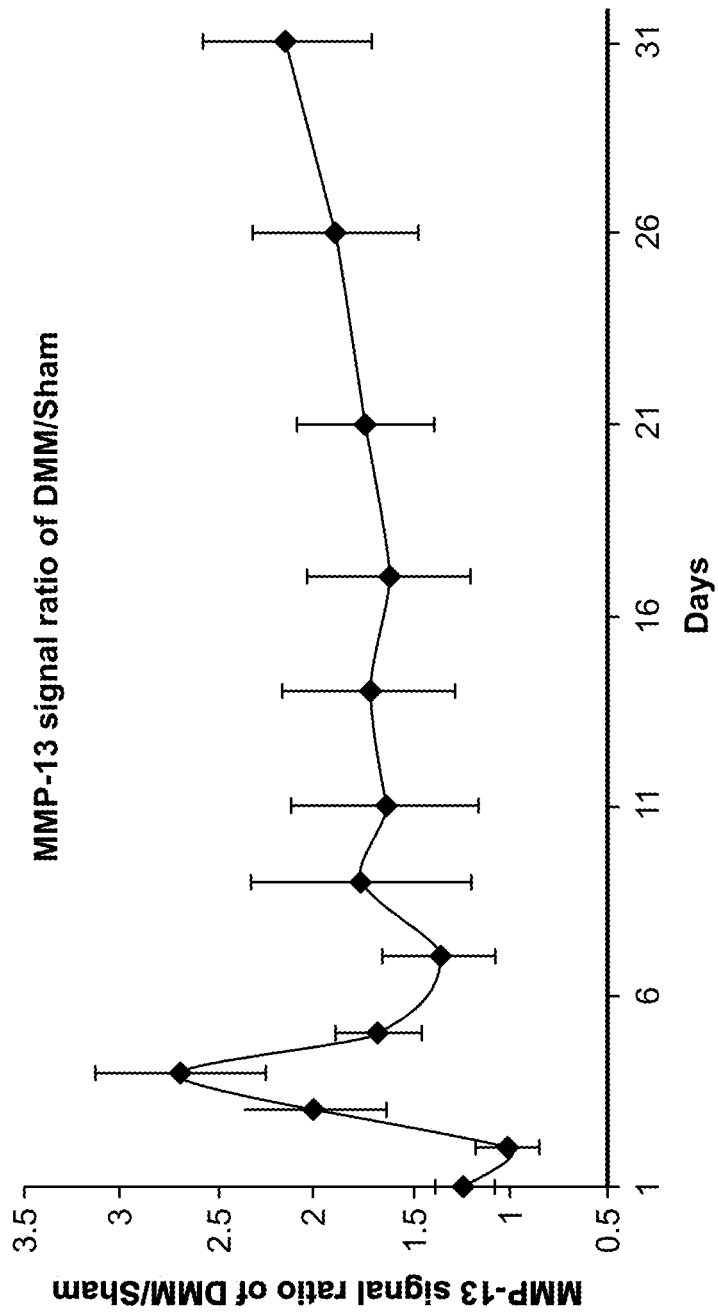
FIG. 31 is a graph showing DMM/Sham MMP-13 signal over time.
Figure 32:
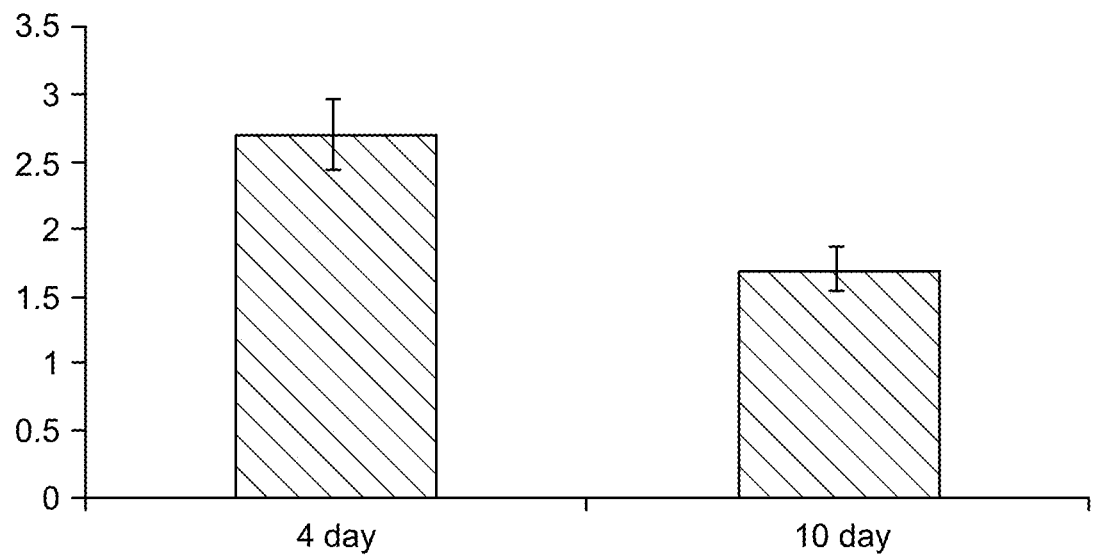
FIG. 32 is a graph showing DMM knee relative MMP-13 expression level.
Figure 33A:
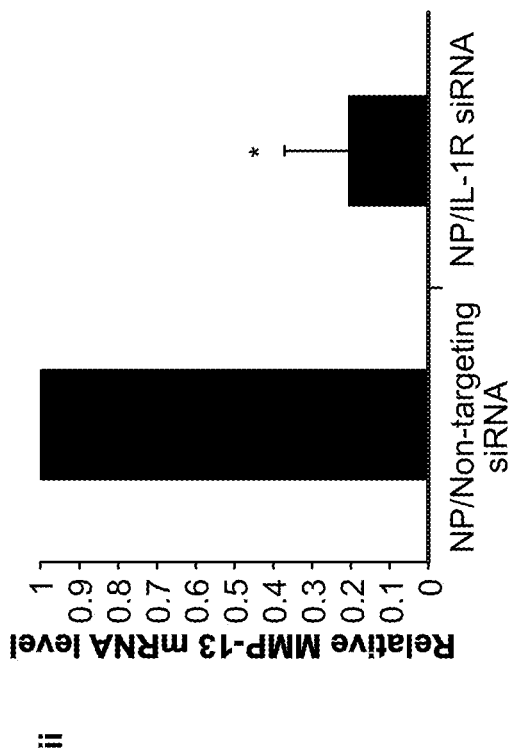
FIGS. 33A-33D area series of graphs showing relative IL-1R, MMP-13, MMP-9 and Col II gene expression level after therapeutically knock down of IL-1R.
Figure 33B:
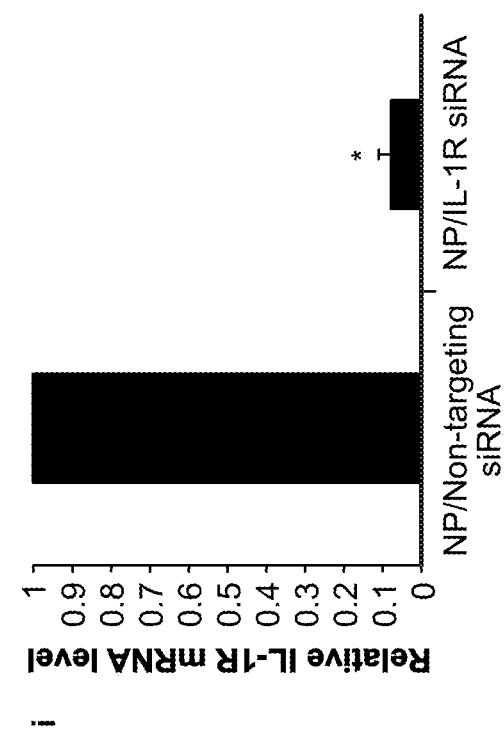
Figure 33C:
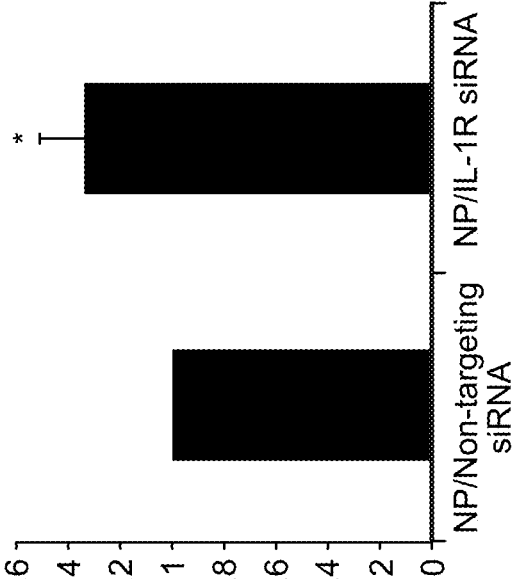
Figure 33D:
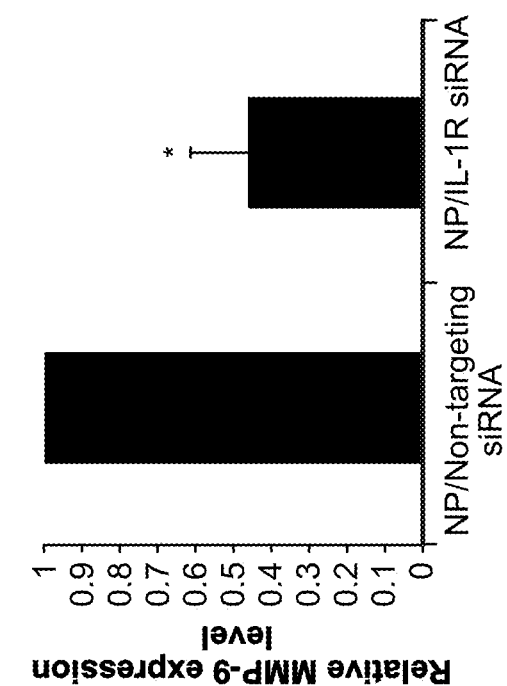

For in vivo diagnosis, the medial meniscus (DMM) was destabilized to induce OA on one knee of the mice, whereas on the other knee a sham surgery was performed. Right after surgery, MMP-13 molecular beacon was delivered for target gene detection together with a non-targeting scrambled molecular beacon as a non-specific signal serving as a negative control. In addition a GAPDH molecular beacon for an internal house-keeping gene control was also administered. After 4 days, the knee with OA induction, showed a significantly stronger signal than the sham knee (FIG. 30). Moreover, using such a real-time, in-situ, non-invasive diagnosis approach, the signals between DMM and sham were quantitatively compared in a time-depend curve (FIG. 31). Methods were provided to continuously monitor a specific gene expression during OA progression in living animals. Moreover, animals were sacrificed at day 4 and day 11 to determine their MMP-13 expression level via real time RT-PCR. Results showed that the non-invasive diagnostic technology described herein accurately detected gene expression level compared with PCR (FIG. 32).

Fluorescence and histology analysis showed that the damaged articular cartilage surface was the area emitting fluorescence signal from MMP-13 molecular beacon (FIGS. 37A-37B and FIG. 38). In FIG. 37A and FIG. 37B, ARROWs indicate the fluorescence signal as a result from MMP-13 molecular beacon. In FIG. 38, the dark grey color in articular cartilage was aggrecan staining DMM surgery resulted in loss of aggrecan staining and damage to articular cartilage.

Figure 42:
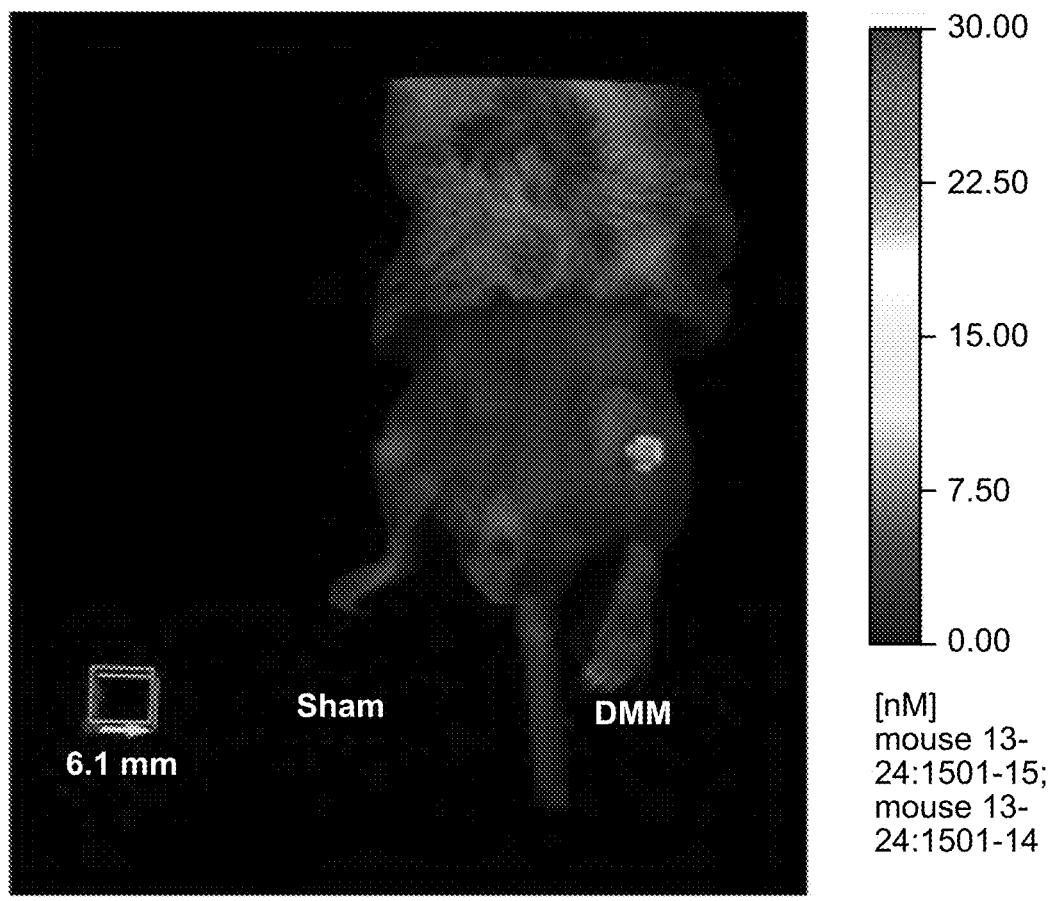
FIG. 42 is an image of fluorescence signal of ADAMTS-5 molecular beacon in DMM and Sham knees on day 6 after surgery.
Figure 43:
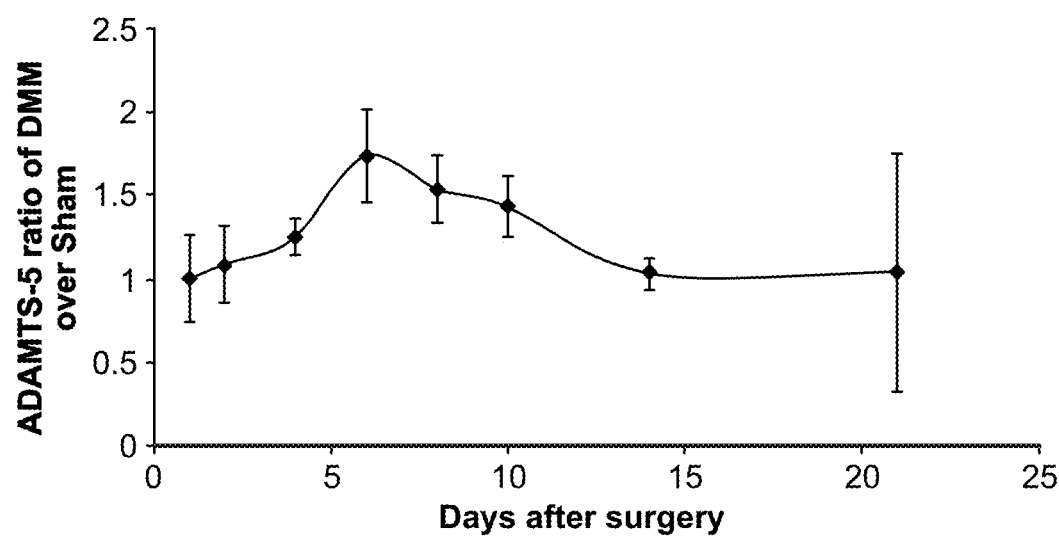
FIG. 43 is a graph showing fluorescence signal ratio of ADAMTS-5 molecular beacon in DMM knees over Sham knees after surgery.
Figure 45B:
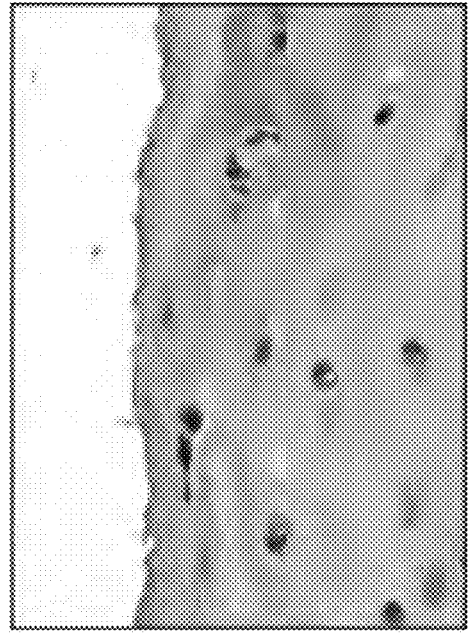
FIGS. 45A-45D are a series of images showing histology results (staining is proteoglycan) of human articular cartilage. ADAMTS-4 siRNA and combination of ADAMTS-4&5 siRNA/Nanopieces greatly inhibited cartilage degradation with cytokine stimulation.
Figure 45D:
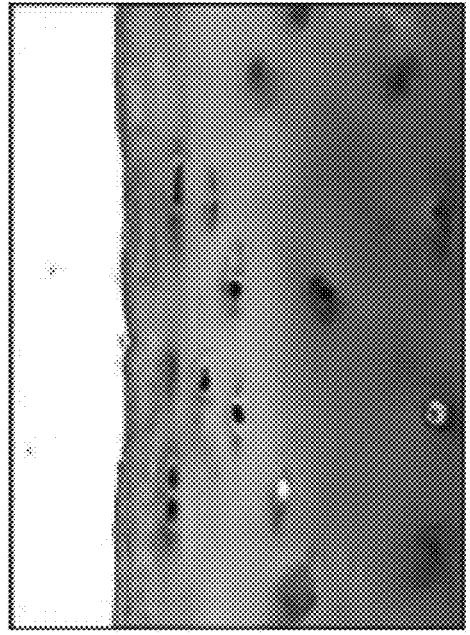
Figure 45A:
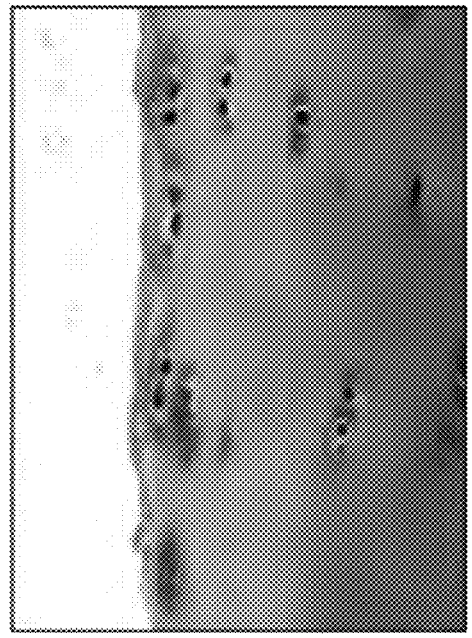
Figure 45C:
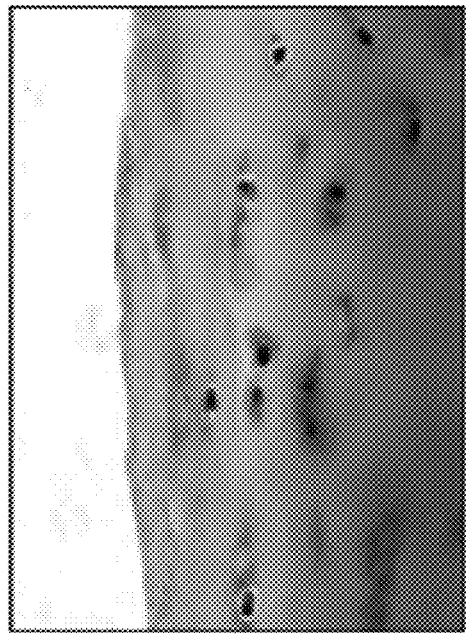

In addition to MMP-13, ADAMTS-5 molecular beacon for OA diagnosis was also shown. Again, the ability of this molecular beacon to detect ADAMTS-5 gene expression in vitro was demonstrated (FIGS. 39A-39C, FIGS. 40A-40C and FIGS. 41A-41C; light grey areas around the cell nuclei in FIGS. 39A-39C, FIGS. 40A-40C and FIGS. 41A-41C are the fluorescence signal from molecular beacons. RED channel showed signal from GAPDH beacons; while GREEN channel showed signal from ADAMTS-5 or Scrambled beacons. The up-regulation pattern of ADAMTS-5 during OA development was also shown (FIG. 42 and FIG. 43).

These data indicate that the methods are useful for accurate and specific gene expression detection, thereby permitting reliable diagnosis in a real-time, in-situ and in a non-invasive manner in living animals.

Example 9.1

Fluorescence labeled GAPDH molecular beacon and fluorescence labeled MMP-13 molecular beacon or fluorescence labeled scrambled molecular beacon delivered with Nanopieces was added into chondrocytes under standard cell culture conditions or stimulated with 10 ng/mL IL-1β (FIG. 29A and FIG. 29B).

Using an established method (Tyagi et al *Nat. Biotech*, 1998, 16:49-53), MBs were designed to target mouse MMP-13 or GAPDH mRNA with a fluorophore/quench pair. Scramble sequence MB (Scramble) was verified to not bind with any mouse mRNA via BLAST. In vitro delivery and validation: MBs were delivered into chondrocytes by Nanopieces. Specifically, after stimulation with IL-1β for 24 hours, chondrocytes were co-transfected GAPDH and scramble MBs or GAPDH and MMP-13 MBs via Nanopieces. Real time RT-PCR and fluorescence microscopy were used to verify the stimulation of MMP-13 expression and the successful fluorescence signal resulted from MMP-13 MB.

To test the efficacy of mRNA detection in chondrocytes using MBs delivered by Nanopieces, primary mouse chondrocytes were transfected with MBs either with or without IL-1β treatment. Before IL-1β treatment, the housekeeping GAPDH MB was detected while the MMP-13 MB was not (FIG. 29A and FIG. 29B, left panels). In contrast, after IL-1β treatment, both GAPDH MB and MMP-13 MB were detected, indicating the induction of MMP-13 mRNA levels by IL-1β (FIG. 29A and FIG. 29B, right panels). Realtime rtPCR showed that MMP-13 mRNA level was up-regulated by about 10 times upon IL-1β stimulation. In contrast, Scramble MB transfection did not show any fluorescence, indicating that the fluorescence of MMP-13 MB was not due to non-specific degradation.

Example 9.2

Figure 55:
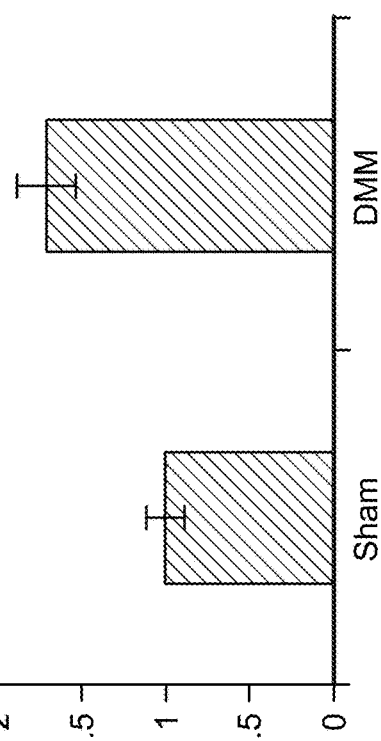
FIG. 55 is a graph showing MMP-expression increase 11 days after surgery.
Figure 54:
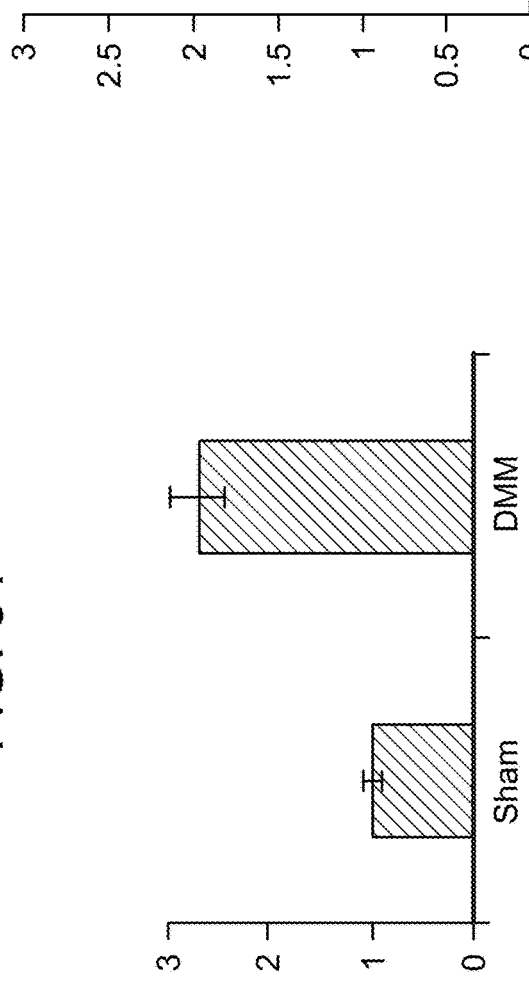
FIG. 54 is a graph showing MMP expression increase 4 days after surgery.

Fluorescence labeled GAPDH, MMP-13 and Scrambled molecular beacon delivered with Nanopieces was injected into mouse knee joints after destabilization of medial meniscus (DMM) surgery or Sham surgery, and then the fluorescence signal was recorded and analyzed via a fluorescence molecular tomography (FIG. 30 and FIG. 31). DMM or sham surgeries were performed on 10-week-old 129S VE male mice to induce osteoarthritis. One week after surgery, MMP-13 and scramble MBs with different fluorophores delivered by Nanopieces were injected into knee joints of mice. Small animal fluorescence molecular tomography (FMT) was used to determine the fluorescence signal that resulted from MMP-13 expression in the live animals for 3 weeks. The Scramble MB showed low fluorescence in both DMM and Sham surgery knee joints. After subtracting Scramble MB basal level signals, MMP-13 MB real signal was about 40 times stronger in the DMM leg than the sham leg (FIG. 50, FIG. 54, and FIG. 55). Such MMP-13 MB signals persisted, even for 3 weeks after injection of MBs.

Example 9.3

Mouse knee joint cartilage was isolated 4 days or 10 days after DMM or Sham surgery, and MMP-13 expression was determined via real time RT-PCR (FIG. 32).

Example 9.4

Fluorescence labeled MMP-13 molecular beacon and Scrambled molecular beacon delivered with Nanopieces was injected into mouse knee joints after DMM or Sham surgery. After 30 days, the animals were sacrificed and their knee joints were sectioned for histology and fluorescence scan (FIGS. 37A-37B and FIG. 38).

Example 9.5

Fluorescence labeled GAPDH molecular beacon, fluorescence labeled ADAMTS-5 molecular beacon or fluorescence labeled Scrambled molecular beacon delivered with Nanopieces was added into chondrocytes under standard cell culture conditions or stimulated with 10 ng/mL IL-1α and 1004 retinoic acid (FIGS. 39A-39C, FIGS. 40A-40C, and FIGS. 41A-41C).

Example 9.6

Fluorescence labeled GAPDH, ADAMTS-5 and Scrambled molecular beacon delivered with Nanopieces was injected into mouse knee joints after DMM or Sham surgery, and then the fluorescence signal was recorded and analyzed via a fluorescence molecular tomography (FIG. 42 and FIG. 43). FIG. 42 shows a stronger fluorescence signal resulting from ADAMTS-5 molecular beacon in DMM surgery leg than Sham leg. FIG. 43 shows the pattern of ADAMTS-5 expression after surgery.

Example 10

Therapeutics

IL-1 receptor (IL-1R) siRNA/Nanopieces were injected into one knee of mice and non-targeting scrambled siRNA/Nanopiece was injected into the other knee. Cartilage degeneration was stimulated with catabolic cytokine (such as IL-1β) in both knees mimicking an inflammation environment during arthritis. Successful knock down of IL-1R in chondrocytes in mouse cartilage was observed with Nanopiece delivery of IL-1R siRNA in vivo (FIGS. 33A-33D). Moreover, cartilage degeneration genes (such as MMP-13 and MMP-9, FIGS. 33A-33D) were down-regulated and cartilage anabolic genes (such as Col II, FIGS. 33A-33D) were up-regulated.

Figure 34B:
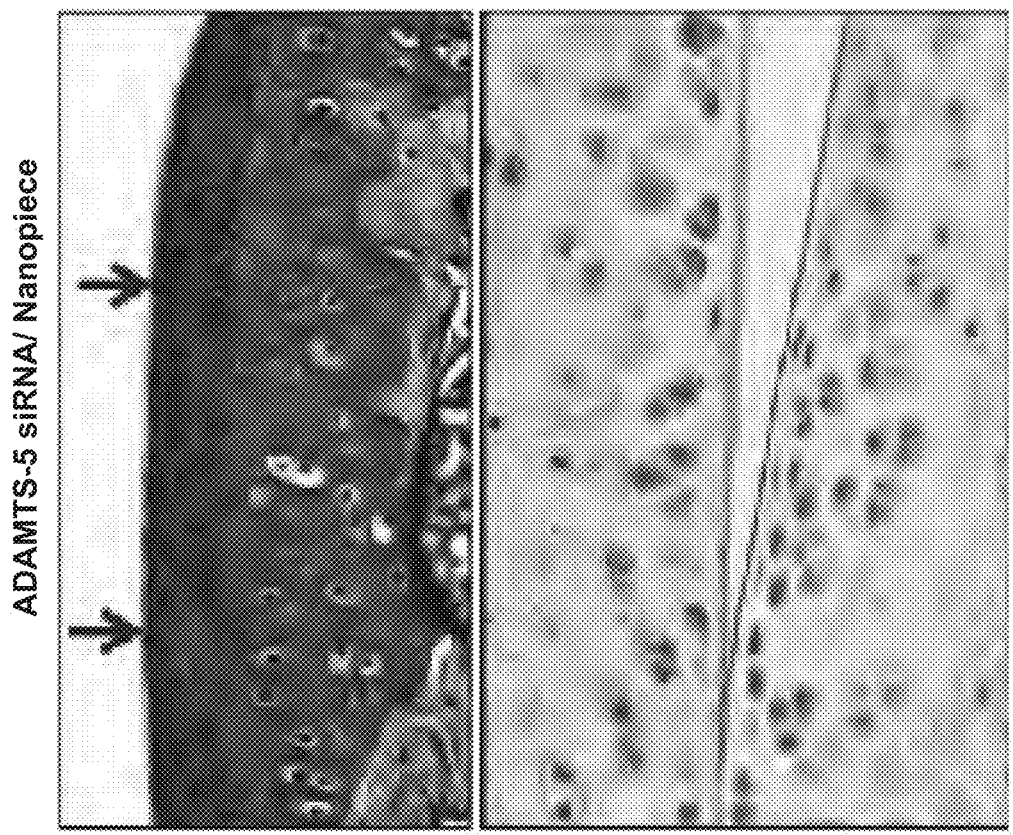
FIGS. 34A and 34B are a series of images showing histology (medium grey staining is proteoglycan) and immunohistochemistry (dark grey staining is epitope from aggrecan cleavage) of mouse knee joints. ADAMTS-5 siRNA/Nanopiece greatly inhibited cartilage degeneration and Aggrecan cleavage with cytokine stimulation.
Figure 34A:
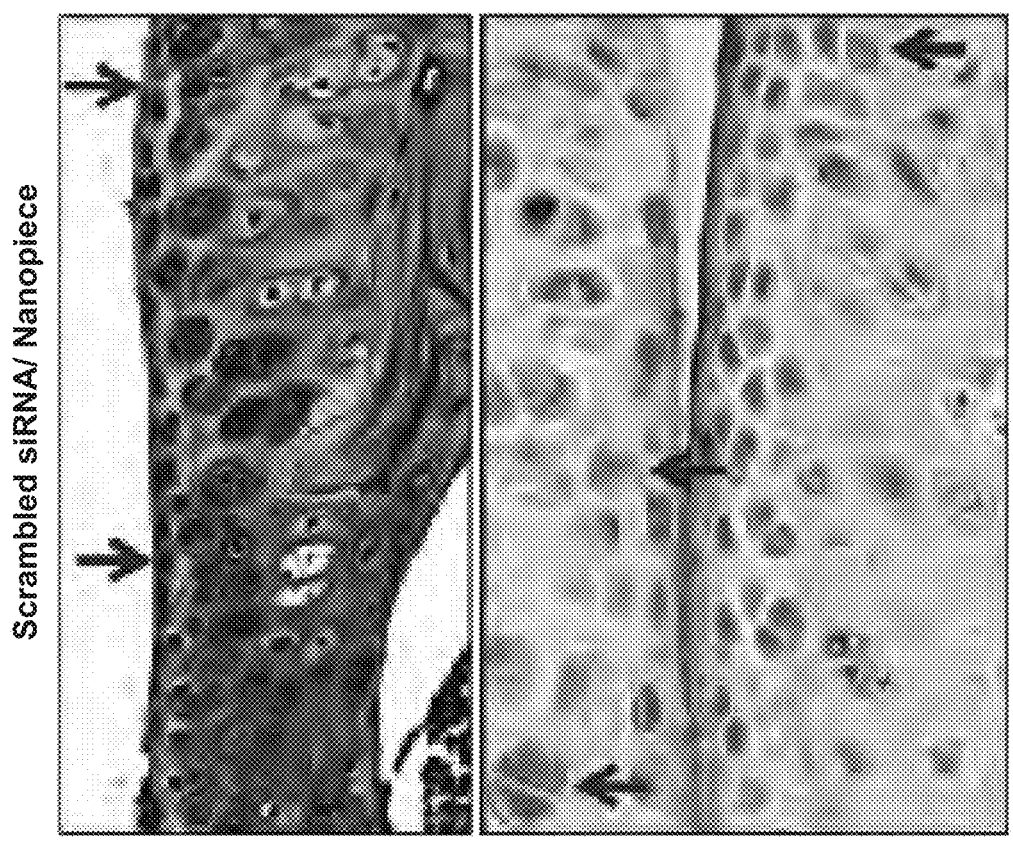
Figure 36:
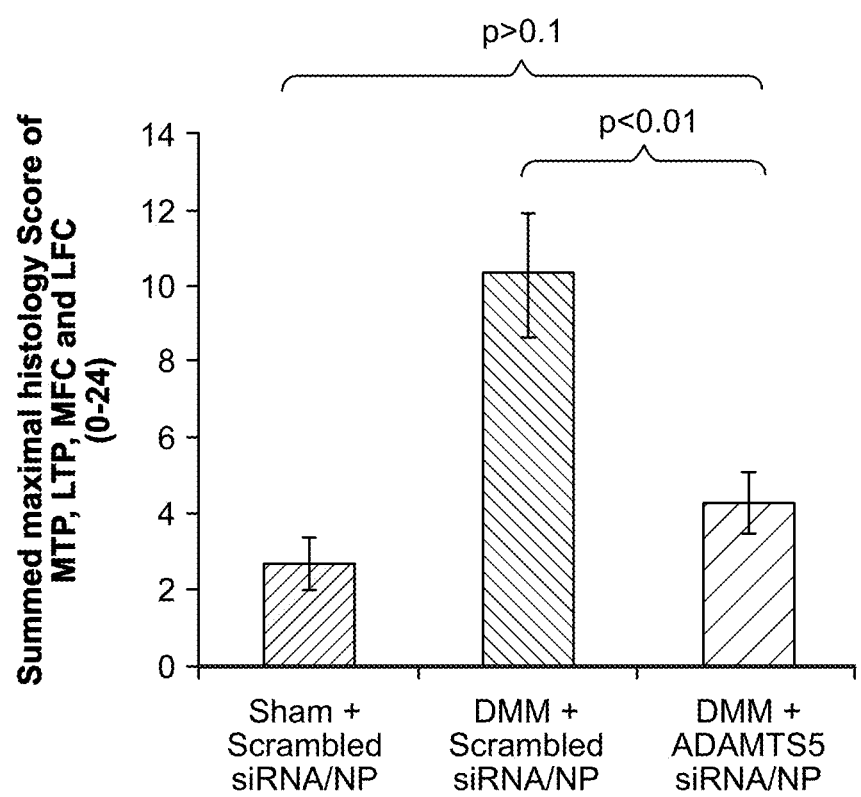
FIG. 36 is a graph showing histology evaluation of mouse knee joints. ADAMTS-5 siRNA/Nanopiece prevents osteoarthritis progression after DMM surgery.

Nanopieces were used to deliver ADAMTS-5 siRNA into knee joints of mice that had been treated with cytokines (IL-1α and retinoic acid). Results showed that cartilage degeneration and aggrecan cleavage was significantly inhibited after ADAMTS-5 siRNA treatment (FIG. 34A and FIG. 34B). In the top two panels, the dark grey color in articular cartilage was aggrecan staining. Without ADAMTS-5 siRNA treatment, aggrecan staining is weaker than the treatment group, indicating loss of aggrecan. In the bottom two panels, dark staining around the cell nuclei was epitope staining from aggrecan cleavage. Without ADAMTS-5 siRNA treatment, the staining is stronger than the treatment group, indicating cleavage of aggrecan.

To mimic osteoarthritis progression, DMM surgery on knee joints of mice was conducted. Osteoarthritis progression was shown to be prevented or slowed with Nanopiece delivery of ADAMTS-5 siRNA (FIGS. 35A-35C and FIG. 36). In FIGS. 35A-35C, the dark greycolor in articular cartilage was aggrecan staining. A RROWs point out loss of aggrecan staining or damage to articular cartilage in the groups without ADAMTS-5 siRNA treatment; while with treatment, there was very little loss of aggrecan or damage to articular cartilage. Also, immunohisology results showed that aggrecan cleavage was inhibited with delivery of ADAMTS-5 siRNA (FIG. 46). In FIGS. 46A-46C, dark staining around cell nuclei was epitope staining from aggrecan cleavage. Without ADAMTS-5 siRNA treatment, the staining is stronger than the treatment group, indicating cleavage of aggrecan.

In addition, ADAMTS-5 siRNA was delivered via Nanopieces to human cartilage ex vivo. Protection of human cartilage from cytokine-induced cartilage degradation was demonstrated (FIGS. 44A-44D and FIGS. 45A-45D). In FIGS. 44A-44D, dark staining around cell nuclei was epitope staining from aggrecan cleavage. Without ADAMTS-4 or 5 siRNA treatment, the staining is stronger than the treatment group, indicating cleavage of aggrecan. In FIGS. 45A-45D, dark color in articular cartilage was aggrecan staining. Without ADAMTS-4 or 5 siRNA treatment, aggrecan staining is weaker than the treatment group, indicating loss of aggrecan.

These data indicate that the methods are useful to prevent and/or inhibit cartilage degeneration and arthritis progression.

Example 11

Synthesis

Example 11.1

RNTs and TBLs to form Nanopieces are made by first synthesizing a module [(e.g., compound of Formula I or compound of Formula II, respectively]. Nanotubes (RNTs or TBLs) are then processed (Processing-1, Processing-2) to make nanorods and Nanopieces, respectively (see, e.g., FIG. 53). A module for making a Nanopiece was synthesized according to methods described in U.S. Pat. No. 6,696,565 and subsequently purified prior to using the same in the preparation of functional Nanopieces. Liquid chromatography purification was used to purify the synthetic products derived from Formula I and/or Formula II to ensure the success of forming functional and low toxic Nanopieces. In liquid chromatography, trifluoroacetic acid (TFA) is usually applied to keep an acidic eluent environment. Due to known toxicity of TFA or fluoride residual, which made isolated materials undesirable for preclinical and clinical studies, a modification to include hydrochloric acid (HCl) or phosphoric acid during the purification process was developed as an alternative TFA.

Liquid chromatography was performed on C18 reverse-phase column, and agilent 1260 Infinity Quaternary HPLC System was used. One example of gradient used in isolation is shown below:

| Time | 0 min | 10 min | 15 min |
| --- | --- | --- | --- |
| Percentage of Solvent A | 90 | 65 | 0 |
| Percentage of Solvent B | 0 | 25 | 90 |
| Percentage of Solvent C | 10 | 10 | 10 |

Figure 47:
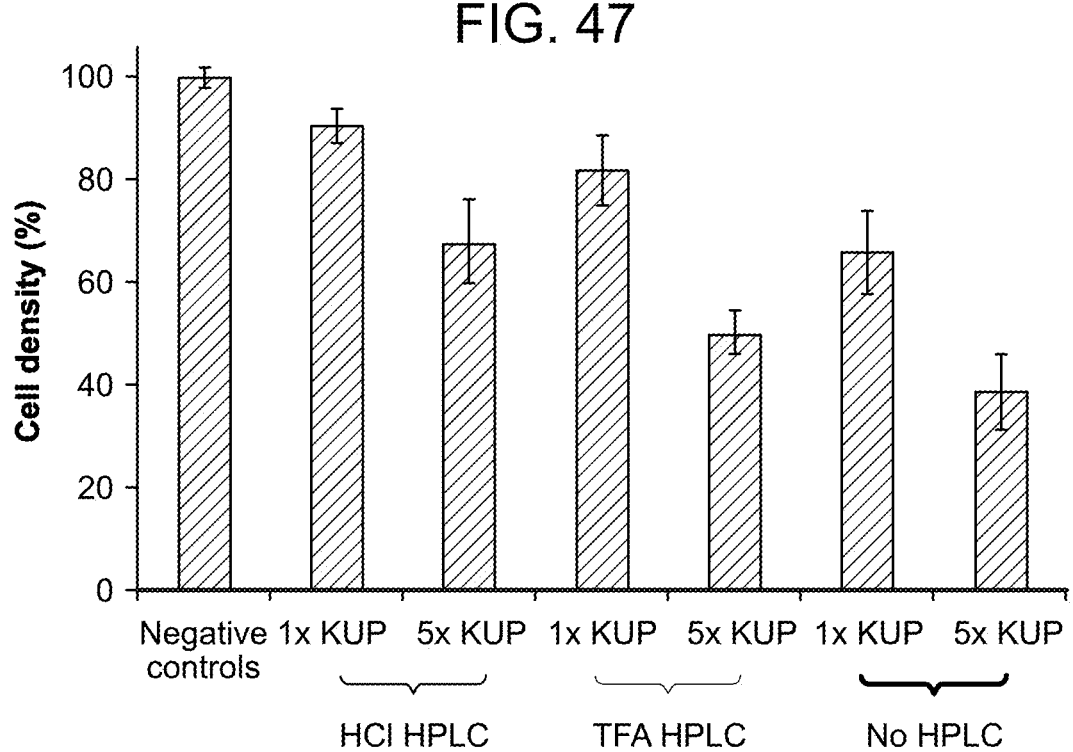
FIG. 47 is a graph showing cell toxicity studies of RNTs purified using HPLC chromatography with HCl or TFA as a modifier.
Figure 48A:
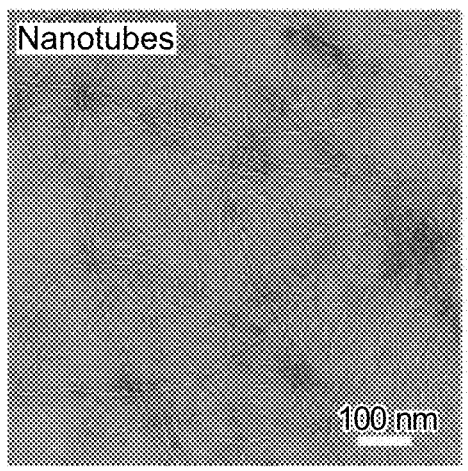
FIG. 48A and FIG. 48B are a series of images showing the conversion of nanotubes to nanorods.
Figure 48B:
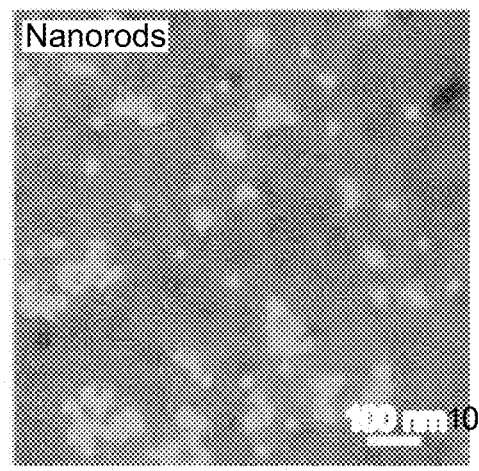

*Solvent A is $H_2O$, Solvent B is 100% acetonitrile, and Solvent C is 0.05N hydrochloric acid. The cell toxicity was evaluated using a standard cell viability test. ATDC5 cells were treated with RNTs, and after 48 hours cell viability normalized to negative controls (as 100). Results are showed in FIG. 47. These results demonstrate successful isolation of modules using a modified HPLC purification method to obtain RNTs. Using HCl instead of TFA in this purification process avoided the presence of fluorine containing contaminates within the module, which contributed to the toxicity of the resulting nanotube. Thus, use of HPLC decreased the toxicity of RNTs and use of HCl versus TFA further decreased the cytotoxicity. Molecular modules, e.g, TBLs were therefore isolated by applying HCl in liquid chromatography purification. This purification scheme is applicable for module I compounds (for RNT assembly and for module II compounds for TBL assembly) to yield functional Nanopieces with low toxicity.

Example 11.2

Figure 53:
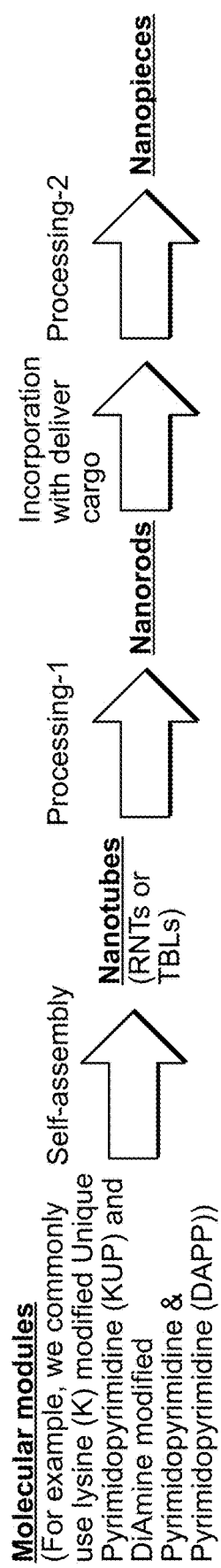
FIG. 53 is flow design of self-assembly, processing-1, processing-2 to yield nanopieces.

Conversion of nanotubes (such as RNTs and TBLs) into nanorods was accomplished according to a process called "processing-1" (FIG. 53). In Processing-1, nanotubes are converted into short and homogeneous nanorods. This is very important to produce Nanopieces small enough to penetrate some types of tissue matrices for introduction of therapeutics into the tissue. Conversion of nanotubes to nanorods can be accomplished by altering pH, temperature, and/or using physical methods (such as sonicating, heating and blending (e.g. homogenizer)), and/or addition of aromatic chemicals. Different sizes of Nanopieces can be produced (FIGS. 5A-5B, FIGS. 6A-6B and FIGS. 48A-48B). Based on the Nanopiece assembly mechanism, the processing approach may include at least one of the following: 1) before assembly, controlling the length and bundle of RNTs via changing physical and/or chemical conditions such as temperature, molecule motion and/or vibration (like sonication) and pH; 2) during assembly, adjusting assembly conditions via changing physical and/or chemical conditions including concentrations, pH and ionic strength to enhance and/or reduce the formation and stacking of Nanopieces; 3) after assembly, breaking long or stacked Nanopieces by via changing physical and/or chemical conditions including enhancing molecule motion/vibration (like sonication).

Example 11.3

Preparation of Nanopieces was accomplished by a process called "processing-2" (FIG. 55). Processing-2 occurs after the incorporation between nanotubes or nanorods with delivery cargo and formation of bundles, ribbons or other agglomerates. These agglomerates can then be transformed to Nanopieces (FIG. 49A and FIG. 49B). The size of the Nanopieces can be changed with changes in pH, ionic strength, temperature and concentration (FIG. 4, FIGS. 7A-7B, FIGS. 8A-8B, and FIGS. 9A-9B).

FIGS. 15A-FIG. 23F and FIG. 26A-FIG. 32 demonstrated the successful tissue delivery after combining the above methods in Examples 11.1-11.3.

Example 11.4

Preparation of small and large lipid Nanoparticles was accomplished using the procedures described below.
Preparation of Large Lipid Nanoparticles with IL-1R siRNA (Sphere Shape 110 nm to 180 nm Diameter):
1) Dissolve siRNA in 20 mM citrate buffer (pH 5.0, nuclease free) to achieve a concentration of 5004.
2) Dissolve DSPC, cholesterol, DODMA, and DSG-PEG (20:48:2:30 molar ratio) in absolute, anhydrous ethanol, and then add nuclease free water to achieve a concentration of 90% ethanol.
3) The total concentration of lipid in solution is then adjusted to 20 mM.
4) 1 μL of siRNA and 1 μL of lipid solutions are heated to 37° C., then mix at the same temperature and dilute with 8 uL nuclease free water. Sit at least 30 minutes before use.
Preparation of Small Lipid Nanoparticles with IL-1R siRNA (Sphere Shape 70 nm to 120 nm Diameter):
1) Dissolve siRNA in 10 mM citrate, 30 mM NaCl (pH 6.0, nuclease free) to achieve a concentration of 5004.
2) Dissolve DSPC, DSG-PEG, cholesterol, SPDiOC18, and DOTMA (10:10:39.8:0.2:40 molar ratio) in absolute, anhydrous ethanol, and then add an aqueous buffer (50 mM citrate, pH 4.0, nuclease free) to achieve a final concentration of 40% ethanol.
3) The total concentration of lipid in solution is then adjusted to 20 mM.
4) Extrude the lipid solution through two nuclepore polycarbonate filters (100 nm, 10 passes).
5) 1 μL extruded lipid solution and 1 μL siRNA are mixed under constant vortex, then dialyzed in PBS overnight to increase the pH to about 7.4.

Figure 67:
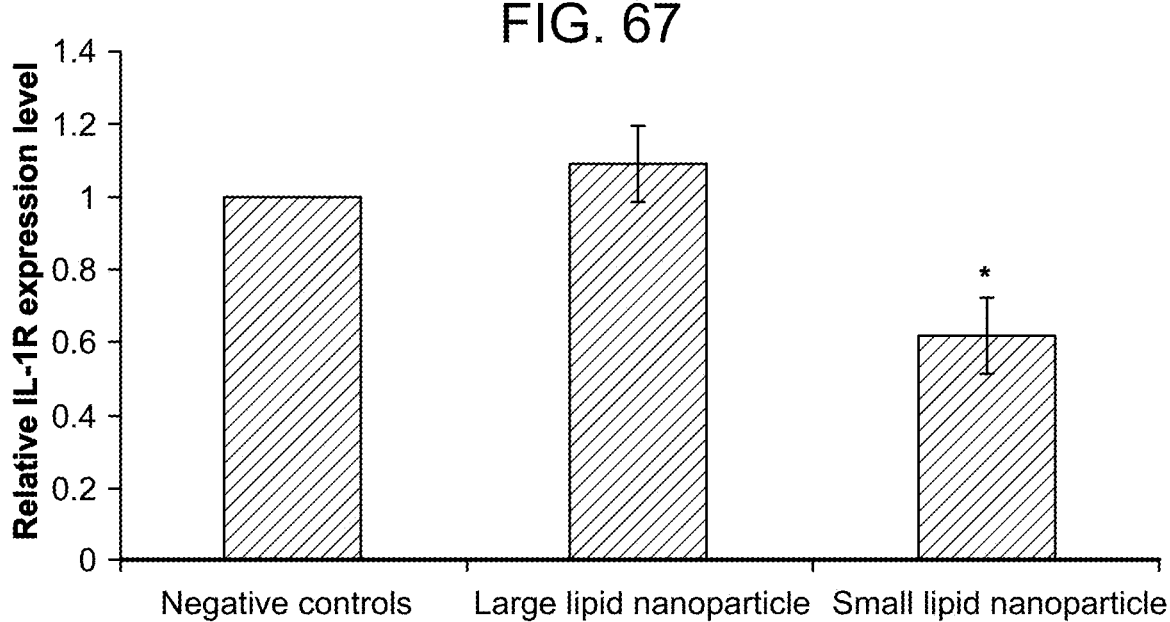
FIG. 67 is a bar graph showing PCR results of IL-1R expression levels of large and small lipid nanoparticles (* p<0.05 compared to negative controls and large lipid nanoparticle).

FIG. 67 shows successful localization/delivery of cargo to cartilage tissue using nucleic acid-loaded lipid nanoparticles. The small siRNA lipid nanoparticles localized to, penetrated cartilage tissue, and inhibited expression of the target gene.

Example 11.5

Preparation of small and large polymer Nanoparticles was accomplished using the procedures described below.
Preparation of Large and Small Polymer Nanoparticles with IL-1R siRNA:
1) Dissolve poly-lysine (PLL) (molecular weight, 15 kDa-30 kDa) in nuclease free water to 0.2 mg/mL.
2) Dialyze to remove salt (HBr).
3) Lyophilize
To prepare large PLL/siRNA nanoparticles (100-250 nm diameter):
1) Dissolve siRNA and PLL in 0.15M NaCl to concentrations of 1004 and 2504, respectively.
2) Quickly add 1 uL 5004 siRNA solution to 15 uL 100 μg/mL PLL and pipette well at room temperature.
3) Pipette and let sit for at least 30 minutes before use.
To prepare small PLL/siRNA nanoparticles (50-75 nm diameter):
1) Dissolve siRNA and PLL in nuclease free water to concentrations of 5004 and 100 μg/mL, respectively.
2) Quickly add 1 uL 5004 siRNA solution to 15 uL 100 μg/mL PLL and pipette well at room temperature.
3) Use within 30 minutes of reaction.

Figure 68:
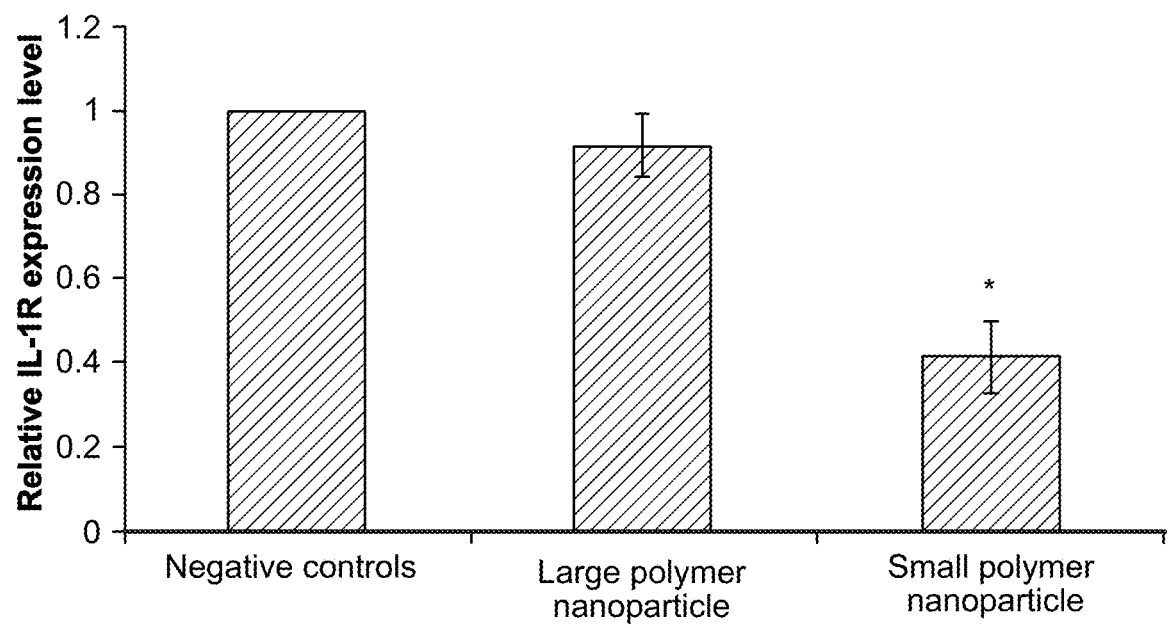
FIG. 68 is a bar graph showing PCR results of IL-1R expression levels of large and small polymer nanoparticles (* p<0.05 compared to negative controls and large polymer nanoparticle).

FIG. 68 shows successful localization/delivery of cargo to cartilage tissue using nucleic acid-loaded polymer nanoparticles. The small siRNA polymer nanoparticles localized to, penetrated cartilage tissue, and inhibited expression of the target gene.

FIG. 67 and FIG. 68 demonstrated the successful tissue delivery of the above prepared lipid or polymer nanoparticles. Animals were injected with prepared large/small lipid or polymer nanoparticles delivered with IL-1R siRNA to right knees of mice. (Animal left knees were used as negative controls). After 24 hours, euthanize animals were euthanized and their knee cartilage was collected for real time RT-PCR. These data indicate that cargo-loaded nanostructures such as RNTs comprising compounds of Formula I, TBLs comprising compounds of Formula II, as well as lipid nanoparticles, and polymer nanoparticles successfully deliver cargo to target tissues.

Example 12

A Non-Invasive, Early, and Sensitive Detection of Osteoarthritis Through In Vivo Imaging of MMP-13 mRNA Levels by Molecular Beacon (MB) and Nanopiece Delivery Technology MBs were designed to target MMP-13 or GAPDH mRNA with a fluorophore/quench pair using a mouse model. Scramble sequence MB (Scramble) was verified to not bind with any mouse mRNA via BLAST. To demonstrate in vitro delivery and validation; MBs were delivered into chondrocytes by Nanopieces. After stimulation with IL-1β for 24 hours, chondrocytes were co-transfected GAPDH (red) and scramble (green) MBs or GAPDH (red) and MMP-13 (green) MBs via Nanopieces. Real time RT-PCR and fluorescence microscopy were used to verify the stimulation of MMP-13 expression, and a successful fluorescence signal resulted from using a MMP-13 MB.

Destabilization of the medial meniscus (DMM) surgery and in vivo delivery: DMM or sham surgeries were performed on 10-week-old 129SVE male mice to induce osteoarthritis. One week after surgery, MMP-13 and scramble MBs with different fluorophores delivered by Nanopieces were injected into knee joints of mice small animal fluorescence molecular tomography (FMT) was used to determine the fluorescence signal resulted from MMP-13 expression in the live animals for 3 weeks.

To test the in vitro efficacy of mRNA detection in chondrocytes using MBs delivered by Nanopieces, primary mouse chondrocytes were transfected with MBs either with or without IL-1β treatment. Before IL-1β treatment, the housekeeping GAPDH MB (red) was detected while the MMP-13 MB (green) was not. In contrast, after IL-1β treatment, both GAPDH MB (red) and MMP-13 MB (green) were detected, indicating the induction of MMP-13 mRNA levels by Realtime rtPCR showed that MMP-13 mRNA level was up-regulated by about 10 times upon IL-1β stimulation. In contrast, Scramble MB transfection did not show any green fluorescence, suggesting that the fluorescence of MMP-13 MB was not due to non-specific degradation.

To evaluate in vivo efficacy, the following studies were carried out. After DMM surgery, MMP-13 MB was delivered intra-articularly to the knee joint of adult mice with Scramble MB that emits fluorescence at a different wavelength than MMP-13 MB. Only a week after surgery, the DMM surgery leg displayed a strong MMP-13 signal than the contralateral Sham surgery leg (FIG. 2, left panel). In contrast, the Scramble MB showed very low fluorescence in both DMM and Sham surgery knee joints. After subtracting Scramble MB basal level signals, MMP-13 MB real signal was about 40 times stronger in the DMM leg than the sham leg. Such MMP-13 MB signals persist, even for 3 weeks after injection of MBs.

MMP-13 MB delivered by Nanopiece technology represents a sensitive tool to detect pro-inflammatory degenerative conditions as evidenced with chondrocytes in vitro and in OA animal models in vivo. This technology detects pathogenesis of OA at an early stage (within a week) in a mild OA model (DMM). A high sensitivity was achieved due to the detection at the mRNA level and the high efficiency of MB intracellular delivery by Nanopieces. The combination of molecular beacon and Nanopieces technology provided a powerful tool for early detection of OA in vivo in a specific and sensitive manner without harming any joint tissues.

Matrix metalloproteinases (MMP) are the major enzymes that degrade the components of the extracellular matrix during arthritis progression. MMP-13, which is usually produced by cartilage and bone, degrade interstitial collagens (types I, II and III) in both OA and RA. Expression of MMP-13 is low in normal cells, whereas in pathologic condition excess MMP-13 production is associated with inflammation. Thus, mRNA level of MMP-13 is useful as a diagnostic and prognostic tool for assessment of arthritis development. Therefore MMP-13 is recognized as a reliable target in early diagnosis of arthritis. These data indicate that intra-articular injection of Nanopieces+payload were successfully introduced into joint tissue and that the payload was functionally active after delivery.

The system and compositions described herein overcame the difficulty of accurately translating molecular beacon signal into MMP-13 mRNA expression level. MMP-13 upregulation pattern was demonstrated during OA progression using the Nanopiece—delivered beacons. Compared to earlier and current research and clinical methods, Nanopiece-Molecular Beacon technology achieved much earlier and more sensitive detection.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

What is claimed:

1. A method of treating joint disease comprising administration to a subject of an effective amount of a nanopiece, wherein said nanopiece comprises i) a compound of Formula I or Formula II or a combination thereof, and ii) a nucleic acid:

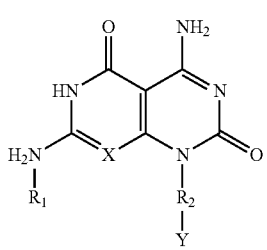

(I)

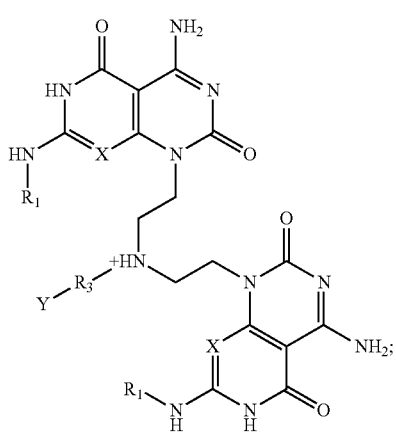

(II)

wherein, X is CH or N;
R$_2$ is hydrogen or a linker group;

Y is absent when R₂ is hydrogen or is an amino acid side chain, amino acid or polypeptide; and R₁ is hydrogen or aliphatic, wherein the nanopiece has a size in at least one dimension between 0.1 nm and 150 nm, wherein a ratio of the compound to nucleic acid ranges from 4.4 to 30 μg compound per to 0.1 nmol of the nucleic acid;

wherein the nanopiece is positively charged at pH 7-7.5.

2. The method of claim 1, wherein said joint disease comprises autoimmune, degenerative, inflammatory, infectious, cancerous, viral, fungal, injured, trauma, genetic, trauma, mechanical, nutritional or mal-alignment derived.

3. The method of claim 1, wherein said joint disease comprises rheumatoid arthritis, osteoarthritis, juvenile onset of rheumatoid arthritis (JRA), reactive arthritis (RA), septic arthritis, tendinitis, or herniation.

4. The method of claim 1, wherein the nucleic acid is a diagnostic agent or a therapeutic agent.

5. The method of claim 1, wherein the nanopiece has a net positive charge of a Zeta potential>+8 mV.

6. The method of claim 1, wherein the compound is selected from:

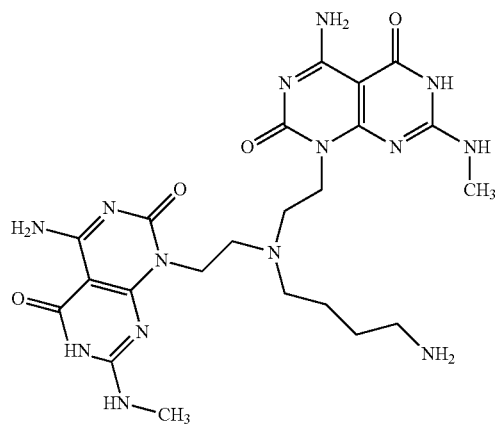

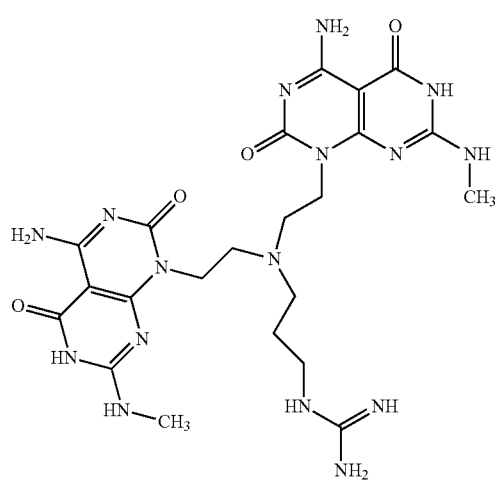

-continued

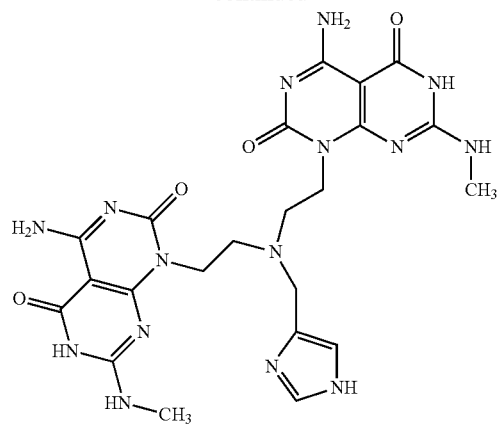

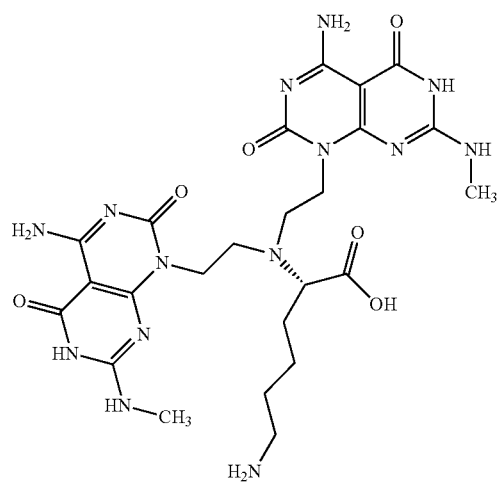

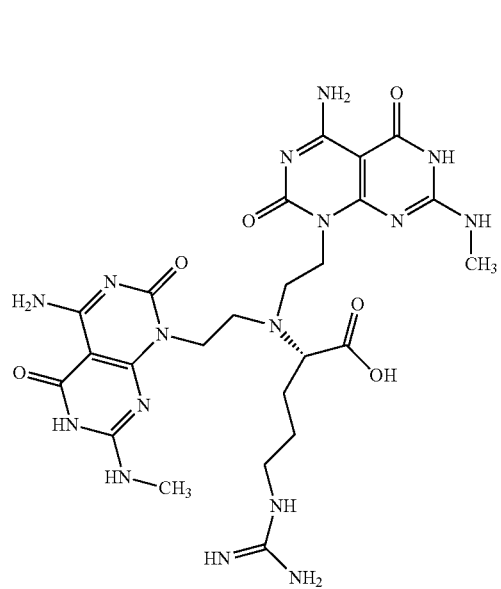

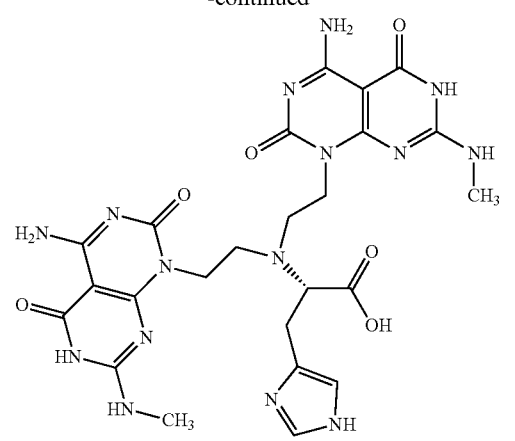
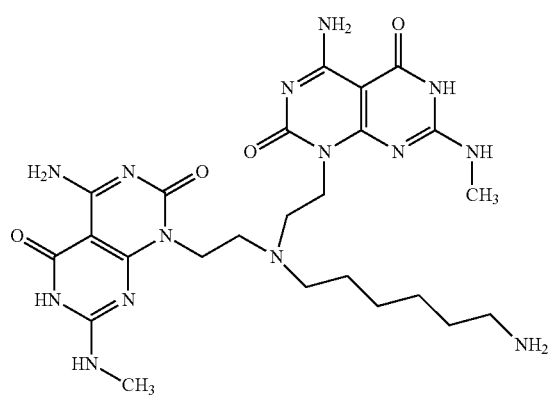
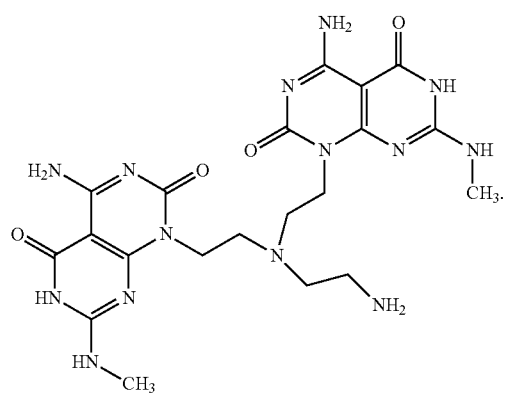
7. The method of claim 1, wherein R$_2$ comprises an amino acid side chain or is selected from:
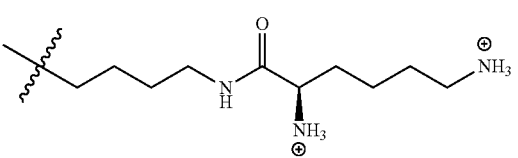
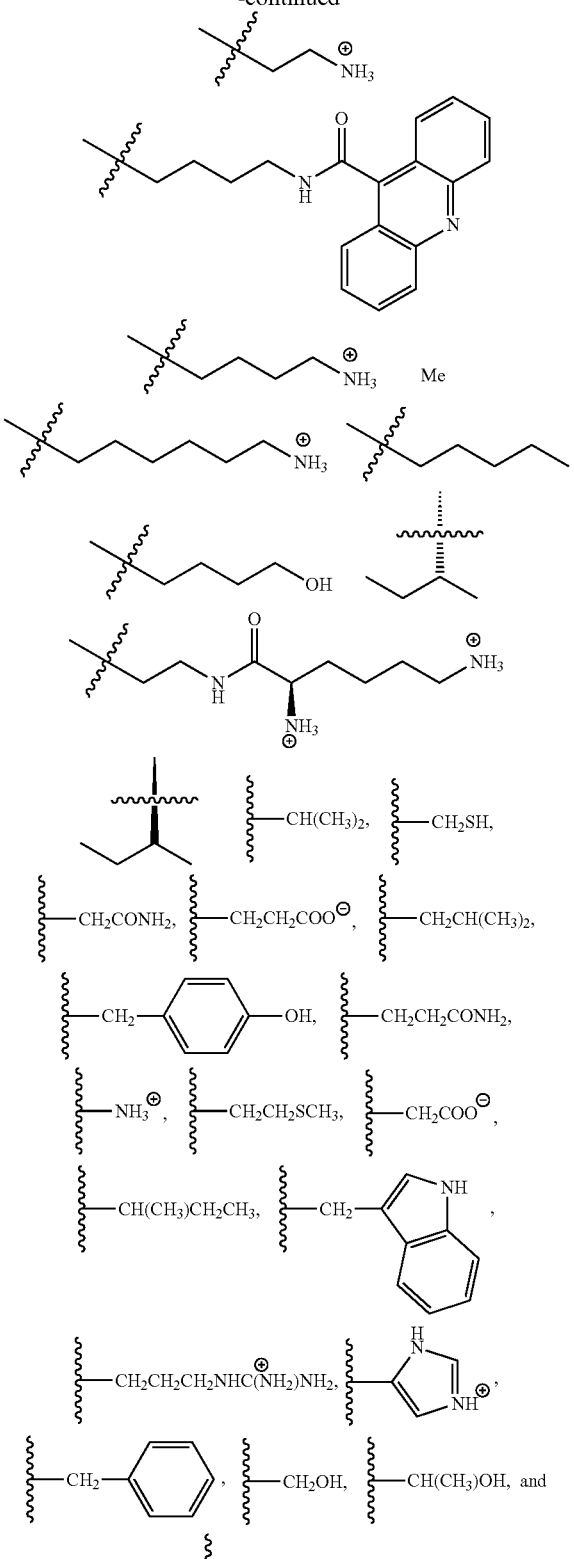
wherein Y is absent.

8. The method of claim 1, wherein the compound is selected from

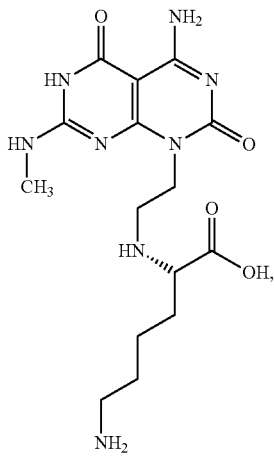

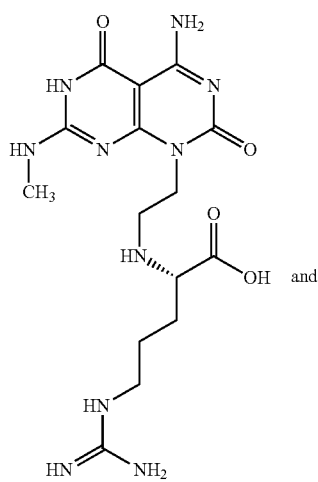 and

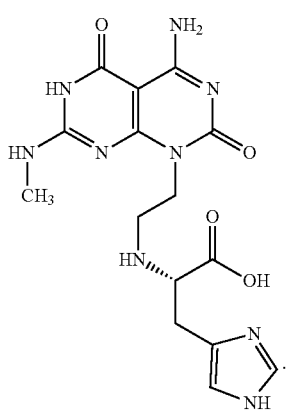

9. The method of claim 1, wherein $R_1$ is $C_1$ to $C_{10}$ alkyl.

10. The method of claim 1, wherein the nucleic acid comprises siRNA.

11. The method of claim 10, wherein the nucleic acid comprises an IL-1 receptor siRNA, ADAMTS-5 siRNA, Matrilin-3 siRNA or a siRNA targeting a FGF receptor.

12. The method of claim 1, wherein the nucleic acid comprises a molecular probe or a molecular beacon.

13. The method of claim 12, wherein the nucleic acid is the molecular beacon detecting MMP-13 or ADAMTS-5.

14. The method of claim 1, further comprising administering one or more analgesic agents, anti-inflammatory agents, immunosuppressive agents, antifungal agents, antibiotic agents, lubricants, anti-cancer agents, NMDA receptor antagonists, or antiviral agents.

15. The method of claim 1, wherein the nanopiece comprises a size of <30 nm in at least one dimension.

16. The method of claim 1, wherein the nanopiece has a size of 1 to 30 nm in at least one dimension.

17. The method of claim 1, wherein a ratio of the compound to nucleic acid ranges from 4.4 to 30 μg compound per to 0.1 nmol of the nucleic acid.

18. The method of claim 1, wherein the nucleic acid comprises microRNA-365.

19. The method of claim 1, wherein the nucleic acid comprises microRNA-146a.

20. The method of claim 1, wherein the nucleic acid comprises microRNA-140.

21. The method of claim 1, wherein the nucleic acid comprises an anti-microRNA.

22. The method of claim 1, wherein the joint disease is selected from polymyalgia rheumatica, rheumatoid arthritis, multiple sclerosis, Charcot's Joint, osteoarthritis, juvenile onset of rheumatoid arthritis (JRA), system lupus erythematosus (SLE), psoriatic arthritis, inflammatory bowel disease (IBS) arthritis, Whipple's disease, intestinal lipodystrupjy, ankylosing spondylitis (AS), reactive arthritis (RA), Still's disease, avascular necrosis, bursitis, fibromyalgia, gout, hemochromatosis, hypothyroidism, lupus, Lyme disease, Fifths disease, osteomalacia, osteomyelitis, Paget's disease of bone, pseudogout, rickets, septic arthritis, tendinitis, diabetes, Ehlers-Danlos syndrome, costochondritis, Perthes' disease, Marfan syndrome, rheumatic fever, tubercular arthritis, pigmented villonodular synovitis, scleroderma, polymyositis, erythema nodosum, neuropathic arthropathy, sickle-cell disease, acromegaly, amyloidosis, acute crystal synovitis, pyogenic bacterial infection, scurvy, hemophilia, achondroplasia, herniation, diffuse iodophatic skeletal hyperostosis (DISH), ganglion, lumbar spinal stenosis, sacrolilac joint pain, SAPHO syndrome, polycythemia, Raynaud's phenomenon, hydroxyapatite, Behcet's syndrome, Felt's syndrome, hepatitis B, primary Sjoegrens, and polychondritis.

23. The method of claim 1, wherein the joint disease is resulted from genetics, trauma, mechanical injury, nutrition deficiencies, or joint mal-alignment.

24. The method of claim 1, wherein the effective amount of the nanopiece is administered by injection or infusion into a localized tissue site, inhalation, transdermally, orally, rectally, transmucosally, intestinally, parenterally, intramuscularly, intra-articularly, subcutaneously, or intravenously.

25. The method of claim 1, wherein the joint disease comprises arthritis.

26. The method of claim 1, wherein the joint disease comprises osteoarthritis.

27. The method of claim 1, wherein the joint disease comprises rheumatoid arthritis.

28. The method of claim 1, wherein the joint disease comprises osteosarcoma.

29. The method of claim 1, wherein the nanopiece is administered intravenously.

30. A method of treating a joint disease comprising (i) providing a cell from a subject;

(ii) introducing siRNA into a cell by contacting the cell with a nanopiece comprising the siRNA and a compound of Formula I or Formula II or a combination thereof,

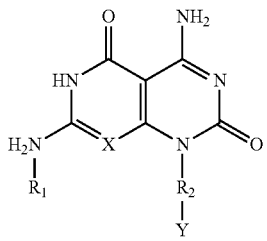
(I)

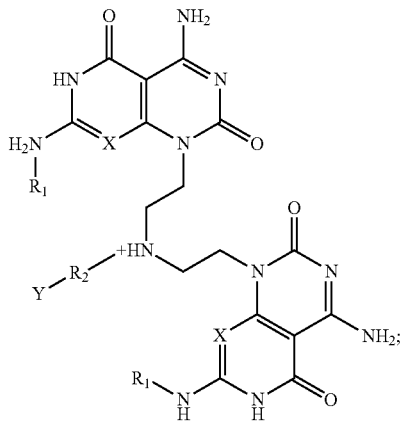
(II)

wherein, X is CH or N;
$R_2$ is hydrogen or a linker group;
Y is absent when $R_2$ is hydrogen or is an amino acid side chain, amino acid or poly peptide; and
$R_1$ is hydrogen or aliphatic; and (iii) reintroducing the cell into the subject,
wherein the nanopiece has a size in at least one dimension between 0.1 nm and 150 nm,
wherein a ratio of the compound to the siRNA ranges from 4.4 to 30 µg compound per to 0.1 nmol of the siRNA;
wherein the nanopiece is positively charged at pH 7-7.5.

31. The method of claim 1, wherein the nanopiece is positively charged at pH 7.4.

32. The method of claim 30, wherein the nanopiece is positively charged at pH 7.4.

* * * * *

SEQUENCE LISTING

```
<160> NUMBER OF SEQ ID NOS: 227

<210> SEQ ID NO 1
<211> LENGTH: 9663
<212> TYPE: DNA
<213> ORGANISM: Homo sapiens

<400> SEQUENCE: 1
ataaattcat tgttccacct cctcgcatct tcacagcgct cgcgctgctc tcggcgctcg      60
cagctgccga ctggggatga cggcgggcag gaggagaccg cagccgaagg gacacagaca     120
cgccgcttca ccagctcgcc tcaggctgcc ccctgcatt tttgttttaa ttttacggc      180 tttttcccct ctctttcttc ccttcctcct ggtcccagca gagccaagga aacccacaaa     240
```

```
ataagaaagg aagtgggccc cggagcttgg aacctccaca gccggcttgt ccagcgcagc    300 gcggggcgg gaggctgcgc gcaccagttg ccagcccggt gcgcggtacc tttccttact    360
tttcttgaaa cagcgatcgt gcctgcattt ggtggttttt tggttttgt ttttttcctt    420 ttcccgtatt tgctgaatct ccactatccg actttttttt tttaatcttt tctttccccc    480 ccccccacc ccacctcttt ctggagcacg aatccaaaca ttttcccaag caacaaagaa    540
aagttcgcac gctggcaccg cagcccggac aggctggcgc tgctgccggg ccccctccc    600 tccgacactt gactcaatcc tgcaagcaag tgtgtgtgtg tccccatccc ccgccccgtt    660
aacttcatag caaataacaa atacccataa agtcccagtc gcgcagcccc tccccgcggg    720
cagcgcacta tgctgctcgg gtgggcgtcc ctgctgctgt gcgcgttccg cctgcccctg    780
gccgcggtcg gccccgccgc gacacctgcc caggataaag ccgggcagcc tccgactgct    840
gcagcagccg cccagcccg ccggcggcag ggggaggagg tgcaggagcg agccgagcct    900 cccgccacc cgcaccccct ggcgcagcgg cgcaggagca aggggctggt gcagaacatc    960
gaccaactct actccggcgg cggcaaggtg ggctacctcg tctacgcggg cggccggagg   1020
ttcctcttgg acctggagcg agatggttcg gtgggcattg ctggcttcgt gcccgcagga   1080
ggcgggacga gtgcgccctg gcgccaccgg agccactgct tctatcgggg cacagtggac   1140
ggtagtcccc gctctctggc tgtctttgac ctctgtgggg gtctcgacgg cttcttcgcg   1200
gtcaagcacg cgcgctacac cctaaagcca ctgctgcgcg gaccctgggc ggaggaagaa   1260
aaggggcgcg tgtacgggga tgggtccgca cggatcctgc acgtctacac ccgcgagggc   1320
ttcagcttcg aggccctgcc gccgcgcgcc agctgcgaaa ccccgcgtc cacaccggag   1380 gcccacgagc atgctccggc gcacagcaac ccgagcggac gcgcagcact ggcctcgcag   1440
ctcttggacc agtccgctct ctcgcccgct gggggctcag gaccgcagac gtggtggcgg   1500
cggcggcgcc gctccatctc ccgggcccgc caggtggagc tgcttctggt ggctgacgcg   1560
tccatggcgc ggttgtatgg ccgggcctg cagcattacc tgctgaccct ggcctccatc   1620
gccaataggc tgtacagcca tgctagcatc gagaaccaca tccgcctggc cgtggtgaag   1680
gtggtggtgc taggcgacaa ggacaagagc ctggaagtga gcaagaacgc tgccaccaca   1740
ctcaagaact tttgcaagtg gcagcaccaa cacaaccagc tgggagatga ccatgaggag   1800
cactacgatg cagctatcct gtttactcgg gaggatttat gtgggcatca ttcatgtgac   1860
accctgggaa tggcagacgt tgggaccata tgttctccag agcgcagctg tgctgtgatt   1920
gaagacgatg gcctccacgc agccttcact gtggctcacg aaatcggaca tttacttggc   1980
ctctcccatg acgattccaa attctgtgaa gagacctttg gttccacaga agataagcgc   2040
ttaatgtctt ccatccttac cagcattgat gcatctaagc cctggtccaa atgcacttca   2100
gccaccatca cagaattcct ggatgatggc catggtaact gtttgctgga cctaccacga   2160
aagcagatcc tggccccga agaactccca ggacagacct acgatgccac ccagcagtgc   2220
aacctgacat tcgggcctga gtactccgtg tgtcccggca tggatgtctg tgctcgcctg   2280
tggtgtgctg tggtacgcca gggccagatg gtctgtctga ccaagaagct gcctgcggtg   2340
gaagggacgc cttgtggaaa ggggagaatc tgcctgcagg gcaaatgtgt ggacaaaacc   2400
aagaaaaaat attattcaac gtcaagccat ggcaactggg gatcttgggg atcctggggc   2460
cagtgttctc gctcatgtgg aggaggagtg cagtttgcct atcgtcactg taataacct   2520 gctcccagaa acaacggacg ctactgcaca gggaagaggg ccatctaccg ctcctgcagt   2580
```

```
ctcatgccct gcccacccaa tggtaaatca tttcgtcatg aacagtgtga ggccaaaaat   2640
ggctatcagt ctgatgcaaa aggagtcaaa acttttgtgg aatgggttcc caaatatgca   2700
ggtgtcctgc cagcggatgt gtgcaagctg acctgcagag ccaagggcac tggctactat   2760
gtggtatttt ctccaaaggt gaccgatggc actgaatgta ggctgtacag taattccgtc   2820
tgcgtccggg ggaagtgtgt gagaactggc tgtgacggca tcattggctc aaagctgcag   2880
tatgacaagt gcggagtatg tggaggagac aactccagct gtacaaagat tgttggaacc   2940
tttaataaga aaagtaaggg ttacactgac gtggtgagga ttcctgaagg ggcaacccac   3000
ataaaagttc gacagttcaa agccaaagac cagactagat tcactgccta tttagccctg   3060
aaaaagaaaa acggtgagta ccttatcaat ggaaagtaca tgatctccac ttcagagact   3120
atcattgaca tcaatggaac agtcatgaac tatagcggtt ggagccacag ggatgacttc   3180
ctgcatggca tgggctactc tgccacgaag gaaattctaa tagtgcagat tcttgcaaca   3240
gaccccacta aaccattaga tgtccgttat agcttttttg ttcccaagaa gtccactcca   3300
aaagtaaact ctgtcactag tcatggcagc aataaagtgg gatcacacac ttcgcagccg   3360
cagtgggtca cgggcccatg gctcgcctgc tctaggacct gtgacacagg ttggcacacc   3420
agaacggtgc agtgccagga tggaaaccgg aagttagcaa aaggatgtcc tctctcccaa   3480
aggccttctg cgtttaagca atgcttgttg aagaaatgtt agcctgtggt tatgatctta   3540
tgcacaaaga taactggagg attcagcact gatgcagtcg tggtgaacag gaggtctacc   3600
taacgcacag aaagtcatgc ttcagtgaca ttgtcaacag gagtccaatt atgggcagaa   3660
tctgctctct gtgaccaaaa gaggatgtgc actgcttcac gtgacagtgg tgaccttgca   3720
atatagaaaa acttgggagt tattgaacat cccctgggct acaagaaac actgatgaat    3780
gtaaaatcag gggacatttg aagatggcag aactgtctcc cccttgtcac ctacctctga   3840
tagaatgtct ttaatggtat cataatcatt ttcacccata atacacagta gcttcttctt   3900
actgtttgta aatacattct cccttggtat gtcactttat atcccctggt tctattaaaa   3960
tatccatata tatttctata aaaaagtgt ttgaccaaag taggtctgca gctatttcaa    4020
cttccttccg tttccagaaa gagctgtgga tattttactg gaaattaaga acttgctgct   4080
gttttaataa gatgtagtat attttctgac tacaggagat aaaatttcag tcaaaaaacc   4140
attttgacag caagtatctt ctgagaaatt ttgaaaagta aatagatctc agtgtatcta   4200
gtcacttaaa tacatacacg ggttcattta cttaaacctt tgactgcctg tattttttc    4260
aggtagctag ccaaattaat gcataatttc agatgtagaa gtagggtttg cgtgtgtgtg   4320
tgtgatcata ctcaagagtc taaaaactag tttccttgtg ttggaaattt aaaaggaaaa   4380
aaatcgtatt tcactgtgtt ttcaatttat attttcacaa ctactttctc tctccagagc   4440
tttcatctga tatctcacaa tgtatgatat acgtacaaaa cacacagcaa gttttctatc   4500
atgtccaaca cattcaacac tggtatacct cctaccagca agcctttaaa atgcatttgt   4560
gtttgcttat ttgttttgtt caagggttca gtaagaccta caatgttttg tatttcttga   4620
cttattttat tagaaacatt aaagatcact tggtagttag ccacattgag aagtggttat   4680
cattgttaat gtggttaatg ccaaaaagtg gttaatatta ataagactgt ttccacacca   4740
taggcaataa tttcttaatt taaaaaatct aagtatattc ctattgtact aaatattttt   4800
cccaactgga aagcacttga ttgtacccgt aagtgtttga gtgatgacat gtgatgattt   4860
tcagaaagtt gttgttttg tttccatagc ctgtttaagt aggttgtaag tttgaatagt    4920
tagacatgga aattatttta taagcacaca cctaaagata tctttttaga tgataaaatg   4980
```

```
tacaccccc catcaccaac ctcacaactt agaaaatcta agttgtttga tttctttggg    5040
atttcttttg ttgtgaaaca ctgcaaagcc aatttttctt tataaaaatt catagtaatc    5100
ctgccaaatg tgcctattgt taaagatttg catgtgaaga tcttagggaa ccactgtttg    5160
agttctacaa gctcatgaga gtttatttt attataagat gttttaata taaaagaatt    5220 atgtaactga tcactatatt acatcatttc agtgggccag gaaaatagat gtcttgctgt    5280
tttcagtatt ttcttaagaa attgctttta aaacaaataa ttgttttaca aaaccaataa    5340
ttatcctttg aattttcata gactgacttt gcttttgacg tagaaatttt ttttctcaat    5400
aaattatcac tttgagaaat gaggcctgta caaggctgat aacctatatg tgatggagat    5460
cacccaatgc caagggcaga aagcaaacct agttaaatag gtgagaaaaa aataataat    5520 cccagtgcca tttgtctgtg caaagagaat taggagagag gttaatgtta ctttttttcca    5580 ttttggaaat aattttaatc aagtaactca aatgtgacaa aatttatttt tatttttgt    5640 ggttatattc ccaacaacat taaaaatac tcgaggcata aatgtagttg tctcctactc    5700
tgcttctctt actatactca tacatttta atatggttta tcaatgattc atgtttccct    5760
caaatagtga tggtttacac ctgtcatgga aacaatccta gagagctcag agcaattaaa    5820
ccactattcc atgcttttaa gtagttttct ccaccttttt cttatgagtc tcactagatt    5880
gactgaggaa tgtatgtcta aattcctgga gaagatgata tggattggaa actgaaattc    5940
agagaaatgg agtgttcaat agataccacg aattgtgaac aaagggaaaa ttctatacaa    6000
ctcaatctaa gtcagtccac tttgacttcg tactgtcttt ccctttcca ttgttgcatc    6060 ttgaattttt taaaatgtct agaattcagg atgctagggg ctacttcttt aaaaaaaaaa    6120 aaaaaaaga attcgtctga aaatgctcag gtttgtaaga atctaatctc acttacataa    6180
ctaagcactc cataataagt tttattaagt acaaagggag ccagaaaaaa tgacatttat    6240
ttcttctaga tcagaaaaat ttaaattaag ccctgccttg ctgtttagaa atatgtgggc    6300
attgttataa tttattcaat aaatttatgt tcctttgcct tcctgtggaa acagttttat    6360
cccactaaac taggaattag gggataaatc acaaacaaaa aaaagttgc agcactgaaa    6420 aaaagtaatt tattgttttt gcaactggta tgtgaatttg tgtgataaaa ttattattc    6480 ttatttaaca aaaatatgtt caaattttc tatatttaaa atgttttgct gttgtcctac    6540
ttttaatttt atgcttcatg tttgtgtata aagtacactt ttacactttg tgagtttaca    6600
taatatacag cactggttgc ttttgtattt ttttacagaa agctttctgt gtgaagcagg    6660
tgtatatgta tatattcctc atgtattctt attctgatac tatcattttt ctttccaagg    6720
aaattttaat ctgtcatgac caatagtgtt cattacttgt gcctatgata ataggttttt    6780
tacatcacat taacactatt ttttccaagt cacaaataag aaaaacactt attcaatgaa    6840
acaaggtgca agttttaaat ttgggtacac aaatagccta gaagcttcct acagacgcta    6900
agacacagcc aataatcaga tcctttcact tcatcgagaa acttggacaa gtcgatattg    6960
atgtattaga tgaaagttgt ctacacacaa cttctgaggg atacaaacga taataaaacc    7020
aaatgttgtc tgtttctcct ttagaaacac ctcctaaaat taatatcatt tagtctctag    7080
tgtctgtagg attctacaga tgagcacaaa tagattgggt tgtataaca aatgctaata    7140 gtcataactg tttctacaaa tatggggtgt ccattaagag aatgtgatgt tttcctactg    7200
ctgttgaatc ccatggggtg attataggac ttgaaatagg cagagtcacc tctgatgaca    7260
tcagcttgcc tctgtgattt cacagtctga tcctggcaac aagacaaagc acccttggac    7320
```

```
acacagccaa tctctggttg tgatatttcc ccattgattc cttccttgtt aacaaggtca    7380
tttaatggt tcaggtgagg acagcagcca gattcaaagt ccagaatttg tgctgttaca     7440
tagagttcac actgtcaaat aacattgaat ttaataatga tcaaattttt ctagtagtct    7500
ttggcagagt gtataatctc attggcatga ttggtgaata ttactaatct ctttataatg    7560
aaagatgctt tacaaatacc ttatatttgc taacatttca aaactactaa ataaatgaaa    7620
tagccatgtg tacagaaatg gtcatttaaa gctttaatag aaccaaattc aagacaatgt    7680
atcatttaga cacacagaaa aggaacttgt atgttttccc tattattttt ctcatttgcc    7740
aacaatctat agttttaggt tatcaaacag atagatcaac ttaactggct agtacattga    7800
aaaatcttcc taagaatcct tgttagcat aatctataga gataatttct caaattatat     7860
catcatgatg catataaact ctataatgta taattgtgtt tcatttattt aatgtatgag    7920
aacatattga aatacaaaac catgcattag ccaaaaaatt ggaatacagg tagtgttcag    7980
atcagcaaaa cattcagtct ggtaaatgcc tgcctggggc tatgatatca ttctcaatgc    8040
aggttttatg gaaaaactaa agaatatgt tgttagatga tgttggtttt gaaaaaaaaa     8100
agacattaac atacacatta gttagcccag ttaattgcat tctactaata tagttgcaca    8160
ttagcaataa ttttgctgtc tctggtcttt attttgtggc ttcaactaac tggaccatgt    8220
ggactgtaaa ggtcaaatgg aaaaaacgag cagtggcccc tcatcctgta aggtactgct    8280
acatcagagt gacctaaaag tctaacactg tgaggaaaac tgtgatttgt aggaaaaaaa    8340
aaaaaaacaa ataaaaaaca gggcatgctt ttaattttt ttccactttc ctttggcaca     8400
cccaatgaac aattctaatt tttattgagg tgctaacatc tttcgtgacc gactgtcaaa    8460
tgtggtattt ttgagttact atttttctac atgattttac agtttgcaag aaagacctct    8520
aagctttgtg tcacggtagg gcacaacttg atactcaaaa tttgaaaaat aagcacatcc    8580
aatgattgtt ttgaccaaca gtggtcagtg acgtaaactg catgtgcatc tgaggacatt    8640
taagggtca ttaaaatttg aggagcatca ggccggagta gcagactttt agatgagtca     8700
tatttcagca ttcactaagt cctcagcatt ccattcaaac tgtcgtgtat atttggcctg    8760
attttttttc aagctttgca ataatttatg ttattggtaa acacttggtg actatatctc    8820
agccttttct ttaacaactc acaatatatt agaaacacgt ctacctatac tgagagtata    8880
tttacaatag aagaacatac tgtatgtgac tttgtaaagc tagacttttg attaagaaat    8940
atataatctc tggatgctat ttttgcatta tacactcagg cacaacgtaa accttgatgg    9000
ctcatcttgc tacaattacg agttgaaaaa cactacttac gtatttgtat gacctattag    9060
tcagaggaaa tcatacatat gctttgtaaa tagactttgc agataactaa atagactgaa    9120
gaaatatgtt gcatttgata gaagcaattg cataaatatt tggtttctat attagagtct    9180
gtgagtaaag tcaagtaata aacctaagta ggtataacag ttttaaac cttgaaactt      9240
gctttgatgg tagagaaaat cattgaagat ttacatactg tatataagat gtaaaatgta    9300
cgctgcttat taccctcaat tttccagaag caatggtata taatgcagtt gaaaaaccaa    9360
aaatcttgga aaactaagac gggtcttgtt taaaatgtct ctcagctttg caaccttca     9420
aatcttaatc aactatttaa agcattactg tgtcttgtag cctgcattcc acaacagctc    9480
tgttattcag gtaaaagact tgaactgagc cgtttgggac ctatactgta atattttcat    9540
tgaggaacaa tatcctatt tgtaaagcat ttccctatgt gtgactttaa actgtaaaat     9600
taaacactgc ttttgtgggt tcagtgggca taataaaat aaattgtaaa ctaggttaaa     9660
gta                                                                  9663
```

<210> SEQ ID NO 2
<211> LENGTH: 930
<212> TYPE: PRT
<213> ORGANISM: Homo sapiens

<400> SEQUENCE: 2

```
Met Leu Leu Gly Trp Ala Ser Leu Leu Cys Ala Phe Arg Leu Pro
1               5                   10                  15

Leu Ala Ala Val Gly Pro Ala Ala Thr Pro Ala Gln Asp Lys Ala Gly
                20                  25                  30

Gln Pro Pro Thr Ala Ala Ala Ala Gln Pro Arg Arg Arg Gln Gly
            35                  40                  45

Glu Glu Val Gln Glu Arg Ala Glu Pro Pro Gly His Pro His Pro Leu
    50                  55                  60

Ala Gln Arg Arg Arg Ser Lys Gly Leu Val Gln Asn Ile Asp Gln Leu
65                  70                  75                  80

Tyr Ser Gly Gly Lys Val Gly Tyr Leu Val Tyr Ala Gly Gly Arg
                85                  90                  95

Arg Phe Leu Leu Asp Leu Glu Arg Asp Gly Ser Val Gly Ile Ala Gly
                100                 105                 110

Phe Val Pro Ala Gly Gly Gly Thr Ser Ala Pro Trp Arg His Arg Ser
            115                 120                 125

His Cys Phe Tyr Arg Gly Thr Val Asp Gly Ser Pro Arg Ser Leu Ala
        130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
```

```
            370                 375                 380
Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
                420                 425                 430

Thr Glu Asp Lys Arg Leu Met Ser Ser Ile Leu Thr Ser Ile Asp Ala
                435                 440                 445

Ser Lys Pro Trp Ser Lys Cys Thr Ser Ala Thr Ile Thr Glu Phe Leu
                450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Val Arg Gln Gly Gln Met Val
                515                 520                 525

Cys Leu Thr Lys Lys Leu Pro Ala Val Glu Gly Thr Pro Cys Gly Lys
                530                 535                 540

Gly Arg Ile Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Ser Trp
                565                 570                 575

Gly Gln Cys Ser Arg Ser Cys Gly Gly Val Gln Phe Ala Tyr Arg
                580                 585                 590

His Cys Asn Asn Pro Ala Pro Arg Asn Gly Arg Tyr Cys Thr Gly
                595                 600                 605

Lys Arg Ala Ile Tyr Arg Ser Cys Ser Leu Met Pro Cys Pro Pro Asn
                610                 615                 620

Gly Lys Ser Phe Arg His Glu Gln Cys Glu Ala Lys Asn Gly Tyr Gln
625                 630                 635                 640

Ser Asp Ala Lys Gly Val Lys Thr Phe Val Glu Trp Val Pro Lys Tyr
                645                 650                 655

Ala Gly Val Leu Pro Ala Asp Val Cys Lys Leu Thr Cys Arg Ala Lys
                660                 665                 670

Gly Thr Gly Tyr Tyr Val Val Phe Ser Pro Lys Val Thr Asp Gly Thr
                675                 680                 685

Glu Cys Arg Leu Tyr Ser Asn Ser Val Cys Val Arg Gly Lys Cys Val
                690                 695                 700

Arg Thr Gly Cys Asp Gly Ile Ile Gly Ser Lys Leu Gln Tyr Asp Lys
705                 710                 715                 720

Cys Gly Val Cys Gly Gly Asp Asn Ser Ser Cys Thr Lys Ile Val Gly
                725                 730                 735

Thr Phe Asn Lys Lys Ser Lys Gly Tyr Thr Asp Val Val Arg Ile Pro
                740                 745                 750

Glu Gly Ala Thr His Ile Lys Val Arg Gln Phe Lys Ala Lys Asp Gln
                755                 760                 765

Thr Arg Phe Thr Ala Tyr Leu Ala Leu Lys Lys Lys Asn Gly Glu Tyr
                770                 775                 780

Leu Ile Asn Gly Lys Tyr Met Ile Ser Thr Ser Glu Thr Ile Ile Asp
785                 790                 795                 800
```

```
Ile Asn Gly Thr Val Met Asn Tyr Ser Gly Trp Ser His Arg Asp Asp
                805                 810                 815

Phe Leu His Gly Met Gly Tyr Ser Ala Thr Lys Glu Ile Leu Ile Val
            820                 825                 830

Gln Ile Leu Ala Thr Asp Pro Thr Lys Pro Leu Asp Val Arg Tyr Ser
        835                 840                 845

Phe Phe Val Pro Lys Lys Ser Thr Pro Lys Val Asn Ser Val Thr Ser
    850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
            900                 905                 910

Cys Pro Leu Ser Gln Arg Pro Ser Ala Phe Lys Gln Cys Leu Leu Lys
        915                 920                 925

Lys Cys
    930

<210> SEQ ID NO 3
<211> LENGTH: 19
<212> TYPE: DNA
<213> ORGANISM: Artificial Sequence
<220> FEATURE:
<223> OTHER INFORMATION: chemically synthesized

<400> SEQUENCE: 3
gcucaaagcu gcaguauga                                              19

<210> SEQ ID NO 4
<211> LENGTH: 19
<212> TYPE: DNA
<213> ORGANISM: Artificial Sequence
<220> FEATURE:
<223> OTHER INFORMATION: chemically synthesized

<400> SEQUENCE: 4
gaaguccacu ccaaaagua                                              19

<210> SEQ ID NO 5
<211> LENGTH: 19
<212> TYPE: DNA
<213> ORGANISM: Artificial Sequence
<220> FEATURE:
<223> OTHER INFORMATION: chemically synthesized

<400> SEQUENCE: 5
gcacuacgau gcagcuauc                                              19

<210> SEQ ID NO 6
<211> LENGTH: 19
<212> TYPE: DNA
<213> ORGANISM: Artificial Sequence
<220> FEATURE:
<223> OTHER INFORMATION: chemically synthesized

<400> SEQUENCE: 6
cgaaggaaau ucuaauagu                                              19

<210> SEQ ID NO 7
<211> LENGTH: 32
```

```
<212> TYPE: DNA
<213> ORGANISM: Artificial Sequence
<220> FEATURE:
<223> OTHER INFORMATION: chemically synthesized

<400> SEQUENCE: 7
ccggtctaac atttcttcaa caagcagacc gg                                    32

<210> SEQ ID NO 8
<211> LENGTH: 32
<212> TYPE: DNA
<213> ORGANISM: Artificial Sequence
<220> FEATURE:
<223> OTHER INFORMATION: chemcially synthesized

<400> SEQUENCE: 8
ccggtcttat acacaaacat gaagcagacc gg                                    32

<210> SEQ ID NO 9
<211> LENGTH: 32
<212> TYPE: DNA
<213> ORGANISM: Artificial Sequence
<220> FEATURE:
<223> OTHER INFORMATION: chemcially synthesized

<400> SEQUENCE: 9
ccggtctaca tcttattaaa acagcagacc gg                                    32

<210> SEQ ID NO 10
<211> LENGTH: 4410
<212> TYPE: DNA
<213> ORGANISM: Homo sapiens

<400> SEQUENCE: 10
ggggagaacc cacagggaga cccacagaca catatgcacg agagagacag aggaggaaag        60
agacagagac aaaggcacag cggaagaagg cagagacagg gcaggcacag aagcggccca       120
gacagagtcc tacagaggga gaggccagag aagctgcaga gacacaggc agggagagac        180 aaagatccag gaaaggaggg ctcaggagga gagtttggag aagccagacc cctgggcacc       240
tctcccaagc ccaaggacta agttttctcc atttccttta acggtcctca gcccttctga       300
aaactttgcc tctgaccttg gcaggagtcc aagcccccag gctacagaga ggagctttcc       360
aaagctaggg tgtggaggac ttggtgccct agacggcctc agtccctccc agctgcagta       420
ccagtgccat gtcccagaca ggctcgcatc ccgggagggg cttggcaggg cgctggctgt       480
ggggagccca accctgcctc ctgctcccca ttgtgccgct ctcctggctg gtgtggctgc       540
ttctgctact gctggcctct ctcctgccct cagcccggct ggccagcccc ctccccgggg       600
aggaggagat cgtgtttcca gagaagctca acggcagcgt cctgcctggc tcgggcgccc       660
ctgccaggct gttgtgccgc ttgcaggcct ttggggagac gctgctacta gagctggagc       720
aggactccgg tgtgcaggtc gagggggctga cagtgcagta cctgggccag gcgcctgagc       780
tgctgggtgg agcagagcct ggcacctacc tgactggcac catcaatgga gatccggagt       840
cggtggcatc tctgcactgg gatggggag ccctgttagg cgtgttacaa tatcgggggg        900
ctgaactcca cctccagccc ctggaggag caccccctaa ctctgctggg gaccctgggg        960
ctcacatcct acgccggaag agtcctgcca gcggtcaagg tcccatgtgc aacgtcaagg      1020
ctcctcttgg aagccccagc cccagacccc gaagagccaa cgcctttgct tcactgagta      1080
gatttgtgga gacactggtg gtggcagatg acaagatggc cgcattccac ggtgcgggc       1140
```

| | |
|---|---|
| taaagcgcta cctgctaaca gtgatggcag cagcagccaa ggccttcaag cacccaagca | 1200 |
| tccgcaatcc tgtcagcttg gtggtgactc ggctagtgat cctggggtca ggcgaggagg | 1260 |
| ggccccaagt ggggcccagt gctgcccaga ccctgcgcag cttctgtgcc tggcagcggg | 1320 |
| gcctcaacac ccctgaggac tcggaccctg accactttga cacagccatt ctgtttaccc | 1380 |
| gtcaggacct gtgtggagtc tccacttgcg acacgctggg tatggctgat gtgggcaccg | 1440 |
| tctgtgaccc ggctcggagc tgtgccattg tggaggatga tgggctccag tcagccttca | 1500 |
| ctgctgctca tgaactgggt catgtcttca acatgctcca tgacaactcc aagccatgca | 1560 |
| tcagtttgaa tgggcctttg agcacctctc gccatgtcat ggcccctgtg atggctcatg | 1620 |
| tggatcctga ggagccctgg tcccctgca gtgcccgctt catcactgac ttcctggaca | 1680 |
| atggctatgg gcactgtctc ttagacaaac cagaggctcc attgcatctg cctgtgactt | 1740 |
| tccctggcaa ggactatgat gctgaccgcc agtgccagct gaccttcggg cccgactcac | 1800 |
| gccattgtcc acagctgccg ccgccctgtg ctgccctctg gtgctctggc cacctcaatg | 1860 |
| gccatgccat gtgccagacc aaacactcgc cctgggccga tggcacaccc tgcgggcccg | 1920 |
| cacaggcctg catgggtggt cgctgcctcc acatggacca gctccaggac ttcaatattc | 1980 |
| cacaggctgg tggctggggt ccttggggac catggggtga ctgctctcgg acctgtgggg | 2040 |
| gtggtgtcca gttctcctcc cgagactgca cgaggcctgt cccccggaat ggtggcaagt | 2100 |
| actgtgaggg ccgccgtacc cgcttccgct cctgcaacac tgaggactgc caactggct | 2160 |
| cagccctgac cttccgcgag gagcagtgtg ctgcctacaa ccaccgcacc gacctcttca | 2220 |
| agagcttccc agggccatg gactgggttc ctcgctacac aggcgtggcc ccccaggacc | 2280 |
| agtgcaaact cacctgccag gcccaggcac tgggctacta ctatgtgctg gagccacggg | 2340 |
| tggtagatgg gaccccctgt tccccggaca gctcctcggt ctgtgtccag ggccgatgca | 2400 |
| tccatgctgg ctgtgatcgc atcattggct ccaagaagaa gtttgacaag tgcatggtgt | 2460 |
| gcggagggga cggttctggt tgcagcaagc agtcaggctc cttcaggaaa ttcaggtacg | 2520 |
| gatacaacaa tgtggtcact atccccgcgg gggccaccca cattcttgtc cggcagcagg | 2580 |
| gaaaccctgg ccaccggagc atctacttgg ccctgaagct gccagatggc tcctatgccc | 2640 |
| tcaatggtga atacacgctg atgccctccc ccacagatgt ggtactgcct ggggcagtca | 2700 |
| gcttgcgcta cagcggggcc actgcagcct cagagacact gtcaggccat gggccactgg | 2760 |
| cccagccttt gacactgcaa gtcctagtgg ctggcaaccc ccaggacaca cgcctccgat | 2820 |
| acagcttctt cgtgccccgg ccgacccctt caacgccacg ccccactccc caggactggc | 2880 |
| tgcaccgaag agcacagatt ctggagatcc ttcggcggcg cccctgggcg ggcaggaaat | 2940 |
| aacctcacta tcccggctgc cctttctggg caccggggcc tcggacttag ctgggagaaa | 3000 |
| gagagagctt ctgttgctgc tcatgctaa gactcagtgg ggaggggctg tgggcgtgag | 3060 |
| acctgcccct cctctctgcc ctaatgcgca ggctggccct gccctggttt cctgccctgg | 3120 |
| gaggcagtga tgggttagtg gatggaaggg gctgacagac agccctccat ctaaactgcc | 3180 |
| ccctctgccc tgcgggtcac aggagggagg gggaaggcag ggagggcctg ggccccagtt | 3240 |
| gtatttattt agtatttatt cacttttatt tagcaccagg gaaggggaca aggactaggg | 3300 |
| tcctggggaa cctgaccct gacccctcat agccctcacc ctggggctag gaaatccagg | 3360 |
| gtggtggtga taggtataag tggtgtgtgt atgcgtgtgt gtgtgtgtga aaatgtgtgt | 3420 |
| gtgcttatgt atgaggtaca acctgttctg cttttcctctt cctgaatttt atttttttggg | 3480 |
| aaaagaaaag tcaagggtag ggtgggcctt cagggagtga gggattatct tttttttttt | 3540 |

-continued

```
ttctttctttt ctttctttttt ttttttttgag acagaatctc gctctgtcgc ccaggctgga    3600
gtgcaatggc acaatctcgg ctcactgcat cctccgcctc ccgggttcaa gtgattctca      3660
tgcctcagcc tcctgagtag ctgggattac aggctcctgc caccacgccc ggctaatttt      3720
tgttttgttt tgtttggaga cagagtctcg ctattgtcac cagggctgga atgatttcag     3780
ctcactgcaa ccttcgccac ctgggttcca gcaattctcc tgcctcagcc tcccgagtag      3840
ctgagattat aggcacctac caccacgccc ggctaatttt tgtattttta gtagagacgg      3900
ggtttcacca tgttggccag gctggtctcg aactcctgac cttaggtgat ccactcgcct      3960
tcatctccca aagtgctggg attacaggcg tgagccaccg tgcctggcca cgcccaacta      4020
attttgtat tttagtaga cagggtttt caccatgttg gccaggctgc tcttgaactc         4080
ctgacctcag gtaatcgacc tgcctcggcc tcccaaagtg ctgggattac aggtgtgagc      4140
caccacgccc ggtacatatt ttttaaattg aattctacta tttatgtgat ccttttggag     4200
tcagacagat gtggttgcat cctaactcca tgtctctgag cattagattt ctcatttgcc     4260
aataataata cctcccttag aagtttgttg tgaggattaa ataatgtaaa taagaactaa     4320
gcataacact caaaaaaaaa aaaaaaaaaa aaaaaaaaaa aaaaaaaaaa aaaaaaaaaa     4380
aaaaaaaaaa aaaaaaaaaa aaaaaaaaaa                                      4410
```

<210> SEQ ID NO 11
<211> LENGTH: 837
<212> TYPE: PRT
<213> ORGANISM: Homo sapiens

<400> SEQUENCE: 11

```
Met Ser Gln Thr Gly Ser His Pro Gly Arg Gly Leu Ala Gly Arg Trp
1               5                   10                  15

Leu Trp Gly Ala Gln Pro Cys Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Gly Ala Glu Pro Gly Thr Tyr Leu
        115                 120                 125

Thr Gly Thr Ile Asn Gly Asp Pro Glu Ser Val Ala Ser Leu His Trp
130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
```

```
            210                 215                 220
Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
                260                 265                 270

Gly Ser Gly Glu Glu Gly Pro Gln Val Gly Pro Ser Ala Ala Gln Thr
                275                 280                 285

Leu Arg Ser Phe Cys Ala Trp Gln Arg Gly Leu Asn Thr Pro Glu Asp
            290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
                340                 345                 350

Leu Gln Ser Ala Phe Thr Ala Ala His Glu Leu Gly His Val Phe Asn
            355                 360                 365

Met Leu His Asp Asn Ser Lys Pro Cys Ile Ser Leu Asn Gly Pro Leu
370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
                420                 425                 430

His Leu Pro Val Thr Phe Pro Gly Lys Asp Tyr Asp Ala Asp Arg Gln
                435                 440                 445

Cys Gln Leu Thr Phe Gly Pro Asp Ser Arg His Cys Pro Gln Leu Pro
            450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
                500                 505                 510

Gln Asp Phe Asn Ile Pro Gln Ala Gly Gly Trp Gly Pro Trp Gly Pro
            515                 520                 525

Trp Gly Asp Cys Ser Arg Thr Cys Gly Gly Val Gln Phe Ser Ser
530                 535                 540

Arg Asp Cys Thr Arg Pro Val Pro Arg Asn Gly Gly Lys Tyr Cys Glu
545                 550                 555                 560

Gly Arg Arg Thr Arg Phe Arg Ser Cys Asn Thr Glu Asp Cys Pro Thr
                565                 570                 575

Gly Ser Ala Leu Thr Phe Arg Glu Glu Gln Cys Ala Ala Tyr Asn His
                580                 585                 590

Arg Thr Asp Leu Phe Lys Ser Phe Pro Gly Pro Met Asp Trp Val Pro
                595                 600                 605

Arg Tyr Thr Gly Val Ala Pro Gln Asp Gln Cys Lys Leu Thr Cys Gln
                610                 615                 620

Ala Gln Ala Leu Gly Tyr Tyr Tyr Val Leu Glu Pro Arg Val Val Asp
625                 630                 635                 640
```

```
Gly Thr Pro Cys Ser Pro Asp Ser Ser Val Cys Val Gln Gly Arg
                645                 650                 655

Cys Ile His Ala Gly Cys Asp Arg Ile Ile Gly Ser Lys Lys Phe
            660                 665                 670

Asp Lys Cys Met Val Cys Gly Gly Asp Gly Ser Gly Cys Ser Lys Gln
        675                 680                 685

Ser Gly Ser Phe Arg Lys Phe Arg Tyr Gly Tyr Asn Asn Val Val Thr
690                 695                 700

Ile Pro Ala Gly Ala Thr His Ile Leu Val Arg Gln Gln Gly Asn Pro
705                 710                 715                 720

Gly His Arg Ser Ile Tyr Leu Ala Leu Lys Leu Pro Asp Gly Ser Tyr
                725                 730                 735

Ala Leu Asn Gly Glu Tyr Thr Leu Met Pro Ser Pro Thr Asp Val Val
            740                 745                 750

Leu Pro Gly Ala Val Ser Leu Arg Tyr Ser Gly Ala Thr Ala Ala Ser
        755                 760                 765

Glu Thr Leu Ser Gly His Gly Pro Leu Ala Gln Pro Leu Thr Leu Gln
770                 775                 780

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
                805                 810                 815

Trp Leu His Arg Arg Ala Gln Ile Leu Glu Ile Leu Arg Arg Arg Pro
            820                 825                 830

Trp Ala Gly Arg Lys
        835

<210> SEQ ID NO 12
<211> LENGTH: 19
<212> TYPE: DNA
<213> ORGANISM: Artificial Sequence
<220> FEATURE:
<223> OTHER INFORMATION: chemcically synthesized

<400> SEQUENCE: 12
ccgcaauccu gucagcuug                                                  19

<210> SEQ ID NO 13
<211> LENGTH: 19
<212> TYPE: DNA
<213> ORGANISM: Artificial Sequence
<220> FEATURE:
<223> OTHER INFORMATION: chemically synthesized

<400> SEQUENCE: 13
gcgcuuugcu ucacugagu                                                  19

<210> SEQ ID NO 14
<211> LENGTH: 19
<212> TYPE: DNA
<213> ORGANISM: Artificial Sequence
<220> FEATURE:
<223> OTHER INFORMATION: chemcially synthesized

<400> SEQUENCE: 14
ggacacacgc cuccgauac                                                  19

<210> SEQ ID NO 15
<211> LENGTH: 19
```

```
<212> TYPE: DNA
<213> ORGANISM: Artificial Sequence
<220> FEATURE:
<223> OTHER INFORMATION: chemically synthesized

<400> SEQUENCE: 15
gcaccgaaga gcacagauu                                                    19

<210> SEQ ID NO 16
<211> LENGTH: 32
<212> TYPE: DNA
<213> ORGANISM: Artificial Sequence
<220> FEATURE:
<223> OTHER INFORMATION: chemcially synthesized

<400> SEQUENCE: 16
ccggtctttt cacacacaca cacacggacc gg                                     32

<210> SEQ ID NO 17
<211> LENGTH: 32
<212> TYPE: DNA
<213> ORGANISM: Artificial Sequence
<220> FEATURE:
<223> OTHER INFORMATION: chemcially synthesized

<400> SEQUENCE: 17
ccggtctaaa aatacaaaaa ttagccgacc gg                                     32

<210> SEQ ID NO 18
<211> LENGTH: 32
<212> TYPE: DNA
<213> ORGANISM: Artificial Sequence
<220> FEATURE:
<223> OTHER INFORMATION: chemically synthesized

<400> SEQUENCE: 18
ccggtcttgt ctctgtctct ttcctcgacc gg                                     32

<210> SEQ ID NO 19
<211> LENGTH: 2735
<212> TYPE: DNA
<213> ORGANISM: Homo sapiens

<400> SEQUENCE: 19
acaacagtcc ccaggcatca ccattcaaga tgcatccagg ggtcctggct gccttcctct        60
tcttgagctg gactcattgt cgggccctgc cccttcccag tggtggtgat gaagatgatt       120
tgtctgagga agacctccag tttgcagagc gctacctgag atcatactac catcctacaa       180
atctcgcggg aatcctgaag gagaatgcag caagctccat gactgagagg ctccgagaaa       240
tgcagtcttt cttcggctta gaggtgactg gcaaacttga cgataacacc ttagatgtca       300
tgaaaaagcc aagatgcggg gttcctgatg tgggtgaata caatgttttc cctcgaactc       360
ttaaatggtc caaaatgaat ttaacctaca gaattgtgaa ttacccccct gatatgactc       420
attctgaagt cgaaaaggca ttcaaaaaag ccttcaaagt ttggtccgat gtaactcctc       480
tgaattttac cagacttcac gatggcattg ctgacatcat gatctctttt ggaattaagg       540
agcatggcga cttctaccca tttgatgggc cctctggcct gctggctcat gcttttcctc       600
ctgggccaaa ttatggagga gatgcccatt ttgatgatga tgaaacctgg acaagtagtt       660
ccaaaggcta caacttgttt cttgttgctg cgcatgagtt cggccactcc ttaggtcttg       720
accactccaa ggaccctgga gcactcatgt ttcctatcta cacctacacc ggcaaaagcc       780
```

```
actttatgct tcctgatgac gatgtacaag ggatccagtc tctctatggt ccaggagatg    840
aagaccccaa ccctaaacat ccaaaaacgc cagacaaatg tgacccttcc ttatcccttg    900
atgccattac cagtctccga ggagaaacaa tgatctttaa agacagattc ttctggcgcc    960
tgcatcctca gcaggttgat gcggagctgt ttttaacgaa atcattttgg ccagaacttc   1020
ccaaccgtat tgatgctgca tatgagcacc cttctcatga cctcatcttc atcttcagag   1080
gtagaaaatt ttgggctctt aatggttatg acattctgga aggttatccc aaaaaaatat   1140
ctgaactggg tcttccaaaa gaagttaaga agataagtgc agctgttcac tttgaggata   1200
caggcaagac tctcctgttc tcaggaaacc aggtctggag atatgatgat actaaccata   1260
ttatggataa agactatccg agactaatag aagaagactt cccaggaatt ggtgataaag   1320
tagatgctgt ctatgagaaa aatggttata tctatttttt caacggaccc atacagtttg   1380
aatacagcat ctggagtaac cgtattgttc gcgtcatgcc agcaaattcc attttgtggt   1440
gttaagtgtc ttttaaaaa ttgttattta atcctgaag agcatttggg gtaatacttc   1500
cagaagtgcg gggtagggga agaagagcta tcaggagaaa gcttggttct gtgaacaagc   1560
ttcagtaagt tatctttgaa tatgtagtat ctatatgact atgcgtggct ggaaccacat   1620
tgaagaatgt tagagtaatg aaatggagga tctctaaaga gcatctgatt cttgttgctg   1680
tacaaaagca atggttgatg atacttccca caccacaaat gggacacatg gtctgtcaat   1740
gagagcataa tttaaaaata tatttataag gaaattttac aagggcataa agtaaataca   1800
tgcatataat gaataaatca ttcttactaa aaagtataaa atagtatgaa atggaaatt   1860
tgggagagcc atacataaaa gaaataaacc aaaggaaaat gtctgtaata atagactgta   1920
acttccaaat aaataatttt catttgcac tgaggatatt cagatgtatg tgcccttctt   1980
cacacagaca ctaacgaaat atcaaagtca ttaaagacag gagacaaaag agcagtggta   2040
agaatagtag atgtggcctt tgaattctgt ttaatttca cttttggcaa tgactcaaag   2100
tctgctctca tataagacaa atattccttt gcatattata aaggataaag aaggatgatg   2160
tcttttatt aaaatatttc aggttcttca gaagtcacac attacaaagt taaaattgtt   2220
atcaaaatag tctaaggcca tggcatccct ttttcataaa ttatttgatt atttaagact   2280
aaaagttgca ttttaacct atttaccta gctaattatt taattgtcca gtttgtcttg   2340
gatatatagg ctatttcta aagacttgta tagcatgaaa taaatatat cttataaagt   2400
ggaagtatgt atattaaaaa agagacatcc aaatttttt ttaaagcagt ctactagatt   2460
gtgatccctt gagatatgga aggatgcctt tttttctctg catttaaaaa aatcccccag   2520
cacttcccac agtgcctatt gatacttggg gagggtgctt ggcacttatt gaatatatga   2580
tcggccatca agggaagaac tattgtgctc agagacactg ttgataaaaa ctcaggcaaa   2640
gaaaatgaaa tgcatatttg caaagtgtat taggaagtgt ttatgttgtt tataataaaa   2700
atatattttc aacagacaaa aaaaaaaaaa aaaaa                               2735
```

<210> SEQ ID NO 20
<211> LENGTH: 471
<212> TYPE: PRT
<213> ORGANISM: Homo sapiens

<400> SEQUENCE: 20

Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
            35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
            115                 120                 125

Met Thr His Ser Glu Val Glu Lys Ala Phe Lys Lys Ala Phe Lys Val
        130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Asp Glu Thr Trp Thr
            195                 200                 205

Ser Ser Ser Lys Gly Tyr Asn Leu Phe Leu Val Ala Ala His Glu Phe
        210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
        275                 280                 285

Ser Leu Asp Ala Ile Thr Ser Leu Arg Gly Glu Thr Met Ile Phe Lys
        290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
            340                 345                 350

Lys Phe Trp Ala Leu Asn Gly Tyr Asp Ile Leu Glu Gly Tyr Pro Lys
            355                 360                 365

Lys Ile Ser Glu Leu Gly Leu Pro Lys Glu Val Lys Lys Ile Ser Ala
        370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
            420                 425                 430

Ala Val Tyr Glu Lys Asn Gly Tyr Ile Tyr Phe Phe Asn Gly Pro Ile
            435                 440                 445

Gln Phe Glu Tyr Ser Ile Trp Ser Asn Arg Ile Val Arg Val Met Pro
            450                 455                 460

Ala Asn Ser Ile Leu Trp Cys
465                 470

<210> SEQ ID NO 21
<211> LENGTH: 20
<212> TYPE: DNA
<213> ORGANISM: Artificial Sequence
<220> FEATURE:
<223> OTHER INFORMATION: chemically synthesized

<400> SEQUENCE: 21
uuucacacac acacacacgc                                              20

<210> SEQ ID NO 22
<211> LENGTH: 20
<212> TYPE: DNA
<213> ORGANISM: Artificial Sequence
<220> FEATURE:
<223> OTHER INFORMATION: chemically synthesized

<400> SEQUENCE: 22
uuuucacaca cacacacacg                                              20

<210> SEQ ID NO 23
<211> LENGTH: 20
<212> TYPE: DNA
<213> ORGANISM: Artificial Sequence
<220> FEATURE:
<223> OTHER INFORMATION: chemically synthesized

<400> SEQUENCE: 23
uaaaaauaca aaaauuagcc                                              20

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized

<400> SEQUENCE: 24
uuugucucug ucucuuuccu                                              20

<210> SEQ ID NO 25
<211> LENGTH: 32
<212> TYPE: DNA
<213> ORGANISM: Artificial Sequence
<220> FEATURE:
<223> OTHER INFORMATION: chemically synthesized

<400> SEQUENCE: 25
ccggtctaca cacaccactt atacctgacc gg                                32

<210> SEQ ID NO 26
<211> LENGTH: 32
<212> TYPE: DNA
<213> ORGANISM: Artificial Sequence
<220> FEATURE:
<223> OTHER INFORMATION: chemcially synthesized

<400> SEQUENCE: 26
ccggtctata atctcagcta ctcggggacc gg                                32

```
<210> SEQ ID NO 27
<211> LENGTH: 32
<212> TYPE: DNA
<213> ORGANISM: Artificial Sequence
<220> FEATURE:
<223> OTHER INFORMATION: chemcially synthesized

<400> SEQUENCE: 27
ccggtcaaac aaaacaaaaa ttagccgacc gg                                     32

<210> SEQ ID NO 28
<211> LENGTH: 1903
<212> TYPE: DNA
<213> ORGANISM: Homo sapiens

<400> SEQUENCE: 28
agcatgagtc agacagcctc tggctttctg gaagggcaag gactctatat atacagaggg       60
agcttcctag ctgggatatt ggagcagcaa gaggctggga agccatcact taccttgcac      120
tgagaaagaa gacaaaggca agttgaaaag cggagaaata gtgcccagt ggttgaaaaa       180 ttgaagcaaa tgcaggaatt ctttgggctg aaagtgactg gaaaccaga tgctgaaacc       240 ctgaaggtga tgaagcagcc cagatgtgga gtgcctgatg tggctcagtt tgtcctcact      300
gaggggaacc ctcgctggga gcaaacacat ctgacctaca ggattgaaaa ttacacgcca      360
gatttgccaa gagcagatgt ggaccatgcc attgagaaag ccttccaact ctggagtaat      420
gtcacacctc tgacattcac caaggtctct gagggtcaag cagacatcat gatatctttt      480
gtcaggggag atcatcggga caactctcct tttgatggac ctggaggaaa tcttgctcat      540
gcttttcaac caggcccagg tattggaggg gatgctcatt ttgatgaaga tgaaaggtgg      600
accaacaatt tcagagagta caacttacat cgtgttgcag ctcatgaact cggccattct      660
cttggactct cccattctac tgatatcggg gctttgatgt accctagcta caccttcagt      720
ggtgatgttc agctagctca ggatgacatt gatggcatcc aagccatata tggacgttcc      780
caaaatcctg tccagcccat cggcccacaa accccaaaag cgtgtgacag taagctaacc      840
tttgatgcta taactacgat tcggggagaa gtgatgttct ttaaagacag attctacatg      900
cgcacaaatc ccttctaccc ggaagttgag ctcaatttca tttctgtttt ctggccacaa      960
ctgccaaatg gcttgaagc tgcttacgaa tttgccgaca gagatgaagt ccggttttc      1020 aaagggaata agtactgggc tgttcaggga cagaatgtgc tacacggata ccccaaggac     1080
atctacagct cctttggctt ccctagaact gtgaagcata tcgatgctgc tctttctgag     1140
gaaaacactg gaaaacccta cttctttgtt gctaacaaat actggaggta tgatgaatat     1200
aaacgatcta tggatccagg ttatcccaaa atgatagcac atgactttcc tggaattggc     1260
cacaaagttg atgcagtttt catgaaagat ggatttttct atttctttca tggaacaaga     1320
caatacaaat ttgatcctaa aacgaagaga attttgactc tccagaaagc taatagctgg     1380
ttcaactgca ggaaaaattg aacattacta atttgaatgg aaaacacatg gtgtgagtcc     1440
aaagaaggtg ttttcctgaa gaactgtcta ttttctcagt catttttaac ctctagagtc     1500
actgatacac agaatataat cttatttata cctcagtttg catattttt tactatttag     1560 aatgtagccc ttttttgtact gatataaattt agttccacaa atggtgggta caaaaagtca     1620
agtttgtggc ttatggattc atataggcca gagttgcaaa gatcttttcc agagtatgca     1680
actctgacgt tgatcccaga gagcagcttc agtgacaaac atatcctttc aagacagaaa     1740
gagacaggag acatgagtct tgccggagg aaaagcagct caagaacaca tgtgcagtca     1800
```

```
ctggtgtcac cctggatagg caagggataa ctcttctaac acaaataag tgttttatgt    1860 ttggaataaa gtcaaccttg tttctactgt tttatacact ttc                    1903
```

<210> SEQ ID NO 29
<211> LENGTH: 403
<212> TYPE: PRT
<213> ORGANISM: Homo sapiens

<400> SEQUENCE: 29

```
Met Gln Glu Phe Phe Gly Leu Lys Val Thr Gly Lys Pro Asp Ala Glu
1               5                   10                  15

Thr Leu Lys Val Met Lys Gln Pro Arg Cys Gly Val Pro Asp Val Ala
                20                  25                  30

Gln Phe Val Leu Thr Glu Gly Asn Pro Arg Trp Glu Gln Thr His Leu
            35                  40                  45

Thr Tyr Arg Ile Glu Asn Tyr Thr Pro Asp Leu Pro Arg Ala Asp Val
        50                  55                  60

Asp His Ala Ile Glu Lys Ala Phe Gln Leu Trp Ser Asn Val Thr Pro
65                  70                  75                  80

Leu Thr Phe Thr Lys Val Ser Glu Gly Gln Ala Asp Ile Met Ile Ser
                85                  90                  95

Phe Val Arg Gly Asp His Arg Asp Asn Ser Pro Phe Asp Gly Pro Gly
                100                 105                 110

Gly Asn Leu Ala His Ala Phe Gln Pro Gly Pro Gly Ile Gly Gly Asp
            115                 120                 125

Ala His Phe Asp Glu Asp Glu Arg Trp Thr Asn Asn Phe Arg Glu Tyr
        130                 135                 140

Asn Leu His Arg Val Ala Ala His Glu Leu Gly His Ser Leu Gly Leu
145                 150                 155                 160

Ser His Ser Thr Asp Ile Gly Ala Leu Met Tyr Pro Ser Tyr Thr Phe
                165                 170                 175

Ser Gly Asp Val Gln Leu Ala Gln Asp Asp Ile Asp Gly Ile Gln Ala
            180                 185                 190

Ile Tyr Gly Arg Ser Gln Asn Pro Val Gln Pro Ile Gly Pro Gln Thr
        195                 200                 205

Pro Lys Ala Cys Asp Ser Lys Leu Thr Phe Asp Ala Ile Thr Thr Ile
    210                 215                 220

Arg Gly Glu Val Met Phe Phe Lys Asp Arg Phe Tyr Met Arg Thr Asn
225                 230                 235                 240

Pro Phe Tyr Pro Glu Val Glu Leu Asn Phe Ile Ser Val Phe Trp Pro
                245                 250                 255

Gln Leu Pro Asn Gly Leu Glu Ala Ala Tyr Glu Phe Ala Asp Arg Asp
            260                 265                 270

Glu Val Arg Phe Phe Lys Gly Asn Lys Tyr Trp Ala Val Gln Gly Gln
        275                 280                 285

Asn Val Leu His Gly Tyr Pro Lys Asp Ile Tyr Ser Ser Phe Gly Phe
    290                 295                 300

Pro Arg Thr Val Lys His Ile Asp Ala Ala Leu Ser Glu Glu Asn Thr
305                 310                 315                 320

Gly Lys Thr Tyr Phe Val Ala Asn Lys Tyr Trp Arg Tyr Asp Glu
                325                 330                 335

Tyr Lys Arg Ser Met Asp Pro Gly Tyr Pro Lys Met Ile Ala His Asp
            340                 345                 350

Phe Pro Gly Ile Gly His Lys Val Asp Ala Val Phe Met Lys Asp Gly
```

```
                    355                 360                 365
Phe Phe Tyr Phe Phe His Gly Thr Arg Gln Tyr Lys Phe Asp Pro Lys
        370                 375                 380

Thr Lys Arg Ile Leu Thr Leu Gln Lys Ala Asn Ser Trp Phe Asn Cys
385                 390                 395                 400

Arg Lys Asn

<210> SEQ ID NO 30
<211> LENGTH: 19
<212> TYPE: DNA
<213> ORGANISM: Artificial Sequence
<220> FEATURE:
<223> OTHER INFORMATION: chemcially synthesized

<400> SEQUENCE: 30
uuagcuuacu gucacacgc                                                       19

<210> SEQ ID NO 31
<211> LENGTH: 19
<212> TYPE: DNA
<213> ORGANISM: Artificial Sequence
<220> FEATURE:
<223> OTHER INFORMATION: chemcialy synthesized

<400> SEQUENCE: 31
uuauauucau cauaccucc                                                       19

<210> SEQ ID NO 32
<211> LENGTH: 19
<212> TYPE: DNA
<213> ORGANISM: Artificial Sequence
<220> FEATURE:
<223> OTHER INFORMATION: chemically synthesized

<400> SEQUENCE: 32
uugucuucuu ucucagugc                                                       19

<210> SEQ ID NO 33
<211> LENGTH: 19
<212> TYPE: DNA
<213> ORGANISM: Artificial Sequence
<220> FEATURE:
<223> OTHER INFORMATION: chemcially synthesized

<400> SEQUENCE: 33
uucguaagca gcuucaagc                                                       19

<210> SEQ ID NO 34
<211> LENGTH: 31
<212> TYPE: DNA
<213> ORGANISM: Artificial Sequence
<220> FEATURE:
<223> OTHER INFORMATION: chemcially synthesized

<400> SEQUENCE: 34
ccggtcttcg taagcagctt caagcgaccg g                                         31

<210> SEQ ID NO 35
<211> LENGTH: 30
<212> TYPE: DNA
<213> ORGANISM: Artificial Sequence
<220> FEATURE:
<223> OTHER INFORMATION: chemcially synthesized

<400> SEQUENCE: 35
```

```
ccggtctaaa gaacatcact ttccgaccgg                                    30
```

<210> SEQ ID NO 36
<211> LENGTH: 31
<212> TYPE: DNA
<213> ORGANISM: Artificial Sequence
<220> FEATURE:
<223> OTHER INFORMATION: chemcially synthesized

<400> SEQUENCE: 36

```
ccggtctaaa acagtagaaa caagggaccg g                                  31
```

<210> SEQ ID NO 37
<211> LENGTH: 2387
<212> TYPE: DNA
<213> ORGANISM: Homo sapiens

<400> SEQUENCE: 37

```
agacacctct gccctcacca tgagcctctg gcagcccctg gtcctggtgc tcctggtgct    60
gggctgctgc tttgctgccc ccagacagcg ccagtccacc cttgtgctct ccctggaga   120
cctgagaacc aatctcaccg acaggcagct ggcagaggaa tacctgtacc gctatggtta   180
cactcgggtg gcagagatgc gtggagagtc gaaatctctg gggcctgcgc tgctgcttct   240
ccagaagcaa ctgtccctgc ccgagaccgg tgagctggat agcgccacgc tgaaggccat   300
gcgaacccca cggtgcgggg tcccagacct gggcagattc caaacctttg agggcgacct   360
caagtggcac caccacaaca tcacctattg gatccaaaac tactcggaag acttgccgcg   420
ggcggtgatt gacgacgcct tgcccgcgc cttcgcactg tggagcgcgg tgacgccgct   480
caccttcact cgcgtgtaca gccgggacgc agacatcgtc atccagtttg gtgtcgcgga   540
gcacggagac gggtatccct tcgacgggaa ggacgggctc ctggcacacg cctttcctcc   600
tggccccggc attcagggag acgcccattt cgacgatgac gagttgtggt ccctgggcaa   660
gggcgtcgtg gttccaactc ggtttggaaa cgcagatggc gcggcctgcc acttccccctt   720
catcttcgag ggccgctcct actctgcctg caccaccgac ggtcgctccg acggcttgcc   780
ctggtgcagt accacggcca actacgacac cgacgaccgg tttggcttct gcccagcga    840
gagactctac acccaggacg gcaatgctga tgggaaaccc tgccagtttc cattcatctt   900
ccaaggccaa tcctactccg cctgcaccac ggacggtcgc tccgacggct accgctggtg   960
cgccaccacc gccaactacg accgggacaa gctcttcggc ttctgcccga cccgagctga  1020
ctcgacggtg atggggggca actcggcggg ggagctgtgc gtcttccccct tcacttttcct  1080
gggtaaggag tactcgacct gtaccagcga gggccgcgga gatgggcgcc tctggtgcgc  1140
taccacctcg aactttgaca cgacaagaa gtggggcttc tgcccggacc aaggatacag  1200
tttgttcctc gtggcggcgc atgagttcgg ccacgcgctg ggcttagatc attcctcagt  1260
gccggaggcg ctcatgtacc ctatgtaccg cttcactgag gggcccccct gcataagga   1320
cgacgtgaat ggcatccggc acctctatgg tcctcgccct gaacctgagc cacggcctcc  1380
aaccaccacc acaccgcagc ccacggctcc cccgacggtc tgccccaccg accccccac   1440
tgtccacccc tcagagcgcc ccacagctgg ccccacaggt ccccccctcag ctggccccac  1500
aggtccccccc actgctggcc cttctacggc cactactgtg cctttgagtc cggtggacga  1560
tgcctgcaac gtgaacatct tcgacgccat cgcggagatt gggaaccagc tgtatttgtt  1620
caaggatggg aagtactggc gattctctga gggcaggggg agccggccgc agggccccctt  1680
```

```
cottatcgcc gacaagtggc ccgcgctgcc ccgcaagctg gactcggtct ttgaggagcg   1740
gctctccaag aagcttttct tcttctctgg gcgccaggtg tgggtgtaca caggcgcgtc   1800
ggtgctgggc ccgaggcgtc tggacaagct gggcctggga gccgacgtgg cccaggtgac   1860
cggggccctc cggagtggca gggggaagat gctgctgttc agcggggcgg cctctggag    1920 gttcgacgtg aaggcgcaga tggtggatcc ccggagcgcc agcgaggtgg accggatgtt   1980 ccccgggggtg cctttggaca cgcacgacgt cttccagtac cgagagaaag cctatttctg  2040
ccaggaccgc ttctactggc gcgtgagttc ccggagtgag ttgaaccagg tggaccaagt   2100
gggctacgtg acctatgaca tcctgcagtg ccctgaggac tagggctccc gtcctgcttt   2160
ggcagtgcca tgtaaatccc cactgggacc aaccctgggg aaggagccag tttgccggat   2220
acaaactggt attctgttct ggaggaaagg gaggagtgga ggtgggctgg ccctctctt    2280 ctcacctttg ttttttgttg gagtgtttct aataaacttg gattctctaa cctttaaaaa   2340
aaaaaaaaaa aaaaaaaaaa aaaaaaaaaa aaaaaaaaaa aaaaaaa                 2387
```

<210> SEQ ID NO 38
<211> LENGTH: 707
<212> TYPE: PRT
<213> ORGANISM: Homo sapiens

<400> SEQUENCE: 38

```
Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255
```

Ser Thr Thr Ala Asn Tyr Asp Thr Asp Asp Arg Phe Gly Phe Cys Pro
                260                 265                 270

Ser Glu Arg Leu Tyr Thr Gln Asp Gly Asn Ala Asp Gly Lys Pro Cys
            275                 280                 285

Gln Phe Pro Phe Ile Phe Gln Gly Gln Ser Tyr Ser Ala Cys Thr Thr
        290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
                435                 440                 445

Pro Glu Pro Arg Pro Pro Thr Thr Thr Pro Gln Pro Thr Ala Pro Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

-continued

```
Phe Cys Gln Asp Arg Phe Tyr Trp Arg Val Ser Ser Ser Arg Ser Glu Leu
            675                 680                 685

Asn Gln Val Asp Gln Val Gly Tyr Val Thr Tyr Asp Ile Leu Gln Cys
        690                 695                 700

Pro Glu Asp
705

<210> SEQ ID NO 39
<211> LENGTH: 21
<212> TYPE: DNA
<213> ORGANISM: Artificial Sequence
<220> FEATURE:
<223> OTHER INFORMATION: chemcially synthesized

<400> SEQUENCE: 39
uugucgcugu caaaguucga g                                           21

<210> SEQ ID NO 40
<211> LENGTH: 21
<212> TYPE: DNA
<213> ORGANISM: Artificial Sequence
<220> FEATURE:
<223> OTHER INFORMATION: chemcially synthesized

<400> SEQUENCE: 40
uucuugucgc ugucaaaguu c                                           21

<210> SEQ ID NO 41
<211> LENGTH: 21
<212> TYPE: DNA
<213> ORGANISM: Artificial Sequence
<220> FEATURE:
<223> OTHER INFORMATION: chemically synthesized

<400> SEQUENCE: 41
uucaacucac uccgggaacu c                                           21

<210> SEQ ID NO 42
<211> LENGTH: 21
<212> TYPE: DNA
<213> ORGANISM: Artificial Sequence
<220> FEATURE:
<223> OTHER INFORMATION: chemcially synthesized

<400> SEQUENCE: 42
uucacgucgu ccuuaugcaa g                                           21

<210> SEQ ID NO 43
<211> LENGTH: 31
<212> TYPE: DNA
<213> ORGANISM: Artificial Sequence
<220> FEATURE:
<223> OTHER INFORMATION: chemcially synthesized

<400> SEQUENCE: 43
ccggtcttgt cgctgtcaaa gttcggaccg g                                31

<210> SEQ ID NO 44
<211> LENGTH: 31
<212> TYPE: DNA
<213> ORGANISM: Artificial Sequence
<220> FEATURE:
<223> OTHER INFORMATION: chemcially synthesized

<400> SEQUENCE: 44
```

```
ccggtcttat tagaaacact ccaacgaccg g                                      31
```

<210> SEQ ID NO 45
<211> LENGTH: 31
<212> TYPE: DNA
<213> ORGANISM: Artificial Sequence
<220> FEATURE:
<223> OTHER INFORMATION: chemically synthesized

<400> SEQUENCE: 45

```
ccggtcattc acgtcgtcct tatgcgaccg g                                      31
```

<210> SEQ ID NO 46
<211> LENGTH: 1828
<212> TYPE: DNA
<213> ORGANISM: Homo sapiens

<400> SEQUENCE: 46

```
ctacaaggag gcaggcaaga cagcaaggca tagagacaac atagagctaa gtaaagccag       60
tggaaatgaa gagtcttcca atcctactgt tgctgtgcgt ggcagtttgc tcagcctatc      120
cattggatgg agctgcaagg ggtgaggaca ccagcatgaa ccttgttcag aaatatctag      180
aaaactacta cgacctcaaa aaagatgtga acagtttgt taggagaaag acagtggtc       240
ctgttgttaa aaaaatccga gaaatgcaga agttccttgg attggaggtg acggggaagc      300
tggactccga cactctggag gtgatgcgca agcccaggtg tggagttcct gatgttggtc      360
acttcagaac ctttcctggc atcccgaagt ggaggaaaac ccaccttaca tacaggattg      420
tgaattatac accagatttg ccaaaagatg ctgttgattc tgctgttgag aaagctctga      480
aagtctggga gaggtgact ccactcacat tctccaggct gtatgaagga gaggctgata      540
taatgatctc ttttgcagtt agagaacatg gagactttta ccctttgat ggacctggaa      600
atgttttggc ccatgcctat gcccctgggc agggattaa tggagatgcc cactttgatg      660
atgatgaaca atggacaaag gatacaacag ggaccaattt atttctcgtt gctgctcatg      720
aaattggcca ctccctgggt ctctttcact cagccaacac tgaagctttg atgtacccac      780
tctatcactc actcacagac ctgactcggt tccgcctgtc tcaagatgat ataaatggca      840
ttcagtccct ctatggacct cccctgact cccctgagac cccctggta cccacggaac      900
ctgtccctcc agaacctggg acgccagcca actgtgatcc tgctttgtcc tttgatgctg      960
tcagcactct gagggagaa atcctgatct ttaaagacag gcactttggg cgcaaatccc     1020
tcaggaagct tgaacctgaa ttgcatttga tctcttcatt ttggccatct cttccttcag     1080
gcgtggatgc cgcatatgaa gttactagca aggacctcgt tttcatttt aaaggaaatc     1140
aattctgggc tatcagagga aatgaggtac gagctggata cccaagaggc atccacaccc     1200
taggtttccc tccaaccgtg aggaaaatcg atgcagccat ttctgataag gaaaagaaca     1260
aaacatattt ctttgtagag gacaaatact ggagatttga tgaagagaga aattccatgg     1320
agccaggctt tcccaagcaa atagctgaag actttccagg gattgactca agattgatg     1380
ctgttttga agaatttggg ttctttatt tctttactgg atcttcacag ttggagtttg     1440
acccaaatgc aaagaaagtg acacacactt tgaagagtaa cagctggctt aattgttgaa     1500
agagatatgt agaaggcaca atatgggcac tttaaatgaa gctaataatt cttcacctaa     1560
gtctctgtga attgaaatgt tcgttttctc ctgcctgtgc tgtgactcga gtcacactca     1620
agggaacttg agcgtgaatc tgtatcttgc cggtcatttt tatgttatta cagggcattc     1680
aaatgggctg ctgcttagct tgcaccttgt cacatagagt gatctttccc aagagaaggg     1740
```

```
gaagcactcg tgtgcaacag acaagtgact gtatctgtgt agactatttg cttatttaat    1800
aaagacgatt tgtcagttat tttatctt                                       1828
```

<210> SEQ ID NO 47
<211> LENGTH: 477
<212> TYPE: PRT
<213> ORGANISM: Homo sapiens

<400> SEQUENCE: 47

```
Met Lys Ser Leu Pro Ile Leu Leu Leu Cys Val Ala Val Cys Ser
1               5                   10                  15

Ala Tyr Pro Leu Asp Gly Ala Ala Arg Gly Glu Asp Thr Ser Met Asn
                20                  25                  30

Leu Val Gln Lys Tyr Leu Glu Asn Tyr Asp Leu Lys Lys Asp Val
            35                  40                  45

Lys Gln Phe Val Arg Arg Lys Asp Ser Gly Pro Val Val Lys Lys Ile
    50                  55                  60

Arg Glu Met Gln Lys Phe Leu Gly Leu Glu Val Thr Gly Lys Leu Asp
65                  70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
        115                 120                 125

Ala Val Asp Ser Ala Val Glu Lys Ala Leu Lys Val Trp Glu Glu Val
    130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
            180                 185                 190

Gly Asp Ala His Phe Asp Asp Glu Gln Trp Thr Lys Asp Thr Thr
        195                 200                 205

Gly Thr Asn Leu Phe Leu Val Ala Ala His Glu Ile Gly His Ser Leu
    210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
                245                 250                 255

Asn Gly Ile Gln Ser Leu Tyr Gly Pro Pro Pro Asp Ser Pro Glu Thr
            260                 265                 270

Pro Leu Val Pro Thr Glu Pro Val Pro Pro Glu Pro Gly Thr Pro Ala
        275                 280                 285

Asn Cys Asp Pro Ala Leu Ser Phe Asp Ala Val Ser Thr Leu Arg Gly
    290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
            340                 345                 350
```

Phe Ile Phe Lys Gly Asn Gln Phe Trp Ala Ile Arg Gly Asn Glu Val
            355                 360                 365

Arg Ala Gly Tyr Pro Arg Gly Ile His Thr Leu Gly Phe Pro Pro Thr
370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Pro Gly
            420                 425                 430

Ile Asp Ser Lys Ile Asp Ala Val Phe Glu Glu Phe Gly Phe Tyr
            435                 440                 445

Phe Phe Thr Gly Ser Ser Gln Leu Glu Phe Asp Pro Asn Ala Lys Lys
450                 455                 460

Val Thr His Thr Leu Lys Ser Asn Ser Trp Leu Asn Cys
465                 470                 475

<210> SEQ ID NO 48
<211> LENGTH: 20
<212> TYPE: DNA
<213> ORGANISM: Artificial Sequence
<220> FEATURE:
<223> OTHER INFORMATION: chemcially synthesized

<400> SEQUENCE: 48
uucaucauca ucaaagugggg                                          20

<210> SEQ ID NO 49
<211> LENGTH: 20
<212> TYPE: DNA
<213> ORGANISM: Artificial Sequence
<220> FEATURE:
<223> OTHER INFORMATION: chemically synthesized

<400> SEQUENCE: 49
uaauaacaua aaaaugaccg                                           20

<210> SEQ ID NO 50
<211> LENGTH: 20
<212> TYPE: DNA
<213> ORGANISM: Artificial Sequence
<220> FEATURE:
<223> OTHER INFORMATION: chemcially synthesized

<400> SEQUENCE: 50
uagucuacac agauacaguc                                           20

<210> SEQ ID NO 51
<211> LENGTH: 20
<212> TYPE: DNA
<213> ORGANISM: Artificial Sequence
<220> FEATURE:
<223> OTHER INFORMATION: chemically synthesized

<400> SEQUENCE: 51
uauaucaucu ugagacaggc                                           20

<210> SEQ ID NO 52
<211> LENGTH: 32
<212> TYPE: DNA
<213> ORGANISM: Artificial Sequence
<220> FEATURE:
<223> OTHER INFORMATION: chemcially synthesized

<400> SEQUENCE: 52
ccggtctata tcatcttgag acaggcgacc gg    32

<210> SEQ ID NO 53
<211> LENGTH: 32
<212> TYPE: DNA
<213> ORGANISM: Artificial Sequence
<220> FEATURE:
<223> OTHER INFORMATION: chemcially synthesized

<400> SEQUENCE: 53
ccggtctttc tcttctcatc aaatctgacc gg    32

<210> SEQ ID NO 54
<211> LENGTH: 32
<212> TYPE: DNA
<213> ORGANISM: Artificial Sequence
<220> FEATURE:
<223> OTHER INFORMATION: chemcially synthesized

<400> SEQUENCE: 54
ccggtctaac aaactgtttc acatctgacc gg    32

<210> SEQ ID NO 55
<211> LENGTH: 2943
<212> TYPE: DNA
<213> ORGANISM: Homo sapiens

<400> SEQUENCE: 55
accaggcaac accattgaag gctcatatgt aaaaatccat gccttccttt ctcccaatct    60
ccattcccaa acttagccac tggcttctgg ctgaggcctt acgcatacct cccggggctt   120
gcacacacct tcttctacag aagacacacc ttgggcatat cctacagaag accaggcttc   180
tctctggtcc ttggtagagg gctactttac tgtaacaggg ccagggtgga gagttctctc   240
ctgaagctcc atcccctcta taggaaatgt gttgacaata ttcagaagag taagaggatc   300
aagacttctt tgtgctcaaa taccactgtt ctcttctcta ccctgcccta accaggagct   360
tgtcacccca aactctgagg tgatttatgc cttaatcaag caaacttccc tcttcagaaa   420
agatggctca ttttccctca aaagttgcca ggagctgcca agtattctgc caattcaccc   480
tggagcacaa tcaacaaatt cagccagaac acaactacag ctactattag aactattatt   540
attaataaat tcctctccaa atctagcccc ttgacttcgg atttcacgat ttctcccttc   600
ctcctagaaa cttgataagt ttcccgcgct tcccttttc taagactaca tgtttgtcat   660
cttataaagc aaaggggtga ataaatgaac caaatcaata acttctggaa tatctgcaaa   720
caacaataat atcagctatg ccatctttca ctattttagc cagtatcgag ttgaatgaac   780
atagaaaaat acaaaactga attcttccct gtaaattccc cgttttgacg acgcacttgt   840
agccacgtag ccacgcctac ttaagacaat tacaaaaggc gaagaagact gactcaggct   900
taagctgcca gccagagagg gagtcatttc attggcgttt gagtcagcaa agaagtcaag   960
atggccaaag ttccagacat gtttgaagac ctgaagaact gttacagtga aaatgaagaa  1020
gacagttcct ccattgatca tctgtctctg aatcagaaat ccttctatca tgtaagctat  1080
ggcccactcc atgaaggctg catggatcaa tctgtgtctc tgagtatctc tgaaacctct  1140
aaaacatcca agcttacctt caaggagagc atggtggtag tagcaaccaa cgggaaggtt  1200
ctgaagaaga cacggttgag tttaagccaa tccatcactg atgatgacct ggaggccatc  1260

```
gccaatgact cagaggaaga atcatcaag cctaggtcag caccttttag cttcctgagc    1320
aatgtgaaat acaactttat gaggatcatc aaatacgaat tcatcctgaa tgacgccctc    1380
aatcaaagta taattcgagc caatgatcag tacctcacgg ctgctgcatt acataatctg    1440
gatgaagcag tgaaatttga catgggtgct tataagtcat caaggatgat gctaaaatt    1500 accgtgattc taagaatctc aaaaactcaa ttgtatgtga ctgcccaaga tgaagaccaa    1560
ccagtgctgc tgaaggagat gcctgagata cccaaaacca tcacaggtag tgagaccaac    1620
ctcctcttct tctgggaaac tcacggcact aagaactatt tcacatcagt tgcccatcca    1680
aacttgttta ttgccacaaa gcaagactac tgggtgtgct tggcagggg gccaccctct    1740 atcactgact ttcagatact ggaaaaccag gcgtaggtct ggagtctcac ttgtctcact    1800
tgtgcagtgt tgacagttca tatgtaccat gtacatgaag aagctaaatc ctttactgtt    1860
agtcatttgc tgagcatgta ctgagccttg taattctaaa tgaatgttta cactctttgt    1920
aagagtggaa ccaacactaa catataatgt tgttatttaa agaacaccct atattttgca    1980
tagtaccaat cattttaatt attattcttc ataacaattt taggaggacc agagctactg    2040
actatggcta ccaaaaagac tctacccata ttacagatgg gcaaattaag gcataagaaa    2100
actaagaaat atgcacaata gcagttgaaa caagaagcca cagacctagg atttcatgat    2160
ttcatttcaa ctgtttgcct tctactttta agttgctgat gaactcttaa tcaaatagca    2220
taagtttctg ggacctcagt tttatcattt tcaaaatgga gggaataata cctaagcctt    2280
cctgccgcaa cagtttttta tgctaatcag ggaggtcatt ttggtaaaat acttcttgaa    2340
gccgagcctc aagatgaagg caaagcacga aatgttattt tttaattatt atttatatat    2400
gtatttataa atatatttaa gataattata atatactata tttatgggaa ccccttcatc    2460
ctctgagtgt gaccaggcat cctccacaat agcagacagt gttttctggg ataagtaagt    2520
ttgatttcat taatacaggg cattttggtc caagttgtgc ttatcccata gccaggaaac    2580
tctgcattct agtactgggg agacctgtaa tcatataata aatgtacatt aattaccttg    2640
agccagtaat tggtccgatc tttgactctt ttgccattaa acttacctgg gcattcttgt    2700
ttcaattcca cctgcaatca agtcctacaa gctaaaatta gatgaactca actttgacaa    2760
ccatgagacc actgttatca aaactttctt ttctggaatg taatcaatgt ttcttctagg    2820
ttctaaaaat tgtgatcaga ccataatgtt acattattat caacaatagt gattgataga    2880
gtgttatcag tcataactaa ataaagcttg caacaaaatt ctctgacaaa aaaaaaaaa    2940 aaa    2943
```

<210> SEQ ID NO 56
<211> LENGTH: 271
<212> TYPE: PRT
<213> ORGANISM: Homo sapiens

<400> SEQUENCE: 56

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Val Ala Thr Asn Gly Lys Val
```

```
                65                  70                  75                  80
Leu Lys Lys Arg Arg Leu Ser Leu Ser Gln Ser Ile Thr Asp Asp
                    85                  90                  95

Leu Glu Ala Ile Ala Asn Asp Ser Glu Glu Ile Ile Lys Pro Arg
                100                 105                 110

Ser Ala Pro Phe Ser Phe Leu Ser Asn Val Lys Tyr Asn Phe Met Arg
                115                 120                 125

Ile Ile Lys Tyr Glu Phe Ile Leu Asn Asp Ala Leu Asn Gln Ser Ile
                130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                    165                 170                 175

Asp Ala Lys Ile Thr Val Ile Leu Arg Ile Ser Lys Thr Gln Leu Tyr
                180                 185                 190

Val Thr Ala Gln Asp Glu Asp Gln Pro Val Leu Leu Lys Glu Met Pro
                    195                 200                 205

Glu Ile Pro Lys Thr Ile Thr Gly Ser Glu Thr Asn Leu Leu Phe Phe
210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                    245                 250                 255

Gly Pro Pro Ser Ile Thr Asp Phe Gln Ile Leu Glu Asn Gln Ala
                260                 265                 270

<210> SEQ ID NO 57
<211> LENGTH: 20
<212> TYPE: DNA
<213> ORGANISM: Artificial Sequence
<220> FEATURE:
<223> OTHER INFORMATION: chemically synthesized

<400> SEQUENCE: 57
uuucuauguu cauucaacuc                                                    20

<210> SEQ ID NO 58
<211> LENGTH: 20
<212> TYPE: DNA
<213> ORGANISM: Artificial Sequence
<220> FEATURE:
<223> OTHER INFORMATION: chemically synthesized

<400> SEQUENCE: 58
ucauucaacu cgauacuggc                                                    20

<210> SEQ ID NO 59
<211> LENGTH: 20
<212> TYPE: DNA
<213> ORGANISM: Artificial Sequence
<220> FEATURE:
<223> OTHER INFORMATION: chemcially synthesized

<400> SEQUENCE: 59
uucauucaac ucgauacugg                                                    20

<210> SEQ ID NO 60
<211> LENGTH: 20
<212> TYPE: DNA
<213> ORGANISM: Artificial Sequence
```

```
<220> FEATURE:
<223> OTHER INFORMATION: chemically synthesized

<400> SEQUENCE: 60
uaauaguucu aauaguagcu                                              20

<210> SEQ ID NO 61
<211> LENGTH: 32
<212> TYPE: DNA
<213> ORGANISM: Artificial Sequence
<220> FEATURE:
<223> OTHER INFORMATION: chemcially synthesized

<400> SEQUENCE: 61
ccggtctttc ttagttttct tatgccgacc gg                                32

<210> SEQ ID NO 62
<211> LENGTH: 31
<212> TYPE: DNA
<213> ORGANISM: Artificial Sequence
<220> FEATURE:
<223> OTHER INFORMATION: chemcially synthesized

<400> SEQUENCE: 62
ccggtctaat agttctaata gtagcgaccg g                                 31

<210> SEQ ID NO 63
<211> LENGTH: 31
<212> TYPE: DNA
<213> ORGANISM: Artificial Sequence
<220> FEATURE:
<223> OTHER INFORMATION: chemcially synthesized

<400> SEQUENCE: 63
ccggtctatg aactgtcaac actgcgaccg g                                 31

<210> SEQ ID NO 64
<211> LENGTH: 1498
<212> TYPE: DNA
<213> ORGANISM: Homo sapiens

<400> SEQUENCE: 64
accaaacctc ttcgaggcac aaggcacaac aggctgctct gggattctct tcagccaatc    60
ttcattgctc aagtgtctga agcagccatg gcagaagtac ctgagctcgc cagtgaaatg   120
atggcttatt acagtggcaa tgaggatgac ttgttctttg aagctgatgg ccctaaacag   180
atgaagtgct cctccaggac cctggacctc tgccctctgg atggcggcat ccagctacga   240
atctccgacc accactacag caagggcttc aggcaggccg cgtcagttgt tgtggccatg   300
gacaagctga ggaagatgct ggttccctgc ccacagacct tccaggagaa tgacctgagc   360
accttctttc ccttcatctt tgaagaagaa cctatcttct tcgacacatg ggataacgag   420
gcttatgtgc acgatgcacc tgtacgatca ctgaactgca cgctccggga ctcacagcaa   480
aaaagcttgg tgatgtctgg tccatatgaa ctgaaagctc tccacctcca gggacaggat   540
atggagcaac aagtggtgtt ctccatgtcc tttgtacaag gagaagaaag taatgacaaa   600
ataccgtgtg ccttgggcct caaggaaaag aatctgtacc tgtcctgcgt gttgaaagat   660
gataagccca ctctacagct ggagagtgta gatcccaaaa attacccaaa gaagaagatg   720
gaaaagcgat tgtcttcaa caagataaga atcaataaca agctgaatt tgagtctgcc    780
cagttcccca ctggtacat cagcacctct caagcagaaa acatgccgt cttcctggga   840
```

```
gggaccaaag gcggccagga tataactgac ttcaccatgc aatttgtgtc ttcctaaaga    900
gagctgtacc cagagagtcc tgtgctgaat gtggactcaa tccctagggc tggcagaaag    960
ggaacagaaa ggttttgag tacggctata gcctggactt tcctgttgtc tacaccaatg   1020
cccaactgcc tgccttaggg tagtgctaag aggatctcct gtccatcagc caggacagtc   1080
agctctctcc tttcagggcc aatccccagc ccttttgttg agccaggcct ctctcacctc   1140
tcctactcac ttaaagcccg cctgacagaa accacggcca catttggttc taagaaaccc   1200
tctgtcattc gctcccacat tctgatgagc aaccgcttcc ctatttattt atttatttgt   1260
ttgtttgttt tattcattgg tctaatttat tcaaaggggg caagaagtag cagtgtctgt   1320
aaaagagcct agttttaat agctatgaa tcaattcaat ttggactggt gtgctctctt   1380
taaatcaagt cctttaatta agactgaaaa tatataagct cagattattt aaatgggaat   1440
atttataaat gagcaaatat catactgttc aatggttctg aaataaactt cactgaag     1498
```

<210> SEQ ID NO 65
<211> LENGTH: 269
<212> TYPE: PRT
<213> ORGANISM: Homo sapiens

<400> SEQUENCE: 65

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
```

<210> SEQ ID NO 66
<211> LENGTH: 21
<212> TYPE: DNA
<213> ORGANISM: Artificial Sequence
<220> FEATURE:
<223> OTHER INFORMATION: chemcially synthesized

<400> SEQUENCE: 66
uuaucaucuu ucaacacgca g                                    21

<210> SEQ ID NO 67
<211> LENGTH: 21
<212> TYPE: DNA
<213> ORGANISM: Artificial Sequence
<220> FEATURE:
<223> OTHER INFORMATION: chemcially synthesized

<400> SEQUENCE: 67
uuuuacagac acugcuacuu c                                    21

<210> SEQ ID NO 68
<211> LENGTH: 21
<212> TYPE: DNA
<213> ORGANISM: Artificial Sequence
<220> FEATURE:
<223> OTHER INFORMATION: chemcially synthesized

<400> SEQUENCE: 68
uuugucauua cuuucuucuc c                                    21

<210> SEQ ID NO 69
<211> LENGTH: 21
<212> TYPE: DNA
<213> ORGANISM: Artificial Sequence
<220> FEATURE:
<223> OTHER INFORMATION: chemcially synthesized

<400> SEQUENCE: 69
uacagacacu gcuacuucuu g                                    21

<210> SEQ ID NO 70
<211> LENGTH: 33
<212> TYPE: DNA
<213> ORGANISM: Artificial Sequence
<220> FEATURE:
<223> OTHER INFORMATION: chemcially synthesized

<400> SEQUENCE: 70
ccggtctttt gtcattactt tcttctcgac cgg                       33

<210> SEQ ID NO 71
<211> LENGTH: 33
<212> TYPE: DNA
<213> ORGANISM: Artificial Sequence
<220> FEATURE:
<223> OTHER INFORMATION: chemcially synthesized

<400> SEQUENCE: 71
ccggtctttc agtcttaatt aaaggacgac cgg                       33

<210> SEQ ID NO 72
<211> LENGTH: 32
<212> TYPE: DNA
<213> ORGANISM: Artificial Sequence
<220> FEATURE:
<223> OTHER INFORMATION: chemcially synthesized

<400> SEQUENCE: 72

```
ccggtcttac ataaattaac tcagctgacc gg                                    32
```

<210> SEQ ID NO 73
<211> LENGTH: 1201
<212> TYPE: DNA
<213> ORGANISM: Homo sapiens

<400> SEQUENCE: 73

```
aatattagag tctcaacccc caataaatat aggactggag atgtctgagg ctcattctgc      60
cctcgagccc accgggaacg aaagagaagc tctatctccc ctccaggagc ccagctatga     120
actccttctc cacaagcgcc ttcggtccag ttgccttctc cctggggctg ctcctggtgt     180
tgcctgctgc cttccctgcc ccagtacccc aggagaaga ttccaaagat gtagccgccc      240
cacacagaca gccactcacc tcttcagaac gaattgacaa acaaattcgg tacatcctcg     300
acggcatctc agccctgaga aggagacat gtaacaagag taacatgtgt gaaagcagca      360
aagaggcact ggcagaaaac aacctgaacc ttccaaagat ggctgaaaaa gatggatgct     420
tccaatctgg attcaatgag gagacttgcc tggtgaaaat catcactggt cttttggagt     480
ttgaggtata cctagagtac ctccagaaca gatttgagag tagtgaggaa caagccagag     540
ctgtgcagat gagtacaaaa gtcctgatcc agttcctgca gaaaaaggca agaatctag     600
atgcaataac caccccctgac ccaaccacaa atgccagcct gctgacgaag ctgcaggcac     660
agaaccagtg gctgcaggac atgacaactc atctcattct gcgcagcttt aaggagttcc     720
tgcagtccag cctgagggct cttcggcaaa tgtagcatgg gcacctcaga ttgttgttgt     780
taatgggcat tccttcttct ggtcagaaac ctgtccactg gcacagaac ttatgttgtt      840
ctctatggag aactaaaagt atgagcgtta ggacactatt ttaattattt ttaatttatt     900
aatatttaaa tatgtgaagc tgagttaatt tatgtaagtc atatttatat ttttaagaag     960
taccacttga acatttat gtattagttt tgaaataata atggaaagtg gctatgcagt      1020
ttgaatatcc tttgtttcag agccagatca tttcttggaa agtgtaggct tacctcaaat    1080
aaatggctaa cttatacata tttttaaaga aatatttata ttgtatttat ataatgtata    1140
aatggttttt ataccaataa atggcatttt aaaaaattca gcaaaaaaaa aaaaaaaaa     1200
a                                                                     1201
```

<210> SEQ ID NO 74
<211> LENGTH: 212
<212> TYPE: PRT
<213> ORGANISM: Homo sapiens

<400> SEQUENCE: 74

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80
```

-continued

```
Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

```
<210> SEQ ID NO 75
<211> LENGTH: 21
<212> TYPE: DNA
<213> ORGANISM: Artificial Sequence
<220> FEATURE:
<223> OTHER INFORMATION: chemcially synthesized

<400> SEQUENCE: 75
uaaaauagug uccuaacgcu c                                              21

<210> SEQ ID NO 76
<211> LENGTH: 21
<212> TYPE: DNA
<213> ORGANISM: Artificial Sequence
<220> FEATURE:
<223> OTHER INFORMATION: chemcially synthesized

<400> SEQUENCE: 76
ucacuacucu caaaucuguu c                                              21

<210> SEQ ID NO 77
<211> LENGTH: 21
<212> TYPE: DNA
<213> ORGANISM: Artificial Sequence
<220> FEATURE:
<223> OTHER INFORMATION: chemcially synthesized

<400> SEQUENCE: 77
uuacucuugu uacaugucuc c                                              21

<210> SEQ ID NO 78
<211> LENGTH: 21
<212> TYPE: DNA
<213> ORGANISM: Artificial Sequence
<220> FEATURE:
<223> OTHER INFORMATION: chemcially synthesized

<400> SEQUENCE: 78
uaacgcucau acuuuuaguu c                                              21

<210> SEQ ID NO 79
<211> LENGTH: 33
```

<210> SEQ ID NO 79
<211> LENGTH: 33
<212> TYPE: DNA
<213> ORGANISM: Artificial Sequence
<220> FEATURE:
<223> OTHER INFORMATION: chemically synthesized

<400> SEQUENCE: 79
ccggtcttac tcttgttaca tgtcyccgac ctt     33

<210> SEQ ID NO 80
<211> LENGTH: 33
<212> TYPE: DNA
<213> ORGANISM: Artificial Sequence
<220> FEATURE:
<223> OTHER INFORMATION: chemically synthesized

<400> SEQUENCE: 80
ccggtcttac tcttgttaca tgtctccgac ctt     33

<210> SEQ ID NO 81
<211> LENGTH: 33
<212> TYPE: DNA
<213> ORGANISM: Artificial Sequence
<220> FEATURE:
<223> OTHER INFORMATION: chemcially synthesized

<400> SEQUENCE: 81
ccggtctaca taaaatgttt caagtgggac ctt     33

<210> SEQ ID NO 82
<211> LENGTH: 1718
<212> TYPE: DNA
<213> ORGANISM: Homo sapiens

<400> SEQUENCE: 82
gagggtgcat aagttctcta gtagggtgat gatataaaaa gccaccggag cactccataa     60
ggcacaaact ttcagagaca gcagagcaca caagcttcta ggacaagagc caggaagaaa    120
ccaccggaag gaaccatctc actgtgtgta acatgactt ccaagctggc cgtggctctc    180
ttggcagcct tcctgatttc tgcagctctg tgtgaaggtg cagttttgcc aaggagtgct    240
aaagaactta gatgtcagtg cataaagaca tactccaaac ctttccaccc caaatttatc    300
aaagaactga gagtgattga gagtggacca cactgcgcca acacagaaat tattgtaaag    360
ctttctgatg gaagagagct ctgtctggac cccaaggaaa ctgggtgca gagggttgtg    420
gagaagtttt tgaagagggc tgagaattca taaaaaaatt cattctctgt ggtatccaag    480
aatcagtgaa gatgccagtg aaacttcaag caaatctact tcaacacttc atgtattgtg    540
tgggtctgtt gtagggttgc cagatgcaat acaagattcc tggttaaatt tgaatttcag    600
taaacaatga atagtttttc attgtaccat gaaatatcca gaacatactt atatgtaaag    660
tattatttat ttgaatctac aaaaaacaac aaataatttt taaatataag gattttccta    720
gatattgcac gggagaatat acaaatagca aaattgaggc caagggccaa gagaatatcc    780
gaactttaat ttcaggaatt gaatgggttt gctagaatgt gatatttgaa gcatcacata    840
aaaatgatgg gacaataaat tttgccataa agtcaaattt agctggaaat cctggatttt    900
tttctgttaa atctggcaac cctagtctgc tagccaggat ccacaagtcc ttgttccact    960
gtgccttggt ttctccttta tttctaagtg gaaaaagtat tagccaccat cttacctcac   1020
agtgatgttg tgaggacatg tggaagcact ttagtttttt tcatcataac ataaattatt   1080
ttcaagtgta acttattaac ctatttatta tttatgtatt tatttaagca tcaaatattt   1140

```
gtgcaagaat ttggaaaaat agaagatgaa tcattgattg aatagttata aagatgttat    1200
agtaaattta ttttatttta gatattaaat gatgttttat tagataaatt tcaatcaggg    1260
tttttagatt aaacaaacaa acaattgggt acccagttaa atttcatttt cagataaaca    1320
acaaataatt tttagtata agtacattat tgtttatctg aaatttaat tgaactaaca      1380 atcctagttt gatactccca gtcttgtcat tgccagctgt gttggtagtg ctgtgttgaa    1440
ttacggaata atgagttaga actattaaaa cagccaaaac tccacagtca atattagtaa    1500
tttcttgctg gttgaaactt gtttattatg tacaaataga ttcttataat attatttaaa    1560
tgactgcatt tttaaataca aggctttata ttttaacttt taagatgttt ttatgtgctc    1620
tccaaatttt ttttactgtt tctgattgta tggaaatata aaagtaaata tgaaacattt    1680
aaaatataat ttgttgtcaa agtaaaaaaa aaaaaaaa                             1718
```

<210> SEQ ID NO 83
<211> LENGTH: 99
<212> TYPE: PRT
<213> ORGANISM: Homo sapiens

<400> SEQUENCE: 83

```
Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 84
<211> LENGTH: 20
<212> TYPE: DNA
<213> ORGANISM: Artificial Sequence
<220> FEATURE:
<223> OTHER INFORMATION: chemcially synthesized

<400> SEQUENCE: 84

```
uuuguuuaau cuaaaaaccc                                                 20
```

<210> SEQ ID NO 85
<211> LENGTH: 20
<212> TYPE: DNA
<213> ORGANISM: Artificial Sequence
<220> FEATURE:
<223> OTHER INFORMATION: chemcially synthesized

<400> SEQUENCE: 85

```
uuuacacaca gugagauggu                                                 20
```

<210> SEQ ID NO 86
<211> LENGTH: 20
<212> TYPE: DNA
<213> ORGANISM: Artificial Sequence
<220> FEATURE:
<223> OTHER INFORMATION: chemcially synthesized

```
<400> SEQUENCE: 86
uucaaauauc acauucuagc                                              20

<210> SEQ ID NO 87
<211> LENGTH: 20
<212> TYPE: DNA
<213> ORGANISM: Artificial Sequence
<220> FEATURE:
<223> OTHER INFORMATION: chemcialy synthesized

<400> SEQUENCE: 87
uuaugcacug acaucuaagu                                              20

<210> SEQ ID NO 88
<211> LENGTH: 32
<212> TYPE: DNA
<213> ORGANISM: Artificial Sequence
<220> FEATURE:
<223> OTHER INFORMATION: chemcially synthesized

<400> SEQUENCE: 88
ccggtctatc acattctagc aaacccgacc gg                                32

<210> SEQ ID NO 89
<211> LENGTH: 32
<212> TYPE: DNA
<213> ORGANISM: Artificial Sequence
<220> FEATURE:
<223> OTHER INFORMATION: chemcially synthesized

<400> SEQUENCE: 89
ccggtctact agagaactta tgcaccgacc gg                                32

<210> SEQ ID NO 90
<211> LENGTH: 32
<212> TYPE: DNA
<213> ORGANISM: Artificial Sequence
<220> FEATURE:
<223> OTHER INFORMATION: chemically synthesized

<400> SEQUENCE: 90
ccggtctagt tctaactcat tattccgacc gg                                32

<210> SEQ ID NO 91
<211> LENGTH: 5170
<212> TYPE: DNA
<213> ORGANISM: Homo sapiens

<400> SEQUENCE: 91
gtggccggcg gccggagccg actcggagcg cgcggcgccg gccggaggga gccggagagc    60
ggccgggccg ggcggtgggg gcgccggcct gccccgcgcg ccccagggag cggcaggaat   120
gtgacaatcg cgcgcccgcg caccgaagca ctcctcgctc ggctcctagg gctctcgccc   180
ctctgagctg agccgggttc cgcccggggc tgggatccca tcaccctcca cggccgtccg   240
tccaggtaga cgcaccctct gaagatggtg actccctcct gagaagctgg acccttggt    300 aaaagacaag gccttctcca agaagaatat gaaagtgtta ctcagactta tttgtttcat   360
agctctactg atttcttctc tggaggctga taaatgcaag gaacgtgaag aaaaaataat   420
tttagtgtca tctgcaaatg aaattgatgt tcgtccctgt cctcttaacc caaatgaaca   480
caaaggcact ataacttggt ataaagatga cagcaagaca cctgtatcta cagaacaagc   540
```

-continued

```
ctccaggatt catcaacaca aagagaaact ttggtttgtt cctgctaagg tggaggattc    600
aggacattac tattgcgtgg taagaaattc atcttactgc ctcagaatta aaataagtgc    660
aaaatttgtg gagaatgagc ctaacttatg ttataatgca caagccatat ttaagcagaa    720
actacccgtt gcaggagacg gaggacttgt gtgcccttat atggagtttt ttaaaaatga    780
aaataatgag ttacctaaat tacagtggta taaggattgc aaacctctac ttcttgacaa    840
tatacacttt agtggagtca aagataggct catcgtgatg aatgtggctg aaaagcatag    900
agggaactat acttgtcatg catcctacac atacttgggc aagcaatatc ctattacccg    960
ggtaatagaa tttattactc tagaggaaaa caaacccaca aggcctgtga ttgtgagccc   1020
agctaatgag acaatggaag tagacttggg atcccagata caattgatct gtaatgtcac   1080
cggccagttg agtgacattg cttactgaa gtggaatggg tcagtaattg atgaagatga    1140
cccagtgcta ggggaagact attacagtgt ggaaaatcct gcaaacaaaa aaggagtac    1200 cctcatcaca gtgcttaata tatcggaaat tgaaagtaga ttttataaac atccatttac   1260
ctgttttgcc aagaatacac atggtataga tgcagcatat atccagttaa tatatccagt   1320
cactaatttc cagaagcaca tgattggtat atgtgtcacg ttgacagtca taattgtgtg   1380
ttctgttttc atctataaaa tcttcaagat tgacattgtg ctttggtaca gggattcctg   1440
ctatgatttt ctcccaataa aagcttcaga tggaaagacc tatgacgcat atatactgta   1500
tccaaagact gttggggaag ggtctaccct tgactgtgat attttttgtgt ttaaagtctt   1560 gcctgaggtc ttggaaaaac agtgtggata taagctgttc atttatggaa gggatgacta   1620
cgttggggaa gacattgttg aggtcattaa tgaaaacgta aagaaaagca gaagactgat   1680 tatcattta gtcagagaaa catcaggctt cagctggctg ggtggttcat ctgaagagca   1740
aatagccatg tataatgctc ttgttcagga tggaattaaa gttgtcctgc ttgagctgga   1800
gaaaatccaa gactatgaga aaatgccaga atcgattaaa ttcattaagc agaaacatgg   1860
ggctatccgc tggtcagggg actttacaca gggaccacag tctgcaaaga caaggttctg   1920
gaagaatgtc aggtaccaca tgccagtcca gcgacggtca ccttcatcta aacaccagtt   1980
actgtcacca gccactaagg agaaactgca aagagaggct cacgtgcctc tcgggtagca   2040
tggagaagtt gccaagagtt cttttaggtgc ctcctgtctt atggcgttgc aggccaggtt   2100
atgcctcatg ctgacttgca gagttcatgg aatgtaacta tatcatcctt tatccctgag   2160
gtcacctgga atcagattat aagggaata agccatgacg tcaatagcag cccagggcac   2220
ttcagagtag agggcttggg aagatctttt aaaaaggcag taggcccggt gtggtggctc   2280
acgcctataa tcccagcact ttgggaggct gaagtgggtg gatcaccaga ggtcaggagt   2340
tcgagaccag cccagccaac atggcaaaac cccatctcta ctaaaaatac aaaaatgagc   2400
taggcatggt ggcacacgcc tgtaatccca gctacacctg aggctgaggc aggagaattg   2460
cttgaaccgg ggagacggag gttgcagtga gccgagtttg gccactgca ctctagcctg   2520 gcaacagagc aagactccgt ctcaaaaaaa gggcaataaa tgccctctct gaatgtttga   2580
actgccaaga aaaggcatgg agacagcgaa ctagaagaaa gggcaagaag gaaatagcca   2640
ccgtctacag atggcttagt taagtcatcc acagcccaag ggcggggcta tgccttgtct   2700
ggggaccctg tagagtcact gaccctggag cggctctcct gagaggtgct gcaggcaaag   2760
tgagactgac acctcactga ggaagggaga catattcttg gagaactttc catctgcttg   2820 tatttttccat acacatcccc agccagaagt tagtgtccga agaccgaatt ttatttaca   2880 gagcttgaaa actcacttca atgaacaaag ggattctcca ggattccaaa gttttgaagt   2940
```

```
catcttagct tccacagga gggagagaac ttaaaaaagc aacagtagca gggaattgat   3000
ccacttctta atgctttcct ccctggcatg accatcctgt cctttgttat tatcctgcat   3060
tttacgtctt tggaggaaca gctccctagt ggcttcctcc gtctgcaatg tcccttgcac   3120
agcccacaca tgaaccatcc ttcccatgat gccgctcttc tgtcatcccg ctcctgctga   3180
aacacctccc aggggctcca cctgttcagg agctgaagcc catgctttcc caccagcatg   3240
tcactcccag accacctccc tgccctgtcc tccagcttcc cctcgctgtc ctgctgtgtg   3300
aattcccagg ttggcctggt ggccatgtcg cctgccccca gcactcctct gtctctgctc   3360
ttgcctgcac ccttcctcct cctttgccta ggaggccttc tcgcattttc tctagctgat   3420
cagaatttta ccaaaattca gaacatcctc caattccaca gtctctggga gactttccct   3480
aagaggcgac ttcctctcca gccttctctc tctggtcagg cccactgcag agatggtggt   3540
gagcacatct gggaggctgg tctccctcca gctggaattg ctgctctctg agggagaggc   3600
tgtggtggct gtctctgtcc ctcactgcct tccaggagca atttgcacat gtaacataga   3660
tttatgtaat gctttatgtt taaaaacatt ccccaattat cttatttaat ttttgcaatt   3720
attctaattt tatatataga gaaagtgacc tatttttaa aaaaatcaca ctctaagttc   3780
tattgaacct aggacttgag cctccatttc tggcttctag tctggtgttc tgagtacttg   3840
atttcaggtc aataacggtc ccccctcact ccacactggc acgtttgtga agaaaatga   3900 cattttgcta ggaagtgacc gagtctagga atgcttttat tcaagacacc aaattccaaa   3960
cttctaaatg ttggaatttt caaaaattgt gtttagattt tatgaaaaac tcttctactt   4020
tcatctattc tttccctaga ggcaaacatt tcttaaaatg tttcattttc attaaaaatg   4080
aaagccaaat ttatatgcca ccgattgcag gacacaagca cagttttaag agttgtatga   4140
acatggagag gacttttggt ttttatattt ctcgtattta atatgggtga acaccaactt   4200
ttatttggaa taataatttt cctcctaaac aaaacacat tgagtttaag tctctgactc   4260
ttgcctttcc acctgctttc tcctgggccc gctttgcctg cttgaaggaa cagtgctgtt   4320
ctggagctgc tgttccaaca gacagggcct agctttcatt tgacacacag actcagccaa   4380
gaagcccatg gagcagggat gtcacgtctt gaaaagccta ttagatgttt tacaaattta   4440
attttgcaga ttattttagt ctgtcatcca gaaaatgtgt cagcatgcat agtgctaaga   4500
aagcaagcca atttggaaac ttaggttagt gacaaaattg gccagagagt gggggtgatg   4560
atgaccaaga attacaagta gaatggcagc tggaatttaa ggaggacaa gaatcaatgg   4620 ataagcgtgg gtggaggaag atccaaacag aaaagtgcaa agttattccc catcttccaa   4680
gggttgaatt ctggaggaag aagacacatt cctagttccc cgtgaacttc ctttgactta   4740
ttgtccccac taaacaaaa caaaaaactt ttaatgcctt ccacattaat tagattttct   4800
tgcagttttt ttatggcatt ttttttaaga tgccctaagt gttgaagaag agtttgcaaa   4860
tgcaacaaaa tatttaatta ccggttgtta aaactggttt agcacaattt atattttccc   4920
tctcttgcct ttcttatttg caataaaagg tattgagcca ttttttaaat gacattttg    4980 ataaattatg tttgtactag ttgatgaagg agttttttt aacctgttta tataattttg   5040
cagcagaagc caaatttttt gtatattaaa gcaccaaatt catgtacagc atgcatcacg   5100
gatcaataga ctgtacttat tttccaataa aatttcaaa ctttgtactg ttaaaaaaaa   5160
aaaaaaaaaa                                                         5170
```

<210> SEQ ID NO 92

```
<211> LENGTH: 569
<212> TYPE: PRT
<213> ORGANISM: Homo sapiens

<400> SEQUENCE: 92

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
370                 375                 380

Tyr Asp Ala Tyr Ile Leu Tyr Pro Lys Thr Val Gly Glu Gly Ser Thr
```

| | | 385 | | | 390 | | | 395 | | | 400 |
|---|---|---|---|---|---|---|---|---|---|---|---|
| Ser | Asp | Cys | Asp | Ile | Phe | Val | Phe | Lys | Val | Leu | Glu |
| | | | | 405 | | | | 410 | | | 415 |

Val Leu Glu

Lys Gln Cys Gly Tyr Lys Leu Phe Ile Tyr Gly Arg Asp Asp Tyr Val
           420                425               430

Gly Glu Asp Ile Val Glu Val Ile Asn Glu Asn Val Lys Lys Ser Arg
               435               440               445

Arg Leu Ile Ile Ile Leu Val Arg Glu Thr Ser Gly Phe Ser Trp Leu
       450               455               460

Gly Gly Ser Ser Glu Glu Gln Ile Ala Met Tyr Asn Ala Leu Val Gln
465               470               475               480

Asp Gly Ile Lys Val Val Leu Leu Glu Leu Glu Lys Ile Gln Asp Tyr
               485               490               495

Glu Lys Met Pro Glu Ser Ile Lys Phe Ile Lys Gln Lys His Gly Ala
               500               505               510

Ile Arg Trp Ser Gly Asp Phe Thr Gln Gly Pro Gln Ser Ala Lys Thr
       515               520               525

Arg Phe Trp Lys Asn Val Arg Tyr His Met Pro Val Gln Arg Arg Ser
       530               535               540

Pro Ser Ser Lys His Gln Leu Leu Ser Pro Ala Thr Lys Glu Lys Leu
545               550               555               560

Gln Arg Glu Ala His Val Pro Leu Gly
               565

<210> SEQ ID NO 93
<211> LENGTH: 20
<212> TYPE: DNA
<213> ORGANISM: Artificial Sequence
<220> FEATURE:
<223> OTHER INFORMATION: chemcially synthesized

<400> SEQUENCE: 93
uuucuucuca caaacgugcc                                              20

<210> SEQ ID NO 94
<211> LENGTH: 20
<212> TYPE: DNA
<213> ORGANISM: Artificial Sequence
<220> FEATURE:
<223> OTHER INFORMATION: chemcially synthesized

<400> SEQUENCE: 94
uuauaccaag uuauagugcc                                              20

<210> SEQ ID NO 95
<211> LENGTH: 20
<212> TYPE: DNA
<213> ORGANISM: Artificial Sequence
<220> FEATURE:
<223> OTHER INFORMATION: chemcially synthesized

<400> SEQUENCE: 95
uuguaaaaca ucuaauaggc                                              20

<210> SEQ ID NO 96
<211> LENGTH: 20
<212> TYPE: DNA
<213> ORGANISM: Artificial Sequence
<220> FEATURE:
<223> OTHER INFORMATION: chemcially synthesized

<400> SEQUENCE: 96
uuuccacacu guaauagucu                                                    20

<210> SEQ ID NO 97
<211> LENGTH: 31
<212> TYPE: DNA
<213> ORGANISM: Artificial Sequence
<220> FEATURE:
<223> OTHER INFORMATION: chemically synthesized

<400> SEQUENCE: 97
ccggtctttc ttctcacaaa cgtgcgaccg g                                       31

<210> SEQ ID NO 98
<211> LENGTH: 31
<212> TYPE: DNA
<213> ORGANISM: Artificial Sequence
<220> FEATURE:
<223> OTHER INFORMATION: chemcially synthesized

<400> SEQUENCE: 98
ccggtcttaa acacaaaaat atcacgaccg g                                       31

<210> SEQ ID NO 99
<211> LENGTH: 31
<212> TYPE: DNA
<213> ORGANISM: Artificial Sequence
<220> FEATURE:
<223> OTHER INFORMATION: checmially synthesized

<400> SEQUENCE: 99
ccggtctttc cacactgtaa tagtcgaccg g                                       31

<210> SEQ ID NO 100
<211> LENGTH: 1686
<212> TYPE: DNA
<213> ORGANISM: Homo sapiens

<400> SEQUENCE: 100
cagacgctcc ctcagcaagg acagcagagg accagctaag agggagagaa gcaactacag        60
accccccctg aaaacaaccc tcagacgcca catcccctga caagctgcca ggcaggttct       120
cttcctctca catactgacc cacggctcca ccctctctcc cctggaaagg acaccatgag       180
cactgaaagc atgatccggg acgtggagct ggccgaggag gcgctcccca gaagacagg        240 ggggccccag ggctccaggc ggtgcttgtt cctcagcctc ttctccttcc tgatcgtggc       300
aggcgccacc acgctcttct gcctgctgca ctttggagtg atcggccccc agagggaaga       360
gttccccagg gacctctctc taatcagccc tctggcccag gcagtcagat catcttctcg       420
aaccccgagt gacaagcctg tagcccatgt tgtagcaaac cctcaagctg agggcagct        480 ccagtggctg aaccgccggg ccaatgccct cctggccaat ggcgtggagc tgagagataa       540
ccagctggtg gtgccatcag agggcctgta cctcatctac tcccaggtcc tcttcaaggg       600
ccaaggctgc ccctccaccc atgtgctcct cacccacacc atcagccgca tcgccgtctc       660
ctaccagacc aaggtcaacc tcctctctgc catcaagagc ccctgccaga gggagacccc       720 agaggggggct gaggccaagc cctggtatga gcccatctat ctgggagggg tcttccagct       780
ggagaagggt gaccgactca gcgctgagat caatcggccc gactatctcg actttgccga       840
gtctgggcag gtctactttg ggatcattgc cctgtgagga ggacgaacat ccaaccttcc       900
caaacgcctc ccctgcccca tcccttttat tacccctcc ttcagacacc ctcaaccctct       960

-continued

```
tctggctcaa aaagagaatt gggggcttag ggtcggaacc caagcttaga actttaagca    1020
acaagaccac cacttcgaaa cctgggattc aggaatgtgt ggcctgcaca gtgaagtgct    1080
ggcaaccact aagaattcaa actggggcct ccagaactca ctggggccta cagctttgat    1140
ccctgacatc tggaatctgg agaccaggga gcctttggtt ctggccagaa tgctgcagga    1200
cttgagaaga cctcacctag aaattgacac aagtggacct taggccttcc tctctccaga    1260
tgtttccaga cttccttgag acacggagcc cagccctccc catggagcca gctccctcta    1320
tttatgtttg cacttgtgat tatttattat ttatttatta tttatttatt tacagatgaa    1380
tgtatttatt tgggagaccg gggtatcctg ggggacccaa tgtaggagct gccttggctc    1440
agacatgttt tccgtgaaaa cggagctgaa caataggctg ttcccatgta gccccctggc    1500
ctctgtgcct tcttttgatt atgttttta aaatatttat ctgattaagt tgtctaaaca     1560
atgctgattt ggtgaccaac tgtcactcat tgctgagcct ctgctcccca ggggagttgt    1620
gtctgtaatc gccctactat tcagtggcga gaaataaagt ttgcttagaa aagaaaaaaa    1680
aaaaaa                                                               1686
```

<210> SEQ ID NO 101
<211> LENGTH: 233
<212> TYPE: PRT
<213> ORGANISM: Homo sapiens

<400> SEQUENCE: 101

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

```
<210> SEQ ID NO 102
<211> LENGTH: 19
<212> TYPE: DNA
<213> ORGANISM: Artificial Sequence
<220> FEATURE:
<223> OTHER INFORMATION: chemically synthesized

<400> SEQUENCE: 102
aauaaauaau cacaagugc                                                   19

<210> SEQ ID NO 103
<211> LENGTH: 19
<212> TYPE: DNA
<213> ORGANISM: Artificial Sequence
<220> FEATURE:
<223> OTHER INFORMATION: chemically synthesized

<400> SEQUENCE: 103
uaaaaaacau aaucaaaag                                                   19

<210> SEQ ID NO 104
<211> LENGTH: 19
<212> TYPE: DNA
<213> ORGANISM: Artificial Sequence
<220> FEATURE:
<223> OTHER INFORMATION: chemcially synthesized

<400> SEQUENCE: 104
uaauaaauaa ucacaagug                                                   19

<210> SEQ ID NO 105
<211> LENGTH: 19
<212> TYPE: DNA
<213> ORGANISM: Artificial Sequence
<220> FEATURE:
<223> OTHER INFORMATION: chemcially synthesized

<400> SEQUENCE: 105
uuuucuuuuc uaagcaaac                                                   19

<210> SEQ ID NO 106
<211> LENGTH: 31
<212> TYPE: DNA
<213> ORGANISM: Artificial Sequence
<220> FEATURE:
<223> OTHER INFORMATION: chemcially synhtesized

<400> SEQUENCE: 106
ccggtcaaac ataatcaaaa gaagggaccg g                                     31

<210> SEQ ID NO 107
<211> LENGTH: 31
<212> TYPE: DNA
<213> ORGANISM: Artificial Sequence
<220> FEATURE:
<223> OTHER INFORMATION: chemically synthesized

<400> SEQUENCE: 107
ccggtctaaa aacataatc aaaaggaccg g                                      31

<210> SEQ ID NO 108
<211> LENGTH: 31
<212> TYPE: DNA
<213> ORGANISM: Artificial Sequence
<220> FEATURE:
```

<223> OTHER INFORMATION: chemically synthesized

<400> SEQUENCE: 108
ccggtctatt ttaaaaaaca taatcgaccg g                                   31

<210> SEQ ID NO 109
<211> LENGTH: 3677
<212> TYPE: DNA
<213> ORGANISM: Homo sapiens

<400> SEQUENCE: 109

| | | | | | |
|---|---|---|---|---|---|
| tcgcggaggc | ttggggcagc | cgggtagctc | ggaggtcgtg | gcgctggggg | ctagcaccag | 60 |
| cgctctgtcg | ggaggcgcag | cggttaggtg | gaccggtcag | cggactcacc | ggccagggcg | 120 |
| ctcggtgctg | gaatttgata | ttcattgatc | cgggttttat | ccctcttctt | ttttcttaaa | 180 |
| catttttttt | taaaactgta | ttgtttctcg | ttttaattta | ttttgcttg | ccattcccca | 240 |
| cttgaatcgg | gccgacggct | tggggagatt | gctctacttc | cccaaatcac | tgtggatttt | 300 |
| ggaaaccagc | agaaagagga | aagagtagc | aagagctcca | gagagaagtc | gaggaagaga | 360 |
| gagacggggt | cagagagagc | gcgcgggcgt | gcgagcagcg | aaagcgacag | gggcaaagtg | 420 |
| agtgacctgc | ttttgggggt | gaccgccgga | gcgcggcgtg | agccctcccc | cttgggatcc | 480 |
| cgcagctgac | cagtcgcgct | gacggacaga | cagacagaca | ccgcccccag | cccagctac | 540 |
| cacctcctcc | ccggccggcg | gcggacagtg | gacgcggcgg | cgagccgcgg | gcaggggccg | 600 |
| gagcccgcgc | ccggaggcgg | ggtggagggg | gtcgggctc | gcggcgtcgc | actgaaactt | 660 |
| ttcgtccaac | ttctgggctg | ttctcgcttc | ggaggagccg | tggtccgcgc | ggggaagcc | 720 |
| gagccgagcg | gagccgcgag | aagtgctagc | tcggccgggg | aggagccgca | gccggaggag | 780 |
| gggaggagg | aagaagagaa | ggaagaggag | aggggccgc | agtggcgact | cggcgctcgg | 840 |
| aagccgggct | catggacggg | tgaggcggcg | gtgtgcgcag | acagtgctcc | agccgcgcgc | 900 |
| gctcccagg | ccctggcccg | ggcctcgggc | cgggaggaa | gagtagctcg | ccgaggcgcc | 960 |
| gaggagagcg | ggccgcccca | cagcccgagc | cggagaggga | gcgcgagccg | cgccggcccc | 1020 |
| ggtcgggcct | ccgaaaccat | gaactttctg | ctgtcttggg | tgcattggag | ccttgccttg | 1080 |
| ctgctctacc | tccaccatgc | caagtggtcc | caggctgcac | ccatggcaga | aggaggaggg | 1140 |
| cagaatcatc | acgaagtggt | gaagttcatg | gatgtctatc | agcgcagcta | ctgccatcca | 1200 |
| atcgagaccc | tggtggacat | cttccaggag | taccctgatg | agatcgagta | catcttcaag | 1260 |
| ccatcctgtg | tgccccctgat | gcgatgcggg | ggctgctgca | atgacgaggg | cctggagtgt | 1320 |
| gtgcccactg | aggagtccaa | catcaccatg | cagattatgc | ggatcaaacc | tcaccaaggc | 1380 |
| cagcacatag | agagatgag | cttcctacag | cacaacaaat | gtgaatgcag | accaaagaaa | 1440 |
| gatagagcaa | gacaagaaaa | aaaatcagtt | cgaggaaagg | gaaaggggca | aaaacgaaag | 1500 |
| cgcaagaaat | cccggtataa | gtcctggagc | gtgtacgttg | gtgcccgctg | ctgtctaatg | 1560 |
| ccctggagcc | tccctggccc | ccatccctgt | gggccttgct | cagagcggag | aaagcatttg | 1620 |
| tttgtacaag | atccgcagac | gtgtaaatgt | tcctgcaaaa | acacagactc | gcgttgcaag | 1680 |
| gcgaggcagc | ttgagttaaa | cgaacgtact | tgcagatgtg | acaagccgag | gcggtgagcc | 1740 |
| gggcaggagg | aaggagcctc | cctcagggtt | tcgggaacca | gatctctcac | caggaaagac | 1800 |
| tgatacagaa | cgatcgatac | agaaaccacg | ctgccgccac | cacaccatca | ccatcgacag | 1860 |
| aacagtcctt | aatccagaaa | cctgaaatga | aggaagagga | gactctgcgc | agagcacttt | 1920 |
| gggtccggag | ggcgagactc | cggcggaagc | attcccgggc | gggtgaccca | gcacggtccc | 1980 |

```
tcttggaatt ggattcgcca ttttattttt cttgctgcta aatcaccgag cccggaagat    2040
tagagagttt tatttctggg attcctgtag acacacccac ccacatacat acatttatat    2100
atatatatat tatatatata taaaaataaa tatctctatt ttatatatat aaaatatata    2160 tattctttt ttaaattaac agtgctaatg ttattggtgt cttcactgga tgtatttgac     2220
tgctgtggac ttgagttggg aggggaatgt tcccactcag atcctgacag gaagaggag     2280 gagatgagag actctggcat gatctttttt ttgtcccact tggtggggcc agggtcctct    2340
cccctgccca ggaatgtgca aggccagggc atggggcaa atatgaccca gttttgggaa     2400
caccgacaaa cccagccctg cgctgagcc tctctacccc aggtcagacg gacagaaaga    2460
cagatcacag gtacagggat gaggacaccg gctctgacca ggagtttggg gagcttcagg    2520
acattgctgt gctttgggga ttccctccac atgctgcacg cgcatctcgc ccccaggggc    2580
actgcctgga agattcagga gcctgggcgg ccttcgctta ctctcacctg cttctgagtt    2640
gcccaggaga ccactggcag atgtcccggc gaagagaaga gacacattgt tggaagaagc    2700
agcccatgac agctcccctt cctgggactc gccctcatcc tcttcctgct ccccttcctg    2760
gggtgcagcc taaaaggacc tatgtcctca caccattgaa accactagtt ctgtcccccc    2820
aggagacctg gttgtgtgtg tgtgagtggt tgaccttcct ccatcccctg gtccttccct    2880
tcccttcccg aggcacagag agacagggca ggatccacgt gcccattgtg gaggcagaga    2940
aaagagaaag tgttttatat acggtactta tttaatatcc cttttaatt agaaattaaa     3000 acagttaatt taattaaaga gtagggtttt ttttcagtat tcttggttaa tatttaattt    3060
caactattta tgagatgtat cttttgctct ctcttgctct cttatttgta ccggtttttg    3120
tatataaaat tcatgtttcc aatctctctc tccctgatcg gtgacagtca ctagcttatc    3180
ttgaacagat atttaatttt gctaacactc agctctgccc tccccgatcc cctggctccc    3240
cagcacacat tcctttgaaa taaggtttca atatacatct acatactata tatatatttg    3300
gcaacttgta tttgtgtgta tatatatata tatatgttta tgtatatatg tgattctgat    3360
aaaatagaca ttgctattct gtttttata tgtaaaaaca aaacaagaaa aaatagagaa     3420
ttctacatac taaatctctc tccttttta atttaatat ttgttatcat ttatttattg     3480
gtgctactgt ttatccgtaa taattgtggg gaaaagatat taacatcacg tctttgtctc    3540
tagtgcagtt tttcgagata ttccgtagta catatttatt tttaaacaac gacaaagaaa    3600
tacagatata tcttaaaaaa aaaaagcat tttgtattaa agaatttaat tctgatctca     3660 aaaaaaaaa aaaaaaa                                                    3677
```

<210> SEQ ID NO 110
<211> LENGTH: 412
<212> TYPE: PRT
<213> ORGANISM: Homo sapiens

<400> SEQUENCE: 110

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
            85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
            130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
            290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
            355                 360                 365

Glu Arg Arg Lys His Leu Phe Val Gln Asp Pro Gln Thr Cys Lys Cys
370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 111
<211> LENGTH: 21
<212> TYPE: DNA
<213> ORGANISM: Artificial Sequence
<220> FEATURE:
<223> OTHER INFORMATION: chemically synthesized

<400> SEQUENCE: 111
uaaaacucuc uaaucuuccg g                                              21

```
<210> SEQ ID NO 112
<211> LENGTH: 21
<212> TYPE: DNA
<213> ORGANISM: Artificial Sequence
<220> FEATURE:
<223> OTHER INFORMATION: chemically synthesized

<400> SEQUENCE: 112
uuccuucucu ucuuccuccu c                                              21

<210> SEQ ID NO 113
<211> LENGTH: 21
<212> TYPE: DNA
<213> ORGANISM: Artificial Sequence
<220> FEATURE:
<223> OTHER INFORMATION: chemically synthesized

<400> SEQUENCE: 113
uauacacaca aauacaaguu g                                              21

<210> SEQ ID NO 114
<211> LENGTH: 21
<212> TYPE: DNA
<213> ORGANISM: Artificial Sequence
<220> FEATURE:
<223> OTHER INFORMATION: chemcially synthesized

<400> SEQUENCE: 114
uuaaaacgag aacaauaca g                                               21

<210> SEQ ID NO 115
<211> LENGTH: 31
<212> TYPE: DNA
<213> ORGANISM: Artificial Sequence
<220> FEATURE:
<223> OTHER INFORMATION: chemcially synthesized

<400> SEQUENCE: 115
ccggtctaaa actctctaat cttccgaccg g                                   31

<210> SEQ ID NO 116
<211> LENGTH: 31
<212> TYPE: DNA
<213> ORGANISM: Artificial Sequence
<220> FEATURE:
<223> OTHER INFORMATION: chemcially synhesized

<400> SEQUENCE: 116
ccggtctttg atccgcataa tctgcgaccg g                                   31

<210> SEQ ID NO 117
<211> LENGTH: 31
<212> TYPE: DNA
<213> ORGANISM: Artificial Sequence
<220> FEATURE:
<223> OTHER INFORMATION: chemically synthesized

<400> SEQUENCE: 117
ccggtcttga aattaaatat taaccgaccg g                                   31

<210> SEQ ID NO 118
<211> LENGTH: 2583
<212> TYPE: DNA
<213> ORGANISM: Homo sapiens

<400> SEQUENCE: 118
```

-continued

| | |
|---|---|
| agccggtccc cgccgccgcc gcccttcgcg ccctgggcca tctccctccc acctccctcc | 60 |
| gcggagcagc cagacagcga gggccccggc cggggcagg gggacgccc cgtccggggc | 120 |
| accccccgg ctctgagccg cccgcgggc cggcctcggc ccggagcgga ggaaggagtc | 180 |
| gccgaggagc agcctgaggc cccagagtct gagacgagcc gccgccgccc ccgccactgc | 240 |
| ggggaggagg gggaggagga gcgggaggag ggacgagctg gtcgggagaa gaggaaaaaa | 300 |
| acttttgaga cttttccgtt gccgctggga gccggaggcg cggggacctc ttggcgcgac | 360 |
| gctgccccgc gaggaggcag gacttgggga ccccagaccg cctcccttg ccgccgggga | 420 |
| cgcttgctcc ctccctgccc cctacacggc gtccctcagg cgccccatt ccggaccagc | 480 |
| cctcgggagt cgccgacccg gcctcccgca aagactttc cccagacctc gggcgcaccc | 540 |
| cctgcacgcc gccttcatcc ccggcctgtc tcctgagccc ccgcgcatcc tagacccttt | 600 |
| ctcctccagg agacggatct ctctccgacc tgccacagat cccctattca agaccaccca | 660 |
| ccttctggta ccagatcgcg cccatctagg ttatttccgt gggatactga gacacccccg | 720 |
| gtccaagcct cccctccacc actgcgccct tctccctgag gacctcagct ttccctcgag | 780 |
| gccctcctac cttttgccgg gagaccccca gcccctgcag gggcggggcc tccccaccac | 840 |
| accagccctg ttcgcgctct cggcagtgcc ggggggcgcc gcctccccca tgccgccctc | 900 |
| cgggctgcgg ctgctgccgc tgctgctacc gctgctgtgg ctactggtgc tgacgcctgg | 960 |
| ccggccggcc gcgggactat ccacctgcaa gactatcgac atggagctgg tgaagcggaa | 1020 |
| gcgcatcgag gccatccgcg gccagatcct gtccaagctg cggctcgcca gccccccgag | 1080 |
| ccaggggag gtgccgcccg gcccgctgcc cgaggccgtg ctcgccctgt acaacagcac | 1140 |
| ccgcgaccgg gtggccgggg agagtgcaga accggagccc gagcctgagg ccgactacta | 1200 |
| cgccaaggag gtcacccgcg tgctaatggt ggaaacccac aacgaaatct atgacaagtt | 1260 |
| caagcagagt acacacagca tatatatgtt cttcaacaca tcagagctcc gagaagcggt | 1320 |
| acctgaaccc gtgttgctct cccggggcaga gctgcgtctg ctgaggctca agttaaaagt | 1380 |
| ggagcagcac gtggagctgt accagaaata cagcaacaat tcctggcgat acctcagcaa | 1440 |
| ccggctgctg gcacccagcg actcgccaga gtggttatct tttgatgtca ccggagttgt | 1500 |
| gcggcagtgg ttgagccgtg gagggggaaat tgagggcttt cgccttagcg cccactgctc | 1560 |
| ctgtgacagc agggataaca cactgcaagt ggacatcaac gggttcacta ccggccgccg | 1620 |
| aggtgacctg gccaccattc atggcatgaa ccggcctttc ctgcttctca tggccaccc | 1680 |
| gctggagagg gcccagcatc tgcaaagctc ccggcaccgc cgagccctgg acaccaacta | 1740 |
| ttgcttcagc tccacggaga gaactgctg cgtgcggcag ctgtacattg acttccgcaa | 1800 |
| ggacctcggc tggaagtgga tccacgagcc caagggctac catgccaact tctgcctcgg | 1860 |
| gccctgcccc tacatttgga gcctggacac gcagtacagc aaggtcctgg ccctgtacaa | 1920 |
| ccagcataac ccgggcgcct cggcggcgcc gtgctgcgtg ccgcaggcgc tggagccgct | 1980 |
| gcccatcgtg tactacgtgg gccgcaagcc caaggtggag cagctgtcca acatgatcgt | 2040 |
| gcgctcctgc aagtgcagct gaggtcccgc cccgcccgc cccgcccgg caggcccggc | 2100 |
| cccacccgc cccgccccg ctgccttgcc catgggggct gtatttaagg acaccgtgc | 2160 |
| cccaagccca cctggggccc cattaaagat ggagagagga ctgcggatct ctgtgtcatt | 2220 |
| gggcgcctgc ctggggtctc catccctgac gttcccccac tcccactccc tctctctccc | 2280 |
| tctctgcctc ctcctgcctg tctgcactat tcctttgccc ggcatcaagg cacagggac | 2340 |
| cagtggggaa cactactgta gttagatcta tttattgagc accttgggca ctgttgaagt | 2400 |

```
gccttacatt aatgaactca ttcagtcacc atagcaacac tctgagatgc agggactctg   2460
ataacaccca tttaaaggt gaggaaacaa gcccagagag gttaagggag gagttcctgc    2520
ccaccaggaa cctgctttag tgggggatag tgaagaagac aataaaagat agtagttcag   2580
gcc                                                                 2583

<210> SEQ ID NO 119
<211> LENGTH: 390
<212> TYPE: PRT
<213> ORGANISM: Homo sapiens

<400> SEQUENCE: 119

Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335
```

```
Ser Lys Val Leu Ala Leu Tyr Asn Gln His Asn Pro Gly Ala Ser Ala
        340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 120
<211> LENGTH: 19
<212> TYPE: DNA
<213> ORGANISM: Artificial Sequence
<220> FEATURE:
<223> OTHER INFORMATION: chemcially synhtesized

<400> SEQUENCE: 120
uauugucuuc uucacuauc                                               19

<210> SEQ ID NO 121
<211> LENGTH: 19
<212> TYPE: DNA
<213> ORGANISM: Artificial Sequence
<220> FEATURE:
<223> OTHER INFORMATION: chemcially synthesized

<400> SEQUENCE: 121
uagaucuaac uacaguagu                                               19

<210> SEQ ID NO 122
<211> LENGTH: 19
<212> TYPE: DNA
<213> ORGANISM: Artificial Sequence
<220> FEATURE:
<223> OTHER INFORMATION: chemcially synthesized

<400> SEQUENCE: 122
uauaugcugu guguacucu                                               19

<210> SEQ ID NO 123
<211> LENGTH: 19
<212> TYPE: DNA
<213> ORGANISM: Artificial Sequence
<220> FEATURE:
<223> OTHER INFORMATION: chemcially synthesized

<400> SEQUENCE: 123
uauauaugcu guguguacu                                               19

<210> SEQ ID NO 124
<211> LENGTH: 31
<212> TYPE: DNA
<213> ORGANISM: Artificial Sequence
<220> FEATURE:
<223> OTHER INFORMATION: chemcially synthesized

<400> SEQUENCE: 124
ccggtcatat atgctgtgtg tactcgaccg g                                 31

<210> SEQ ID NO 125
<211> LENGTH: 31
<212> TYPE: DNA
<213> ORGANISM: Artificial Sequence
<220> FEATURE:
```

<223> OTHER INFORMATION: chemcially synthesized

<400> SEQUENCE: 125
ccggtctttt attgtcttct tcactgaccg g                             31

<210> SEQ ID NO 126
<211> LENGTH: 31
<212> TYPE: DNA
<213> ORGANISM: Artificial Sequence
<220> FEATURE:
<223> OTHER INFORMATION: chemcially synthesized

<400> SEQUENCE: 126
ccggtctata tatgctgtgt gtactgaccg g                             31

<210> SEQ ID NO 127
<211> LENGTH: 5966
<212> TYPE: DNA
<213> ORGANISM: Homo sapiens

<400> SEQUENCE: 127

| | |
|---|---|
| gtgatgttat ctgctggcag cagaaggttc gctccgagcg gagctccaga agctcctgac | 60 |
| aagagaaaga cagattgaga tagagataga aagagaaaga gagaaagaga cagcagagcg | 120 |
| agagcgcaag tgaaagaggc aggggagggg gatggagaat attagcctga cggtctaggg | 180 |
| agtcatccag gaacaaactg aggggctgcc cggctgcaga caggaggaga cagagaggat | 240 |
| ctattttagg gtggcaagtg cctacctacc ctaagcgagc aattccacgt tggggagaag | 300 |
| ccagcagagg ttgggaaagg gtgggagtcc aagggagccc ctgcgcaacc ccctcaggaa | 360 |
| taaaactccc cagccagggt gtcgcaaggg ctgccgttgt gatccgcagg gggtgaacgc | 420 |
| aaccgcgacg gctgatcgtc tgtggctggg ttggcgtttg gagcaagaga aggaggagca | 480 |
| ggagaaggag ggagctggag gctggaagcg tttgcaagcg gcggcggcag caacgtggag | 540 |
| taaccaagcg ggtcagcgcg cgcccgccag ggtgtaggcc acgagcgca gctcccagag | 600 |
| caggatccgc gccgcctcag cagcctctgc ggcccctgcg gcacccgacc gagtaccgag | 660 |
| cgccctgcga agcgcaccct cctccccgcg gtgcgctggg ctcgccccca gcgcgcgcac | 720 |
| acgcacacac acacacacac acacacacgc acgcacacac gtgtgcgctt ctctgctccg | 780 |
| gagctgctgc tgctcctgct ctcagcgccg cagtggaagg caggaccgaa ccgctccttc | 840 |
| tttaaatata taaatttcag cccaggtcag cctcggcggc ccccctcacc gcgctcccgg | 900 |
| cgccctccc gtcagttcgc cagctgccag ccccgggacc ttttcatctc ttccctttg | 960 |
| gccggaggag ccgagttcag atccgccact ccgcacccga gactgacaca ctgaactcca | 1020 |
| cttcctcctc ttaaatttat ttctacttaa tagccactcg tctctttttt tcccatctc | 1080 |
| attgctccaa gaatttttt cttcttactc gccaaagtca gggttccctc tgcccgtccc | 1140 |
| gtattaatat ttccactttt ggaactactg gccttttctt tttaaaggaa ttcaagcagg | 1200 |
| atacgttttt ctgttgggca ttgactagat tgtttgcaaa agtttcgcat caaaaacaac | 1260 |
| aacaacaaaa aaccaaacaa ctctcccttga tctatacttt gagaattgtt gatttctttt | 1320 |
| ttttattctg acttttaaaa acaactttttt tttccactttt tttaaaaaat gcactactgt | 1380 |
| gtgctgagcg cttttctgat cctgcatctg gtcacggtcg cgctcagcct gtctacctgc | 1440 |
| agcacactcg atatggacca gttcatgcgc aagaggatcg aggcgatccg cgggcagatc | 1500 |
| ctgagcaagc tgaagctcac cagtcccccca gaagactatc ctgagcccga ggaagtcccc | 1560 |
| ccggaggtga tttccatcta caacagcacc agggacttgc tccaggagaa ggcgagccgg | 1620 |

```
agggcggccg cctgcgagcg cgagaggagc gacgaagagt actacgccaa ggaggtttac    1680
aaaatagaca tgccgccctt cttcccctcc gaaactgtct gcccagttgt tacaacaccc    1740
tctggctcag tgggcagctt gtgctccaga cagtcccagg tgctctgtgg gtaccttgat    1800
gccatcccgc ccactttcta cagaccctac ttcagaattg ttcgatttga cgtctcagca    1860
atggagaaga atgcttccaa tttggtgaaa gcagagttca gagtctttcg tttgcagaac    1920
ccaaaagcca gagtgcctga acaacggatt gagctatatc agattctcaa gtccaaagat    1980
ttaacatctc caacccagcg ctacatcgac agcaaagttg tgaaaacaag agcagaaggc    2040
gaatggctct ccttcgatgt aactgatgct gttcatgaat ggcttcacca taaagacagg    2100
aacctgggat ttaaaataag cttacactgt ccctgctgca cttttgtacc atctaataat    2160
tacatcatcc caaataaaag tgaagaacta gaagcaagat ttgcaggtat tgatggcacc    2220
tccacatata ccagtggtga tcagaaaact ataaagtcca ctaggaaaaa aaacagtggg    2280
aagaccccac atctcctgct aatgttattg ccctcctaca gacttgagtc acaacagacc    2340
aaccggcgga agaagcgtgc tttggatgcg gcctattgct ttagaaatgt gcaggataat    2400
tgctgcctac gtccactttta cattgatttc aagagggatc tagggtggaa atggatacac    2460
gaacccaaag ggtacaatgc caacttctgt gctggagcat gcccgtattt atggagttca    2520
gacactcagc acagcagggt cctgagctta tataatacca taaatccaga agcatctgct    2580
tctccttgct gcgtgtccca agatttagaa cctctaacca ttctctacta cattggcaaa    2640
acacccaaga ttgaacagct ttctaatatg attgtaaagt cttgcaaatg cagctaaaat    2700
tcttggaaaa gtggcaagac caaaatgaca atgatgatga taatgatgat gacgacgaca    2760
acgatgatgc ttgtaacaag aaaacataag agagccttgg ttcatcagtg ttaaaaaatt    2820
tttgaaaagg cggtactagt tcagacactt tggaagtttg tgttctgttt gttaaaactg    2880
gcatctgaca caaaaaaagt tgaaggcctt attctacatt tcacctactt tgtaagtgag    2940
agagacaaga agcaaatttt ttttaaagaa aaaaataaac actggaagaa tttattagtg    3000
ttaattatgt gaacaacgac aacaacaaca acaacaacaa acaggaaaat cccattaagt    3060
ggagttgctg tacgtaccgt tcctatcccg cgcctcactt gattttttctg tattgctatg    3120 caataggcac ccttcccatt cttactctta gagttaacag tgagttattt attgtgtgtt    3180
actatataat gaacgtttca ttgcccttgg aaaataaaac aggtgtataa agtggagacc    3240
aaatactttg ccagaaactc atggatggct taaggaactt gaactcaaac gagccagaaa    3300
aaaagaggtc atattaatgg gatgaaaacc caagtgagtt attatatgac cgagaaagtc    3360
tgcattaaga taaagaccct gaaaacacat gttatgtatc agctgcctaa ggaagcttct    3420
tgtaaggtcc aaaaactaaa aagactgtta ataaaagaaa ctttcagtca gaataagtct    3480
gtaagttttt ttttttcttt ttaattgtaa atggttcttt gtcagtttag taaaccagtg    3540
aaatgttgaa atgttttgac atgtactggt caaacttcag accttaaaat attgctgtat    3600
agctatgcta taggtttttt cctttgtttt ggtatatgta accataccta tattattaaa    3660
atagatggat atagaagcca gcataattga aaacacatct gcagatctct tttgcaaact    3720
attaaatcaa acattaact actttatgtg taatgtgtaa attttttacca tattttttat    3780 attctgtaat aatgtcaact atgatttaga ttgacttaaa tttgggctct tttaatgat    3840 cactcacaaa tgtatgtttc ttttagctgg ccagtacttt tgagtaaagc ccctatagtt    3900
tgacttgcac tacaaatgca ttttttttttt aataacattt gccctacttg tgctttgtgt    3960
```

```
ttctttcatt attatgacat aagctacctg ggtccacttg tctttttcttt ttttttgtttc    4020
acagaaaaga tgggttcgag ttcagtggtc ttcatcttcc aagcatcatt actaaccaag    4080
tcagacgtta acaaatttt atgttaggaa aaggaggaat gttatagata catagaaaat    4140
tgaagtaaaa tgttttcatt ttagcaagga tttagggttc taactaaaac tcagaatctt    4200
tattgagtta agaaaagttt ctctaccttg gtttaatcaa tatttttgta aaatcctatt    4260
gttattacaa agaggacact tcataggaaa catctttttc tttagtcagg ttttttaatat   4320
tcaggggaa attgaaagat atatatttta gtcgattttt caaaggggga aaaaagtcca    4380
ggtcagcata agtcatttg tgtatttcac tgaagttata aggttttat aaatgttctt    4440
tgaaggggaa aaggcacaag ccaatttttc ctatgatcaa aaaattcttt ctttcctctg    4500
agtgagagtt atctatatct gaggctaaag tttaccttgc tttaataaat aatttgccac    4560
atcattgcag aagaggtatc ctcatgctgg ggttaataga atatgtcagt ttatcacttg    4620
tcgcttattt agctttaaaa taaaaattaa taggcaaagc aatggaatat ttgcagtttc    4680
acctaaagag cagcataagg aggcgggaat ccaaagtgaa gttgtttgat atggtctact    4740
tcttttttgg aatttcctga ccattaatta aagaattgga tttgcaagtt tgaaaactgg    4800
aaaagcaaga gatgggatgc cataatagta aacagcccct gtgttggatg taacccaatc    4860
ccagatttga gtgtgtgttg attattttt tgtcttccac ttttctatta tgtgtaaatc    4920
acttttattt ctgcagacat tttcctctca gataggatga cattttgttt tgtattattt    4980
tgtctttcct catgaatgca ctgataatat tttaaatgct ctattttaag atctcttgaa    5040
tctgtttttt tttttttaaa tttgggggtt ctgtaaggtc tttatttccc ataagtaaat    5100
attgccatgg gaggggggtg gaggtggcaa ggaagggtg aagtgctagt atgcaagtgg    5160
gcagcaatta ttttttgtgtt aatcagcagt acaatttgat cgttggcatg gttaaaaaat    5220
ggaatataag attagctgtt ttgtattttg atgaccaatt acgctgtatt ttaacacgat    5280
gtatgtctgt ttttgtggtg ctctagtggt aaataaatta tttcgatgat atgtggatgt    5340
cttttttccta tcagtaccat catcgagtct agaaaacacc tgtgatgcaa taagactatc    5400
tcaagctgga aaagtcatac cacctttccg attgccctct gtgctttctc ccttaaggac    5460
agtcacttca gaagtcatgc tttaaagcac aagagtcagg ccatatccat caaggataga    5520
agaaatccct gtgccgtctt tttattccct tatttattgc tatttggtaa ttgtttgaga    5580
tttagttccc atccagcttg actgccgacc agaaaaaatg cagagagatg tttgcaccat    5640
gctttggctt tctggttcta tgttctgcca acgccagggc caaaagaact ggtctagaca    5700
gtatcccctg tagccccata acttggatag ttgctgagcc agccagatat aacaagagcc    5760
acgtgctttc tggggttggt tgtttgggat cagctacttg cctgtcagtt tcactggtac    5820
cactgcacca caaacaaaaa aacccaccct atttcctcca atttttttgg ctgctaccta    5880
caagaccaga ctcctcaaac gagttgccaa tctcttaata aataggatta ataaaaaaag    5940
taattgtgac tcaaaaaaaa aaaaaa                                         5966
```

<210> SEQ ID NO 128
<211> LENGTH: 442
<212> TYPE: PRT
<213> ORGANISM: Homo sapiens

<400> SEQUENCE: 128

Met His Tyr Cys Val Leu Ser Ala Phe Leu Ile Leu His Leu Val Thr
1               5                   10                  15

-continued

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
                35                  40                  45

Lys Leu Thr Ser Pro Pro Glu Asp Tyr Pro Glu Pro Glu Glu Val Pro
        50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
                100                 105                 110

Pro Ser Glu Thr Val Cys Pro Val Val Thr Thr Pro Ser Gly Ser Val
        115                 120                 125

Gly Ser Leu Cys Ser Arg Gln Ser Gln Val Leu Cys Gly Tyr Leu Asp
        130                 135                 140

Ala Ile Pro Pro Thr Phe Tyr Arg Pro Tyr Phe Arg Ile Val Arg Phe
145                 150                 155                 160

Asp Val Ser Ala Met Glu Lys Asn Ala Ser Asn Leu Val Lys Ala Glu
                165                 170                 175

Phe Arg Val Phe Arg Leu Gln Asn Pro Lys Ala Arg Val Pro Glu Gln
                180                 185                 190

Arg Ile Glu Leu Tyr Gln Ile Leu Lys Ser Lys Asp Leu Thr Ser Pro
                195                 200                 205

Thr Gln Arg Tyr Ile Asp Ser Lys Val Val Lys Thr Arg Ala Glu Gly
        210                 215                 220

Glu Trp Leu Ser Phe Asp Val Thr Asp Ala Val His Glu Trp Leu His
225                 230                 235                 240

His Lys Asp Arg Asn Leu Gly Phe Lys Ile Ser Leu His Cys Pro Cys
                245                 250                 255

Cys Thr Phe Val Pro Ser Asn Asn Tyr Ile Ile Pro Asn Lys Ser Glu
                260                 265                 270

Glu Leu Glu Ala Arg Phe Ala Gly Ile Asp Gly Thr Ser Thr Tyr Thr
        275                 280                 285

Ser Gly Asp Gln Lys Thr Ile Lys Ser Thr Arg Lys Lys Asn Ser Gly
        290                 295                 300

Lys Thr Pro His Leu Leu Leu Met Leu Leu Pro Ser Tyr Arg Leu Glu
305                 310                 315                 320

Ser Gln Gln Thr Asn Arg Arg Lys Lys Arg Ala Leu Asp Ala Ala Tyr
                325                 330                 335

Cys Phe Arg Asn Val Gln Asp Asn Cys Cys Leu Arg Pro Leu Tyr Ile
                340                 345                 350

Asp Phe Lys Arg Asp Leu Gly Trp Lys Trp Ile His Glu Pro Lys Gly
                355                 360                 365

Tyr Asn Ala Asn Phe Cys Ala Gly Ala Cys Pro Tyr Leu Trp Ser Ser
        370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
                405                 410                 415

Thr Ile Leu Tyr Tyr Ile Gly Lys Thr Pro Lys Ile Glu Gln Leu Ser
        420                 425                 430

Asn Met Ile Val Lys Ser Cys Lys Cys Ser

<210> SEQ ID NO 129
<211> LENGTH: 20
<212> TYPE: DNA
<213> ORGANISM: Artificial Sequence
<220> FEATURE:
<223> OTHER INFORMATION: chemcially synthesized

<400> SEQUENCE: 129
uaucucuauc ucaaucuguc                                               20

<210> SEQ ID NO 130
<211> LENGTH: 20
<212> TYPE: DNA
<213> ORGANISM: Artificial Sequence
<220> FEATURE:
<223> OTHER INFORMATION: checmially synthesized

<400> SEQUENCE: 130
uucuaucucu aucucaaucu                                               20

<210> SEQ ID NO 131
<211> LENGTH: 20
<212> TYPE: DNA
<213> ORGANISM: Artificial Sequence
<220> FEATURE:
<223> OTHER INFORMATION: chemcially synhtesized

<400> SEQUENCE: 131
uucucuuucu aucucuaucu                                               20

<210> SEQ ID NO 132
<211> LENGTH: 20
<212> TYPE: DNA
<213> ORGANISM: Artificial Sequence
<220> FEATURE:
<223> OTHER INFORMATION: chemically synthesized

<400> SEQUENCE: 132
ucuaucucua ucucaaucug                                               20

<210> SEQ ID NO 133
<211> LENGTH: 31
<212> TYPE: DNA
<213> ORGANISM: Artificial Sequence
<220> FEATURE:
<223> OTHER INFORMATION: chemcially synthesizerd

<400> SEQUENCE: 133
ccggtcttct atctctatct caatcgaccg g                                  31

<210> SEQ ID NO 134
<211> LENGTH: 31
<212> TYPE: DNA
<213> ORGANISM: Artificial Sequence
<220> FEATURE:
<223> OTHER INFORMATION: chemcially synthesized

<400> SEQUENCE: 134
ccggtctatc tctatctcaa tctgtgaccg g                                  31

<210> SEQ ID NO 135
<211> LENGTH: 31
<212> TYPE: DNA
<213> ORGANISM: Artificial Sequence

```
<220> FEATURE:
<223> OTHER INFORMATION: chemcially synthesized

<400> SEQUENCE: 135
ccggtcttct ctttctatct ctatcgaccg g                              31

<210> SEQ ID NO 136
<211> LENGTH: 7321
<212> TYPE: DNA
<213> ORGANISM: Homo sapiens

<400> SEQUENCE: 136
ttttgtagat aaatgtgagg attttctcta aatccctctt ctgtttgcta aatctcactg    60
tcactgctaa attcagagca gatagagcct gcgcaatgga ataaagtcct caaaattgaa   120
atgtgacatt gctctcaaca tctcccatct ctctggattt cttttttgctt cattattcct   180 gctaaccaat tcattttcag actttgtact tcagaagcaa tgggaaaaat cagcagtctt   240
ccaacccaat tatttaagtg ctgcttttgt gatttcttga aggtgaagat gcacaccatg   300
tcctcctcgc atctcttcta cctggcgctg tgcctgctca ccttcaccag ctctgccacg   360 gctgaccgg agacgctctg cggggctgag ctggtggatg ctcttcagtt cgtgtgtgga   420
gacaggggct tttatttcaa caagcccaca gggtatggct ccagcagtcg gagggcgcct   480
cagacaggca tcgtggatga gtgctgcttc cggagctgtg atctaaggag ctggagatg   540 tattgcgcac ccctcaagcc tgccaagtca gctcgctctg tccgtgccca gccacacc   600 gacatgccca gacccagaa ggaagtacat ttgaagaacg caagtagagg gagtgcagga   660
aacaagaact acaggatgta ggaagaccct cctgaggagt gaagagtgac atgccaccgc   720
aggatccttt gctctgcacg agttaccgt taaactttgg aacacctacc aaaaaataag   780
tttgataaca tttaaaagat gggcgtttcc cccaatgaaa tacacaagta aacattccaa   840
cattgtcttt aggagtgatt tgcaccttgc aaaaatggtc ctggagttgg tagattgctg   900
ttgatctttt atcaataatg ttctatagaa aagaaaaaaa aatatatat atatatatat   960 cttagtccct gcctctcaag agccacaaat gcatgggtgt tgtatagatc cagttgcact  1020
aaattcctct ctgaatcttg gctgctggag ccattcattc agcaaccttg tctaagtggt  1080
ttatgaattg tttccttatt tgcacttctt tctacacaac tcgggctgtt tgttttacag  1140
tgtctgataa tcttgttagt ctatacccac cacctccctt cataaccttt atatttgccg  1200
aatttggcct cctcaaaagc agcagcaagt cgtcaagaag cacaccaatt ctaacccaca  1260
agattccatc tgtggcattt gtaccaaata taagttggat gcattttatt ttagacacaa  1320
agctttattt ttccacatca tgcttacaaa aagaataat gcaaatagtt gcaactttga  1380
ggccaatcat ttttaggcat atgttttaaa catagaaagt tcttcaact caaaagagtt  1440 ccttcaaatg atgagttaat gtgcaaccta attagtaact ttcctcttt tattttttcc  1500 atatagagca ctatgtaaat ttagcatatc aattatacag gatatatcaa acagtatgta  1560
aaactctgtt ttttagtata atggtgctat tttgtagttt gttatatgaa agagtctggc  1620
caaaacggta atacgtgaaa gcaaaacaat aggggaagcc tggagccaaa gatgacacaa  1680
ggggaagggt actgaaaaca ccatccattt gggaaagaag gcaaagtccc cccagttatg  1740
ccttccaaga ggaacttcag acacaaaagt ccactgatgc aaattggact ggcgagtcca  1800
gagaggaaac tgtggaatgg aaaaagcaga aggctaggaa ttttagcagt cctggtttct  1860
ttttctcatg gaagaaatga acatctgcca gctgtgtcat ggactcacca ctgtgtgacc  1920
```

```
ttgggcaagt cacttcacct ctctgtgcct cagtttcctc atctgcaaaa tgggggcaat    1980
atgtcatcta cctacctcaa aggggtggta taaggtttaa aaagataaag attcagattt    2040 tttttacccct gggttgctgt aagggtgcaa catcagggcg cttgagttgc tgagatgcaa   2100
ggaattctat aaataaccca ttcatagcat agctagagat tggtgaattg aatgctcctg    2160
acatctcagt tcttgtcagt gaagctatcc aaataactgg ccaactagtt gttaaaagct    2220
aacagctcaa tctcttaaaa cacttttcaa aatatgtggg aagcatttga ttttcaattt    2280
gattttgaat tctgcatttg gttttatgaa tacaaagata agtgaaaaga gagaaaggaa    2340
aagaaaaagg agaaaaacaa agagatttct accagtgaaa ggggaattaa ttactctttg    2400
ttagcactca ctgactcttc tatgcagtta ctacatatct agtaaaacct cgtttaatac    2460
tataaataat attctattca ttttgaaaaa cacaatgatt ccttcttttc taggcaatat    2520
aaggaaagtg atccaaaatt tgaaatatta aataatatc taataaaaag tcacaaagtt     2580
atcttcttta acaaacttta ctcttattct tagctgtata tacatttttt taaaagtttg    2640
ttaaaatatg cttgactaga gtttccagtt gaaaggcaaa aacttccatc acaacaagaa    2700
atttcccatg cctgctcaga agggtagccc ctagctctct gtgaatgtgt tttatccatt    2760
caactgaaaa ttggtatcaa gaaagtccac tggttagtgt actagtccat catagcctag    2820
aaaatgatcc ctatctgcag atcaagattt tctcattaga acaatgaatt atccagcatt    2880
cagatctttc tagtcacctt agaacttttt ggttaaaagt acccaggctt gattatttca    2940
tgcaaattct atattttaca ttcttggaaa gtctatatga aaaacaaaaa taacatcttc    3000 agttttctc ccactgggtc acctcaagga tcagaggcca ggaaaaaaaa aaaaaagact     3060
ccctggatct ctgaatatat gcaaaagaa ggccccattt agtggagcca gcaatcctgt     3120
tcagtcaaca agtattttaa ctctcagtcc aacattattt gaattgagca cctcaagcat    3180
gcttagcaat gttctaatca ctatggacag atgtaaaaga aactatacat cattttttgcc   3240 ctctgcctgt tttccagaca tacaggttct gtggaataag atactggact cctcttccca    3300
agatggcact tctttttatt tcttgtcccc agtgtgtacc ttttaaaatt attccctctc    3360
aacaaaactt tataggcagt cttctgcaga cttaacgtgt tttctgtcat agttagatgt    3420
gataattcta agagtgtcta tgacttattt ccttcactta attctatcca cagtcaaaaa    3480
tcccccaagg aggaaagctg aaagatgcac tgccatatta tctttcttaa cttttttccaa   3540 cacataatcc tctccaactg gattataaat aaattgaaaa taactcatta taccaattca    3600
ctattttatt ttttaatgaa ttaaaactag aaaacaaatt gatgcaaacc ctggaagtca    3660
gttgattact atatactaca gcagaatgac tcagatttca tagaaaggag caaccaaaat    3720
gtcacaaccc aaaactttac aagctttgct tcagaattag attgctttat aattcttgaa    3780
tgaggcaatt tcaagatatt tgtaaaagaa cagtaaacat tggtaagaat gagctttcaa    3840
ctcataggct tatttccaat ttaattgacc atactggata cttaggtcaa atttctgttc    3900
tctcttcccc aaataatatt aaagtattat ttgaactttt taagatgagg cagttcccct    3960
gaaaaagtta atgcagctct ccatcagaat ccactcttct agggatatga aaatctctta    4020
acacccaccc tacatacaca gacacacaca cacacacaca cacacacaca cacacacaca    4080
ttcaccctaa ggatccaatg gaatactgaa aagaaatcac ttccttgaaa attttattaa    4140
aaaacaaaca aacaaacaaa aagcctgtcc acccttgaga atccttcctc tccttggaac    4200
gtcaatgttt gtgtagatga aaccatctca tgctctgtgg ctccagggtt tctgttacta    4260
ttttatgcac ttgggagaag gcttagaata aaagatgtag cacatttgc tttcccattt     4320
```

```
attgtttggc cagctatgcc aatgtggtgc tattgtttct ttaagaaagt acttgactaa    4380
aaaaaaaaga aaaaagaaa aaaagaaag catagacata ttttttttaaa gtataaaaac    4440 aacaattcta tagatagatg gcttaataaa atagcattag gtctatctag ccaccaccac    4500
ctttcaactt tttatcactc acaagtagtg tactgttcac caaattgtga atttgggggt    4560 gcagggggcag gagttggaaa tttttttaaag ttagaaggct ccattgtttt gttggctctc    4620
aaacttagca aaattagcaa tatattatcc aatcttctga acttgatcaa gagcatggag    4680
aataaacgcg ggaaaaaaga tcttataggc aaatagaaga atttaaaaga taagtaagtt    4740
ccttattgat ttttgtgcac tctgctctaa aacagatatt cagcaagtgg agaaaataag    4800
aacaaagaga aaaatacat agatttacct gcaaaaaata gcttctgcca aatccccctt    4860
gggtattctt tggcatttac tggttttatag aagacattct cccttcaccc agacatctca    4920
aagagcagta gctctcatga aaagcaatca ctgatctcat ttgggaaatg ttggaaagta    4980
tttccttatg agatgggggt tatctactga taaagaaaga atttatgaga aattgttgaa    5040
agagatggct aacaatctgt gaagattttt tgtttcttgt ttttgttttt ttttttttt    5100 tactttatac agtctttatg aatttcttaa tgttcaaaat gacttggttc ttttcttctt    5160
tttttatatc agaatgagga ataataagtt aaacccacat agactcttta aaactatagg    5220
ctagatagaa atgtatgttt gacttgttga agctataatc agactattta aaatgttttg    5280 ctattttaa tcttaaaaga ttgtgctaat ttattagagc agaacctgtt tggctctcct    5340
cagaagaaag aatctttcca ttcaaatcac atggctttcc accaatattt tcaaaagata    5400
aatctgattt atgcaatggc atcatttatt ttaaaacaga agaattgtga aagtttatgc    5460
ccctcccttg caaagaccat aaagtccaga tctggtaggg gggcaacaac aaaaggaaaa    5520
tgttgttgat tcttggtttt ggattttgtt ttgttttcaa tgctagtgtt taatcctgta    5580
gtacatattt gcttattgct attttaatat tttataagac cttcctgtta ggtattagaa    5640
agtgatacat agatatcttt tttgtgtaat ttctatttaa aaaagagaga agactgtcag    5700
aagctttaag tgcatatggt acaggataaa gatatcaatt taaataacca attcctatct    5760
ggaacaatgc ttttgttttt taagaaaacc tctcacagat aagacagagg cccagggggat    5820 ttttgaagct gtctttattc tgcccccatc ccaacccagc ccttattatt ttagtatctg    5880
cctcagaatt ttatagaggg ctgaccaagc tgaaactcta gaattaaagg aacctcactg    5940
aaaacatata tttcacgtgt tccctctttt tttttttcct ttttgtgaga tgggggtctcg    6000 cactgtcccc caggctggag tgcagtggca tgatctcggc tcactgcaac ctccacctcc    6060
tgggtttaag cgattctcct gcctcagcct cctgagtagc tgggattaca ggcacccacc    6120
actatgcccg gctaattttt tggatttta atagagacgg ggttttacca tgttggccag    6180
gttggtctca aactcctgac cttgtgattt gcccgcctca gcctcccaaa ttgctgggat    6240
tacaggcatg agccaccaca ccctgcccat gtgttccctc ttaatgtatg attacatgga    6300
tcttaaacat gatccttctc tcctcattct tcaactatct ttgatggggt ctttcaaggg    6360
gaaaaaaatc caagctttt taaagtaaaa aaaaaaaaag agaggacaca aaaccaaatg    6420
ttactgctca actgaaatat gagttaagat ggagacagag tttctcctaa taaccggagc    6480
tgaattacct ttcactttca aaaacatgac cttccacaat ccttagaatc tgccttttttt    6540 tatattactg aggcctaaaa gtaaacatta ctcattttat tttgcccaaa atgcactgat    6600
gtaaagtagg aaaaataaaa acagagctct aaaatcccctt tcaagccacc cattgacccc    6660
```

```
actcaccaac tcatagcaaa gtcacttctg ttaatccctt aatctgattt tgtttggata    6720
tttatcttgt acccgctgct aaacacactg caggagggac tctgaaacct caagctgtct    6780
acttacatct tttatctgtg tctgtgtatc atgaaaatgt ctattcaaaa tatcaaaacc    6840
tttcaaatat cacgcagctt atattcagtt tacataaagg ccccaaatac catgtcagat    6900 cttttttggta aaagagttaa tgaactatga gaattgggat tacatcatgt attttgcctc    6960
atgtattttt atcacactta taggccaagt gtgataaata aacttacaga cactgaatta    7020
atttcccctg ctactttgaa accagaaaat aatgactggc cattcgttac atctgtctta    7080
gttgaaaagc atattttta ttaaattaat tctgattgta tttgaaatta ttattcaatt    7140
cacttatggc agaggaatat caatcctaat gacttctaaa aatgtaacta attgaatcat    7200
tatcttacat ttactgttta ataagcatat tttgaaaatg tatggctaga gtgtcataat    7260
aaaatggtat atctttcttt agtaattaca ttaaaattag tcatgtttga ttaattagtt    7320
c                                                                   7321
```

<210> SEQ ID NO 137
<211> LENGTH: 153
<212> TYPE: PRT
<213> ORGANISM: Homo sapiens

<400> SEQUENCE: 137

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
        130                 135                 140

Ser Ala Gly Asn Lys Asn Tyr Arg Met
145                 150

<210> SEQ ID NO 138
<211> LENGTH: 19
<212> TYPE: DNA
<213> ORGANISM: Artificial Sequence
<220> FEATURE:
<223> OTHER INFORMATION: chemically synhtesized

<400> SEQUENCE: 138
uaaacugaau auaagcugc                                                19

<210> SEQ ID NO 139
<211> LENGTH: 19
<212> TYPE: DNA
<213> ORGANISM: Artificial Sequence -continued

```
<220> FEATURE:
<223> OTHER INFORMATION: chemcially synthesized

<400> SEQUENCE: 139
uaaaaaaaua ugucuaugc                                                19

<210> SEQ ID NO 140
<211> LENGTH: 19
<212> TYPE: DNA
<213> ORGANISM: Artificial Sequence
<220> FEATURE:
<223> OTHER INFORMATION: chemcially synthesized

<400> SEQUENCE: 140
uuuaacaggu aacucgugc                                                19

<210> SEQ ID NO 141
<211> LENGTH: 19
<212> TYPE: DNA
<213> ORGANISM: Artificial Sequence
<220> FEATURE:
<223> OTHER INFORMATION: chemcially synthesized

<400> SEQUENCE: 141
uaacaaacua caaaauagc                                                19

<210> SEQ ID NO 142
<211> LENGTH: 32
<212> TYPE: DNA
<213> ORGANISM: Artificial Sequence
<220> FEATURE:
<223> OTHER INFORMATION: chemcially synthesized

<400> SEQUENCE: 142
ccggtctaaa ctgaatataa gctgcggacc gg                                 32

<210> SEQ ID NO 143
<211> LENGTH: 32
<212> TYPE: DNA
<213> ORGANISM: Artificial Sequence
<220> FEATURE:
<223> OTHER INFORMATION: chemcially synthesized

<400> SEQUENCE: 143 ccggtctta aattcttcta tttgccgacc gg                                  32

<210> SEQ ID NO 144
<211> LENGTH: 32
<212> TYPE: DNA
<213> ORGANISM: Artificial Sequence
<220> FEATURE:
<223> OTHER INFORMATION: chemcially synthesized

<400> SEQUENCE: 144
ccggtctaat caactgactt ccaggggacc gg                                 32

<210> SEQ ID NO 145
<211> LENGTH: 3150
<212> TYPE: DNA
<213> ORGANISM: Homo sapiens

<400> SEQUENCE: 145
ccacaaaggg cacttggccc cagggctagg agagcgaggg gagagcacag ccacccgcct   60
cggcggcccg ggactcggct cgactcgccg gagaatgcgc ccgaggacga cggggcgcca  120
```

```
gagccgcggt gctttcaact ggcgagcgcg aatgggggtg cactggagta aggcagagtg    180
atgcgggggg gcaactcgcc tggcaccgag atcgccgccg tgcccttccc tggacccggc    240
gtcgcccagg atggctgccc cgagccatgg gccgcggcgg agctagcgcg gagcgcccga    300
ccctcgaccc ccgagtcccg gagccggccc cgcgcggggc cacgcgtccc tcgggcgctg    360
gttcctaagg aggacgacag caccagcttc tcctttctcc cttcccttcc ctgccccgca    420
ctcctccccc tgctcgctgt tgttgtgtgt cagcacttgg ctggggactt cttgaacttg    480
cagggagaat aacttgcgca ccccactttg cgccggtgcc tttgccccag cggagcctgc    540
ttcgccatct ccgagcccca ccgcccctcc actcctcggc cttgcccgac actgagacgc    600
tgttcccagc gtgaaaagag agactgcgcg gccggcaccc gggagaagga ggaggcaaag    660
aaaaggaacg gacattcggt ccttgcgcca ggtcctttga ccagagtttt tccatgtgga    720
cgctctttca atggacgtgt ccccgcgtgc ttcttagacg gactgcggtc tcctaaaggt    780
cgaccatggt ggccgggacc cgctgtcttc tagcgttgct gcttcccag gtcctcctgg     840
gcggcgcggc tggcctcgtt ccggagctgg gccgcaggaa gttcgcggcg cgtcgtcgg     900
gccgcccctc atcccagccc tctgacgagg tcctgagcga gttcgagttg cggctgctca    960
gcatgttcgg cctgaaacag agacccaccc ccagcaggga cgccgtggtg ccccctaca    1020
tgctagacct gtatcgcagg cactcaggtc agccgggctc acccgcccca gaccaccggt    1080
tggagagggc agccagccga gccaacactg tgcgcagctt ccaccatgaa gaatctttgg    1140
aagaactacc agaaacgagt gggaaaacaa cccggagatt cttctttaat ttaagttcta    1200
tccccacgga ggagtttatc acctcagcag agcttcaggt tttccgagaa cagatgcaag    1260
atgctttagg aaacaatagc agtttccatc accgaattaa tatttatgaa atcataaaac    1320
ctgcaacagc caactcgaaa ttccccgtga ccagactttt ggacaccagg ttggtgaatc    1380
agaatgcaag caggtgggaa agttttgatg tcaccccgc tgtgatgcgg tggactgcac    1440
agggacacgc caaccatgga ttcgtggtgg aagtggccca cttggaggag aaacaaggtg    1500
tctccaagag acatgttagg ataagcaggt cttttgcacca agatgaacac agctggtcac    1560
agataaggcc attgctagta acttttggcc atgatggaaa agggcatcct ctccacaaaa    1620
gagaaaaacg tcaagccaaa cacaaacagc ggaaacgcct taagtccagc tgtaagagac    1680
acccttgta cgtggacttc agtgacgtgg ggtggaatga ctggattgtg ctcccccgg    1740
ggtatcacgc ctttactgc cacggagaat gccctttcc tctggctgat catctgaact    1800
ccactaatca tgccattgtt cagacgttgg tcaactctgt taactctaag attcctaagg   1860
catgctgtgt cccgacagaa ctcagtgcta tctcgatgct gtaccttgac gagaatgaaa   1920
aggttgtatt aaagaactat caggacatgg ttgtgggggg ttgtgggtgt cgctagtaca   1980
gcaaaattaa atacataaat atatatatat atatatattt tagaaaaaag aaaaaaacaa   2040
acaaacaaaa aaccccacc ccagttgaca ctttaatatt tcccaatgaa gactttattt    2100
atggaatgga atgaaaaaa aaacagctat tttgaaaata tatttatatc tacgaaagaa    2160
agttgggaaa acaaatattt taatcagaga attattcctt aaagatttaa aatgtattta   2220
gttgtacatt ttatatgggt tcaaccccag cacatgaagt ataatggtca gatttatttt   2280
gtatttattt actattataa ccacttttta ggaaaaaaat agctaatttg tatttatatg   2340
taatcaaaag aagtatcggg tttgtacata atttttccaaa aattgtagtt gttttcagtt   2400
gtgtgtattt aagatgaaaa gtctacatgg aaggttactc tggcaaagtg cttagcacgt   2460
ttgctttttt gcagtgctac tgttgagttc acaagttcaa gtccagaaaa aaaaagtgga   2520
```

```
taatccactc tgctgacttt caagattatt atattattca attctcagga atgttgcaga      2580
gtgattgtcc aatccatgag aatttacatc cttattaggt ggaatatttg gataagaacc      2640
agacattgct gatctattat agaaactctc ctcctgcccc ttaatttaca gaaagaataa      2700
agcaggatcc atagaaataa ttaggaaaac gatgaacctg caggaaagtg aatgatggtt      2760
tgttgttctt ctttcctaaa ttagtgatcc cttcaaaggg gctgatctgg ccaaagtatt      2820
caataaaacg taagatttct tcattattga tattgtggtc atatatattt aaaattgata      2880
tctcgtggcc ctcatcaagg gttggaaatt tatttgtgtt ttacctttac ctcatctgag      2940
agctctttat tctccaaaga acccagtttt ctaacttttt gcccaacacg cagcaaaatt      3000
atgcacatcg tgttttctgc ccaccctctg ttctctgacc tatcagcttg cttttctttc      3060
caaggttgtg tgtttgaaca catttctcca aatgttaaac ctatttcaga taataaatat      3120
caaatctctg gcatttcatt ctataaagtc                                       3150
```

<210> SEQ ID NO 146
<211> LENGTH: 396
<212> TYPE: PRT
<213> ORGANISM: Homo sapiens

<400> SEQUENCE: 146

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255
```

-continued

```
Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
            325                 330                 335

Leu Asn Ser Thr Asn His Ala Ile Val Gln Thr Leu Val Asn Ser Val
        340                 345                 350

Asn Ser Lys Ile Pro Lys Ala Cys Cys Val Pro Thr Glu Leu Ser Ala
    355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 147
<211> LENGTH: 19
<212> TYPE: DNA
<213> ORGANISM: Artificial Sequence
<220> FEATURE:
<223> OTHER INFORMATION: chemcially synthesized

<400> SEQUENCE: 147
uugugaacuc aacaguagc                                              19

<210> SEQ ID NO 148
<211> LENGTH: 19
<212> TYPE: DNA
<213> ORGANISM: Artificial Sequence
<220> FEATURE:
<223> OTHER INFORMATION: chemcially synthesized

<400> SEQUENCE: 148
uuaauuuugc uguacuagc                                              19

<210> SEQ ID NO 149
<211> LENGTH: 19
<212> TYPE: DNA
<213> ORGANISM: Artificial Sequence
<220> FEATURE:
<223> OTHER INFORMATION: chemcially synthesized

<400> SEQUENCE: 149
uaaaacacaa auaaauuuc                                              19

<210> SEQ ID NO 150
<211> LENGTH: 19
<212> TYPE: DNA
<213> ORGANISM: Artificial Sequence
<220> FEATURE:
<223> OTHER INFORMATION: chemcially synthesized

<400> SEQUENCE: 150
uucuuucugu aaauuaagg                                              19

<210> SEQ ID NO 151
<211> LENGTH: 30
<212> TYPE: DNA
```

```
<213> ORGANISM: Artificial Sequence
<220> FEATURE:
<223> OTHER INFORMATION: chemcially synthesized

<400> SEQUENCE: 151
ccggtctaat acaaaataaa tctggaccgg                                         30

<210> SEQ ID NO 152
<211> LENGTH: 31
<212> TYPE: DNA
<213> ORGANISM: Artificial Sequence
<220> FEATURE:
<223> OTHER INFORMATION: chemcially synthesized

<400> SEQUENCE: 152
ccggtcaaaa cacaaataaa tttccgaccg g                                       31

<210> SEQ ID NO 153
<211> LENGTH: 31
<212> TYPE: DNA
<213> ORGANISM: Artificial Sequence
<220> FEATURE:
<223> OTHER INFORMATION: chemically synthesized

<400> SEQUENCE: 153
ccggtcttca ttctcgtcaa ggtacgaccg g                                       31

<210> SEQ ID NO 154
<211> LENGTH: 1957
<212> TYPE: DNA
<213> ORGANISM: Homo sapiens

<400> SEQUENCE: 154
aagaggagga aggaagatgc gagaaggcag aggaggaggg agggagggaa ggagcgcgga        60
gcccggcccg gaagctaggt gagtgtggca tccgagctga gggacgcgag cctgagacgc       120
cgctgctgct ccggctgagt atctagcttg tctccccgat gggattcccg tccaagctat       180
ctcgagcctg cagcgccaca gtccccggcc ctcgcccagg ttcactgcaa ccgttcagag       240
gtccccagga gctgctgctg gcgagcccgc tactgcaggg acctatggag ccattccgta       300
gtgccatccc gagcaacgca ctgctgcagc ttccctgagc cttttcagca agtttgttca       360
agattggctg tcaagaatca tggactgtta ttatatgcct tgttttctgt caagacacca       420
tgattcctgg taaccgaatg ctgatggtcg ttttattatg ccaagtcctg ctaggaggcg       480
cgagccatgc tagtttgata cctgagacgg ggaagaaaaa agtcgccgag attcagggcc       540
acgcgggagg acgccgctca gggcagagcc atgagctcct gcgggacttc gaggcgacac       600
ttctgcagat gtttgggctg cgccgccgcc cgcagcctag caagagtgcc gtcattccgg       660
actacatgcg ggatctttac cggcttcagt ctggggagga ggaggaagag cagatccaca       720
gcactggtct tgagtatcct gagcgcccgg ccagccgggc caacaccgtg aggagcttcc       780
accacgaaga acatctggag aacatcccag ggaccagtga aaactctgct tttcgtttcc       840
tctttaacct cagcagcatc cctgagaacg aggtgatctc ctctgcagag cttcggctct       900
tccgggagca ggtggaccag ggccctgatt gggaaagggg cttccaccgt ataaacattt       960
atgaggttat gaagcccca gcagaagtgg tgcctgggca cctcatcaca cgactactgg      1020
acacagagct ggtccaccac aatgtgacac ggtgggaaac ttttgatgtg agccctgcgg      1080
tccttcgctg gacccgggag aagcagccaa actatgggct agccattgag gtgactcacc      1140
tccatcagac tcggacccac cagggccagc atgtcaggat tagccgatcg ttacctcaag      1200
```

```
ggagtgggaa ttgggcccag ctccggcccc tcctggtcac ctttggccat gatggccggg    1260
gccatgcctt gacccgacgc cggagggcca agcgtagccc taagcatcac tcacagcggg    1320
ccaggaagaa gaataagaac tgccggcgcc actcgctcta tgtggacttc agcgatgtgg    1380
gctggaatga ctggattgtg ccccaccag gctaccaggc cttctactgc catgggact      1440 gccccttttcc actggctgac cacctcaact caaccaacca tgccattgtg cagaccctgg   1500
tcaattctgt caattccagt atccccaaag cctgttgtgt gcccactgaa ctgagtgcca    1560
tctccatgct gtacctggat gagtatgata aggtggtact gaaaaattat caggagatgg    1620
tagtagaggg atgtgggtgc cgctgagatc aggcagtcct tgaggataga cagatataca    1680
caccacacac acacaccaca tacaccacac acacgttc ccatccactc acccacacac      1740
tacacagact gcttccttat agctggactt ttatttaaaa aaaaaaaaaa aaaaggaaaa    1800
aatccctaaa cattcacctt gaccttattt atgactttac gtgcaaatgt tttgaccata    1860
ttgatcatat attttgacaa aatatattta taactacgta ttaaaagaaa aaaataaaat    1920
gagtcattat tttaaaggta aaaaaaaaaa aaaaaaa                             1957
```

<210> SEQ ID NO 155
<211> LENGTH: 408
<212> TYPE: PRT
<213> ORGANISM: Homo sapiens

<400> SEQUENCE: 155

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240
```

Leu His Gln Thr Arg Thr His Gln Gly Gln His Val Arg Ile Ser Arg
            245                 250                 255

Ser Leu Pro Gln Gly Ser Gly Asn Trp Ala Gln Leu Arg Pro Leu Leu
        260                 265                 270

Val Thr Phe Gly His Asp Gly Arg Gly His Ala Leu Thr Arg Arg Arg
    275                 280                 285

Arg Ala Lys Arg Ser Pro Lys His His Ser Gln Arg Ala Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 156
<211> LENGTH: 20
<212> TYPE: DNA
<213> ORGANISM: Artificial Sequence
<220> FEATURE:
<223> OTHER INFORMATION: chemcially synthesized

<400> SEQUENCE: 156
uaauaaaacg accaucagca                                               20

<210> SEQ ID NO 157
<211> LENGTH: 20
<212> TYPE: DNA
<213> ORGANISM: Artificial Sequence
<220> FEATURE:
<223> OTHER INFORMATION: chemcially synthesized

<400> SEQUENCE: 157
uaucugucua uccucaagga                                               20

<210> SEQ ID NO 158
<211> LENGTH: 20
<212> TYPE: DNA
<213> ORGANISM: Artificial Sequence
<220> FEATURE:
<223> OTHER INFORMATION: chemcially synthesized

<400> SEQUENCE: 158
uucuuauucu ucuuccuggc                                               20

<210> SEQ ID NO 159
<211> LENGTH: 19
<212> TYPE: DNA
<213> ORGANISM: Artificial Sequence
<220> FEATURE:
<223> OTHER INFORMATION: chemcially synthesized

<400> SEQUENCE: 159

| | |
|---|---|
| uaauaaaacg accaucagc | 19 |

<210> SEQ ID NO 160
<211> LENGTH: 31
<212> TYPE: DNA
<213> ORGANISM: Artificial Sequence
<220> FEATURE:
<223> OTHER INFORMATION: chemically synthesized

<400> SEQUENCE: 160

| | |
|---|---|
| ccggtctatc tgtctatcct caagggaccg g | 31 |

<210> SEQ ID NO 161
<211> LENGTH: 31
<212> TYPE: DNA
<213> ORGANISM: Artificial Sequence
<220> FEATURE:
<223> OTHER INFORMATION: chemically synthesized

<400> SEQUENCE: 161

| | |
|---|---|
| ccggtctctc aggtatcaaa ctagcgaccg g | 31 |

<210> SEQ ID NO 162
<211> LENGTH: 31
<212> TYPE: DNA
<213> ORGANISM: Artificial Sequence
<220> FEATURE:
<223> OTHER INFORMATION: chemcially synthesized

<400> SEQUENCE: 162

| | |
|---|---|
| ccggtctttg tcaaaatata tgatcgaccg g | 31 |

<210> SEQ ID NO 163
<211> LENGTH: 4049
<212> TYPE: DNA
<213> ORGANISM: Homo sapiens

<400> SEQUENCE: 163

| | |
|---|---|
| agcgcgtacc actctggcgc tcccgaggcg gcctcttgtg cgatccaggg cgcacaaggc | 60 |
| tgggagagcg ccccggggcc cctgctatcc gcgccggagg ttggaagagg gtgggttgcc | 120 |
| gccgcccgag ggcgagagcg ccagaggagc gggaagaagg agcgctcgcc cgcccgcctg | 180 |
| cctcctcgct gcctccccgg cgttggctct ctggactcct aggcttgctg gctgctcctc | 240 |
| ccacccgcgc ccgcctcctc actcgccttt tcgttcgccg gggctgcttt ccaagccctg | 300 |
| cggtgcgccc gggcgagtgc ggggcgaggg gcccggggcc agcaccgagc aggggcgggg | 360 |
| ggtccgggca gagcgcggcc ggccgggag gggccatgtc tggcgcgggc gcagcggggc | 420 |
| ccgtctgcag caagtgaccg agcggcgcgg acggccgcct gccccctctg ccacctgggg | 480 |
| cggtgcgggc ccggagcccg gagcccgggt agcgcgtaga gccggcgcga tgcacgtgcg | 540 |
| ctcactgcga gctgcggcgc cgcacagctt cgtggcgctc tgggcacccc tgttcctgct | 600 |
| gcgctccgcc ctggccgact tcagcctgga caacgaggtg cactcgagct tcatccaccg | 660 |
| gcgcctccgc agccaggagc ggcgggagat gcagcgcgag atcctctcca ttttgggctt | 720 |
| gccccaccgc ccgcgcccgc acctccaggg caagcacaac tcggcaccca tgttcatgct | 780 |
| ggacctgtac aacgccatgg cggtggagga gggcggcggg cccggcggcc agggcttctc | 840 |
| ctaccccta c aaggccgtct tcagtaccca gggccccct ctggccagcc tgcaagatag | 900 |
| ccatttcctc accgacgccg acatggtcat gagcttcgtc aacctcgtgg aacatgacaa | 960 |

```
ggaattcttc cacccacgct accaccatcg agagttccgg tttgatcttt ccaagatccc    1020
agaaggggaa gctgtcacgg cagccgaatt ccggatctac aaggactaca tccgggaacg    1080
cttcgacaat gagacgttcc ggatcagcgt ttatcaggtg ctccaggagc acttgggcag    1140
ggaatcggat ctcttcctgc tcgacagccg taccctctgg gcctcggagg agggctggct    1200
ggtgtttgac atcacagcca ccagcaacca ctgggtggtc aatccgcggc acaacctggg    1260
cctgcagctc tcggtggaga cgctggatgg gcagagcatc aaccccaagt tggcgggcct    1320
gattgggcgg cacgggcccc agaacaagca gcccttcatg gtggctttct tcaaggccac    1380
ggaggtccac ttccgcagca tccggtccac ggggagcaaa cagcgcagcc agaaccgctc    1440
caagacgccc aagaaccagg aagccctgcg gatggccaac gtggcagaga cagcagcag    1500 cgaccagagg caggcctgta agaagcacga gctgtatgtc agcttccgag acctgggctg    1560
gcaggactgg atcatcgcgc tgaaggcta cgccgcctac tactgtgagg gggagtgtgc    1620
cttccctctg aactcctaca tgaacgccac caaccacgcc atcgtgcaga cgctggtcca    1680
cttcatcaac ccggaaacgg tgcccaagcc ctgctgtgcg cccacgcagc tcaatgccat    1740
ctccgtcctc tacttcgatg acagctccaa cgtcatcctg aagaaataca gaaacatggt    1800
ggtccgggcc tgtggctgcc actagctcct ccgagaattc agacccttg gggccaagtt    1860 tttctggatc ctccattgct cgccttggcc aggaaccagc agaccaactg cctttgtga    1920 gaccttcccc tccctatccc caactttaaa ggtgtgagag tattaggaaa catgagcagc    1980
atatggcttt tgatcagttt ttcagtggca gcatccaatg aacaagatcc tacaagctgt    2040
gcaggcaaaa cctagcagga aaaaaaaaca acgcataaag aaaaatggcc gggccaggtc    2100
attggctggg aagtctcagc catgcacgga ctcgtttcca gaggtaatta tgagcgccta    2160
ccagccaggc cacccagccg tgggaggaag ggggcgtggc aaggggtggg cacattggtg    2220
tctgtgcgaa aggaaaattg acccggaagt tcctgtaata aatgtcacaa taaaacgaat    2280
gaatgaaaat ggttaggacg ttacagatat attttcctaa acaatttatc cccatttctc    2340
ggtttatcct gatgcgtaaa cagaagctgt gtcaagtgga gggcggggag gtccctctcc    2400
attccctaca gttttcatcc tgaggcttgc agaggcccag tgtttaccga ggtttgccca    2460
aatccaagat ctagtgggag gggaaagagc aaatgtctgc tccgaggagg gcggtgtgtt    2520
gatctttgga ggaaaaatat gttctgttgt tcagctggat ttgccgtggc agaaatgaaa    2580
ctaggtgtgt gaaatacccg cagacatttg ggattggctt ttcacctcgc cccagtggta    2640
gtaaatccat gtgaaattgc agaggggaca aggacagcaa gtaggatgga acttgcaact    2700
caaccctgtt gttaagaagc accaatgggc cgggcacagt agctcccacc tgtaatccca    2760
gcactttggg aggctgaggt gggcggatca tttgaggtca ggagttcgag accagcctgg    2820
ccaacatggt gaaaccccat ctctactaaa aatacaaaaa ttagccgggc atggtggcac    2880
gcacctgtaa tcccagctac tctggaggct gaggcaggag aattgcttga ccccagagg    2940 tggaggttgc agtgagccaa gatcgtccca ctgcactcca gcttgggtga caaaacaaga    3000
ctccatctca aagaaaaaa aaacagcac caatgaagcc tagttctcca cgggagtggg    3060
gtgagcagga gcactgcaca tcgcccagt ggaccctctg gtctttgtct gcagtggcat    3120
tccaaggctg ggccctggca agggcacccg tggctgtctc ttcatttgca gaccctgatc    3180
agaagtctct gcaaacaaat ttgctccttg aattaagggg gagatggcat aataggaggt    3240
ctgatgggtg caggatgtgc tggacttaca ttgcaaatag aagccttgtt gagggtgaca    3300
tcctaaccaa gtgtcccgat ttggaggtgg catttctgac gtggctcttg gtgtaagcct    3360
```

```
gccttgcctt ggctggtgag tcccataaat agtatgcact cagcctccgg ccacaaacac    3420
aaggcctagg ggagggctag actgtctgca aacgttttct gcatctgtaa agaaaacaag    3480
gtgatcgaaa actgtggcca tgtggaaccc ggtcttgtgg gggactgttt ctccatcttg    3540
actcagacag ttcctggaaa caccggggct ctgtttttat tttctttgat gtttttcttc    3600
tttagtagct tgggctgcag cctccactct ctagtcactg gggaggagta ttttttgtta    3660
tgtttggttt catttgctgg cagagctggg gcttttttgtg tgatccctct tggtgtgagt    3720
tttctgaccc aaccagcctc tggttagcat catttgtaca tttaaacctg taaatagttg    3780
ttacaaagca aagagattat ttatttccat ccaaagctct tttgaacacc ccccccctt    3840 taatccctcg ttcaggacga tgagcttgct ttccttcaac ctgtttgttt tcttatttaa    3900
gactatttat taatggttgg accaatgtac tcacagctgt tgcgtcgagc agtccttagt    3960
gaaaattctg tataaataga caaatgaaa agggtttgac cttgcaataa aaggagacgt    4020
ttggttctgg caaaaaaaaa aaaaaaaa                                       4049
```

<210> SEQ ID NO 164
<211> LENGTH: 431
<212> TYPE: PRT
<213> ORGANISM: Homo sapiens

<400> SEQUENCE: 164

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
```

```
                245                 250                 255
Ile Asn Pro Lys Leu Ala Gly Leu Ile Gly Arg His Gly Pro Gln Asn
        260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
        290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 165
<211> LENGTH: 19
<212> TYPE: DNA
<213> ORGANISM: Artificial Sequence
<220> FEATURE:
<223> OTHER INFORMATION: chemically synthesized

<400> SEQUENCE: 165
uuccuaauac ucucacacc                                                19

<210> SEQ ID NO 166
<211> LENGTH: 19
<212> TYPE: DNA
<213> ORGANISM: Artificial Sequence
<220> FEATURE:
<223> OTHER INFORMATION: chemically synthesized

<400> SEQUENCE: 166
uaacaaaaaa uacuccucc                                                19

<210> SEQ ID NO 167
<211> LENGTH: 20
<212> TYPE: DNA
<213> ORGANISM: Artificial Sequence
<220> FEATURE:
<223> OTHER INFORMATION: chemcially synthesized

<400> SEQUENCE: 167
uaaauaagaa aacaaacagg                                               20

<210> SEQ ID NO 168
<211> LENGTH: 20
<212> TYPE: DNA
<213> ORGANISM: Artificial Sequence
<220> FEATURE:
<223> OTHER INFORMATION: chemcially synthesized
```

<400> SEQUENCE: 168
uuccuaauac ucucacaccu                                        20

<210> SEQ ID NO 169
<211> LENGTH: 32
<212> TYPE: DNA
<213> ORGANISM: Artificial Sequence
<220> FEATURE:
<223> OTHER INFORMATION: chemcially synthesized

<400> SEQUENCE: 169
ccggtctaac aaaaaatact cctcccgacc gg                          32

<210> SEQ ID NO 170
<211> LENGTH: 32
<212> TYPE: DNA
<213> ORGANISM: Artificial Sequence
<220> FEATURE:
<223> OTHER INFORMATION: chemcially synthesized

<400> SEQUENCE: 170
ccggtcttgt aacaacuatt tacagggacc gg                          32

<210> SEQ ID NO 171
<211> LENGTH: 31
<212> TYPE: DNA
<213> ORGANISM: Artificial Sequence
<220> FEATURE:
<223> OTHER INFORMATION: chemcially synthesized

<400> SEQUENCE: 171
ccggtctaaa taagaaaaca aacaggaccg g                           31

<210> SEQ ID NO 172
<211> LENGTH: 1802
<212> TYPE: DNA
<213> ORGANISM: Homo sapiens

<400> SEQUENCE: 172
gggcagctcc accctgggag ggactgtggc ccaggtactg cccgggtgct actttatggg    60
cagcagctca gttgagttag agtctggaag acctcagaag acctcctgtc ctatgaggcc   120
ctccccatgg ctttagagac gatctgccga ccctctggga gaaaatccag caagatgcaa   180
gccttcagaa tctgggatgt taaccagaag accttctatc tgaggaacaa ccaactagtt   240
gctggatact tgcaaggacc aaatgtcaat ttagaagaaa agatagatgt ggtacccatt   300
gagcctcatg ctctgttctt gggaatccat ggagggaaga tgtgcctgtc ctgtgtcaag   360
tctggtgatg agaccagact ccagctggag gcagttaaca tcactgacct gagcgagaac   420
agaaagcagg acaagcgctt cgccttcatc cgctcagaca gtggcccac caccagtttt   480 gagtctgccg cctgccccgg ttggttcctc tgcacagcga tggaagctga ccagcccgtc   540
agcctcacca atatgcctga cgaaggcgtc atggtcacca aattctactt ccaggaggac   600
gagtagtact gcccaggcct gcctgttccc attcttgcat ggcaaggact gcagggactg   660
ccagtccccc tgcccaggg ctccggcta tggggcact gaggaccagc cattgagggg   720
tggaccctca gaaggcgtca caacaacctg gtcacaggac tctgcctcct cttcaactga   780
ccagcctcca tgctgcctcc agaatggtct ttctaatgtg tgaatcagag cacagcagcc   840
cctgcacaaa gcccttccat gtcgcctctg cattcaggat caaaccccga ccacctgccc   900
aacctgctct cctcttgcca ctgcctcttc ctccctcatt ccaccttccc atgccctgga   960

```
tccatcaggc cacttgatga ccccaacca agtggctccc acaccctgtt ttacaaaaaa    1020
gaaaagacca gtccatgagg gaggttttta agggtttgtg gaaatgaaa attaggattt    1080 catgattttt ttttttcagt ccccgtgaag gagagccctt catttggaga ttatgttctt    1140
tcggggagag gctgaggact taaaatattc ctgcatttgt gaaatgatgg tgaaagtaag    1200
tggtagcttt tcccttcttt ttcttctttt tttgtgatgt cccaacttgt aaaaattaaa    1260
agttatggta ctatgttagc cccataattt ttttttcct tttaaaacac ttccataatc     1320
tggactcctc tgtccaggca ctgctgccca gcctccaagc tccatctcca ctccagattt    1380
tttacagctg cctgcagtac tttacctcct atcagaagtt tctcagctcc caaggctctg    1440
agcaaatgtg gctcctgggg gttctttctt cctctgctga aggaataaat tgctccttga    1500
cattgtagag cttctggcac ttggagactt gtatgaaaga tggctgtgcc tctgcctgtc    1560
tcccccaccg ggctgggagc tctgcagagc aggaaacatg actcgtatat gtctcaggtc    1620
cctgcagggc caagcaccta gcctcgctct tggcaggtac tcagcgaatg aatgctgtat    1680
atgttgggtg caaagttccc tacttcctgt gacttcagct ctgttttaca ataaaatctt    1740
gaaaatgcct aaaaaaaaaa aaaaaaaaaa aaaaaaaaaa aaaaaaaaaa aaaaaaaaaa    1800
aa                                                                   1802
```

<210> SEQ ID NO 173
<211> LENGTH: 159
<212> TYPE: PRT
<213> ORGANISM: Homo sapiens

<400> SEQUENCE: 173

Met Ala Leu Glu Thr Ile Cys Arg Pro Ser Gly Arg Lys Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155

<210> SEQ ID NO 174
<211> LENGTH: 100
<212> TYPE: DNA
<213> ORGANISM: Homo sapiens

<400> SEQUENCE: 174
ugugucucuc ucuguguccu gccagugguu uuacccuaug guagguuacg ucaugcuguu    60
cuaccacagg guagaaccac ggacaggaua ccggggcacc         100

<210> SEQ ID NO 175
<211> LENGTH: 22
<212> TYPE: DNA
<213> ORGANISM: Homo sapiens

<400> SEQUENCE: 175
cagugguuuu acccuauggu ag                            22

<210> SEQ ID NO 176
<211> LENGTH: 87
<212> TYPE: DNA
<213> ORGANISM: Homo sapiens

<400> SEQUENCE: 176
accgcaggga aaugaggga cuuuuggggg cagauguguu ccauuccac uaucauaaug    60 ccccuaaaaa uccuuauugc ucuugca                       87

<210> SEQ ID NO 177
<211> LENGTH: 23
<212> TYPE: DNA
<213> ORGANISM: Homo sapiens

<400> SEQUENCE: 177
agggacuuuu gggggcagau gug                           23

<210> SEQ ID NO 178
<211> LENGTH: 86
<212> TYPE: DNA
<213> ORGANISM: Homo sapiens

<400> SEQUENCE: 178
ugccagucuc uagguccoug agcccuuua accugugagg acauccaggg ucacagguga   60
gguucuuggg agccuggcgu cuggcc                        86

<210> SEQ ID NO 179
<211> LENGTH: 24
<212> TYPE: DNA
<213> ORGANISM: Homo sapiens

<400> SEQUENCE: 179
ucccugagac ccuuuaaccu guga                          24

<210> SEQ ID NO 180
<211> LENGTH: 22
<212> TYPE: DNA
<213> ORGANISM: Homo sapiens

<400> SEQUENCE: 180
acaggugagg uucuugggag cc                            22

<210> SEQ ID NO 181
<211> LENGTH: 1968
<212> TYPE: DNA
<213> ORGANISM: Homo sapiens

<400> SEQUENCE: 181
actccgggtg gcaggcgccc gggggaatcc cagctgactc gctcactgcc ttcgaagtcc  60
ggcgcccccc gggagggaac tgggtggccg caccctcccg gctgcggtgg ctgtcgcccc  120 ccacccctgca gccaggactc gatggaggta cagagctcgg cttctttgcc ttgggagggg 180

-continued

```
agtggtggtg gttgaaaggg cgatggaatt ttccccgaaa gcctacgccc agggcccctc      240
ccagctccag cgttaccctc cggtctatcc tactggccga gctgccccgc cttctcatgg      300
ggaaaactta gccgcaactt caattttttgg tttttccttt aatgacactt ctgaggctct      360
cctagccatc ctcccgcttc cggaggagcg cagatcgcag gtccctttgc ccctggcgtg      420
cgactcccta ctgcgctgcg ctcttacggc gttccaggct gctggctagc gcaaggcggg      480
ccgggcaccc cgcgctccgc tgggagggtg agggacgcgc gtctggcggc cccagccaag      540
ctgcgggttt ctgagaagac gctgtcccgc agccctgagg ctgagttct gcacccagtc       600 aagctcagga aggccaagaa aagaatccat tccaatatat ggccatgtgg ctctttggag      660
caatgttcca tcatgttcca tgctgctgac gtcacatgga gcacagaaat caatgttagc      720
agatagccag cccatacaag atcgtattgt attgtaggag gcatcgtgga tggatggctg      780
ctggaaaccc cttgccatag ccagctcttc ttcaatactt aaggatttac cgtggctttg      840
agtaatgaga atttcgaaac cacatttgag aagtatttcc atccagtgct acttgtgttt      900
acttctaaac agtcattttc taactgaagc tggcattcat gtcttcattt tgggctgttt      960
cagtgcaggg cttcctaaaa cagaagccaa ctgggtgaat gtaataagtg atttgaaaaa     1020
aattgaagat cttattcaat ctatgcatat tgatgctact ttatatacgg aaagtgatgt     1080 tcacccccagt tgcaaagtaa cagcaatgaa gtgctttctc ttggagttac aagttatttc    1140
acttgagtcc ggagatgcaa gtattcatga tacagtagaa atctgatca tcctagcaaa      1200 caacagtttg tcttctaatg ggaatgtaac agaatctgga tgcaaagaat gtgaggaact     1260
ggaggaaaaa aatattaaag aattttttgca gagttttgta catattgtcc aaatgttcat    1320
caacacttct tgattgcaat tgattctttt taaagtgttt ctgttattaa caaacatcac     1380
tctgctgctt agacataaca aaacactcgg catttcaaat gtgctgtcaa acaagttttt    1440
tctgtcaaga gatgatcag accttggatc agatgaactc ttagaaatga aggcagaaaa    1500
atgtcattga gtaatatagt gactatgaac ttctctcaga cttactttac tcatttttt     1560 aatttattat tgaaattgta catatttgtg gaataatgta aaatgttgaa taaaatatg     1620 tacaagtgtt gttttttaag ttgcactgat attttaccctc ttattgcaaa atagcatttg    1680
tttaagggtg atagtcaaat tatgtattgg tggggctggg taccaatgct gcaggtcaac     1740
agctatgctg gtaggctcct gcctgtgtgg aaccactgac tactggctct cattgacttc     1800
cttactaagc atagcaaaca gaggaagaat ttgttatcag taagaaaaag aagaactata    1860
tgtgaatcct cttctttaca ctgtaattta gttattgatg tataaagcaa ctgttatgaa    1920
ataaagaaat tgcaataact ggcaaaaaaa aaaaaaaaaa aaaaaaa                  1968
```

<210> SEQ ID NO 182
<211> LENGTH: 162
<212> TYPE: PRT
<213> ORGANISM: Homo sapiens

<400> SEQUENCE: 182

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
```

```
                50                  55                  60
Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                     85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```

<210> SEQ ID NO 183
<211> LENGTH: 1252
<212> TYPE: DNA
<213> ORGANISM: Homo sapiens

<400> SEQUENCE: 183

| | | | | | |
|---|---|---|---|---|---|
| ctttgaattc | ctagctcctg | tggtctccag | atttcaggcc | taagatgaaa | gcctctagtc | 60 |
| ttgccttcag | ccttctctct | gctgcgtttt | atctcctatg | gactccttcc | actggactga | 120 |
| agacactcaa | tttgggaagc | tgtgtgatcg | ccacaaacct | tcaggaaata | cgaaatggat | 180 |
| tttctgagat | acggggcagt | gtgcaagcca | aagatggaaa | cattgacatc | agaatcttaa | 240 |
| ggaggactga | gtctttgcaa | gacacaaagc | ctgcgaatcg | atgctgcctc | ctgcgccatt | 300 |
| tgctaagact | ctatctggac | agggtattta | aaaactacca | gaccctgac | cattatactc | 360 |
| tccggaagat | cagcagcctc | gccaattcct | ttcttaccat | caagaaggac | ctccggctct | 420 |
| gtcatgccca | catgacatgc | cattgtgggg | aggaagcaat | gaagaaatac | agccagattc | 480 |
| tgagtcactt | tgaaaagctg | gaacctcagg | cagcagttgt | gaaggctttg | ggggaactag | 540 |
| acattcttct | gcaatggatg | gaggagacag | aataggagga | aagtgatgct | gctgctaaga | 600 |
| atattcgagg | tcaagagctc | cagtcttcaa | tacctgcaga | ggaggcatga | ccccaaacca | 660 |
| ccatctcttt | actgtactag | tcttgtgctg | gtcacagtgt | atcttatta | tgcattactt | 720 |
| gcttccttgc | atgattgtct | ttatgcatcc | ccaatcttaa | ttgagaccat | acttgtataa | 780 |
| gatttttgta | atatctttct | gctattggat | atatttatta | gttaatatat | ttatttattt | 840 |
| tttgctattt | aatgtatttta | ttttttact | tggacatgaa | actttaaaaa | aattcacaga | 900 |
| ttatatttat | aacctgacta | gagcaggtga | tgtattttta | tacagtaaaa | aaaaaaaacc | 960 |
| ttgtaaattc | tagaagagtg | gctaggggggg | ttattcattt | gtattcaact | aaggacatat | 1020 |
| ttactcatgc | tgatgctctg | tgagatattt | gaaattgaac | caatgactac | ttaggatggg | 1080 |
| ttgtggaata | agttttgatg | tggaattgca | catctacctt | acaattactg | accatcccca | 1140 |
| gtagactccc | cagtcccata | attgtgtatc | ttccagccag | gaatcctaca | cggccagcat | 1200 |
| gtatttctac | aaataaagtt | ttctttgcat | aacaaaaaaa | aaaaaaaaaa | aa | 1252 |

<210> SEQ ID NO 184
<211> LENGTH: 176
<212> TYPE: PRT
<213> ORGANISM: Homo sapiens

<400> SEQUENCE: 184

```
Met Lys Ala Ser Ser Leu Ala Phe Ser Leu Leu Ser Ala Ala Phe Tyr
1               5                   10                  15
Leu Leu Trp Thr Pro Ser Thr Gly Leu Lys Thr Leu Asn Leu Gly Ser
            20                  25                  30
Cys Val Ile Ala Thr Asn Leu Gln Glu Ile Arg Asn Gly Phe Ser Glu
        35                  40                  45
Ile Arg Gly Ser Val Gln Ala Lys Asp Gly Asn Ile Asp Ile Arg Ile
    50                  55                  60
Leu Arg Arg Thr Glu Ser Leu Gln Asp Thr Lys Pro Ala Asn Arg Cys
65                  70                  75                  80
Cys Leu Leu Arg His Leu Leu Arg Leu Tyr Leu Asp Arg Val Phe Lys
                85                  90                  95
Asn Tyr Gln Thr Pro Asp His Tyr Thr Leu Arg Lys Ile Ser Ser Leu
            100                 105                 110
Ala Asn Ser Phe Leu Thr Ile Lys Lys Asp Leu Arg Leu Cys His Ala
        115                 120                 125
His Met Thr Cys His Cys Gly Glu Glu Ala Met Lys Lys Tyr Ser Gln
130                 135                 140
Ile Leu Ser His Phe Glu Lys Leu Glu Pro Gln Ala Ala Val Val Lys
145                 150                 155                 160
Ala Leu Gly Glu Leu Asp Ile Leu Leu Gln Trp Met Glu Glu Thr Glu
                165                 170                 175

<210> SEQ ID NO 185
<211> LENGTH: 2265
<212> TYPE: DNA
<213> ORGANISM: Homo sapiens

<400> SEQUENCE: 185
acagccagag ggacgagcta gcccgacgat ggcccagggg acattgatcc gtgtgacccc      60
agagcagccc acccatgccg tgtgtgtgct gggcaccttg actcagcttg acatctgcag     120
ctctgcccct gaggactgca cgtccttcag catcaacgcc tccccagggg tggtcgtgga     180
tattgcccac ggccctccag ccaagaagaa atccacaggt tcctccacat ggcccctgga     240
ccctggggta gaggtgaccc tgacgatgaa agtggccagt ggtagcacag gcgaccagaa     300
ggttcagatt tcatactacg acccaagac tccaccagtc aaagctctac tctacctcac     360
cggggtggaa atctccttgt gcgcagacat caccgcacc ggcaaagtga agccaaccag     420
agctgtgaaa gatcagagga cctggacctg gggccttgt ggacagggtg ccatcctgct     480
ggtgaactgt gacagagaca atctcgaatc ttctgccatg gactgcgagg atgatgaagt     540
gcttgacagc gaagacctgc aggacatgtc gctgatgacc ctgagcacga agacccccaa     600
ggacttcttc acaaaccata cactggtgct ccacgtggcc aggtctgaga tggacaaagt     660
gagggtgttt caggccacac ggggcaaact gtcctccaag tgcagcgtag tcttgggtcc     720
caagtggccc tctcactacc tgatggtccc cggtggaaag cacaacatgg acttctacgt     780
ggaggccctc gctttcccgg acaccgactt cccggggctc attaccctca ccatctccct     840
gctggacacg tccaacctgg agctccccga gctgtggtg ttccaagaca gcgtggtctt     900
ccgcgtggcg ccctggatca tgaccccaa cacccagccc ccgcaggagg tgtacgcgtg     960
cagtattttt gaaaatgagg acttcctgaa gtcagtgact actctggcca tgaaagccaa    1020
gtgcaagctg accatctgcc ctgaggagga gaacatggat gaccagtgga tgcaggatga    1080
aatggagatc ggctacatcc aagccccaca caaaacgctg cccgtggtct tcgactctcc    1140
```

```
aaggaacaga ggcctgaagg agtttcccat caaacgcgtg atgggtccag attttggcta    1200
tgtaactcga gggcccccaaa caggggggtat cagtggactg gactcctttg ggaacctgga   1260
agtgagcccc ccagtcacag tcaggggcaa ggaatacccg ctgggcagga ttctcttcgg    1320
ggacagctgt tatcccagca atgacagccg gcagatgcac caggccctgc aggacttcct    1380
cagtgcccag caggtgcagg cccctgtgaa gctctattct gactggctgt ccgtgggcca    1440
cgtggacgag ttcctgagct tgtgccagc acccgacagg aagggcttcc ggctgctcct     1500
ggccagcccc aggtcctgct acaaactgtt ccaggagcag cagaatgagg ccacgggga     1560 ggccctgctg ttcgaaggga tcaagaaaaa aaaacagcag aaaataaaga acattctgtc    1620
aaacaagaca ttgagagaac ataattcatt tgtggagaga tgcatcgact ggaaccgcga    1680
gctgctgaag cgggagctgg gcctggccga gagtgacatc attgacatcc cgcagctctt    1740
caagctcaaa gagttctcta aggcggaagc tttttttcccc aacatggtga acatgctggt    1800
gctagggaag cacctgggca tccccaagcc cttcgggccc gtcatcaacg ccgctgctg    1860 cctggaggag aaggtgtgtt ccctgctgga gccactgggc tccagtgca ccttcatcaa     1920 cgacttcttc acctaccaca tcaggcatgg ggaggtgcac tgcggcacca acgtgcgcag   1980
aaagcccttc tccttcaagt ggtggaacat ggtgccctga gccatcttc cctggcgtcc    2040 tctccctcct ggccagatgt cgctgggtcc tctgcagtgt ggcaagcaag agctcttgtg    2100
aatattgtgg ctccctgggg gcggccagcc ctcccagcag tggcttgctt tcttctcctg    2160
tgatgtccca gtttcccact ctgaagatcc aacatggtc ctagcactgc acactcagtt     2220
ctgctctaag aagctgcaat aaagttttt taagtcactt tgtac                    2265
```

<210> SEQ ID NO 186
<211> LENGTH: 663
<212> TYPE: PRT
<213> ORGANISM: Homo sapiens

<400> SEQUENCE: 186

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
                20                  25                  30

Ala Pro Glu Asp Cys Thr Ser Phe Ser Ile Asn Ala Ser Pro Gly Val
            35                  40                  45

Val Val Asp Ile Ala His Gly Pro Pro Ala Lys Lys Ser Thr Gly
        50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Ser Glu Asp
                165                 170                 175

```
Leu Gln Asp Met Ser Leu Met Thr Leu Ser Thr Lys Thr Pro Lys Asp
                180                 185                 190
Phe Phe Thr Asn His Thr Leu Val Leu His Val Ala Arg Ser Glu Met
            195                 200                 205
Asp Lys Val Arg Val Phe Gln Ala Thr Arg Gly Lys Leu Ser Ser Lys
        210                 215                 220
Cys Ser Val Val Leu Gly Pro Lys Trp Pro Ser His Tyr Leu Met Val
225                 230                 235                 240
Pro Gly Gly Lys His Asn Met Asp Phe Tyr Val Glu Ala Leu Ala Phe
                245                 250                 255
Pro Asp Thr Asp Phe Pro Gly Leu Ile Thr Leu Thr Ile Ser Leu Leu
            260                 265                 270
Asp Thr Ser Asn Leu Glu Leu Pro Glu Ala Val Val Phe Gln Asp Ser
        275                 280                 285
Val Val Phe Arg Val Ala Pro Trp Ile Met Thr Pro Asn Thr Gln Pro
    290                 295                 300
Pro Gln Glu Val Tyr Ala Cys Ser Ile Phe Glu Asn Glu Asp Phe Leu
305                 310                 315                 320
Lys Ser Val Thr Thr Leu Ala Met Lys Ala Lys Cys Lys Leu Thr Ile
                325                 330                 335
Cys Pro Glu Glu Glu Asn Met Asp Asp Gln Trp Met Gln Asp Glu Met
            340                 345                 350
Glu Ile Gly Tyr Ile Gln Ala Pro His Lys Thr Leu Pro Val Val Phe
        355                 360                 365
Asp Ser Pro Arg Asn Arg Gly Leu Lys Glu Phe Pro Ile Lys Arg Val
    370                 375                 380
Met Gly Pro Asp Phe Gly Tyr Val Thr Arg Gly Pro Gln Thr Gly Gly
385                 390                 395                 400
Ile Ser Gly Leu Asp Ser Phe Gly Asn Leu Glu Val Ser Pro Pro Val
                405                 410                 415
Thr Val Arg Gly Lys Glu Tyr Pro Leu Gly Arg Ile Leu Phe Gly Asp
            420                 425                 430
Ser Cys Tyr Pro Ser Asn Asp Ser Arg Gln Met His Gln Ala Leu Gln
        435                 440                 445
Asp Phe Leu Ser Ala Gln Gln Val Gln Ala Pro Val Lys Leu Tyr Ser
    450                 455                 460
Asp Trp Leu Ser Val Gly His Val Asp Glu Phe Leu Ser Phe Val Pro
465                 470                 475                 480
Ala Pro Asp Arg Lys Gly Phe Arg Leu Leu Leu Ala Ser Pro Arg Ser
                485                 490                 495
Cys Tyr Lys Leu Phe Gln Glu Gln Gln Asn Glu Gly His Gly Glu Ala
            500                 505                 510
Leu Leu Phe Glu Gly Ile Lys Lys Lys Gln Gln Lys Ile Lys Asn
        515                 520                 525
Ile Leu Ser Asn Lys Thr Leu Arg Glu His Asn Ser Phe Val Glu Arg
    530                 535                 540
Cys Ile Asp Trp Asn Arg Glu Leu Leu Lys Arg Glu Leu Gly Leu Ala
545                 550                 555                 560
Glu Ser Asp Ile Ile Asp Ile Pro Gln Leu Phe Lys Leu Lys Glu Phe
                565                 570                 575
Ser Lys Ala Glu Ala Phe Phe Pro Asn Met Val Asn Met Leu Val Leu
            580                 585                 590
```

```
Gly Lys His Leu Gly Ile Pro Lys Pro Phe Gly Pro Val Ile Asn Gly
            595                 600                 605

Arg Cys Cys Leu Glu Glu Lys Val Cys Ser Leu Leu Glu Pro Leu Gly
    610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655

Lys Trp Trp Asn Met Val Pro
            660
```

<210> SEQ ID NO 187
<211> LENGTH: 801
<212> TYPE: DNA
<213> ORGANISM: Homo sapiens

<400> SEQUENCE: 187

```
atggtgtgtc tgaggctccc tggaggctcc tgcatggcag ttctgacagt gacactgatg      60
gtgctgagct ccccactggc tttggctggg acaccagac cacgtttctt ggaggaggtt     120
aagtttgagt gtcatttctt caacgggacg agcgggtgc ggttgctgga agacgcgtc      180
cataaccaag aggagtacgc gcgctacgac agcgacgtgg gggagtaccg ggcggtgacg     240
gagctggggc ggcctgatgc cgagtactgg aacagccaga aggacctcct ggagcggagg     300
cgtgccgcgg tggacaccta ctgcagacac aactacgggg ttggtgagag cttcacagtg     360
cagcggcgag ttcaacctaa ggtgactgtg tatccttcaa agacccagcc cctgcagcac     420
cacaacctcc tggtctgttc tgtgaatggt ttctatccag gcagcattga agtcaggtgg     480
ttccggaacg gccaggaaga gaagactggg gtggtgtcca cgggcctgat ccagaatgga     540
gactggacct tccagaccct ggtgatgctg gaaacagttc ctcagagtgg agaggtttac     600
acctgccaag tggagcaccc aagtgtgatg agccctctca cagtggaatg gagagcacgg     660
tctgaatctg cacagagcaa gatgctgagt ggagtcgggg ctttgtgct gggcctgctc     720
ttccttgggg ccgggctgtt catctacttc aggaatcaga aggacactc tggacttccg     780
ccaacaggat tcctgagctg a                                              801
```

<210> SEQ ID NO 188
<211> LENGTH: 266
<212> TYPE: PRT
<213> ORGANISM: Homo sapiens

<400> SEQUENCE: 188

```
Met Val Cys Leu Arg Leu Pro Gly Gly Ser Cys Met Ala Val Leu Thr
1               5                   10                  15

Val Thr Leu Met Val Leu Ser Ser Pro Leu Ala Leu Ala Gly Asp Thr
            20                  25                  30

Arg Pro Arg Phe Leu Glu Glu Val Lys Phe Glu Cys His Phe Asn
        35                  40                  45

Gly Thr Glu Arg Val Arg Leu Leu Glu Arg Arg Val His Asn Gln Glu
    50                  55                  60

Glu Tyr Ala Arg Tyr Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Arg Arg Arg Ala Ala Val Asp Thr Tyr Cys Arg His Asn Tyr
            100                 105                 110
```

```
Gly Val Gly Glu Ser Phe Thr Val Gln Arg Arg Val Gln Pro Lys Val
            115                 120                 125
Thr Val Tyr Pro Ser Lys Thr Gln Pro Leu Gln His His Asn Leu Leu
        130                 135                 140
Val Cys Ser Val Asn Gly Phe Tyr Pro Gly Ser Ile Glu Val Arg Trp
145                 150                 155                 160
Phe Arg Asn Gly Gln Glu Glu Lys Thr Gly Val Val Ser Thr Gly Leu
                165                 170                 175
Ile Gln Asn Gly Asp Trp Thr Phe Gln Thr Leu Val Met Leu Glu Thr
            180                 185                 190
Val Pro Gln Ser Gly Glu Val Tyr Thr Cys Gln Val Glu His Pro Ser
        195                 200                 205
Val Met Ser Pro Leu Thr Val Glu Trp Arg Ala Arg Ser Glu Ser Ala
210                 215                 220
Gln Ser Lys Met Leu Ser Gly Val Gly Gly Phe Val Leu Gly Leu Leu
225                 230                 235                 240
Phe Leu Gly Ala Gly Leu Phe Ile Tyr Phe Arg Asn Gln Lys Gly His
                245                 250                 255
Ser Gly Leu Pro Pro Thr Gly Phe Leu Ser
            260                 265

<210> SEQ ID NO 189
<211> LENGTH: 3436
<212> TYPE: DNA
<213> ORGANISM: Homo sapiens

<400> SEQUENCE: 189
ggtgtctcgg ccatgacaca catttgacat gccctccctc aacctactta tagactattt      60
ttcttgctct gcagcatgga ccaaagagaa attctgcaga agttcctgga tgaggcccaa     120
agcaagaaaa ttactaaaga ggagtttgcc aatgaatttc tgaagctgaa aaggcaatct     180
accaagtaca aggcagacaa aacctatcct acaactgtgg ctgagaagcc caagaatatc     240
aagaaaaaca gatataagga tattttgccc tatgattata gccgggtaga actatccctg     300
ataacctctg atgaggattc cagctacatc aatgccaact tcattaaggg agtttatgga     360
cccaaggctt atattgccac ccagggtcct ttatctacaa ccctcctgga cttctggagg     420
atgatttggg aatatagtgt ccttatcatt gttatggcat gcatggagta tgaaatggga     480
aagaaaaagt gtgagcgcta ctgggctgag ccaggagaga tgcagctgga atttggccct     540
ttctctgtat cctgtgaagc tgaaaaaagg aaatctgatt atataatcag gactctaaaa     600
gttaagttca atagtgaaac tcgaactatc taccagtttc attacaagaa ttggccagac     660
catgatgtac cttcatctat agaccctatt cttgagctca tctgggatgt acgttgttac     720
caagaggatg acagtgttcc catatgcatt cactgcagtg ctggctgtgg aaggactggt     780
gttatttgtg ctattgatta tatggatgtt gctaaaag atgggagtca agcaaagcat     840
tgtattcctg agaaaaatca cactctccaa gcagactctt attctcctaa tttaccaaaa     900
agtaccacaa aagcagcaaa aatgatgaac caacaaagga caaaaatgga aatcaaagaa     960
tcttcttcct ttgactttag gacttctgaa ataagtgcaa agaagagct agttttgcac    1020 cctgctaaat caagcacttc ttttgacttt ctggagctaa attacagttt tgacaaaaat    1080
gctgacacaa ccatgaaatg gcagacaaag gcatttccaa tagttgggga gcctcttcag    1140
aagcatcaaa gtttggattt gggctctctt ttgtttgagg atgttctaa ttctaaacct    1200
```

```
gtaaatgcag caggaagata ttttaattca aggtgccaa taacacggac caaatcaact      1260
ccttttgaat tgatacagca gagagaaacc aaggaggtgg acagcaagga aaacttttct      1320
tatttggaat ctcaaccaca tgattcttgt tttgtagaga tgcaggctca aaaagtaatg      1380
catgtttctt cagcagaact gaattattca ctgccatatg actctaaaca ccaaatacgt      1440
aatgcctcta atgtaaagca ccatgactct agtgctcttg gtgtatattc ttacatacct      1500
ttagtggaaa atccttattt ttcatcatgg cctccaagtg gtaccagttc taagatgtct      1560
cttgatttac ctgagaagca agatggaact gttttccctt cttctctgtt gccaacatcc      1620
tctacatccc tcttctctta ttacaattca catgattctt tatcactgaa ttctccaacc      1680
aatatttcct cactattgaa ccaggagtca gctgtactag caactgctcc aaggatagat      1740
gatgaaatcc cccctccact tcctgtacgg acacctgaat catttattgt ggttgaggaa      1800
gctggagaat tctcaccaaa tgttcccaaa tccttatcct cagctgtgaa ggtaaaaatt      1860
ggaacatcac tggaatgggg tggaacatct gaaccaaaga aatttgatga ctctgtgata      1920
cttagaccaa gcaagagtgt aaaactccga agtcctaaat cagaactaca tcaagatcgt      1980
tcttctcccc cacctcctct cccagaaaga actctagagt ccttctttct tgccgatgaa      2040
gattgtatgc aggcccaatc tatagaaaca tattctacta gctatcctga caccatggaa      2100
aattcaacat cttcaaaaca gacactgaag actcctggaa aaagtttcac aaggagtaag      2160
agtttgaaaa ttttgcgaaa catgaaaaag agtatctgta attcttgccc accaaacaag      2220
cctgcagaat ctgttcagtc aaataactcc agctcatttc tgaattttgg ttttgcaaac      2280
cgttttcaa acccaaagg accaaggaat ccaccaccaa cttggaatat ttaataaaac      2340
tccagattta taataatatg ggctgcaagt acacctgcaa ataaaactac tagaatactg      2400
ctagttaaaa taagtgctct atatgcataa tatcaaatat gaagatatgc taatgtgtta      2460
atagctttta aagaaaagc aaaatgccaa taagtgccag ttttgcattt tcatatcatt      2520
tgcattgagt tgaaaactgc aaataaaagt ttgtcacttg agcttatgta cagaatgcta      2580
tatgagaaac acttttagaa tggatttatt tttcattttt gccagttatt tttatttttct      2640
tttacttttt tacataaaca taaacttcaa aaggtttgta agatttggat ctcaactaat      2700
ttctacattg ccagaatata ctataaaaag ttaaaaaaaa aacttacttt gtgggttgca      2760
atacaaactg ctcttgacaa tgactattcc ctgacagtta ttttgccta atgagtat       2820
accttgtaaa tcttcccaaa tgttgtggaa aactggaata ttaagaaaat gagaaattat      2880
atttattaga ataaaatgtg caaataatga caattatttg aatgtaacaa ggaattcaac      2940
tgaaatcctg ataagttta accaaagtca ttaaattacc aattctagaa agtaatcaa       3000
tgaaatataa tagctatctt ttggtagcaa aagatataaa ttgtatatgt ttatacagga      3060
tctttcagat catgtgcaat ttttatctaa ccaatcagaa atactagttt aaaatgaatt      3120
tctatatgaa tatggatctg ccataagaaa atcagttca actctaattt tatgtagtaa       3180
ataaattggc aggtaattgt ttttacaaag aatccacctg acttccccta atgcattaaa      3240
aatatttta tttaaataac tttatttata acttttagaa acatgtagta ttgtttaaac      3300
atcatttgtt cttcagtatt tttcatttgg aagtccaata gggcaaattg aatgaagtat      3360
tattatctgt ctccttgtagt acaatgtatc caacagacac tcaataaact ttttggttgt      3420
taaaaaaaaaa aaaaaa                                                    3436

<210> SEQ ID NO 190
<211> LENGTH: 752
```

<212> TYPE: PRT
<213> ORGANISM: Homo sapiens

<400> SEQUENCE: 190

```
Met Asp Gln Arg Glu Ile Leu Gln Lys Phe Leu Asp Glu Ala Gln Ser
1               5                   10                  15

Lys Lys Ile Thr Lys Glu Glu Phe Ala Asn Glu Phe Leu Lys Leu Lys
                20                  25                  30

Arg Gln Ser Thr Lys Tyr Lys Ala Asp Lys Thr Tyr Pro Thr Thr Val
            35                  40                  45

Ala Glu Lys Pro Lys Asn Ile Lys Lys Asn Arg Tyr Lys Asp Ile Leu
        50                  55                  60

Pro Tyr Asp Tyr Ser Arg Val Glu Leu Ser Leu Ile Thr Ser Asp Glu
65                  70                  75                  80

Asp Ser Ser Tyr Ile Asn Ala Asn Phe Ile Lys Gly Val Tyr Gly Pro
                85                  90                  95

Lys Ala Tyr Ile Ala Thr Gln Gly Pro Leu Ser Thr Thr Leu Leu Asp
            100                 105                 110

Phe Trp Arg Met Ile Trp Glu Tyr Ser Val Leu Ile Ile Val Met Ala
        115                 120                 125

Cys Met Glu Tyr Glu Met Gly Lys Lys Cys Glu Arg Tyr Trp Ala
130                 135                 140

Glu Pro Gly Glu Met Gln Leu Glu Phe Gly Pro Phe Ser Val Ser Cys
145                 150                 155                 160

Glu Ala Glu Lys Arg Lys Ser Asp Tyr Ile Ile Arg Thr Leu Lys Val
                165                 170                 175

Lys Phe Asn Ser Glu Thr Arg Thr Ile Tyr Gln Phe His Tyr Lys Asn
            180                 185                 190

Trp Pro Asp His Asp Val Pro Ser Ser Ile Asp Pro Ile Leu Glu Leu
        195                 200                 205

Ile Trp Asp Val Arg Cys Tyr Gln Glu Asp Asp Ser Val Pro Ile Cys
210                 215                 220

Ile His Cys Ser Ala Gly Cys Gly Arg Thr Gly Val Ile Cys Ala Ile
225                 230                 235                 240

Asp Tyr Thr Trp Met Leu Leu Lys Asp Gly Ser Gln Ala Lys His Cys
                245                 250                 255

Ile Pro Glu Lys Asn His Thr Leu Gln Ala Asp Ser Tyr Ser Pro Asn
            260                 265                 270

Leu Pro Lys Ser Thr Thr Lys Ala Ala Lys Met Met Asn Gln Gln Arg
        275                 280                 285

Thr Lys Met Glu Ile Lys Glu Ser Ser Ser Phe Asp Phe Arg Thr Ser
290                 295                 300

Glu Ile Ser Ala Lys Glu Leu Val Leu His Pro Ala Lys Ser Ser
305                 310                 315                 320

Thr Ser Phe Asp Phe Leu Glu Leu Asn Tyr Ser Phe Asp Lys Asn Ala
                325                 330                 335

Asp Thr Thr Met Lys Trp Gln Thr Lys Ala Phe Pro Ile Val Gly Glu
            340                 345                 350

Pro Leu Gln Lys His Gln Ser Leu Asp Leu Gly Ser Leu Leu Phe Glu
        355                 360                 365

Gly Cys Ser Asn Ser Lys Pro Val Asn Ala Ala Gly Arg Tyr Phe Asn
370                 375                 380

Ser Lys Val Pro Ile Thr Arg Thr Lys Ser Thr Pro Phe Glu Leu Ile
385                 390                 395                 400
```

Gln Gln Arg Glu Thr Lys Glu Val Asp Ser Lys Glu Asn Phe Ser Tyr
            405                 410                 415

Leu Glu Ser Gln Pro His Asp Ser Cys Phe Val Glu Met Gln Ala Gln
        420                 425                 430

Lys Val Met His Val Ser Ser Ala Glu Leu Asn Tyr Ser Leu Pro Tyr
            435                 440                 445

Asp Ser Lys His Gln Ile Arg Asn Ala Ser Asn Val Lys His His Asp
        450                 455                 460

Ser Ser Ala Leu Gly Val Tyr Ser Tyr Ile Pro Leu Val Glu Asn Pro
465                 470                 475                 480

Tyr Phe Ser Ser Trp Pro Pro Ser Gly Thr Ser Lys Met Ser Leu
            485                 490                 495

Asp Leu Pro Glu Lys Gln Asp Gly Thr Val Phe Pro Ser Ser Leu Leu
        500                 505                 510

Pro Thr Ser Ser Thr Ser Leu Phe Ser Tyr Tyr Asn Ser His Asp Ser
            515                 520                 525

Leu Ser Leu Asn Ser Pro Thr Asn Ile Ser Ser Leu Leu Asn Gln Glu
        530                 535                 540

Ser Ala Val Leu Ala Thr Ala Pro Arg Ile Asp Asp Glu Ile Pro Pro
545                 550                 555                 560

Pro Leu Pro Val Arg Thr Pro Glu Ser Phe Ile Val Val Glu Glu Ala
            565                 570                 575

Gly Glu Phe Ser Pro Asn Val Pro Lys Ser Leu Ser Ser Ala Val Lys
        580                 585                 590

Val Lys Ile Gly Thr Ser Leu Glu Trp Gly Thr Ser Glu Pro Lys
            595                 600                 605

Lys Phe Asp Asp Ser Val Ile Leu Arg Pro Ser Lys Ser Val Lys Leu
        610                 615                 620

Arg Ser Pro Lys Ser Glu Leu His Gln Asp Arg Ser Ser Pro Pro
625                 630                 635                 640

Pro Leu Pro Glu Arg Thr Leu Glu Ser Phe Phe Leu Ala Asp Glu Asp
            645                 650                 655

Cys Met Gln Ala Gln Ser Ile Glu Thr Tyr Ser Thr Ser Tyr Pro Asp
        660                 665                 670

Thr Met Glu Asn Ser Thr Ser Ser Lys Gln Thr Leu Lys Thr Pro Gly
            675                 680                 685

Lys Ser Phe Thr Arg Ser Lys Ser Leu Lys Ile Leu Arg Asn Met Lys
        690                 695                 700

Lys Ser Ile Cys Asn Ser Cys Pro Pro Asn Lys Pro Ala Glu Ser Val
705                 710                 715                 720

Gln Ser Asn Asn Ser Ser Phe Leu Asn Phe Gly Phe Ala Asn Arg
            725                 730                 735

Phe Ser Lys Pro Lys Gly Pro Arg Asn Pro Pro Thr Trp Asn Ile
            740                 745                 750

<210> SEQ ID NO 191
<211> LENGTH: 3825
<212> TYPE: DNA
<213> ORGANISM: Homo sapiens

<400> SEQUENCE: 191
ccggagaggt gttggagagc acaatggctg aacaagtcct tcctcaggct ttgtatttga    60
gcaatatgcg gaaagctgtg aagatacggg agagaactcc agaagacatt tttaaaccta   120

```
ctaatgggat cattcatcat tttaaaacca tgcaccgata cacactggaa atgttcagaa    180
cttgccagtt ttgtcctcag tttcgggaga tcatccacaa agccctcatc gacagaaaca    240
tccaggccac cctggaaagc cagaagaaac tcaactggtg tcgagaagtc cggaagcttg    300
tggcgctgaa aacgaacggt gacggcaatt gcctcatgca tgccacttct cagtacatgt    360
ggggcgttca ggacacagac ttggtactga ggaaggcgct gttcagcacg ctcaaggaaa    420
cagacacacg caactttaaa ttccgctggc aactggagtc tctcaaatct caggaatttg    480
ttgaaacggg gctttgctat gatactcgga actggaatga tgaatgggac aatcttatca    540
aaatggcttc cacagacaca cccatggccc gaagtggact tcagtacaac tcactggaag    600
aaatacacat atttgtcctt tgcaacatcc tcagaaggcc aatcattgtc atttcagaca    660
aaatgctaag aagtttggaa tcaggttcca atttcgcccc tttgaaagtg ggtgaattt    720
acttgcctct ccactggcct gcccaggaat gctacagata ccccattgtt ctcggctatg    780
acagccatca ttttgtaccc ttggtgaccc tgaaggacag tgggcctgaa atccgagctg    840
ttccacttgt taacagagac cggggaagat ttgaagactt aaaagttcac ttttttgacag    900
atcctgaaaa tgagatgaag gagaagctct aaaagagta cttaatggtg atagaaatcc    960
ccgtccaagg ctgggaccat ggcacaactc atctcatcaa tgccgcaaag ttggatgaag   1020
ctaacttacc aaaagaaatc aatctggtag atgattactt tgaacttgtt cagcatgagt   1080
acaagaaatg gcaggaaaac agcgagcagg ggaggagaga ggggcacgcc cagaatccca   1140
tggaacctcc cgtgccccag ctttctctca tggatgtaaa atgtgaaacg cccaactgcc   1200
ccttcttcat gtctgtgaac acccagcctt tatgccatga gtgctcagag aggcggcaaa   1260
agaatcaaaa caaactccca aagctgaact ccaagccggg ccctgagggg ctccctggca   1320
tggcgctcgg ggcctctcgg ggagaagcct atgagccctt ggcgtggaac cctgaggagt   1380
ccactggggg gcctcattcg gccccaccga cagcacccag cccttttctg ttcagtgaga   1440
ccactgccat gaagtgcagg agccccggct gcccctccac actgaatgtg cagcacaacg   1500
gattttgtga acgttgccac aacgcccggc aacttcacgc cagccacgcc cagaccaca   1560
caaggcactt ggatcccggg aagtgccaag cctgcctcca ggatgttacc aggacattta   1620
atgggatctg cagtacttgc ttcaaaagga ctacagcaga ggcctcctcc agcctcagca   1680
ccagcctccc tccttcctgt caccagcgtt ccaagtcaga tccctcgcgg ctcgtccgga   1740
gcccctcccc gcattcttgc cacagagctg gaaacgacgc cctgctggc tgcctgtctc   1800
aagctgcacg gactcctggg gacaggacgg ggacgagcaa gtgcagaaaa gccggctgcg   1860
tgtattttgg gactccagaa acaagggct tttgcacact gtgtttcatc gagtacagag   1920
aaaacaaaca ttttgctgct gcctcaggga agtcagtcc cacagcgtcc aggttccaga   1980
acaccattcc gtgcctgggg agggaatgcg gcacccttgg aagcaccatg tttgaaggat   2040
actgccagaa gtgtttcatt gaagctcaga atcagagatt tcatgaggcc aaaaggacag   2100
aagagcaact gagatcgagc cagcgcagag atgtgcctcg aaccacacaa agcacctcaa   2160
ggcccaagtg cgcccgggcc tcctgcaaga acatcctggc ctgccgcagc gaggagctct   2220
gcatggagtc tcagcatccc aaccagagga tgggccctgg ggccaccgg ggtgagcctg   2280
cccccgaaga ccccccaag cagcgttgcc gggcccccgc ctgtgatcat tttggcaatg   2340
ccaagtgcaa cggctactgc aacgaatgct tcagttcaa gcagatgtat ggctaaccgg   2400
aaacaggtgg gtcacctcct gcaagaagtg gggcctcgag ctgtcagtca tcatggtgct   2460
atcctctgaa cccctcagct gccactgcaa cagtgggctt aagggtgtct gagcaggaga   2520
```

```
ggaaagataa gctcttcgtg gtgcccacga tgctcaggtt tggtaacccg ggagtgttcc    2580
caggtggcct tagaaagcaa agcttgtaac tggcaaggga tgatgtcaga ttcagcccaa    2640
ggttcctcct ctcctaccaa gcaggaggcc aggaacttct ttggacttgg aaggtgtgcg    2700
gggactggcc gaggcccctg caccctgcgc atcaggactg cttcatcgtc ttggctgaga    2760
aagggaaaag acacacaagt cgcgtgggtt ggagaagcca gagccattcc acctcccctc    2820
ccccagcatc tctcagagat gtgaagccag atcctcatgg cagcgaggcc ctctgcaaga    2880
agctcaagga agctcaggga aaatggacgt attcagagag tgtttgtagt tcatggtttt    2940
tccctacctg cccggttcct ttcctgagga cccggcagaa atgcagaacc atccatggac    3000
tgtgattctg aggctgctga gactgaacat gttcacattg acagaaaaac aagctgctct    3060
ttataatatg caccttttaa aaaattagaa tattttactg ggaagacgtg taactctttg    3120
ggttattact gtctttactt ctaaagaagt tagcttgaac tgaggagtaa aagtgtgtac    3180
atatataata taccccttaca ttatgtatga gggattttttt taaattatat tgaaatgctg    3240
ccctagaagt acaataggaa ggctaaataa taataacctg ttttctggtt gttgttgggg    3300
catgagcttg tgtatacact gcttgcataa actcaaccag ctgccttttt aaagggagct    3360
ctagtccttt ttgtgtaatt cactttattt attttattac aaacttcaag attatttaag    3420
cgaagatatt tcttcagctc tggggaaaat gccacagtgt tctcctgaga gaacatcctt    3480
gctttgagtc aggctgtggg caagttcctg accacaggga gtaaattggc ctctttgata    3540 cactttttgct tgcctcccca ggaaagaagg aattgcatcc aaggtataca tacatattca    3600
tcgatgtttc gtgcttctcc ttatgaaact ccagctatgt aataaaaaac tatactctgt    3660
gttctgttaa tgcctctgag tgtcctacct ccttggagat gagatagggga aggagcaggg    3720 atgagactgg caatggtcac agggaaagat gtggccttttt gtgatggttt tattttctgt    3780
taacactgtg tcctgggggg gctgggaagt cccctgcatc ccatg                   3825
```

<210> SEQ ID NO 192
<211> LENGTH: 790
<212> TYPE: PRT
<213> ORGANISM: Homo sapiens

<400> SEQUENCE: 192

```
Met Ala Glu Gln Val Leu Pro Gln Ala Leu Tyr Leu Ser Asn Met Arg
1               5                   10                  15

Lys Ala Val Lys Ile Arg Glu Arg Thr Pro Glu Asp Ile Phe Lys Pro
            20                  25                  30

Thr Asn Gly Ile Ile His His Phe Lys Thr Met His Arg Tyr Thr Leu
        35                  40                  45

Glu Met Phe Arg Thr Cys Gln Phe Cys Pro Gln Phe Arg Glu Ile Ile
    50                  55                  60

His Lys Ala Leu Ile Asp Arg Asn Ile Gln Ala Thr Leu Glu Ser Gln
65                  70                  75                  80

Lys Lys Leu Asn Trp Cys Arg Glu Val Arg Lys Leu Val Ala Leu Lys
                85                  90                  95

Thr Asn Gly Asp Gly Asn Cys Leu Met His Ala Thr Ser Gln Tyr Met
            100                 105                 110

Trp Gly Val Gln Asp Thr Asp Leu Val Leu Arg Lys Ala Leu Phe Ser
        115                 120                 125

Thr Leu Lys Glu Thr Asp Thr Arg Asn Phe Lys Phe Arg Trp Gln Leu
    130                 135                 140
```

```
Glu Ser Leu Lys Ser Gln Glu Phe Val Glu Thr Gly Leu Cys Tyr Asp
145                 150                 155                 160

Thr Arg Asn Trp Asn Asp Glu Trp Asp Asn Leu Ile Lys Met Ala Ser
            165                 170                 175

Thr Asp Thr Pro Met Ala Arg Ser Gly Leu Gln Tyr Asn Ser Leu Glu
            180                 185                 190

Glu Ile His Ile Phe Val Leu Cys Asn Ile Leu Arg Arg Pro Ile Ile
            195                 200                 205

Val Ile Ser Asp Lys Met Leu Arg Ser Leu Glu Ser Gly Ser Asn Phe
210                 215                 220

Ala Pro Leu Lys Val Gly Gly Ile Tyr Leu Pro Leu His Trp Pro Ala
225                 230                 235                 240

Gln Glu Cys Tyr Arg Tyr Pro Ile Val Leu Gly Tyr Asp Ser His His
            245                 250                 255

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
            275                 280                 285

His Phe Leu Thr Asp Pro Glu Asn Glu Met Lys Glu Lys Leu Leu Lys
290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
            325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
            355                 360                 365

Ala Gln Asn Pro Met Glu Pro Ser Val Pro Gln Leu Ser Leu Met Asp
370                 375                 380

Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
            405                 410                 415

Lys Leu Pro Lys Leu Asn Ser Lys Pro Gly Pro Glu Gly Leu Pro Gly
            420                 425                 430

Met Ala Leu Gly Ala Ser Arg Gly Glu Ala Tyr Glu Pro Leu Ala Trp
            435                 440                 445

Asn Pro Glu Glu Ser Thr Gly Gly Pro His Ser Ala Pro Pro Thr Ala
            450                 455                 460

Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
            485                 490                 495

Arg Cys His Asn Ala Arg Gln Leu His Ala Ser His Ala Pro Asp His
            500                 505                 510

Thr Arg His Leu Asp Pro Gly Lys Cys Gln Ala Cys Leu Gln Asp Val
            515                 520                 525

Thr Arg Thr Phe Asn Gly Ile Cys Ser Thr Cys Phe Lys Arg Thr Thr
            530                 535                 540

Ala Glu Ala Ser Ser Ser Leu Ser Thr Ser Leu Pro Pro Ser Cys His
545                 550                 555                 560
```

```
Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
            580                 585                 590

Gln Ala Ala Arg Thr Pro Gly Asp Arg Thr Gly Thr Ser Lys Cys Arg
        595                 600                 605

Lys Ala Gly Cys Val Tyr Phe Gly Thr Pro Glu Asn Lys Gly Phe Cys
    610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655

Cys Leu Gly Arg Glu Cys Gly Thr Leu Gly Ser Thr Met Phe Glu Gly
            660                 665                 670

Tyr Cys Gln Lys Cys Phe Ile Glu Ala Gln Asn Gln Arg Phe His Glu
        675                 680                 685

Ala Lys Arg Thr Glu Glu Gln Leu Arg Ser Ser Gln Arg Asp Val
    690                 695                 700

Pro Arg Thr Thr Gln Ser Thr Ser Arg Pro Lys Cys Ala Arg Ala Ser
705                 710                 715                 720

Cys Lys Asn Ile Leu Ala Cys Arg Ser Glu Glu Leu Cys Met Glu Cys
                725                 730                 735

Gln His Pro Asn Gln Arg Met Gly Pro Gly Ala His Arg Gly Glu Pro
            740                 745                 750

Ala Pro Glu Asp Pro Pro Lys Gln Arg Cys Arg Ala Pro Ala Cys Asp
        755                 760                 765

His Phe Gly Asn Ala Lys Cys Asn Gly Tyr Cys Asn Glu Cys Phe Gln
    770                 775                 780

Phe Lys Gln Met Tyr Gly
785                 790

<210> SEQ ID NO 193
<211> LENGTH: 2588
<212> TYPE: DNA
<213> ORGANISM: Homo sapiens

<400> SEQUENCE: 193
gctttctcct agggactgtg aggggcgctt ctgactttgg acttgagcac tgcctgggac      60
ctgtgctgag agagcgctag catgtctcag tggaatcaag tccaacagtt agaaatcaag     120
tttttggagc aggtggatca attctatgat gacaactttc ccatggaaat tcggcatctg     180
ttggcccaat ggattgaaaa tcaagactgg gaggcagctt ctaacaatga accatggca      240 acgattcttc ttcaaaactt gttaatacaa ctggatgaac agttaggtcg tgtttccaaa     300
gagaaaaacc tactcttgat acacaatcta aaaagaatta ggaaggtcct tcagggaaaa     360
tttcatggaa atccaatgca gtagctgtg gttatttcaa actgtttaag ggaagagagg     420
agaatattgg ctgcagccaa catgcctgtc aggggcctc tagagaaatc cttacaaagt     480
tcttcagttt cagaaagaca gaggaatgtg agcacaaag tggctgccat taaaaacagt     540
gtgcagatga cagaacaaga taccaaatac ttagaagatc tgcaagacga atttgactac     600
aggtataaaa caattcagac aatggatcag agtgacaaga atagtgccat ggtgaatcag     660
gaagttttga cactgcagga aatgcttaac agcctcgatt tcaagagaaa ggaggctctc     720
agtaaaatga cccaaatcat ccatgagaca gacctgttaa tgaacaccat gctcatagaa     780
```

```
gagctgcaag actggaagcg gcggcagcaa atcgcctgca tcgggggtcc actccacaat      840
gggctcgacc agcttcagaa ctgctttaca ctattggcag aaagtctttt ccaactgaga      900
aggcaattgg agaaactaga ggagcaatct accaaaatga catatgaagg tgatcccatt      960
ccaatgcaaa gaactcacat gctagaaaga gtcaccttct tgatctacaa ccttttcaag     1020
aactcatttg tggttgagcg acagccatgt atgccaaccc accctcagag gccgttggta     1080
cttaaaaccc taattcagtt cactgtaaaa ctaaggctac taataaaatt gccagaacta     1140
aactatcagg taaaggttaa ggcatcaatt gacaagaatg tttcaactct aagcaaccga     1200
agatttgtac tttgtggaac taatgtcaaa gccatgtcta ttgaagaatc ttccaatggg     1260
agtctctcag tagaatttcg acatttgcaa ccaaaggaaa tgaagtccag tgctggaggt     1320
aaaggaaatg agggctgtca catggtgact gaagaacttc attccataac gtttgaaaca     1380
cagatctgcc tctatggcct gaccatagat ttggagacca gctcattgcc tgtggtgatg     1440
atttccaatg tcagtcagtt acctaatgct tgggcatcca tcatttggta caacgtgtca     1500
accaacgatt cccagaactt ggtttccttt aataatcctc cacctgccac attgagtcaa     1560
ctactggagg tgatgagctg gcagttttca tcgtacgttg gtcgtggtct taactcagat     1620
caactccata tgctggcaga agcttaca gtccaatcta gctacagtga tggtcacctc       1680
acctgggcca agttctgcaa ggaacattta cctggtaaat catttacctt ttggacatgg     1740
cttgaagcaa tattggatct aattaagaaa cacattcttc ccctttggat tgatgggtat     1800
gtcatgggct tgttagcaa agagaaggaa cggctgttgc taaaggataa aatgcctggc      1860
acctttttat taagattcag tgaaagccat ctcggaggaa taactttcac ctgggtggac     1920
cattctgaaa gtggggaagt gagattccac tctgtagaac cctacaataa aggccggttg     1980
tctgctctgc cattcgctga catcctgcga gactacaaag ttattatggc tgaaaacatt     2040
cctgaaaacc ctctgaagta cctatatcct gacattccca agacaaagc cttcggtaaa     2100
cactacagct ctcagccttg cgaagtttca agaccaacag aaaggggtga caaaggttat     2160
gttccttctg tttttatccc catctcaaca atccgaagtg attcaacaga gccacattct     2220
ccatcagacc ttcttcccat gtctccaagt gtgtatgcgg tgttgagaga aaacctgagt     2280
cccacaacaa ttgaaactgc aatgaagtct ccttattctg ctgaatgaca ggataaactc     2340
tgacgcacca agaaaggaag caatgaaaa agtttaaaga ctgttctttg cccaataacc      2400
acatttatt tcttcagctt tgtaaatacc aggttctagg aaatgtttga catctgaagc      2460
tctcttcaca ctcccgtggc actcctcaat tgggagtgtt gtgactgaaa tgcttgaaac     2520
caaagcttca gataaacttg caagataaga caactttaag aaaccagtgt taataacaat     2580
attaacag                                                              2588
```

<210> SEQ ID NO 194
<211> LENGTH: 748
<212> TYPE: PRT
<213> ORGANISM: Homo sapiens

<400> SEQUENCE: 194

```
Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Asn Gln Asp Trp Glu Ala Ala Ser Asn
        35                  40                  45
```

```
Asn Glu Thr Met Ala Thr Ile Leu Leu Gln Asn Leu Leu Ile Gln Leu
 50                  55                  60

Asp Glu Gln Leu Gly Arg Val Ser Lys Glu Lys Asn Leu Leu Leu Ile
 65                  70                  75                  80

His Asn Leu Lys Arg Ile Arg Lys Val Leu Gln Gly Lys Phe His Gly
                 85                  90                  95

Asn Pro Met His Val Ala Val Ile Ser Asn Cys Leu Arg Glu Glu
            100                 105                 110

Arg Arg Ile Leu Ala Ala Ala Asn Met Pro Val Gln Gly Pro Leu Glu
            115                 120                 125

Lys Ser Leu Gln Ser Ser Val Ser Glu Arg Gln Arg Asn Val Glu
130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
            195                 200                 205

Arg Lys Glu Ala Leu Ser Lys Met Thr Gln Ile Ile His Glu Thr Asp
210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270

Arg Arg Gln Leu Glu Lys Leu Glu Glu Gln Ser Thr Lys Met Thr Tyr
            275                 280                 285

Glu Gly Asp Pro Ile Pro Met Gln Arg Thr His Met Leu Glu Arg Val
290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
            340                 345                 350

Leu Asn Tyr Gln Val Lys Val Lys Ala Ser Ile Asp Lys Asn Val Ser
            355                 360                 365

Thr Leu Ser Asn Arg Arg Phe Val Leu Cys Gly Thr Asn Val Lys Ala
370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Gly Lys Gly Asn
                405                 410                 415

Glu Gly Cys His Met Val Thr Glu Glu Leu His Ser Ile Thr Phe Glu
            420                 425                 430

Thr Gln Ile Cys Leu Tyr Gly Leu Thr Ile Asp Leu Glu Thr Ser Ser
            435                 440                 445

Leu Pro Val Val Met Ile Ser Asn Val Ser Gln Leu Pro Asn Ala Trp
450                 455                 460

Ala Ser Ile Ile Trp Tyr Asn Val Ser Thr Asn Asp Ser Gln Asn Leu
```

```
                465                 470                 475                 480
        Val Phe Phe Asn Asn Pro Pro Ala Thr Leu Ser Gln Leu Leu Glu
                            485                 490                 495
        Val Met Ser Trp Gln Phe Ser Ser Tyr Val Gly Arg Gly Leu Asn Ser
                        500                 505                 510
        Asp Gln Leu His Met Leu Ala Glu Lys Leu Thr Val Gln Ser Ser Tyr
                    515                 520                 525
        Ser Asp Gly His Leu Thr Trp Ala Lys Phe Cys Lys Glu His Leu Pro
                530                 535                 540
        Gly Lys Ser Phe Thr Phe Trp Thr Trp Leu Glu Ala Ile Leu Asp Leu
        545                 550                 555                 560
        Ile Lys Lys His Ile Leu Pro Leu Trp Ile Asp Gly Tyr Val Met Gly
                            565                 570                 575
        Phe Val Ser Lys Glu Lys Glu Arg Leu Leu Leu Lys Asp Lys Met Pro
                        580                 585                 590
        Gly Thr Phe Leu Leu Arg Phe Ser Glu Ser His Leu Gly Gly Ile Thr
                    595                 600                 605
        Phe Thr Trp Val Asp His Ser Glu Ser Gly Glu Val Arg Phe His Ser
                610                 615                 620
        Val Glu Pro Tyr Asn Lys Gly Arg Leu Ser Ala Leu Pro Phe Ala Asp
        625                 630                 635                 640
        Ile Leu Arg Asp Tyr Lys Val Ile Met Ala Glu Asn Ile Pro Glu Asn
                            645                 650                 655
        Pro Leu Lys Tyr Leu Tyr Pro Asp Ile Pro Lys Asp Lys Ala Phe Gly
                        660                 665                 670
        Lys His Tyr Ser Ser Gln Pro Cys Glu Val Ser Arg Pro Thr Glu Arg
                    675                 680                 685
        Gly Asp Lys Gly Tyr Val Pro Ser Val Phe Ile Pro Ile Ser Thr Ile
                690                 695                 700
        Arg Ser Asp Ser Thr Glu Pro His Ser Pro Ser Asp Leu Leu Pro Met
        705                 710                 715                 720
        Ser Pro Ser Val Tyr Ala Val Leu Arg Glu Asn Leu Ser Pro Thr Thr
                            725                 730                 735
        Ile Glu Thr Ala Met Lys Ser Pro Tyr Ser Ala Glu
                        740                 745

<210> SEQ ID NO 195
<211> LENGTH: 1125
<212> TYPE: DNA
<213> ORGANISM: Homo sapiens

<400> SEQUENCE: 195
atgagcgggg aatcaatgaa tttcagcgat gttttcgact ccagtgaaga ttattttgtg      60
tcagtcaata cttcatatta ctcagttgat tctgagatgt tactgtgctc cttgcaggag    120
gtcaggcagt tctccaggct atttgtaccg attgcctact ccttgatctg tgtctttggc    180
ctcctgggga atattctggt ggtgatcacc tttgcttttt ataagaaggc caggtctatg    240
acagacgtct atctcttgaa catggccatt gcagacatcc tctttgttct tactctccca    300
ttctgggcag tgagtcatgc cactggtgcg tgggttttca gcaatgccac gtgcaagttg    360
ctaaaaggca tctatgccat caactttaac tgcgggatgc tgcctctgac ttgcattagc    420
atggaccggt acatcgccat gtacaggcg actaagtcat tccggctccg atccagaaca    480
ctaccgcgca gcaaaatcat ctgccttgtt gtgtggggc tgtcagtcat catctccagc    540
```

```
tcaactttg tcttcaacca aaatacaac acccaaggca gcgatgtctg tgaacccaag    600
taccagactg tctcggagcc catcaggtgg aagctgctga tgttggggct tgagctactc   660
tttggtttct ttatcccttt gatgttcatg atattttgtt acacgttcat tgtcaaaacc   720
ttggtgcaag ctcagaattc taaaaggcac aaagccatcc gtgtaatcat agctgtggtg   780
cttgtgtttc tggcttgtca gattcctcat aacatggtcc tgcttgtgac ggctgcaaat   840
ttgggtaaaa tgaaccgatc ctgccagagc gaaaagctaa ttggctatac gaaaactgtc   900
acagaagtcc tggctttcct gcactgctgc ctgaaccctg tgctctacgc ttttattggg   960
cagaagttca gaaactactt tctgaagatc ttgaaggacc tgtggtgtgt gagaaggaag  1020
tacaagtcct caggcttctc ctgtgccggg aggtactcag aaaacatttc tcggcagacc  1080
agtgagaccg cagataacga caatgcgtcg tccttcacta tgtga                 1125
```

<210> SEQ ID NO 196
<211> LENGTH: 374
<212> TYPE: PRT
<213> ORGANISM: Homo sapiens

<400> SEQUENCE: 196

```
Met Ser Gly Glu Ser Met Asn Phe Ser Asp Val Phe Asp Ser Glu
1               5                  10                 15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
            180                 185                 190

Gly Ser Asp Val Cys Glu Pro Lys Tyr Gln Thr Val Ser Glu Pro Ile
        195                 200                 205

Arg Trp Lys Leu Leu Met Leu Gly Leu Glu Leu Leu Phe Gly Phe Phe
    210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
            260                 265                 270
```

| | | | | | | | | | | | | |
|---|---|---|---|---|---|---|---|---|---|---|---|---|
|Val|Leu|Leu|Val|Thr|Ala|Ala|Asn|Leu|Gly|Lys|Met|Asn|Arg|Ser|Cys|
| | |275| | | |280| | | |285| | | | | |

Gln Ser Glu Lys Leu Ile Gly Tyr Thr Lys Thr Val Thr Glu Val Leu
    290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
            340                 345                 350

Ser Glu Asn Ile Ser Arg Gln Thr Ser Glu Thr Ala Asp Asn Asp Asn
        355                 360                 365

Ala Ser Ser Phe Thr Met
    370

<210> SEQ ID NO 197
<211> LENGTH: 2258
<212> TYPE: DNA
<213> ORGANISM: Homo sapiens

<400> SEQUENCE: 197

```
ctcctccagc tcttcctgtc ccgctgttgc aacactgcct cactcttccc ctcccacctt      60
ctctcccctc ctctctgctt taattttctc agaattctct ggactgaggc tccagttctg     120
gcctttgggg ttcaagatca ctgggaccag gccgtgatct ctatgcccga gtctcaaccc     180
tcaactgtca ccccaaggca cttgggacgt cctggacaga ccgagtcccg ggaagcccca     240
gcactgccgc tgccacactg ccctgagccc aaatggggga gtgagaggcc atagctgtct     300
ggcatgggcc tctccaccgt gcctgacctg ctgctgccac tggtgctcct ggagctgttg     360
gtgggaatat accctcagg ggttattgga ctggtccctc acctagggga cagggagaag     420
agagatagtg tgtgtcccca aggaaaatat atccaccctc aaaataattc gatttgctgt     480
accaagtgcc acaaaggaac ctacttgtac aatgactgtc caggcccggg gcaggatacg     540
gactgcaggg agtgtgagag cggctccttc accgcttcag aaaaccacct cagacactgc     600
ctcagctgct ccaaatgccg aaaggaaatg ggtcaggtgg agatctcttc ttgcacagtg     660
gaccgggaca ccgtgtgtgg ctgcaggaag aaccagtacc ggcattattg gagtgaaaac     720
cttttccagt gcttcaattg cagcctctgc ctcaatggga ccgtgcacct ctcctgccag     780
gagaaacaga acaccgtgtg cacctgccat gcaggtttct ttctaagaga aaacgagtgt     840
gtctcctgta gtaactgtaa gaaaagcctg gagtgcacga agttgtgcct accccagatt     900
gagaatgtta agggcactga ggactcaggc accacagtgc tgttgcccct ggtcattttc     960
tttggtcttt gctttttatc cctcctcttc attggtttaa tgtatcgcta ccaacggtgg    1020
aagtccaagc tctactccat tgtttgtggg aaatcgacac tgaaaaaga ggggagctt    1080
gaaggaacta ctactaagcc cctggcccca aacccaagct tcagtcccac tccaggcttc    1140
acccccaccc tgggcttcag tccgtgccc agttccacct tcacctccag ctccacctat    1200
accccggtg actgtcccaa ctttgcggct cccgcagag aggtggcacc accctatcag    1260
ggggctgacc ccatccttgc gacagccctc gcctccgacc ccatcccaa ccccccttcag    1320
aagtgggagg acagcgccca caagccacag agcctagaca ctgatgaccc cgcgacgctg    1380
tacgccgtgg tggagaacgt gccccgttg cgctggaaga aattcgtgcg cgcgcctaggg    1440
ctgagcgacc acgagatcga tcggctggag ctgcagaacg gcgctgcct gcgcgaggcg    1500
```

```
caatacagca tgctggcgac ctggaggcgg cgcacgccgc ggcgcgaggc cacgctggag    1560
ctgctgggac gcgtgctccg cgacatggac ctgctgggct gcctggagga catcgaggag    1620
gcgctttgcg gccccgccgc cctcccgccc gcgcccagtc ttctcagatg aggctgcgcc    1680
cctgcgggca gctctaagga ccgtcctgcg agatcgcctt ccaacccac tttttctgg      1740 aaaggagggg tcctgcaggg gcaagcagga gctagcagcc gcctacttgg tgctaacccc    1800
tcgatgtaca tagcttttct cagctgcctg cgcgccgccg acagtcagcg ctgtgcgcgc    1860
ggagagaggt gcgccgtggg ctcaagagcc tgagtgggtg gtttgcgagg atgagggacg    1920
ctatgcctca tgcccgtttt gggtgtcctc accagcaagg ctgctcgggg gcccctggtt    1980
cgtccctgag cctttttcac agtgcataag cagttttttt tgttttttgtt ttgttttgtt   2040 ttgtttttaa atcaatcatg ttacactaat agaaacttgg cactcctgtg ccctctgcct    2100
ggacaagcac atagcaagct gaactgtcct aaggcagggg cgagcacgga acaatggggc    2160
cttcagctgg agctgtggac ttttgtacat acactaaaat tctgaagtta aagctctgct    2220
cttggaaaaa aaaaaaaaaa aaaaaaaaaa aaaaaaaa                            2258
```

<210> SEQ ID NO 198
<211> LENGTH: 455
<212> TYPE: PRT
<213> ORGANISM: Homo sapiens

<400> SEQUENCE: 198

```
Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240
```

```
Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
        260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Thr Tyr Thr Pro Gly Asp Cys
        290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
        340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
        420                 425                 430

Cys Leu Glu Asp Ile Glu Glu Ala Leu Cys Gly Pro Ala Ala Leu Pro
        435                 440                 445

Pro Ala Pro Ser Leu Leu Arg
450                 455

<210> SEQ ID NO 199
<211> LENGTH: 2394
<212> TYPE: DNA
<213> ORGANISM: Homo sapiens

<400> SEQUENCE: 199
gaattcggcg cagcggagcc tggagagaag gcgctgggct gcgagggcgc gagggcgcga    60
gggcaggggg caaccggacc ccgcccgcac ccatggcgcc cgtcgccgtc tgggccgcgc   120
tggccgtcgg actggagctc tgggctgcgg cgcacgcctt gcccgcccag gtggcattta   180
caccctacgc cccggagccc gggagcacat gccggctcag agaatactat gaccagacag   240
ctcagatgtg ctgcagcaag tgctcgccgg ccaacatgc aaaagtcttc tgtaccaaga   300
cctcggacac cgtgtgtgac tcctgtgagg acagcacata cacccagctc tggaactggg   360
ttcccgagtg cttgagctgt ggctcccgct gtagctctga ccaggtggaa actcaagcct   420
gcactcggga acagaaccgc atctgcacct gcaggcccgg ctggtactgc gcgctgagca   480
agcaggaggg gtgccggctg tgcgcgccgc tgcgcaagtg ccgcccgggc ttcggcgtgg   540
ccagaccagg aactgaaaca tcagacgtgg tgtgcaagcc ctgtgccccg ggacgttct   600 ccaacacgac ttcatccacg gatatttgca ggccccacca gatctgtaac gtggtggcca   660
tccctgggaa tgcaagcagg gatgcagtct gcacgtccac gtcccccacc cggagtatgg   720
ccccaggggc agtacactta ccccagccag tgtccacacg atcccaacac acgcagccaa   780
ctccagaacc cagcactgct ccaagcacct ccttcctgct cccaatgggc cccagccccc   840
cagctgaagg gagcactggc gacttcgctc ttccagttgg actgattgtg ggtgtgacag   900
```

-continued

```
ccttgggtct actaataata ggagtggtga actgtgtcat catgacccag gtgaaaaaga      960
agcccttgtg cctgcagaga gaagccaagg tgcctcactt gcctgccgat aaggcccggg     1020
gtacacaggg ccccgagcag cagcacctgc tgatcacagc gccgagctcc agcagcagct     1080
ccctggagag ctcggccagt gcgttggaca aagggcgcc cactcggaac cagccacagg      1140
caccaggcgt ggaggccagt ggggccgggg aggcccgggc cagcaccggg agctcagatt     1200
cttcccctgg tggccatggg acccaggtca atgtcacctg catcgtgaac gtctgtagca     1260
gctctgacca cagctcacag tgctcctccc aagccagctc acaatggga gacacagatt      1320
ccagcccctc ggagtccccg aaggacgagc aggtcccctt ctccaaggag gaatgtgcct     1380
ttcggtcaca gctggagacg ccagagaccc tgctggggag caccgaagag aagcccctgc     1440
cccttggagt gcctgatgct gggatgaagc cagttaacc aggccggtgt gggctgtgtc      1500
gtagccaagg tgggctgagc cctggcagga tgaccctgcg aaggggccct ggtccttcca     1560
ggcccccacc actaggactc tgaggctctt tctgggccaa gttcctctag tgccctccac     1620
agccgcagcc tccctctgac ctgcaggcca agagcagagg cagcgggttg tggaaagcct     1680
ctgctgccat ggtgtgtccc tctcggaagg ctggctgggc atggacgttc ggggcatgct     1740
ggggcaagtc cctgactctc tgtgacctgc cccgcccagc tgcacctgcc agcctggctt     1800
ctggagccct tgggtttttt gtttgtttgt ttgtttgttt gtttgtttct cccctgggc     1860
tctgccccag ctctggcttc cagaaaaccc cagcatcctt ttctgcagag gggctttctg     1920
gagaggaggg atgctgcctg agtcacccat gaagacagga cagtgcttca gcctgaggct     1980
gagactgcgg gatggtcctg gggctctgtg caggaggag gtggcagccc tgtagggaac      2040
ggggtccttc aagttagctc aggaggcttg gaaagcatca cctcaggcca ggtgcagtcc     2100
ctcacgccta tgatcccagc actttgggag gctgaggcgg gtggatcacc tgaggttagg     2160
agttcgagac cagcctggcc aacatggtaa acccccatct ctactaaaaa tacagaaatt     2220
agccgggcgt ggtggcgggc acctatagtc ccagctactc agaagcctga ggctgggaaa     2280
tcgtttgaac ccgggaagcg gaggttgcag ggagccgaga tcacgccact gcactccagc     2340
ctgggcgaca gagcgagagt ctgtctcaaa agaaaaaaaa aaaaaaccga attc            2394
```

<210> SEQ ID NO 200
<211> LENGTH: 461
<212> TYPE: PRT
<213> ORGANISM: Homo sapiens

<400> SEQUENCE: 200

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110
```

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
370                 375                 380

Val Asn Val Cys Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
450                 455                 460

<210> SEQ ID NO 201
<211> LENGTH: 1240
<212> TYPE: DNA
<213> ORGANISM: Homo sapiens

<400> SEQUENCE: 201
gacgtgaaga gtttaaagaa agagtattca aacgaaaatg cagttgtgaa gagaatgcag        60
tctcttcaac ttgattgtgt ggcagtacct tcaagccggt caaattcagc cacagaacag       120

```
cctggttcac tgcacagttc ccagggactt gggatgggtc ctgtggagga gtcctggttt      180
gctccttccc tggagcaccc acaagaagag aatgagccca gcctgcagag taaactccaa      240
gacgaagcca actaccatct ttatggcagc cgcatggaca ggcagacgaa acagcagccc      300
agacagaatg tggcttacaa cagagaggag gaaaggagac gcagggtctc ccatgaccct      360
tttgcacagc aaagacctta cgagaatttt cagaatacag agggaaaagg cactgtttat      420
tccagtgcag ccagtcatgg taatgcagtg caccagccat cagggctcac cagccaacct      480
caagtactgt atcagaacaa tggattatat agctcacatg gctttggaac aagaccactg      540
gatccaggaa cagcaggtcc cagagtttgg tacaggccaa ttccaagtca tatgcctagt      600
ctgcataata tcccagtgcc tgagaccaac tatctaggaa attctcccac catgccattc      660
agctccttgc caccaacaga tgaatctata aaatatacca tatacaatag tactggcatt      720
cagattggag cctacaatta tatggagatt ggtgggacga gttcatcact actagacagc      780
acaaatacga acttcaaaga agagccagct gctaagtacc aagctatctt tgataatacc      840
actagtctga cggataaaca cctggaccca atcagggaaa atctgggaaa gcactggaaa      900
aactgtgccc gtaaactggg cttcacacag tctcagattg atgaaattga ccatgactat      960
gagcgagatg gactgaaaga aaaggtttac cagatgctcc aaaagtgggt gatgagggaa     1020
ggcataaagg gagccacggt ggggaagctg gcccaggcgc tccaccagtg ttccaggatc     1080
gaccttctga gcagcttgat ttacgtcagc cagaactaac cctggatggg ctacggcagc     1140
tgaagtggac gcctcactta gtggataacc ccagaaagtt ggctgcctca gagcattcag     1200
aattctgtcc tcactgatag gggttctgtg tctgcagaaa                          1240
```

<210> SEQ ID NO 202
<211> LENGTH: 372
<212> TYPE: PRT
<213> ORGANISM: Homo sapiens

<400> SEQUENCE: 202

```
Asp Val Lys Ser Leu Lys Lys Glu Tyr Ser Asn Glu Asn Ala Val Val
1               5                   10                  15

Lys Arg Met Gln Ser Leu Gln Leu Asp Cys Val Ala Val Pro Ser Ser
            20                  25                  30

Arg Ser Asn Ser Ala Thr Glu Gln Pro Gly Ser Leu His Ser Ser Gln
        35                  40                  45

Gly Leu Gly Met Gly Pro Val Glu Glu Ser Trp Phe Ala Pro Ser Leu
    50                  55                  60

Glu His Pro Gln Glu Glu Asn Glu Pro Ser Leu Gln Ser Lys Leu Gln
65                  70                  75                  80

Asp Glu Ala Asn Tyr His Leu Tyr Gly Ser Arg Met Asp Arg Gln Thr
                85                  90                  95

Lys Gln Gln Pro Arg Gln Asn Val Ala Tyr Asn Arg Glu Glu Glu Arg
            100                 105                 110

Arg Arg Arg Val Ser His Asp Pro Phe Ala Gln Gln Arg Pro Tyr Glu
        115                 120                 125

Asn Phe Gln Asn Thr Glu Gly Lys Gly Thr Val Tyr Ser Ser Ala Ala
    130                 135                 140

Ser His Gly Asn Ala Val His Gln Pro Ser Gly Leu Thr Ser Gln Pro
145                 150                 155                 160

Gln Val Leu Tyr Gln Asn Asn Gly Leu Tyr Ser Ser His Gly Phe Gly
                165                 170                 175
```

Thr Arg Pro Leu Asp Pro Gly Thr Ala Gly Pro Arg Val Trp Tyr Arg
            180                 185                 190

Pro Ile Pro Ser His Met Pro Ser Leu His Asn Ile Pro Val Pro Glu
        195                 200                 205

Thr Asn Tyr Leu Gly Asn Ser Pro Thr Met Pro Phe Ser Ser Leu Pro
    210                 215                 220

Pro Thr Asp Glu Ser Ile Lys Tyr Thr Ile Tyr Asn Ser Thr Gly Ile
225                 230                 235                 240

Gln Ile Gly Ala Tyr Asn Tyr Met Glu Ile Gly Thr Ser Ser Ser
                245                 250                 255

Leu Leu Asp Ser Thr Asn Thr Asn Phe Lys Glu Glu Pro Ala Ala Lys
                260                 265                 270

Tyr Gln Ala Ile Phe Asp Asn Thr Thr Ser Leu Thr Asp Lys His Leu
            275                 280                 285

Asp Pro Ile Arg Glu Asn Leu Gly Lys His Trp Lys Asn Cys Ala Arg
        290                 295                 300

Lys Leu Gly Phe Thr Gln Ser Gln Ile Asp Glu Ile Asp His Asp Tyr
305                 310                 315                 320

Glu Arg Asp Gly Leu Lys Glu Lys Val Tyr Gln Met Leu Gln Lys Trp
                325                 330                 335

Val Met Arg Glu Gly Ile Lys Gly Ala Thr Val Gly Lys Leu Ala Gln
            340                 345                 350

Ala Leu His Gln Cys Ser Arg Ile Asp Leu Leu Ser Leu Ile Tyr
        355                 360                 365

Val Ser Gln Asn
    370

<210> SEQ ID NO 203
<211> LENGTH: 1496
<212> TYPE: DNA
<213> ORGANISM: Homo sapiens

<400> SEQUENCE: 203
gcacacccgg aagcggcgga gtagagcgga gcctggcggg cgtgggaacc caggccccgc    60
cgaggcggcc aggaggtgag atggcagctg ggcaaaatgg gcacgaagag tgggtgggca   120
gcgcatacct gtttgtggag tcctcgctgg acaaggtggt cctgtcggat gcctacgcgc   180 accccagca gaaggtggca gtgtacaggg ctctgcaggc tgccttggca gagagcggcg   240
ggagcccgga cgtgctgcag atgctgaaga tccaccgcag cgacccgcag ctgatcgtgc   300
agctgcgatt ctgcgggcgg cagccctgtg ccgcttcct ccgcgcctac cgcgaggggg   360
cgctgcgcgc cgcgctgcag aggagcctgg cggccgcgct cgcccagcac tcggtgccgc   420
tgcaactgga gctgcgcgcc ggcgccgagc ggctggacgc tttgctggcg gacgaggagc   480
gctgtttgag ttgcatccta gcccagcagc ccgaccggct ccgggatgaa gaactggctg   540
agctggagga tgcgctgcga aatctgaagt gcggctcggg ggcccgggt ggcgacgggg   600 aggtcgcttc ggccccttg cagccccgg tgccctctct gtcggaggtg aagccgccgc   660
cgccgccgcc acctgcccag actttttctgt tccagggtca gcctgtagtg aatcggccgc   720
tgagcctgaa ggaccaacag acgttcgcgc gctctgtggg tctcaaatgg cgcaaggtgg   780
ggcgctcact gcagcgaggc tgccgggcgc tgcgggaccc ggcgctggac tcgctggcct   840
acgagtacga gcgcgaggga ctgtacgagc aggccttcca gctgctgcgg cgcttcgtgc   900
aggccgaggg ccgccgcgcc acgctgcagc gcctggtgga ggcactcgag gagaacgagc   960

| | | |
|---|---|---|
| tcaccagcct ggcagaggac ttgctgggcc tgaccgatcc caatggcggc ctggcctaga | 1020 |
| ccagggtgc agccagcttt tggagaacct ggatggcctt agggttcctt ctgcggctat | 1080 |
| tgctgaaccc ctgtccatcc acgggaccct gaaactccac ttggcctatc tgctggacct | 1140 |
| gctggggcag agttgattgc cttccccagg agccagacca ctgggggtgc atcattgggg | 1200 |
| attctgcctc aggtactttg atagagtgtg gggtgggggg gacctgcttt ggagatcagc | 1260 |
| ctcaccttct cccatcccag aagcggggct tacagccagc ccttacagtt tcactcatga | 1320 |
| agcaccttga tctttggtgt cctggacttc atcctgggtg ctgcagatac tgcagtgaag | 1380 |
| taaaacagga atcaatcttg cctgccccca gctcacactc agcgtgggac cccgaatgtt | 1440 |
| aagcaatgat aataaagtat aacacggatt ttgatgtgag aaaaaaaaaa aaaaaa | 1496 |

<210> SEQ ID NO 204
<211> LENGTH: 312
<212> TYPE: PRT
<213> ORGANISM: Homo sapiens

<400> SEQUENCE: 204

Met Ala Ala Gly Gln Asn Gly His Glu Glu Trp Val Gly Ser Ala Tyr
1               5                   10                  15

Leu Phe Val Glu Ser Ser Leu Asp Lys Val Val Leu Ser Asp Ala Tyr
                20                  25                  30

Ala His Pro Gln Gln Lys Val Ala Val Tyr Arg Ala Leu Gln Ala Ala
            35                  40                  45

Leu Ala Glu Ser Gly Gly Ser Pro Asp Val Leu Gln Met Leu Lys Ile
        50                  55                  60

His Arg Ser Asp Pro Gln Leu Ile Val Gln Leu Arg Phe Cys Gly Arg
65                  70                  75                  80

Gln Pro Cys Gly Arg Phe Leu Arg Ala Tyr Arg Glu Gly Ala Leu Arg
                85                  90                  95

Ala Ala Leu Gln Arg Ser Leu Ala Ala Leu Ala Gln His Ser Val
            100                 105                 110

Pro Leu Gln Leu Glu Leu Arg Ala Gly Ala Glu Arg Leu Asp Ala Leu
        115                 120                 125

Leu Ala Asp Glu Glu Arg Cys Leu Ser Cys Ile Leu Ala Gln Gln Pro
    130                 135                 140

Asp Arg Leu Arg Asp Glu Glu Leu Ala Glu Leu Glu Asp Ala Leu Arg
145                 150                 155                 160

Asn Leu Lys Cys Gly Ser Gly Ala Arg Gly Gly Asp Gly Glu Val Ala
                165                 170                 175

Ser Ala Pro Leu Gln Pro Pro Val Pro Ser Leu Ser Glu Val Lys Pro
            180                 185                 190

Pro Pro Pro Pro Pro Ala Gln Thr Phe Leu Phe Gln Gly Gln Pro
        195                 200                 205

Val Val Asn Arg Pro Leu Ser Leu Lys Asp Gln Gln Thr Phe Ala Arg
    210                 215                 220

Ser Val Gly Leu Lys Trp Arg Lys Val Gly Arg Ser Leu Gln Arg Gly
225                 230                 235                 240

Cys Arg Ala Leu Arg Asp Pro Ala Leu Asp Ser Leu Ala Tyr Glu Tyr
                245                 250                 255

Glu Arg Glu Gly Leu Tyr Glu Gln Ala Phe Gln Leu Leu Arg Arg Phe
            260                 265                 270

Val Gln Ala Glu Gly Arg Arg Ala Thr Leu Gln Arg Leu Val Glu Ala
        275                 280                 285

```
Leu Glu Glu Asn Glu Leu Thr Ser Leu Ala Glu Asp Leu Leu Gly Leu
    290                 295                 300

Thr Asp Pro Asn Gly Gly Leu Ala
305                 310
```

<210> SEQ ID NO 205
<211> LENGTH: 4363
<212> TYPE: DNA
<213> ORGANISM: Homo sapiens

<400> SEQUENCE: 205

| | | | | | |
|---|---|---|---|---|---|
| gcaggctgct | ggagaaggcg | cacctgctgc | aggtgctccc | ggccgccccg | gaccagcgag | 60 |
| cgcgggcact | gcggcgggga | ggatgctgcg | cgagcggacc | gtgcggctgc | agtacgggag | 120 |
| ccgcgtggag | gcggtgtacg | tgctgggcac | ctacctctgg | accgatgtct | acagcgcggc | 180 |
| cccagccggg | gcccaaacct | tcagcctgaa | gcactcggaa | cacgtgtggg | tggaggtggt | 240 |
| gcgtgatggg | gaggctgagg | aggtggccac | caatggcaag | cagcgctggc | ttctctcgcc | 300 |
| cagcaccacc | ctgcgggtca | ccatgagcca | ggcgagcacc | gaggccagca | gtgacaaggt | 360 |
| caccgtcaac | tactatgacg | aggaaggag | cattcccatc | gaccaggcgg | ggctcttcct | 420 |
| cacagccatt | gagatctccc | tggatgtgga | cgcagaccgg | gatggtgtgg | tggagaagaa | 480 |
| caacccaaag | aaggcatcct | ggacctgggg | ccccgagggc | caggggggcca | tcctgctggt | 540 |
| gaactgtgac | cgagagacac | cctggttgcc | caaggaggac | tgccgtgatg | agaaggtcta | 600 |
| cagcaaggaa | gatctcaagg | acatgtccca | gatgatcctg | cggaccaaag | ccccgaccg | 660 |
| cctcccgcc | ggatacgaga | tagttctgta | catttccatg | tcagactcag | acaaagtggg | 720 |
| cgtgttctac | gtggagaacc | cgttcttcgg | ccaacgctat | atccacatcc | tgggccggcg | 780 |
| gaagctctac | catgtggtca | gtacacgggg | tggctccgcg | gagctgctgt | tcttcgtgga | 840 |
| aggcctctgt | ttccccgacg | agggcttctc | aggcctggtc | tccatccatg | tcagcctgct | 900 |
| ggagtacatg | gcccaggaca | ttcccctgac | tcccatcttc | acggacaccg | tgatattccg | 960 |
| gattgctccg | tggatcatga | cccccaacat | cctgcctccc | gtgtcggtgt | ttgtgtgctg | 1020 |
| catgaaggat | aattacctgt | tcctgaaaga | ggtgaagaac | cttgtggaga | aaaccaactg | 1080 |
| tgagctgaag | gtctgcttcc | agtacctaaa | ccgaggcgat | cgctggatcc | aggatgaaat | 1140 |
| tgagtttggc | tacatcgagg | cccccataa | aggcttcccc | gtggtgctgg | actctccccg | 1200 |
| agatggaaac | ctaaaggact | tccctgtgaa | ggagctcctg | ggcccagatt | ttggctacgt | 1260 |
| gacccgggag | cccctctttg | agtctgtcac | cagccttgac | tcatttggaa | acctggaggt | 1320 |
| cagtccccca | gtgaccgtga | acggcaagac | atacccgctt | ggccgcatcc | tcatcgggag | 1380 |
| cagctttcct | ctgtctggtg | gtcggaggat | gaccaaggtg | gtgcgtgact | tcctgaaggc | 1440 |
| ccagcaggtg | caggcgcccg | tggagctcta | tcagactgg | ctgactgtgg | ccacgtgga | 1500 |
| tgagttcatg | tcctttgtcc | ccatccccgg | cacaaagaaa | ttcctgctac | tcatggccag | 1560 |
| cacctcggcc | tgctacaagc | tcttccgaga | gaagcagaag | gacggccatg | agaggccat | 1620 |
| catgttcaaa | ggcttgggtg | ggatgagcag | caagcgaatc | accatcaaca | agattctgtc | 1680 |
| caacgagagc | cttgtgcagg | agaacctgta | cttccagcgc | tgcctagact | ggaaccgtga | 1740 |
| catcctcaag | aaggagctgg | gactgacaga | gcaggacatc | attgacctgc | ccgctctgtt | 1800 |
| caagatggac | gaggaccacc | gtgccagagc | cttcttccca | aacatggtga | acatgatcgt | 1860 |
| gctggacaag | gacctgggca | tccccaagcc | attcgggcca | caggttgagg | aggaatgctg | 1920 |

```
cctggagatg cacgtgcgtg gcctcctgga gccctgggc ctcgaatgca ccttcatcga    1980
cgacatttct gcctaccaca aatttctggg ggaagtccac tgtggcacca acgtccgcag    2040
gaagcccttc accttcaagt ggtggcacat ggtgccctga cctgccaggg gccctggcgt    2100
ttgcctcctt cgcttagttc tccagaccct ccctcacacg cccagagcct tctgctgaca    2160
tggactggac agccccgctg ggagaccttt gggacgtggg gtggaatttg gggtatctgt    2220
gccttgccct ccctgagagg ggcctcagtg tcctctgaag ccatccccag tgagcctcga    2280
ctctgtccct gctgaaaata gctgggccag tgtctctgta gccctgacat aaggaacaga    2340
acacaacaaa acacagcaaa ccatgtgccc aaactgctcc ccaaagaatt ttgagtctct    2400
aatctgacac tgaatgaggg gagaagggaa ggagattctg ggattgccag ttcttccagc    2460
agccatgctc tgaaaatcaa ggtagaatcc atggaaaggg accccaggac cccgggaccc    2520
tagacgtatc ttgaactgcc atcgtcattt caaatacatc tccctcaggg tttccaggtg    2580
gccaccccca attattcatt ccttaccaac ctctcaaatc ctcttggctt tctctctgca    2640
gtgtggacac tgttggctag tcctccccac tccctgaggg tccagtaagt tagcttagaa    2700
ccttcctgga aacatttcat ctgagcaggt ttccccacgt gtgggatgct ccttttgcct    2760
catctgtctc agggatgcag gctccccgc atgcatgggg atttctcccc agaccagcat    2820
acttgtgacc tgagagttca atgcgtaaag atgcccctgg tcagccatat ccatcttctc    2880
ttgcctggtc cttgattctc tggccgctcc ctgaccttcc tccttccact gccttgactt    2940
tcttcctttt tattcctggt gccatctgtc caggcagcta acaagaact tgttcgccag    3000
cagccagatt caggccttcc caggggcata ataagtgacc agcccctcct ctccggacat    3060
cagatccaac acataaggac cctggcctac cctccagccc aacagccagt tctgggtcag    3120
ctgccaactt aggggtggtt tgattatccc attgaaattc accagtgcct ttgccaaaga    3180
ccctctcatt tggacatacc cagattcatt ccctggctcc aactgaaaag actcagtttc    3240
aatcgttaaa agttcccttta gggccagaag aataaatgaa ttataatccc attttgaaga    3300
accgatttat aaccaatgaa aaggttataa tgtaatttat attcttggag gaacaagatt    3360
ttcatttggg attatttcct tcaaccattc aacaaacatt tgttgtatgc cactaagcgc    3420
caggcacggc gttgggctct gcaaacacag tggttagtag cagtctggac ctggtcccta    3480
ctggcatgga acccatcact ccccaacatg caaagcccac attaaaggc cagcctctgc    3540
cccttcagtg atgcgctctt tagaaatgcc agtccactat attcagaaat ccgcagggca    3600
caaaacttcc agcaagtcac tgttgtggtg aaatgggcag tggggtggg gggtcttctt    3660
taaacaggcc cccttcccat ctacctagcc agtacccatc caatgagtcc ccagagcctc    3720
cagaagctgt tgtctcctct ctggggacag cagctcctgc cttggaggc caaagcccca    3780
gatctctcca gccccagagc tgaaaacacc aagtgcctat ttgagggtgt ctgtctggag    3840
acttagagtt tgtcatgtgt gtgtgtgtgt ttggttaatg tgggtttatg ggttttcttt    3900
cttttttttc ttttttttt tagtctacat taggggaag tgagcgcctc ccatgtgcag    3960
acagtgtgtc tttatagatt tttctaaggc tttccccaat gatgtcggta atttctgatg    4020
tttctgaagt tccaggact cacacacccg ttcccatctc acttgcccac ccagtgtgac    4080
aaccctcggt gtggatatac cccgtggac tcatggctct tccccacccc cactttctat    4140
aaatgtaggc ctagaatacg cttctctgtt gcaaaactca gctaagttcc tgcttccacc    4200
ttgatgttga aatatcttat gtaagagggc aggggatgtc gtgaagatgg caagaagaac    4260
acagtttcaa atttctggaa aagagcctgt ggtggagatc taaagatgtt tagggaagag    4320
```
ctcgactaaa gaacaatgaa ataaatggtc caaggggaag tca 4363

<210> SEQ ID NO 206
<211> LENGTH: 665
<212> TYPE: PRT
<213> ORGANISM: Homo sapiens

<400> SEQUENCE: 206

Met Leu Arg Glu Arg Thr Val Arg Leu Gln Tyr Gly Ser Arg Val Glu
1               5                   10                  15

Ala Val Tyr Val Leu Gly Thr Tyr Leu Trp Thr Asp Val Tyr Ser Ala
                20                  25                  30

Ala Pro Ala Gly Ala Gln Thr Phe Ser Leu Lys His Ser Glu His Val
            35                  40                  45

Trp Val Glu Val Val Arg Asp Gly Glu Ala Glu Val Ala Thr Asn
50                  55                  60

Gly Lys Gln Arg Trp Leu Leu Ser Pro Ser Thr Thr Leu Arg Val Thr
65                  70                  75                  80

Met Ser Gln Ala Ser Thr Glu Ala Ser Ser Asp Lys Val Thr Val Asn
                85                  90                  95

Tyr Tyr Asp Glu Glu Gly Ser Ile Pro Ile Asp Gln Ala Gly Leu Phe
                100                 105                 110

Leu Thr Ala Ile Glu Ile Ser Leu Asp Val Asp Ala Asp Arg Asp Gly
            115                 120                 125

Val Val Glu Lys Asn Asn Pro Lys Lys Ala Ser Trp Thr Trp Gly Pro
130                 135                 140

Glu Gly Gln Gly Ala Ile Leu Leu Val Asn Cys Asp Arg Glu Thr Pro
145                 150                 155                 160

Trp Leu Pro Lys Glu Asp Cys Arg Asp Glu Lys Val Tyr Ser Lys Glu
                165                 170                 175

Asp Leu Lys Asp Met Ser Gln Met Ile Leu Arg Thr Lys Gly Pro Asp
            180                 185                 190

Arg Leu Pro Ala Gly Tyr Glu Ile Val Leu Tyr Ile Ser Met Ser Asp
        195                 200                 205

Ser Asp Lys Val Gly Val Phe Tyr Val Glu Asn Pro Phe Phe Gly Gln
210                 215                 220

Arg Tyr Ile His Ile Leu Gly Arg Arg Lys Leu Tyr His Val Val Lys
225                 230                 235                 240

Tyr Thr Gly Gly Ser Ala Glu Leu Leu Phe Phe Val Glu Gly Leu Cys
                245                 250                 255

Phe Pro Asp Glu Gly Phe Ser Gly Leu Val Ser Ile His Val Ser Leu
            260                 265                 270

Leu Glu Tyr Met Ala Gln Asp Ile Pro Leu Thr Pro Ile Phe Thr Asp
        275                 280                 285

Thr Val Ile Phe Arg Ile Ala Pro Trp Ile Met Thr Pro Asn Ile Leu
290                 295                 300

Pro Pro Val Ser Val Phe Val Cys Cys Met Lys Asp Asn Tyr Leu Phe
305                 310                 315                 320

Leu Lys Glu Val Lys Asn Leu Val Glu Lys Thr Asn Cys Glu Leu Lys
                325                 330                 335

Val Cys Phe Gln Tyr Leu Asn Arg Gly Asp Arg Trp Ile Gln Asp Glu
            340                 345                 350

Ile Glu Phe Gly Tyr Ile Glu Ala Pro His Lys Gly Phe Pro Val Val
        355                 360                 365

Leu Asp Ser Pro Arg Asp Gly Asn Leu Lys Asp Phe Pro Val Lys Glu
    370                 375                 380

Leu Leu Gly Pro Asp Phe Gly Tyr Val Thr Arg Glu Pro Leu Phe Glu
385                 390                 395                 400

Ser Val Thr Ser Leu Asp Ser Phe Gly Asn Leu Glu Val Ser Pro Pro
            405                 410                 415

Val Thr Val Asn Gly Lys Thr Tyr Pro Leu Gly Arg Ile Leu Ile Gly
        420                 425                 430

Ser Ser Phe Pro Leu Ser Gly Gly Arg Arg Met Thr Lys Val Val Arg
            435                 440                 445

Asp Phe Leu Lys Ala Gln Gln Val Gln Ala Pro Val Glu Leu Tyr Ser
450                 455                 460

Asp Trp Leu Thr Val Gly His Val Asp Glu Phe Met Ser Phe Val Pro
465                 470                 475                 480

Ile Pro Gly Thr Lys Lys Phe Leu Leu Met Ala Ser Thr Ser Ala
                485                 490                 495

Cys Tyr Lys Leu Phe Arg Glu Lys Gln Lys Asp Gly His Gly Glu Ala
            500                 505                 510

Ile Met Phe Lys Gly Leu Gly Gly Met Ser Ser Lys Arg Ile Thr Ile
    515                 520                 525

Asn Lys Ile Leu Ser Asn Glu Ser Leu Val Gln Glu Asn Leu Tyr Phe
530                 535                 540

Gln Arg Cys Leu Asp Trp Asn Arg Asp Ile Leu Lys Lys Glu Leu Gly
545                 550                 555                 560

Leu Thr Glu Gln Asp Ile Ile Asp Leu Pro Ala Leu Phe Lys Met Asp
                565                 570                 575

Glu Asp His Arg Ala Arg Ala Phe Phe Pro Asn Met Val Asn Met Ile
            580                 585                 590

Val Leu Asp Lys Asp Leu Gly Ile Pro Lys Pro Phe Gly Pro Gln Val
        595                 600                 605

Glu Glu Glu Cys Cys Leu Glu Met His Val Arg Gly Leu Leu Glu Pro
610                 615                 620

Leu Gly Leu Glu Cys Thr Phe Ile Asp Asp Ile Ser Ala Tyr His Lys
625                 630                 635                 640

Phe Leu Gly Glu Val His Cys Gly Thr Asn Val Arg Arg Lys Pro Phe
                645                 650                 655

Thr Phe Lys Trp Trp His Met Val Pro
            660                 665

<210> SEQ ID NO 207
<211> LENGTH: 3189
<212> TYPE: DNA
<213> ORGANISM: Homo sapiens

<400> SEQUENCE: 207
agtgttgggg ttggcggcca cagctaagtc caacaccagc atgtcgctgc agagaatcgt    60
gcgtgtgtcc ctggagcatc ccaccagcgc ggtgtgtgtg gctggcgtgg agaccctcgt   120
ggacatttat gggtcagtgc ctgagggcac agaaatgttt gaggtctatg ggacgcctgg   180
cgtggacatc tacatctctc ccaacatgga gggggccggg agcgtgcaga caccaggcg    240 gtggcgcttt gacgcgactt tggagatcat cgtggtcatg aactccccca gcaatgacct   300
caacgacagc catgttcaga tttcctacca ctccagccat gagcctctgc ccctggccta   360
tgcggtgctc tacctcacct gtgttgacat ctctctggat tgcgacctga actgtgaggg   420

```
aaggcaggac aggaactttg tagacaagcg gcagtgggtc tgggggccca gtgggtatgg    480
cggcatcttg ctggtgaact gtgaccgtga tgatccgagc tgtgatgtcc aggacaattg    540
tgaccagcac gtgcactgcc tgcaagacct ggaagacatg tctgtcatgg tcctgcggac    600
gcagggccct gcagccctct tgatgacca caaacttgtc ctccataccct ccagctatga    660
tgccaaacgg gcacaggtct tccacatctg cggtcctgag gatgtgtgtg aggcctatag    720
gcatgtgctg ggccaagata aggtgtccta tgaggtaccc cgcttgcatg ggatgaggaa    780
gcgcttcttc gtggaaggcc tgtccttccc tgatgccggc ttcacaggac tcatctcctt    840
ccatgtcact ctgctggacg actccaacga ggatttctcg gcatcccta tcttcactga    900
cactgtggtg ttccgagtgg caccctggat catgacgccc agcactctgc caccctaga     960
ggtgtatgtg tgccgtgtga ggaacaacac gtgttttgtg gatgcggtgg cagagctggc   1020
caggaaggcc ggctgcaagc tgaccatctg cccacaggcc gagaaccgca cgaccgctg    1080
gatccaggat gagatggagc tgggctacgt tcaggcgccg cacaagaccc tcccggtggt   1140
ctttgactcc ccaaggaatg gggaactgca ggatttccct tacaaaagaa tcctgggtcc   1200
agattttggt tacgtgactc gggaaccacg cgacaggtct gtgagtggcc tggactcctt   1260
tgggaacctg gaggtcagcc ctccagtggt ggccaatggg aaagagtacc ccctggggag   1320
gatcctcatt gggggcaacc tgcctgggtc aagtggccgc agggtcaccc aggtggtgcg   1380
ggacttcctc catgcccaga aggtgcagcc cccgtggag ctctttgtgg actggttggc    1440
cgtgggccat gtggatgagt ttctgagctt tgtccctgcc cccgatggga agggcttccg   1500
gatgctcctg gccagccctg gggcctgctt caagctcttc aggaaaagc agaagtgtgg    1560
ccacgggagg gccctcctgt tccaggggt tgttgatgat gagcaggtca agaccatctc   1620
catcaaccag gtgctctcca taaagacct catcaactac aataagtttg tgcagagctg    1680
catcgactgg aaccgtgagg tgctgaagcg ggagctgggc ctggcagagt gtgacatcat   1740
tgacatccca cagctcttca agaccgagag gaaaaagca acggccttct tccctgactt    1800
ggtgaacatg ctggtgctgg ggaagcacct gggcatcccc aagcccttg ggcccatcat    1860
caatggctgc tgctgcctgg aggagaaggt gcggtccctg ctggagccgc tgggcctcca   1920
ctgcaccttc attgatgact tcactccata ccacatgctg catggggagg tgcactgtgg   1980
caccaatgtg tgcagaaagc ccttctcttt caagtggtgg aacatggtgc ctgagacag    2040
ctcccaccca ccatcctgtc cccctggggc gggcattggc ccaggtggtg gagacagaga   2100
caggcccctg aacgataagc accaagagac cccaaggctc cagatggaac actgagggtg   2160
accgtccctc tcagaagcct tttccctgga agtgtccatg cctcacctgc aacccatgtg   2220
gttctcagac ttgaatcttc tcggccccc aaaaagaagg acctcatttc ttatagcctc    2280
tcctgtgatt caacacaacc catggagatg tccccttctc actctgaaat catccatttg   2340
gggacaaatc cacattgggg tctagaaaca tccacgtatc tcatcagcca tcttgtcctg   2400
tgcatcctaa cagaggaagg atccatgatt ctgctttggt ccaattgctt cctctctgca   2460
gaggaacaac cctaaaacca gaccactcca cgcaggacag gcaggagaga ttcttcctaa   2520
agcctccccc ataaaagggg agctgtggat ccacttagat cagggcggaa ccatctttca   2580
cccggccaag ctcctgccca gatgttgacc ctcacccagc gtgagctgtc acatagtagg   2640
agcttctaga tgcatgtgga agcaatgaga gttgtcccctt agccttataa actccccatg   2700
atctgacatg cagaaatcca gccttgtcca gaatcctcct ggaatttctt ggagacgaaa   2760
```

-continued

```
gtatctgggg gattgttggg tactagggag actgggtaca agggtgaaaa gtagttccca    2820
taatacacat ggttgactat ggtgatccac cttgtgatgg ttaatattag gtgtctggag    2880
aaggttgctt cattggccct gggacttctc tctgcaggag gagagaacgc tgcctctcct    2940
ctggattggt ctcaggctct ctgttggcct ttggtcagcg tttccacatc ctgctctgct    3000
gcaggagagg gggctaaggg gctggatcca ccaaggcagc tcacagcggg aaaactctgg    3060
gaatgaacca ctgaattcag gggatggggg tggggggggcg gttctcgagg tgtgtgccag    3120
ctacacgtgt gttctgtatg ggtccagctg cgtttccatc actcgctaat aaatcaacag    3180
aaacacaaa                                                             3189
```

<210> SEQ ID NO 208
<211> LENGTH: 664
<212> TYPE: PRT
<213> ORGANISM: Homo sapiens

<400> SEQUENCE: 208

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
                20                  25                  30

Val Pro Glu Gly Thr Glu Met Phe Glu Val Tyr Gly Thr Pro Gly Val
            35                  40                  45

Asp Ile Tyr Ile Ser Pro Asn Met Glu Arg Gly Glu Arg Ala Asp
        50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
```

```
              290                 295                 300
Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Arg Ser Leu Leu Glu Pro Leu
    610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660

<210> SEQ ID NO 209
<211> LENGTH: 1296
<212> TYPE: DNA
<213> ORGANISM: Homo sapiens

<400> SEQUENCE: 209
```

```
atgcccaacc ccaggcctgg caagccctcg gccccttcct tggcccttgg cccatcccca      60
ggagcctcgc ccagctggag ggctgcaccc aaagcctcag acctgctggg ggcccggggc     120
ccaggggggaa ccttccaggg ccgagatctt cgaggcgggg cccatgcctc ctcttcttcc    180
ttgaacccca tgccaccatc gcagctgcag ctgcccacac tgcccctagt catggtggca     240
ccctccgggg cacggctggg ccccttgccc cacttacagg cactcctcca ggacaggcca     300
catttcatgc accagctctc aacggtggat gcccacgccc ggaccctgt gctgcaggtg      360
cacccctgg agagcccagc catgatcagc ctcacaccac ccaccaccgc cactggggtc      420
ttctccctca aggccggcc tggcctccca cctgggatca acgtggccag cctggaatgg      480
gtgtccaggg agccggcact gctctgcacc ttcccaaatc ccagtgcacc caggaaggac     540
agcacccttt cggctgtgcc ccagagctcc tacccactgc tggcaaatgg tgtctgcaag     600
tggcccggat gtgagaaggt cttcgaagag ccagaggact tcctcaagca ctgccaggcg     660
gaccatcttc tggatgagaa gggcagggca caatgtctcc tccagagaga gatggtacag     720
tctctggagc agcagctggt gctggagaag gagaagctga gtgccatgca ggcccacctg     780
gctgggaaaa tggcactgac caaggcttca tctgtggcat catccgacaa gggctcctgc     840
tgcatcgtag ctgctggcag ccaaggccct gtcgtcccag cctggtctgg ccccgggag     900
gcccctgaca gctgtttgc tgtccggagg cacctgtggg gtagccatgg aaacagcaca     960
ttcccagagt tcctccacaa catggactac ttcaagttcc acaacatgcg accccctttc    1020
acctacgcca cgctcatccg ctgggccatc ctggaggctc agagaagca gcggacactc    1080
aatgagatct accactggtt cacacgcatg tttgccttct tcagaaacca tcctgccacc    1140
tggaagaacg ccatccgcca aacctgagt ctgcacaagt gctttgtgcg ggtggagagc    1200
gagaagggggg ctgtgtggac cgtggatgag ctggagttcc gcaagaaacg gagccagagg   1260
cccagcaggt gttccaaccc tacacctggc ccctga                             1296
```

<210> SEQ ID NO 210
<211> LENGTH: 431
<212> TYPE: PRT
<213> ORGANISM: Homo sapiens

<400> SEQUENCE: 210

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
            85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

```
Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
                260                 265                 270

Ala Ser Ser Asp Lys Gly Ser Cys Cys Ile Val Ala Ala Gly Ser Gln
            275                 280                 285

Gly Pro Val Val Pro Ala Trp Ser Gly Pro Arg Glu Ala Pro Asp Ser
        290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
                340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430

<210> SEQ ID NO 211
<211> LENGTH: 3216
<212> TYPE: DNA
<213> ORGANISM: Homo sapiens

<400> SEQUENCE: 211
ggcagtttcc tggctgaaca cgccagccca atacttaaag agagcaactc ctgactccga     60
tagagactgg atggacccac aagggtgaca gcccaggcgg accgatcttc ccatcccaca    120
tcctccggcg cgatgccaaa agaggctgac ggcaactgg ccttctgca gagaaagacc      180 tccgcttcac tgccccggct ggtcccaagg gtcaggaaga tggattcata cctgctgatg    240
tggggactgc tcacgttcat catggtgcct ggctgccagg cagagctctg tgacgatgac    300
ccgccagaga tcccacacgc cacattcaaa gccatggcct acaaggaagg aaccatgttg    360
aactgtgaat gcaagagagg tttccgcaga ataaaaagcg ggtcactcta tatgctctgt    420
acaggaaact ctagccactc gtcctgggac aaccaatgtc aatgcacaag ctctgccact    480
cggaacacaa cgaaacaagt gacacctcaa cctgaagaac agaaagaaag gaaaccaca    540
```

```
gaaatgcaaa gtccaatgca gccagtggac caagcgagcc ttccaggtca ctgcagggaa      600
cctccaccat gggaaaatga agccacagag agaatttatc atttcgtggt ggggcagatg      660
gtttattatc agtgcgtcca gggatacagg gctctacaca gaggtcctgc tgagagcgtc      720
tgcaaaatga cccacgggaa gacaaggtgg acccagcccc agctcatatg cacaggtgaa      780
atggagacca gtcagtttcc aggtgaagag aagcctcagg caagccccga aggccgtcct      840
gagagtgaga cttcctgcct cgtcacaaca acagattttc aaatacagac agaaatggct      900
gcaaccatgg agacgtccat atttacaaca gagtaccagg tagcagtggc cggctgtgtt      960
ttcctgctga tcagcgtcct cctcctgagt gggctcacct ggcagcggag acagaggaag     1020
agtagaagaa caatctagaa aaccaaaaga acaagaattt cttggtaaga agccgggaac     1080
agacaacaga agtcatgaag cccaagtgaa atcaaaggtg ctaaatggtc gcccaggaga     1140
catccgttgt gcttgcctgc gttttggaag ctctgaagtc acatcacagg acacggggca     1200
gtggcaacct tgtctctatg ccagctcagt cccatcagag agcgagcgct acccacttct     1260
aaatagcaat ttcgccgttg aagaggaagg gcaaaaccac tagaactctc atcttatttt     1320
tcatgtatat gtgttcatta aagcatgaat ggtatgaaac tctctccacc ctatatgtag     1380
tataaagaaa agtaggttta cattcatctc attccaactt cccagttcag gagtcccaag     1440
gaaagcccca gcactaacgt aaatacacaa cacacacact ctaccctata caactggaca     1500
ttgtctgcgt ggttcctttc tcagccgctt ctgactgctg attctcccgt tcacgttgcc     1560
taataaacat ccttcaagaa ctctgggctg ctacccagaa atcattttac ccttggctca     1620
atcctctaag ctaacccccct tctactgagc cttcagtctt gaatttctaa aaaacagagg     1680
ccatggcaga ataatctttg ggtaacttca aaacggggca gccaaaccca tgaggcaatg     1740
tcaggaacag aaggatgaat gaggtcccag gcagagaatc atacttagca aagttttacc     1800
tgtgcgttac taattggcct ctttaagagt tagtttcttt gggattgcta tgaatgatac     1860
cctgaatttg gcctgcacta atttgatgtt tacaggtgga cacacaaggt gcaaatcaat     1920
gcgtacgttt cctgagaagt gtctaaaaac accaaaaagg gatccgtaca ttcaatgttt     1980
atgcaaggaa ggaaagaaag aaggaagtga agagggagaa gggatggagg tcacactggt     2040
agaacgtaac cacggaaaag agcgcatcag gcctggcacg gtggctcagg cctataaccc     2100
cagctcccta ggagaccaag gcgggagcat ctcttgaggc caggagtttg agaccagcct     2160
gggcagcata gcaagacaca tccctacaaa aaattagaaa ttggctggat gtggtggcat     2220
acgcctgtag tcctagccac tcaggaggct gaggcaggag gattgcttga gcccaggagt     2280
tcgaggctgc agtcagtcat gatggcacca ctgcactcca gcctgggcaa cagagcaaga     2340
tcctgtcttt aaggaaaaaa agacaagatg agcataccag cagtccttga acattatcaa     2400
aaagttcagc atattagaat caccgggagg ccttgttaaa agagttcgct gggcccatct     2460
tcagagtctc tgagttgttg gtctggaata gagccaaatg ttttgtgtgt ctaacaattc     2520
ccaggtgctg ttgctgctgc tactattcca ggaacacact ttgagaacca ttgtgttatt     2580
gctctgcacg cccacccact ctcaactccc acgaaaaaaa tcaacttcca gagctaagat     2640
ttcggtggaa gtcctggttc catatctggt gcaagatctc ccctcacgaa tcagttgagt     2700
caacattcta gctcaacaac atcacacgat taacattaac gaaaattatt catttgggaa     2760
actatcagcc agttttcact tctgaagggg caggagagtg ttatgagaaa tcacggcagt     2820
tttcagcagg gtccagattc agattaaata actattttct gtcatttctg tgaccaacca     2880
```

-continued

```
catacaaaca gactcatctg tgcactctcc ccctcccct tcaggtatat gttttctgag    2940
taaagttgaa aagaatctca gaccagaaaa tatagatata tatttaaatc ttacttgagt    3000
agaactgatt acgacttttg ggtgttgagg ggtctataag atcaaaactt ttccatgata    3060
atactaagat gttatcgacc atttatctgt ccttctctca aaagtgtatg gtggaatttt    3120
ccagaagcta tgtgatacgt gatgatgtca tcactctgct gttaacatat aataaattta    3180
ttgctattgt ttataaaaga ataaatgata tttttt                              3216
```

<210> SEQ ID NO 212
<211> LENGTH: 272
<212> TYPE: PRT
<213> ORGANISM: Homo sapiens

<400> SEQUENCE: 212

Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 213
<211> LENGTH: 2740
<212> TYPE: DNA
<213> ORGANISM: Homo sapiens

<400> SEQUENCE: 213

```
aagaacgccc ccaaaatctg tttctaattt tacagaaatc ttttgaaact tggcacggta      60
ttcaaaagtc cgtggaaaga aaaaaacctt gtcctggctt cagcttccaa ctacaaagac     120
agacttggtc cttttcaacg gttttcacag atccagtgac ccacgctctg aagacagaat     180
tagctaactt tcaaaaacat ctggaaaaat aagacttggg gtaaaaatcg tatttggagt     240
tgccacctct gctgtgcttg ccttattggt gatgtgcatt gtcttacgcc cttcaagagt     300
tcataactct gaagaaaata caatgagagc actcacactg aaggatattt taaatggaac     360
attttcttat aaaacatttt ttccaaactg gatttcagga caagaatatc ttcatcaatc     420
tgcagataac aatatagtac tttataatat tgaaacagga caatcatata ccattttgag     480
taatagaacc atgctttgga gatactctta cacagcaaca tattacatct atgaccttag     540
caatggagaa tttgtaagag gaaatgagct tcctcgtcca attcagtatt tatgctggtc     600
gcctgttggg agtaaattag catatgtcta tcaaaacaat atctatttga aacaaagacc     660
aggagatcca cctttcaaa taacatttaa tggaagagaa aataaaatat ttaatggaat     720
cccagactgg gtttatgaag aggaaatgct tgctacaaaa tatgctctct ggtggtctcc     780
taatggaaaa ttttttggcat atgcggaatt taatgatacg gatataccag ttattgccta     840
ttcctattat ggcgatgaac aatatcctag aacaataaat attccatacc caaggctgg     900
agctaagaat cccgttgttc ggatatttat tatcgatacc acttaccctg cgtatgtagg     960
tccccaggaa gtgcctgttc cagcaatgat agcctcaagt gattattatt tcagttggct    1020
cacgtgggtt actgatgaac gagtatgttt gcagtggcta aaaagagtcc agaatgtttc    1080
ggtcctgtct atatgtgact tcagggaaga ctggcagaca tgggattgtc caagaccca    1140
ggagcatata gaagaaagca gaactggatg ggctggtgga ttctttgttt caacaccagt    1200
tttcagctat gatgccattt cgtactacaa aatatttagt gacaaggatg ctacaaaca    1260
tattcactat atcaaagaca ctgtggaaaa tgctattcaa attacaagtg gcaagtggga    1320
ggccataaat atattcagag taacacagga ttcactgttt tattctagca atgaatttga    1380
agaatacct ggaagaagaa acatctacag aattagcatt ggaagctatc ctccaagcaa    1440
gaagtgtgtt acttgccatc taaggaaaga aaggtgccaa tattacacag caagtttcag    1500
cgactacgcc aagtactatg cacttgtctg ctacggccca ggcatcccca tttccaccct    1560
tcatgatgga cgcactgatc aagaaattaa aatcctggaa gaaacaagg aattggaaaa    1620
tgctttgaaa aatatccagc tgcctaaaga ggaaattaag aaacttgaag tagatgaaat    1680
tactttatgg tacaagatga ttcttcctcc tcaatttgac agatcaaaga gtatcccctt    1740
gctaattcaa gtgtatggtg gtccctgcag tcagagtgta aggtctgtat ttgctgttaa    1800
ttggatatct tatcttgcaa gtaaggaagg gatggtcatt gccttggtgg atggtcgagg    1860
aacagctttc caaggtgaca aactcctcta tgcagtgtat cgaaagctgg gtgtttatga    1920
agttgaagac cagattacag ctgtcagaaa attcatagaa atgggttttca ttgatgaaaa    1980
aagaatagcc atatgggct ggtcctatgg aggatacgtt tcatcactgg cccttgcatc    2040
tggaactggt cttttcaaat gtggtatagc agtggctcca gtctccagct gggaatatta    2100
cgcgtctgtc tacacagaga gattcatggg tctcccaaca aaggatgata atcttgagca    2160
ctataagaat tcaactgtga tggcaagagc agaatatttc agaaatgtag actatcttct    2220
catccacgga acagcagatg ataatgtgca ctttcaaaac tcagcacaga ttgctaaagc    2280
tctggttaat gcacaagtgg atttccaggc aatgtggtac tctgaccaga accacggctt    2340
atccggcctg tccacgaacc acttatacac ccacatgacc cacttcctaa agcagtgttt    2400
```

```
ctctttgtca gactaaaaac gatgcagatg caagcctgta tcagaatctg aaaaccttat      2460
ataaacccct cagacagttt gcttatttta ttttttatgt tgtaaaatgc tagtataaac      2520
aaacaaatta atgttgttct aaaggctgtt aaaaaaaaga tgaggactca gaagttcaag      2580
ctaaatattg tttacatttt ctggtactct gtgaaagaag agaaaaggga gtcatgcatt      2640
ttgctttgga cacagtgttt tatcacctgt tcatttgaag aaaaataata aagtcagaag      2700
ttcaagtgct aaaaaaaaaa aaaaaaaaaa aaaaaaaaa                             2740

<210> SEQ ID NO 214
<211> LENGTH: 735
<212> TYPE: PRT
<213> ORGANISM: Homo sapiens

<400> SEQUENCE: 214
```

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
            20                  25                  30

Asn Ser Glu Glu Asn Thr Met Arg Ala Leu Thr Leu Lys Asp Ile Leu
        35                  40                  45

Asn Gly Thr Phe Ser Tyr Lys Thr Phe Phe Pro Asn Trp Ile Ser Gly
    50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Leu
                85                  90                  95

Trp Arg Tyr Ser Tyr Thr Ala Thr Tyr Tyr Ile Tyr Asp Leu Ser Asn
            100                 105                 110

Gly Glu Phe Val Arg Gly Asn Glu Leu Pro Arg Pro Ile Gln Tyr Leu
        115                 120                 125

Cys Trp Ser Pro Val Gly Ser Lys Leu Ala Tyr Val Tyr Gln Asn Asn
    130                 135                 140

Ile Tyr Leu Lys Gln Arg Pro Gly Asp Pro Pro Phe Gln Ile Thr Phe
145                 150                 155                 160

Asn Gly Arg Glu Asn Lys Ile Phe Asn Gly Ile Pro Asp Trp Val Tyr
                165                 170                 175

Glu Glu Glu Met Leu Ala Thr Lys Tyr Ala Leu Trp Trp Ser Pro Asn
            180                 185                 190

Gly Lys Phe Leu Ala Tyr Ala Glu Phe Asn Asp Thr Asp Ile Pro Val
        195                 200                 205

Ile Ala Tyr Ser Tyr Tyr Gly Asp Glu Gln Tyr Pro Arg Thr Ile Asn
    210                 215                 220

Ile Pro Tyr Pro Lys Ala Gly Ala Lys Asn Pro Val Val Arg Ile Phe
225                 230                 235                 240

Ile Ile Asp Thr Thr Tyr Pro Ala Tyr Val Gly Pro Gln Glu Val Pro
                245                 250                 255

Val Pro Ala Met Ile Ala Ser Ser Asp Tyr Tyr Phe Ser Trp Leu Thr
            260                 265                 270

Trp Val Thr Asp Glu Arg Val Cys Leu Gln Trp Leu Lys Arg Val Gln
        275                 280                 285

Asn Val Ser Val Leu Ser Ile Cys Asp Phe Arg Glu Asp Trp Gln Thr
    290                 295                 300

Trp Asp Cys Pro Lys Thr Gln Glu His Ile Glu Glu Ser Arg Thr Gly

```
                   305                 310                 315                 320
Trp Ala Gly Gly Phe Phe Val Ser Thr Pro Val Phe Ser Tyr Asp Ala
                325                 330                 335
Ile Ser Tyr Tyr Lys Ile Phe Ser Asp Lys Asp Gly Tyr Lys His Ile
                340                 345                 350
His Tyr Ile Lys Asp Thr Val Glu Asn Ala Ile Gln Ile Thr Ser Gly
                355                 360                 365
Lys Trp Glu Ala Ile Asn Ile Phe Arg Val Thr Gln Asp Ser Leu Phe
                370                 375                 380
Tyr Ser Ser Asn Glu Phe Glu Glu Tyr Pro Gly Arg Arg Asn Ile Tyr
            385                 390                 395                 400
Arg Ile Ser Ile Gly Ser Tyr Pro Pro Ser Lys Lys Cys Val Thr Cys
                405                 410                 415
His Leu Arg Lys Glu Arg Cys Gln Tyr Tyr Thr Ala Ser Phe Ser Asp
                420                 425                 430
Tyr Ala Lys Tyr Tyr Ala Leu Val Cys Tyr Gly Pro Gly Ile Pro Ile
                435                 440                 445
Ser Thr Leu His Asp Gly Arg Thr Asp Gln Glu Ile Lys Ile Leu Glu
            450                 455                 460
Glu Asn Lys Glu Leu Glu Asn Ala Leu Lys Asn Ile Gln Leu Pro Lys
465                 470                 475                 480
Glu Glu Ile Lys Lys Leu Glu Val Asp Glu Ile Thr Leu Trp Tyr Lys
                485                 490                 495
Met Ile Leu Pro Pro Gln Phe Asp Arg Ser Lys Lys Tyr Pro Leu Leu
                500                 505                 510
Ile Gln Val Tyr Gly Gly Pro Cys Ser Gln Ser Val Arg Ser Val Phe
                515                 520                 525
Ala Val Asn Trp Ile Ser Tyr Leu Ala Ser Lys Glu Gly Met Val Ile
                530                 535                 540
Ala Leu Val Asp Gly Arg Gly Thr Ala Phe Gln Gly Asp Lys Leu Leu
545                 550                 555                 560
Tyr Ala Val Tyr Arg Lys Leu Gly Val Tyr Glu Val Glu Asp Gln Ile
                565                 570                 575
Thr Ala Val Arg Lys Phe Ile Glu Met Gly Phe Ile Asp Glu Lys Arg
                580                 585                 590
Ile Ala Ile Trp Gly Trp Ser Tyr Gly Gly Tyr Val Ser Ser Leu Ala
                595                 600                 605
Leu Ala Ser Gly Thr Gly Leu Phe Lys Cys Gly Ile Ala Val Ala Pro
            610                 615                 620
Val Ser Ser Trp Glu Tyr Tyr Ala Ser Val Tyr Thr Glu Arg Phe Met
625                 630                 635                 640
Gly Leu Pro Thr Lys Asp Asp Asn Leu Glu His Tyr Lys Asn Ser Thr
                645                 650                 655
Val Met Ala Arg Ala Glu Tyr Phe Arg Asn Val Asp Tyr Leu Leu Ile
                660                 665                 670
His Gly Thr Ala Asp Asp Asn Val His Phe Gln Asn Ser Ala Gln Ile
                675                 680                 685
Ala Lys Ala Leu Val Asn Ala Gln Val Asp Phe Gln Ala Met Trp Tyr
                690                 695                 700
Ser Asp Gln Asn His Gly Leu Ser Gly Leu Ser Thr Asn His Leu Tyr
705                 710                 715                 720
Thr His Met Thr His Phe Leu Lys Gln Cys Phe Ser Leu Ser Asp
                725                 730                 735
```

<210> SEQ ID NO 215
<211> LENGTH: 3913
<212> TYPE: DNA
<213> ORGANISM: Homo sapiens

<400> SEQUENCE: 215

```
ctttcactgg caagagacgg agtcctgggt ttcagttcca gttgcctgcg gtgggctgtg      60
tgagtttgcc aaagtccccct gccctctctg ggtctcggtt ccctcgcctg tccacgtgag    120
gttggaggag ctgaacgccg acgtcatttt tagctaagag ggagcagggt ccccgagtcg    180
ccggcccagg gtctgcgcat ccgaggccgc gcgccctttc cctccccca cggctcctcc    240
gggccccgca ctctgcgccc cggctgccgc ccagcgccct acaccgccct caggggccc    300
tcgcgggctc ccccggccg ggatgccagt gccccgcgcc acgcgcgcct gctcccgcgc    360
cgcctgccct gcagcctgcc cgcggcgcct ttatacccag cgggctcggc gctcactaat    420
gtttaactcg gggccgaaac ttgccagcgg cgagtgactc caccgcccgg agcagcggtg    480
caggacgcgc gtctccgccg cccgcggtga cttctgcctg cgctccttct ctgaacgctc    540
acttccgagg agacgccgac gatgaagaca ccgtggaagg ttcttctggg actgctgggt    600
gctgctgcgc ttgtcaccat catcaccgtg cccgtggttc tgctgaacaa aggcacagat    660
gatgctacag ctgacagtcg caaaacttac actctaactg attacttaaa aaatacttat    720
agactgaagt tatactcctt aagatggatt tcagatcatg aatatctcta caaacaagaa    780
aataatatct tggtattcaa tgctgaatat ggaaacagct cagttttctt ggagaacagt    840
acatttgatg agtttgggaca ttctatcaat gattattcaa tatctcctga tgggcagttt    900
attctcttag aatacaacta cgtgaagcaa tggaggcatt cctacacagc ttcatatgac    960
atttatgatt taaataaaag gcagctgatt acagaagaga ggattccaaa caacacacag   1020
tgggtcacat ggtcaccagt gggtcataaa ttggcatatg tttggaacaa tgacatttat   1080
gttaaaattg aaccaaattt accaagttac agaatcacat ggacggggaa agaagatata   1140
atatataatg gaataactga ctgggtttat gaagaggaag tcttcagtgc ctactctgct   1200
ctgtggtggt ctccaaacgg cacttttttta gcatatgccc aatttaacga cacagaagtc   1260
ccacttattg aatactcctt ctactctgat gagtcactgc agtacccaaa gactgtacgg   1320
gttccatatc caaaggcagg agctgtgaat ccaactgtaa agttctttgt tgtaaataca   1380
gactctctca gctcagtcac caatgcaact tccatacaaa tcactgctcc tgcttctatg   1440
ttgataggggg atcactactt gtgtgatgtg acatgggcaa cacaagaaag aatttctttg   1500
cagtggctca ggaggattca gaactattcg gtcatggata tttgtgacta tgatgaatcc   1560
agtgaaagat ggaactgctt agtggcacgg caacacattg aaatgagtac tactggctgg   1620
gttggaagat ttaggccttc agaacctcat tttacccttg atggtaatag cttctacaag   1680
atcatcagca tgaagaagg ttacagacac atttgctatt ccaaataga taaaaaagac   1740
tgcacattta ttacaaaagg cacctgggaa gtcatcggga tagaagctct aaccagtgat   1800
tatctatact acattagtaa tgaatataaa ggaatgccag gaggaaggaa tctttataaa   1860
atccaactta gtgactatac aaaagtgaca tgcctcagtt gtgagctgaa tccggaaagg   1920
tgtcagtact attctgtgtc attcagtaaa gaggcgaagt attatcagct gagatgttcc   1980
ggtcctggtc tgcccctcta tactctacac agcagcgtga atgataaagg gctgagagtc   2040
ctggaagaca attcagcttt ggataaaatg ctgcagaatg tccagatgcc ctccaaaaaa   2100
```

```
ctggacttca ttattttgaa tgaaacaaaa ttttggtatc agatgatctt gcctcctcat    2160
tttgataaat ccaagaaata tcctctacta ttagatgtgt atgcaggccc atgtagtcaa    2220
aaagcagaca ctgtcttcag actgaactgg gccacttacc ttgcaagcac agaaaacatt    2280
atagtagcta gctttgatgg cagaggaagt ggttaccaag gagataagat catgcatgca    2340
atcaacagaa gactgggaac atttgaagtt gaagatcaaa ttgaagcagc cagacaattt    2400
tcaaaaatgg gatttgtgga caacaaacga attgcaattt ggggctggtc atatggaggg    2460
tacgtaacct caatggtcct gggatcggga agtggcgtgt tcaagtgtgg aatagccgtg    2520
gcgcctgtat cccggtggga gtactatgac tcagtgtaca cagaacgtta catgggtctc    2580
ccaactccag aagacaacct tgaccattac agaaattcaa cagtcatgag cagagctgaa    2640
aattttaaac aagttgagta cctccttatt catggaacag cagatgataa cgttcacttt    2700
cagcagtcag ctcagatctc caaagccctg gtcgatgttg gagtggattt ccaggcaatg    2760
tggtatactg atgaagacca tggaatagct agcagcacag cacaccaaca tatatatacc    2820
cacatgagcc acttcataaa acaatgtttc tctttacctt agcacctcaa aataccatgc    2880
catttaaagc ttattaaaac tcattttttgt tttcattatc tcaaaactgc actgtcaaga    2940
tgatgatgat ctttaaaata cacactcaaa tcaagaaact taaggttacc tttgttccca    3000
aatttcatac ctatcatctt aagtagggac ttctgtcttc acaacagatt attaccttac    3060
agaagtttga attatccggt cgggttttat tgtttaaaat catttctgca tcagctgctg    3120
aaacaacaaa taggaattgt tttatggag gctttgcata gattccctga gcaggatttt    3180 aatcttttc taactggact ggttcaaatg ttgttctctt ctttaaaggg atggcaagat    3240
gtgggcagtg atgtcactag gcagggaca ggataagagg gattagggag agaagatagc    3300
agggcatggc tgggaaccca gtccaagca taccaacacg agcaggctac tgtcagctcc    3360
cctcggagaa gagctgttca cagccagact ggcacagttt tctgagaaag actattcaaa    3420
cagtctcagg aaatcaaata tgcaaagcac tgacttctaa gtaaaaccac agcagttgaa    3480
aagactccaa agaaatgtaa gggaaactgc cagcaacgca ggcccccagg tgccagttat    3540
ggctataggt gctacaaaaa cacagcaagg gtgatgggaa agcattgtaa atgtgctttt    3600
aaaaaaaaat actgatgttc ctagtgaaag aggcagcttg aaactgagat gtgaacacat    3660
cagcttgccc tgttaaaaga tgaaaatatt tgtatcacaa atcttaactt gaaggagtcc    3720
ttgcatcaat ttttcttatt tcatttcttt gagtgtctta attaaaagaa tattttaact    3780
tccttggact catttttaaaa aatggaacat aaaatacaat gttatgtatt attattccca    3840
ttctacatac tatggaattt ctcccagtca tttaataaat gtgccttcat tttttcagaa    3900 aaaaaaaaa aaa                                                        3913
```

<210> SEQ ID NO 216
<211> LENGTH: 766
<212> TYPE: PRT
<213> ORGANISM: Homo sapiens

<400> SEQUENCE: 216

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

```
Leu Lys Asn Thr Tyr Arg Leu Lys Leu Tyr Ser Leu Arg Trp Ile Ser
 50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                 85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
```

| | | | | | | | | | | | |
|---|---|---|---|---|---|---|---|---|---|---|---|
| | 465 | | | 470 | | | 475 | | | 480 | |
| Thr | Leu | His | Ser | Ser | Val | Asn | Asp | Lys | Gly | Leu | Arg | Val | Leu | Glu | Asp |
| | | | | 485 | | | | | 490 | | | | | 495 | |
| Asn | Ser | Ala | Leu | Asp | Lys | Met | Leu | Gln | Asn | Val | Gln | Met | Pro | Ser | Lys |
| | | | 500 | | | | | 505 | | | | | 510 | | |
| Lys | Leu | Asp | Phe | Ile | Ile | Leu | Asn | Glu | Thr | Lys | Phe | Trp | Tyr | Gln | Met |
| | | | 515 | | | | | 520 | | | | | 525 | | |
| Ile | Leu | Pro | Pro | His | Phe | Asp | Lys | Ser | Lys | Lys | Tyr | Pro | Leu | Leu | Leu |
| | 530 | | | | | 535 | | | | | 540 | | | | |
| Asp | Val | Tyr | Ala | Gly | Pro | Cys | Ser | Gln | Lys | Ala | Asp | Thr | Val | Phe | Arg |
| 545 | | | | | 550 | | | | | 555 | | | | | 560 |
| Leu | Asn | Trp | Ala | Thr | Tyr | Leu | Ala | Ser | Thr | Glu | Asn | Ile | Ile | Val | Ala |
| | | | | 565 | | | | | 570 | | | | | 575 | |
| Ser | Phe | Asp | Gly | Arg | Gly | Ser | Gly | Tyr | Gln | Gly | Asp | Lys | Ile | Met | His |
| | | | | 580 | | | | | 585 | | | | | 590 | |
| Ala | Ile | Asn | Arg | Arg | Leu | Gly | Thr | Phe | Glu | Val | Glu | Asp | Gln | Ile | Glu |
| | | | 595 | | | | | 600 | | | | | 605 | | |
| Ala | Ala | Arg | Gln | Phe | Ser | Lys | Met | Gly | Phe | Val | Asp | Asn | Lys | Arg | Ile |
| | 610 | | | | | 615 | | | | | 620 | | | | |
| Ala | Ile | Trp | Gly | Trp | Ser | Tyr | Gly | Gly | Tyr | Val | Thr | Ser | Met | Val | Leu |
| 625 | | | | | 630 | | | | | 635 | | | | | 640 |
| Gly | Ser | Gly | Ser | Gly | Val | Phe | Lys | Cys | Gly | Ile | Ala | Val | Ala | Pro | Val |
| | | | | 645 | | | | | 650 | | | | | 655 | |
| Ser | Arg | Trp | Glu | Tyr | Tyr | Asp | Ser | Val | Tyr | Thr | Glu | Arg | Tyr | Met | Gly |
| | | | 660 | | | | | 665 | | | | | 670 | | |
| Leu | Pro | Thr | Pro | Glu | Asp | Asn | Leu | Asp | His | Tyr | Arg | Asn | Ser | Thr | Val |
| | | | 675 | | | | | 680 | | | | | 685 | | |
| Met | Ser | Arg | Ala | Glu | Asn | Phe | Lys | Gln | Val | Glu | Tyr | Leu | Leu | Ile | His |
| | 690 | | | | | 695 | | | | | 700 | | | | |
| Gly | Thr | Ala | Asp | Asp | Asn | Val | His | Phe | Gln | Gln | Ser | Ala | Gln | Ile | Ser |
| 705 | | | | | 710 | | | | | 715 | | | | | 720 |
| Lys | Ala | Leu | Val | Asp | Val | Gly | Val | Asp | Phe | Gln | Ala | Met | Trp | Tyr | Thr |
| | | | | 725 | | | | | 730 | | | | | 735 | |
| Asp | Glu | Asp | His | Gly | Ile | Ala | Ser | Ser | Thr | Ala | His | Gln | His | Ile | Tyr |
| | | | | 740 | | | | | 745 | | | | | 750 | |
| Thr | His | Met | Ser | His | Phe | Ile | Lys | Gln | Cys | Phe | Ser | Leu | Pro | | |
| | | | 755 | | | | | 760 | | | | | 765 | | |

<210> SEQ ID NO 217
<211> LENGTH: 2924
<212> TYPE: DNA
<213> ORGANISM: Homo sapiens

<400> SEQUENCE: 217

| | | | | |
|---|---|---|---|---|
| gacgccgacg | atgaagacac | cgtggaaggt | tcttctggga | ctgctgggtg | ctgctgcgct | 60 |
| tgtcaccatc | atcaccgtgc | ccgtggttct | gctgaacaaa | ggcacagatg | atgctacagc | 120 |
| tgacagtcgc | aaaacttaca | ctctaactga | ttacttaaaa | aatacttata | gactgaagtt | 180 |
| atactcctta | agatggattt | cagatcatga | atatctctac | aaacaagaaa | ataatatctt | 240 |
| ggtattcaat | gctgaatatg | aaacagctc | agttttcttg | gagaacagta | catttgatga | 300 |
| gtttggacat | tctatcaatg | attattcaat | atctcctgat | gggcagttta | ttctcttaga | 360 |
| atacaactac | gtgaagcaat | ggaggcattc | ctacacagct | tcatatgaca | tttatgattt | 420 |
| aaataaaagg | cagctgatta | cagaagagag | gattccaaac | aacacacagt | gggtcacatg | 480 |

```
gtcaccagtg ggtcataaat tggcatatgt ttggaacaat gacatttatg ttaaaattga    540
accaaattta ccaagttaca gaatcacatg gacggggaaa gaagatataa tatataatgg    600
aataactgac tgggtttatg aagaggaagt cttcagtgcc tactctgctc tgtggtggtc    660
tccaaacggc acttttttag catatgccca atttaacgac acagaagtcc cacttattga    720
atactccttc tactctgatg agtcactgca gtacccaaag actgtacggg ttccatatcc    780
aaaggcagga gctgtgaatc caactgtaaa gttctttgtt gtaaatacag actctctcag    840
ctcagtcacc aatgcaactt ccatacaaat cactgctcct gcttctatgt tgataggga    900 tcactacttg tgtgatgtga catgggcaac acaagaaaga attctttgc agtggctcag    960 gaggattcag aactattcgg tcatggatat ttgtgactat gatgaatcca gtggaagatg   1020
gaactgctta gtggcacggc aacacattga aatgagtact actggctggg ttggaagatt   1080
taggccttca gaacctcatt ttacccttga tggtaatagc ttctacaaga tcatcagcaa   1140
tgaagaaggt tacagacaca tttgctattt ccaaatagat aaaaaagact gcacatttat   1200
tacaaaaggc acctgggaag tcatcgggat agaagctcta accagtgatt atctatacta   1260
cattagtaat gaatataaag gaatgccagg aggaaggaat cttaatataaaa tccaacttag   1320 tgactataca aaagtgacat gcctcagttg tgagctgaat ccggaaaggt gtcagtacta   1380
ttctgtgtca ttcagtaaag aggcgaagta ttatcagctg agatgttccg gtcctggtct   1440 gccctctat actctacaca gcagcgtgaa tgataaaggg ctgagagtcc tggaagacaa   1500
ttcagctttg gataaaatgc tgcagaatgt ccagatgccc tccaaaaaac tggacttcat   1560 tatttttgaat gaaacaaaat tttggtatca gatgatcttg cctcctcatt ttgataaatc   1620
caagaaatat cctctactat tagatgtgta tgcaggccca tgtagtcaaa aagcagacac   1680
tgtcttcaga ctgaactggg ccacttacct tgcaagcaca gaaaacatta gtagctag   1740 ctttgatggc agaggaagtg gttaccaagg agataagatc atgcatgcaa tcaacagaag   1800
actgggaaca tttgaagttg aagatcaaat tgaagcagcc agacaatttt caaaaatggg   1860
atttgtggac aacaaacgaa ttgcaatttg gggctggtca tatggaggggt acgtaacctc   1920 aatggtcctg ggatcaggaa gtggcgtgtt caagtgtgga atagccgtgg cgcctgtatc   1980
ccggtgggag tactatgact cagtgtacac agaacgttac atgggtctcc caactccaga   2040
agacaacctt gaccattaca gaaattcaac agtcatgagc agagctgaaa attttaaaca   2100
agttgagtac ctccttattc atggaacagc agatgataac gttcactttc agcagtcagc   2160
tcagatctcc aaagccctgg tcgatgttgg agtggatttc caggcaatgt ggtatactga   2220
tgaagaccat ggaatagcta gcagcacagc acaccaacat atatatcccc acatgagcca   2280
cttcataaaa caatgtttct ctttaccta gcacctcaaa ataccatgcc atttaaagct   2340
tattaaaact cattttttgt ttcattatct caaaactgca ctgtcaagat gatgatgatc   2400
tttaaaatac acactcaaat caagaaactt aaggttacct ttgttcccaa atttcatacc   2460
tatcatctta agtagggact tctgtcttca caacagatta ttaccttaca gaagtttgaa   2520
ttatccggtc gggttttatt gtttaaaatc atttctgcat cagctgctga aacaacaaat   2580
aggaattgtt tttatggagg ctttgcatag attccctgag caggatttta atcttttct   2640 aactggactg gttcaaatgt tgttctcttc tttaagggga tggcaagatg tgggcagtga   2700
tgtcactagg gcaggacag ataagagggg attaggaga gaagatagca gggcatggct   2760
gggaacccaa gtccaagcat accaacacga ccaggctact gtcagctccc ctcggagaaa   2820
```

```
actgtgcagt ctgcgtgtga acagctcttc tcctttagag cacaatggat ctcgagggat    2880
cttccatacc taccagttct gcgcctcgag gccgcgactc taga                    2924
```

<210> SEQ ID NO 218
<211> LENGTH: 766
<212> TYPE: PRT
<213> ORGANISM: Homo sapiens

<400> SEQUENCE: 218

```
Met Lys Thr Pro Trp Lys Val Leu Leu Gly Leu Leu Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
```

```
              355                 360                 365
Asn Ser Phe Tyr Lys Ile Ile Ser Asn Glu Glu Gly Tyr Arg His Ile
    370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
                405                 410                 415
Tyr Ile Ser Asn Glu Tyr Lys Gly Met Pro Gly Gly Arg Asn Leu Tyr
            420                 425                 430
Lys Ile Gln Leu Ser Asp Tyr Thr Lys Val Thr Cys Leu Ser Cys Glu
        435                 440                 445
Leu Asn Pro Glu Arg Cys Gln Tyr Tyr Ser Val Ser Phe Ser Lys Glu
    450                 455                 460
Ala Lys Tyr Tyr Gln Leu Arg Cys Ser Gly Pro Gly Leu Pro Leu Tyr
465                 470                 475                 480
Thr Leu His Ser Val Asn Asp Lys Gly Leu Arg Val Leu Glu Asp
                485                 490                 495
Asn Ser Ala Leu Asp Lys Met Leu Gln Asn Val Gln Met Pro Ser Lys
            500                 505                 510
Lys Leu Asp Phe Ile Ile Leu Asn Glu Thr Lys Phe Trp Tyr Gln Met
        515                 520                 525
Ile Leu Pro Pro His Phe Asp Lys Ser Lys Tyr Pro Leu Leu Leu
    530                 535                 540
Asp Val Tyr Ala Gly Pro Cys Ser Gln Lys Ala Asp Thr Val Phe Arg
545                 550                 555                 560
Leu Asn Trp Ala Thr Tyr Leu Ala Ser Thr Glu Asn Ile Ile Val Ala
                565                 570                 575
Ser Phe Asp Gly Arg Gly Ser Gly Tyr Gln Gly Asp Lys Ile Met His
            580                 585                 590
Ala Ile Asn Arg Arg Leu Gly Thr Phe Glu Val Glu Asp Gln Ile Glu
        595                 600                 605
Ala Ala Arg Gln Phe Ser Lys Met Gly Phe Val Asp Asn Lys Arg Ile
    610                 615                 620
Ala Ile Trp Gly Trp Ser Tyr Gly Gly Tyr Val Thr Ser Met Val Leu
625                 630                 635                 640
Gly Ser Gly Ser Gly Val Phe Lys Cys Gly Ile Ala Val Ala Pro Val
                645                 650                 655
Ser Arg Trp Glu Tyr Tyr Asp Ser Val Tyr Thr Glu Arg Tyr Met Gly
            660                 665                 670
Leu Pro Thr Pro Glu Asp Asn Leu Asp His Tyr Arg Asn Ser Thr Val
        675                 680                 685
Met Ser Arg Ala Glu Asn Phe Lys Gln Val Glu Tyr Leu Leu Ile His
    690                 695                 700
Gly Thr Ala Asp Asp Asn Val His Phe Gln Gln Ser Ala Gln Ile Ser
705                 710                 715                 720
Lys Ala Leu Val Asp Val Gly Val Asp Phe Gln Ala Met Trp Tyr Thr
                725                 730                 735
Asp Glu Asp His Gly Ile Ala Ser Ser Thr Ala His Gln His Ile Tyr
            740                 745                 750
Thr His Met Ser His Phe Ile Lys Gln Cys Phe Ser Leu Pro
        755                 760                 765

<210> SEQ ID NO 219
```

<211> LENGTH: 1260
<212> TYPE: DNA
<213> ORGANISM: Homo sapiens

<400> SEQUENCE: 219

```
atgattggca cagatcctcg aacaattctt aaagatttat tgccggaaac aatacctcca      60
cctgagttgg atgatatgac actgtggcag attgttatta atatcctttc agaaccacca     120
aaaaggaaaa aagaaaaga tattaataca attgaagatg ctgtgaaatt actgcaagag     180
tgcaaaaaaa ttatagttct aactggagct ggggtgtctg tttcatgtgg aatacctgac     240
ttcaggtcaa gggatggtat ttatgctcgc cttgctgtag acttcccaga tcttccagat     300
cctcaagcga tgtttgatat tgaatatttc agaaaagatc caagaccatt cttcaagttt     360
gcaaaggaaa tatatcctgg acaattccag ccatctctct gtcacaaatt catagccttg     420
tcagataagg aaggaaaaact acttcgcaac tatacccaga acatagacac gctggaacag     480
gttgcgggaa tccaaaggat aattcagtgt catggttcct ttgcaacagc atcttgcctg     540
atttgtaaat acaaagttga ctgtgaagct gtacgaggag ctctttttag tcaggtagtt     600
cctcgatgtc ctaggtgccc agctgatgaa ccgcttgcta tcatgaaacc agagattgtg     660
tttttggtg aaaatttacc agaacagttt catagagcca tgaagtatga caagatgaa     720
gttgacctcc tcattgttat tgggtcttcc ctcaaagtaa gaccagtagc actaattcca     780
agttccatac cccatgaagt gcctcagata ttaattaata gagaaccttt gcctcatctg     840
cattttgatg tagagcttct tggagactgt gatgtcataa ttaatgaatt gtgtcatagg     900
ttaggtggta aatatgccaa actttgctgt aaccctgtaa agctttcaga aattactgaa     960
aaacctccac gaacacaaaa agaattggct tatttgtcag agttgccacc cacacctctt    1020
catgtttcag aagactcaag ttcaccagaa agaacttcac caccagattc ttcagtgatt    1080
gtcacacttt tagaccaagc agctaagagt aatgatgatt tagatgtgtc tgaatcaaaa    1140
ggttgtatgg aagaaaaacc acaggaagta caaacttcta ggaatgttga agtattgct    1200
gaacagatgg aaaatccgga tttgaagaat gttggttcta gtactgggga gaaaatgaa    1260
```

<210> SEQ ID NO 220
<211> LENGTH: 420
<212> TYPE: PRT
<213> ORGANISM: Homo sapiens

<400> SEQUENCE: 220

Met Ile Gly Thr Asp Pro Arg Thr Ile Leu Lys Asp Leu Leu Pro Glu
1               5                   10                  15

Thr Ile Pro Pro Glu Leu Asp Asp Met Thr Leu Trp Gln Ile Val
            20                  25                  30

Ile Asn Ile Leu Ser Glu Pro Pro Lys Arg Lys Lys Arg Lys Asp Ile
        35                  40                  45

Asn Thr Ile Glu Asp Ala Val Lys Leu Leu Gln Glu Cys Lys Lys Ile
    50                  55                  60

Ile Val Leu Thr Gly Ala Gly Val Ser Val Ser Cys Gly Ile Pro Asp
65                  70                  75                  80

Phe Arg Ser Arg Asp Gly Ile Tyr Ala Arg Leu Ala Val Asp Phe Pro
                85                  90                  95

Asp Leu Pro Asp Pro Gln Ala Met Phe Asp Ile Glu Tyr Phe Arg Lys
            100                 105                 110

Asp Pro Arg Pro Phe Phe Lys Phe Ala Lys Glu Ile Tyr Pro Gly Gln
        115                 120                 125

Phe Gln Pro Ser Leu Cys His Lys Phe Ile Ala Leu Ser Asp Lys Glu
    130                 135                 140

Gly Lys Leu Leu Arg Asn Tyr Thr Gln Asn Ile Asp Thr Leu Glu Gln
145                 150                 155                 160

Val Ala Gly Ile Gln Arg Ile Ile Gln Cys His Gly Ser Phe Ala Thr
                165                 170                 175

Ala Ser Cys Leu Ile Cys Lys Tyr Lys Val Asp Cys Glu Ala Val Arg
            180                 185                 190

Gly Ala Leu Phe Ser Gln Val Val Pro Arg Cys Pro Arg Cys Pro Ala
        195                 200                 205

Asp Glu Pro Leu Ala Ile Met Lys Pro Glu Ile Val Phe Phe Gly Glu
    210                 215                 220

Asn Leu Pro Glu Gln Phe His Arg Ala Met Lys Tyr Asp Lys Asp Glu
225                 230                 235                 240

Val Asp Leu Leu Ile Val Ile Gly Ser Ser Leu Lys Val Arg Pro Val
                245                 250                 255

Ala Leu Ile Pro Ser Ser Ile Pro His Glu Val Pro Gln Ile Leu Ile
            260                 265                 270

Asn Arg Glu Pro Leu Pro His Leu His Phe Asp Val Glu Leu Leu Gly
        275                 280                 285

Asp Cys Asp Val Ile Ile Asn Glu Leu Cys His Arg Leu Gly Gly Glu
    290                 295                 300

Tyr Ala Lys Leu Cys Cys Asn Pro Val Lys Leu Ser Glu Ile Thr Glu
305                 310                 315                 320

Lys Pro Pro Arg Thr Gln Lys Glu Leu Ala Tyr Leu Ser Glu Leu Pro
                325                 330                 335

Pro Thr Pro Leu His Val Ser Glu Asp Ser Ser Ser Pro Glu Arg Thr
            340                 345                 350

Ser Pro Pro Asp Ser Ser Val Ile Val Thr Leu Leu Asp Gln Ala Ala
        355                 360                 365

Lys Ser Asn Asp Asp Leu Asp Val Ser Glu Ser Lys Gly Cys Met Glu
    370                 375                 380

Glu Lys Pro Gln Glu Val Gln Thr Ser Arg Asn Val Glu Ser Ile Ala
385                 390                 395                 400

Glu Gln Met Glu Asn Pro Asp Leu Lys Asn Val Gly Ser Ser Thr Gly
                405                 410                 415

Glu Lys Asn Glu
            420

<210> SEQ ID NO 221
<211> LENGTH: 7341
<212> TYPE: DNA
<213> ORGANISM: Homo sapiens

<400> SEQUENCE: 221
gcgcgaggcc gtcgattcgc tcgcggctcc atcgcggcct ggccgggggg cggtgtctgc    60
tgcgccaggt tcgctggccg cacgtcttca ggtcctcctg ttcctgggag gcgggcgcgg   120
caggactggg aggtggcggc agcgggcgag gactcgccga ggacgggggct ccggcccggg   180 ataaccaact ctccttctct cttctttggt gcttcccag gcggcggcgg cggcgcccgg   240
gagccggagc cttcgcggcg tccacgtccc tccccgctg caccccgccc ggcgcgaga   300 ggagagcgcg agagccccag ccgcgggcgg gcgggcggcg aagatggcag aggcaccggc   360
ttccccggcc ccgctctctc cgctcgaagt ggagctggac ccggagttcg agccccagag   420

-continued

```
ccgtccgcga tcctgtacgt ggccctgca aaggccggag ctccaagcga gccctgccaa      480
gccctcgggg gagacggccg ccgactccat gatccccgag gaggaggacg atgaagacga      540
cgaggacggc gggggacggg ccggctcggc catggcgatc ggcggcggcg gcgggagcgg      600
cacgctgggc tccgggctgc tccttgagga ctcggcccgg gtgctggcac ccggagggca      660
agaccccggg tctgggccag ccaccgcggc gggcgggctg agcggggta cacaggcgct       720 gctgcagcct cagcaaccgc tgccaccgcc gcagccgggg gcggctgggg gctccgggca      780
gccgaggaaa tgttcgtcgc ggcggaacgc ctggggaaac ctgtcctacg cggacctgat      840
cacccgcgca atcgagagct ccccggacaa acggctcact ctgtcccaga tctacgagtg      900
gatggtgcgt tgcgtgccct acttcaagga taagggcgac agcaacagct ctgccggctg      960
gaagaactcc atccggcaca acctgtcact gcatagtcga ttcatgcggg tccagaatga     1020
gggaactggc aagagctctt ggtggatcat caaccctgat gggggaaga gcggaaaagc      1080 cccccggcgg cgggctgtct ccatggacaa tagcaacaag tataccaaga gccgtggccg     1140
cgcagccaag aagaaggcag ccctgcagac agcccccgaa tcagctgacg acagtccctc     1200
ccagctctcc aagtggcctg gcagcccac gtcacgcagc agtgatgagc tggatgcgtg      1260
gacggacttc cgttcacgca ccaattctaa cgccagcaca gtcagtggcc gcctgtcgcc     1320
catcatggca agcacagagt tggatgaagt ccaggacgat gatgcgcctc tctcgcccat     1380
gctctacagc agctcagcca gcctgtcacc ttcagtaagc aagccgtgca cggtggaact     1440
gccacggctg actgatatgg caggcaccat gaatctgaat gatgggctga ctgaaaacct     1500
catggacgac ctgctggata acatcacgct cccgccatcc cagccatcgc ccactggggg     1560
actcatgcag cggagctcta gcttcccgta caccaag ggctcgggcc tgggctcccc       1620
aaccagctcc tttaacagca cggtgttcgg accttcatct ctgaactccc tacgccagtc     1680
tcccatgcag accatccaag agaacaagcc agctaccttc tcttccatgt cacactatgg     1740
taaccagaca ctccaggacc tgctcacttc ggactcactt agccacagcg atgtcatgat     1800
gacacagtcg gaccccttga tgtctcaggc cagcaccgct gtgtctgccc agaattcccg     1860
ccggaacgtg atgcttcgca atgatccgat gatgtccttt gctgcccagc ctaaccaggg     1920
aagtttggtc aatcagaact tgctccacca ccagcaccaa acccagggcg ctcttggtgg     1980
cagccgtgcc ttgtcgaatt ctgtcagcaa catgggcttg agtgagtcca gcagccttgg     2040
gtcagccaaa caccagcagc agtctcctgt cagccagtct atgcaaaccc tctcggactc     2100
tctctcaggc tcctccttgt actcaactag tgcaaacctg cccgtcatgg gccatgagaa     2160
gttccccagc gacttggacc tggacatgtt caatgggagc ttggaatgtg acatggagtc     2220
cattatccgt agtgaactca tggatgctga tgggttggat tttaactttg attccctcat     2280
ctccacacag aatgttgttg gtttgaacgt ggggaacttc actggtgcta agcaggcctc     2340
atctcagagc tgggtgccag gctgaaggat cactgaggaa ggggaagtgg caaagcaga     2400 ccctcaaact gacacaagac ctacagagaa aacccttgc caaatctgct ctcagcaagt     2460
ggacagtgat accgtttaca gcttaacacc tttgtgaatc ccacgccatt ttcctaaccc     2520
agcagagact gttaatggcc ccttaccctg ggtgaagcac ttacccttgg aacagaactc     2580
taaaaagtat gcaaaatctt ccttgtacag ggtggtgagc cgcctgccag tggaggacag     2640
cacccctcag caccacccac cctcattcag agcacaccgt gagccccgt cggccattct      2700 gtggtgtttt aatattgcga tggtttatgg gacgttttaa gtgttgttct tgtgtttgtt     2760
```

```
ttcctttgac tttctgagtt tttcacatgc attaacttgc ggtattttc tgttaaaatg      2820 ttaaccgtcc ttccctagc aaatttaaaa acagaaagaa aatgttgtac cagttaccat      2880
tccgggttcg agcatcacaa gcttttgagc gcatggaact ccataaacta acaaattaca     2940
taaactaaag ggggatttc tttcttcttt tgtttggtag aaaattatcc tttctaaaa      3000 actgaacaat ggcacaattg tttgctatgt gcacccgtcc aggacagaac cgtgcatagg     3060
caaaaggagt ggagcacagc gtccggccca gtgtgtttcc ggttctgagt cagggtgatc     3120
tgtggacggg accccagcac caagtctacg ggtgccagat cagtagggcc tgtgatttcc     3180
tgtcagtgtc ctcagctaat gtgaacagtg ttggtctgct ggttagaaac tagaatattg     3240
atattttcag gaaagaaatc agctcagctc tccactcatt gccaaatgtc actaaagggt     3300
ttagttttaa ggagaaagaa aaggaaaaaa aaaaaaaca aaaaagtcct gttttgcttt      3360
gcagaacaaa tgaacttaca ggtgagcatt aagcttgcag tgagaaatgt gcgaagagta     3420
aaaacccaag tcaatgctga ggcagttcta acttcactgt tttcctaaat acacatcctt     3480 gattatttc agccttgcta tataatctga tctgctagaa gtgtatgagt gagaggcaat     3540
agcatacaaa ctgatttttt aaatataagc ttaggttgta attgtacaag tgactcaatg     3600
gaagtacaaa atagggcagt tttaactttt ttttctgctt ctatggattt cattttgttg     3660
tgttttcaaa aagttatggt gctgtatagg tgctttctgt ttaacctgga aagtgtgatt     3720
atattcgtta ccttctttgg tagacggaat agttgggacc acctttggta cataagaaat      3780
tggtataacg atgctctgat tagcacagta tatgcatact tctccaaagt gatatatgaa     3840
gactcttttc tttgcataaa aagcattagg catataaatg tataaatata ttttatcatg     3900
tacagtacaa aaatggaacc ttatgcatgg gccttaggaa tacaggctag tatttcagca    3960
cagacttccc tgcttgagtt cttgctgatg cttgcaccgt gacagtgggc accaacacag     4020
acgtgccacc caaccccctg cacacaccac cggccaccag gggccccctt gtgcgccttg     4080
gctttataac tcctctgggg gtgatattgg tggtgatcac agctcctagc ataatgagag     4140
ttccatttgg tattgtcaca cgtctcctgc ctcgcttggg ttgccatgtt tgagcgatgg     4200
ccctgttgat ttcaccctgc cttttactga atctgtaaat tgttgtgcaa ttgtggttat     4260
agtagactgt agcacattgc cttttctaaa ctgctacatg tttataatct tcatttttaa     4320
agtatgtgta atttttttaa gtatgtattc tattcatatg gtctgcttgt cagtgagcca     4380
gacttgctta ctatattcct ttataataat gctagccact tcctggattc tttagtaatg     4440
tgctgtatgc aagaactttc cagtagcagt gaaggagggt tgcctctcca agcttcctaa     4500
gggatgctgc cctgtgtggg gatgcattgc agaggcacta gtagcatggg ggctagagtg     4560
gggagcgaga tgtaaaaggg tgggggata ggagaattcc agagtgcttc cagcattagg    4620
gtcctgagaa cttctgagtt cagagaaaca tgcaaagtga ctaacaaaat agctacttac     4680
ctttgcagtt ttacagaccc tgggagctgc tttgggagtg agaaaggcaa ccctccaatg     4740
tgtttcaact ttaaaatgtt gaattctttt cagacatggt atctcattta ttctcctttt     4800
ctagcgtttg ttgaatttca ggcagaatgt cttacagaat gtcctagaac cagattatca     4860
tttaatctga aacagctgag gaagggacag agaaggtaca agggcaaggc agcacaaaac     4920
agatcaggag aatgaagagg gaatgctttg gtttttgtt ttgttttgtt ttttcttttt      4980
caagtaacta aaacagcatc tacatgtaga gtgttgtgga gagctgagac cagggtaaag     5040
tcaagtgcag catcagtact gcgagaccca ccagcccctg gagagggtca gccgagaatc     5100
tggtagtgaa gcctgtctag ggtcccggca ccctcaccct cagccacctg cagagaggcc     5160
```

```
agggccccag agactagcct ggttctgaag tgggcagggg tgctgccaga gccctctgcc    5220
ccttatgttg agaccctgct ttcaggacag gccagccgtt ggccaccatg tcacattctg    5280
agtgagtgtc acaggtccct aacaataatt ttctgatctg gagcatatca gcagaatgct    5340
tagcctcaag gggcctggca gctgtaatgt ttgatttatg atgagaacta ccgaggcca     5400
cccttggcct ctaaataagc tgctctaggg agccgcctac tttttgatga gaaattagaa    5460
gagtacctaa tgttgaaaac atgacatgcg ctccttgggat ctgctgttct ctccagggct   5520
ccagaacctg ataccctgtta ccaaagctag gaaagagctt tatcacaagc cttcactgtc   5580
ctggcatgag aactggctgc caggctcagt gtaccccatt aactgtgaat gaatctgagc    5640
ttggtttcct ttattgcttc ctctgcaata tgattgctga aacacatttt aaaaattcag    5700
aagcttgtca ctcctgttaa tgggaggatc agtcacacat gtgtagtaca aggcggactt    5760
tgtgtttgtt tttggtgtta attttttagca ttgtgtgtgt tgcttcccca ccctgaggag   5820
aggacaccat ggcttactac tcaggacaag tatgccccgc tcagggtgtg atttcaggtg    5880
gcttccaaac ttgtacgcag tttaaagatg gtggggacag actttgcctc tacctagtga   5940
accccactta agaataagg agcatttgaa tctcttggaa aaggccatga agaataaagc     6000
agtcaaaaag aagtcctcca tgttggtgcc aaggacttgc gaggggaaat aaaaatgtta   6060
tccagcctga ccaacatgga gaaaccccgt ctccattaaa aatacaaaat tagcctggca   6120
tggtggcgca tgcctgtaat cccagctact ctggaggctg aggcaggaga atcgcttgaa   6180
cccaggaggc ggaggtcgca gtgagccgag atcatgccag tgcactccag cctgggtaac   6240
aagagtgaaa ctccgtgtca aaaaaaaaaa aaaatgttta ctcatcctct ctgaaagcaa    6300
aaaggaaacc ctaacagctc tgaactctgg ttttattttt cttgctgtat ttgggtgaac   6360
attgtatgat taggcataat gttaaaaaaa aaaatttttt tttggtagaa atgcaatcac    6420
cagtaaagag gtacgaaaaa gctagcctct ctcagagacc ggggaggcag agtactacta   6480
gaggaagtga agttctgatg gaatcatgcc tgtcaaatga ggtcttgaag cggatgccca    6540
aataaaagag tatatttat ctaaatctta agtgggtaac atttttatgca gtttaaatga    6600
atggaatatt ttcctcttgt ttagttgtat ctgtttgtat ttttctttga tgaatgattg    6660
gtcatgaggc ctcttgccac actccagaaa tacgtgtgcg gctgctttta agaactatgt    6720
gtctggtcac ttatttctct aaaattatct cattgcctgg caatcagtct tctcttgtat    6780
acttgtccta gcacattatg tacatgggaa atgtaaacaa atgtgaagga ggaccagaaa    6840
aattagttaa tatttaaaaa aatgtattgt gcattttggc ttcacatgtt taactttttt    6900
taagaaaaaa gttgcatgaa tggaaaaaaa aatctgtata cagtatctgt aaaaactatc    6960
ttatctgttt caattccttg ctcatatccc atataatcta gaactaaata tggtgtgtgg    7020
ccatatttaa acacctgaga gtcaagcagt tgagactttg atttgaagca cctcatcctt    7080
cttcaatgc gaacactatc atatggcatt cttactgagg attttgtcta accatatgtt    7140
gccatgaatt aactctgccg cctttcttaa ggatcaaaac cagtttgatt tgggaatctt    7200
cccctttcca aatgaaatag agatgcagta cttaactttc cttggtgttt gtagatattg    7260
ccttgtgtat tccacttaaa accgtaatct agtttgtaaa agagatggtg acgcatgtaa    7320
ataaagcatc agtgacactc t                                             7341
```

<210> SEQ ID NO 222
<211> LENGTH: 673
<212> TYPE: PRT

<213> ORGANISM: Homo sapiens

<400> SEQUENCE: 222

| | | | | | | | | | | | | | | |
|---|---|---|---|---|---|---|---|---|---|---|---|---|---|---|
|Met|Ala|Glu|Ala|Pro|Ala|Ser|Pro|Ala|Pro|Leu|Ser|Pro|Leu|Glu|Val|
|1| | | |5| | | |10| | | |15| | |
|Glu|Leu|Asp|Pro|Glu|Phe|Glu|Pro|Gln|Ser|Arg|Pro|Arg|Ser|Cys|Thr|
| | | |20| | | |25| | | |30| | | |
|Trp|Pro|Leu|Gln|Arg|Pro|Glu|Leu|Gln|Ala|Ser|Pro|Ala|Lys|Pro|Ser|
| | |35| | | |40| | | |45| | | | |
|Gly|Glu|Thr|Ala|Ala|Asp|Ser|Met|Ile|Pro|Glu|Glu|Asp|Asp|Glu|
| |50| | | |55| | | |60| | | | | |
|Asp|Asp|Glu|Asp|Gly|Gly|Arg|Ala|Gly|Ser|Ala|Met|Ala|Ile|Gly|
|65| | | |70| | | |75| | | |80| | |
|Gly|Gly|Gly|Gly|Ser|Gly|Thr|Leu|Gly|Ser|Gly|Leu|Leu|Leu|Glu|Asp|
| | | | |85| | | |90| | | |95| | |
|Ser|Ala|Arg|Val|Leu|Ala|Pro|Gly|Gly|Gln|Asp|Pro|Gly|Ser|Gly|Pro|
| | | |100| | | |105| | | |110| | | |
|Ala|Thr|Ala|Ala|Gly|Gly|Leu|Ser|Gly|Gly|Thr|Gln|Ala|Leu|Leu|Gln|
| | |115| | | |120| | | |125| | | | |
|Pro|Gln|Gln|Pro|Leu|Pro|Pro|Pro|Gln|Pro|Gly|Ala|Ala|Gly|Gly|Ser|
| |130| | | |135| | | |140| | | | | |
|Gly|Gln|Pro|Arg|Lys|Cys|Ser|Ser|Arg|Arg|Asn|Ala|Trp|Gly|Asn|Leu|
|145| | | |150| | | |155| | | |160| | |
|Ser|Tyr|Ala|Asp|Leu|Ile|Thr|Arg|Ala|Ile|Glu|Ser|Ser|Pro|Asp|Lys|
| | | |165| | | |170| | | |175| | | |
|Arg|Leu|Thr|Leu|Ser|Gln|Ile|Tyr|Glu|Trp|Met|Val|Arg|Cys|Val|Pro|
| | |180| | | |185| | | |190| | | | |
|Tyr|Phe|Lys|Asp|Lys|Gly|Asp|Ser|Asn|Ser|Ser|Ala|Gly|Trp|Lys|Asn|
| |195| | | |200| | | |205| | | | | |
|Ser|Ile|Arg|His|Asn|Leu|Ser|Leu|His|Ser|Arg|Phe|Met|Arg|Val|Gln|
|210| | | |215| | | |220| | | | | | |
|Asn|Glu|Gly|Thr|Gly|Lys|Ser|Ser|Trp|Trp|Ile|Ile|Asn|Pro|Asp|Gly|
|225| | | |230| | | |235| | | |240| | |
|Gly|Lys|Ser|Gly|Lys|Ala|Pro|Arg|Arg|Arg|Ala|Val|Ser|Met|Asp|Asn|
| | | |245| | | |250| | | |255| | | |
|Ser|Asn|Lys|Tyr|Thr|Lys|Ser|Arg|Gly|Arg|Ala|Ala|Lys|Lys|Lys|Ala|
| | |260| | | |265| | | |270| | | | |
|Ala|Leu|Gln|Thr|Ala|Pro|Glu|Ser|Ala|Asp|Ser|Pro|Ser|Gln|Leu|
| |275| | | |280| | | |285| | | | | |
|Ser|Lys|Trp|Pro|Gly|Ser|Pro|Thr|Ser|Arg|Ser|Ser|Asp|Glu|Leu|Asp|
|290| | | |295| | | |300| | | | | | |
|Ala|Trp|Thr|Asp|Phe|Arg|Ser|Arg|Thr|Asn|Ser|Asn|Ala|Ser|Thr|Val|
|305| | | |310| | | |315| | | |320| | |
|Ser|Gly|Arg|Leu|Ser|Pro|Ile|Met|Ala|Ser|Thr|Glu|Leu|Asp|Glu|Val|
| | | |325| | | |330| | | |335| | | |
|Gln|Asp|Asp|Asp|Ala|Pro|Leu|Ser|Pro|Met|Leu|Tyr|Ser|Ser|Ser|Ala|
| | |340| | | |345| | | |350| | | | |
|Ser|Leu|Ser|Pro|Ser|Val|Ser|Lys|Pro|Cys|Thr|Val|Glu|Leu|Pro|Arg|
| |355| | | |360| | | |365| | | | | |
|Leu|Thr|Asp|Met|Ala|Gly|Thr|Met|Asn|Leu|Asn|Asp|Gly|Leu|Thr|Glu|
|370| | | |375| | | |380| | | | | | |
|Asn|Leu|Met|Asp|Asp|Leu|Leu|Asp|Asn|Ile|Thr|Leu|Pro|Pro|Ser|Gln|
|385| | | |390| | | |395| | | |400| | |

```
Pro Ser Pro Thr Gly Gly Leu Met Gln Arg Ser Ser Phe Pro Tyr
                405                 410                 415

Thr Thr Lys Gly Ser Gly Leu Gly Ser Pro Thr Ser Ser Phe Asn Ser
            420                 425                 430

Thr Val Phe Gly Pro Ser Ser Leu Asn Ser Leu Arg Gln Ser Pro Met
        435                 440                 445

Gln Thr Ile Gln Glu Asn Lys Pro Ala Thr Phe Ser Ser Met Ser His
    450                 455                 460

Tyr Gly Asn Gln Thr Leu Gln Asp Leu Leu Thr Ser Asp Ser Leu Ser
465                 470                 475                 480

His Ser Asp Val Met Met Thr Gln Ser Asp Pro Leu Met Ser Gln Ala
                485                 490                 495

Ser Thr Ala Val Ser Ala Gln Asn Ser Arg Arg Asn Val Met Leu Arg
            500                 505                 510

Asn Asp Pro Met Met Ser Phe Ala Ala Gln Pro Asn Gln Gly Ser Leu
        515                 520                 525

Val Asn Gln Asn Leu Leu His His Gln His Thr Gln Gly Ala Leu
    530                 535                 540

Gly Gly Ser Arg Ala Leu Ser Asn Ser Val Ser Asn Met Gly Leu Ser
545                 550                 555                 560

Glu Ser Ser Ser Leu Gly Ser Ala Lys His Gln Gln Ser Pro Val
                565                 570                 575

Ser Gln Ser Met Gln Thr Leu Ser Asp Ser Leu Ser Gly Ser Ser Leu
            580                 585                 590

Tyr Ser Thr Ser Ala Asn Leu Pro Val Met Gly His Glu Lys Phe Pro
        595                 600                 605

Ser Asp Leu Asp Leu Asp Met Phe Asn Gly Ser Leu Glu Cys Asp Met
    610                 615                 620

Glu Ser Ile Ile Arg Ser Glu Leu Met Asp Ala Asp Gly Leu Asp Phe
625                 630                 635                 640

Asn Phe Asp Ser Leu Ile Ser Thr Gln Asn Val Val Gly Leu Asn Val
                645                 650                 655

Gly Asn Phe Thr Gly Ala Lys Gln Ala Ser Ser Gln Ser Trp Val Pro
            660                 665                 670

Gly

<210> SEQ ID NO 223
<211> LENGTH: 22
<212> TYPE: DNA
<213> ORGANISM: Homo sapiens
```

```
<400> SEQUENCE: 223
tggctcagtt cagcaggaac ag                                        22

<210> SEQ ID NO 224
<211> LENGTH: 86
<212> TYPE: DNA
<213> ORGANISM: Homo sapiens

<400> SEQUENCE: 224
tgccagtctc taggtccctg agacccttta acctgtgagg acatccaggg tcacaggtga  60
ggttcttggg agcctggcgt ctggcc                                      86

<210> SEQ ID NO 225
<211> LENGTH: 110
<212> TYPE: DNA
<213> ORGANISM: Homo sapiens

<400> SEQUENCE: 225
gtgttgggga ctcgcgcgct gggtccagtg gttcttaaca gttcaacagt tctgtagcgc  60
aattgtgaaa tgtttaggac cactagaccc ggcgggcgcg gcgacagcga            110

<210> SEQ ID NO 226
<211> LENGTH: 100
<212> TYPE: DNA
<213> ORGANISM: Homo sapiens

<400> SEQUENCE: 226
tgtgtctctc tctgtgtcct gccagtggtt ttaccctatg gtaggttacg tcatgctgtt  60
ctaccacagg gtagaaccac ggacaggata ccggggcacc                       100

<210> SEQ ID NO 227
<211> LENGTH: 78
<212> TYPE: DNA
<213> ORGANISM: Homo sapiens

<400> SEQUENCE: 227
ctgaggagca gggcttagct gcttgtgagc agggtccaca ccaagtcgtg ttcacagtgg  60
ctaagttccg ccccccag                                               78
```